US008399650B2

(12) United States Patent
James et al.

(10) Patent No.: US 8,399,650 B2

(45) **Date of Patent: *Mar. 19, 2013**

(54) MYCOBACTERIAL ANTIGENS EXPRESSED DURING LATENCY

(75) Inventors: Brian W. James, Salisbury (GB); Philip Marsh, Salisbury (GB); Tobias Hampshire, Salisbury (GB)

(73) Assignee: Health Protection Agency, Salisbury (GB)

(*) Notice: Subject to any disclaimer, the term of this patent is extended or adjusted under 35 U.S.C. 154(b) by 0 days.

This patent is subject to a terminal disclaimer.

(21) Appl. No.: 13/214,776

(22) Filed: Aug. 22, 2011

(65) Prior Publication Data

US 2012/0034689 A1 Feb. 9, 2012

Related U.S. Application Data

(62) Division of application No. 12/140,163, filed on Jun. 16, 2008, now Pat. No. 8,003,776, which is a division of application No. 10/482,706, filed on Jul. 19, 2004, now Pat. No. 7,393,540.

(30) Foreign Application Priority Data

Jul. 4, 2001 (GB) .................................. 0116385.6
Oct. 5, 2001 (GB) .................................. 0123993.8

(51) Int. Cl.
*C07H 21/04* (2006.01)
*A61K 39/04* (2006.01)
*A61K 39/02* (2006.01)

(52) U.S. Cl. ........ 536/23.7; 536/23.1; 424/9.1; 424/9.2; 424/184.1; 424/185.1; 424/234.1; 424/248.1

(58) Field of Classification Search ................. 536/23.1, 536/23.7; 424/9.1, 9.2, 184.1, 185.1, 234.1, 424/248.1
See application file for complete search history.

(56) References Cited

U.S. PATENT DOCUMENTS

| | | | | |
|---|---|---|---|---|
| 5,783,386 | A | 7/1998 | Jacobs, Jr. et al. | |
| 5,876,991 | A | 3/1999 | DeHoff et al. | |
| 5,998,194 | A | 12/1999 | Summers et al. | |
| 6,183,957 | B1 | 2/2001 | Cole et al. | |
| 6,572,865 | B1 | 6/2003 | Nano | |
| 6,573,361 | B1 | 6/2003 | Bunkers et al. | |
| 6,583,266 | B1 | 6/2003 | Smith et al. | |
| 6,613,553 | B1 | 9/2003 | Rock et al. | |
| 6,892,139 | B2 | 5/2005 | Eisenberg et al. | |
| 7,393,539 | B2 | 7/2008 | James et al. | |
| 7,393,540 | B2 | 7/2008 | James et al. | |
| 7,811,588 | B2 | 10/2010 | James et al. | |
| 8,003,776 | B2 * | 8/2011 | James et al. | 536/23.7 |
| 8,017,753 | B2 | 9/2011 | James et al. | |
| 2004/0241826 | A1 | 12/2004 | James et al. | |
| 2004/0253711 | A1 | 12/2004 | James et al. | |
| 2004/0254349 | A1 | 12/2004 | James et al. | |
| 2009/0054367 | A1 | 2/2009 | James et al. | |
| 2009/0082296 | A1 | 3/2009 | James et al. | |
| 2011/0091881 | A1 | 4/2011 | James et al. | |
| 2012/0088297 | A1 | 4/2012 | James et al. | |

FOREIGN PATENT DOCUMENTS

| | | |
|---|---|---|
| JP | 2000-508525 | 7/2000 |
| WO | WO 92/08484 | 5/1992 |
| WO | WO 94/01441 | 1/1994 |
| WO | WO 96/17951 | 6/1996 |
| WO | WO 97/35611 | 10/1997 |
| WO | WO 98/16645 | 4/1998 |
| WO | WO 98/53076 | 11/1998 |
| WO | WO 98/55624 | 12/1998 |
| WO | WO 99/04005 | 1/1999 |
| WO | WO 99/10536 | 3/1999 |
| WO | WO 99/24067 | 5/1999 |
| WO | WO 99/57130 | 11/1999 |
| WO | WO 00/52139 | 9/2000 |
| WO | WO 02/077183 | 10/2002 |
| WO | WO 03/000721 | 1/2003 |
| WO | WO 03/004520 | 1/2003 |
| WO | WO 03/035681 | 5/2003 |

OTHER PUBLICATIONS

NCBI, Sequence Viewer: Protien NP_334615.1, "Peptidase family M13 endopeptidase (*Mycobacterium turbulosis* CDC1551)", found at http://www.ncbi.nlm.nih.gov, pp. 1-2, printed on Aug. 11, 2011.

NCBI, Sequence Viewer Protein O08411.1, "RecName: Full=Probable low-affinity inorganic phosphate transporter", found at http://www.ncbi.nlm.nih.gov, pp. 1-3, printed on Aug. 11, 2011.

McShane, H. et al., "Recombinant modified vaccinia Ankara expressing antigen 85A boosts BCG-primed and naturally acquired antimycobacterial immunity in humans", Nature Medicine, vol. 10, pp. 1240-1244, (2004).

Pai, M. et al., "Interferon-y assays in the immunodiagnosis of tuberculosis: a systematic review", The Lancet Infectious Diseases, vol. 4, issue 12, pp. 761-766, (2004).

McKinney, J.D., et al., Persistence of *Mycobacterium tuberculosis* in macrophages and mice requires the glyoxylate shunt enzyme isocitrate lyase [see comments]. Nature, 2000. 406(6797): p. 735-8.

(Continued)

*Primary Examiner* — Rodney P. Swartz

(74) *Attorney, Agent, or Firm* — Evan Law Group LLC

(57) ABSTRACT

A method is provided for identifying mycobacterial genes that are induced or up-regulated under culture conditions that are nutrient-starving and which maintain mycobacterial latency, said conditions being obtainable by batch fermentation of a mycobacterium for at least 20 days post-inoculation, when compared with culture conditions that are not nutrient-starving and which support exponential growth of said mycobacterium. Said induced or up-regulated genes form the basis of nucleic acid vaccines, or provide targets to allow preparation of attenuated mycobacteria for vaccines against mycobacterial infections. Similarly, peptides encoded by said induced or up-regulated genes are employed in vaccines. In a further embodiment, the identified genes/peptides provide the means for identifying the presence of a mycobacterial infection in a clinical sample by nucleic acid probe or antibody detection.

19 Claims, 4 Drawing Sheets

OTHER PUBLICATIONS

Pelicic, V., et al., Efficient allelic exchange and transposon mutagensis in *Mycobacterium tuberculosis*. Proc Natl Acad Sci U S A, 1997. 94(20): p. 10955-60.

Lee, M.H., et al., Site-specific integration of mycobacteriophage L5: integration-proficient vectors for *Mycobacterium smegmatis, Mycobacterium tuberculosis*, and bacille Calmette-Guerin. Proc Natl Acad Sci U S A, 1991. 88(8): p. 3111-5.

McShane, H., et al., Enhanced immunogenicity of CDF(+) t-cell responses and protective efficacy of a DNA-modified vaccinia virus Ankara prime-boost vaccination regimen for murine tuberculosis. Infect Immun, 2001. 69(2): p. 681-6.

Movahedzadeh, F., M.J. Colston, and E.O. Davis, Characterization of *Mycobacterium tuberculosis* LexA: recognition of a Cheo (*Bacillus*-type SOS) box. Microbiology, 1997, 143(Pt 3): p. 929-36.

Cunningham, A. F. and C. L. Spreadbury. 1998, Mycobacterial stationary phase induced by low oxygen tension: cell wall thickening and localization of the 16-kilodalton alpha-crystallin homolog. J. Bacteriol. 180:801-808.

Lalvani, A. et al., 2001. Enhanced contact tracing and spatial tracking of *Mycobacterium tuberculosis* infection by enumeration of antigen-specific T cells. The Lancet 357:2017-2021.

Rook, G. A. W. and B. R. Bloom. 1994. Mechanisms of pathogenesis in tuberculosis, pp. 460-485. In B. R. Bloom (ed), Tuberculosis-pathogenesis, protection and control, ASM Press, Washington DC.

Wayne, L. G. 1994. Dormancy of *Mycobacterium tuberculosis* and latency of disease. Eur. J. Clin. Microbiol. Infect. Dis. 13:908-914.

Wayne, L. G. and L. G. Hayes. 1996. An in vitro model for sequential study of shift-down of *Mycobacterium tuberculosis* through two stages of non-replicating persistence. Infect. Immun. 65:2062-2069.

Wayne, L. G. and K. Lin. 1982. Glyoxylate metabolism and adaptation of *Mycobacterium tuberculosis* to survival under anaerobic conditions. Infect. Immun. 37:1042-1049.

Sambrook, J., E. F. Fritsch, and T. Maniatis, 1989. Molecular cloning: a laboratory manual, 2nd ed. Cold Spring Harbour Laboratory Press, Cold Spring Harbour, N. Y.

Lefever, P., O. Denis, L. De Wit, A. Tanghe, P. Vandenbussche, J. Content, and K. Huygen. 2000. Cloning of the gene encoding a 22-kilodalton cell surface antigen of *Mycobacterium bovis* BCG and anaylsis of its potential for DNA vaccination against tuberculosis. Infection and Immunity. 68:1040-1047.

Vordermeire, H. M., P. J. Cockle, A. O. Whelan, S. Rhodes, M. A. Chambers, D. Clifford, K. Huygen, R. Tascon, D. Lowrie, M. J. Colston, and R. G. Hewinson. 2000. Effective DNA vaccination of cattle with the mycobacterial antigens MPB83 and MPB70 does not compromise the specificity of the comparative intradermal tuberculin skin test. Vaccine. 19:1246-1255.

Cheng, W., C. Hung, C. Chai, K. Hsu, L. He, C. Rice, M. Ling, and T. Wu. 2001. Enhancement of Sindbis virus self-replicating RNA vaccine potency by linkage of *Mycobacterium tuberculosis* heat shock protein 70 gene to an antigen. J. Immunol. 166:6218-6226.

Primm et al., "The Stringent Response of *Mycobacterium tuberculosis* Is Requred for Long-Term Survival," Journal of Bacteriology, vol. 182, No. 17, pp. 4889-4898, 2000.

Primm et al., "The Stringent Response of *Mycobacterium tuberculosis* Is Required for Long-Term Survival," Journal of Bacteriology, vol. 162, No. 17, pp. 4889-4898, (2000).

Daniel, T.M., "Soluble Mycobacterial Antigens", in, The Mycobacteria, a sourcebook, Part A, eds. Kubica and Wayne, Marcel Dekker, Inc., New York, pp. 417-465, 1984.

Stedman's Medical Dictionary, $26^{th}$ edition, Williams & Wilkins, Baltimore, MD, 1995, p. 868.

Betts, J.C., et al., "Evaluation of a nutrient starvation model of *Mycobacterium tuberculosis* persistence by gene and protein expression profiling," Mol. Microbiol. 43:717-731, Blackwell Scientific Ltd (Feb. 2002).

Blanton, R., et al., "A 60K Protein is Induced by *Mycobacterium avium* intracellulare by Nutriional Deprivation and Heat Shock," Clin. Res. 38:553A, Charles B. Slack (1990).

Cole, S.T., et al., "Deciphering the biology of *Mycobacterium tuberculosis* from the complete genome sequence," Nature 393:537-544, Nature Pub. Group (1998).

Cole, S.T., et al., "Deciphering the biology of *Mycobacterium tuberculosis* from the complete genome sequence (Erratum)," Nature 396:190-198, Nature Pub. Group (1998).

DeMaio, J., et al., "A stationary-phase stress-response sigma factor from *Mycobacterium tuberculosis*," Proc. Natl. Acad. Sci. 93:2790-2794, National Academy of Sciences (1996).

Gupta, S. et al., "Proteomics analysis of carbon-starved *Mycobacterium smegmatis*: Induction of Dps-like protein," Protein Eng. 15:503-511, Oxford Universtiy Press (Jun. 2002).

Hutter, B., and Dick, T., "Analysis of the dormancy-inducible narK2 promoter in *Mycobacterium bovis* BCG," FEMS Microbiol. Letts 188:144-146, Elsevier Science B.V. (Jul. 15, 2000).

Mahenthiralingam, E., et al., Cloning and sequencing of the gene which encodes the highly inducible acetamidase of *Mycobacterium smegmatis*, J Gen. Microbiol. 139-575-583. SGM (1993).

Michele, T.M., et al., "Exposure to Antibiotic Induces Expression of the *Mycobacterium tuberculosis* sigF Gene: Implications for Chemotherapy against Mycobacterial Persistors," Antimicrobial Agents and Chemotherapy 43:218-225, American Society for Microbiology (1999).

Murugasu-Oei, B., et al., "Upregulation of stress response genes and ABC transporters in anaerobic stationary-phase *Mycobacterium smegmatis*," Mol. Gen. Genet. 262:677-682, Springer-Vertag (1999).

Rivera-Marrero, C.A., et al., "Identification of genes differentially expressed in *Mycobacterium tuberculosis* by differential display PCR," Microb. Pathog 25:307-316, Academic Press (1998).

Sambrook, J., et al., eds., Molecular Cloning: A Laboratory Manual, 2nd Edition, Cold Spring Harbor Laboratory Press, Cold Spring Harbor, NY, pp. 8.48-8.49 (1989).

Sherman, D.R., et al., "Regulation of the *Mycobacterium tuberculosis* hypoxic response gene encoding a-cyrstallin," Proc. Natl. Acad. Sci. 98:7534-7539, National Academy of Sciences (Jun. 19, 2001).

Smeulders, M.J., et al., "Adaptation of *Mycobacterium smegmatis* to Stationary Phase" J. Bacteriol. 181:270-283, American Society for Microbiology (1999).

Yuan, Y. et al., "The 16-kDa a-crystallin (Acr) protein of *Mycobacterium tuberculosis* is required for growth in macrophages," Proc. Natl. Acad. Sci. 95:9578-9583, National Academy of Sciences (1998).

Dialog File 351, Accession No. 9728887, Derwent WPI English language abstract for WO 94/01441 (Document AM1), 2000.

NCBI Entrez, GenBank Report, Accession No. P71591, from Cole, S.T., et al. (1998).

Search Report under Section 17(6) for Application No. GB 0116385.6, The Patent Office, United Kingdom, mailed May 29, 2002.

EBI Accession No. AAW73663, Alderson, M.R., et al., "*M. tuberculosis* antigen clone Tb436 protein sequence" (First entered Mar. 24, 1999).

EBI Entry, Accession No. ABU34862, Wang, L., et al., "Protein encoded by Prokaryotic essential gene #20389" (First entered Jun. 19, 2003).

EBI Entry, Accession No. ABU36420, Wang, L., et al., "Protein encoded by Prokaryotic essential gene #21947" (First entered Jun. 19, 2003).

UniProt Accession No. 053633, Cole, S.T., et al., "UniProtKB/TrEMBL entry 053633" (First entered Jun. 1, 1998).

McKinney, J.D., et al., Persistence of *Mycobacterium tuberculosis* in macrophages and mice requires the glyoxylate shunt enzyme isocitrate lyase. Nature, 2000. 406(6797): p. 735-8.

Pelicic, V., et al., Efficient allelic exchange and transposon mutagenesis in *Mycobacterium tuberculosis*, Proc Natl Acad Sci U S A, 1997. 94(20): p. 10955-60.

McShane, H., et al., Enhanced immunogenicity of CD4(+) t-cell responses and protective efficacy of a DNA-modified vaccinia virus Ankara primeboost vaccination regimen for murine tuberculosis. Infect Immun, 2001. 69(2): p. 681-6.

Movahedzadeh, F., M.J. Colston, and E.O. Davis, Characterizaion of *Mycobacterium tuberculosis* LexA: recognition of Cheo (*Bacillus*-type SOS) box. Microbiology. 1997. 143(Pt 3): p. 929-36.

Cunningham, A. F. and C. L. Spreadbury. 1998. Mycobacterial stationary phase induced by low oxygen tension: cell wall thickening and localization of the 16-kilodalton alpha-crystallin homolog. J. Bacteriol. 180:801-808.

Rook. G. A. W. and B. R. Bloom. 1994. Mechanisms of pathogenesis in tuberculosis, pp. 460-485. In B. R. Bloom (ed), Tuberculosis-pathogenesis, protection and control, ASM Press, Washington DC.
Wayne, L. G. and L. G. Hayes. 1996. An in vitro model for sequential study of shift-down of *Mycobacterium tuberculosis* through two stages of non-replicating persistence. Infect. Immun. 64:2062-2069.
Sambrook, J., E. F. Fritsch, and T. Maniatis. 1989. Molecular cloning: a laboratory manual, 2nd ed. Cold Spring Harbour Laboratory Press, Cold Spring Harbour, N. Y.
Lefevre, P., O. Denis, L. De Wit, A. Tanghe, P. Vandenbussche, J. Content, and K. Huygen. 2000. Cloning of the gene encoding a 22-kilodalton cell surface antigen of *Mycobacterium bovis* BCG and analysis of its potential for DNA vaccination against tuberculosis. Infection and Immunity, 68:1040-1047.
Vordermeier, H. M., P. J. Cockle. A. O. Whelan, S. Rhodes, M. A. Chambers, D. Clifford, K. Huygen, R. Tascon, D. Lowrie, M. J. Colston, and R. G. Hewinson. 2001. Effective DNA vaccination of cattle with the mycobacterial antigens MPB83 and MPB70 does not compromise the specifity of the comparative intradermal tuberculin skin test. Vaccine. 19:1246-1255.
Boon, C. et al., "Proteins of *Mycobacterium bovis* BCG induced in the wayne dormancy model", Journal of Bacteriology, vol. 183, No. 8, pp. 2672-2676, (2001).
Barker, L.P. et al., "The identification of *Mycobacterium marinum* genes differentially expressed in macrophage phagosomes using promoter fusions to green fluorescent protein", Molecular Microbiology, vol. 29, No. 5, pp. 1167-1177, (1998).
Smith, T.F. et al., "Comparison of biosequences", Advances in Applied Mathematics, vol. 2, issue 5, pp. 482-489, (1981).
Needleman, S.B. et al., "A general method applicable to the search for similarities in the amino acid sequence of two proteins", Journal of Molecular Biology, vol. 48, issue 3, pp. 443-453, (1970).
Pearson, W.R. et al., "Improved tools for biological sequence comparison", Proceedings of the National Academy of Science, vol. 85, pp. 2444-2448, (1988).
Altschul, S.F. et al., "Basic local alignment search tool", Journal of Molecular Biology, vol. 215, issue 3, pp. 403-410, (1990).
Kanehisa, M. "Use of statistical criteria for screening potential homologies in nucleic acid sequences", Nucleic Acids Research, vol. 12, No. 1, part 1, pp. 203-213, (1984).
Wetmur, J.G. et al., "Kinetics of renaturation of DNA", Journal of Molecular Biology, vol. 31, issue 3, pp. 349-370, (1968).
Mujumdar, R.B. et al., "Cyanine dye labeling reagents: Sulfoindocyanine succinimidyl esters", Bioconjugate Chemistry, vol. 4, No. 2, pp. 105-111, (1993).
Yu, H. et al., "Cyanine dye dUTP analogs for enzymatic labeling of DNA probes" Nucleic Acids Research, vol. 22, No. 15, pp. 3226-3232, (1994).
Zhu, Z. et al., "Directly labeled DNA probes using fluorescent nucleotides with different length linkers", Nucleic Acids Research, vol. 22, No. 16, pp. 3418-3422, (1994).
Jungblut, P.R. et al., "Proteomics reveals open reading frames in *Mycobacterium tuberculosis* H37Rv not predicted by genomics", Infection and Immunity, vol. 69, No. 9, pp. 5905-5907, (2001).
James, B.W. et al., "The physiology and pathogenicity of *Mycobacterium tuberculosis* grown under controlled conditions in a defined medium", Journal of Applied Microbiology, vol. 88, pp. 669-677, The Society of Applied Microbiology, (2000).
EMBL Database Accession No. Z75555, Cole, S.T. et al., "*Mycobacterium tuberculosis* H37Rv complete genome; segment 60/162", Jun. 30, 1996.
Bacon, J. et al., "The influence of reduced oxygen abailibility on pathogenicity and gene expression in *Mycobacterium tuberculosis*", Tuberculosis, vol. 4, pp. 205-217, (2004).
Chaitra, et al., "Modulation of immune responses in mice to recomnbinant antigens from PE and PPE families of proteins of *Mycobacterium tuberculosis* by the ribi adjuvant", Vaccine, vol. 25, pp. 7168-7176, (2007).
Ramakrishnan, L. et al., "Granuloma-specific expression of *Mycobacterium* virulence proteins from the glycine-rich PE-PGRS family", Science, vol. 288, pp. 1436-1439, (2000).
Vipond, et al., "Selection of novel TB vaccine candidates and their evaluation as DNA vaccines against aerosol challenge", Vaccine, vol. 24, pp. 6340-6350, (2006).
Dialog file 351, accession No. 8374384, WPI English language abstract for JP 2000-508525, 1998.
European Search Report for European application No. 02747549, Mailed Jan. 10, 2008, European Patent Office, Munich, DE.
Database Uniprot, Accession No. O53247, "Possible conserved transmembrane protein", 4 pages, (first available 1998).
Database EMBL Accession No. Z97188, "*Mycobacterium tuberculosis* H37Rv complete genome; segment 158/162", 20 pages, (1998).
Database EMBL, Accession No. AL021287, "*Mycobacterium tuberculosis* H37Rv complete genome; segment 132/162", 50 pages, (1999).
Flynn, J.L. et al., "Tuberculosis: Latency and reactivation", Infect. Immun., vol. 69, pp. 4195-4201, (2001).
Ohno, H. et al., "Trends in research concerning pulmonary myocobacteriosis genome and pathogenicity of tuberculosis", Resp. Moled. Med., vol. 6, pp. 202-209, (2002).
Unverified English language translation of Ohno, H. et al., "Trends in research concerning pulmonary myocobacteriosis genome and pathogenicity of tuberculosis", Resp. Mold. Med., vol. 6, pp. 202-209, (2002).
Wilson, M. et al., "Exploring drug-induced alterations in gene expression in *Mycobacteriums tuberulosis* by microarray hybridization", Proceedings of the National Academy of Science, vol. 96, pp. 12833-12838, (1999).
Ojha, A.K. et al., "High intracellular level of guanosine tetraphosphate in *Mycobacterium smegmatis* changes the morphology of the bacterium", Infection and Immunity, vol. 68, pp. 4084-4091, (2000).
Honore, N. et al., "Nucleotide sequence of the first cosmid from the *Mycobacterium leprae* genome project: structure and function of the Rif-Str regions", Molecular Micro, 7, No. 2, pp. 207-214, (1993).
Ohara, N. et al., "Isolation and amino acid sequence of the 30S ribosomal protein S19 from *Mycobacterium bovis* BCG", FEBS Letters, vol. 331, No. 1,2, pp. 9-14, (1993).
Hutter, B. et al., "Up-regulation of marX, encoding a putative "fused nitrate reductase" in anaerobic dormant *Muycobacterium bovis* BCG", FEMS Microbiology Letters, vol. 178, pp. 63-69, (1999).
Talaat, A.M. et al., "Genome-directed primers for selective labeling of bacterial transcripts for DNA microarray analysis", Nat. Biotechnology, vol. 18, pp. 679-682, (2000).
EMBL Online Database Sequence, Accession No. O53607, "Putative cellulose of *Mycobacterium tuberculosis*", created Jun. 1, 1998.
McMurray, D., "Recent progress in the development and testing of vaccines against human tuberculosis", International Journal for Parasitology, vol. 33, pp. 547-554, (2003).
von Reyn, C.F. et al., "New vaccines for the prevention of tuberculosis", Clinical Infectious Diseases, vol. 35, pp. 465-474, (2002).
Orme, I.M. et al., "Tuberculosis vaccine development: recent progress", Trends in Microbiology, vol. 9, No. 3, pp. 115-118, (2001).
Hampshire, T. et al., "Stationary phase gene expression of *Mycobacterium tuberculosis* following a progressive nutrient depletion: a model for persistent organisms?" Tuberculosis, vol. 84, pp. 228-238, (2004).
European Search Report for European Application No. 0123993.8, 3 pages, dated May 31, 2002.
European Search Report for European Application No. 0116385.6, 4 pages, dated Feb. 28, 2002.
European Search Report for European Application No. 0116385.6, 2 pages, dated May 29, 2002.
International Search Report dated Apr. 22, 2003 for PCT application No. PCT/GB02/03052.
International Search Report dated Mar. 25, 2003 for PCT application No. PCT/GB02/04718.
European Search Report for European Application No. 02747549.0, 7 pages, Jan. 10, 2008.
U.S. Appl. No. 13/220,894, Mailed Nov. 14, 2012, 6 pages.

* cited by examiner

SEQUENCE LISTING

```
<160> NUMBER OF SEQ ID NOS: 282

<210> SEQ ID NO 1
<211> LENGTH: 322
<212> TYPE: PRT
<213> ORGANISM: Mycobacterium tuberculosis

<400> SEQUENCE: 1

Val Val Leu Ser Thr Ala Phe Ser Gln Met Phe Gly Ile Asp Tyr Pro
1               5                   10                  15

Ile Val Ser Ala Pro Met Asp Leu Ile Ala Gly Gly Glu Leu Ala Ala
            20                  25                  30

Ala Val Ser Gly Ala Gly Gly Leu Gly Leu Ile Gly Gly Gly Tyr Gly
        35                  40                  45

Asp Arg Asp Trp Leu Ala Arg Gln Phe Asp Leu Ala Ala Gly Ala Pro
    50                  55                  60

Val Gly Cys Gly Phe Ile Thr Trp Ser Leu Ala Arg Gln Pro Gln Leu
65                  70                  75                  80

Leu Asp Leu Ala Leu Gln Tyr Glu Pro Val Ala Val Met Leu Ser Phe
                85                  90                  95

Gly Asp Pro Ala Val Phe Ala Asp Ala Ile Lys Ser Ala Gly Thr Arg
            100                 105                 110

Leu Val Cys Gln Ile Gln Asn Arg Thr Gln Ala Glu Arg Ala Leu Gln
        115                 120                 125

Val Gly Ala Asp Val Leu Val Ala Gln Gly Thr Glu Ala Gly Gly His
    130                 135                 140

Gly His Gly Pro Arg Ser Thr Leu Thr Leu Val Pro Glu Ile Val Asp
145                 150                 155                 160

Leu Val Thr Ala Arg Gly Thr Asp Ile Pro Val Ile Ala Ala Gly Gly
                165                 170                 175

Ile Ala Asp Gly Arg Gly Leu Ala Ala Ala Leu Met Leu Gly Ala Ala
            180                 185                 190
```

Gly Val Leu Val Gly Thr Arg Phe Tyr Ala Thr Val Glu Ala Leu Ser
195 200 205

Thr Pro Gln Ala Arg Asp Pro Leu Leu Ala Ala Thr Gly Asp Asp Met
210 215 220

Cys Arg Thr Thr Ile Tyr Asp Gln Leu Arg Arg Tyr Pro Trp Pro Gln
225 230 235 240

Gly His Thr Met Ser Val Leu Ser Asn Ala Leu Thr Asp Gln Phe Glu
245 250 255

Asp Thr Glu Leu Asp Ile Leu His Arg Glu Glu Ala Met Ala Arg Tyr
260 265 270

Trp Arg Ala Val Ala Ala Arg Asp Tyr Ser Ile Ala Asn Val Thr Ala
275 280 285

Gly Gln Ala Ala Gly Leu Val Asn Ala Val Leu Pro Ala Ala Asp Val
290 295 300

Ile Thr Gly Met Ala Gln Gln Ala Ala Arg Thr Leu Thr Ala Met Arg
305 310 315 320

Ala Val

<210> SEQ ID NO 2
<211> LENGTH: 966
<212> TYPE: DNA
<213> ORGANISM: Mycobacterium tuberculosis

<400> SEQUENCE: 2
gtggtgctat cgacggcctt tagccagatg ttcggaatcg actatccgat agtgtccgcg 60
ccaatggact tgatcgccgg cggtgagctg gctgccgcgg taagtggcgc agggggactc 120
ggcctcatcg gggcggcta tggggaccgg gattggttgg cccggcagtt cgatctcgcc 180
gctggagcgc cggtgggctg cgggttcatc acctggtctt tggcccgcca accgcagctg 240
ctcgacctcg cgctgcagta tgagccggtg gcggtgatgc tgtcgttcgg ggaccccgcg 300
gttttcgctg acgccatcaa gtccgccgga acgcggttgg tctgccagat ccaaaaccgg 360
acccaggccg agcgagccct gcaggtcggc gccgatgtgt tggtggctca gggcaccgag 420
gccggtgggc acggccacgg tccacgttcc accctgacct tggtacccga aatcgtcgac 480
ctggtcaccg cgcggggaac tgatatcccg gtgatcgccg ccgggggcat cgccgacggc 540
cggggccttg ccgccgcgtt gatgttgggc gccgccgggg tattggtcgg tacgcgcttc 600
tacgccacgg tcgaagcgtt atccacaccg caggcgcggg acccgctgct ggcggccact 660
ggcgacgaca tgtgccgcac cactatctac gatcagctac ggcgctatcc ctggccgcaa 720
ggacacacga tgagcgtgct aagcaacgcc ctcaccgacc aattcgagga caccgaactc 780
gacattctcc atcgcgaaga agccatggcc agatattggc gagccgttgc tgcgcgtgac 840
tacagcatcg ccaatgtcac cgccggtcaa gccgcgggcc tggtcaatgc cgtcctgcca 900
gccgccgacg tgataaccgg tatggcgcaa caagcggcga ggacgctgac cgcgatgcgc 960
gccgtg 966

<210> SEQ ID NO 3
<211> LENGTH: 365
<212> TYPE: PRT
<213> ORGANISM: Mycobacterium tuberculosis

<400> SEQUENCE: 3

Val Ala Ile Phe Gly Arg Trp Ser Ala Arg Gln Arg Leu Arg Arg Ala
1 5 10 15

-continued

```
Thr Arg Glu Ser Leu Thr Ile Pro Thr Phe Ser Ser Ser Leu Asp Cys
            20                  25                  30

Thr Thr Arg Val Ile Gly Gly Leu Trp Pro Ala Glu Leu Ser Ser Asn
        35                  40                  45

Thr Ala Glu Thr Ala Thr Leu Ala Glu His Leu Lys Ala Asp Leu His
    50                  55                  60

Arg Ile Val Gly Ser Ala Asn Asp Glu Leu Met Val Ile Trp Arg Ala
65                  70                  75                  80

Gly Met Ala Asp Ser Thr Arg Arg Ala Glu Glu Asp Arg Val Ile Asp
                85                  90                  95

Arg Ala Arg Ala Ser Ala Met Arg Arg Val Glu Ser Ala Met Arg Glu
            100                 105                 110

Leu Arg Gln Ile Thr Gly Arg Val Pro Val Glu Ile Pro Arg Met Arg
        115                 120                 125

Gly Ala Gly Gly Ser Asp Leu Asp Thr Thr Arg Leu Met Pro Ala Val
    130                 135                 140

Thr Val Val Gln Pro Ala Asp Gln Ala Cys Thr Asp Trp Pro Val Ala
145                 150                 155                 160

Ala Ala Glu Asp Asp Glu Ala Arg Leu Gln Arg Leu Leu Ala Phe Val
                165                 170                 175

Ala Arg Gln Glu Pro Arg Leu Asn Trp Ala Val Gly Val His Ala Asp
            180                 185                 190

Gly Thr Thr Val Leu Val Thr Asp Val Ala His Gly Trp Ile Pro Pro
        195                 200                 205

Gly Ile Ala Leu Pro Glu Gly Val Arg Leu Leu Ala Pro Ala Arg Arg
    210                 215                 220

Ala Gly Arg Ala Pro Glu Leu Val Gly Ile Thr Thr Cys Cys Lys Thr
225                 230                 235                 240

Tyr Thr Pro Gly Asp Ser Leu Arg Arg Ala Val Asp Ser Thr Ala Pro
                245                 250                 255

Thr Ser Ser Val Gln Pro Arg Ala Leu Pro Ala Ile Ala Gly Leu Ser
            260                 265                 270

Val Glu Leu Gly Ile Ala Thr Gln Arg His Asp Gly Leu Pro Lys Ile
        275                 280                 285

Val His Ala Met Ala Thr Ala Ala Gly Asn Gly Ala Ala Ala Glu Glu
    290                 295                 300

Val Asp Leu Leu Arg Val His Val Asp Thr Ala Leu His His Val Leu
305                 310                 315                 320

Ala Gln Tyr Pro Arg Val Asp Pro Ala Leu Leu Leu Asn Cys Met Leu
                325                 330                 335

Leu Ala Ala Thr Glu Arg Ser Val Thr Gly Asp Pro Ile Ala Ala Asn
            340                 345                 350

Tyr His Phe Ala Trp Phe Arg Glu Leu Asp Ser Arg Arg
        355                 360                 365
```

<210> SEQ ID NO 4
<211> LENGTH: 1095
<212> TYPE: DNA
<213> ORGANISM: Mycobacterium tuberculosis

<400> SEQUENCE: 4

```
gtggcgatct tcggtcgatg gagtgcgcgc cagcgactcc ggagagcgac ccgggaatcc      60

ctcacgattc cgacgtttag ctcctcgctg gattgcacca cacgggtaat tggcgggctc     120

tggcccgctg agctttcgtc taacaccgcc gaaaccgcca cgcttgcaga acatctgaaa     180
```

-continued gcggatctgc atcggatagt tggttctgcc aacgacgagc tgatggtcat ctggcgtgcg 240
gggatggctg attcgacgcg acgcgcagaa gaagacagag tgatcgaccg cgcccgcgcg 300
tcggcgatgc gtcgcgtcga gtcggcgatg cgcgagcttc ggcagataac ggggcgcgtt 360
cccgtggaaa ttccgcgtat gcgcggcgcc ggcggctcgg atctggacac gacacgactc 420
atgccggccg tcacggtagt tcagcccgct gaccaggcct gtacggattg gccggttgcc 480
gccgccgagg atgacgaagc ccgactgcag cgcctcctgg cgttcgtggc tcgtcaggag 540
ccacggctga actgggcggt cggcgttcac gcggacggca cgacggtcct ggtcaccgac 600
gtcgcccatg gttggatacc tccgggcatc gcccttcccg aaggcgtgcg attgttggca 660
ccggcgcgac gcgccggcag agcccccgag ttggtcggta tcacgacgtg ttgcaagacg 720
tacacccccg gtgactcgct gcgtcgggcg gtcgattcaa ccgcgccgac gtcctcggtg 780
cagccgcgag cgttgccagc gatcgccggc ctgagtgtgg agctgggcat agcgacccag 840
cggcacgacg gcttaccgaa gatcgtgcac gccatggcca cggcggccgg caacggcgcc 900
gccgccgagg aagtcgacct gttgcgggtg cacgtcgata ccgcgctcca ccacgtcttg 960
gcccagtatc cccgggtcga tccggcgtta ctgctcaact gtatgttgtt ggccgccacc 1020
gagcgcagcg tcacgggaga cccgatcgcg gcgaactatc acttcgcgtg gttccgggaa 1080
ctcgattcac gccga 1095

<210> SEQ ID NO 5
<211> LENGTH: 129
<212> TYPE: PRT
<213> ORGANISM: Mycobacterium tuberculosis

<400> SEQUENCE: 5

Met Pro Ala Val Thr Thr Pro Ser Asn His Trp Gly Asp Glu Arg Arg
1 5 10 15

Lys Leu Ser His Gln Pro Pro Val Arg Gly Gln Ile Leu Gly Arg Arg
20 25 30

Gln Ala Arg Arg Leu Ser Gln His Phe Ala Arg Val Gly Val Glu Ala
35 40 45

Pro Pro Lys Arg Leu Gln Glu Met Leu Leu Gly Ala Pro Ala Ala Asp
50 55 60

Glu Glu Trp Thr Asp Val Lys Phe Ala Leu Ile Val Thr Gln Leu Asn
65 70 75 80

His Glu Lys Arg Val Ala Lys Phe His Arg Leu Gln Arg Arg Ala Thr
85 90 95

His Ser Leu Ile Cys Leu Gly Leu Val Leu Val Ala Leu Asn Phe Leu
100 105 110

Ile Cys Leu Ala Tyr Ile Phe Phe Ser Leu Thr Gln His Ala Ala Ala
115 120 125

Leu

<210> SEQ ID NO 6
<211> LENGTH: 387
<212> TYPE: DNA
<213> ORGANISM: Mycobacterium tuberculosis

<400> SEQUENCE: 6
atgcccgctg tgacgacccc gtccaaccac tgggggggacg aacgaaggaa gctctcgcat 60
cagccaccgg tgcggggtca gattcttggc cgcaggcaag cccggcggct gagccagcac 120
ttcgcgcggg tcggcgtcga agccccgccg aagcgccttc aggaaatgct gttgggcgct 180

-continued cccgccgccg acgaagaatg gaccgacgtc aagttcgcac tgatcgtgac ccagctgaac 240
catgagaagc gcgtcgcgaa attccaccgc ctacaacgcc gagccacgca ttcactaatc 300
tgtctgggtt tggttctcgt ggcactgaac ttcctgatct gcctcgccta catcttcttc 360
agcctgaccc aacacgccgc agcgttg 387

<210> SEQ ID NO 7
<211> LENGTH: 685
<212> TYPE: PRT
<213> ORGANISM: Mycobacterium tuberculosis

<400> SEQUENCE: 7

Val Pro Ala Arg Ser Val Pro Arg Pro Arg Trp Val Ala Pro Val Arg
1 5 10 15

Arg Val Gly Arg Leu Ala Val Trp Asp Arg Pro Glu Arg Arg Ser Gly
20 25 30

Ile Pro Ala Leu Asp Gly Leu Arg Ala Ile Ala Val Ala Leu Val Leu
35 40 45

Ala Ser His Gly Gly Ile Pro Gly Met Gly Gly Gly Phe Ile Gly Val
50 55 60

Asp Ala Phe Phe Val Leu Ser Gly Phe Leu Ile Thr Ser Leu Leu Leu
65 70 75 80

Asp Glu Leu Gly Arg Thr Gly Arg Ile Asp Leu Ser Gly Phe Trp Ile
85 90 95

Arg Arg Ala Arg Arg Leu Leu Pro Ala Leu Val Leu Met Val Leu Thr
100 105 110

Val Ser Ala Ala Arg Ala Leu Phe Pro Asp Gln Ala Leu Thr Gly Leu
115 120 125

Arg Ser Asp Ala Ile Ala Ala Phe Leu Trp Thr Ala Asn Trp Arg Phe
130 135 140

Val Ala Gln Asn Thr Asp Tyr Phe Thr Gln Gly Ala Pro Pro Ser Pro
145 150 155 160

Leu Gln His Thr Trp Ser Leu Gly Val Glu Glu Gln Tyr Tyr Val Val
165 170 175

Trp Pro Leu Leu Leu Ile Gly Ala Thr Leu Leu Leu Ala Ala Arg Ala
180 185 190

Arg Arg Arg Cys Arg Arg Ala Thr Val Gly Gly Val Arg Phe Ala Ala
195 200 205

Phe Leu Ile Ala Ser Leu Gly Thr Met Ala Ser Ala Thr Ala Ala Val
210 215 220

Ala Phe Thr Ser Ala Ala Thr Arg Asp Arg Ile Tyr Phe Gly Thr Asp
225 230 235 240

Thr Arg Ala Gln Ala Leu Leu Ile Gly Ser Ala Ala Ala Ala Leu Leu
245 250 255

Val Arg Asp Trp Pro Ser Leu Asn Arg Gly Trp Cys Leu Ile Arg Thr
260 265 270

Arg Trp Gly Arg Arg Ile Ala Arg Leu Leu Pro Phe Val Gly Leu Ala
275 280 285

Gly Leu Ala Val Thr Thr His Val Ala Thr Gly Ser Val Gly Glu Phe
290 295 300

Arg His Gly Leu Leu Ile Val Val Ala Gly Ala Ala Val Ile Val Val
305 310 315 320

Ala Ser Val Ala Met Glu Gln Arg Gly Ala Val Ala Arg Ile Leu Ala
325 330 335

Trp Arg Pro Leu Val Trp Leu Gly Thr Ile Ser Tyr Gly Val Tyr Leu

-continued

```
            340                 345                 350

Trp His Trp Pro Ile Phe Leu Ala Leu Asn Gly Gln Arg Thr Gly Trp
        355                 360                 365

Ser Gly Pro Ala Leu Phe Ala Ala Arg Cys Ala Ala Thr Val Val Leu
    370                 375                 380

Ala Gly Ala Ser Trp Trp Leu Ile Glu Gln Pro Ile Arg Arg Trp Arg
385                 390                 395                 400

Pro Ala Arg Val Pro Leu Leu Pro Leu Ala Ala Ala Thr Val Ala Ser
                405                 410                 415

Ala Ala Ala Val Thr Met Leu Val Val Pro Val Gly Ala Gly Pro Gly
            420                 425                 430

Leu Arg Glu Ile Gly Leu Pro Pro Gly Val Ser Ala Val Ala Ala Val
        435                 440                 445

Ser Pro Ser Pro Pro Glu Ala Ser Gln Pro Ala Pro Gly Pro Arg Asp
    450                 455                 460

Pro Asn Arg Pro Phe Thr Val Ser Val Phe Gly Asp Ser Ile Gly Trp
465                 470                 475                 480

Thr Leu Met His Tyr Leu Pro Pro Thr Pro Gly Phe Arg Phe Ile Asp
                485                 490                 495

His Thr Val Ile Gly Cys Ser Leu Val Arg Gly Thr Pro Tyr Arg Tyr
            500                 505                 510

Ile Gly Gln Thr Leu Glu Gln Arg Ala Glu Cys Asp Gly Trp Pro Ala
        515                 520                 525

Arg Trp Ser Ala Gln Val Asn Arg Asp Gln Pro Asp Val Ala Leu Leu
    530                 535                 540

Ile Val Gly Arg Trp Glu Thr Val Asp Arg Val Asn Glu Gly Arg Trp
545                 550                 555                 560

Thr His Ile Gly Asp Pro Thr Phe Asp Ala Tyr Leu Asn Ala Glu Leu
                565                 570                 575

Gln Arg Ala Leu Ser Ile Val Gly Ser Thr Gly Val Arg Val Met Val
            580                 585                 590

Thr Thr Val Pro Tyr Ser Arg Gly Gly Glu Lys Pro Asp Gly Arg Leu
        595                 600                 605

Tyr Pro Glu Asp Gln Pro Glu Arg Val Asn Lys Trp Asn Ala Met Leu
    610                 615                 620

His Asn Ala Ile Ser Gln His Ser Asn Val Gly Met Ile Asp Leu Asn
625                 630                 635                 640

Lys Lys Leu Cys Pro Asp Gly Val Tyr Thr Ala Lys Val Asp Gly Ile
                645                 650                 655

Lys Val Arg Ser Asp Gly Val His Leu Thr Gln Glu Gly Val Lys Trp
            660                 665                 670

Leu Ile Pro Trp Leu Glu Asp Ser Val Arg Val Ala Ser
        675                 680                 685


<210> SEQ ID NO 8
<211> LENGTH: 2055
<212> TYPE: DNA
<213> ORGANISM: Mycobacterium tuberculosis

<400> SEQUENCE: 8

gtgccggcac gttctgttcc ccggccccgt tgggtggccc cggtgcgccg ggtcggtcgg      60

ctggccgtat gggatcggcc ggagcggcgc agcggaattc cagcgttaga tggccttcgt     120

gcgatagcgg tcgcgctggt actcgccagc catggcggca tccccggtat gggcggcggg     180

ttcatcggcg tcgacgcctt cttcgtcttg agcggatttc tcatcacctc gctgctgctc     240
```

-continued

```
gacgagctgg ggcgcaccgg tcgtatcgat ctgagcgggt tctggattcg ccgtgcgcgg    300
cggctgctgc cggcgctggt gctgatggtt ctcaccgtga gcgccgcacg cgcactattt    360
cctgaccaag ctctcaccgg gctacggagc gatgcgatcg ccgcgttcct atggacggcg    420
aattggcggt ttgtggccca aaataccgat tacttcaccc agggcgctcc accctcgccc    480
ctacagcaca cctggtcgtt gggggtggag gagcagtatt acgttgtctg gccactgttg    540
ctgatcgggg cgacgctact gttggcggcc cgggcgaggc gccgttgcag acgggccacg    600
gtgggcgggg ttcggttcgc cgcgttcctg attgccagtc tcggcacgat ggcttccgcc    660
accgccgcgg tcgcatttac ctcggcggcc acccgcgacc ggatttactt cggcaccgat    720
acccgtgcgc aggcgttgct gatcggctcc gcggcagcgg ctctgctggt gcgggattgg    780
ccatcgctga accgcgggtg gtgcctgatc cggactcgct ggggacggcg gattgcccgt    840
ctgttgccgt tcgtcgggct ggctgggctg gcggtgacga ctcacgtcgc aacgggcagt    900
gtgggcgagt tccgccatgg tctgctgatc gtggtggcag gtgcggccgt catcgtggtt    960
gcctcggtag ccatggagca gcgcggagcg gtggcccgca tcctggcctg gcgaccgttg   1020
gtgtggctgg gcaccatatc gtacggcgtc tatctgtggc actggccaat ctttctggcg   1080
ctcaacggcc aacgtacggg ctggtcgggc ccggccctgt ttgccgctag gtgtgcagcc   1140
acggtggtgc tggccggtgc gtcgtggtgg ctgatcgagc aacctattcg gcgctggcga   1200
ccggcacggg ttccgctgtt gccgctggca gcggcgaccg ttgccagcgc tgccgccgtg   1260
acgatgctcg ttgttccggt cggagccgga ccggggctac gcgagatcgg ccttccgccc   1320
ggcgtttcgg cggtcgccgc ggtctcgccg tcgccgccgg aagcgagtca gcccgcgccc   1380
gggccacgag atcccaaccg gccgttcacc gtttcggtat tcggtgattc gatcgggtgg   1440
actttgatgc attacctgcc gccgactccc ggattccggt tcatcgacca caccgtcatc   1500
ggctgcagcc tggtacgcgg cacaccgtat cggtacatcg gtcaaaccct ggagcagagg   1560
gcggaatgcg acggctggcc ggccagatgg tcggcgcagg tcaaccggga ccaaccggac   1620
gttgcgttgc tgatcgtcgg ccgctgggag acggtagacc gggtcaatga ggggcggtgg   1680
acacatatcg gcgacccgac cttcgatgcg tacctcaacg ccgagctaca gcgagcgctc   1740
agcatcgttg gatccaccgg ggttcgagtg atggtcacca ccgtgcccta cagccgcggc   1800
ggcgaaaagc cggacggccg cttgtatccg gaggatcaac ccgagcgtgt gaacaaatgg   1860
aacgccatgt tacataacgc cattagccaa cactcgaacg tcggaatgat cgacctcaac   1920
aaaaagcttt gtccagacgg cgtttacacg gccaaggtcg acggcatcaa ggtccgcagt   1980
gatggtgttc atctcaccca ggaaggcgtg aagtggctga taccgtggct tgaggattcg   2040
gtgcgggtcg ccagt                                                    2055
```

<210> SEQ ID NO 9
<211> LENGTH: 449
<212> TYPE: PRT
<213> ORGANISM: Mycobacterium tuberculosis

<400> SEQUENCE: 9

```
Met Leu Thr Ser Leu Val Ser Ala Val Gly Ser His His Val Thr Thr
1               5                   10                  15

Asp Pro Asp Val Leu Ala Gly Arg Ser Val Asp His Thr Gly Arg Tyr
            20                  25                  30

Arg Gly Arg Ala Ser Ala Leu Val Arg Pro Gly Ser Ala Glu Glu Val
        35                  40                  45
```

```
Ala Glu Val Leu Arg Val Cys Arg Asp Ala Gly Ala Tyr Val Thr Val
    50                  55                  60

Gln Gly Gly Arg Thr Ser Leu Val Ala Gly Thr Val Pro Glu His Asp
65                  70                  75                  80

Asp Val Leu Leu Ser Thr Glu Arg Leu Cys Val Val Ser Asp Val Asp
                85                  90                  95

Thr Val Glu Arg Arg Ile Glu Ile Gly Ala Gly Val Thr Leu Ala Ala
            100                 105                 110

Val Gln His Ala Ala Ser Thr Ala Gly Leu Val Phe Gly Val Asp Leu
        115                 120                 125

Ser Ala Arg Asp Thr Ala Thr Val Gly Gly Met Ala Ser Thr Asn Ala
    130                 135                 140

Gly Gly Leu Arg Thr Val Arg Tyr Gly Asn Met Gly Glu Gln Val Val
145                 150                 155                 160

Gly Leu Asp Val Ala Leu Pro Asp Gly Thr Val Leu Arg Arg His Ser
                165                 170                 175

Arg Val Arg Arg Asp Asn Thr Gly Tyr Asp Leu Pro Ala Leu Phe Val
            180                 185                 190

Gly Ala Glu Gly Thr Leu Gly Val Ile Thr Ala Leu Asp Leu Arg Leu
        195                 200                 205

His Pro Thr Pro Ser His Arg Val Thr Ala Val Cys Gly Phe Ala Glu
    210                 215                 220

Leu Ala Ala Leu Val Asp Ala Gly Arg Met Phe Arg Asp Val Glu Gly
225                 230                 235                 240

Ile Ala Ala Leu Glu Leu Ile Asp Gly Arg Ala Ala Ala Leu Thr Arg
                245                 250                 255

Glu His Leu Gly Val Arg Pro Pro Val Glu Ala Asp Trp Leu Leu Leu
            260                 265                 270

Val Glu Leu Ala Ala Asp His Asp Gln Thr Asp Arg Leu Ala Asp Leu
        275                 280                 285

Leu Gly Gly Ala Arg Met Cys Gly Glu Pro Ala Val Gly Val Asp Ala
    290                 295                 300

Ala Ala Gln Gln Arg Leu Trp Arg Thr Arg Glu Ser Leu Ala Glu Val
305                 310                 315                 320

Leu Gly Val Tyr Gly Pro Pro Leu Lys Phe Asp Val Ser Leu Pro Leu
                325                 330                 335

Ser Ala Ile Ser Gly Phe Ala Arg Asp Ala Val Ala Leu Val His Arg
            340                 345                 350

His Val Pro Asp Ser Pro Glu Ala Leu Pro Leu Leu Phe Gly His Ile
        355                 360                 365

Gly Glu Gly Asn Leu His Leu Asn Val Leu Arg Cys Pro Pro Asp Arg
    370                 375                 380

Glu Pro Ala Leu Tyr Ala Lys Met Met Gly Leu Ile Ala Glu Cys Gly
385                 390                 395                 400

Gly Asn Val Ser Ser Glu His Gly Val Gly Ser Arg Lys Arg Ala Tyr
                405                 410                 415

Leu Gly Met Ser Arg Gln Ala Asn Asp Val Ala Ala Met Arg Arg Val
            420                 425                 430

Lys Ala Ala Leu Asp Pro Thr Gly Tyr Leu Asn Ala Ala Val Leu Phe
        435                 440                 445

Asp
```

<210> SEQ ID NO 10
<211> LENGTH: 1347

-continued

<212> TYPE: DNA
<213> ORGANISM: Mycobacterium tuberculosis

<400> SEQUENCE: 10
atgctaacca gcttggtgag tgcggtcgga tcgcatcacg tcaccaccga ccctgacgtg 60
ctggccggcc gcagcgtcga ccacaccggc cgctatcggg gccgggccag cgcgctggtg 120
cggcccggct cggctgaaga ggtcgccgaa gtgctgcggg tgtgccggga cgctggagcc 180
tatgtcaccg ttcaaggcgg ccgcacctca ctggtggcgg gcaccgttcc cgaacacgac 240
gacgtgctgc tgtctaccga acggctttgc gtcgtcagcg atgtcgatac cgttgagcgc 300
cgaatcgaga tcggtgccgg ggtcacactg gccgcggtgc agcacgccgc gtcaacggct 360
gggctggtgt tcggcgtgga tttgtcggcc cgggataccg cgaccgtcgg tggcatggcc 420
tcgacgaacg ccggcggatt gcgcacggtc cgttacggca acatgggcga gcaggttgtc 480
gggctagacg tcgcgctgcc cgacggtacg gtgctgcgcc ggcacagccg ggtgcgtcgc 540
gacaacaccg gctacgacct gcccgcgctg ttcgtcgggg ccgaaggcac cctgggggtt 600
atcaccgcgc tggatctgcg gctgcacccc accccgtcgc atcgggtgac agccgtgtgc 660
gggttcgccg agctggcagc gctggtcgat gccggccgaa tgttccgcga cgtggagggc 720
atcgcggcgt tggaattgat tgacggtcgg gccgccgcgc taacccgtga acatcttggc 780
gttcgccccc ccgtcgaggc tgactggttg ctattggtgg aactggccgc cgaccacgat 840
cagaccgacc ggctcgccga cctgctcggc ggtgcacgga tgtgcgggga gcccgcggtc 900
ggtgtggatg ccgctgcgca gcaacggttg tggcgcaccc gtgaatcgct ggccgaggtg 960
ctcggtgtgt acggcccgcc gctgaagttc gacgtctcgc tgccattgtc ggcgatcagc 1020
ggcttcgccc gagatgcggt cgcgttggtt caccgacacg tcccggattc tccggaggcg 1080
ttgccgctgt tgttcggtca catcggtgag ggcaacctgc acctgaacgt gctgcgttgc 1140
ccgcctgatc gggaaccggc gttgtacgca aagatgatgg gcctcatcgc cgaatgcggc 1200
ggtaacgtca gttcagaaca tggggtgggc agccgcaagc gtgcctacct gggaatgtcc 1260
cggcaggcca acgacgtcgc cgcgatgcgg agggtcaagg cggcgttgga cccgaccggg 1320
taccttaacg ccgcggtctt gttcgac 1347

<210> SEQ ID NO 11
<211> LENGTH: 323
<212> TYPE: PRT
<213> ORGANISM: Mycobacterium tuberculosis

<400> SEQUENCE: 11

Val Thr His Gly Met Val Leu Gly Lys Phe Met Pro Pro His Ala Gly
1               5                   10                  15

His Val Tyr Leu Cys Glu Phe Ala Arg Arg Trp Val Asp Glu Leu Thr
            20                  25                  30

Ile Val Val Gly Ser Thr Ala Ala Glu Pro Ile Pro Gly Ala Gln Arg
        35                  40                  45

Val Ala Trp Met Arg Glu Leu Phe Pro Phe Asp Arg Val Val His Leu
    50                  55                  60

Ala Asn Glu Asn Pro Gln Arg Pro Trp Glu His Pro Asp Phe Trp Asp
65                  70                  75                  80

Ile Trp Lys Ala Ser Leu Gln Gly Val Leu Ala Thr Arg Pro Asp Phe
                85                  90                  95

Val Phe Gly Ala Glu Pro Tyr Asn Ala Asp Phe Ala Gln Val Leu Gly
            100                 105                 110

-continued

```
Ala Arg Phe Val Ala Val Asp His Gly Arg Thr Val Val Pro Val Thr
        115                 120                 125

Ala Thr Asp Ile Arg Ala Asp Pro Leu Gly His Trp Gln His Ile Pro
    130                 135                 140

Arg Cys Val Arg Pro Ala Phe Val Lys Arg Val Ser Ile Ile Gly Pro
145                 150                 155                 160

Glu Ser Thr Gly Lys Thr Thr Leu Ala Gln Ala Val Ala Glu Lys Leu
                165                 170                 175

Arg Thr Lys Trp Val Pro Glu Arg Ala Lys Met Leu Arg Glu Leu Asn
            180                 185                 190

Gly Gly Ser Leu Ile Gly Leu Glu Trp Ala Glu Ile Val Arg Gly Gln
        195                 200                 205

Ile Ala Ser Glu Glu Ala Leu Ala Arg Asp Ala Asp Arg Val Leu Ile
    210                 215                 220

Cys Asp Thr Asp Pro Leu Ala Thr Thr Val Trp Ala Glu Phe Leu Ala
225                 230                 235                 240

Gly Gly Cys Pro Gln Glu Leu Arg Asp Leu Ala Arg Arg Pro Tyr Asp
                245                 250                 255

Leu Thr Leu Leu Thr Thr Pro Asp Val Pro Trp Asp Ala Asp Asp Gly
            260                 265                 270

Arg Cys Val Pro Gly Ala Arg Gly Thr Phe Phe Ala Arg Cys Glu Gln
        275                 280                 285

Ala Leu Arg Ala Ala Gly Arg Ser Phe Val Val Ile Thr Gly Gly Trp
    290                 295                 300

Glu Glu Arg Leu Ser Val Ser Leu Arg Ala Val Glu Glu Leu Val Arg
305                 310                 315                 320

Ala Arg Arg
```

<210> SEQ ID NO 12
<211> LENGTH: 969
<212> TYPE: DNA
<213> ORGANISM: Mycobacterium tuberculosis

<400> SEQUENCE: 12

```
gtgacacacg gaatggtgct cggcaagttc atgccgcccc atgcgggaca cgtctacctt      60

tgcgagttcg cgcggcgatg ggtggatgag ctgaccatcg tcgtcggatc aacggcagca     120

gagccgattc cgggcgccca gcgcgttgca tggatgcggg agctgttccc cttcgatcgc     180

gtggtccatc tggccaacga gaacccgcag cgcccgtggg agcacccgga cttctgggac     240

atctggaagg cgagcctgca gggcgtgctg gcaacccgcc ccgacttcgt cttcggtgcc     300

gagccctaca acgcggactt tgcccaggtc ctcggagcgc gtttcgtggc ggtcgatcac     360

ggtcgcaccg tcgttcccgt gactgcaacc gacatccgcg cggacccgct tggccactgg     420

caacacatcc cacggtgcgt gcggccggcc ttcgtcaaac gcgtgagcat catcggaccc     480

gaatccaccg ggaagaccac gctggcacag gcggttgcgg aaaagctccg aacgaagtgg     540

gtcccggagc gggcgaaaat gttgcgggag ctcaatggcg gctcactgat aggactggag     600

tgggccgaaa tcgttcgcgg acagatcgcg tcggaggaag ccttggctcg tgacgccgat     660

cgcgtcctga tctgcgacac ggatccgctc gcgacgaccg tgtgggccga gttcctggcg     720

ggcggctgcc cgcaagagct ccgtgatcta gctcggcgtc cctacgatct cacactgctc     780

accacgcccg atgtgccctg ggacgccgac gacggacgct gtgtccccgg cgcacgcggt     840

acctttttcg cccgctgcga gcaggctctc cgcgccgcgg gacgatcatt cgtggtgatc     900

acgggcggtt gggaagagag gctttcggtg tctttgcgcg ctgtcgaaga acttgtgcgt     960
```

-continued gcccgccgc 969

<210> SEQ ID NO 13
<211> LENGTH: 407
<212> TYPE: PRT
<213> ORGANISM: Mycobacterium tuberculosis

<400> SEQUENCE: 13

Met Gly Pro Ala Asp Glu Ser Gly Ala Pro Ile Arg Pro Gln Thr Pro
1 5 10 15

His Arg His Thr Val Leu Val Thr Asn Gly Gln Val Val Gly Gly Thr
20 25 30

Arg Gly Phe Leu Pro Ala Val Glu Gly Met Arg Ala Cys Ala Ala Val
35 40 45

Gly Val Val Val Thr His Val Ala Phe Gln Thr Gly His Ser Ser Gly
50 55 60

Val Gly Gly Arg Leu Phe Gly Arg Phe Asp Leu Ala Val Ala Val Phe
65 70 75 80

Phe Ala Val Ser Gly Phe Leu Leu Trp Arg Gly His Ala Ala Ala Ala
85 90 95

Arg Asp Leu Arg Ser His Pro Arg Thr Gly Pro Tyr Leu Arg Ser Arg
100 105 110

Val Ala Arg Ile Met Pro Ala Tyr Val Val Ala Val Val Val Ile Leu
115 120 125

Ser Leu Leu Pro Asp Ala Asp His Ala Ser Leu Thr Val Trp Leu Ala
130 135 140

Asn Leu Thr Leu Thr Gln Ile Tyr Val Pro Leu Thr Leu Thr Gly Gly
145 150 155 160

Leu Thr Gln Met Trp Ser Leu Ser Val Glu Val Ala Phe Tyr Ala Ala
165 170 175

Leu Pro Val Leu Ala Leu Leu Gly Arg Arg Ile Pro Val Gly Ala Arg
180 185 190

Val Pro Ala Ile Ala Ala Leu Ala Ala Leu Ser Trp Ala Trp Gly Trp
195 200 205

Leu Pro Leu Asp Ala Gly Ser Gly Ile Asn Pro Leu Thr Trp Pro Pro
210 215 220

Ala Phe Phe Ser Trp Phe Ala Ala Gly Met Leu Leu Ala Glu Trp Ala
225 230 235 240

Tyr Ser Pro Val Gly Leu Pro His Arg Trp Ala Arg Arg Arg Val Ala
245 250 255

Met Ala Val Thr Ala Leu Leu Gly Tyr Leu Val Ala Ala Ser Pro Leu
260 265 270

Ala Gly Pro Glu Gly Leu Val Pro Gly Thr Ala Ala Gln Phe Ala Val
275 280 285

Lys Thr Ala Met Gly Ser Leu Val Ala Phe Ala Leu Val Ala Pro Leu
290 295 300

Val Leu Asp Arg Pro Asp Thr Ser His Arg Leu Leu Gly Ser Pro Ala
305 310 315 320

Met Val Thr Leu Gly Arg Trp Ser Tyr Gly Leu Phe Ile Trp His Leu
325 330 335

Ala Ala Leu Ala Met Val Phe Pro Val Ile Gly Ala Phe Pro Phe Thr
340 345 350

Gly Arg Met Pro Thr Val Leu Val Leu Thr Leu Ile Phe Gly Phe Ala
355 360 365

-continued

```
Ile Ala Ala Val Ser Tyr Ala Leu Val Glu Ser Pro Cys Arg Glu Ala
    370                 375                 380

Leu Arg Arg Trp Glu Arg Arg Asn Glu Pro Ile Ser Val Gly Glu Leu
385                 390                 395                 400

Gln Ala Asp Ala Ile Ala Pro
                405


<210> SEQ ID NO 14
<211> LENGTH: 1221
<212> TYPE: DNA
<213> ORGANISM: Mycobacterium tuberculosis

<400> SEQUENCE: 14

atgggcccgg cggacgaatc gggtgcaccg attcgcccgc aaacacctca caggcacact      60

gtgttggtga ccaacggcca ggtggtgggt gggacccgtg gctttctgcc cgccgtcgag     120

ggaatgcgcg catgcgcggc cgtcggcgtc gtggtcactc acgtcgcgtt ccagaccggg     180

cactctagcg gtgtgggcgg gcggctgttc ggccgcttcg atctggcggt ggcggtgttc     240

ttcgccgtgt cgggattctt gttgtggcgc ggacacgccg cagcggcgcg agatctgcgg     300

tcacacccgc gaaccggtcc gtatctgcga tcgcgggtgg cgcgcatcat gccggcctat     360

gtggtggcgg tggtcgtcat cctgtccctg ctgcccgacg cggatcatgc cagcctgacc     420

gtgtggctgg ccaacctgac gctcacccag atctatgtgc cgctgaccct gaccggcggc     480

ctgacccaga tgtggagcct gtccgtggag gtcgccttct atgcggcgct gccggtctta     540

gcgttgctgg gccgccgaat tccggtcggt gcccgagtgc cggcgatcgc ggcgctggcg     600

gcgctcagct gggcgtgggg ctggctcccg ttggacgccg ggtcggggat caacccgttg     660

acctggccgc cggcgttctt ctcgtggttc gccgcgggaa tgttgctggc ggagtgggcc     720

tacagcccgg tcgggttgcc gcatcggtgg gcgcgccgcc gcgtggcgat ggcggttacc     780

gcgctgctgg gttacctggt ggcggcctcg ccgttggcgg gtccggaggg cctggttccg     840

ggcacggcgg cacaattcgc ggtgaagacc gcgatgggct cgctggtagc gttcgcgctg     900

gtggcgccgc tggtgctgga ccggcccgac acgtcgcacc ggctgctggg cagccccgcg     960

atggtgaccc tgggccgttg gtcctatggc ctgttcatct ggcatctggc cgcgctggcc    1020

atggtgtttc ccgtgatcgg agcgttcccg tttaccgggc gaatgccgac ggtgctggtg    1080

ttgacgctga tcttcggttt cgcgatcgcc gcggtcagct acgccctggt cgagtcgccc    1140

tgccgggaag cgttgcgccg ctgggagcgc cgcaacgaac ccatatcggt cggcgaactt    1200

caggcggacg cgattgcacc c                                              1221


<210> SEQ ID NO 15
<211> LENGTH: 381
<212> TYPE: PRT
<213> ORGANISM: Mycobacterium tuberculosis

<400> SEQUENCE: 15

Met Ala Gln Ala His Ser Ala Pro Leu Thr Gly Tyr Arg Ile Ala Val
1               5                   10                  15

Thr Ser Ala Arg Arg Ala Glu Glu Leu Cys Ala Leu Leu Arg Arg Gln
            20                  25                  30

Gly Ala Glu Val Cys Ser Ala Pro Ala Ile Lys Met Ile Ala Leu Pro
        35                  40                  45

Asp Asp Asp Glu Leu Gln Asn Asn Thr Glu Ala Leu Ile Ala Asp Pro
    50                  55                  60

Pro Asp Ile Leu Val Ala His Thr Gly Ile Gly Phe Arg Gly Trp Leu
```

-continued

```
65                  70                  75                  80

Ala Ala Ala Glu Gly Trp Gly Leu Ala Asn Glu Leu Leu Glu Ser Leu
                85                  90                  95

Ser Ser Ala Arg Ile Ile Ser Arg Gly Pro Lys Ala Thr Gly Ala Leu
            100                 105                 110

Arg Ala Ala Gly Leu Arg Glu Glu Trp Ser Pro Asp Ser Glu Ser Ser
        115                 120                 125

His Glu Val Leu Glu Tyr Leu Leu Glu Ser Gly Val Ser Arg Thr Arg
    130                 135                 140

Ile Ala Val Gln Leu His Gly Ala Ala Asp Ser Trp Asp Pro Phe Pro
145                 150                 155                 160

Glu Phe Leu Gly Gly Leu Arg Phe Ala Gly Ala Gln Val Val Pro Ile
                165                 170                 175

Arg Val Tyr Arg Trp Lys Pro Ala Pro Leu Gly Gly Val Phe Asp His
            180                 185                 190

Leu Val Thr Gly Ile Ala Arg Arg Gln Phe Asp Ala Val Thr Phe Thr
        195                 200                 205

Ser Ala Pro Ala Ala Ala Ala Val Leu Glu Arg Ser Arg Glu Leu Asp
    210                 215                 220

Ile Glu Asp Gln Leu Leu Ala Ala Leu Arg Thr Asp Val His Ala Met
225                 230                 235                 240

Cys Val Gly Pro Val Thr Ser Arg Pro Leu Ile Arg Lys Gly Val Pro
                245                 250                 255

Thr Ser Ala Pro Glu Arg Met Arg Leu Gly Ala Leu Ala Arg His Ile
            260                 265                 270

Ala Glu Glu Leu Pro Leu Leu Gly Ser Cys Thr Phe Lys Ala Ala Gly
        275                 280                 285

His Val Ile Glu Ile Arg Gly Thr Ser Val Leu Val Asp Asp Ser Val
    290                 295                 300

Lys Pro Leu Ser Pro Ser Gly Met Ala Ile Leu Arg Ala Leu Val His
305                 310                 315                 320

Arg Pro Gly Gly Val Val Ser Arg Gly Asp Leu Leu Arg Val Leu Pro
                325                 330                 335

Gly Asp Gly Ser Asp Thr His Ala Val Asp Thr Ala Val Leu Arg Leu
            340                 345                 350

Arg Thr Ala Leu Gly Asp Lys Asn Ile Val Ala Thr Val Val Lys Arg
        355                 360                 365

Gly Tyr Arg Leu Ala Val Asp Ser Arg His Asp Asp Val
    370                 375                 380
```

<210> SEQ ID NO 16
<211> LENGTH: 1143
<212> TYPE: DNA
<213> ORGANISM: Mycobacterium tuberculosis

<400> SEQUENCE: 16

```
atggcccagg cacactcggc gccactgacc ggctaccgga tcgcggtgac atccgctcgc      60

cgcgccgaag agctgtgcgc attgcttcgc cgccagggcg ccgaggtctg tagtgcccca     120

gcgatcaaga tgatcgcgct tcccgacgac gatgaactgc agaacaacac cgaggcgttg     180

atcgccgacc cgcctgacat tctggtcgcc cacaccggca tcggatttcg cggctggttg     240

gccgcggccg aggggtgggg gctggccaac gagctcctgg aatcgttgtc gtcggcccgg     300

atcatctccc gcggaccaaa ggcaactggt gcgctgcgtg ccgccggcct gcgtgaagag     360

tggtcccccg actctgaatc gtcgcatgaa gtgctggaat atctgctcga atcgggggtg     420
```

```
tcccgtacgc gtattgccgt ccagctgcac ggtgccgccg acagctggga cccgtttccg    480

gaatttctgg gcgggttacg tttcgccggc gcgcaagtgg tgccgatccg ggtttaccgg    540

tggaagccgg cgccactagg cggcgtgttc gaccatttag tcaccgggat cgcgcgacga    600

caattcgacg cggtcacctt cacgtcggca cctgccgcag ccgcggtgct agaacgcagc    660

cgtgaattgg atatcgagga ccaactgttg gctgcgctgc gtaccgacgt gcacgcgatg    720

tgtgtcggcc cggtaacttc gcggccgttg atccgaaagg gcgtcccgac gtcggctccc    780

gagcgaatgc ggttgggagc cttagcccgc cacattgccg aggagctgcc gctgctgggt    840

tcgtgcacgt tcaaagcagc cggccacgtg atcgagatcc gtggaacctc tgtgctggtg    900

gatgattcgg tgaagccact atcgccgtcc ggaatggcga ttttgcgcgc gttggtacat    960

cgccccggcg gcgtcgtctc tcgtggcgac ttgctacgcg tcctacccgg cgacggcagc   1020

gacacccacg ccgtggacac cgccgtcctg cggctacgaa cggctctggg cgacaagaac   1080

atcgtggcaa cagtggtgaa acgtggctac cgtctcgccg ttgacagccg gcacgatgac   1140

gta                                                                 1143
```

<210> SEQ ID NO 17
<211> LENGTH: 409
<212> TYPE: PRT
<213> ORGANISM: Mycobacterium tuberculosis

<400> SEQUENCE: 17

```
Met Ser Gln Ser Arg Tyr Ala Gly Leu Ser Arg Ser Glu Leu Ala Val
1               5                   10                  15

Leu Leu Pro Glu Leu Leu Leu Ile Gly Gln Leu Ile Asp Arg Ser Gly
            20                  25                  30

Met Ala Trp Cys Ile Gln Ala Phe Gly Arg Gln Glu Met Leu Gln Ile
        35                  40                  45

Ala Ile Glu Glu Trp Ala Gly Ala Ser Pro Ile Tyr Thr Lys Arg Met
    50                  55                  60

Gln Lys Ala Leu Asn Phe Glu Gly Asp Asp Val Pro Thr Ile Phe Lys
65                  70                  75                  80

Gly Leu Gln Leu Asp Ile Gly Ala Pro Pro Gln Phe Met Asp Phe Arg
                85                  90                  95

Phe Thr Leu His Asp Arg Trp His Gly Glu Phe His Leu Asp His Cys
            100                 105                 110

Gly Ala Leu Leu Asp Val Glu Pro Met Gly Asp Asp Tyr Val Val Gly
        115                 120                 125

Met Cys His Thr Ile Glu Asp Pro Thr Phe Asp Ala Thr Ala Ile Ala
    130                 135                 140

Thr Asn Pro Arg Ala Gln Val Arg Pro Ile His Arg Pro Pro Arg Lys
145                 150                 155                 160

Pro Ala Asp Arg His Pro His Cys Ala Trp Thr Val Ile Ile Asp Glu
                165                 170                 175

Ser Tyr Pro Glu Ala Glu Gly Ile Pro Ala Leu Asp Ala Val Arg Glu
            180                 185                 190

Thr Lys Ala Ala Thr Trp Glu Leu Asp Asn Val Asp Ala Ser Asp Asp
        195                 200                 205

Gly Leu Val Asp Tyr Ser Gly Pro Leu Val Ser Asp Leu Asp Phe Gly
    210                 215                 220

Ala Phe Ser His Ser Ala Leu Val Arg Met Ala Asp Glu Val Cys Leu
225                 230                 235                 240
```

-continued

```
Gln Met His Leu Leu Asn Leu Ser Phe Ala Ile Ala Val Arg Lys Arg
                245                 250                 255

Ala Lys Ala Asp Ala Gln Leu Ala Ile Ser Val Asn Thr Arg Gln Leu
            260                 265                 270

Ile Gly Val Ala Gly Leu Gly Ala Glu Arg Ile His Arg Ala Met Ala
        275                 280                 285

Leu Pro Gly Gly Ile Glu Gly Ala Leu Gly Val Leu Glu Leu His Pro
    290                 295                 300

Leu Leu Asn Pro Ala Gly Tyr Val Leu Ala Glu Thr Ser Pro Asp Arg
305                 310                 315                 320

Leu Val Val His Asn Ser Pro Ala His Ala Asp Gly Ala Trp Ile Ser
                325                 330                 335

Leu Cys Thr Pro Ala Ser Val Gln Pro Leu Gln Ala Ile Ala Thr Ala
            340                 345                 350

Val Asp Pro His Leu Lys Val Arg Ile Ser Gly Thr Asp Thr Asp Trp
        355                 360                 365

Thr Ala Glu Leu Ile Glu Ala Asp Ala Pro Ala Ser Glu Leu Pro Glu
    370                 375                 380

Val Leu Val Ala Lys Val Ser Arg Gly Ser Val Phe Gln Phe Glu Pro
385                 390                 395                 400

Arg Arg Ser Leu Pro Leu Thr Val Lys
                405
```

<210> SEQ ID NO 18
<211> LENGTH: 1227
<212> TYPE: DNA
<213> ORGANISM: Mycobacterium tuberculosis

<400> SEQUENCE: 18

```
atgagccaat cccggtacgc ggggttgtcc cgcagcgagc tggcagttct gttacccgag     60

ctgttgttga tcggccagct gatcgaccga tcgggcatgg cctggtgtat acaggcattc    120

ggccgccagg agatgctgca gatcgccatc gaggagtggg cgggcgccag cccgatctac    180

accaagcgca tgcaaaaggc gctgaacttc gagggcgacg acgtgcccac catcttcaag    240

gggctacagc tcgacatcgg cgcgccgccg caattcatgg acttccgttt caccctgcac    300

gaccgctggc acggcgagtt tcacctcgac cactgcggtg cgctgctcga cgtggagccg    360

atgggcgacg actacgtcgt cggcatgtgc cacaccatcg aagatccgac gttcgacgcc    420

accgcgatcg cgaccaaccc gcgcgcgcag gtgcgcccca tccaccggcc gccccgcaag    480

ccggccgacc ggcatccgca ctgtgcgtgg accgtcatca tcgacgagtc ctatcccgag    540

gctgagggta ttccggcgct ggacgcggtc cgtgaaacca aagctgccac ctgggaatta    600

gacaacgtcg atgcgtctga cgacgggctg gtggactatt cgggtccgct ggtgtccgac    660

ctggacttcg gggcgttctc gcattccgca ctggtgcgga tggccgatga ggtctgcctg    720

caaatgcacc tgctgaatct gtcgttcgcc attgccgtgc ggaaacgggc caaagccgat    780

gctcaactgg ccatttcggt gaacacccgc cagttgatcg gagtggccgg gctgggcgca    840

gaacgcattc accgtgcgat ggctttaccc ggcggaatcg aaggcgcgtt aggtgtgctg    900

gagctacacc cgctgctcaa cccggccggt tacgtgctgg ccgaaacgtc gccggaccgt    960

ctggtggtgc acaactcgcc agcccacgcc gacggcgcct ggatttcgtt gtgcacaccg   1020

gcatccgtgc agccgttgca ggccatcgcc accgctgtag acccgcatct gaaggttcgg   1080

atcagcggga cggacaccga ctggaccgcg gaactcatcg aggccgatgc cccagcgagc   1140

gaactgccgg aggtgttggt agccaaggtc agtcgcggat cggtcttcca gttcgagccg   1200
```

-continued aggcgctcac tgccgttgac cgtgaaa 1227

<210> SEQ ID NO 19
<211> LENGTH: 443
<212> TYPE: PRT
<213> ORGANISM: Mycobacterium tuberculosis

<400> SEQUENCE: 19

Val Arg Cys Ser Val Phe Gly Thr Gly Tyr Leu Gly Ala Thr His Ala
1 5 10 15

Val Gly Met Ala Gln Leu Gly His Glu Val Val Gly Val Asp Ile Asp
20 25 30

Pro Gly Lys Val Ala Lys Leu Ala Gly Gly Asp Ile Pro Phe Tyr Glu
35 40 45

Pro Gly Leu Arg Lys Leu Leu Thr Asp Asn Leu Ala Ala Gly Arg Leu
50 55 60

Arg Phe Thr Thr Asp Tyr Asp Met Ala Ala Asp Phe Ala Asp Val His
65 70 75 80

Phe Leu Gly Val Gly Thr Pro Gln Lys Ile Gly Glu Tyr Gly Ala Asp
85 90 95

Leu Arg His Val His Ala Val Ile Asp Ala Leu Val Pro Arg Leu Val
100 105 110

Arg Ala Ser Ile Leu Val Gly Lys Ser Thr Val Pro Val Gly Thr Ala
115 120 125

Ala Glu Leu Gly His Arg Ala Gly Ala Leu Ala Pro Arg Gly Val Asp
130 135 140

Val Glu Ile Ala Trp Asn Pro Glu Phe Leu Arg Glu Gly Phe Ala Val
145 150 155 160

His Asp Thr Leu Asn Pro Asp Arg Ile Val Leu Gly Val Gln Asp Asp
165 170 175

Ser Thr Arg Ala Glu Val Ala Val Arg Glu Leu Tyr Ala Pro Leu Leu
180 185 190

Ala Ala Gly Val Pro Phe Leu Val Thr Asp Leu Gln Thr Ala Glu Leu
195 200 205

Val Lys Val Ser Ala Asn Ala Phe Leu Ala Thr Lys Ile Ser Phe Ile
210 215 220

Asn Ala Ile Ser Glu Val Cys Glu Ala Ala Gly Ala Asp Val Ser Gln
225 230 235 240

Leu Ala Asp Ala Leu Gly Tyr Asp Pro Arg Ile Gly Arg Gln Cys Leu
245 250 255

Asn Ala Gly Leu Gly Phe Gly Gly Gly Cys Leu Pro Lys Asp Ile Arg
260 265 270

Ala Phe Met Ala Arg Ala Gly Glu Leu Gly Ala Asp Gln Ala Leu Thr
275 280 285

Phe Leu Arg Glu Val Asp Ser Ile Asn Met Arg Arg Arg Thr Lys Met
290 295 300

Val Glu Leu Ala Thr Thr Ala Cys Gly Gly Ser Leu Leu Gly Ala Asn
305 310 315 320

Ile Ala Val Leu Gly Ala Ala Phe Lys Pro Glu Ser Asp Asp Val Arg
325 330 335

Asp Ser Pro Ala Leu Asn Val Ala Gly Gln Leu Gln Leu Asn Gly Ala
340 345 350

Thr Val His Val Tyr Asp Pro Lys Ala Leu Asp Asn Ala His Arg Leu
355 360 365

-continued

Phe Pro Thr Leu Asn Tyr Ala Val Ser Val Ala Glu Ala Cys Glu Arg
370 375 380

Ala Asp Ala Val Leu Val Leu Thr Glu Trp Arg Glu Phe Ile Asp Leu
385 390 395 400

Glu Pro Ala Asp Leu Ala Asn Arg Val Arg Ala Arg Val Ile Val Asp
405 410 415

Gly Arg Asn Cys Leu Asp Val Thr Arg Trp Arg Arg Ala Gly Trp Arg
420 425 430

Val Phe Arg Leu Gly Val Pro Arg Leu Gly His
435 440

<210> SEQ ID NO 20
<211> LENGTH: 1329
<212> TYPE: DNA
<213> ORGANISM: Mycobacterium tuberculosis

<400> SEQUENCE: 20
gtgcgatgca gcgtcttcgg cactgggtat ctgggtgcca cccacgccgt cggtatggcg 60
caactgggac acgaggtcgt cggggtcgat atcgatcccg gtaaggtcgc caagctcgcc 120
gggggtgaca ttccgttcta cgaacccggc ctgcgaaagc tgttgactga taacctggct 180
gccggccgct tgcggttcac caccgactac gacatggcgg ccgatttcgc cgacgtgcat 240
ttcctggggg tcggcacgcc gcaaaagata ggcgaatatg gcgccgacct gcggcatgtc 300
cacgccgtca tcgatgcgct ggtgccgcgt ctggtcaggg cgtcgattct ggtcggcaag 360
tcgacagtcc cagtgggcac cgcagccgaa ctgggacatc gggccggtgc actggcaccc 420
cggggagtcg acgtggaaat tgcctggaat ccggaattcc tgcgcgaggg cttcgcggtg 480
cacgacaccc tcaaccccga ccgtatcgtc cttggggtac aagatgattc gacgcgcgcc 540
gaggtagccg tccgcgagct gtacgcgccg ctgctggcag cgggcgtgcc gtttctggtg 600
accgatctgc agaccgcgga gttggtcaag gtatccgcca atgcctttct ggcgaccaag 660
atttcgttta tcaatgcgat ctccgaagtg tgcgaggcgg cgggtgccga cgttagccag 720
ctggccgatg cgctcggata cgacccgcgg atcggacgcc aatgcctcaa cgcgggcttg 780
ggtttcggcg gcggctgctt gcccaaggac atccgcgctt tcatggcccg cgccggcgaa 840
ctgggagccg accaggcgtt gacgttcctg cgtgaagtgg acagcatcaa catgcgccgg 900
cgcaccaaga tggtggaact ggccaccacc gcatgcggtg gctcgttgct gggcgccaat 960
attgcggtgc tcggcgcggc gttcaaaccc gaatccgatg acgtgcgcga ttcgcccgcc 1020
ctcaatgtgg cgggccagct gcagctcaac ggcgccacgg tccacgtgta cgatccaaag 1080
gccttggaca acgcccaccg actgttccct accttgaact atgcggtttc ggttgcggag 1140
gcctgcgagc gcgcggacgc cgtgttggtg cttaccgaat ggcgggagtt catcgatctc 1200
gaacccgctg atctagccaa ccgggtgcgg gcccgggtga tcgtggacgg ccgcaactgc 1260
ctcgacgtga cccgctggcg gcgggcaggc tggcgggtgt tccggctggg agtgccgcga 1320
ttagggcac 1329

<210> SEQ ID NO 21
<211> LENGTH: 74
<212> TYPE: PRT
<213> ORGANISM: Mycobacterium tuberculosis

<400> SEQUENCE: 21

Val Gly Pro Lys Gly Ser Leu Arg Leu Val Lys Arg Gln Pro Glu Leu
1 5 10 15

-continued

```
Leu Val Ala Gln His Glu His Trp Gln Asp Thr Tyr Arg Ala His Pro
            20                  25                  30

Val Leu Tyr Gly Thr Arg Pro Ser Glu Pro Gly Val Tyr Ala Ala Glu
        35                  40                  45

Val Phe Asn Ala Asp Gly Val Gln Arg Val Leu Glu Leu Ala Ala Gly
    50                  55                  60

His Gly Arg Asp Thr Leu Tyr Phe Ala Gly
65                  70


<210> SEQ ID NO 22
<211> LENGTH: 222
<212> TYPE: DNA
<213> ORGANISM: Mycobacterium tuberculosis

<400> SEQUENCE: 22

gtggggccga agggaagtct acgtttggtg aagcggcagc cagaactgct cgttgcccag     60

catgaacact ggcaggacac ctaccgagcg catccggtgc tgtacggaac ccgcccgtca    120

gagccggggg tatatgccgc cgaggtgttc aatgccgacg gcgtgcagcg ggtgctggag    180

ttggcggccg gtcatgggcg tgacaccctg tatttcgctg gc                       222


<210> SEQ ID NO 23
<211> LENGTH: 419
<212> TYPE: PRT
<213> ORGANISM: Mycobacterium tuberculosis

<400> SEQUENCE: 23

Val Ile Asp Gly Trp Thr Glu Glu Gln His Glu Pro Thr Val Arg His
1               5                   10                  15

Glu Arg Pro Ala Ala Pro Gln Asp Val Arg Arg Val Met Leu Leu Gly
            20                  25                  30

Ser Ala Glu Pro Ser Arg Glu Leu Ala Ile Ala Leu Gln Gly Leu Gly
        35                  40                  45

Ala Glu Val Ile Ala Val Asp Gly Tyr Val Gly Ala Pro Ala His Arg
    50                  55                  60

Ile Ala Asp Gln Ser Val Val Val Thr Met Thr Asp Ala Glu Glu Leu
65                  70                  75                  80

Thr Ala Val Ile Arg Arg Leu Gln Pro Asp Phe Leu Val Thr Val Thr
                85                  90                  95

Ala Ala Val Ser Val Asp Ala Leu Asp Ala Val Glu Gln Ala Asp Gly
            100                 105                 110

Glu Cys Thr Glu Leu Val Pro Asn Ala Arg Ala Val Arg Cys Thr Ala
        115                 120                 125

Asp Arg Glu Gly Leu Arg Arg Leu Ala Ala Asp Gln Leu Gly Leu Pro
    130                 135                 140

Thr Ala Pro Phe Trp Phe Val Gly Ser Leu Gly Glu Leu Gln Ala Val
145                 150                 155                 160

Ala Val His Ala Gly Phe Pro Leu Leu Val Ser Pro Val Ala Gly Val
                165                 170                 175

Ala Gly Gln Gly Ser Ser Val Val Ala Gly Pro Asn Glu Val Glu Pro
            180                 185                 190

Ala Trp Gln Arg Ala Ala Gly His Gln Val Gln Pro Gln Thr Gly Gly
        195                 200                 205

Val Ser Pro Arg Val Cys Ala Glu Ser Val Val Glu Ile Glu Phe Leu
    210                 215                 220

Val Thr Met Ile Val Val Cys Ser Gln Gly Pro Asn Gly Pro Leu Ile
225                 230                 235                 240
```

-continued

```
Glu Phe Cys Ala Pro Ile Gly His Arg Asp Ala Asp Ala Gly Glu Leu
                245                 250                 255

Glu Ser Trp Gln Pro Gln Lys Leu Ser Thr Ala Ala Leu Asp Ala Ala
            260                 265                 270

Lys Ser Ile Ala Ala Arg Ile Val Lys Ala Leu Gly Gly Arg Gly Val
        275                 280                 285

Phe Gly Val Glu Leu Met Ile Asn Gly Asp Glu Val Tyr Phe Ala Asp
    290                 295                 300

Val Thr Val Cys Pro Ala Gly Ser Ala Trp Val Thr Val Arg Ser Gln
305                 310                 315                 320

Arg Leu Ser Val Phe Glu Leu Gln Ala Arg Ala Ile Leu Gly Leu Ala
                325                 330                 335

Val Asp Thr Leu Met Ile Ser Pro Gly Ala Ala Arg Val Ile Asn Pro
            340                 345                 350

Asp His Thr Ala Gly Arg Ala Ala Val Gly Ala Ala Pro Pro Ala Asp
        355                 360                 365

Ala Leu Thr Gly Ala Leu Gly Val Pro Glu Ser Asp Val Val Ile Phe
    370                 375                 380

Gly Arg Gly Leu Gly Val Ala Leu Ala Thr Ala Pro Glu Val Ala Ile
385                 390                 395                 400

Ala Arg Glu Arg Ala Arg Glu Val Ala Ser Arg Leu Asn Val Pro Asp
               405                 410                 415

Ser Arg Glu
```

<210> SEQ ID NO 24
<211> LENGTH: 1257
<212> TYPE: DNA
<213> ORGANISM: Mycobacterium tuberculosis

<400> SEQUENCE: 24

```
gtgatcgacg gctggacgga agaacagcac gaacccaccg ttaggcatga gcgcccagca     60

gctccccaag acgttcggcg ggtgatgttg ctgggttcgg ccgaacccag ccgggagctg    120

gcgatcgcgt tgcagggctt gggcgcggag gtgatcgccg tcgacggcta tgtcggcgcg    180

cctgcccacc ggatagccga ccagtcggtg gtggtcacca tgaccgatgc tgaagagctg    240

acggcggtga tccggcggct gcaaccggat ttcttggtga cggtcaccgc cgcggtgtct    300

gtggatgctc tcgatgccgt cgagcaagcc gacggcgagt gcactgagct ggtgccgaac    360

gcccgtgccg tccggtgcac ggccgaccgg gagggcctgc gccggctggc cgccgatcag    420

ctcggcctgc ccacagcccc gttctggttc gtcggatccc ttggcgaact tcaagcggtg    480

gccgtccatg ctgggtttcc gttgctggtg agcccggtgg caggggtggc tggccagggt    540

agctcggtgg tcgccgggcc caacgaggtc gagcccgcct ggcagcgcgc ggcaggccat    600

caagtacagc cgcagactgg gggagtgagc cctcgggtgt gcgccgagtc ggtggtcgag    660

atcgagtttt tggtcaccat gatcgttgtg tgcagtcagg gcccgaacgg gccgctcatc    720

gagttctgtg cacctatcgg tcatcgcgac gccgatgccg gtgagttgga atcctggcaa    780

ccgcagaagc tgagcacggc ggcgctggac gcggccaagt cgatcgccgc gcgcatcgtc    840

aaggcgctcg gggacgcgg ggttttcggc gtcgaattga tgatcaacgg cgatgaggtg    900

tatttcgccg atgtcaccgt gtgtcctgcc gggagtgcct gggtcaccgt gcgcagccag    960

cggctttcgg tgttcgaact gcaggcccgg gcgatcctgg gtctggcggt ggacaccctg   1020

atgatctcgc cgggtgccgc gcgggtgatc aacccggacc acacggcagg ccgggcagcg   1080
```

gtcggcgccg caccacctgc cgatgcgctg accggtgcgc tcggtgtgcc ggaaagcgac 1140
gtcgtgatat tcggccgcgg gcttggggtg gcgctggcca ccgcacccga ggtggcaatc 1200
gcccgcgaac gcgcccgcga agttgcatct cggctaaatg tgccagactc acgcgag 1257

<210> SEQ ID NO 25
<211> LENGTH: 140
<212> TYPE: PRT
<213> ORGANISM: Mycobacterium tuberculosis

<400> SEQUENCE: 25

Val Ser Tyr Ala Gly Asp Ile Thr Pro Leu Gln Ala Trp Glu Met Leu
1 5 10 15

Ser Asp Asn Pro Arg Ala Val Leu Val Asp Val Arg Cys Glu Ala Glu
20 25 30

Trp Arg Phe Val Gly Val Pro Asp Leu Ser Ser Leu Gly Arg Glu Val
35 40 45

Val Tyr Val Glu Trp Ala Thr Ser Asp Gly Thr His Asn Asp Asn Phe
50 55 60

Leu Ala Glu Leu Arg Asp Arg Ile Pro Ala Asp Ala Asp Gln His Glu
65 70 75 80

Arg Pro Val Ile Phe Leu Cys Arg Ser Gly Asn Arg Ser Ile Gly Ala
85 90 95

Ala Glu Val Ala Thr Glu Ala Gly Ile Thr Pro Ala Tyr Asn Val Leu
100 105 110

Asp Gly Phe Glu Gly His Leu Asp Ala Glu Gly His Arg Gly Ala Thr
115 120 125

Gly Trp Arg Ala Val Gly Leu Pro Trp Arg Gln Gly
130 135 140

<210> SEQ ID NO 26
<211> LENGTH: 420
<212> TYPE: DNA
<213> ORGANISM: Mycobacterium tuberculosis

<400> SEQUENCE: 26
gtgagctacg ccggagatat cacgccactt caggcctggg agatgctcag cgataatccg 60
cgggcggtcc tggtcgacgt gcgctgcgag gcggaatggc gcttcgtcgg tgtgcccgac 120
ttgtcgagcc ttggtcgtga agtggtctat gtcgaatggg cgacgtccga cgggacgcac 180
aacgacaact tcctcgccga gttgcgggac cgcatcccgg cggacgctga tcagcacgag 240
cggcccgtta ttttcttgtg tcgctccggt aaccgctcca tcggcgcggc cgaggtcgcg 300
accgaggcgg gcatcacgcc ggcctataac gtgctggacg gcttcgaagg gcatctcgac 360
gctgagggtc atcgaggcgc aacgggctgg cgggcggtgg gactgccgtg gagacaggga 420

<210> SEQ ID NO 27
<211> LENGTH: 134
<212> TYPE: PRT
<213> ORGANISM: Mycobacterium tuberculosis

<400> SEQUENCE: 27

Met Asp Trp Met Pro Leu Gly Asp Tyr Glu Thr Phe Arg His Trp Ser
1 5 10 15

Gly Lys Pro Arg Ala Trp Gly Pro Gln Glu Ser Gly Trp Arg Ala Trp
20 25 30

Phe Gly Gly Lys Ile Val Asp Gly Leu Cys Glu Val Leu Asp Glu His
35 40 45

Leu Ala Val Arg Arg Arg Gly Val Pro Ala Ala Ile Gly Cys Val Pro
    50                  55                  60

Trp Leu Ser Ser Glu Ala Val Ala Glu Thr Leu Leu Ala Leu Ser Val
65                  70                  75                  80

Phe Cys Val Val Ile Asp Lys Gly Thr Ser Phe Pro Ser Arg Leu Arg
                85                  90                  95

Asn Pro Asp Lys Gly Phe Pro Asn Val Ala Leu Leu Arg Leu Arg Asp
            100                 105                 110

Met Ala Pro Ser Glu His Gly Ser Arg Cys Ser Ser Ala Arg Gly Arg
        115                 120                 125

Leu Cys Leu Ser Met Ser
    130

<210> SEQ ID NO 28
<211> LENGTH: 402
<212> TYPE: DNA
<213> ORGANISM: Mycobacterium tuberculosis

<400> SEQUENCE: 28
atggattgga tgccgctcgg cgactacgag actttccggc attggtcggg gaagccccgc      60
gcatgggggc cgcaagagtc ggggtggcgc gcgtggttcg gcgggaagat agtcgatggg     120
ctctgcgagg tactcgacga gcacctcgcg gtgcggcgtc gtggtgttcc agccgcgatc     180
ggctgcgtgc cctggctgag tagcgaggcg gtcgccgaga cgctgctcgc attgagcgtc     240
ttttgcgtgg tgatcgacaa gggaacctcg ttcccgtcgc gactgcgtaa ccctgacaaa     300
gggtttccca acgtcgccct attgcggctt cgcgacatgg cgccctccga gcatggctca     360
cgctgctcct cggcccgtgg tcgtctatgc ctgagcatga gc                        402

<210> SEQ ID NO 29
<211> LENGTH: 340
<212> TYPE: PRT
<213> ORGANISM: Mycobacterium tuberculosis

<400> SEQUENCE: 29

Val Pro Ala Cys Pro Ala Pro Ala Arg Ala Gly Thr Ala Arg Ser Ser
1               5                   10                  15

Pro Gly Ala Ser Trp Ile Ala Arg Leu Leu Arg Ala Pro Val Arg Arg
            20                  25                  30

Ala Arg Arg Arg Ala Gln Ala Gly Leu Pro Gly Ser Cys Ala Arg Arg
        35                  40                  45

Cys Gly Ala Leu Val Ala Gly Pro Arg Leu Ala Arg Met Arg Ile Ala
    50                  55                  60

Leu Ala Gln Ile Arg Ser Gly Thr Asp Pro Ala Ala Asn Leu Gln Leu
65                  70                  75                  80

Val Gly Lys Tyr Ala Gly Glu Ala Ala Thr Ala Gly Ala Gln Leu Val
                85                  90                  95

Val Phe Pro Glu Ala Thr Met Cys Arg Leu Gly Val Pro Leu Arg Gln
            100                 105                 110

Val Ala Glu Pro Val Asp Gly Pro Trp Ala Asn Gly Val Arg Arg Ile
        115                 120                 125

Ala Thr Glu Ala Gly Ile Thr Val Ile Ala Gly Met Phe Thr Pro Thr
    130                 135                 140

Gly Asp Gly Arg Val Thr Asn Thr Leu Ile Ala Ala Gly Pro Gly Thr
145                 150                 155                 160

Pro Asn Gln Pro Asp Ala His Tyr His Lys Ile His Leu Tyr Asp Ala
                165                 170                 175

-continued

Phe Gly Phe Thr Glu Ser Arg Thr Val Ala Pro Gly Arg Glu Pro Val
180 185 190

Val Val Val Val Asp Gly Val Arg Val Gly Leu Thr Val Cys Tyr Asp
195 200 205

Ile Arg Phe Pro Ala Leu Tyr Thr Glu Leu Ala Arg Arg Gly Ala Gln
210 215 220

Leu Ile Ala Val Cys Ala Ser Trp Gly Ser Gly Pro Gly Lys Leu Glu
225 230 235 240

Gln Trp Thr Leu Leu Ala Arg Ala Arg Ala Leu Asp Ser Met Ser Tyr
245 250 255

Val Ala Ala Ala Gly Gln Ala Asp Pro Gly Asp Ala Arg Thr Gly Val
260 265 270

Gly Ala Ser Ser Ala Ala Pro Thr Gly Val Gly Gly Ser Leu Val Ala
275 280 285

Ser Pro Leu Gly Glu Val Val Val Ser Ala Gly Thr Gln Pro Gln Leu
290 295 300

Leu Val Ala Asp Ile Asp Val Asp Asn Val Ala Ala Ala Arg Asp Arg
305 310 315 320

Ile Ala Val Leu Arg Asn Gln Thr Asp Phe Val Gln Ile Asp Lys Ala
325 330 335

Gln Ser Arg Gly
340

<210> SEQ ID NO 30
<211> LENGTH: 1020
<212> TYPE: DNA
<213> ORGANISM: Mycobacterium tuberculosis

<400> SEQUENCE: 30
gtgccagctt gcccggctcc tgcgcgcgcc ggtacggcgc gctcgtcgcc gggcgcaagc 60
tggattgccc ggctcctgcg cgcgccggtg cggcgcgctc gtcgccgggc gcaagctgga 120
ttgcccggct cctgcgcgcg ccggtgcggc gcgctcgtcg ccgggcctag gctggcgcgc 180
atgcgaatcg cgttggcgca aatccgcagc ggtaccgacc ccgccgccaa tctgcaactg 240
gtcggcaagt acgccggcga agccgccacc gcgggcgcac agctggtggt gtttcctgag 300
gcgaccatgt gccggctcgg tgtcccgctg cggcaggtcg ccgagcccgt cgacggaccc 360
tgggcaaacg gagtccgacg gatcgcgacc gaggcgggca tcaccgtgat cgccggcatg 420
ttcaccccga ccggcgacgg gcgggtaaca aacacgctga tcgcagccgg cccgggcacg 480
cccaatcagc cggacgcgca ctaccacaag atccacctct atgacgcgtt cggcttcacc 540
gagtcacgta ccgtcgcacc cgggcgcgaa ccggtggtag tcgtggtcga cggcgtgcgg 600
gtgggtttga ccgtttgcta cgacattcgc tttcccgccc tttataccga gctggcgcgg 660
cgcggggccc aactgatcgc ggtctgtgca tcctggggtt ccggtccggg caaactcgaa 720
cagtggacgt tgctggcccg cgcccgggcg ctagactcca tgagttacgt cgccgcggcc 780
ggccaagcag acccaggtga tgcccgcacc ggcgtggggg cgagctcggc tgcaccgacc 840
ggggtaggcg gcagcctggt ggcctcgccg ctaggcgagg tggtggtgtc agctggcacc 900
cagccgcaac tgctggtcgc cgacatcgat gtcgacaatg tggccgcggc tcgcgaccgc 960
attgcggtgc tacgcaacca gacagacttc gttcagatcg ataaggcaca atcgcgtggg 1020

<210> SEQ ID NO 31
<211> LENGTH: 329
<212> TYPE: PRT

<213> ORGANISM: Mycobacterium tuberculosis

<400> SEQUENCE: 31

```
Val Gly Glu Ser Thr Thr Gln Pro Ala Gly Gly Ala Ala Val Asp Asp
1               5                   10                  15

Glu Thr Arg Ser Ala Ala Leu Pro Arg Trp Arg Gly Ala Ala Gly Arg
            20                  25                  30

Leu Glu Val Trp Tyr Ala Thr Leu Ser Asp Pro Leu Thr Arg Thr Gly
        35                  40                  45

Leu Trp Val His Cys Glu Thr Val Ala Pro Thr Thr Gly Gly Pro Tyr
    50                  55                  60

Ala His Gly Trp Val Thr Trp Phe Pro Pro Asp Ala Pro Pro Gly Thr
65                  70                  75                  80

Glu Arg Phe Gly Pro Gln Pro Ala Gln Pro Ala Ala Gly Pro Ala Trp
                85                  90                  95

Phe Asp Ile Ala Gly Val Arg Met Ala Pro Ala Glu Leu Thr Gly Arg
            100                 105                 110

Thr Arg Ser Leu Ala Trp Glu Leu Ser Trp Lys Asp Thr Ala Ala Pro
        115                 120                 125

Leu Trp Thr Phe Pro Arg Val Ala Trp Glu Arg Glu Leu Leu Pro Gly
    130                 135                 140

Ala Gln Val Val Ile Ala Pro Thr Ala Val Phe Ala Gly Ser Leu Ala
145                 150                 155                 160

Val Gly Glu Thr Thr His Arg Val Asp Ser Trp Arg Gly Ser Val Ala
                165                 170                 175

His Ile Tyr Gly His Gly Asn Ala Lys Arg Trp Gly Trp Ile His Ala
            180                 185                 190

Asp Leu Gly Asp Gly Asp Val Leu Glu Val Val Thr Ala Val Ser His
        195                 200                 205

Lys Pro Gly Leu Arg Arg Leu Ala Pro Leu Ala Phe Val Arg Phe Arg
    210                 215                 220

Ile Asp Gly Lys Asp Trp Pro Ala Ser Pro Leu Pro Ser Leu Arg Met
225                 230                 235                 240

Arg Thr Thr Leu Gly Val Arg His Trp Gln Leu Glu Gly Arg Ile Gly
                245                 250                 255

Gly Arg Glu Ala Leu Ile Arg Val Asp Gln Pro Pro Glu Arg Cys Val
            260                 265                 270

Ser Leu Gly Tyr Thr Asp Pro Asp Gly Ala Lys Ala Val Cys Thr Asn
        275                 280                 285

Thr Glu Gln Ala Asp Ile His Ile Glu Leu Gly Gly Arg His Trp Ser
    290                 295                 300

Val Leu Gly Thr Gly His Ala Glu Val Gly Leu Arg Gly Thr Ala Ala
305                 310                 315                 320

Pro Ala Ile Lys Glu Gly Thr Pro Ala
                325
```

<210> SEQ ID NO 32
<211> LENGTH: 987
<212> TYPE: DNA
<213> ORGANISM: Mycobacterium tuberculosis

<400> SEQUENCE: 32

```
gtgggcgaat cgacaactca gccagcagga ggtgccgcag tggacgatga aacgcggtcg      60

gcggccttgc cgcggtggcg cggtgcagcc gggcgcctgg aagtctggta tgcgactctg     120

tcggatccac tgacgcgtac cggcctatgg gtgcactgtg agacggtggc cccgacgacc     180
```

-continued

```
ggcgggccct acgcgcacgg ctgggtgacc tggtttccac cggatgcccc gccgggcacc    240

gagcgcttcg gcccccagcc cgcccaaccc gcggccggcc ccgcctggtt cgacatcgcc    300

ggtgtacgaa tggcgccagc ggagctgacc ggacgtaccc gatcactcgc atgggagctg    360

tcctggaagg acaccgcggc gccactgtgg acgtttcctc gcgtggcctg ggagcgcgag    420

ttgctgcccg gcgcccaagt ggtgatcgca cccaccgccg tcttcgctgg ctccttggcc    480

gtcggcgaaa ccacccaccg cgtcgacagc tggcgcggca gtgtggccca catctacgga    540

catggcaatg ccaagcggtg gggatggatc catgccgatc tcggcgacgg cgacgtccta    600

gaggtggtga ccgcggtatc acacaagccg ggcctacgca ggctcgcgcc gctagcgttc    660

gttcgcttcc gcatcgacgg aaaggattgg cccgcaagtc ctttaccgtc gctgcgaatg    720

cggacaacgc tcggcgtgcg gcactggcaa ctggaaggac gcatcggcgg ccgggaggcg    780

ctaatccggg tagaccagcc gccggagcgg tgcgtaagcc tgggatacac cgatcccgac    840

ggggccaagg cggtgtgcac caacaccgag caggccgaca tccacatcga gctcggcggc    900

cggcactggt cggtgctggg caccggacac gccgaagtcg gcctgcgggg aaccgcggca    960

ccggctatca aggaagggac gccagca                                          987
```

<210> SEQ ID NO 33
<211> LENGTH: 292
<212> TYPE: PRT
<213> ORGANISM: Mycobacterium tuberculosis

<400> SEQUENCE: 33

```
Val Ala Ser Phe Ala Gln Trp Val Ser Gly Ala Arg Pro Arg Thr Leu
1               5                   10                  15

Pro Asn Ala Ile Ala Pro Val Val Ala Gly Thr Gly Ala Ala Ala Trp
            20                  25                  30

Leu His Ala Ala Val Trp Trp Lys Ala Leu Leu Ala Leu Ala Val Ala
        35                  40                  45

Val Ala Leu Val Ile Gly Val Asn Tyr Ala Asn Asp Tyr Ser Asp Gly
    50                  55                  60

Ile Arg Gly Thr Asp Asp Asp Arg Val Gly Pro Val Arg Leu Val Gly
65                  70                  75                  80

Ser Arg Leu Ala Thr Pro Arg Ser Val Leu Thr Ala Ala Met Thr Ser
                85                  90                  95

Leu Ala Leu Gly Ala Leu Ala Gly Leu Val Leu Ala Leu Leu Ser Ala
            100                 105                 110

Pro Trp Leu Ile Ala Val Gly Ala Ile Cys Ile Ala Gly Ala Trp Leu
        115                 120                 125

Tyr Thr Gly Gly Ser Lys Pro Tyr Gly Tyr Ala Gly Phe Gly Glu Leu
    130                 135                 140

Ala Val Phe Val Phe Phe Gly Pro Val Ala Val Leu Gly Thr Gln Tyr
145                 150                 155                 160

Thr Gln Ala Leu Arg Val Asp Trp Val Gly Leu Ala Gln Ala Val Ala
                165                 170                 175

Thr Gly Ala Leu Ser Cys Ser Val Leu Val Ala Asn Asn Leu Arg Asp
            180                 185                 190

Ile Pro Thr Asp Ala Arg Ala Asp Lys Ile Thr Leu Ala Val Arg Leu
        195                 200                 205

Gly Asp Ala Arg Thr Arg Met Leu Tyr Gln Gly Leu Leu Ala Val Ala
    210                 215                 220

Gly Val Leu Thr Phe Val Leu Met Leu Ala Thr Pro Trp Cys Val Val
```

-continued

```
225                 230                 235                 240

Gly Leu Val Ala Ala Pro Leu Ala Leu Arg Ala Ala Gly Pro Val Arg
                245                 250                 255

Ser Gly Arg Gly Gly Arg Glu Leu Ile Pro Val Leu Arg Asp Thr Gly
            260                 265                 270

Leu Ala Met Leu Val Trp Ala Leu Ala Val Ala Gly Ala Leu Ala Phe
        275                 280                 285

Gly Gln Leu Ser
    290
```

<210> SEQ ID NO 34
<211> LENGTH: 876
<212> TYPE: DNA
<213> ORGANISM: Mycobacterium tuberculosis

<400> SEQUENCE: 34

```
gtggccagtt tcgcacagtg ggtctccggc gcgcggcccc gaacgctgcc gaacgcgatc      60

gcgccagtgg ttgccggcac cggcgccgcg gcctggctgc acgcggccgt gtggtggaaa     120

gcgctgttgg cactggctgt tgcggtggcg ctggtcattg ggtcaatta cgccaatgac     180

tactccgacg gcatccgcgg caccgatgac gacagggtgg gtccggtgcg gttggtgggc     240

tcgcggctgg cgaccccgcg ctcggtgctg accgctgcca tgacgagcct ggcgctcggt     300

gcgctggccg ggctggtttt ggcgctgctc agcgcgccgt ggctgattgc ggtgggtgcg     360

atctgcatcg ccggggcctg gctctacacc ggcgggtcaa aaccctacgg ctatgcgggc     420

ttcggcgaac tggcggtgtt tgtgttcttc gggccggtcg ccgtgctcgg tacccagtac     480

acgcaggcat tgcgggtgga ctgggtgggg ctggcacagg cggtagcaac gggtgcgttg     540

tcgtgctcgg tgctggtggc caacaacctg cgcgacatcc ccaccgacgc gcgggccgac     600

aagatcacgc tggcggtgcg gctgggagac gcccggaccc ggatgcttta ccagggcctg     660

ctggcggtcg ccggggtgct gacgttcgtg ctaatgctgg ccacgccgtg gtgtgtggtg     720

ggcttggtgg ccgcgccttt ggcgctgcgc gctgccggac cggtgcgatc cgggcgcggc     780

gggcgcgagc tgatcccggt actgcgtgac actgggctgg ccatgctggt gtgggcgttg     840

gcggtggcgg gggcattggc gtttggtcag ttgagc                               876
```

<210> SEQ ID NO 35
<211> LENGTH: 378
<212> TYPE: PRT
<213> ORGANISM: Mycobacterium tuberculosis

<400> SEQUENCE: 35

```
Val Cys Gly Val Arg Val Ala Ile Val Ala Glu Ser Phe Leu Pro Gln
1               5                   10                  15

Val Asn Gly Val Ser Asn Ser Val Val Lys Val Leu Glu His Leu Arg
            20                  25                  30

Arg Thr Gly His Glu Ala Leu Val Ile Ala Pro Asp Thr Pro Pro Gly
        35                  40                  45

Glu Asp Arg Ala Glu Arg Leu His Asp Gly Val Arg Val His Arg Val
    50                  55                  60

Pro Ser Arg Met Phe Pro Lys Val Thr Thr Leu Pro Leu Gly Val Pro
65                  70                  75                  80

Thr Phe Arg Met Leu Arg Ala Leu Arg Gly Phe Asp Pro Asp Val Val
                85                  90                  95

His Leu Ala Ser Pro Ala Leu Leu Gly Tyr Gly Gly Leu His Ala Ala
            100                 105                 110
```

-continued

```
Arg Arg Leu Gly Val Pro Thr Val Ala Val Tyr Gln Thr Asp Val Pro
        115                 120                 125

Gly Phe Ala Ser Ser Tyr Gly Ile Pro Met Thr Ala Arg Ala Ala Trp
    130                 135                 140

Ala Trp Phe Arg His Leu His Arg Leu Ala Asp Arg Thr Leu Ala Pro
145                 150                 155                 160

Ser Thr Ala Thr Met Glu Ser Leu Ile Ala Gln Gly Ile Pro Arg Val
                165                 170                 175

His Arg Trp Ala Arg Gly Val Asp Val Gln Arg Phe Ala Pro Ser Ala
            180                 185                 190

Arg Asn Glu Val Leu Arg Arg Arg Trp Ser Pro Asp Gly Lys Pro Ile
        195                 200                 205

Val Gly Phe Val Gly Arg Leu Ala Pro Glu Lys His Val Asp Arg Leu
    210                 215                 220

Thr Gly Leu Ala Ala Ser Gly Ala Val Arg Leu Val Ile Val Gly Asp
225                 230                 235                 240

Gly Ile Asp Arg Ala Arg Leu Gln Ser Ala Met Pro Thr Ala Val Phe
                245                 250                 255

Thr Gly Ala Arg Tyr Gly Lys Glu Leu Ala Glu Ala Tyr Ala Ser Met
            260                 265                 270

Asp Val Phe Val His Ser Gly Glu His Glu Thr Phe Cys Gln Val Val
        275                 280                 285

Gln Glu Ala Leu Ala Ser Gly Leu Pro Val Ile Ala Pro Asp Ala Gly
    290                 295                 300

Gly Pro Arg Asp Leu Ile Thr Pro His Arg Thr Gly Leu Leu Leu Pro
305                 310                 315                 320

Val Gly Glu Phe Glu His Arg Leu Pro Asp Ala Val Ala His Leu Val
                325                 330                 335

His Glu Arg Gln Arg Tyr Ala Leu Ala Ala Arg Arg Ser Val Leu Gly
            340                 345                 350

Arg Ser Trp Pro Val Val Cys Asp Glu Leu Leu Gly His Tyr Glu Ala
        355                 360                 365

Val Arg Gly Arg Arg Thr Thr Gln Ala Ala
    370                 375
```

<210> SEQ ID NO 36
<211> LENGTH: 1134
<212> TYPE: DNA
<213> ORGANISM: Mycobacterium tuberculosis

<400> SEQUENCE: 36

```
gtgtgtggcg tgcgcgttgc gatcgtcgcc gagtcgttcc tcccgcaggt gaacggcgtc      60

agcaactcgg tggtcaaggt actcgaacat ctgcgtcgaa ccggtcatga agccctggtg     120

atcgcgcccg acacgccgcc aggtgaagac cgcgccgagc gacttcacga cggtgtccgg     180

gtgcaccggg tgccgtcgcg gatgttccca aaggtgacca cgttgccgct cggcgtgccc     240

accttccgaa tgctgagagc gctgcgcgga ttcgatccgg atgtcgtgca tctggcgtcg     300

ccggcgctgc ttggctacgg tggactccat gccgctcggc ggctaggggt gcccacggtc     360

gcggtctacc aaaccgatgt tccgggtttc gcgtccagct acggcattcc gatgacagca     420

cgggcggcgt gggcatggtt ccgccacttg catcgcctgg ctgaccgcac tctggcgccg     480

tccacagcga caatggaatc ccttattgcc cagggcattc cgcgagtaca ccggtgggca     540

cgcggggtgg acgtgcaacg tttcgcgccg tcggcgcgaa acgaggtgtt gaggcgacgg     600
```

```
tggtcaccgg acggcaaacc catcgtcggc tttgtgggtc ggcttgctcc ggagaagcat    660

gtcgaccggc tcacgggtct ggcggcctcc ggcgccgtgc ggctggtgat cgtcggcgac    720

ggcatcgacc gggcaagatt gcaatcagca atgcccacag cggttttcac cggagcacgg    780

tatggcaaag agctcgccga ggcgtatgcc agcatggacg tcttcgtaca ttccggtgag    840

cacgagacgt tctgccaagt cgtgcaggaa gcgctggcgt cggggctacc ggtgatcgct    900

ccggacgccg gcggaccgcg tgatctgata accccgcacc gcaccgggct gctgttgccg    960

gtcggcgagt tcgagcaccg gcttcctgac gccgtcgccc acctggtgca cgaacgccag   1020

cgctacgcgc tggccgcccg gcgcagtgtg ctgggccgca gttggccggt ggtctgcgat   1080

gagctgctcg gccactacga ggcggtgcga ggtcggcgca cgacccaggc cgcg         1134


<210> SEQ ID NO 37
<211> LENGTH: 330
<212> TYPE: PRT
<213> ORGANISM: Mycobacterium tuberculosis

<400> SEQUENCE: 37

Leu Pro Ala Ile Pro Phe Gln Gly Glu Ala Arg Ala Gly Arg Arg Pro
1               5                   10                  15

Gly Arg Pro Arg Arg Cys Pro Ala Gly Val Val Arg Cys Arg Pro Arg
            20                  25                  30

Ser Met Gly His Val Arg Pro Gly Phe Ser Pro Arg Leu Gly Ser His
        35                  40                  45

Arg Thr Leu Arg Pro Arg Trp Pro Pro Tyr Ala Ala Ala Ser Arg Gly
    50                  55                  60

Leu Thr Ser Gly Thr Ser Arg Trp Gly Trp Pro Arg Leu Gly Phe Gly
65                  70                  75                  80

Val Val Thr Ala Pro Thr Arg Trp Thr Leu Ala Asp Gly Arg Glu Leu
                85                  90                  95

Leu Phe Phe Ser Leu Pro Gly Pro Arg Thr Ser Gly Thr Ala Ala Glu
            100                 105                 110

Arg Val Ala Arg His Ala Gln Ala Gln Thr Phe Ala Gly Asp Ile Arg
        115                 120                 125

Gln Arg Ala Ile Gln Leu Val Val Ser Glu Gln Glu Val Ala Ser Lys
    130                 135                 140

Ile Thr Ala Ala Thr Ala Gly Ile Ala Thr Thr Thr Phe Pro Glu Thr
145                 150                 155                 160

Pro Ser Ile Asp Asp Thr Ile Ile Gly Asn Asp Asn Arg Asp Thr Gly
                165                 170                 175

Val Arg Leu Val Asp Val Lys Gln Asp Gly Gly Thr Ser Pro Pro Pro
            180                 185                 190

Pro Phe Ala Pro Trp Asp Thr Pro Asp Gly Thr Pro Pro Pro Gly Thr
        195                 200                 205

Gly Leu Ser Pro Thr Leu Gln Gln Met Ile Leu Gly Gly Asp Pro Ala
    210                 215                 220

Asn Leu Thr Gly Gln Gly Leu Ala Asp Asn Val Gln Arg Phe Val Gln
225                 230                 235                 240

Ser Leu Pro Ala Asn Asp Pro Asn Thr Ala Trp Leu Arg Gly Gln Val
                245                 250                 255

Ala Asp Leu Gln Ala His Val Ala Asp Ile Glu Tyr Ala Arg Thr His
            260                 265                 270

Cys Ser Thr Asn Asp Trp Ile Asp Arg Thr Ala Gln Phe Ala Ser Gly
        275                 280                 285
```

-continued

Ala Ile Val Phe Ser Ile Gly Val Leu Thr Ala Glu Thr Gly Ala Gly
    290                 295                 300

Val Val Ala Ala Ala Ala Gly Gly Val Gly Ala Ala Thr Ala Gly Val
305                 310                 315                 320

Ser Leu Leu Gln Cys Leu Val Gly Ser Lys
                325                 330

<210> SEQ ID NO 38
<211> LENGTH: 990
<212> TYPE: DNA
<213> ORGANISM: Mycobacterium tuberculosis

<400> SEQUENCE: 38
ttgccggcca ttccgtttca aggcgaagcg cgcgcaggac ggcgtccggg tcggccacgc 60
cgctgtccag caggcgtcgt gcgatgtcgt cctcgctcaa tgggccatgt tcggccagga 120
ttctcgccac ggcttgggtc gcatcgaacg cttcggccac ggtggccacc ttatgccgcg 180
gccagccgag gcttgacgtc gggcaccagc cgatggggct ggcctcgcct agggttcggc 240
gttgtgacgg cgccgacgcg gtggaccctg gccgacggac gtgagctgct gttcttttcg 300
ctgcccgggc cccgcaccag cggcaccgcc gcagaacggg tggctcgcca cgctcaagcg 360
caaacgttcg ccggcgatat ccgccagcgc gccatacagc tggtcgtgtc cgaacaagaa 420
gtggcaagca aaatcaccgc cgctaccgcc ggaatcgcca ccaccacctt cccggaaaca 480
cccagcatcg acgacaccat catcggcaac gacaaccgcg acactggggt ccggttggtc 540
gacgtcaaac aagatggcgg cactagtccc ccgcccccat ttgcgccgtg ggacacccct 600
gatggaacac cgccgccggg cactggccta agccctacgc tgcagcagat gatcctcggc 660
ggtgatccag ctaatctgac cggccagggt cttgcggaca acgtgcaacg gttcgtacag 720
tcgctgcccg caaacgaccc caacacagcg tggttgcgcg gtcaggttgc ggatctgcag 780
gcgcacgtcg ccgatattga gtacgcccgc acccattgca gcaccaacga ctggatcgac 840
cggaccgccc agttcgcctc gggcgccata gtcttcagca tcggcgtgtt gaccgcagag 900
accggggcgg gggtcgtggc tgccgcggcc ggtggtgtcg gcgcggccac ggcgggcgtg 960
agtcttctac aatgcctggt ggggagcaag 990

<210> SEQ ID NO 39
<211> LENGTH: 354
<212> TYPE: PRT
<213> ORGANISM: Mycobacterium tuberculosis

<400> SEQUENCE: 39

Met Ala Gly Asp Arg Gly Ala Asp Pro Gly Pro Ala Asn Val Thr Pro
1               5                   10                  15

Gly Ala Asp Asp His Ala Gln His Ala Ser Pro Thr Val Leu Cys Pro
            20                  25                  30

Gln Gly His Val Asn Ala Trp Asp Tyr Arg Phe Cys Glu Arg Cys Gly
        35                  40                  45

Ser Pro Ile Gly Val Val Pro Trp Pro Ser Glu Glu Ser Gly Thr Arg
    50                  55                  60

Gln Thr Ala Pro Ala Arg Ser Phe Val Pro Leu Val Val Leu Ala Ala
65                  70                  75                  80

Thr Leu Leu Val Val Ala Val Val Val Thr Ala Val Gly Tyr Ala Val
                85                  90                  95

Thr Arg Pro Ala Arg Asn Asp Arg Glu Glu Pro Ser Ser Ala Arg Gly
            100                 105                 110

```
Ala Ala Thr Thr Gly Val Pro Phe Ala Gln Ala Glu Ala Ala Ser Cys
        115                 120                 125

Pro Asp Asp Pro Val Leu Glu Ala Glu Ser Ile Asp Leu Thr Ser Asp
    130                 135                 140

Gly Leu Ala Val Ser Ala Ala Phe Met Ser Ala Cys Ala Gly Gly Asp
145                 150                 155                 160

Val Glu Ser Asn Ser Ala Leu Glu Val Thr Val Ala Asp Gly Arg Arg
                165                 170                 175

Asp Val Ala Ala Gly Ser Phe Asp Phe Ser Ala Asp Pro Leu Arg Ile
            180                 185                 190

Glu Pro Gly Val Pro Ala Arg Arg Thr Leu Val Phe Pro Pro Gly Met
        195                 200                 205

Tyr Trp Arg Thr Pro Asp Met Leu Ser Gly Ala Pro Ala Leu Ala Ala
    210                 215                 220

Thr Arg Lys Gly Arg Ser Asp Arg Ser Ala Ala Arg Gly Gly Ser Ala
225                 230                 235                 240

Arg Thr Thr Met Val Ala Ala Ala Ser Ala Ala Pro Ala Tyr Gly Ser
                245                 250                 255

Ile Asn Ala Val Ala Gly Ala Val Leu Val Glu Leu Arg Asp Ser Asp
            260                 265                 270

Phe Pro Tyr Val Arg Val Gly Ile Ala Asn Arg Trp Val Pro Gln Val
        275                 280                 285

Ser Ser Lys Arg Val Gly Leu Val Ala Ala Gly Lys Thr Trp Thr Ser
    290                 295                 300

Ala Asp Ile Leu Arg Asp His Leu Ala Leu Arg Gln Arg Phe Gly Gly
305                 310                 315                 320

Ala Arg Leu Val Trp Ser Gly His Trp Thr Thr Phe Ser Gly Pro Asp
                325                 330                 335

Phe Trp Val Thr Val Val Gly Pro Ala Gln Pro Thr Ala Ala Glu Ala
            340                 345                 350

Asn Arg
```

<210> SEQ ID NO 40
<211> LENGTH: 1062
<212> TYPE: DNA
<213> ORGANISM: Mycobacterium tuberculosis

<400> SEQUENCE: 40

```
atggcaggcg atcgaggcgc tgaccccggt ccggcgaatg tgactccggg tgcggatgac      60

catgcacagc atgcgtcgcc gacggtgcta tgtccccagg gtcacgtgaa cgcatgggac     120

tacaggttct gtgagcggtg cggctcgccg atcggcgtgg tgccctggcc gtcggaggaa     180

tcaggcacac gccagacggc gcccgcgcga tccttcgtcc ccctcgtcgt cctcgcggcg     240

acgctgctcg tggtcgccgt cgtcgtgacg gccgtcggct acgcggtgac gcgaccggct     300

cgcaacgacc gtgaggagcc cagttccgcg cggggcgccg ccacgacggg tgtgccgttc     360

gcacaggccg aggccgcgag ttgcccggac gatccggtgc ttgaagcgga gtcgatcgac     420

ctgacgtccg acgggcttgc ggtgagtgcc gcgttcatgt cggcatgcgc cggcggcgat     480

gtcgagtcga actcggcgct cgaggtcacc gtcgccgacg gacggcgcga cgtggcggcc     540

ggaagcttcg acttctcggc agatccgctg aggatcgagc ccggcgtgcc cgcccgtcga     600

accctggtct ttccgcccgg aatgtattgg cgaacgcccg acatgttgtc cggcgcaccg     660

gcattggcgg ccacacggaa gggcaggtcc gatcgttcgg ccgcacgagg cggatcggca     720

cggacgacca tggtcgcggc cgcgtccgcg gcaccggctt acggcagcat caacgccgtt     780
```

```
gccggggcgg tgctggtgga gctacgtgac tcggacttcc cctacgtgcg agtcggtatc    840

gccaatcgct gggtgccgca ggtgagttcg aagcgcgtcg gcctggtcgc cgcggggaaa    900

acgtggacga gcgccgatat tcttcgcgat cacctggccc tgcggcagcg gttcgggggc    960

gcccgcctgg tgtggtcggg gcactggacc accttcagcg gacccgattt ctgggtgacg   1020

gtggttgggc cggcgcagcc caccgcagct gaggccaatc gc                      1062
```

```
<210> SEQ ID NO 41
<211> LENGTH: 341
<212> TYPE: PRT
<213> ORGANISM: Mycobacterium tuberculosis

<400> SEQUENCE: 41

Met Thr Val Ser Arg Ser Ser Ser Ala Pro Ser Leu Ala Arg Arg Ala
1               5                   10                  15

Arg Arg Cys Thr Gly Ser Asp Asp Ala Ala Met Ser Phe Cys Val Tyr
            20                  25                  30

Cys Gly Ala Glu Leu Ala Asp Pro Thr Arg Cys Gly Ala Cys Gly Ala
        35                  40                  45

Tyr Lys Ile Gly Ser Thr Trp His Arg Thr Thr Thr Pro Thr Val Gly
    50                  55                  60

Ala Ala Thr Thr Ala Thr Gly Trp Arg Pro Asp Pro Thr Gly Arg His
65                  70                  75                  80

Glu Gly Arg Tyr Phe Val Ala Gly Gln Pro Thr Asp Leu Val Arg Glu
                85                  90                  95

Gly Asp Ala Glu Ala Val Asp Pro Leu Gly Gln Gln Gln Leu Asp Gln
            100                 105                 110

Ser Gly Ala Val Gly Val Ser Pro Ser Ala Val Ser Gly Trp Val Arg
        115                 120                 125

Ser Gly His Arg Arg Leu Trp Trp Ala Leu Ala Gly Val Val Ala Phe
    130                 135                 140

Leu Gly Leu Val Gly Ala Gly Val Val Gly Thr Leu Phe Leu Asn Arg
145                 150                 155                 160

Asp Arg Glu Ser Ile Asp Asp Lys Tyr Leu Ala Ala Leu Arg Arg Ser
                165                 170                 175

Gly Leu Thr Gly Glu Phe Asn Ser Asp Ala Asn Ala Ile Ala Arg Gly
            180                 185                 190

Lys Gln Val Cys Arg Gln Leu Gln Asp Gly Gly Glu Gln Gln Gly Met
        195                 200                 205

Pro Val Asp Gln Val Ala Val Gln Tyr Tyr Cys Pro Gln Phe Ser Asp
    210                 215                 220

Gly Phe His Ile Leu Glu Thr Ile Thr Val Thr Gly Ser Phe Thr Leu
225                 230                 235                 240

Lys Asp Glu Ser Pro Asn Val Tyr Ala Pro Ala Ile Thr Val Ser Gly
                245                 250                 255

Ser Gly Cys Ser Gly Ser Ala Gly Tyr Ala Asp Ile Asp Arg Gly Thr
            260                 265                 270

Gln Val Thr Val Lys Asn Gly Gln Gly Asp Ile Leu Ala Thr Ala Phe
        275                 280                 285

Leu Gln Ala Gly Gln Gly Gly Arg Phe Leu Cys Thr Phe Pro Phe Ser
    290                 295                 300

Phe Glu Ile Thr Glu Gly Glu Asp Arg Tyr Val Val Ser Val Ser Arg
305                 310                 315                 320

Arg Gly Glu Met Ser Tyr Ser Phe Ala Asp Leu Lys Ala Asn Gly Leu
```

-continued 325 330 335

Ser Leu Val Leu Gly
340

<210> SEQ ID NO 42
<211> LENGTH: 1023
<212> TYPE: DNA
<213> ORGANISM: Mycobacterium tuberculosis

<400> SEQUENCE: 42
atgactgttt cgcgaagttc atcagcaccc tcgttggcgc gaagggcacg acggtgtacc 60
ggaagtgacg acgctgccat gagtttctgc gtgtattgcg gtgccgagct tgccgacccg 120
accaggtgcg gggcgtgcgg cgcatacaag attggttcaa cctggcatcg gaccacgacg 180
ccgacggtcg gcgccgcgac gacggcaacg ggatggcgac ccgatcccac cggtcgccac 240
gagggacgct acttcgtcgc cgggcagccg accgacctcg ttcgcgaggg cgacgccgaa 300
gccgttgacc cacttggtca gcagcagctg gatcagtcag gtgccgttgg tgtttcgccg 360
tcagcggtgt cggggtgggt gcgttctggg caccgtcgac tgtggtgggc gcttgcgggc 420
gtggtggcgt ttctcgggct ggtgggagcc ggtgtcgtcg ggacgctgtt cctgaatcga 480
gaccgggagt ccatcgacga caagtacctc gccgccttga ggcggtccgg actcaccggt 540
gagttcaact ccgacgcgaa cgccatcgcc cgcggcaagc aggtgtgccg ccagttgcaa 600
gacggtggcg aacagcaggg gatgccggtc gatcaggtcg ccgtgcaata ctactgcccg 660
cagttcagcg atggcttcca tatcctggaa accataactg tcactggaag tttcaccctc 720
aaggatgaat cgccaaacgt gtacgcaccg gcgatcaccg tgtcgggctc cgggtgctca 780
gggtcagccg gctacgccga catcgaccgg ggaacgcagg tgacggtgaa aaacggtcag 840
ggggacatcc tggccacggc cttcctgcag gcgggtcagg gcggccgatt cttgtgcacc 900
ttccctttct cgtttgaaat caccgagggc gaagaccgct acgtcgtgtc ggtcagtcgt 960
cgaggcgaaa tgagttactc gttcgccgat ctgaaggcca atgggctatc gctcgtcttg 1020
ggc 1023

<210> SEQ ID NO 43
<211> LENGTH: 479
<212> TYPE: PRT
<213> ORGANISM: Mycobacterium tuberculosis

<400> SEQUENCE: 43

Val Thr Ala Ala Val Arg His Ser Asp Val Leu Val Val Gly Ala Gly
1 5 10 15

Ser Ala Gly Ser Val Val Ala Glu Arg Leu Ser Met Asp Ser Ser Cys
20 25 30

Val Val Thr Val Leu Glu Ala Gly Pro Gly Leu Ala Asp Pro Gly Leu
35 40 45

Leu Ala Gln Thr Ala Asn Gly Leu Gln Leu Pro Ile Gly Ala Gly Ser
50 55 60

Pro Leu Val Glu Arg Tyr Arg Thr Arg Leu Thr Asp Arg Pro Val Arg
65 70 75 80

His Leu Pro Ile Val Arg Gly Ala Thr Val Gly Gly Ser Gly Ala Ile
85 90 95

Asn Gly Gly Tyr Phe Cys Arg Gly Leu Pro Ser Asp Phe Asp Arg Ala
100 105 110

Ser Ile Pro Gly Trp Ala Trp Ser Asp Val Leu Glu His Phe Arg Ala
115 120 125

```
Ile Glu Thr Asp Leu Asp Phe Glu Thr Pro Val His Gly Arg Ser Gly
    130                 135                 140

Pro Ile Pro Val Arg Arg Thr His Glu Met Thr Gly Ile Thr Glu Ser
145                 150                 155                 160

Phe Met Ala Ala Ala Glu Asp Ala Gly Phe Ala Trp Ile Ala Asp Leu
                165                 170                 175

Asn Asp Val Gly Pro Glu Met Pro Ser Gly Val Gly Ala Val Pro Leu
            180                 185                 190

Asn Ile Val Asn Gly Val Arg Thr Ser Ser Ala Val Gly Tyr Leu Met
        195                 200                 205

Pro Ala Leu Gly Arg Pro Asn Leu Thr Leu Leu Ala Arg Thr Arg Ala
    210                 215                 220

Val Arg Leu Arg Phe Ser Ala Thr Thr Ala Val Gly Val Asp Ala Ile
225                 230                 235                 240

Gly Pro Gly Gly Pro Val Ser Leu Ser Ala Asp Arg Ile Val Leu Cys
                245                 250                 255

Ala Gly Ala Ile Gln Ser Ala His Leu Leu Met Leu Ser Gly Val Gly
            260                 265                 270

Glu Glu Glu Val Leu Arg Ser Ala Gly Val Lys Val Leu Met Ala Leu
        275                 280                 285

Pro Val Gly Met Gly Cys Ser Asp His Pro Glu Trp Val Met Pro Thr
    290                 295                 300

Asn Trp Ala Val Ala Val Asp Arg Pro Val Leu Glu Val Leu Leu Ser
305                 310                 315                 320

Thr His Asp Gly Ile Glu Ile Arg Pro Tyr Thr Gly Gly Phe Val Ala
                325                 330                 335

Met Thr Gly Asp Gly Thr Ala Gly His Arg Asp Trp Pro His Ile Gly
            340                 345                 350

Val Ala Leu Met Gln Pro Arg Ala Arg Gly Arg Ile Thr Leu Val Ser
        355                 360                 365

Ser Asp Pro Gln Ile Pro Val Arg Ile Glu His Arg Tyr Asp Ser Glu
    370                 375                 380

Pro Ala Asp Val Ala Ala Leu Arg Gln Gly Ser Ala Leu Ala His Glu
385                 390                 395                 400

Leu Cys Gly Ala Ala Thr Arg Ile Gly Pro Ala Val Trp Ala Thr Ser
                405                 410                 415

Gln His Leu Cys Gly Ser Ala Pro Met Gly Thr Asp Asp Asp Pro Arg
            420                 425                 430

Ala Val Val Asp Pro Arg Cys Arg Val Arg Gly Ile Glu Asn Leu Trp
        435                 440                 445

Val Ile Asp Gly Ser Val Leu Pro Ser Ile Thr Ser Arg Gly Pro His
    450                 455                 460

Ala Thr Ile Val Met Leu Gly His Arg Ala Ala Glu Phe Val Gln
465                 470                 475
```

<210> SEQ ID NO 44
<211> LENGTH: 1437
<212> TYPE: DNA
<213> ORGANISM: Mycobacterium tuberculosis

<400> SEQUENCE: 44

```
gtgactgcgg cggtccggca tagcgatgtg ctggtcgtcg gtgctggaag tgctggatcg      60

gttgttgccg agcgtctttc catggactcg agctgtgtgg tgaccgtgct tgaggctggc     120

cccgggctgg ccgatccggg gttgctggct cagacggcca atgggttgca actgccgatc     180
```

ggagctggca gccctctggt tgagcgttat cggacgcggc tcaccgatcg accggttcgc 240
cacttgccga tcgtgcgggg tgcgacggtc ggcggttccg gcgcaatcaa cggcggctat 300
ttctgccgcg gactgcccag cgatttcgac cgtgcctcga taccaggctg ggcatggtct 360
gacgttctgg agcacttccg ggctatcgag acagatctgg atttcgagac gcctgtgcat 420
ggccgtagtg gccccatccc agttcgccgc acacacgaaa tgactggcat cactgaaagt 480
ttcatggctg ccgcagagga cgcagggttc gcttggatcg ctgacctcaa cgatgttggg 540
ccggaaatgc cttcgggtgt aggcgcggtc ccgctcaaca tcgttaacgg cgtacgcacc 600
agctcggcgg tcggctatct gatgcccgcg ctgggacggc cgaatctgac actgctggcc 660
cggacgcggg cggtgcggtt gcgcttttcc gccaccaccg cggtgggtgt cgacgcgatc 720
ggcccaggag gcccggtaag cctgagcgct gaccgaatcg tattgtgcgc cggagcgatt 780
cagtcagctc atctgttgat gctctcgggc gtcggcgagg aggaggtgtt gcgatccgcc 840
ggtgtgaagg tgcttatggc gttgccggtt ggcatgggct gcagtgacca cccggaatgg 900
gtgatgccga ccaactgggc ggtggctgtc gatcggccgg tgttagaggt gctgctgagc 960
actcatgacg gcatcgaaat aaggccgtac acaggcggct tcgttgcgat gaccggcgac 1020
ggtacagccg ggcatcgcga ttggccgcat atcggggtgg cgctcatgca gccgcgggca 1080
cgcggacgca tcacgttggt ctcgagtgat ccccagatac cagtccgcat cgagcaccga 1140
tacgacagtg aacctgccga tgtcgcggcc ctgcgccagg gtagcgcatt ggcccacgaa 1200
ttatgcggtg cggcaacgcg catcggtcca gccgtatggg cgacatcgca gcatctgtgt 1260
ggtagtgccc caatgggcac cgacgatgac ccacgagccg tcgtcgaccc gaggtgtcgg 1320
gtccgcggca tcgaaaacct atgggtgata gacggatctg tccttccgtc gatcaccagt 1380
cgcggtccac acgcaacgat cgtaatgctg ggccaccgcg cggccgaatt tgttcag 1437

<210> SEQ ID NO 45
<211> LENGTH: 203
<212> TYPE: PRT
<213> ORGANISM: Mycobacterium tuberculosis

<400> SEQUENCE: 45

Leu Gly Arg Arg Gly Asn Arg Arg Val His Val Asp Arg Val Arg Leu
1 5 10 15

Thr Gly Thr Glu Arg Glu Leu Arg Ala Glu Asn Gln Ser Pro Pro Ile
20 25 30

Phe Arg Pro Gln Asn Thr Leu Gly Asp Gly Ala Asn Gly Leu Pro Leu
35 40 45

Ala Val Cys Thr Thr Thr Ala His Thr Cys His Thr Ser His Thr His
50 55 60

Pro Ser Arg Trp Thr Pro Asn Pro Val Pro Ala Thr Lys Gly Val Pro
65 70 75 80

Ala Gly Leu Val Gln Ala Thr Phe Ile Ile Glu Asn Leu Asp Pro Gly
85 90 95

Asn Asn Asp Thr Pro Thr Pro Pro Thr Pro Lys Leu Arg Leu Ala Arg
100 105 110

Lys Pro Gly His His Arg Arg Ser Glu Tyr Asp Ala Asp Ser Val Leu
115 120 125

Arg Arg Lys Asp Thr Ser Arg Arg Cys Val Gln Ala Asp Asp Val Arg
130 135 140

Cys Val Gln Leu Val Gln Asp Pro Arg Arg Gly Arg Val Glu Leu Gly
145 150 155 160

-continued

```
Gly Tyr Arg Ala Glu Leu Thr Val Gly Arg Arg Ala Ala Val Asn Cys
                165                 170                 175

Gln Arg Pro Gln Tyr Gly Ala Asp Gly Trp Pro Val Arg Leu Gly Cys
            180                 185                 190

Gly Val Gly Gly Ala Ala Arg Gly Asp Gln Arg
        195                 200


<210> SEQ ID NO 46
<211> LENGTH: 609
<212> TYPE: DNA
<213> ORGANISM: Mycobacterium tuberculosis

<400> SEQUENCE: 46

ttgggtcgca ggggtaaccg aagggtgcac gttgaccgcg tgaggctaac cggcaccgag      60

cgtgaactga gggcggagaa tcagagcccc ccgattttcc gcccgcagaa cacgttgggc     120

gacggcgcca acgggctgcc actggccgtg tgcaccacga cggctcacac gtgccacact     180

tcccatactc acccatcgcg gtggacccca aacccagtgc cggccaccaa gggcgtcccc     240

gctggattgg tgcaagcaac cttcatcatc gaaaaccttg accccggcaa caacgacacg     300

ccgacccccc ctacacccaa actgcgatta gcccgaaaac ctgggcacca taggcgatct     360

gaatacgatg cggattcggt gctgcggaga aaggatacat cgcgccgatg cgtccaggcg     420

gatgacgtcc gatgcgtgca gctggtccag gatccgcggc gcggacgtgt cgaactcggt     480

ggttaccgcg ccgagcttac tgttggccga cgggcggcgg tgaattgcca acgcccgcaa     540

tatggtgcgg atggatggcc cgttcggttg ggttgcgggg taggcggcgc cgcgcgaggc     600

gatcagcgc                                                             609


<210> SEQ ID NO 47
<211> LENGTH: 250
<212> TYPE: PRT
<213> ORGANISM: Mycobacterium tuberculosis

<400> SEQUENCE: 47

Met Thr Met Pro Leu Arg Gly Leu Gly Pro Pro Asp Asp Thr Gly Val
1               5                   10                  15

Arg Glu Val Ser Thr Gly Asp Asp His His Tyr Ala Met Trp Asp Ala
            20                  25                  30

Ala Tyr Val Leu Gly Ala Leu Ser Ala Ala Asp Arg Arg Glu Phe Glu
        35                  40                  45

Ala His Leu Ala Gly Cys Pro Glu Cys Arg Gly Ala Val Thr Glu Leu
    50                  55                  60

Cys Gly Val Pro Ala Leu Leu Ser Gln Leu Asp Arg Asp Glu Val Ala
65                  70                  75                  80

Ala Ile Ser Glu Ser Ala Pro Thr Val Val Ala Ser Gly Leu Ser Pro
                85                  90                  95

Glu Leu Leu Pro Ser Leu Leu Ala Ala Val His Arg Arg Arg Arg Arg
            100                 105                 110

Thr Arg Leu Ile Thr Trp Val Ala Ser Ser Ala Ala Ala Ala Val Leu
        115                 120                 125

Ala Ile Gly Val Leu Val Gly Val Gln Gly His Ser Ala Ala Pro Gln
    130                 135                 140

Arg Ala Ala Val Ser Ala Leu Pro Met Ala Gln Val Gly Thr Gln Leu
145                 150                 155                 160

Leu Ala Ser Thr Val Ser Ile Ser Gly Glu Pro Trp Gly Thr Phe Ile
                165                 170                 175
```

Asn Leu Arg Cys Val Cys Leu Ala Pro Pro Tyr Ala Ser His Asp Thr
180 185 190

Leu Ala Met Val Val Val Gly Arg Asp Gly Ser Gln Thr Arg Leu Ala
195 200 205

Thr Trp Leu Ala Glu Pro Gly His Thr Ala Thr Pro Ala Gly Ser Ile
210 215 220

Ser Thr Pro Val Asp Gln Ile Ala Ala Val Gln Val Val Ala Ala Asp
225 230 235 240

Thr Gly Gln Val Leu Leu Gln Arg Ser Leu
245 250

<210> SEQ ID NO 48
<211> LENGTH: 750
<212> TYPE: DNA
<213> ORGANISM: Mycobacterium tuberculosis

<400> SEQUENCE: 48
atgacgatgc cgctacgagg acttggcccg cccgatgaca ccggtgtgcg cgaggtgtcg 60
acgggtgatg atcaccacta cgcgatgtgg gatgcagctt acgtgttggg agcattgtct 120
gcggccgacc gccgcgaatt cgaagcgcac ctggccggtt gccccgaatg ccggggggcc 180
gtcaccgaac tctgcggggt gcccgccctg ctgtcccagc tcgatcgtga cgaagtggcc 240
gcgattagcg aatccgcccc gactgtggtg gcttcggggc tgtcgccgga gttgttgccg 300
tcgttgctgg cggcggtgca caggcgtcgg cgccgtaccc ggctgatcac ctgggtggcc 360
tcgtccgccg ctgccgcggt gctggcgatc ggtgtgctag tcggtgtgca gggccactcc 420
gcggcaccgc agcgggcggc cgtgtcggcg ctgccgatgg cccaggtcgg cacgcagctg 480
ttggcgtcca cggtgtcgat cagcggcgag ccttggggga cgttcatcaa cctgcggtgc 540
gtctgcctgg cgccgccgta tgcttcccac gacacgctgg ccatggttgt ggtgggtcgt 600
gacggcagcc agacacggct ggcgacttgg ttggccgaac ccggtcacac cgcgacaccc 660
gccggcagca tttcgacacc ggttgaccag atcgccgccg tgcaagtggt tgccgccgat 720
accggccagg ttctgctgca gcgttcgctc 750

<210> SEQ ID NO 49
<211> LENGTH: 294
<212> TYPE: PRT
<213> ORGANISM: Mycobacterium tuberculosis

<400> SEQUENCE: 49

Met Thr Thr Ile Ala Phe Leu Gly Leu Gly Asn Met Gly Ala Pro Met
1 5 10 15

Ser Ala Asn Leu Val Gly Ala Gly His Val Val Arg Gly Phe Asp Pro
20 25 30

Ala Pro Thr Ala Ala Ser Gly Ala Ala Ala His Gly Val Ala Val Phe
35 40 45

Arg Ser Ala Pro Glu Ala Val Ala Glu Ala Asp Val Val Ile Thr Met
50 55 60

Leu Pro Thr Gly Glu Val Val Arg Arg Cys Tyr Thr Asp Val Leu Ala
65 70 75 80

Ala Ala Arg Pro Ala Thr Leu Phe Ile Asp Ser Ser Thr Ile Ser Val
85 90 95

Thr Asp Ala Arg Glu Val His Ala Leu Ala Glu Ser His Gly Met Leu
100 105 110

Gln Leu Asp Ala Pro Val Ser Gly Gly Val Lys Gly Ala Ala Ala Ala

```
        115                 120                 125

Thr Leu Ala Phe Met Val Gly Gly Asp Glu Ser Thr Leu Arg Arg Ala
    130                 135                 140

Arg Pro Val Leu Glu Pro Met Ala Gly Lys Ile Ile His Cys Gly Ala
145                 150                 155                 160

Ala Gly Ala Gly Gln Ala Ala Lys Val Cys Asn Asn Met Val Leu Ala
                165                 170                 175

Val Gln Gln Ile Ala Ile Ala Glu Ala Phe Val Leu Ala Glu Lys Leu
            180                 185                 190

Gly Leu Ser Ala Gln Ser Leu Phe Asp Val Ile Thr Gly Ala Thr Gly
        195                 200                 205

Asn Cys Trp Ala Val His Thr Asn Cys Pro Val Pro Gly Pro Val Pro
    210                 215                 220

Thr Ser Pro Ala Asn Asn Asp Phe Lys Pro Gly Phe Ser Thr Ala Leu
225                 230                 235                 240

Met Asn Lys Asp Leu Gly Leu Ala Met Asp Ala Val Ala Ala Thr Gly
                245                 250                 255

Ala Thr Ala Pro Leu Gly Ser His Ala Ala Asp Ile Tyr Ala Lys Phe
            260                 265                 270

Ala Ala Asp His Ala Asp Leu Asp Phe Ser Ala Val Ile His Thr Leu
        275                 280                 285

Arg Ala Arg Ala Asp Ala
    290
```

<210> SEQ ID NO 50
<211> LENGTH: 882
<212> TYPE: DNA
<213> ORGANISM: Mycobacterium tuberculosis

<400> SEQUENCE: 50

```
atgacgacca tcgccttcct aggtttgggc aacatgggtg cgccgatgtc ggcgaatctg      60

gttggtgcgg gccacgtcgt gcgtggattc gacccggcac ccacggcggc gtccggcgcc     120

gccgcgcacg gtgtcgcggt gtttcgtagc gcgcccgaag cggtggccga ggccgacgtg     180

gtcatcacca tgctgcccac cggcgaggtg gtccggcgct gctacaccga cgtgctggcc     240

gccgcgcgtc cggcaacgct gttcatcgac agctccacga tctcggtcac cgatgcccgt     300

gaggtgcacg cgctggccga atcgcacggc atgctccaac tggatgcgcc ggtctccggc     360

ggggtgaagg gcgccgccgc cgcgacgctg gcattcatgg tcggcggcga cgagtccacg     420

ctacggcggg cacgcccggt actagagccc atggcgggca agatcattca ctgcggcgcc     480

gccggtgccg gacaggccgc caaggtgtgc aacaacatgg tgctggcggt gcagcagatc     540

gcgatcgccg aggcgttcgt gctggccgag aagctcgggc tgtccgcaca atcgttgttc     600

gacgtcatca ccggcgcgac cggcaattgc tgggcggtgc acaccaattg cccggtgccg     660

ggcccggtgc ccacctcacc ggccaacaac gacttcaagc ccgggttttc gaccgcgttg     720

atgaacaagg acctgggcct ggcgatggat gcggtggccg ccaccggtgc gacggccccg     780

ctgggcagcc acgccgccga catctacgcc aaattcgccg ccgaccacgc cgacctggac     840

ttcagcgcgg tgatccacac gttgcgcgcg cgagcagacg ca                        882
```

<210> SEQ ID NO 51
<211> LENGTH: 207
<212> TYPE: PRT
<213> ORGANISM: Mycobacterium tuberculosis

<400> SEQUENCE: 51

```
Met Gly Val Thr Ala Ala Val Thr Pro Lys Gly Glu Arg Arg Arg Tyr
1               5                   10                  15

Ala Leu Val Ser Ala Ala Ala Glu Leu Leu Gly Glu Gly Gly Phe Glu
            20                  25                  30

Ala Val Arg His Arg Ala Val Ala Arg Arg Ala Gly Leu Pro Leu Ala
        35                  40                  45

Ser Thr Thr Tyr Tyr Phe Ser Ser Leu Asp Asp Leu Ile Ala Arg Ala
    50                  55                  60

Val Glu His Ile Gly Met Ile Glu Val Ala Gln Leu Arg Ala Arg Val
65                  70                  75                  80

Ser Ala Leu Ser Arg Arg Arg Arg Gly Pro Glu Thr Thr Ala Val Val
                85                  90                  95

Leu Val Asp Leu Leu Val Gly Glu Met Ser Ser Pro Gly Leu Ala Glu
            100                 105                 110

Gln Leu Ile Ser Arg Tyr Glu Arg His Ile Ala Cys Thr Arg Leu Pro
        115                 120                 125

Asp Leu Arg Glu Ser Met Arg Arg Ser Leu Arg Gln Arg Ala Glu Ala
    130                 135                 140

Val Ala Glu Ala Ile Glu Arg Ser Gly Arg Ser Ala Gln Ile Glu Leu
145                 150                 155                 160

Val Cys Thr Leu Ile Cys Ala Val Asp Gly Ser Val Val Ser Ala Leu
                165                 170                 175

Val Glu Gly Arg Asp Pro Arg Ala Ala Ala Leu Ala Thr Val Val Asp
            180                 185                 190

Leu Ile Asp Val Leu Ala Pro Val Asp Gln Arg Pro Val Pro Phe
        195                 200                 205
```

<210> SEQ ID NO 52
<211> LENGTH: 621
<212> TYPE: DNA
<213> ORGANISM: Mycobacterium tuberculosis

<400> SEQUENCE: 52

```
atgggcgtga cagcagcggt cactccaaaa ggagaacgtc ggcggtatgc gttggtcagc      60

gccgccgcgg agctgctcgg cgagggcggg ttcgaggcgg tacgccaccg ggcggtggcg     120

cggcgggccg gtttgccgtt ggcgtctacc acctactact tctcgtcgct cgacgatttg     180

atcgctcgcg cggtcgaaca catcggaatg atcgaggtgg ctcagctgcg agcccgggtc     240

agtgcgctgt cccggcgacg tcgggggccc gagaccaccg ccgttgtgct ggttgacctg     300

ctggtggggg aaatgtccag tccggggctt gccgagcagc tgatctcacg atacgagcgc     360

catatcgcct gtacccgcct gcctgacctg cgcgaaagca tgcgccgcag cctgcgtcag     420

cgcgctgagg ccgtggccga ggccatcgag cgctccggcc gctccgcaca gatcgaactg     480

gtgtgtacgt tgatctgtgc ggtcgacgga tcggtggtct cggcgctggt cgaagggcgg     540

gacccgcgtg ccgctgcgct ggcgacggtg gtcgacctca tcgacgtgct cgcgcccgtc     600

gaccagcgtc cggtgccgtt c                                               621
```

<210> SEQ ID NO 53
<211> LENGTH: 259
<212> TYPE: PRT
<213> ORGANISM: Mycobacterium tuberculosis

<400> SEQUENCE: 53

```
Met Tyr Phe Val Gly Val Asp Leu Ala Trp Ala Gly Arg Asn Pro Thr
1               5                   10                  15
```

Gly Val Ala Ala Val Asp Ala Asp Gly Cys Leu Val Gly Val Gly Ala
            20                  25                  30

Ala Arg Asp Asp Ala Ser Val Leu Ala Ala Leu Arg Pro Tyr Val Val
        35                  40                  45

Gly Asp Cys Leu Val Ala Phe Asp Ala Pro Leu Val Val Ala Asn Arg
    50                  55                  60

Thr Gly Gln Arg Pro Ala Glu Ala Ala Leu Asn Arg Asp Phe Arg Gln
65                  70                  75                  80

Phe Glu Ala Gly Ala Tyr Pro Ala Asn Thr Glu Lys Pro Glu Phe Ala
                85                  90                  95

Asp Val Pro Arg Ala Ala Arg Leu Ala Arg Gln Leu Ala Leu Asp Met
            100                 105                 110

Asp Pro Leu Ser Ser Ala Thr Arg Arg Ala Ile Glu Val Tyr Pro His
        115                 120                 125

Pro Ala Thr Val Ala Leu Phe Arg Leu Pro Arg Ala Leu Lys Tyr Lys
    130                 135                 140

Ala Lys Pro Gly Arg Ser Val Asp Leu Leu Lys Ser Glu Leu Leu Arg
145                 150                 155                 160

Leu Met Asp Gly Val Glu Gly Leu Ala Gln Ala Gly Val Arg Met Gln
                165                 170                 175

Val Ala Gly Gln Pro Asp Trp Val Ser Leu Arg Arg Gln Val Thr Val
            180                 185                 190

Ala Gln Arg Lys Ser Asp Leu Arg Ala Ala Glu Asp Pro Ile Asp Ala
        195                 200                 205

Val Val Cys Ala Tyr Val Ala Leu Tyr Ala Gln Arg Arg Pro Ala Asp
    210                 215                 220

Val Thr Ile Tyr Gly Asp Phe Thr Thr Gly Tyr Ile Val Thr Pro Ser
225                 230                 235                 240

Leu Pro Thr Asp Phe Arg Thr Ala Pro Asp Ala Gly Arg Arg Ala Arg
                245                 250                 255

Ala Arg Arg

<210> SEQ ID NO 54
<211> LENGTH: 777
<212> TYPE: DNA
<213> ORGANISM: Mycobacterium tuberculosis

<400> SEQUENCE: 54
atgtacttcg tcggcgtgga cctcgcctgg gccggccgca atccgaccgg tgtcgcggct 60
gtcgacgcgg acgggtgtct ggtgggggtc ggtgccgctc gcgacgatgc ctccgtgctg 120
gcggcgctgc ggccctacgt tgtgggcgat tgcctggtcg ccttcgacgc gccgctggtg 180
gtggccaacc gcaccggcca gcggccggcg gaggccgcac tgaatcgaga cttccgacaa 240
ttcgaggccg gcgcgtatcc ggccaacacc gaaaagcccg agtttgccga cgttccacgc 300
gccgcccggc tggcccgcca actggcgctg gatatggatc ctctttcgtc cgccacgcgg 360
cgggccatcg aggtctatcc gcacccggct acggtggcgc tgtttcggct accccgcgcg 420
ctgaagtaca aggccaagcc gggacgcagc gttgacctgc tcaaatcgga gctattgcga 480
ctgatggacg gcgtcgaggg gctcgcccag gccggggttc ggatgcaggt agccggtcag 540
ccggattggg tctcgttgcg ccggcaggtg acggtcgcgc agcgaaaaag cgacctgcgg 600
gccgccgagg atccgatcga cgccgtcgta tgcgcctacg tggcgttgta cgcccaacgc 660
cggcccgccg atgtcacgat ctatggggac ttcaccaccg ggtacattgt cacgccgtcg 720

-continued ctgcccaccg acttcagaac ggcaccggac gctggtcgac gggcgcgagc acgtcga 777

<210> SEQ ID NO 55
<211> LENGTH: 566
<212> TYPE: PRT
<213> ORGANISM: Mycobacterium tuberculosis

<400> SEQUENCE: 55

Val Ala Leu Thr Cys Thr Asp Met Ser Asp Ala Val Ala Gly Ser Asp
1 5 10 15

Ala Glu Gly Leu Thr Ala Asp Ala Ile Val Val Gly Ala Gly Leu Ala
20 25 30

Gly Leu Val Ala Ala Cys Glu Leu Ala Asp Arg Gly Leu Arg Val Leu
35 40 45

Ile Leu Asp Gln Glu Asn Arg Ala Asn Val Gly Gly Gln Ala Phe Trp
50 55 60

Ser Phe Gly Gly Leu Phe Leu Val Asn Ser Pro Glu Gln Arg Arg Leu
65 70 75 80

Gly Ile Arg Asp Ser His Glu Leu Ala Leu Gln Asp Trp Leu Gly Thr
85 90 95

Ala Ala Phe Asp Arg Pro Glu Asp Tyr Trp Pro Glu Gln Trp Ala His
100 105 110

Ala Tyr Val Asp Phe Ala Ala Gly Glu Lys Arg Ser Trp Leu Arg Ala
115 120 125

Arg Gly Leu Lys Ile Phe Pro Leu Val Gly Trp Ala Glu Arg Gly Gly
130 135 140

Tyr Asp Ala Gln Gly His Gly Asn Ser Val Pro Arg Phe His Ile Thr
145 150 155 160

Trp Gly Thr Gly Pro Ala Leu Val Asp Ile Phe Val Arg Gln Leu Arg
165 170 175

Asp Arg Pro Thr Val Arg Phe Ala His Arg His Gln Val Asp Lys Leu
180 185 190

Ile Val Glu Gly Asn Ala Val Thr Gly Val Arg Gly Thr Val Leu Glu
195 200 205

Pro Ser Asp Glu Pro Arg Gly Ala Pro Ser Ser Arg Lys Ser Val Gly
210 215 220

Lys Phe Glu Phe Arg Ala Ser Ala Val Ile Val Ala Ser Gly Gly Ile
225 230 235 240

Gly Gly Asn His Glu Leu Val Arg Lys Asn Trp Pro Arg Arg Met Gly
245 250 255

Arg Ile Pro Lys Gln Leu Leu Ser Gly Val Pro Ala His Val Asp Gly
260 265 270

Arg Met Ile Gly Ile Ala Gln Lys Ala Gly Ala Ala Val Ile Asn Pro
275 280 285

Asp Arg Met Trp His Tyr Thr Glu Gly Ile Thr Asn Tyr Asp Pro Ile
290 295 300

Trp Pro Arg His Gly Ile Arg Ile Ile Pro Gly Pro Ser Ser Leu Trp
305 310 315 320

Leu Asp Ala Ala Gly Lys Arg Leu Pro Val Pro Leu Phe Pro Gly Phe
325 330 335

Asp Thr Leu Gly Thr Leu Glu Tyr Ile Thr Lys Ser Gly His Asp Tyr
340 345 350

Thr Trp Phe Val Leu Asn Ala Lys Ile Ile Glu Lys Glu Phe Ala Leu
355 360 365

Ser Gly Gln Glu Gln Asn Pro Asp Leu Thr Gly Arg Arg Leu Gly Gln

-continued

```
    370                 375                 380

Leu Leu Arg Ser Arg Ala His Ala Gly Pro Pro Gly Pro Val Gln Ala
385                 390                 395                 400

Phe Ile Asp Arg Gly Val Asp Cys Val His Ala Asn Ser Leu Arg Glu
                405                 410                 415

Leu Val Ala Ala Met Asn Glu Leu Pro Asp Val Val Pro Leu Asp Tyr
            420                 425                 430

Glu Thr Val Ala Ala Ala Val Thr Ala Arg Asp Arg Glu Val Val Asn
        435                 440                 445

Lys Tyr Ser Lys Asp Gly Gln Ile Thr Ala Ile Arg Ala Ala Arg Arg
    450                 455                 460

Tyr Arg Gly Asp Arg Phe Gly Arg Val Val Ala Pro His Arg Leu Thr
465                 470                 475                 480

Asp Pro Lys Ala Gly Pro Leu Ile Ala Val Lys Leu His Ile Leu Thr
                485                 490                 495

Arg Lys Thr Leu Gly Gly Ile Glu Thr Asp Leu Asp Ala Arg Val Leu
            500                 505                 510

Lys Ala Asp Gly Thr Pro Leu Ala Gly Leu Tyr Ala Ala Gly Glu Val
        515                 520                 525

Ala Gly Phe Gly Gly Gly Gly Val His Gly Tyr Arg Ala Leu Glu Gly
    530                 535                 540

Thr Phe Leu Gly Gly Cys Ile Phe Ser Gly Arg Ala Ala Gly Arg Gly
545                 550                 555                 560

Ala Ala Glu Asp Ile Arg
                565


<210> SEQ ID NO 56
<211> LENGTH: 1698
<212> TYPE: DNA
<213> ORGANISM: Mycobacterium tuberculosis

<400> SEQUENCE: 56

gtggcgttaa cctgtaccga catgagcgat gctgtagccg gttcagatgc cgaggggctc      60

accgctgatg ccattgtcgt gggagccgga ttagcgggcc tggtagccgc ttgtgagttg     120

gccgaccgcg gcctacgggt gctgatcctc gaccaggaga atcgggccaa cgtgggcggg     180

caggccttct ggtcgttcgg cggtttgttc ttggtcaaca gtcccgagca gcgccgcttg     240

ggcatccgtg atagccatga gcttgctctg caggattggc tggggacggc ggcgttcgac     300

cggcccgagg actactggcc cgaacaatgg gcgcatgctt acgtcgattt cgcggcgggg     360

gagaagcgca gctggctgcg ggcccgcggg ctgaagatct ttccgctggt gggctgggcc     420

gagcgtggtg gttacgacgc gcaggggcac ggcaactcgg tgccccgttt ccacatcacc     480

tggggtactg ggccggctct ggtcgacata ttcgtgcgtc agctgcgtga tcgcccccacg    540

gtgcgctttg cgcaccgcca ccaggtcgac aaactgatcg tcgagggtaa cgcggtgaca     600

ggcgttcggg gtaccgtgct ggagccctcg gatgagccgc gcggcgcgcc ttcgtcgcga     660

aagtctgtgg ggaaattcga gtttcgcgcg tcagcggtga tcgtcgccag tggtggtatc     720

ggtggcaatc atgagctggt gcgcaaaaac tggccgagac ggatgggccg cattcccaag     780

caactgttga gcggggtgcc cgcgcacgtt gatggcagga tgatcggcat cgctcaaaag     840

gccggggctg cggtgatcaa tccggaccgg atgtggcatt acaccgaagg cattaccaac     900

tacgacccga tctggccgcg gcacggtatc cggattattc cggggccgtc gtcgctatgg     960

ctggatgccg cgggcaagcg gttgccggta ccgttgtttc ccgggttcga caccctcggc    1020
```

```
acattggagt acatcaccaa gtctggacat gactacacct ggttcgtgtt gaatgccaag   1080

ataatcgaga aggaattcgc gctgtccggt caggagcaga accctgactt gaccggtcgg   1140

cgcctgggcc agctgttgcg ctctcgggct cacgccggcc cgcccggacc ggtgcaggca   1200

ttcatcgatc gtggtgtgga ctgcgtccac gcgaactcgt tgcgcgagtt ggtggccgcg   1260

atgaacgagt tgcccgatgt ggtgccgctg gactacgaga cggtggcagc cgcggtcact   1320

gcgcgcgatc gtgaggtggt caataagtac agcaaggatg gacagatcac cgcgattcgt   1380

gccgctcgcc gctaccgagg cgaccgattt ggccgggtgg tggcgccaca tcggttgacc   1440

gatccgaagg ccgggccgct gatcgcggtc aagctgcaca tcctgactcg aaagacgttg   1500

ggtggcatcg aaactgactt agatgctcgg gtgctcaagg ccgacggtac gccactggcc   1560

gggttgtatg cagccggcga ggtcgccggg ttcggcgggg gcggtgtcca tggctaccgg   1620

gccttggagg gcaccttcct gggtggatgc atattttccg gccgcgctgc cggccgcggg   1680

gccgccgagg atatccgc                                                  1698


<210> SEQ ID NO 57
<211> LENGTH: 242
<212> TYPE: PRT
<213> ORGANISM: Mycobacterium tuberculosis

<400> SEQUENCE: 57

Met Thr Leu Ala Asn Asn Gly Thr Gly Met Asp His Phe Leu Thr Pro
1               5                   10                  15

Thr Glu Tyr Leu Asp Ala Gly His Pro Leu Val Arg Thr Thr Ala Ala
            20                  25                  30

Thr Leu Ile Arg Asp Ala Val Ser Asp Thr Glu Arg Val Arg Arg Ile
        35                  40                  45

Tyr Tyr Tyr Val Arg Asp Val Pro Tyr Asp Val Leu Ala Ser Phe Arg
    50                  55                  60

Tyr Leu Ala Gln Gly His His Arg Ala Ser Asp Val Ile Gly His Gly
65                  70                  75                  80

Val Ala Phe Cys Met Gly Lys Ala Ser Ser Phe Val Ala Leu Cys Arg
                85                  90                  95

Ala Ala Gly Val Pro Ala Arg Ile Ala Phe Gln Thr Ile Asp Ala Pro
            100                 105                 110

Asp Lys Glu Phe Leu Ser Pro Gln Val Arg Ala Leu Trp Gly Gly Arg
        115                 120                 125

Thr Gly Arg Pro Phe Pro Trp His Ser Leu Gly Glu Ala Tyr Leu Gly
    130                 135                 140

Arg Arg Trp Val Lys Leu Asp Ala Thr Ile Asp Ala Pro Thr Ala Ala
145                 150                 155                 160

Arg Leu Gly Lys Pro Tyr Arg Gln Glu Phe Asp Gly Ala Thr Pro Ile
                165                 170                 175

Pro Thr Val Glu Gly Thr Ile Leu Arg Glu Asn Gly Ser Tyr Ala Asp
            180                 185                 190

Tyr Pro Ser Ala Val Ala Gln Trp Tyr Glu Arg Ile Ala Gln Ser Val
        195                 200                 205

Leu Lys Ala Leu Gln Ser Thr Glu Val His Ala Leu Val Ala Ala Asp
    210                 215                 220

Glu Glu Leu Trp Thr Gly Pro Pro Val Glu Leu Ala Asp Ala Thr His
225                 230                 235                 240

Arg Leu
```

-continued

<210> SEQ ID NO 58
<211> LENGTH: 726
<212> TYPE: DNA
<213> ORGANISM: Mycobacterium tuberculosis

<400> SEQUENCE: 58

```
atgacgctag ccaacaatgg aaccggcatg gaccactttc tgacgcccac ggagtacctc      60

gacgcgggcc atccgctcgt tcgtacgacg gcagcaaccc tcatccggga cgcggtgtcg     120

gataccgagc gggtcaggcg gatctactac tacgtgcgcg acgtgccata cgacgtcctc     180

gcgtcctttc gctacctcgc gcagggacat caccgcgcca gcgacgtgat cggccacggg     240

gtcgccttct gcatgggcaa ggcaagttcc ttcgtcgccc tgtgccgagc cgccggtgtc     300

ccggcccgta tcgcgttcca gacgatcgac gcccccgata aggagtttct gtccccgcag     360

gtacgtgccc tatggggagg ccgaactggc cggcccttcc cgtggcactc gctgggtgag     420

gcatatcttg gtcggcgatg ggtcaagctg gacgccacca tcgacgcacc caccgccgcc     480

cgcctcggca agccctaccg gcaagaattc gacggagcta ccccgatccc gacggtggaa     540

ggaaccatcc tgcgggaaaa cggcagctac gccgactatc ccagcgcggt cgcgcaatgg     600

tacgaacgaa tcgctcagtc ggtcctgaag gcgttgcagt ccaccgaagt acacgccttg     660

gtagccgctg acgaggaact gtggaccggc cccccggttg aattggccga cgcaacccac     720

cgactg                                                                726
```

<210> SEQ ID NO 59
<211> LENGTH: 499
<212> TYPE: PRT
<213> ORGANISM: Mycobacterium tuberculosis

<400> SEQUENCE: 59

```
Met Thr Ala Ala Gln Gln Asp Gln Ala Pro Met Ala Thr Pro Gly Cys
1               5                   10                  15

Arg Glu Gly Glu Thr Tyr Asp Val Val Val Leu Gly Ala Gly Pro Val
            20                  25                  30

Gly Gln Asn Val Ala Asp Arg Ala Arg Ala Gly Gly Leu Arg Val Ala
        35                  40                  45

Val Val Glu Arg Glu Leu Val Gly Gly Glu Cys Ser Tyr Trp Ala Cys
    50                  55                  60

Val Pro Ser Lys Ala Leu Leu Arg Pro Val Ile Ala Ile Ser Asp Ala
65                  70                  75                  80

Arg Arg Val Asp Gly Ala Arg Glu Ala Val Asp Gly Ser Ile Asn Thr
                85                  90                  95

Ala Gly Val Phe Gly Arg Arg Asn Arg Tyr Val Ala His Trp Asp Asp
            100                 105                 110

Thr Gly Gln Ala Asp Trp Val Ser Gly Ile Gly Ala Thr Leu Ile Arg
        115                 120                 125

Gly Asp Gly Arg Leu Asp Gly Pro Arg Arg Val Val Val Thr Lys Ser
    130                 135                 140

Ser Gly Glu Ser Val Ala Leu Thr Ala Arg His Ala Val Val Ile Cys
145                 150                 155                 160

Thr Gly Ser Arg Pro Ala Leu Pro Asp Leu Pro Gly Ile Thr Glu Ala
                165                 170                 175

Arg Pro Trp Thr Asn Arg Gln Ala Thr Asp Asn Ser Thr Val Pro Asp
            180                 185                 190

Arg Leu Ala Ile Val Gly Ala Gly Gly Val Gly Val Glu Met Ala Thr
        195                 200                 205
```

-continued

```
Ala Trp Gln Gly Leu Gly Ala Ser Val Thr Leu Leu Ala Arg Gly Ser
    210                 215                 220

Gly Leu Leu Pro Arg Met Glu Pro Phe Val Gly Glu Leu Ile Gly Arg
225                 230                 235                 240

Gly Leu Ala Asp Ala Gly Val Asp Val Arg Val Gly Val Ser Val Arg
                245                 250                 255

Ala Leu Gly Arg Pro Asn Pro Thr Gly Pro Val Val Leu Glu Leu Asp
            260                 265                 270

Asp Gly Thr Glu Leu Arg Val Asp Glu Val Leu Phe Ala Thr Gly Arg
        275                 280                 285

Ala Pro Arg Thr Asp Asp Ile Gly Leu Glu Thr Ile Gly Leu Thr Pro
    290                 295                 300

Gly Ser Trp Leu Asp Val Asp Asp Thr Cys Arg Val Arg Ala Val Asp
305                 310                 315                 320

Asp Gly Trp Leu Tyr Ala Ala Gly Asp Val Asn His Arg Ala Leu Leu
                325                 330                 335

Thr His Gln Gly Lys Tyr Gln Ala Arg Ile Ala Gly Thr Ala Ile Gly
            340                 345                 350

Ala Arg Ala Ala Gly Arg Pro Leu Asp Thr Thr Ser Trp Gly Met His
        355                 360                 365

Ala Thr Thr Ala Asp His His Ala Val Pro Gln Ala Phe Phe Thr Asp
    370                 375                 380

Pro Glu Ala Ala Ala Val Gly Leu Thr Ala Asp Gln Ala Ala Gln Ala
385                 390                 395                 400

Gly His Arg Ile Lys Ala Ile Asp Val Glu Ile Gly Asp Val Val Met
                405                 410                 415

Gly Ala Lys Leu Phe Ala Asp Gly Tyr Thr Gly Arg Ala Arg Met Val
            420                 425                 430

Val Asp Val Asp Arg Gly His Leu Leu Gly Val Thr Met Val Gly Pro
        435                 440                 445

Gly Ala Ala Glu Leu Leu His Ser Ala Thr Val Ala Val Ala Gly Gln
    450                 455                 460

Val Pro Ile Asp Arg Leu Trp His Ala Val Pro Cys Phe Pro Thr Ile
465                 470                 475                 480

Ser Glu Leu Trp Leu Arg Leu Leu Glu Ser Tyr Arg Asp Ser Phe Tyr
                485                 490                 495

Leu Leu Val
```

<210> SEQ ID NO 60
<211> LENGTH: 1497
<212> TYPE: DNA
<213> ORGANISM: Mycobacterium tuberculosis

<400> SEQUENCE: 60

```
atgaccgcgg cccaacagga ccaggcgcca atggcaacac ccggctgccg tgagggtgaa      60

acgtatgacg tcgtcgtgct cggcgcggga cccgttggac agaacgtcgc cgatcgtgcc     120

cgcgcggggg gcctgcgtgt cgcggtggtg gagcgcgaac tcgtcggggg tgaatgctcc     180

tattgggcct gtgtgcccag caaagccttg ctgcgtccgg tcatcgcgat ctctgacgcc     240

cgacgggtcg acggcgcgcg cgaagcagtc gacggctcga tcaacacagc cggcgtcttt     300

ggccgccgca accgctatgt ggcccactgg gacgacaccg gccaggccga ctgggtgagt     360

ggaatcggcg cgacgctgat acgcggtgac gggcgattgg acggtccgcg ccgcgtcgtc     420

gtcaccaagt cgagcggcga aagcgtggcg ctgaccgccc ggcatgccgt tgtcatctgc     480
```

-continued

```
accggaagcc ggccagcact ccccgacctt cctggcatca ccgaagcccg gccatggacc    540

aatcgccaag ccaccgacaa cagtacggtc cccgaccggc ttgcgatcgt cggcgccggc    600

ggcgtcggtg tggagatggc gaccgcctgg cagggactgg gcgcctcggt gaccctgctg    660

gctcggggat ctggcctgct gccccgaatg gaaccgtttg tgggggaact catcggtcgc    720

ggactggccg acgccggcgt tgacgtgcgc gtgggagtat cggtacgcgc gctgggccgc    780

cccaacccaa ctggcccagt ggtcctcgag ctggacgacg gtaccgagct gcgggtcgac    840

gaggtactct tcgccaccgg ccgagcaccg cgaaccgacg acatcggctt ggagacaata    900

ggactgacgc cgggcagctg gctggacgtc gatgacacct gccgagtgcg ggctgttgac    960

gacggctggc tctatgccgc cggcgacgtc aaccatcgcg cgttgctgac ccaccaaggc   1020

aaataccagg cgcggatcgc cggcaccgcg atcggcgccc gtgccgccgg acgaccgcta   1080

gacaccacgt cgtggggcat gcacgcgacc accgccgacc atcacgcggt gccgcaggca   1140

ttctttaccg accccgaagc cgcagcggtc ggcctgacag ctgatcaggc cgcacaggct   1200

ggtcaccgga tcaaagcgat cgatgtcgaa atcggcgatg tcgttatggg agccaagctc   1260

tttgccgacg gatacaccgg cagggcgcgc atggtggtcg acgtcgatcg gggccatctg   1320

ctgggcgtga ccatggttgg cccgggcgcc gccgagctgt tgcattcggc caccgtcgcc   1380

gtcgccggcc aggtgccaat cgatcggttg tggcacgccg ttccgtgctt cccgaccatc   1440

agcgaactgt ggctgagact tcttgaatcc taccgagatt cgttttacct gctggta      1497
```

<210> SEQ ID NO 61
<211> LENGTH: 108
<212> TYPE: PRT
<213> ORGANISM: Mycobacterium tuberculosis

<400> SEQUENCE: 61

```
Met Ser Gly Gly Ser Ser Arg Arg Tyr Pro Pro Glu Leu Arg Glu Arg
1               5                   10                  15

Ala Val Arg Met Val Ala Glu Ile Arg Gly Gln His Asp Ser Glu Trp
            20                  25                  30

Ala Ala Ile Ser Glu Val Ala Arg Leu Leu Gly Val Gly Cys Ala Glu
        35                  40                  45

Thr Val Arg Lys Trp Val Arg Gln Ala Gln Val Asp Ala Gly Ala Arg
    50                  55                  60

Pro Gly Thr Thr Thr Glu Glu Ser Ala Glu Leu Lys Arg Leu Arg Arg
65                  70                  75                  80

Asp Asn Ala Glu Leu Arg Arg Ala Asn Ala Ile Leu Lys Thr Ala Ser
                85                  90                  95

Ala Phe Phe Ala Ala Glu Leu Asp Arg Pro Ala Arg
            100                 105
```

<210> SEQ ID NO 62
<211> LENGTH: 324
<212> TYPE: DNA
<213> ORGANISM: Mycobacterium tuberculosis

<400> SEQUENCE: 62

```
atgtcaggtg gttcatcgag gaggtacccg ccggagctgc gtgagcgggc ggtgcggatg     60

gtcgcagaga tccgcggtca gcacgattcg gagtgggcag cgatcagtga ggtcgcccgt    120

ctacttggtg ttggctgcgc ggagacggtg cgtaagtggg tgcgccaggc gcaggtcgat    180

gccggcgcac ggcccgggac cacgaccgaa gaatccgctg agctgaagcg cttgcggcgg    240

gacaacgccg aattgcgaag ggcgaacgcg attttaaaga ccgcgtcggc tttcttcgcg    300
```

gccgagctcg accggccagc acgc 324

<210> SEQ ID NO 63
<211> LENGTH: 217
<212> TYPE: PRT
<213> ORGANISM: Mycobacterium tuberculosis

<400> SEQUENCE: 63

Met Leu Val Gly Ala Gln Cys Arg Asp Leu Leu His Trp Arg Phe Cys
1 5 10 15

Arg Gly Val Pro Pro Arg Ala Thr Asn Asp Thr Asp Ile Ala Gly Thr
20 25 30

Leu Asn Asn Trp Asp His Phe Glu Ala Ile Arg Ala Thr Phe Arg Ala
35 40 45

Leu Gly Ser Thr Gly His Arg Phe Leu Ile Ala Asp Arg Ala Val Asp
50 55 60

Ala Leu Pro Phe Gly Glu Val Glu Ser Pro Thr Gly Thr Thr Arg His
65 70 75 80

Pro Pro Gly Asn Gln Leu Met Asn Val His Gly Cys Thr Asp Ala Tyr
85 90 95

Leu Arg Ala Asp Val Leu Pro Leu Pro Gly Gly Leu Thr Val His Leu
100 105 110

Pro Gln Pro Pro Asn Tyr Ala Val Leu Lys Leu His Ala Trp Leu Asp
115 120 125

Arg Ser Ala Asp His Asp Tyr Lys Asp Gly Pro Asp Leu Ala Leu Val
130 135 140

Val His Trp Tyr Ala Gly Asp Leu Asp Arg Leu Tyr Ala Lys Pro Asp
145 150 155 160

Gln Trp Ala Leu Arg Arg His Asp Phe Asp Leu Arg Thr Ala Ala Ala
165 170 175

Ala Leu Leu Gly His Asp Met Arg Ala Ser Val Ser Ala Pro Glu Ala
180 185 190

Ala Val Leu Ala Thr Arg Ala Thr Gln Ala Asp His Asp Leu Leu Ala
195 200 205

Gln His Phe Ala Val Gly Arg Pro Gly
210 215

<210> SEQ ID NO 64
<211> LENGTH: 651
<212> TYPE: DNA
<213> ORGANISM: Mycobacterium tuberculosis

<400> SEQUENCE: 64
atgctcgtcg gggcacagtg ccgcgatcta ctgcactggc gcttctgccg cggggtgccg 60
ccgcgggcca ccaacgacac cgatatcgca gggaccctga acaattggga ccacttcgag 120
gcaattcggg ccaccttccg cgccctgggc agcaccgggc accgattcct gatcgccgac 180
cgcgccgtcg atgccctccc gttcggcgag gtggagtcgc ccaccggcac aacccgccat 240
cccccaggca accagctcat gaacgtccac ggatgcaccg acgcctacct gcgtgccgat 300
gttctgcctc tccctggcgg cctgacagtc caccttcccc aaccgccgaa ctatgcggtc 360
ctcaaactgc acgcatggct cgatcggtcc gcggaccacg actacaaaga cggcccagat 420
ctggccttgg tggtgcactg gtacgccggc gacctcgacc ggctttacgc caaaccagac 480
cagtgggcgc tacgccgtca cgacttcgac ctacgcaccg ccgctgccgc gctgctcggc 540
cacgacatgc gcgccagtgt cagcgcaccg gaggccgccg tgctggcgac gcgcgccaca 600
caggccgacc acgacctgct ggcccagcac ttcgccgtgg gtcgaccggg c 651

<210> SEQ ID NO 65
<211> LENGTH: 342
<212> TYPE: PRT
<213> ORGANISM: Mycobacterium tuberculosis

<400> SEQUENCE: 65

Met Asp Gln Ile Gly Ala Asp Leu Ala Glu Ala Val Glu Arg His Leu
1 5 10 15

Thr Glu Tyr Gly Val Arg Val Leu Gly Gly Leu Ser Ala Leu Asn Ser
20 25 30

Ala His Pro Glu Ser Leu Asp Leu Glu Ile Asp Ala His Pro Leu Thr
35 40 45

Ile Thr Ala Leu Tyr Leu Pro His Leu Ser Ala Thr Ala Ala Leu Gln
50 55 60

Ala Trp Asp Thr Ala Gly Ala Gly Ser Pro Leu Leu Val Val Gly Pro
65 70 75 80

Arg Leu His Pro Ser Ser Ala Glu Thr Leu Arg Ala Arg Gly Leu Trp
85 90 95

Tyr Ile Asp Gly Ala Gly Asn Ala Tyr Leu Arg His Gln Gly Gly Leu
100 105 110

Leu Ile Asp Val Arg Gly Arg Arg Ser Ala Val Ser Ala Gln Pro Gly
115 120 125

Thr Leu Gly Asp Gly Leu His Ser Asp Gly Pro Arg Asn Pro Phe Thr
130 135 140

Pro Lys Arg Ala Gln Val Val Cys Val Leu Leu Asp Ala Pro Gln Leu
145 150 155 160

Val Asp Ala Pro Leu Arg Ala Ile Ala Ala Ser Ala Gly Val Ser Val
165 170 175

Gly Met Ala Lys Glu Thr Met Asp Thr Leu Arg Thr Thr Gly Phe Phe
180 185 190

Glu His Leu Gly Ser Arg Arg Arg Leu Val Arg Thr Asp Glu Leu Leu
195 200 205

Asp Leu Trp Ala Ala Ala Tyr Pro Gly Gly Leu Gly Arg Ala Asn Lys
210 215 220

Leu Leu Val Ala Ser Gly Asp Ile His Thr Trp Ser Ala Pro Asp Gly
225 230 235 240

Leu Ala Val Ala Val Ser Gly Glu Gln Ala Leu Pro Asp Glu Ile Arg
245 250 255

Asn Pro Glu Ser Leu Met Leu Tyr Val Asp Thr Pro Ala Pro Gly Leu
260 265 270

Pro Ala Asp Leu Leu Ile His Asn Arg Trp His Arg Asp Pro His Gly
275 280 285

Ser Ile Val Ile Arg Lys Leu Phe Trp Arg Asn Leu Pro Asp Glu Gln
290 295 300

Pro Gly Leu Ala Pro Thr Ala Leu Ile Tyr Ala Asp Leu Leu Ala Ser
305 310 315 320

Arg Glu Pro Arg Gln Val Glu Val Ala His Leu Met Arg Arg Gln Asp
325 330 335

Glu Arg Leu Ala Arg Leu
340

<210> SEQ ID NO 66
<211> LENGTH: 1026

<212> TYPE: DNA
<213> ORGANISM: Mycobacterium tuberculosis

<400> SEQUENCE: 66
atggatcaga tcggggctga cctcgctgag gccgtcgagc gtcacctcac cgaatacgga 60
gtgcgggtgc tcggtggcct atcagcattg aactccgcgc atcccgaatc actagacctt 120
gagatcgacg ctcacccccct cacgatcact gccctctacc ttcctcacct gtcggcaacg 180
gcagcactgc aggcctggga taccgccggc gctggttcgc cgctgcttgt ggtgggcccg 240
cgtctgcatc cgtcgagcgc tgaaacgctg cgggctcgcg gactctggta catcgacgga 300
gctgggaacg cttatttgcg gcaccagggt ggcctgctca tcgacgtgcg cggccgacgg 360
tcagctgtgt ccgcacaacc gggcaccctc ggtgacggac tgcacagcga tggaccgcgt 420
aacccgttta cccccaagcg cgcgcaggtt gtctgcgtac tgcttgacgc accgcaactg 480
gtcgacgcgc cgctgcgtgc gatcgccgcg agcgccggcg tctcggtcgg tatggccaag 540
gagacgatgg atacgttgcg cactaccggc ttcttcgaac acctcggctc ccgccgcagg 600
ctggtgcgca ccgatgagct gctggacctg tgggcggctg cctatccggg gggtctgggc 660
cgggccaaca aactcctggt cgccagtggt gatatccaca cgtggtccgc acccgacgga 720
ctcgcagtgg cggtcagcgg ggaacaggcc ctgcccgacg aaatccgcaa tcccgaatca 780
ctgatgctct acgtcgacac cccagcgccc gggctacccg ccgacctgct tatacacaac 840
cgctggcacc gcgacccaca cggcagcatc gtgatccgaa agctattctg gcgcaaccta 900
cctgacgagc aaccggggtt ggctcccacg gccttgatct atgccgacct ccttgcctcg 960
cgcgagccgc gccaggtcga agtcgcccac ctcatgagaa ggcaggatga gcgactcgcc 1020
cgatta 1026

<210> SEQ ID NO 67
<211> LENGTH: 286
<212> TYPE: PRT
<213> ORGANISM: Mycobacterium tuberculosis

<400> SEQUENCE: 67

Val Glu Gly Thr Ile Ala Val Pro Gly Gly Arg Val Trp Phe Gln Arg
1 5 10 15

Ile Gly Gly Gly Pro Gly Arg Pro Leu Leu Val Val His Gly Gly Pro
20 25 30

Gly Leu Pro His Asn Tyr Leu Ala Pro Leu Arg Arg Leu Ser Asp Glu
35 40 45

Arg Glu Val Ile Phe Trp Asp Gln Leu Gly Cys Gly Asn Ser Ala Cys
50 55 60

Pro Ser Asp Val Asp Leu Trp Thr Met Asn Arg Ser Val Ala Glu Met
65 70 75 80

Ala Thr Val Ala Glu Ala Leu Ala Leu Thr Arg Phe His Ile Phe Ser
85 90 95

His Ser Trp Gly Gly Met Leu Ala Gln Gln Tyr Val Leu Asp Lys Ala
100 105 110

Pro Asp Ala Val Ser Leu Thr Ile Ala Asn Ser Thr Ala Ser Ile Pro
115 120 125

Glu Phe Ser Ala Ser Leu Val Ser Leu Lys Ser Cys Leu Asp Val Ala
130 135 140

Thr Arg Ser Ala Ile Asp Arg His Glu Ala Ala Gly Thr Thr His Ser
145 150 155 160

Ala Glu Tyr Gln Ala Ala Ile Arg Thr Trp Asn Glu Thr Tyr Leu Cys

```
                165                 170                 175

Arg Thr Arg Pro Trp Pro Arg Glu Leu Thr Glu Ala Phe Ala Asn Met
            180                 185                 190

Gly Thr Glu Ile Phe Glu Thr Met Phe Gly Pro Ser Asp Phe Arg Ile
        195                 200                 205

Val Gly Asn Val Arg Asp Trp Asp Val Val Asp Arg Leu Ala Asp Ile
    210                 215                 220

Ala Val Pro Thr Leu Leu Val Val Gly Arg Phe Asp Glu Cys Ser Pro
225                 230                 235                 240

Glu His Met Arg Glu Met Gln Gly Arg Ile Ala Gly Ser Arg Leu Glu
                245                 250                 255

Phe Phe Glu Ser Ser Ser His Met Pro Phe Ile Glu Glu Pro Ala Arg
            260                 265                 270

Phe Asp Arg Val Met Arg Glu Phe Leu Arg Leu His Asp Ile
        275                 280                 285


<210> SEQ ID NO 68
<211> LENGTH: 858
<212> TYPE: DNA
<213> ORGANISM: Mycobacterium tuberculosis

<400> SEQUENCE: 68

gtggagggga caatcgcggt cccgggtgga cgcgtctggt tccagcggat tggtggcggt      60

cctggtcgtc cgctgcttgt agtgcacggt gggccgggct tgccgcacaa ctacttggcc     120

ccactgcgac ggttgtctga tgagcgggag gtcatcttct gggaccagct cggttgcgga     180

aattccgcat gtccgtcaga cgtagacctt tggacgatga accgctcagt ggccgagatg     240

gcaaccgtgg cggaagccct tgcccttacc cgctttcaca tcttcagcca ttcgtggggt     300

gggatgctgg cacagcagta cgtgctcgac aaggcgcctg acgccgtcag tctgaccatc     360

gcgaacagca cggcttcgat acccgaattt tcggccagtc tggtcagctt gaagtcgtgc     420

ttggacgtgg caactcgctc ggcaattgac cgtcacgagg cggccggcac cacccattcc     480

gccgaatacc aggccgcgat cagaacctgg aacgagactt atctgtgccg cacccgcccc     540

tggccccggg aactcacgga agcattcgcc aacatgggaa ccgagatctt cgagacgatg     600

tttgggccca gcgactttcg catcgttggg aatgttcgag actgggacgt cgtcgaccgg     660

ttggccgaca tcgcggtgcc gaccttgctg gtggtgggcc gtttcgacga atgttcgcct     720

gagcacatgc gagaaatgca gggccggatt gcgggctcgc gattggaatt cttcgagtcc     780

agttcccaca tgccgttcat cgaagagccg gcgcgattcg accgggtgat gcgtgaattc     840

cttcggctgc acgatatt                                                   858


<210> SEQ ID NO 69
<211> LENGTH: 419
<212> TYPE: PRT
<213> ORGANISM: Mycobacterium tuberculosis

<400> SEQUENCE: 69

Met Gly Ala Arg Ala Ile Phe Arg Gly Phe Asn Arg Pro Ser Arg Val
1               5                   10                  15

Leu Met Ile Asn Gln Phe Gly Ile Asn Ile Gly Phe Tyr Met Leu Met
            20                  25                  30

Pro Tyr Leu Ala Asp Tyr Leu Ala Gly Pro Leu Gly Leu Ala Ala Trp
        35                  40                  45

Ala Val Gly Leu Val Met Gly Val Arg Asn Phe Ser Gln Gln Gly Met
    50                  55                  60
```

-continued

Phe Phe Val Gly Gly Thr Leu Ala Asp Arg Phe Gly Tyr Lys Pro Leu
65 70 75 80

Ile Ile Ala Gly Cys Leu Ile Arg Thr Gly Gly Phe Ala Leu Leu Val
85 90 95

Val Ala Gln Ser Leu Pro Ser Val Leu Ile Ala Ala Ala Ala Thr Gly
100 105 110

Phe Ala Gly Ala Leu Phe Asn Pro Ala Val Arg Gly Tyr Leu Ala Ala
115 120 125

Glu Ala Gly Glu Arg Lys Ile Glu Ala Phe Ala Met Phe Asn Val Phe
130 135 140

Tyr Gln Ser Gly Ile Leu Leu Gly Pro Leu Val Gly Leu Val Leu Leu
145 150 155 160

Ala Leu Asp Phe Arg Ile Thr Val Leu Ala Ala Ala Gly Val Phe Gly
165 170 175

Leu Leu Thr Val Ala Gln Leu Val Ala Leu Pro Gln His Arg Ala Asp
180 185 190

Ser Glu Arg Glu Lys Thr Ser Ile Leu Gln Asp Trp Arg Val Val Val
195 200 205

Arg Asn Arg Pro Phe Leu Thr Leu Ala Ala Ala Met Thr Gly Cys Tyr
210 215 220

Ala Leu Ser Phe Gln Ile Tyr Leu Ala Leu Pro Met Gln Ala Ser Ile
225 230 235 240

Leu Met Pro Arg Asn Gln Tyr Leu Leu Ile Ala Ala Met Phe Ala Val
245 250 255

Ser Gly Leu Val Ala Val Gly Gly Gln Leu Arg Ile Thr Arg Trp Phe
260 265 270

Ala Val Arg Trp Gly Ala Glu Arg Ser Leu Val Val Gly Ala Thr Ile
275 280 285

Leu Ala Ala Ser Phe Ile Pro Val Ala Val Ile Pro Asn Gly Gln Arg
290 295 300

Phe Gly Val Ala Val Ala Val Met Ala Leu Val Leu Ser Ala Ser Leu
305 310 315 320

Leu Ala Val Ala Ser Ala Ala Leu Phe Pro Phe Glu Met Arg Ala Val
325 330 335

Val Ala Leu Ser Gly Asp Arg Leu Val Ala Thr His Tyr Gly Phe Tyr
340 345 350

Ser Thr Ile Val Gly Val Gly Val Leu Val Gly Asn Leu Ala Ile Gly
355 360 365

Ser Leu Met Ser Ala Ala Arg Arg Leu Asn Thr Asp Glu Ile Val Trp
370 375 380

Gly Gly Leu Ile Leu Val Gly Ile Val Ala Val Ala Gly Leu Arg Arg
385 390 395 400

Leu Asp Thr Phe Thr Ser Gly Ser Gln Asn Met Thr Gly Arg Trp Ala
405 410 415

Ala Pro Arg

<210> SEQ ID NO 70
<211> LENGTH: 1257
<212> TYPE: DNA
<213> ORGANISM: Mycobacterium tuberculosis

<400> SEQUENCE: 70
atgggagcgc gcgctatatt ccgcgggttc aaccgcccga gccgggtgtt gatgatcaac 60
cagttcggca tcaacatcgg cttctacatg ctgatgccgt acctggccga ctacctagcc 120

```
gggccactgg ggctagccgc gtgggcggtg ggtctggtga tgggcgtgcg caatttctcc    180

cagcagggca tgttcttcgt gggtggcacg ctggccgatc ggttcggcta caagccactg    240

atcatcgccg gatgtctgat ccgcaccggc gggtttgcct tgctggtggt cgcccagtcg    300

ctgcccagtg tgctgatcgc cgcggctgcc acgggctttg ccggcgcgct gttcaatccc    360

gcggtgcgcg gctatctcgc ggccgaagcc ggggaacgca agatcgaagc gttcgcgatg    420

ttcaacgtct tctaccagtc ggggatcctg ctcggcccgc tggttggatt agtattgctg    480

gcgctggatt tccggatcac ggtgctggcc gccgccggtg tgttcggcct actcaccgtc    540

gcgcagctgg tcgcactgcc ccaacaccgg gccgactcgg agcgcgaaaa aacatcgatc    600

ctgcaggact ggcgggtcgt cgttcgcaac cgtccgtttc tgacgttagc cgccgccatg    660

accggatgct atgcgctgtc gttccagatc tatctggctc tgcccatgca ggcgtcgatc    720

ctcatgccac gcaaccaata tctcttgatt gcggcgatgt tcgcggtatc gggtctggtc    780

gccgtcggcg ggcagctgcg catcacccgc tggttcgccg tcagatgggg ggccgagcgc    840

agcctggtag tcggcgcgac gattttggcg gcctcgttca tcccggttgc agtcatccca    900

aacggccagc ggttcggcgt cgccgttgcg gtcatggcat tggtgctgtc ggcgagtctg    960

ctggcggttg cctcggcagc gttgtttcct ttcgaaatgc gtgccgtggt cgcactgtcg   1020

ggcgaccggc tggtggcgac ccactacggg ttctacagca ccatcgtggg cgtcggagtc   1080

ctcgtcggaa atctggcgat cggatcgctc atgagcgccg cgcgccgctt aaataccgat   1140

gaaattgttt ggggcggatt gattctggtg ggcatcgttg cggtggccgg gctccgtcgg   1200

ttggacacat tcacctcggg ttcccagaac atgaccggtc ggtgggctgc accccgg      1257
```

<210> SEQ ID NO 71
<211> LENGTH: 593
<212> TYPE: PRT
<213> ORGANISM: Mycobacterium tuberculosis

<400> SEQUENCE: 71

```
Met Ser Ala Lys Glu Arg Gly Asp Gln Asn Ala Val Val Asp Ala Leu
1               5                   10                  15

Arg Ser Ile Gln Pro Ala Val Phe Ile Pro Ala Ser Val Val Ile Val
            20                  25                  30

Ala Met Ile Val Val Ser Val Val Tyr Ser Ser Val Ala Glu Asn Ala
        35                  40                  45

Phe Val Arg Leu Asn Ser Ala Ile Thr Gly Gly Val Gly Trp Trp Tyr
    50                  55                  60

Ile Leu Val Ala Thr Gly Phe Val Val Phe Ala Leu Tyr Cys Gly Ile
65                  70                  75                  80

Ser Arg Ile Gly Thr Ile Arg Leu Gly Arg Asp Asp Glu Leu Pro Glu
                85                  90                  95

Phe Ser Phe Trp Ala Trp Leu Ala Met Leu Phe Ser Ala Gly Met Gly
            100                 105                 110

Ile Gly Leu Val Phe Tyr Gly Val Ala Glu Pro Leu Ser His Tyr Leu
        115                 120                 125

Arg Pro Pro Arg Ser Arg Gly Val Pro Ala Leu Thr Asp Ala Ala Ala
    130                 135                 140

Asn Gln Ala Met Ala Leu Thr Val Phe His Trp Gly Leu His Ala Trp
145                 150                 155                 160

Ala Ile Tyr Val Val Val Gly Leu Gly Met Ala Tyr Met Thr Tyr Arg
                165                 170                 175
```

-continued

```
Arg Gly Arg Pro Leu Ser Val Arg Trp Leu Leu Glu Pro Val Val Gly
            180                 185                 190

Arg Gly Arg Val Glu Gly Ala Leu Gly His Ala Val Asp Val Ile Ala
        195                 200                 205

Ile Val Gly Thr Leu Phe Gly Val Ala Thr Ser Leu Gly Phe Gly Ile
    210                 215                 220

Thr Gln Ile Ala Ser Gly Leu Glu Tyr Leu Gly Trp Ile Arg Val Asp
225                 230                 235                 240

Asn Trp Trp Met Val Gly Met Ile Ala Ala Ile Thr Ala Thr Ala Thr
                245                 250                 255

Ala Ser Val Val Ser Gly Val Ser Lys Gly Leu Lys Trp Leu Ser Asn
            260                 265                 270

Ile Asn Met Ala Leu Ala Ala Ala Leu Ala Leu Phe Val Leu Leu Leu
        275                 280                 285

Gly Pro Thr Leu Phe Leu Leu Gln Ser Trp Val Gln Asn Leu Gly Gly
    290                 295                 300

Tyr Val Gln Ser Leu Pro Gln Phe Met Leu Arg Thr Ala Pro Phe Ser
305                 310                 315                 320

His Asp Gly Trp Leu Gly Asp Trp Thr Ile Phe Tyr Trp Gly Trp Trp
                325                 330                 335

Ile Ser Trp Ala Pro Phe Val Gly Met Phe Ile Ala Arg Ile Ser Arg
            340                 345                 350

Gly Arg Thr Ile Arg Glu Phe Ile Gly Ala Val Leu Leu Val Pro Thr
        355                 360                 365

Val Ile Ala Ser Leu Trp Phe Thr Ile Phe Gly Asp Ser Ala Leu Leu
    370                 375                 380

Arg Gln Arg Asn Asn Gly Asp Met Leu Val Asn Gly Ala Val Asp Thr
385                 390                 395                 400

Asn Thr Ser Leu Phe Arg Leu Leu Asp Gly Leu Pro Ile Gly Ala Ile
                405                 410                 415

Thr Ser Val Leu Ala Val Leu Val Ile Val Phe Phe Phe Val Thr Ser
            420                 425                 430

Ser Asp Ser Gly Ser Leu Val Ile Asp Ile Leu Ser Ala Gly Gly Glu
        435                 440                 445

Leu Asp Pro Pro Lys Leu Thr Arg Val Tyr Trp Ala Val Leu Glu Gly
    450                 455                 460

Val Ala Ala Ala Val Leu Leu Leu Ile Gly Gly Ala Gly Ser Leu Thr
465                 470                 475                 480

Ala Leu Arg Thr Ala Ala Ile Ala Thr Ala Leu Pro Phe Ser Ile Val
                485                 490                 495

Met Val Val Ala Cys Tyr Ala Met Thr Lys Ala Phe His Phe Asp Leu
            500                 505                 510

Ala Ala Thr Pro Arg Leu Leu His Val Thr Val Pro Asp Val Val Ala
        515                 520                 525

Ala Gly Asn Arg Arg Arg His Asp Ile Ser Ala Thr Leu Ser Gly Leu
    530                 535                 540

Ile Ala Val Arg Asp Val Asp Ser Gly Thr Tyr Ile Val His Pro Asp
545                 550                 555                 560

Thr Gly Ala Leu Thr Val Thr Ala Pro Pro Asp Pro Leu Asp Asp His
                565                 570                 575

Val Phe Glu Ser Asp Arg His Val Thr Arg Arg Asn Thr Thr Ser Ser
            580                 585                 590

Arg
```

<210> SEQ ID NO 72
<211> LENGTH: 1779
<212> TYPE: DNA
<213> ORGANISM: Mycobacterium tuberculosis

<400> SEQUENCE: 72
atgtcagcga aagaacgcgg tgaccagaac gccgtcgtcg acgccctgcg gagtattcag 60
cccgcagtct tcattccggc ttcagtggtc atcgtcgcca tgatcgtcgt ttccgtggtg 120
tactcgagcg tcgccgagaa tgcgttcgtt cggctgaact ccgcgatcac cggcggcgtc 180
gggtggtggt acatcctggt tgccaccggg tttgtggtat tcgcgctgta ctgcggcatt 240
tcccggattg gcactatccg gctgggccgc gacgatgagc tccccgagtt cagcttctgg 300
gcatggctgg caatgctgtt tagtgccggt atgggtatcg gcctggtctt ctacggggtg 360
gccgagccgc tcagccacta cctgcggcca ccgcggtcac gcggcgtgcc cgcgcttact 420
gatgcggcgg ctaaccaggc gatggcgctg acagtgttcc actggggcct gcacgcctgg 480
gcaatttatg tcgtggttgg cctcggtatg gcgtacatga cctatcggcg gggtcgcccc 540
ttgtcggtgc gctggctgct ggagccggtc gtgggtcggg gccgtgtaga gggcgccttg 600
gggcacgcgg tggacgtcat cgccattgtc ggaacactct ttggtgtcgc cacgtcactg 660
ggcttcggta tcactcagat cgcctccggc ctggaatatc tcggctggat ccgggtggac 720
aactggtgga tggtcggcat gatcgccgcc atcaccgcca ctgcgacggc gtcggtggtc 780
agtggggtca gcaagggttt gaagtggctg tcgaacatca atatggcgct ggccgccgca 840
ttggccctgt tcgtgttgtt gctcgggccg acactttttct tgctgcagtc gtgggtgcaa 900
aatttgggag gctacgtcca gtcgcttccg caattcatgc tgcgcaccgc gccgttctcg 960
cacgacggct ggctcggcga ctggactatc ttctactggg gttggtggat cagctgggct 1020
ccgtttgtcg ggatgttcat cgcgcggatt tcgcggggac ggacgatccg ggagttcatc 1080
ggggcggtgc tgctcgttcc caccgtgatc gcctcgctat ggtttacgat cttcggtgac 1140
tcggcgttgt tgcggcaacg caacaacggc gacatgctcg tcaacggggc ggtagacacc 1200
aacacatcgc ttttccgatt gctggacggt ttgcctatcg ggggctattac cagcgttctt 1260 gctgtgctgg tgatcgtgtt cttcttcgtt acgtcgtcgg actccggttc gttggtcatc 1320
gacatcttgt cagcgggtgg tgagctggac ccgcccaagc tgaccagggt ctactgggcg 1380
gtgttggagg gggtagccgc ggccgttttg ctcctgatcg gaggtgctgg gtcactgacc 1440
gcgttgcgga cggccgctat tgccacggcc ctgccgttct caatcgtcat ggtggtggcg 1500
tgctatgcga tgaccaaagc gttccacttc gacctggccg ccacacctag gctgctgcac 1560
gtcaccgtgc ctgacgtggt tgcggcagga aaccggcgac gccacgatat ctcggcgacg 1620
ctgtcggggc tcattgccgt ccgtgatgtc gatagcggca catatatagt ccaccccgac 1680
accggcgctc tcaccgtcac tgcaccacca gatccgttgg acgatcatgt ttttgagtct 1740
gatcggcacg taacgcgaag aaacacaaca tcatcgaga 1779

<210> SEQ ID NO 73
<211> LENGTH: 331
<212> TYPE: PRT
<213> ORGANISM: Mycobacterium tuberculosis

<400> SEQUENCE: 73

Met Ser Phe Val Asn Val Ala Pro Gln Leu Val Ser Thr Ala Ala Ala
1 5 10 15

Asp Ala Ala Arg Ile Gly Ser Ala Ile Asn Thr Ala Asn Thr Ala Ala

-continued

```
            20                  25                  30

Ala Ala Thr Thr Gln Val Leu Ala Ala Ala Gln Asp Glu Val Ser Thr
        35                  40                  45

Ala Ile Ala Ala Leu Phe Gly Ser His Gly Gln His Tyr Gln Ala Ile
    50                  55                  60

Ser Ala Gln Val Ala Ala Tyr Gln Gln Arg Phe Val Leu Ala Leu Ser
65                  70                  75                  80

Gln Ala Gly Ser Thr Tyr Ala Val Ala Glu Ala Ala Ser Ala Thr Pro
                85                  90                  95

Leu Gln Asn Val Leu Asp Ala Ile Asn Ala Pro Val Gln Ser Leu Thr
            100                 105                 110

Gly Arg Pro Leu Ile Gly Asp Gly Ala Asn Gly Ile Asp Gly Thr Gly
        115                 120                 125

Gln Ala Gly Gly Asn Gly Gly Trp Leu Trp Gly Asn Gly Gly Asn Gly
    130                 135                 140

Gly Ser Gly Ala Pro Gly Gln Ala Gly Gly Ala Gly Gly Ala Ala Gly
145                 150                 155                 160

Leu Ile Gly Asn Gly Gly Ala Gly Gly Thr Gly Gly Ala Val Ser Leu
                165                 170                 175

Ala Arg Ala Gly Thr Ala Gly Gly Ala Gly Arg Gly Pro Val Gly Gly
            180                 185                 190

Ile Gly Gly Ala Gly Gly Val Gly Gly Ala Gly Gly Ala Ala Gly Ala
        195                 200                 205

Val Thr Thr Ile Thr His Ala Ser Phe Asn Asp Pro His Gly Val Ala
    210                 215                 220

Val Asn Pro Gly Gly Asn Val Tyr Val Thr Asn Phe Gly Ser Gly Thr
225                 230                 235                 240

Val Ser Val Ile Asn Pro Ala Thr Asn Thr Val Thr Gly Ser Pro Ile
                245                 250                 255

Thr Ile Gly Asn Gly Pro Ser Gly Val Ala Val Ser Pro Val Thr Gly
            260                 265                 270

Leu Val Phe Val Thr Asn Phe Asp Ser Asn Thr Val Ser Val Ile Asp
        275                 280                 285

Pro Thr Thr Asn Thr Val Thr Gly Ser Pro Ile Thr Val Gly Thr Ala
    290                 295                 300

Pro Thr Gly Val Ala Val Asn Pro Val Thr Gly Glu Val Tyr Val Thr
305                 310                 315                 320

Asn Phe Ala Gly Asp Thr Val Ser Val Ile Ser
                325                 330
```

<210> SEQ ID NO 74
<211> LENGTH: 993
<212> TYPE: DNA
<213> ORGANISM: Mycobacterium tuberculosis

<400> SEQUENCE: 74

```
atgtcgtttg tcaacgtggc cccacagtta gtgtccacag ccgcggccga tgcagcgcgg     60

atcggctcgg cgatcaacac cgccaacacc gcggcggcgg cgaccaccca ggtgttggcc    120

gccgcccaag acgaggtgtc aacggcgatc gccgcgctgt tcggcagcca cggccagcac    180

tatcaagcga tcagcgcgca ggtcgcggcc tatcagcaac ggttcgtgct ggccttaagc    240

caagctggca gcacctacgc ggtcgccgaa gcggccagcg caacaccgct gcagaacgtg    300

ctcgatgcga tcaacgcacc cgttcagtcg ctgaccgggc gcccattgat cggcgacggc    360

gcgaacggga tcgacgggac cgggcaagcc ggcggtaacg gcgggtggct gtggggcaac    420
```

ggcggcaacg gcgggtcggg ggcacccgga caggccggcg gcgccggcgg ggcggccggg 480
ttgatcggca acggtggggc cggcggcacc ggcggcgcgg tcagcctcgc ccgcgccggc 540
acggccggcg gtgccggccg cggcccggtc ggcggtatcg gcggtgcggg tggggtcggc 600
ggtgccggtg gggccgccgg cgccgtcacc accatcaccc acgccagctt caacgatccg 660
cacggggtgg cggtcaaccc gggcggcaac gtctacgtca ccaatttcgg cagcggcacg 720
gtgtcggtga tcaaccccgc caccaacacc gtcaccggct cccccatcac catcggcaac 780
ggtccaagcg gggtggcggt cagccccgtc accggcctgg tcttcgtgac caacttcgac 840
agcaacacgg tgtcggtgat cgacccgacc accaacaccg tcaccggctc ccccatcacc 900
gtcggcaccg ctccgaccgg ggtggcggtc aaccccgtca ccggcgaggt ttatgtcacc 960
aacttcgccg gcgacacggt gtcggtaatc agc 993

<210> SEQ ID NO 75
<211> LENGTH: 251
<212> TYPE: PRT
<213> ORGANISM: Mycobacterium tuberculosis

<400> SEQUENCE: 75

Met Arg Ala Asp Val Thr Ala Glu His Leu Thr Gln Val Val Arg Asp
1 5 10 15

Ile Ala Val Ile Asp Ile Asp Asp Gly Val Ala Phe Asn Leu Asp Thr
20 25 30

Ser Ser Val Gln Glu Ile Arg Glu Arg Ala Asp Tyr Pro Gly Leu Arg
35 40 45

Val Arg Val Ala Met Ser Val Gly Pro Trp Gln Gly Ile Ala Ala Trp
50 55 60

Asp Val Ser Thr Gly Glu Pro Ile Ala Pro Trp Pro Thr Arg Val Thr
65 70 75 80

Ile Asp Arg Ile Leu Gly Glu Pro Ile Thr Leu Leu Gly Tyr Ala Pro
85 90 95

Glu Thr Ile Ile Ala Glu Lys Gly Val Thr Ile Leu Glu Arg Gly Ile
100 105 110

Thr Ser Thr Arg Trp Arg Asp Tyr Val Asp Ile Val Gln Leu Asp Arg
115 120 125

Arg Gly Ile Asp Asp Asp Glu Leu Leu Arg Ser Ala Arg Ala Val Ala
130 135 140

Gln Tyr Arg Gly Ala Thr Leu Glu Pro Val Ala Pro His Leu Ala Gly
145 150 155 160

Tyr Gly Ala Val Ala Gln Ala Lys Trp Ala Thr Glu His Gly Arg Cys
165 170 175

Gln His Cys Trp Arg His Trp Lys Pro Ala His Val Gly Arg Arg Asn
180 185 190

Met Asp Leu Leu Asp Ala Lys Gln Val Ser Glu Met Ile Gly Val Pro
195 200 205

Val Gly Thr Leu Arg His Trp Arg His Ser Asp Ile Gly Pro Ala Ser
210 215 220

Phe Thr Leu Gly Arg Arg Val Val Tyr Arg Arg Asp Glu Val Ser Arg
225 230 235 240

Trp Ile Ser Lys Arg Glu Ser Ala Thr Arg Arg
245 250

<210> SEQ ID NO 76
<211> LENGTH: 753

<212> TYPE: DNA
<213> ORGANISM: Mycobacterium tuberculosis

<400> SEQUENCE: 76

```
atgcgcgccg acgtcaccgc cgagcatctc acccaggtgg ttcgcgacat cgccgtgatc      60

gacatcgacg acggggtggc gttcaacctc gacacgagca gcgtgcagga aattcgcgag     120

cgggccgact acccgggcct gcgcgtgcga gtcgctatgt cggtcggacc gtggcagggc     180

atcgcggcct gggatgtgtc caccggcgaa ccgatcgcgc cgtggcccac acgggtgacc     240

atcgaccgga tcctcggcga gccgatcaca ctcctgggct acgcgcccga gaccatcatc     300

gccgagaagg gagtgaccat cctcgaacgc ggcatcacca gcacccgctg gcgggactac     360

gtcgacatcg tccaactcga ccgccggggc atcgacgacg acgagctgct ccgctcggcc     420

agggcagtcg cacaataccg cggcgccact ctcgaacccg tcgcgcctca cctggccggt     480

tatggcgcag tcgcgcaagc gaaatgggcg accgaacacg gacgctgcca gcactgttgg     540

agacattgga aaccagccca tgtcgggagg agaaacatgg atctgctgga cgcaaaacaa     600

gtttcggaga tgatcggcgt tcccgtcggc actctacggc actggcggca ctcggacatc     660

ggaccggcga gcttcacctt gggacggcgc gtcgtgtacc ggcgcgacga ggtgtcgcgc     720

tggatctcaa agcgggagag cgcaactcga cgt                                  753
```

<210> SEQ ID NO 77
<211> LENGTH: 254
<212> TYPE: PRT
<213> ORGANISM: Mycobacterium tuberculosis

<400> SEQUENCE: 77

```
Met Ser Val Asp Tyr Pro Gln Met Ala Ala Thr Arg Gly Arg Ile Glu
1               5                   10                  15

Pro Ala Pro Arg Arg Val Arg Gly Tyr Leu Gly His Val Leu Val Phe
            20                  25                  30

Asp Thr Ser Ala Ala Arg Tyr Val Trp Glu Val Pro Tyr Tyr Pro Gln
        35                  40                  45

Tyr Tyr Ile Pro Leu Ala Asp Val Arg Met Glu Phe Leu Arg Asp Glu
    50                  55                  60

Asn His Pro Gln Arg Val Gln Leu Gly Pro Ser Arg Leu His Ser Leu
65                  70                  75                  80

Val Ser Ala Gly Gln Thr His Arg Ser Ala Ala Arg Val Phe Asp Val
                85                  90                  95

Asp Gly Asp Ser Pro Val Ala Gly Thr Val Arg Phe Asn Trp Asp Pro
            100                 105                 110

Leu Arg Trp Phe Glu Glu Asp Glu Pro Ile Tyr Gly His Pro Arg Asn
        115                 120                 125

Pro Tyr Gln Arg Ala Asp Ala Leu Arg Ser His Arg His Val Arg Val
    130                 135                 140

Glu Leu Asp Gly Ile Val Leu Ala Asp Thr Arg Ser Pro Val Leu Leu
145                 150                 155                 160

Phe Glu Thr Gly Ile Pro Thr Arg Tyr Tyr Ile Asp Pro Ala Asp Ile
                165                 170                 175

Ala Phe Glu His Leu Glu Pro Thr Ser Thr Gln Thr Leu Cys Pro Tyr
            180                 185                 190

Lys Gly Thr Thr Ser Gly Tyr Trp Ser Val Arg Val Gly Asp Ala Val
        195                 200                 205

His Arg Asp Leu Ala Trp Thr Tyr His Tyr Pro Leu Pro Ala Val Ala
    210                 215                 220
```

```
Pro Ile Ala Gly Leu Val Ala Phe Tyr Asn Glu Lys Val Asp Leu Thr
225                 230                 235                 240

Val Asp Gly Val Ala Leu Pro Arg Pro His Thr Gln Phe Ser
                245                 250


<210> SEQ ID NO 78
<211> LENGTH: 762
<212> TYPE: DNA
<213> ORGANISM: Mycobacterium tuberculosis

<400> SEQUENCE: 78

atgagcgtgg attaccccca aatggctgct acccggggaa gaatagaacc ggccccgcgg      60

cgagttcgcg gctatctcgg acatgtgctc gtcttcgaca ccagtgcggc gcgctatgtc     120

tgggaggttc cctactaccc gcagtactac atcccgctgg cggatgtccg catggagttc     180

ctgcgcgacg agaaccaccc gcagcgagtg cagctgggtc cgtcgcggct gcactccttg     240

gtaagcgccg gtcagaccca ccgatcggcg gcgcgggtat tcgatgtcga cggcgacagc     300

ccggtggcgg gcaccgtgcg tttcaactgg gatccgctgc ggtggttcga ggaggacgag     360

ccgatctacg gccatccgcg caatccctat cagcgggccg atgcgctgcg ctcgcaccga     420

cacgtccgtg tcgagctgga cggcattgtg ctcgctgaca cccgatcgcc cgttctgcta     480

ttcgaaactg ggatacccac aaggtattac atcgatccgg ccgacatcgc tttcgagcat     540

ctggagccca cctcgacgca gacgttgtgt ccgtacaagg ggacgacgtc gggctattgg     600

tctgtgcgcg tcggcgacgc cgtgcaccgc gacctggcct ggacgtatca ctatccactg     660

cccgccgttg ccccgatcgc cggcctggtg gcgttttaca acgagaaggt cgacctcacc     720

gtcgacggcg tcgccctgcc gcggccgcac actcagttca gc                        762


<210> SEQ ID NO 79
<211> LENGTH: 120
<212> TYPE: PRT
<213> ORGANISM: Mycobacterium tuberculosis

<400> SEQUENCE: 79

Ser Phe Ala Gly Ala Glu Ala Ala Asn Ala Ser Gln Leu Gln Ser Ile
1               5                   10                  15

Ala Arg Gln Val Arg Gly Ala Val Asn Ala Val Ala Gly Gln Val Thr
            20                  25                  30

Gly Asn Gly Gly Ser Gly Asn Ser Gly Thr Ser Ala Ala Ala Ala Asn
        35                  40                  45

Pro Asn Ser Asp Asn Thr Ala Ser Ile Ala Asp Arg Gly Thr Ser Ala
    50                  55                  60

Ile Met Thr Thr Ala Ser Ala Thr Ala Ser Ser Thr Gly Val Asp Gly
65                  70                  75                  80

Gly Ile Ala Ala Thr Tyr Ala Val Ala Ser Gln Trp Asp Gly Gly Tyr
                85                  90                  95

Val Ala Asn Tyr Thr Ile Thr Gln Phe Gly Arg Asp Phe Asp Asp Arg
            100                 105                 110

Leu Ala Val Ala Ile His Phe Ala
        115                 120


<210> SEQ ID NO 80
<211> LENGTH: 360
<212> TYPE: DNA
<213> ORGANISM: Mycobacterium tuberculosis

<400> SEQUENCE: 80
```

-continued

```
tctttcgccg gcgccgaggc cgccaatgcg tcacagctgc agagcatcgc gcggcaggtg     60

cggggcgccg tcaacgccgt cgccggtcag gtgacgggca atggcggctc cggcaacagc    120

ggcacttcgg ctgcggcggc caacccgaat tccgacaaca cagcgagcat cgccgatagg    180

ggcacaagcg ccatcatgac cacggcaagc gcgaccgcgt cttccacggg cgtcgatggc    240

ggaatagcgg cgacgtatgc ggtcgcctcg caatgggatg gtggctacgt ggccaattac    300

acgatcaccc aattcgggcg cgacttcgat gaccgattgg cggttgcaat tcactttgcc    360
```

<210> SEQ ID NO 81
<211> LENGTH: 470
<212> TYPE: PRT
<213> ORGANISM: Mycobacterium tuberculosis

<400> SEQUENCE: 81

```
Val Ala Thr Val Ala Phe Val Ala Thr Ala Ser Ile Val Ile Thr Pro
1               5                   10                  15

Ala Ala Ile Val Leu Leu Gly Pro Arg Leu Asp Ala Leu Asp Val Arg
            20                  25                  30

Arg Leu Val Arg Arg Leu Leu Gly Arg Pro Asp Pro Val His Lys Pro
        35                  40                  45

Val Lys Gln Leu Phe Trp Tyr Arg Ser Ser Lys Phe Val Met Arg Arg
    50                  55                  60

Trp Leu Pro Val Gly Thr Ala Val Val Ala Leu Leu Val Leu Leu Gly
65                  70                  75                  80

Leu Pro Phe Leu Ser Val Lys Trp Gly Phe Pro Asp Asp Arg Val Leu
                85                  90                  95

Pro Arg Ser Ala Ser Ala Arg Gln Val Gly Asp Ile Leu Arg Asp Asp
            100                 105                 110

Phe Gly His Asp Pro Ala Thr Gln Ile Pro Ile Val Val Pro Asp Ala
        115                 120                 125

Arg Gly Leu Gly Pro Val Glu Leu Asp Ser Tyr Ala Ala Glu Leu Ser
    130                 135                 140

Arg Val Pro Asp Val Ser Ala Val Ala Ala Pro Thr Gly Thr Phe Val
145                 150                 155                 160

Asp Gly Ser Trp Val Gly Thr Pro Arg Gly Ala Thr Gly Leu Ala Glu
                165                 170                 175

Gly Ser Ala Phe Leu Thr Val Ser Ser Thr Ala Pro Leu Phe Ser Arg
            180                 185                 190

Ala Ser Asp Ile Gln Leu Lys Arg Leu His Gln Val Ala Gly Pro Ala
        195                 200                 205

Gly Arg Ser Val Val Met Ala Gly Val Ala Gln Val Asn Arg Asp Ser
    210                 215                 220

Val Asp Ala Val Thr Asp Arg Leu Pro Met Val Leu Gly Leu Ile Ala
225                 230                 235                 240

Ala Ile Thr Tyr Val Leu Leu Phe Leu Leu Thr Gly Ser Val Val Leu
                245                 250                 255

Pro Ala Lys Ala Leu Val Cys Asn Val Leu Ser Leu Thr Ala Ala Phe
            260                 265                 270

Gly Ala Leu Val Trp Ile Phe Gln Glu Gly His Phe Gly Ala Leu Gly
        275                 280                 285

Thr Thr Pro Ser Gly Thr Leu Val Ala Asn Met Pro Val Leu Leu Phe
    290                 295                 300

Cys Ile Ala Phe Gly Leu Ser Met Asp Tyr Glu Val Phe Leu Val Ser
305                 310                 315                 320
```

```
Arg Ile Arg Glu Tyr Trp Leu Glu Ser Gly Ala Ala Arg Pro Ala Arg
                325                 330                 335

Arg Ser Val Ala Glu Val His Ala Ala Asn Asp Glu Ser Val Ala Leu
            340                 345                 350

Gly Val Ala Arg Thr Gly Arg Val Ile Thr Ala Ala Ala Leu Val Met
        355                 360                 365

Ser Met Ser Phe Ala Ala Leu Ile Ala Ala His Val Ser Phe Met Arg
    370                 375                 380

Met Phe Gly Leu Gly Leu Thr Leu Ala Val Ala Ala Asp Ala Thr Leu
385                 390                 395                 400

Val Arg Met Val Val Val Pro Ala Phe Met His Val Thr Gly Arg Trp
                405                 410                 415

Asn Trp Trp Ala Pro Arg Pro Leu Ala Trp Leu His Glu Arg Phe Gly
            420                 425                 430

Val Ser Glu Ala Ala Glu Pro Val Ser Arg Arg Arg Ser His Ala Gly
        435                 440                 445

Gly Leu Gly Lys Ile Ala Gly Arg Ser Asp Gly Gln Thr Ile Pro Ala
    450                 455                 460

Ser Leu Thr Arg Asn Gly
465                 470


<210> SEQ ID NO 82
<211> LENGTH: 1410
<212> TYPE: DNA
<213> ORGANISM: Mycobacterium tuberculosis

<400> SEQUENCE: 82

gtggctaccg tggcattcgt cgcgaccgcg tcgatcgtga tcaccccggc cgcgattgtg      60

ttgctaggtc ctcggctaga tgcgttggac gtgcgccgac tggtgcgtcg gctgctgggc     120

cggcccgatc cggtgcacaa accggtcaag caactgttct ggtaccggtc gagcaagttc     180

gtgatgcgcc gttggctgcc ggtcggtacg gctgttgtcg cgctgctggt gctgctcggg     240

ctgccgttct tgtcggtgaa gtggggtttc ccggacgacc gggtgttgcc gcggtcggcg     300

tcggcccgtc aagtcggcga tatcttgcgc gatgactttg gccacgatcc tgcgacgcag     360

atacccatcg tcgtcccgga cgctcgtggt ctcggcccgg tcgaacttga cagctacgca     420

gccgagttgt cccgggtgcc cgacgtatcc gcggtagccg ccccgacggg cacgttcgta     480

gacggcagct gggtgggaac gccgcgcggg gccaccgggt tggctgaggg cagcgcgttc     540

ctgacggtga gcagcacggc gccgctgttt tcgcgagcct ccgatatcca gctcaagcgg     600

ttgcaccagg tggcagggcc ggccggtcga tccgtcgtga tggccggtgt cgcgcaggtc     660

aaccgcgaca gtgtcgacgc ggtgaccgat cggcttccga tggtgctagg gctaattgcc     720

gcgatcacct acgtactgtt gttcctgctc accggcagcg tggtgctgcc ggcgaaagcg     780

ttggtttgta atgtgttatc gctgaccgcg gcgtttggcg cgttggtgtg gatcttccag     840

gaaggccatt tcggtgccct gggaacgact ccgagcggga cgttggtggc gaatatgccg     900

gtcctactgt tttgcatcgc attcggtttg tccatggact acgaggtgtt tctggtctcc     960

aggattcggg agtactggtt ggaatccgga gccgcgcgac ccgcgcgaag aagcgtcgca    1020

gaggtgcacg ccgccaacga cgagagcgtc gcgctcggcg tggcccgcac cggtcgggtg    1080

atcaccgcgg cagcgttggt gatgtccatg tcgttcgccg cgttgatcgc tgcgcacgtg    1140

tcgttcatgc ggatgttcgg cctcggcctg actttagccg tggctgcaga cgccacactg    1200

gtgcggatgg tcgtggtccc agcattcatg catgtgacgg gccgctggaa ttggtgggca    1260
```

ccgagacccc tggcgtggct gcatgagcgg ttcggtgtca gcgaggcagc agagccggtt 1320
tcgaggagac gttcccacgc cggtgggttg ggcaagattg ccggacgaag cgacggtcag 1380
acgatccctg cctcgctgac gcgcaatggt 1410

<210> SEQ ID NO 83
<211> LENGTH: 216
<212> TYPE: PRT
<213> ORGANISM: Mycobacterium tuberculosis

<400> SEQUENCE: 83

Met Thr Ser Gly Ala Ala Ala Ser Ala Ser Arg Val Asp His Pro Leu
1 5 10 15

Phe Ala Arg Ile Trp Pro Val Val Ala Ala His Glu Ala Glu Ala Ile
20 25 30

Arg Ala Leu Arg Arg Glu Asn Leu Ala Gly Leu Ser Gly Arg Val Leu
35 40 45

Glu Val Gly Ala Gly Val Gly Thr Asn Phe Ala Tyr Tyr Pro Val Ala
50 55 60

Val Glu Gln Val Ile Ala Met Glu Pro Glu Pro Arg Leu Ala Ala Lys
65 70 75 80

Ala Arg Ile Ala Ala Ala Asp Ala Pro Val Pro Ile Val Val Thr Asp
85 90 95

Lys Thr Val Glu Glu Phe Arg Asp Thr Glu Thr Phe Asp Ala Val Val
100 105 110

Cys Ser Leu Val Leu Cys Ser Val Ser Asp Pro Gly Ala Val Leu Ala
115 120 125

His Leu Arg Ser Leu Leu Arg Arg Gly Gly Glu Leu Arg Tyr Leu Glu
130 135 140

His Val Ala Ser Ala Gly Ala Arg Gly Arg Val Gln Arg Phe Val Asp
145 150 155 160

Ala Thr Phe Trp Pro Arg Leu Ala Gly Asn Cys His Thr His Arg His
165 170 175

Thr Glu Arg Ala Ile Leu Asp Ala Gly Phe Val Val Asp Ser Ser Arg
180 185 190

Arg Glu Trp Ala Phe Pro Ala Trp Val Pro Leu Pro Val Ser Glu Leu
195 200 205

Ala Leu Gly Arg Ala His Arg Thr
210 215

<210> SEQ ID NO 84
<211> LENGTH: 648
<212> TYPE: DNA
<213> ORGANISM: Mycobacterium tuberculosis

<400> SEQUENCE: 84
atgacgtcag gcgcggccgc ttcggcgtcc agggtcgacc acccgctttt cgcccggatc 60
tggcccgtgg tcgccgcaca cgaagccgaa gcaatacgag ccctccgccg ggagaatctg 120
gccggtttgt cggggcgggt gttggaagtc ggggccggcg tcgggacgaa ctttgcctac 180
tacccggtgg ccgtcgaaca ggtcatcgcc atggagcccg agccgcggct tgctgccaag 240
gcccgcatcg cggccgctga cgcacccgtt ccgatagtcg tgacggacaa gacggtcgag 300
gagttccgcg acaccgagac gtttgacgcg gtggtttgct cgctggtgct gtgctcggtg 360
agcgacccgg gcgcggtgct ggcgcacctg cgttcgctac tacggcgagg cggggagctg 420
cgctatctcg agcatgtggc cagcgccggc gctcggggcc gggtgcagcg gttcgtcgac 480
gcgacatttt ggcccaggct ggcgggcaac tgtcacacgc atcgccatac cgaacgcgcg 540
atcctcgacg ccggattcgt ggtggacagc tcccggcggg agtgggcatt tcccgcctgg 600
gtgccgctac cggtgtcaga gttggctctg ggccgcgcgc accggacc 648

<210> SEQ ID NO 85
<211> LENGTH: 108
<212> TYPE: PRT
<213> ORGANISM: Mycobacterium tuberculosis

<400> SEQUENCE: 85

Met Ser Gly Gly Ser Ser Arg Arg Tyr Pro Pro Glu Leu Arg Glu Arg
1 5 10 15

Ala Val Arg Met Val Ala Glu Ile Arg Gly Gln His Asp Ser Glu Trp
20 25 30

Ala Ala Ile Ser Glu Val Ala Arg Leu Leu Gly Val Gly Cys Ala Glu
35 40 45

Thr Val Arg Lys Trp Val Arg Gln Ala Gln Val Asp Ala Gly Ala Arg
50 55 60

Pro Gly Thr Thr Thr Glu Glu Ser Ala Glu Leu Lys Arg Leu Arg Arg
65 70 75 80

Asp Asn Ala Glu Leu Arg Arg Ala Asn Ala Ile Leu Lys Thr Ala Ser
85 90 95

Ala Phe Phe Ala Ala Glu Leu Asp Arg Pro Ala Arg
100 105

<210> SEQ ID NO 86
<211> LENGTH: 324
<212> TYPE: DNA
<213> ORGANISM: Mycobacterium tuberculosis

<400> SEQUENCE: 86
atgtcaggtg gttcatcgag gaggtacccg ccggagctgc gtgagcgggc ggtgcggatg 60
gtcgcagaga tccgcggtca gcacgattcg gagtgggcag cgatcagtga ggtcgcccgt 120
ctacttggtg ttggctgcgc ggagacggtg cgtaagtggg tgcgccaggc gcaggtcgat 180
gccggcgcac ggcccgggac cacgaccgaa gaatccgctg agctgaagcg cttgcggcgg 240
gacaacgccg aattgcgaag ggcgaacgcg attttaaaga ccgcgtcggc tttcttcgcg 300
gccgagctcg accggccagc acgc 324

<210> SEQ ID NO 87
<211> LENGTH: 489
<212> TYPE: PRT
<213> ORGANISM: Mycobacterium tuberculosis

<400> SEQUENCE: 87

Val Thr Asn Asp Leu Pro Asp Val Arg Glu Arg Asp Gly Gly Pro Arg
1 5 10 15

Pro Ala Pro Pro Ala Gly Gly Pro Arg Leu Ser Asp Val Trp Val Tyr
20 25 30

Asn Gly Arg Ala Tyr Asp Leu Ser Glu Trp Ile Ser Lys His Pro Gly
35 40 45

Gly Ala Phe Phe Ile Gly Arg Thr Lys Asn Arg Asp Ile Thr Ala Ile
50 55 60

Val Lys Ser Tyr His Arg Asp Pro Ala Ile Val Glu Arg Ile Leu Gln
65 70 75 80

Arg Arg Tyr Ala Leu Gly Arg Asp Ala Thr Pro Arg Asp Ile His Pro

```
                85                  90                  95

Lys His Asn Ala Pro Ala Phe Leu Phe Lys Asp Asp Phe Asn Ser Trp
            100                 105                 110

Arg Asp Thr Pro Lys Tyr Arg Phe Asp Asp Pro Asn Asp Leu Leu His
        115                 120                 125

Arg Val Lys Ala Arg Leu Ala Glu Pro Ala Leu Ala Ala Arg Ile Lys
    130                 135                 140

Arg Met Asp Thr Leu Phe Asn Ala Ile Val Ala Val Leu Ala Val Gly
145                 150                 155                 160

Tyr Phe Ala Val Gln Gly Val Arg Leu Val Glu Pro Ser Trp Met Pro
                165                 170                 175

Leu Trp Ala Phe Val Ile Ala Met Val Leu Leu Arg Ser Ser Leu Ala
            180                 185                 190

Gly Phe Gly His Tyr Ala Leu His Arg Ala Gln Arg Gly Leu Asn Arg
        195                 200                 205

Val Phe Asn Asn Ala Phe Asp Leu Asn Tyr Val Ala Leu Ser Leu Val
    210                 215                 220

Thr Ala Asp Gly His Thr Leu Leu His His Pro Tyr Thr Gln Ser Glu
225                 230                 235                 240

Val Asp Ile Lys Lys Asn Val Phe Thr Met Met Met Arg Leu Pro Trp
                245                 250                 255

Leu Tyr Arg Val Pro Val His Thr Ile His Lys Phe Gly His Met Leu
            260                 265                 270

Ser Gly Met Ala Ile Arg Ile Val Asp Val Phe Arg Ile Thr Arg Lys
        275                 280                 285

Val Gly Val Glu Glu Ser Tyr Gly Ser Trp Arg Ala Ala Leu Pro His
    290                 295                 300

Phe Leu Gly Ser Ala Gly Val Arg Leu Leu Leu Val Ser Glu Leu Val
305                 310                 315                 320

Val Phe Ala Ile Ala Gly Asp Phe Trp Pro Trp Ala Leu Gln Phe Val
                325                 330                 335

Ala Thr Leu Trp Val Ser Thr Phe Leu Val Val Ala Ser His Glu Phe
            340                 345                 350

Glu Asp Asp Thr Gln Gly Gly Ala Val Asn Gly Glu Asp Trp Gly Ile
        355                 360                 365

Asp Gln Leu Glu His Ala Asn Asp Leu Thr Val Ile Gly Asn Arg Tyr
    370                 375                 380

Val Asp Cys Phe Leu Ser Ala Gly Leu Ser Ser His Arg Val His His
385                 390                 395                 400

Val Leu Pro Phe Gln Arg Ser Gly Phe Ala Asn Ile Val Thr Glu Asp
                405                 410                 415

Val Leu Arg Glu Glu Ala Ala Lys Phe Gly Val Glu Trp Leu Pro Ala
            420                 425                 430

Lys Gly Phe Ile Thr Asp Arg Leu Pro Arg Leu Cys Arg Lys Tyr Leu
        435                 440                 445

Leu Thr Pro Ser Arg Gln Ala Lys Glu Arg His Trp Gly Phe Val Arg
    450                 455                 460

Glu His Cys Ser Pro Ala Ala Leu Lys Ala Ser Ala Ser Tyr Val Val
465                 470                 475                 480

Ala Gly Phe Val Gly Ile Gly Ser Val
                485
```

<210> SEQ ID NO 88
<211> LENGTH: 1467

-continued

<212> TYPE: DNA
<213> ORGANISM: Mycobacterium tuberculosis

<400> SEQUENCE: 88
gtgacaaacg acctcccaga cgtccgagag cgtgacggcg gtccacgtcc cgctcctcct 60
gctggcgggc cacgcttgtc agacgtgtgg gtttacaacg ggcgggcgta cgacctgagt 120
gagtggattt ccaagcatcc cggcggcgcc ttcttcattg ggcggaccaa gaaccgcgac 180
atcaccgcaa tcgtcaagtc ctaccatcgt gatccggcga ttgtcgagcg aatcctgcag 240
cggaggtacg cgttgggccg cgacgcaacc cctagggaca tccaccccaa gcacaatgca 300
ccggcatttc tgttcaaaga cgacttcaac agctggcggg acaccccgaa gtatcgattc 360
gacgacccca acgatctgct gcaccgggtc aaagcgcggc tagccgagcc agcgctggcc 420
gcccggatca agcgcatgga cacactcttc aacgccatcg ttgcagtact ggccgtgggt 480
tatttcgcgg ttcagggtgt gcggttggtg gaaccgagct ggatgccgct gtgggccttc 540
gtgattgcga tggttctgct gcgcagttcg ttggccgggt tcggtcatta cgcactgcac 600
cgcgcgcaac gaggcctcaa ccgggttttc aacaatgcct tcgatctcaa ctatgtggcc 660
ttgtccttag tcaccgccga cggacacacc ctgctgcacc acccgtatac ccagagcgag 720
gtggacatca agaagaacgt gttcacgatg atgatgcggc taccgtggtt gtatcgcgtt 780
cccgtacata cgattcacaa atttggccac atgctcagcg gcatggcgat ccggatcgtc 840
gacgtcttca ggatcacgcg caaggtaggt gtcgaggaat cctacggaag ctggcgcgcc 900
gcgcttccac acttccttgg atcggccggg gtgcgcttgc ttctggtgag tgaattggtg 960
gtcttcgcga tcgccggcga cttctggccc tgggcactgc aattcgtagc gacgctgtgg 1020
gttagtacct tcttggtggt ggcgagccat gagttcgagg acgacaccca gggcggtgcc 1080
gtcaacggcg aggactgggg catagatcaa ctcgagcacg ctaatgacct aacggtgatc 1140
gggaaccgct acgtcgactg cttcctgtca gccggcctga gctcccaccg agtccatcac 1200
gtgctgccgt ttcagcgcag cggcttcgcg aacatcgtca ccgaggacgt tttgcgtgag 1260
gaagcagcga agttcggtgt cgagtggctt cccgcaaagg gtttcatcac cgatcggctg 1320
ccgaggctgt gtcggaagta tctgttgacg ccgtcgcgcc aagccaagga gcgtcattgg 1380
ggtttcgtcc gcgagcactg ctcgccggcg gcattgaaag ccagtgccag ctacgtggtt 1440
gcgggtttcg tcggaatcgg gtcggta 1467

<210> SEQ ID NO 89
<211> LENGTH: 393
<212> TYPE: PRT
<213> ORGANISM: Mycobacterium tuberculosis

<400> SEQUENCE: 89

Met Asn Val Ser Ala Glu Ser Gly Ala Pro Arg Arg Ala Gly Gln Arg
1               5                   10                  15

His Glu Val Gly Leu Ala Gln Leu Pro Pro Ala Pro Pro Thr Thr Val
            20                  25                  30

Ala Val Ile Glu Gly Leu Ala Thr Gly Thr Pro Arg Arg Val Val Asn
        35                  40                  45

Gln Ser Asp Ala Ala Asp Arg Val Ala Glu Leu Phe Leu Asp Pro Gly
    50                  55                  60

Gln Arg Glu Arg Ile Pro Arg Val Tyr Gln Lys Ser Arg Ile Thr Thr
65                  70                  75                  80

Arg Arg Met Ala Val Asp Pro Leu Asp Ala Lys Phe Asp Val Phe Arg
                85                  90                  95

```
Arg Glu Pro Ala Thr Ile Arg Asp Arg Met His Leu Phe Tyr Glu His
            100                 105                 110

Ala Val Pro Leu Ala Val Asp Val Ser Lys Arg Ala Leu Ala Gly Leu
        115                 120                 125

Pro Tyr Arg Ala Ala Glu Ile Gly Leu Leu Val Leu Ala Thr Ser Thr
    130                 135                 140

Gly Phe Ile Ala Pro Gly Val Asp Val Ala Ile Val Lys Glu Leu Gly
145                 150                 155                 160

Leu Ser Pro Ser Ile Ser Arg Val Val Val Asn Phe Met Gly Cys Ala
                165                 170                 175

Ala Ala Met Asn Ala Leu Gly Thr Ala Thr Asn Tyr Val Arg Ala His
            180                 185                 190

Pro Ala Met Lys Ala Leu Val Val Cys Ile Glu Leu Cys Ser Val Asn
        195                 200                 205

Ala Val Phe Ala Asp Asp Ile Asn Asp Val Val Ile His Ser Leu Phe
    210                 215                 220

Gly Asp Gly Cys Ala Ala Leu Val Ile Gly Ala Ser Gln Val Gln Glu
225                 230                 235                 240

Lys Leu Glu Pro Gly Lys Val Val Val Arg Ser Ser Phe Ser Gln Leu
                245                 250                 255

Leu Asp Asn Thr Glu Asp Gly Ile Val Leu Gly Val Asn His Asn Gly
            260                 265                 270

Ile Thr Cys Glu Leu Ser Glu Asn Leu Pro Gly Tyr Ile Phe Ser Gly
        275                 280                 285

Val Ala Pro Val Val Thr Glu Met Leu Trp Asp Asn Gly Leu Gln Ile
    290                 295                 300

Ser Asp Ile Asp Leu Trp Ala Ile His Pro Gly Gly Pro Lys Ile Ile
305                 310                 315                 320

Glu Gln Ser Val Arg Ser Leu Gly Ile Ser Ala Glu Leu Ala Ala Gln
                325                 330                 335

Ser Trp Asp Val Leu Ala Arg Phe Gly Asn Met Leu Ser Val Ser Leu
            340                 345                 350

Ile Phe Val Leu Glu Thr Met Val Gln Gln Ala Glu Ser Ala Lys Ala
        355                 360                 365

Ile Ser Thr Gly Val Ala Phe Ala Phe Gly Pro Gly Val Thr Val Glu
    370                 375                 380

Gly Met Leu Phe Asp Ile Ile Arg Arg
385                 390
```

```
<210> SEQ ID NO 90
<211> LENGTH: 1179
<212> TYPE: DNA
<213> ORGANISM: Mycobacterium tuberculosis

<400> SEQUENCE: 90

atgaacgtct cagctgagag cggtgcgccg cgccgggccg gccagaggca tgaggttggc      60

cttgcccagt tgccgccggc tccgcccacc acggtggcgg tgattgaagg gcttgcgacg     120

ggcacgccgc gtcgggtagt caaccagtcc gacgccgccg atcgggtcgc cgagcttttc     180

ctcgatcccg gtcagcggga acggattccg cgggtgtatc aaaaatcgcg gatcaccacg     240

cgccggatgg cggtcgaccc gctcgacgcc aaatttgatg tcttcaggcg ggaacctgcg     300

acgatccgtg atcggatgca tctgttctac gaacacgcgg ttccgctggc ggtggacgtg     360

agcaagcgtg ccctggccgg cctgccatac cgtgccgccg agatcgggct gctggtgttg     420
```

```
gccaccagca ccggattcat cgcgccgggc gtggacgttg cgatcgtcaa agagctcggg    480

ctctccccgt cgatatcacg tgtcgtggtc aatttcatgg gatgtgccgc cgcgatgaat    540

gccctgggca ccgccaccaa ctatgttcgt gcccacccgg ccatgaaggc gctggtggtg    600

tgtatcgaat tgtgctcggt gaacgctgtt tttgccgacg acatcaacga cgtcgtcatt    660

cacagcttgt ttggcgacgg gtgcgcggcg ttggtgatcg gcgccagcca ggttcaggag    720

aagctcgagc caggcaaggt ggtagtccgc agtagtttca gtcagctgct cgacaacacc    780

gaagacggta tcgtgcttgg cgtcaatcac aacggcatca cctgcgagct gtcggagaat    840

ctccccggct acatcttcag cggggtcgca ccggtggtga cagagatgtt atgggacaat    900

ggattacaga tatccgatat cgatctctgg gcgatccatc cgggtggccc caagatcatc    960

gagcagtcgg tgcgctcgct ggggatctcc gcggagctgg cggcgcagag ctgggacgtg   1020

ctcgcccgct tcggcaacat gctcagcgta tcgcttatct ttgtgctaga gacgatggtg   1080

cagcaggcgg agtcggccaa agccatctcg acgggggtgg cgttcgcgtt cgggccgggc   1140

gtcactgtcg aaggcatgct gttcgacatc atccgacgg                          1179
```

<210> SEQ ID NO 91
<211> LENGTH: 326
<212> TYPE: PRT
<213> ORGANISM: Mycobacterium tuberculosis

<400> SEQUENCE: 91

```
Met Asn Ser Glu His Pro Met Thr Asp Arg Val Val Tyr Arg Ser Leu
1               5                   10                  15

Met Ala Asp Asn Leu Arg Trp Asp Ala Leu Gln Leu Arg Asp Gly Asp
            20                  25                  30

Ile Ile Ile Ser Ala Pro Ser Lys Ser Gly Leu Thr Trp Thr Gln Arg
        35                  40                  45

Leu Val Ser Leu Leu Val Phe Asp Gly Pro Asp Leu Pro Gly Pro Leu
    50                  55                  60

Ser Thr Val Ser Pro Trp Leu Asp Gln Thr Ile Arg Pro Ile Glu Glu
65                  70                  75                  80

Val Val Ala Thr Leu Asp Ala Gln Gln His Arg Arg Phe Ile Lys Thr
                85                  90                  95

His Thr Pro Leu Asp Gly Leu Val Leu Asp Asp Arg Val Ser Tyr Ile
            100                 105                 110

Cys Val Gly Arg Asp Pro Arg Asp Ala Ala Val Ser Met Leu Tyr Gln
        115                 120                 125

Ser Ala Asn Met Asn Glu Asp Arg Met Arg Ile Leu His Glu Ala Val
    130                 135                 140

Val Pro Phe His Glu Arg Ile Ala Pro Pro Phe Ala Glu Leu Gly His
145                 150                 155                 160

Ala Arg Ser Pro Thr Glu Glu Phe Arg Asp Trp Met Glu Gly Pro Asn
                165                 170                 175

Gln Pro Pro Pro Gly Ile Gly Phe Thr His Leu Lys Gly Ile Gly Thr
            180                 185                 190

Leu Ala Asn Ile Leu His Gln Leu Gly Thr Val Trp Val Arg Arg His
        195                 200                 205

Leu Pro Asn Val Ala Leu Phe His Tyr Ala Asp Tyr Gln Ala Asp Leu
    210                 215                 220

Ala Gly Glu Leu Leu Arg Pro Ala Arg Val Leu Gly Ile Ala Ala Thr
225                 230                 235                 240

Arg Asp Arg Ala Arg Asp Leu Ala Gln Tyr Ala Thr Leu Asp Ala Met
```

-continued

```
                245                 250                 255

Arg Ser Arg Ala Ser Glu Ile Ala Pro Asn Thr Thr Asp Gly Ile Trp
            260                 265                 270

His Ser Asp Glu Arg Phe Phe Arg Arg Gly Gly Ser Gly Asp Trp Gln
        275                 280                 285

Gln Phe Phe Thr Glu Ala Glu His Leu Arg Tyr Tyr His Arg Ile Asn
    290                 295                 300

Gln Leu Ala Pro Pro Asp Leu Leu Ala Trp Ala His Glu Gly Arg Arg
305                 310                 315                 320

Gly Tyr Asp Pro Ala Asn
                325
```

<210> SEQ ID NO 92
<211> LENGTH: 978
<212> TYPE: DNA
<213> ORGANISM: Mycobacterium tuberculosis

<400> SEQUENCE: 92

```
atgaattcag aacacccgat gaccgaccgg gttgtgtatc gatcgttgat ggccgacaac     60

ctgcgatggg atgccctgca attgcgcgac ggcgacatca ttatctcggc gccgtccaag    120

agcggcctga cctggacaca gcgcctggtg tccctgctgg tgttcgacgg gcccgacttg    180

cccggaccct tgtcgacggt gtccccgtgg ctcgaccaga ccattcggcc catcgaggaa    240

gtggtcgcta ctctcgatgc ccagcagcac cgccggttca tcaagaccca cacgccgttg    300

gacggcctgg tgctcgacga ccgcgtcagc tacatctgcg taggacgcga cccgcgcgat    360

gccgcggtgt caatgctgta ccaatcggcc aacatgaacg aagaccggat gcggattctg    420

cacgaggccg tagtgccgtt tcacgagcga atcgcccccc cgtttgcgga actcggtcat    480

gcgcgcagcc cgaccgagga gttccgggat tggatggagg ggccgaatca gcctccccct    540

ggcataggtt tcacacatct gaaggggatc ggcactctgg ccaacatcct gcaccagcta    600

ggcacggtat gggtccgccg tcacctaccc aacgtggcct tgtttcatta cgccgattac    660

caggcggact tggcgggcga gctgctccgg ccggcaaggg tcctcggtat cgccgcgacc    720

cgcgatcgag cccgggacct ggcgcagtac gccacgctgg atgcgatgcg ctcccgcgcg    780

tcagaaatcg ctcctaacac caccgacggc atctggcaca gtgacgagcg tttcttccgc    840

cggggcggga gtggcgactg gcagcagttc ttcaccgaag ccgagcacct gcgctactac    900

caccgcatca accagctggc gccacctgat ctgctggcct gggcacacga gggccgccgg    960

ggatacgacc cggccaac                                                  978
```

<210> SEQ ID NO 93
<211> LENGTH: 422
<212> TYPE: PRT
<213> ORGANISM: Mycobacterium tuberculosis

<400> SEQUENCE: 93

```
Val Ala Glu Ala Gly Gly Gly Pro Ile Ser Val Ile Ala Arg His Met
1               5                   10                  15

Gln Leu Ile Arg Asp Asp Phe Ile Ser Glu Leu Phe Asp Lys Met Lys
            20                  25                  30

Ala Glu Ile Arg Gly Leu Asp Tyr Asp Ala Arg Met Ala Asp Leu Trp
        35                  40                  45

Arg Ala Ser Ile Thr Glu Asn Phe Val Thr Ala Val His Tyr Leu Asp
    50                  55                  60

Arg Asp Thr Pro Gln Ser Leu Val Glu Ala Pro Ala Ala Ala Leu Ala
```

-continued 65 70 75 80

Tyr Ala Arg Ala Ala Ala Gln Arg Asp Ile Pro Leu Ser Gly Leu Val
85 90 95

Arg Ala His Arg Leu Gly His Ala Arg Phe Leu Glu Val Ala Met Gln
100 105 110

Tyr Val Ser Leu Leu Glu Pro Ala Asp Arg Val Ser Thr Ile Ile Glu
115 120 125

Leu Val Asn Arg Ser Ala Arg Leu Val Asp Leu Val Ala Asp Gln Leu
130 135 140

Ile Val Ala Tyr Glu His Glu His Asp Arg Trp Leu Ser Arg Arg Ser
145 150 155 160

Gly Leu Gln Gln Gln Trp Val Ser Glu Leu Leu Ala Asp Thr Pro Val
165 170 175

Asp Val Pro Arg Ala Glu Arg Ala Leu Gly Tyr Arg Leu Asp Gly Val
180 185 190

His Ile Ala Ala Val Val Trp Val Asp Ser Ala Val Pro Ile Gly Asp
195 200 205

Val Val Ala Gln Phe Asp Gln Val Arg Cys Leu Leu Ala Gly Glu Leu
210 215 220

Gly Pro Glu Leu Gly Pro Val Ala Asn Ser Leu Met Val Pro Thr Asp
225 230 235 240

Glu Arg Glu Ala Arg Leu Trp Phe Ser Pro Ala Pro Thr Arg Ala Phe
245 250 255

Ala Pro Ser Arg Ile Arg Ala Ala Phe Glu Ser Ala Gly Ile Arg Ala
260 265 270

Arg Leu Ala Cys Gly Arg Val Gly Asp Gly Leu Arg Gly Phe Arg Ala
275 280 285

Ser Leu Lys Gln Ala Glu Arg Val Lys Ala Leu Ala Leu Ala Gly Gly
290 295 300

Ala Arg Pro Gly Gly Arg Val Met Phe Tyr Asp Asp Val Ala Pro Val
305 310 315 320

Ala Leu Leu Ala Asp Asp Leu Glu Glu Leu Arg Arg Phe Val Thr Asp
325 330 335

Val Leu Gly Asp Leu Ser Val Asp Asp Glu Arg Asn Ser Trp Leu Arg
340 345 350

Glu Thr Leu Arg Glu Phe Leu Leu Arg Asn Arg Ser Tyr Val Ala Thr
355 360 365

Ala Asp Ala Met Ile Leu His Arg Asn Thr Ile Gln Tyr Arg Val Ile
370 375 380

Gln Ala Met Glu Leu Cys Gly Gln Asn Leu Asp Asp Pro Asp Ala Ala
385 390 395 400

Phe Arg Val Gln Met Ala Leu Glu Val Cys Arg Trp Met Ala Pro Ala
405 410 415

Val Leu Arg Ala Lys Gln
420

<210> SEQ ID NO 94
<211> LENGTH: 1266
<212> TYPE: DNA
<213> ORGANISM: Mycobacterium tuberculosis

<400> SEQUENCE: 94
gtggctgaag ctggtggcgg gcccatttcg gtgatcgccc ggcatatgca gttgattcgc 60
gatgacttca tctccgagtt gtttgacaag atgaaggcgg agattcgggg gctggattac 120

```
gacgcgcgga tggcggacct gtggcgggcg agcatcaccg agaatttcgt gacggccgtt    180

cactatttgg atcgcgatac gccgcagtcc ttggtggagg ctccagcggc cgcgctggca    240

tacgcccgcg ccgcggcgca gcgtgatatt ccgttgtccg ggttggttcg ggcgcaccgg    300

ctcgggcatg cgcgtttctt ggaggtggcg atgcagtacg tgtcgctgct ggagcccgct    360

gaccgggtgt cgacgatcat cgagctggtg aatcgctccg ctcgcctcgt tgacctggtg    420

gccgaccagt tgattgtcgc ctatgagcac gaacacgatc gctggctgag tcgccgcagc    480

ggtctgcaac agcaatgggt cagcgagctg ctcgccgata ccccggtcga cgttccgcgg    540

gccgagcgcg cgttgggcta tcggttggac ggtgtgcata tcgccgcggt ggtatgggtc    600

gattcggcgg tgcccatcgg tgatgtggtg gcgcaattcg accaggtgcg ctgcttgctg    660

gccggggagc tgggccccga actgggcccc gtggcgaact cgctgatggt gccgaccgat    720

gagcgcgagg cacggctgtg gttttcgccc gcgcccacgc gggccttcgc cccgtcgcgg    780

attcgcgcgg cgttcgagtc ggcgggaatc cgggcgcgtt tggcgtgcgg tcgggtaggg    840

gacgggctgc gtgggttccg ggcgtcgttg aaacaggccg aacgagtgaa ggcgttggcc    900

ctggccggtg gcgcccggcc cggcggccgg gtcatgtttt atgacgatgt cgcgccagtc    960

gcgttgctgg ccgacgatct agaggaactg cggcggttcg tcaccgatgt gctgggtgac   1020

ctgagtgttg acgacgagcg caatagctgg ctacgcgaga cgttacggga gttcttgctg   1080

cgtaaccgca gctacgtcgc cacggccgac gcgatgatcc tgcaccgcaa caccattcaa   1140

taccgggtga tccaggcgat ggaactatgc ggacagaatc tcgacgatcc cgatgccgcg   1200

tttcgggtgc agatggcgct ggaggtctgc cgctggatgg caccggcggt gctccgcgcc   1260

aaacaa                                                               1266


<210> SEQ ID NO 95
<211> LENGTH: 287
<212> TYPE: PRT
<213> ORGANISM: Mycobacterium tuberculosis

<400> SEQUENCE: 95

Met Lys Leu Ala Arg Pro Asp Val Phe His Pro Arg Val Val Leu Ala
1               5                   10                  15

Gly Trp Pro Gln Gln Pro Ala Gly Asp Gly Asp Asp Ala Gly Leu Val
            20                  25                  30

Ala Ala Leu Arg His Arg Gly Leu His Ala Gly Trp Leu Ser Trp Asp
        35                  40                  45

Asp Pro Glu Ile Val His Ala Asp Leu Val Ile Leu Arg Ala Thr Arg
    50                  55                  60

Asp Tyr Pro Ala Arg Leu Asp Glu Phe Leu Ala Trp Thr Thr Arg Val
65                  70                  75                  80

Ala Asn Leu Leu Asn Ser Arg Pro Val Val Ala Trp Asn Val Glu Arg
                85                  90                  95

Arg Tyr Leu Arg Asp Leu Met Asp Arg Gly Val Pro Thr Val Pro Gly
            100                 105                 110

Glu Val Tyr Val Pro Gly Glu Pro Val Arg Leu Pro Arg Lys Gly Gln
        115                 120                 125

Val Phe Val Gly Pro Thr Ile Gly Thr Gly Thr Arg Arg Cys Ser Ala
    130                 135                 140

Arg Phe Ala Ala Glu Phe Val Ala Gln Leu His Ala Ala Gly Gln Ala
145                 150                 155                 160

Val Leu Val Gln Pro Gly Gly Ser Gly Asp Glu Thr Val Leu Val Phe
                165                 170                 175
```

-continued

```
Leu Gly Gly Glu Pro Ser His Ala Phe Thr Lys Gln Ala Asp Thr Trp
            180                 185                 190

Arg Gln Thr Glu Pro Asp Phe Glu Ile Trp Asp Val Gly Ala Ala Ala
        195                 200                 205

Val Ala Gly Ala Ala Ala Gln Val Gly Val Asp Pro Gly Glu Leu Leu
    210                 215                 220

Tyr Ala Arg Ala His Ile Thr Gly Gly Ser Arg Asp Pro Arg Leu Leu
225                 230                 235                 240

Glu Leu Gln Leu Val Asp Pro Ser Leu Gly Trp Gln Trp Leu Asp Pro
                245                 250                 255

Asp Ile Arg Asn Leu Ala Gln Arg Asp Phe Ala Leu Cys Val Gln Ser
            260                 265                 270

Ala Leu Glu Arg Leu Gly Leu Gly Pro Phe Ser His Arg Arg Pro
        275                 280                 285
```

<210> SEQ ID NO 96
<211> LENGTH: 861
<212> TYPE: DNA
<213> ORGANISM: Mycobacterium tuberculosis

<400> SEQUENCE: 96

```
atgaagcttg cccggccgga cgtcttccat ccgcgcgtcg ttttggcggg ttggccacag     60

cagcccgccg gtgacggcga cgatgctggg ctggttgcgg ccctgcgcca ccgcggcttg    120

catgctggtt ggctgtcttg ggacgatccc gaaatagtcc acgcggatct ggtgattttg    180

cgggctaccc gcgattaccc cgcgcggctc gacgagtttt tggcctggac tacccgcgtg    240

gccaatctgc tgaactcgcg gccggtggtg gcctggaatg tcgagcgccg ttacctacgt    300

gacctgatgg atcggggggt gccgaccgtg cccggcgagg tgtatgtgcc gggagagccg    360

gtccggttgc cacgcaaagg ccaggtcttc gtcggtccga ccatcggtac cgggacacgg    420

cgctgtagtg cccggttcgc tgccgagttc gtcgcgcaac tgcacgcggc cggccaggcg    480

gtgctcgttc agcccggagg ttccggtgac gagaccgtgt tggtcttcct tggcggtgag    540

ccgtcgcatg cgtttaccaa gcaggccgac acttggcgcc agaccgagcc cgacttcgaa    600

atctgggacg tgggtgcggc cgccgtggcc ggcgcggccg cgcaggtggg tgttgaccca    660

ggtgagctgc tctacgcgcg ggcccacatc acaggtggaa gccgagatcc ccggttgctg    720

gaattgcaat tggtggaccc gtcgctgggc tggcagtggc tggacccaga catccgcaat    780

cttgcccagc gtgacttcgc gctatgcgtc cagtcagcgt tggagcggct ggggctgggc    840

ccgttctccc atcgacgccc a                                              861
```

<210> SEQ ID NO 97
<211> LENGTH: 280
<212> TYPE: PRT
<213> ORGANISM: Mycobacterium tuberculosis

<400> SEQUENCE: 97

```
Met Thr Asp Pro Phe Leu Gly Ser Glu Ala Leu Ala Ala Gly Val Leu
1               5                   10                  15

Thr Pro Tyr Glu Leu Arg Ser Arg Tyr Val Ala Leu His Lys Asp Val
            20                  25                  30

Tyr Val Pro Gln Gly Val Glu Leu Thr Ala Gln Leu Arg Ala Lys Ala
        35                  40                  45

Leu Trp Leu Arg Ser Arg Arg Arg Gly Val Leu Ala Gly Tyr Ser Ala
    50                  55                  60
```

Ser Ala Phe His Gly Ala Lys Trp Ile Asp Ala Asp Leu Pro Ala Ala
65 70 75 80

Ile Ile Asp Thr Asn Arg Arg Arg Ala Pro Gly Leu Gln Val Trp Glu
85 90 95

Glu Arg Ile Glu Pro Asp Glu Ile Cys Val Ile Glu Gly Met Arg Val
100 105 110

Thr Thr Pro Glu Arg Thr Ala Leu Asp Leu Thr Ser Arg Phe Pro Leu
115 120 125

Asp Pro Ala Val Ala Ala Val Asp Ala Leu Ile Gln Ala Thr Asp Leu
130 135 140

Lys Val Ala Asp Val Glu Pro Leu Ile Glu Arg Tyr Arg Gly Arg Arg
145 150 155 160

Gly Met Lys Ala Ala Arg Ala Ala Leu Asp Leu Val Asp Gly Gly Ala
165 170 175

Gln Ser Pro Lys Glu Thr Trp Leu Arg Leu Leu Leu Ile Arg Ala Gly
180 185 190

Phe Pro Arg Pro Gln Thr Gln Ile Ala Val Arg Asn Glu Trp Gly Trp
195 200 205

Ala Glu Ala His Leu Asp Met Gly Trp Gln Asp Ile Lys Val Ala Ala
210 215 220

Glu Tyr Asp Gly Asp His His Leu Thr Ser Arg Tyr His Tyr Arg Lys
225 230 235 240

Asp Ile Leu Arg His Glu Lys Val Gln His Arg Tyr Gly Trp Ile Val
245 250 255

Val Arg Val Val Ala Glu Asp His Pro Ala Asp Ile Ile Arg Arg Val
260 265 270

Gly Glu Ala Arg Ala Phe Arg Ala
275 280

<210> SEQ ID NO 98
<211> LENGTH: 840
<212> TYPE: DNA
<213> ORGANISM: Mycobacterium tuberculosis

<400> SEQUENCE: 98
atgacggatc cctttctggg cagcgaggcc ctggctgcgg gtgtattgac gccctacgaa 60
ttgcgcagca ggtatgtcgc gctacataaa gacgtgtacg tgccgcaggg tgtggaactg 120
accgcgcaat tgcgtgcaaa agcgctgtgg ctgcgctcgc gccgccgcgg cgtgctggcc 180
ggctactcgg cttctgcctt ccatggcgcc aagtggatcg acgcggatct tcccgccgcg 240
atcatcgaca ccaaccgccg ccgtgccccg gggctgcaag tctgggaaga gcgcatcgag 300
cccgacgaga tctgcgtcat cgagggcatg cgcgtgacca caccggagcg aacggcgctc 360
gacctgacca gtcgatttcc attggacccc gccgtcgcgg ccgtcgacgc cctgatacag 420
gccaccgatt tgaaggtggc cgacgtcgag ccgctgatcg agcgctatcg ggccgccgt 480 ggcatgaagg ccgcaagagc cgctctggac ctcgtcgacg gcggtgccca gtcccccaag 540
gaaacctggc tgcgcttgtt gttgatccgc gccggctttc cgcgccccca gacgcagatc 600
gcggtgcgca acgaatgggg ctgggcggaa gcccatttgg atatgggctg gcaagacatc 660
aaggtcgcgg ccgagtatga cggcgaccac catctgacca gtcgctacca ctaccggaaa 720
gacatcctcc ggcacgagaa agtccagcac cgctacgggt ggatcgtggt ccgggtcgtc 780
gccgaggacc accccgctga catcatccgc cgcgtgggcg aggcccgcgc tttccgagcg 840

<210> SEQ ID NO 99

-continued

<211> LENGTH: 334
<212> TYPE: PRT
<213> ORGANISM: Mycobacterium tuberculosis

<400> SEQUENCE: 99

Met Met Ala Ala Ser His Asp Asp Asp Thr Val Asp Gly Leu Ala Thr
1               5                   10                  15

Ala Val Arg Gly Gly Asp Arg Ala Ala Leu Pro Arg Ala Ile Thr Leu
            20                  25                  30

Val Glu Ser Thr Arg Pro Asp His Arg Glu Gln Ala Gln Gln Leu Leu
        35                  40                  45

Leu Arg Leu Leu Pro Asp Ser Gly Asn Ala His Arg Val Gly Ile Thr
    50                  55                  60

Gly Val Pro Gly Val Gly Lys Ser Thr Ala Ile Glu Ala Leu Gly Met
65                  70                  75                  80

His Leu Ile Glu Arg Gly His Arg Val Ala Val Leu Ala Val Asp Pro
                85                  90                  95

Ser Ser Thr Arg Thr Gly Gly Ser Ile Leu Gly Asp Lys Thr Arg Met
            100                 105                 110

Ala Arg Leu Ala Val His Pro Asn Ala Tyr Ile Arg Pro Ser Pro Thr
        115                 120                 125

Ser Gly Thr Leu Gly Gly Val Thr Arg Ala Thr Arg Glu Thr Val Val
    130                 135                 140

Leu Leu Glu Ala Ala Gly Phe Asp Val Ile Leu Ile Glu Thr Val Gly
145                 150                 155                 160

Val Gly Gln Ser Glu Val Ala Val Ala Asn Met Val Asp Thr Phe Val
                165                 170                 175

Leu Leu Thr Leu Ala Arg Thr Gly Asp Gln Leu Gln Gly Ile Lys Lys
            180                 185                 190

Gly Val Leu Glu Leu Ala Asp Ile Val Val Val Asn Lys Ala Asp Gly
        195                 200                 205

Glu His His Lys Glu Ala Arg Leu Ala Ala Arg Glu Leu Ser Ala Ala
    210                 215                 220

Ile Arg Leu Ile Tyr Pro Arg Glu Ala Leu Trp Arg Pro Pro Val Leu
225                 230                 235                 240

Thr Met Ser Ala Val Glu Gly Arg Gly Leu Ala Glu Leu Trp Asp Thr
                245                 250                 255

Val Glu Arg His Arg Gln Val Leu Thr Gly Ala Gly Glu Phe Asp Ala
            260                 265                 270

Arg Arg Arg Asp Gln Gln Val Asp Trp Thr Trp Gln Leu Val Arg Asp
        275                 280                 285

Ala Val Leu Asp Arg Val Trp Ser Asn Pro Thr Val Arg Lys Val Arg
    290                 295                 300

Ser Glu Leu Glu Arg Arg Val Arg Ala Gly Glu Leu Thr Pro Ala Leu
305                 310                 315                 320

Ala Ala Gln Gln Ile Leu Glu Ile Ala Asn Leu Thr Asp Arg
                325                 330

<210> SEQ ID NO 100
<211> LENGTH: 1002
<212> TYPE: DNA
<213> ORGANISM: Mycobacterium tuberculosis

<400> SEQUENCE: 100
atgatggccg catcccacga cgacgacacc gtcgacgggt tggcgacggc cgtgcgcggc      60
ggtgaccgtg cggcgctgcc acgggccatc acactggtcg agtcgacccg ccccgaccat     120

```
cgtgagcagg cgcaacagct gctgctgcga ttgctgccgg actccgggaa cgcccatcgc    180

gtcggcatca ccggggtccc gggggtgggc aagtcgactg ccatcgaggc gctgggcatg    240

catctgatcg agcgcgggca tcgggtggcg gtgctggcgg tcgacccgtc gtcgacccgc    300

acgggtggat cgattcttgg tgataaaacc cggatggcgc ggctggcggt gcacccgaac    360

gcctacatcc ggccgtcccc gacgtcggga acgctgggtg ggtgacgag ggccacccgg     420

gaaacggtgg tgctgttgga ggcggccggt tttgatgtga tcctgatcga aaccgtcggg    480

gtgggccagt ccgaggtcgc ggtggccaac atggtcgaca cgttcgtgtt gctgaccttg    540

gcccgcaccg gtgatcagtt gcagggcatc aagaagggcg tgctggagct cgccgacatc    600

gtggtggtga acaaggccga cggggagcac cacaaagagg cccggctggc cgcccgggag    660

ctgtcggcgg cgatcagatt gatctatcct cgcgaagcac tgtggcgccc accggtgctc    720

accatgagcg cggtggaggg caggggactg gccgagctgt gggacaccgt cgagcgtcat    780

cgccaggtgc tcaccggggc cggcgaattc gacgcccgtc ggcgcgatca gcaggtcgac    840

tggacctggc agctggttcg cgacgccgtc ctggatcggg tgtggtccaa tccgacggtg    900

cgcaaggtcc gctccgagct cgagcgtcgg gtccgcgccg gcgaactgac cccggccctg    960

gcggctcagc aaatactgga gatagctaac ctaacggata gg                      1002


<210> SEQ ID NO 101
<211> LENGTH: 426
<212> TYPE: PRT
<213> ORGANISM: Mycobacterium tuberculosis

<400> SEQUENCE: 101

Met Lys Phe Val Leu Ala Val His Gly Thr Arg Gly Asp Val Glu Pro
1               5                   10                  15

Cys Ala Ala Val Gly Val Glu Leu Arg Arg Arg Gly His Ala Val His
            20                  25                  30

Met Ala Val Pro Pro Asn Leu Ile Glu Phe Val Glu Ser Ala Gly Leu
        35                  40                  45

Thr Gly Val Ala Tyr Gly Pro Asp Ser Asp Glu Gln Ile Asn Thr Val
    50                  55                  60

Ala Ala Phe Val Arg Asn Leu Thr Arg Ala Gln Asn Pro Leu Asn Leu
65                  70                  75                  80

Ala Arg Ala Val Lys Glu Leu Phe Val Glu Gly Trp Ala Glu Met Gly
                85                  90                  95

Thr Thr Leu Thr Thr Leu Ala Asp Gly Ala Asp Leu Val Met Thr Gly
            100                 105                 110

Gln Thr Tyr His Gly Val Ala Ala Asn Val Ala Glu Tyr Tyr Asp Ile
        115                 120                 125

Pro Ala Ala Ala Leu His His Phe Pro Met Gln Val Asn Gly Gln Ile
    130                 135                 140

Ala Ile Pro Ser Ile Pro Thr Pro Ala Thr Leu Val Arg Ala Thr Met
145                 150                 155                 160

Lys Val Ser Trp Arg Leu Tyr Ala Tyr Val Ser Lys Asp Ala Asp Arg
                165                 170                 175

Ala Gln Arg Arg Glu Leu Gly Leu Pro Pro Ala Pro Ala Pro Ala Val
            180                 185                 190

Arg Arg Leu Ala Glu Arg Gly Ala Pro Glu Ile Gln Ala Tyr Asp Pro
        195                 200                 205

Val Phe Phe Pro Gly Leu Ala Ala Glu Trp Ser Asp Arg Arg Pro Phe
    210                 215                 220
```

```
Val Gly Pro Leu Thr Met Glu Leu His Ser Glu Pro Asn Glu Glu Leu
225                 230                 235                 240

Glu Ser Trp Ile Ala Ala Gly Thr Pro Pro Ile Tyr Phe Gly Phe Gly
                245                 250                 255

Ser Thr Pro Val Gln Thr Pro Val Gln Thr Leu Ala Met Ile Ser Asp
            260                 265                 270

Val Cys Ala Gln Leu Gly Glu Arg Ala Leu Ile Tyr Ser Pro Ala Ala
        275                 280                 285

Asn Ser Thr Arg Ile Arg His Ala Asp His Val Lys Arg Val Gly Leu
    290                 295                 300

Val Asn Tyr Ser Thr Ile Leu Pro Lys Cys Arg Ala Val Val His His
305                 310                 315                 320

Gly Gly Ala Gly Thr Thr Ala Ala Gly Leu Arg Ala Gly Met Pro Thr
                325                 330                 335

Leu Ile Leu Trp Asp Val Ala Asp Gln Pro Ile Trp Ala Gly Ala Val
            340                 345                 350

Gln Arg Leu Lys Val Gly Ser Ala Lys Arg Phe Thr Asn Ile Thr Arg
        355                 360                 365

Gly Ser Leu Leu Lys Glu Leu Arg Ser Ile Leu Ala Pro Glu Cys Ala
    370                 375                 380

Ala Arg Ala Arg Glu Ile Ser Thr Arg Met Thr Arg Pro Thr Ala Ala
385                 390                 395                 400

Val Thr Ala Ala Ala Asp Leu Leu Glu Ala Thr Ala Arg Gln Thr Pro
                405                 410                 415

Gly Ser Thr Pro Ser Ser Ser Pro Gly Arg
            420                 425
```

<210> SEQ ID NO 102
<211> LENGTH: 1278
<212> TYPE: DNA
<213> ORGANISM: Mycobacterium tuberculosis

<400> SEQUENCE: 102

```
atgaagtttg tcttggcggt ccacggaacc cgcggtgatg tcgaaccttg cgccgcggtt     60

ggcgtggagc tgcggcggcg aggccacgca gttcatatgg cagtgccgcc caacctgatc    120

gagttcgtcg agtcggcagg tctgaccggc gtcgcctacg gcccggactc ggacgaacag    180

atcaacacgg tcgcggcatt cgtccgcaac ctcaccagag cccagaatcc gctcaacctc    240

gcccgcgccg tcaaggaact attcgtcgaa ggctgggcgg agatgggcac gacgttgacc    300

acgttggccg acggcgccga cctggtgatg acgggccaga catatcatgg tgtggcagcc    360

aacgtcgccg agtactacga cattccggct gcggcactgc atcactttcc gatgcaggtc    420

aacggccaaa tcgcgatccc gtcgataccg acgccggcga ctctggtgcg cgcgacgatg    480

aaggtctcat ggcggctgta tgcgtacgtc agcaaggatg ccgatcgcgc gcaacgacgt    540

gaactgggcc taccgccagc accggcgccg gcggtgcgtc ggctggcgga acgcggagcg    600

cccgaaatcc aagcctacga cccggttttt ttccccggac tggcggccga atggagcgac    660

cgccgcccgt ttgtcggccc gctgaccatg gagttacaca gcgaacccaa cgaagaactc    720

gagtcgtgga tcgccgccgg aacaccaccc atctacttcg gcttcggcag cacgcccgtc    780

caaacgcccg tccaaacgct cgccatgatc tccgatgtct gcgcacagct cggcgagcga    840

gccctgatct attctccggc agccaactcc acccgcattc gtcatgccga ccacgtgaaa    900

cgtgtcggcc tggtcaacta ttcgaccatc cttcccaagt gccgcgcggt cgtccaccac    960
```

ggtggcgccg gtaccaccgc cgccggcctg cgagcgggaa tgcccacgct gattctctgg 1020
gacgtggccg atcaaccgat ctgggccggt gccgtccaac gactcaaagt cggctctgcc 1080
aaacgcttta cgaacatcac ccgcgggtca ttgctcaagg agctacgatc gatcctggcg 1140
ccggaatgcg ccgcgcgggc acgtgagatc tcgacacgga tgacccggcc gacagccgcc 1200
gtcaccgcgg ccgcggacct gctggaggcg acggcacgcc aaacgcctgg gagcacgcct 1260
agcagctcgc cgggcagg 1278

<210> SEQ ID NO 103
<211> LENGTH: 165
<212> TYPE: PRT
<213> ORGANISM: Mycobacterium tuberculosis

<400> SEQUENCE: 103

Val Thr Gln Leu Pro Gln Pro Thr Trp Arg Trp Trp Gln Gln Arg Glu
1 5 10 15

Thr Glu Gln Val Gln Ser Ser His Ile Asp Gly Glu Ile Val Gly Ala
20 25 30

Leu Ile Pro Asp Leu Ala Val Leu His Ser Glu Asp Ala Ser Arg Ala
35 40 45

Ala Val Gly Arg Glu Lys His Arg Cys Ser Leu Asp Pro Leu Gly Gly
50 55 60

Gly Phe Arg Ser Arg Arg Ala Ser Met Pro Ala Gly Ala Leu Leu Leu
65 70 75 80

Ser Ala Val Ile Ala Ile Gln Leu Asp Arg Met Asn Ala Arg Val Phe
85 90 95

Gly Asp Gly Trp Ile Gly Ala Gln Ala Cys Met Trp Val Asn Lys Phe
100 105 110

His Glu Glu Ser Thr Val Thr Ala Leu Ser Pro Ser Ser Pro Ile Ala
115 120 125

Gln Gly Ser Ile Ala Arg His Pro Glu Thr Met Gln Ser Ala Tyr Val
130 135 140

Arg Ile Ala Glu Gly Gly Ser Arg Asp Val Ala Pro Ala Ala Gln Leu
145 150 155 160

Gln Arg Arg Arg Pro
165

<210> SEQ ID NO 104
<211> LENGTH: 495
<212> TYPE: DNA
<213> ORGANISM: Mycobacterium tuberculosis

<400> SEQUENCE: 104
gtgactcagc ttccacaacc aacctggcgc tggtggcagc aaagagagac ggagcaggtg 60
cagtccagcc acatcgacgg agaaatagtc ggcgcgttga tccctgacct ggcggtgctg 120
cacagcgagg atgcctcacg cgcggccgtg ggaagggaaa agcatagatg ctcgttggat 180
cctctaggtg gcggcttccg ttcccgtcgt gcctcgatgc cggccggcgc gcttctgctg 240
tctgcggtca tcgcaataca actggaccgg atgaatgcca gagtattcgg cgatggctgg 300
atcggcgcgc aagcgtgcat gtgggtcaac aagtttcacg aggagagcac cgtcaccgcg 360
ttgtccccca gtagtccgat cgcgcagggc tcgatcgcgc ggcatccaga gacgatgcaa 420
tcggcgtacg tgcgcatcgc cgagggcgga tcgcgcgatg tcgccccagc cgcccagctt 480
cagcgacgac ggcct 495

<210> SEQ ID NO 105
<211> LENGTH: 583
<212> TYPE: PRT
<213> ORGANISM: Mycobacterium tuberculosis

<400> SEQUENCE: 105

Met Thr Ala Gln His Asn Ile Val Val Ile Gly Gly Gly Gly Ala Gly
1               5                   10                  15

Leu Arg Ala Ala Ile Ala Ile Ala Glu Thr Asn Pro His Leu Asp Val
            20                  25                  30

Ala Ile Val Ser Lys Val Tyr Pro Met Arg Ser His Thr Val Ser Ala
        35                  40                  45

Glu Gly Gly Ala Ala Ala Val Thr Gly Asp Asp Asp Ser Leu Asp Glu
    50                  55                  60

His Ala His Asp Thr Val Ser Gly Gly Asp Trp Leu Cys Asp Gln Asp
65                  70                  75                  80

Ala Val Glu Ala Phe Val Ala Glu Ala Pro Lys Glu Leu Val Gln Leu
                85                  90                  95

Glu His Trp Gly Cys Pro Trp Ser Arg Lys Pro Asp Gly Arg Val Ala
            100                 105                 110

Val Arg Pro Phe Gly Gly Met Lys Lys Leu Arg Thr Trp Phe Ala Ala
        115                 120                 125

Asp Lys Thr Gly Phe His Leu Leu His Thr Leu Phe Gln Arg Leu Leu
    130                 135                 140

Thr Tyr Ser Asp Val Met Arg Tyr Asp Glu Trp Phe Ala Thr Thr Leu
145                 150                 155                 160

Leu Val Asp Asp Gly Arg Val Cys Gly Leu Val Ala Ile Glu Leu Ala
                165                 170                 175

Thr Gly Arg Ile Glu Thr Ile Leu Ala Asp Ala Val Ile Leu Cys Thr
            180                 185                 190

Gly Gly Cys Gly Arg Val Phe Pro Phe Thr Thr Asn Ala Asn Ile Lys
        195                 200                 205

Thr Gly Asp Gly Met Ala Leu Ala Phe Arg Ala Gly Ala Pro Leu Lys
    210                 215                 220

Asp Met Glu Phe Val Gln Tyr His Pro Thr Gly Leu Pro Phe Thr Gly
225                 230                 235                 240

Ile Leu Ile Thr Glu Ala Ala Arg Ala Glu Gly Gly Trp Leu Leu Asn
                245                 250                 255

Lys Asp Gly Tyr Arg Tyr Leu Gln Asp Tyr Asp Leu Gly Lys Pro Thr
            260                 265                 270

Pro Glu Pro Arg Leu Arg Ser Met Glu Leu Gly Pro Arg Asp Arg Leu
        275                 280                 285

Ser Gln Ala Phe Val His Glu His Asn Lys Gly Arg Thr Val Asp Thr
    290                 295                 300

Pro Tyr Gly Pro Val Val Tyr Leu Asp Leu Arg His Leu Gly Ala Asp
305                 310                 315                 320

Leu Ile Asp Ala Lys Leu Pro Phe Val Arg Glu Leu Cys Arg Asp Tyr
                325                 330                 335

Gln His Ile Asp Pro Val Val Glu Leu Val Pro Val Arg Pro Val Val
            340                 345                 350

His Tyr Met Met Gly Gly Val His Thr Asp Ile Asn Gly Ala Thr Thr
        355                 360                 365

Leu Pro Gly Leu Tyr Ala Ala Gly Glu Thr Ala Cys Val Ser Ile Asn
    370                 375                 380

Gly Ala Asn Arg Leu Gly Ser Asn Ser Leu Pro Glu Leu Leu Val Phe

```
385                 390                 395                 400

Gly Ala Arg Ala Gly Arg Ala Ala Ala Asp Tyr Ala Ala Arg His Gln
                405                 410                 415

Lys Ser Asp Arg Gly Pro Ser Ser Ala Val Arg Ala Gln Ala Arg Thr
            420                 425                 430

Glu Ala Leu Arg Leu Glu Arg Glu Leu Ser Arg His Gly Gln Gly Gly
        435                 440                 445

Glu Arg Ile Ala Asp Ile Arg Ala Asp Met Gln Ala Thr Leu Glu Ser
    450                 455                 460

Ala Ala Gly Ile Tyr Arg Asp Gly Pro Thr Leu Thr Lys Ala Val Glu
465                 470                 475                 480

Glu Ile Arg Val Leu Gln Glu Arg Phe Ala Thr Ala Gly Ile Asp Asp
                485                 490                 495

His Ser Arg Thr Phe Asn Thr Glu Leu Thr Ala Leu Leu Glu Leu Ser
            500                 505                 510

Gly Met Leu Asp Val Ala Leu Ala Ile Val Glu Ser Gly Leu Arg Arg
        515                 520                 525

Glu Glu Ser Arg Gly Ala His Gln Arg Thr Asp Phe Pro Asn Arg Asp
    530                 535                 540

Asp Glu His Phe Leu Ala His Thr Leu Val His Arg Glu Ser Asp Gly
545                 550                 555                 560

Thr Leu Arg Val Gly Tyr Leu Pro Val Thr Ile Thr Arg Trp Pro Pro
                565                 570                 575

Gly Glu Arg Val Tyr Gly Arg
            580


<210> SEQ ID NO 106
<211> LENGTH: 1749
<212> TYPE: DNA
<213> ORGANISM: Mycobacterium tuberculosis

<400> SEQUENCE: 106

atgaccgccc aacacaacat cgtggttatc ggcggcggtg gtgcgggtct gcgcgccgcg     60

attgcgatag ccgaaaccaa tccgcacctg gatgtggcga tcgtttccaa ggtgtacccg    120

atgcgcagcc acaccgtctc ggctgagggc ggcgccgcgg cggtgaccgg tgacgacgac    180

agcctcgatg aacacgcgca cgacacggta tccggtggcg actggctgtg tgaccaagat    240

gcggtcgagg ctttcgtggc cgaggcgccc aaagagttgg tgcagctcga gcattggggc    300

tgtccgtgga gccgtaaacc agacgggcgc gttgccgttc gcccgttcgg cgggatgaag    360

aagctgcgca cctggtttgc cgccgacaag acgggatttc acctcctgca cacgttgttt    420

caacggctgc tcacctattc cgacgtcatg cgctatgacg agtggttcgc tacgacgctg    480

ctggtcgacg acggcagggt atgtggtctg gtcgctatcg agttggcgac cgggcgcatc    540

gagacgatcc ttgccgacgc ggtgattctg tgcaccggcg gatgcgggcg ggtatttcca    600

ttcaccacca acgcgaacat caagaccggc gacggcatgg cgctcgcatt ccgcgcgggc    660

gcgcccctaa aagacatgga attcgtccaa taccacccca ccggactgcc gttcaccggg    720

atcttgatca ccgaggccgc acgagctgaa ggcggctggc tgctcaacaa agacggctac    780

cgctacctcc aggattacga cctcggcaag cccacgcccg agcccaggct gcgcagtatg    840

gagctcgggc ccagggaccg actgtcgcag gccttcgtac acgagcacaa caaaggaagg    900

acggtcgaca ccccgtacgg ccccgtcgtc tatctagacc tgcggcacct gggggcggac    960

ctgatcgatg caaagttgcc gttcgtacgt gagctgtgcc gcgactacca gcacatcgac   1020
```

```
cccgtggtcg aattggtccc ggtacgaccg gtagtgcact acatgatggg tggcgttcac   1080

accgatatca acggcgccac aacgcttccc gggctatatg ccgcaggtga aacagcctgc   1140

gtgagcatta atggcgccaa ccgcctgggg tcgaactcgc tgcccgagct gctggtgttc   1200

ggggctcgag cgggccgtgc cgccgcggat tacgcagcgc gccaccaaaa gtcggaccgt   1260

ggcccgtcgt cggcagtgcg ggctcaggcc cgcaccgagg ctctacggct agagcgtgag   1320

ctcagccgcc atggccaggg aggcgaacga atcgcggata ttcgggcgga catgcaggcc   1380

accttggaaa gcgccgcggg tatttatcgt gacggaccca ccctcaccaa agcggtcgag   1440

gagattcggg tgctgcagga acgattcgcc acggcgggca tcgacgatca cagccgcaca   1500

ttcaacaccg agctgactgc gctgctcgag ttgtcgggga tgctcgacgt tgcactggcg   1560

atcgtcgaat cgggtttgcg ccgagaagaa tcccgtggcg cacaccagcg aaccgacttt   1620

ccgaaccggg acgacgagca tttcttggcg cacaccttgg ttcatagaga aagcgacgga   1680

acgctgcggg tcggctacct tccggtcact atcactcgct ggccaccggg cgaacgcgtg   1740

tatgggagg                                                           1749
```

<210> SEQ ID NO 107
<211> LENGTH: 386
<212> TYPE: PRT
<213> ORGANISM: Mycobacterium tuberculosis

<400> SEQUENCE: 107

```
Met Lys Ala Ala Thr Gln Ala Arg Ile Asp Asp Ser Pro Leu Ala Trp
1               5                   10                  15

Leu Asp Ala Val Gln Arg Gln Arg His Glu Ala Gly Leu Arg Arg Cys
            20                  25                  30

Leu Arg Pro Arg Pro Ala Val Ala Thr Glu Leu Asp Leu Ala Ser Asn
        35                  40                  45

Asp Tyr Leu Gly Leu Ser Arg His Pro Ala Val Ile Asp Gly Gly Val
    50                  55                  60

Gln Ala Leu Arg Ile Trp Gly Ala Gly Ala Thr Gly Ser Arg Leu Val
65                  70                  75                  80

Thr Gly Asp Thr Lys Leu His Gln Gln Phe Glu Ala Glu Leu Ala Glu
                85                  90                  95

Phe Val Gly Ala Ala Ala Gly Leu Leu Phe Ser Ser Gly Tyr Thr Ala
            100                 105                 110

Asn Leu Gly Ala Val Val Gly Leu Ser Gly Pro Gly Ser Leu Leu Val
        115                 120                 125

Ser Asp Ala Arg Ser His Ala Ser Leu Val Asp Ala Cys Arg Leu Ser
    130                 135                 140

Arg Ala Arg Val Val Val Thr Pro His Arg Asp Val Asp Ala Val Asp
145                 150                 155                 160

Ala Ala Leu Arg Ser Arg Asp Glu Gln Arg Ala Val Val Val Thr Asp
                165                 170                 175

Ser Val Phe Ser Ala Asp Gly Ser Leu Ala Pro Val Arg Glu Leu Leu
            180                 185                 190

Glu Val Cys Arg Arg His Gly Ala Leu Leu Leu Val Asp Glu Ala His
        195                 200                 205

Gly Leu Gly Val Arg Gly Gly Gly Arg Gly Leu Leu Tyr Glu Leu Gly
    210                 215                 220

Leu Ala Gly Ala Pro Asp Val Val Met Thr Thr Thr Leu Ser Lys Ala
225                 230                 235                 240

Leu Gly Ser Gln Gly Gly Val Val Leu Gly Pro Thr Pro Val Arg Ala
```

-continued 245 250 255

His Leu Ile Asp Ala Ala Arg Pro Phe Ile Phe Asp Thr Gly Leu Ala
260 265 270

Pro Ala Ala Val Gly Ala Ala Arg Ala Ala Leu Arg Val Leu Gln Ala
275 280 285

Glu Pro Trp Arg Pro Gln Ala Val Leu Asn His Ala Gly Glu Leu Ala
290 295 300

Arg Met Cys Gly Val Ala Ala Val Pro Asp Ser Ala Met Val Ser Val
305 310 315 320

Ile Leu Gly Glu Pro Glu Ser Ala Val Ala Ala Ala Ala Ala Cys Leu
325 330 335

Asp Ala Gly Val Lys Val Gly Cys Phe Arg Pro Pro Thr Val Pro Ala
340 345 350

Gly Thr Ser Arg Leu Arg Leu Thr Ala Arg Ala Ser Leu Asn Ala Gly
355 360 365

Glu Leu Glu Leu Ala Arg Arg Val Leu Thr Asp Val Leu Ala Val Ala
370 375 380

Arg Arg
385

<210> SEQ ID NO 108
<211> LENGTH: 1158
<212> TYPE: DNA
<213> ORGANISM: Mycobacterium tuberculosis

<400> SEQUENCE: 108
atgaaagccg ccacgcaggc acggatcgac gattcaccgt tggcctggtt ggacgcggtg 60
cagcggcagc gccacgaggc cggactgcgg cgctgcctgc ggccgcgtcc cgcggtcgcc 120
accgagctgg acttggcctc caacgactat ctcggtctgt cccgacatcc cgccgtcatc 180
gacggcggcg tccaggcgct gcggatctgg ggcgccggcg ccaccgggtc gcgcctggtt 240
accggcgaca ccaagctgca ccagcaattc gaggccgagc tcgccgagtt cgtcggcgct 300
gccgcgggat tgctgttctc ctctggctac acggccaacc tgggcgccgt ggtcggcctg 360
tccggcccgg gttccctgct ggtgtccgac gcccgttcgc atgcgtcgtt ggtggatgcc 420
tgtcggctgt cgcgggcgcg ggttgtggtg acgccgcacc gcgacgtcga cgccgtggac 480
gccgcgctgc gatcgcgcga cgagcagcgc gccgtcgtcg tcaccgactc ggtgttcagc 540
gccgacggct cgctggcgcc ggttcgggag ttgcttgagg tctgccggcg tcatggtgcg 600
ctgcttctgg tggacgaggc gcacggcctg ggtgtgcgtg gcggcggacg cgggctgctc 660
tacgagttag gtctagcggg tgcgcccgac gtggtgatga ccaccacgct gtccaaggcg 720
ctgggcagcc agggtggtgt ggtgctcggg ccgacgccgg tgcgggccca tctgatcgat 780
gctgcccggc cgttcatctt cgacaccggt ctggcgccgg cggcggtggg tgccgcacgg 840
gccgcgctgc gcgtcttgca ggccgagccg tggcgaccgc aggcggtgct caaccacgct 900
ggtgaacttg cgcggatgtg cggtgtggct gcggtgccgg actcggcgat ggtgtcggtg 960
atcctgggcg agccggagtc ggcagtggcc gccgcggcgg cctgcctgga cgccggggtc 1020
aaggtgggct gcttccggcc gccgacggtg cccgcgggta cgtcgcggct gcggctgacc 1080
gcgcgcgcat cgctgaacgc cggcgagctc gagctggccc ggcgggtgct gacggatgtt 1140
ctcgccgtgg cgcgccgt 1158

<210> SEQ ID NO 109
<211> LENGTH: 136

<212> TYPE: PRT
<213> ORGANISM: Mycobacterium tuberculosis

<400> SEQUENCE: 109

```
Met Thr Thr Thr Pro Ala Arg Phe Asn His Leu Val Thr Val Thr Asp
1               5                   10                  15

Leu Glu Thr Gly Asp Arg Ala Val Cys Asp Arg Asp Gln Val Ala Glu
            20                  25                  30

Thr Ile Arg Ala Trp Phe Pro Asp Ala Pro Leu Glu Val Arg Glu Ala
        35                  40                  45

Leu Val Arg Leu Gln Ala Ala Leu Asn Arg His Glu His Thr Gly Glu
    50                  55                  60

Leu Glu Ala Phe Leu Arg Ile Ser Val Glu His Ala Asp Ala Ala Gly
65                  70                  75                  80

Gly Asp Glu Cys Gly Pro Ala Ile Leu Ala Gly Arg Ser Gly Pro Glu
                85                  90                  95

Gln Ala Ala Ile Asn Arg Gln Leu Gly Leu Ala Gly Asp Asp Glu Pro
            100                 105                 110

Asp Gly Asp Asp Thr Pro Pro Trp Ser Arg Met Ile Gly Leu Gly Gly
        115                 120                 125

Gly Ser Pro Ala Glu Asp Glu Arg
    130                 135
```

<210> SEQ ID NO 110
<211> LENGTH: 408
<212> TYPE: DNA
<213> ORGANISM: Mycobacterium tuberculosis

<400> SEQUENCE: 110

```
atgaccacca caccagcacg tttcaaccac ttggtgacgg taaccgacct ggaaacgggt      60

gaccgcgccg tctgcgaccg cgaccaggtg gccgagacga tccgggcgtg gttcccggac     120

gcgcccttgg aggtgaggga agcgctcgtt cggctgcagg ccgcgttgaa tcggcacgag     180

cacaccggcg agctcgaagc gttcctgcgg atcagcgtcg agcacgccga cgccgccggc     240

ggcgacgagt gcggcccggc gatcctggcc ggccgctccg ggccggaaca agccgccatc     300

aaccggcaac tcggactcgc cggcgacgac gagcccgacg gcgacgacac cccgccgtgg     360

agccggatga tcgggcttgg cggcggaagc ccagcggaag acgagcgc                  408
```

<210> SEQ ID NO 111
<211> LENGTH: 170
<212> TYPE: PRT
<213> ORGANISM: Mycobacterium tuberculosis

<400> SEQUENCE: 111

```
Met Ala Glu Leu Arg Ser Gly Glu Gly Arg Thr Val His Gly Thr Ile
1               5                   10                  15

Val Pro Tyr Asn Glu Ala Thr Thr Val Arg Asp Phe Asp Gly Glu Phe
            20                  25                  30

Gln Glu Met Phe Ala Pro Gly Ala Phe Arg Arg Ser Ile Ala Glu Arg
        35                  40                  45

Gly His Lys Leu Lys Leu Leu Val Ser His Asp Ala Arg Thr Arg Tyr
    50                  55                  60

Pro Val Gly Arg Ala Val Glu Leu Arg Glu Glu Pro His Gly Leu Phe
65                  70                  75                  80

Gly Ala Phe Glu Ile Ala Asp Thr Pro Asp Gly Asp Glu Ala Leu Ala
                85                  90                  95
```

```
Asn Val Lys Ala Gly Val Val Asp Ser Phe Ser Val Gly Phe Arg Pro
            100                 105                 110

Ile Arg Asp Arg Arg Glu Gly Asp Val Leu Val Arg Val Glu Ala Ala
        115                 120                 125

Leu Leu Glu Val Ser Leu Thr Gly Val Pro Ala Tyr Ser Gly Ala Gln
    130                 135                 140

Ile Ala Gly Val Arg Ala Glu Ser Leu Thr Val Val Ser Arg Ser Thr
145                 150                 155                 160

Ala Glu Ala Trp Leu Ser Leu Leu Asp Trp
                165                 170


<210> SEQ ID NO 112
<211> LENGTH: 510
<212> TYPE: DNA
<213> ORGANISM: Mycobacterium tuberculosis

<400> SEQUENCE: 112

atggccgagc tgcggtctgg cgaaggccga accgtgcacg gcaccatcgt gccctacaac     60

gaggcgacca ccgtccgcga cttcgacggc gagttccagg aaatgttcgc tcctggcgct    120

tttcggcgct ccatcgccga gcgcggccac aaattgaagc tgctggtctc tcacgacgct    180

cgaacccgct acccggtggg ccgggccgtt gagttgcggg aggagcctca cggcttgttc    240

ggggcgttcg agattgcgga cacccccggac ggcgacgagg ctttggcgaa cgtaaaagct    300

ggtgtcgtcg actcgttttc ggtgggtttc cgaccgatcc gggaccgtcg cgaaggggat    360

gtgctggtgc gcgtcgaagc ggcgctgtta gaggtttccc taaccggcgt tccggcctat    420

tcgggggcac aaatcgccgg ggtgcgcgcg gaatcgctta cagtcgtttc ccgttcgaca    480

gccgaagcct ggctgtccct actcgattgg                                     510


<210> SEQ ID NO 113
<211> LENGTH: 115
<212> TYPE: PRT
<213> ORGANISM: Mycobacterium tuberculosis

<400> SEQUENCE: 113

Met Ile Arg Ala Val Trp Asn Gly Thr Val Leu Ala Glu Ala Pro Arg
1               5                   10                  15

Thr Val Arg Val Glu Gly Asn His Tyr Phe Pro Pro Glu Ser Leu His
            20                  25                  30

Arg Glu His Leu Ile Glu Ser Pro Thr Thr Ser Ile Cys Pro Trp Lys
        35                  40                  45

Gly Leu Ala His Tyr Tyr Asn Val Val Val Asp Gly Pro Tyr Gly Pro
    50                  55                  60

Val Asn Pro Asp Ala Ala Trp Tyr Tyr Arg Arg Pro Ser Pro Leu Ala
65                  70                  75                  80

Arg Arg Ile Lys Asn His Val Ala Phe Trp His Gly Val Thr Val Glu
                85                  90                  95

Gly Glu Ser Glu Ser Arg His Gly Leu Ala Arg Arg Val Val Ala Trp
            100                 105                 110

Leu Gly Lys
        115


<210> SEQ ID NO 114
<211> LENGTH: 345
<212> TYPE: DNA
<213> ORGANISM: Mycobacterium tuberculosis

<400> SEQUENCE: 114
```

atgattcgtg ctgtgtggaa tggaacagtg ctcgctgagg cgccgcgaac cgtacgggtg 60
gaaggcaacc actactttcc gcccgagtcg ctgcaccgcg agcatctaat cgaaagcccg 120
accacgtcga tatgcccatg gaagggtctg gcccattact acaacgtcgt cgtggacggc 180
ccctatggtc cggttaaccc ggacgctgcc tggtactacc gccggcccag tccactggct 240
cgccggatca aaaaccatgt tgcgttctgg cacggtgtga cggtcgaagg tgaatccgag 300
agtcggcatg gcttggcgcg ccgggttgtg gcgtggctcg gcaaa 345

<210> SEQ ID NO 115
<211> LENGTH: 236
<212> TYPE: PRT
<213> ORGANISM: Mycobacterium tuberculosis

<400> SEQUENCE: 115

Val Gln Pro Tyr Gly Gln Tyr Cys Pro Val Ala Arg Ala Ala Glu Leu
1 5 10 15

Leu Gly Asp Arg Trp Thr Leu Leu Ile Val Arg Glu Leu Leu Phe Gly
20 25 30

Pro Leu Arg Phe Thr Glu Ile Glu Arg Gly Leu Pro Gly Ile Ser Arg
35 40 45

Ser Val Leu Ala Gln Arg Leu Arg Arg Leu Gln His Asp Arg Ile Ile
50 55 60

Glu Ala Val Pro Glu His Thr Gly Gly Gly Tyr Arg Phe Thr Val Ala
65 70 75 80

Gly Glu Glu Leu Arg Pro Val Leu Gln Thr Leu Gly Asp Trp Val Ser
85 90 95

Arg Trp Leu Met Ala Asp Pro Thr Pro Ala Glu Cys Asp Pro Glu Leu
100 105 110

Leu Thr Leu Trp Ile Ser Arg Arg Val Asn Thr Glu Ala Leu Pro Gly
115 120 125

Arg Arg Val Val Val Glu Phe Arg Tyr His Gly Glu Arg Pro Leu Trp
130 135 140

Ala Trp Leu Val Leu Glu Pro Gly Asp Ile Ser Val Cys Leu His Asp
145 150 155 160

Pro Cys Leu Pro Val Asp Leu Thr Val Arg Gly His Pro Arg Asp Leu
165 170 175

Tyr Arg Val Tyr Ser Gly Arg Ser Thr Leu Ala Ala Glu Ile Ser Ala
180 185 190

Glu Arg Ile Glu Leu Asp Gly Leu Pro Ala Met Arg Arg Ala Phe Pro
195 200 205

Ser Trp Met Ala Trp Ser Pro Phe Ala Pro Ala Met Arg Gln Ala Val
210 215 220

Val Ser Val Asp Gln Met Pro Glu Ala His Gly Gly
225 230 235

<210> SEQ ID NO 116
<211> LENGTH: 708
<212> TYPE: DNA
<213> ORGANISM: Mycobacterium tuberculosis

<400> SEQUENCE: 116
gtgcagccgt acggccagta ctgcccggta gcgcgggcgg cggagctgct gggggaccgc 60
tggacgctgc taatcgtgcg ggagctgctc ttcggcccgc tgcggttcac cgaaatcgag 120
cggggcctgc ccggcatctc ccgctcggtg ctggcccagc ggctacgccg acttcagcac 180

-continued

```
gaccgcatca tcgaagcggt ccccgaacac acgggcgggg gctatcggtt cacggtggcc    240

ggcgaggagc tacgccccgt gctgcagacc ctgggggact gggtctcccg ttggttgatg    300

gccgacccca ctcccgccga atgcgacccc gaactactca cgttgtggat ctcccggcgc    360

gtcaacaccg aggcccttcc cggccggcgg gtggtggtgg agttccgcta ccacggcgag    420

cggccactgt gggcctggct cgtgttggaa cctggggaca tctcggtgtg cctgcacgat    480

ccatgcctac ctgtcgacct cacggtgcgc ggccatcctc gagatctgta tcgggtctac    540

agcggccgca gcacactggc cgccgagatc tccgccgagc gcatcgaact ggacggcctg    600

ccggcgatgc ggcgcgcgtt cccatcctgg atggcttgga gtcccttcgc cccagccatg    660

cggcaagccg tggtgtccgt agaccagatg ccggaggctc atggtggg                 708
```

<210> SEQ ID NO 117
<211> LENGTH: 517
<212> TYPE: PRT
<213> ORGANISM: Mycobacterium tuberculosis

<400> SEQUENCE: 117

```
Leu Cys Pro Pro Ile Ile Leu Ser Ser Ala Thr Pro Thr Gly Thr Arg
1               5                   10                  15

Cys Gly Thr Arg His Gly Arg Ala Val Val Thr Glu Tyr Val Arg Ala
            20                  25                  30

Leu Asp Arg Leu Pro His Glu Ile Ala Thr Ala Val Val Glu Thr Val
        35                  40                  45

Asn Cys Ala Asp Pro Gly Ala Ala Phe Asp Glu Leu Asp Ala Lys Ile
    50                  55                  60

Asn Ala Gly Met Lys Ala Tyr Ala Ile Pro Gly Val Ala Val Ala Val
65                  70                  75                  80

Trp Ala Gly Gly Gln Glu Tyr Val Lys Gly Tyr Gly Val Thr Asn Val
                85                  90                  95

Asp His Pro Met Pro Val Asp Gly Asp Thr Val Phe Arg Ile Gly Ser
            100                 105                 110

Thr Thr Lys Thr Phe Thr Gly Thr Val Met Met Arg Leu Val Glu Arg
        115                 120                 125

Gly Lys Val Asp Leu Asp Ser Pro Val Arg Arg Tyr Ile Pro Asp Phe
    130                 135                 140

Ala Val Ala Asp Glu Ser Ala Ser Ala Thr Val Thr Val Arg Gln Leu
145                 150                 155                 160

Leu Asn His Thr Ala Gly Trp Asp Gly Arg Asn Gly Gln Asp Phe Gly
                165                 170                 175

Arg Gly Asp Asp Ala Val Ala Leu Tyr Val Lys Ala Met Thr Arg Leu
            180                 185                 190

Pro Gln Leu Thr Pro Pro Gly Thr Ala Phe Ala Tyr Asn Asn Ser Gly
        195                 200                 205

Leu Val Val Ala Gly Arg Ile Ile Glu Leu Val Ala Gly Thr Thr Tyr
    210                 215                 220

Glu Ser Thr Val Gln Arg Leu Leu Leu Asp Pro Leu Gln Leu Ala His
225                 230                 235                 240

Thr Arg Tyr Phe Ser Asp Gln Ile Ile Gly Leu Asn Val Ala Ala Ser
                245                 250                 255

His Ser Val Val Asp Gly Lys Pro Ile Ala Val Thr Asp Phe Trp Thr
            260                 265                 270

Phe Pro Arg Ser Cys Asn Pro Thr Gly Gly Leu Met Ser Thr Ala Arg
        275                 280                 285
```

```
Asp Gln Leu Arg Tyr Ala Gln Phe His Leu Gly Asp Gly Arg Ala Pro
    290                 295                 300

Asn Gly Glu Gln Ile Leu Ser Arg Gln Ser Leu Lys Ala Met Arg Ser
305                 310                 315                 320

Asn Pro Gly Ala Gly Gly Thr Leu Trp Val Glu Leu Thr Gly Met Gly
                325                 330                 335

Val Thr Trp Met Leu Arg Pro Ser Ala Glu Asn Val Thr Ile Val Glu
            340                 345                 350

His Gly Gly Thr Trp Lys Gly Gln Arg Ser Gly Phe Val Met Val Pro
        355                 360                 365

Asp Arg Asn Phe Ala Met Thr Val Leu Thr Asn Ser Asp Gly Gly Phe
    370                 375                 380

His Met Ile Asn Asp Leu Phe Ala Ser Asp Trp Ala Leu Gln Arg Phe
385                 390                 395                 400

Ala Gly Leu Ser Asn Leu Pro Ala Thr Pro Gln Arg Leu Gly Ala Val
                405                 410                 415

Asp Leu Ala Pro Tyr Glu Gly Arg Tyr Ile Ala Lys Gln Val Ala Gln
            420                 425                 430

Asn Gly Asp Leu Glu Thr Thr Val Ile Asp Phe Arg Ala Arg Asp Gly
        435                 440                 445

Gln Leu Ala Gly Ser Met Ser Thr Asp Asp Ala Asn Pro Asp Gly Gln
    450                 455                 460

Asn Ser Ala Asn Leu Gly Leu Ala Phe Tyr Arg Pro Asp Tyr Gly Leu
465                 470                 475                 480

Asp Leu Gly Pro Asp Asn Lys Pro Thr Gly Ser Arg Ser Asn Phe Val
                485                 490                 495

Arg Gly Pro Asp Gly Asn Ile Ala Trp Phe Cys Ser Gln His Gly Arg
            500                 505                 510

Leu Phe Arg Arg Gln
        515


<210> SEQ ID NO 118
<211> LENGTH: 1551
<212> TYPE: DNA
<213> ORGANISM: Mycobacterium tuberculosis

<400> SEQUENCE: 118

ttgtgtccgc cgatcatctt gagttccgcg acgccgaccg gcacgcggtg cgggacgcgc      60

catgggcgcg cggtcgtcac cgaatacgtg cgtgcgctag atcgactgcc gcacgaaatc     120

gccactgcag tggttgaaac tgtcaactgc gcagaccctg gtgcagcgtt cgacgaactc     180

gatgcaaaaa tcaacgcggg catgaaggcc tatgcgattc cgggcgtcgc ggttgctgtc     240

tgggccggcg ggcaagaata cgtcaaaggc tacggggtca ccaatgtcga ccatccgatg     300

cctgttgacg gcgacactgt cttcagaatc ggttccacca caaagacttt cacaggtacg     360

gtgatgatgc ggctggtcga gcgaggcaag gtggacctgg attcacctgt gcgccgctac     420

atccccgact tcgcggtagc cgacgaatca gccagcgcta cggttaccgt tcgccaactg     480

ctcaaccata ccgcaggctg ggatggtcgc aatgggcagg actttgggcg cggcgatgac     540

gcggtggcgc tctatgtcaa ggcgatgaca cgcctaccgc agctcacccc tccgggaacc     600

gcgttcgcgt acaacaattc aggtcttgtg gttgcgggcc gcatcatcga gcttgtcgcc     660

ggaacaacct acgaatctac ggttcagagg ctgttgcttg acccgctgca gcttgctcac     720

acgcgctact tttccgacca aataatcggt ctgaatgtgg ccgcatcgca tagcgtggtc     780

gacggcaaac cgattgccgt tactgacttt tggacattcc cgcgcagctg caaccccacc     840
```

```
ggtgggttga tgtccacagc gcgagatcag ctgcgttacg cacagttcca cctcggcgac    900

ggcagggcgc ctaacggtga gcagattctg agccgacaat cgctgaaggc aatgcgctct    960

aaccctgggg cgggcggaac actttgggtg gaactgaccg ggatgggcgt gacctggatg   1020

ctgcggccct ccgcggagaa tgtgaccatc gttgagcacg gcggcacctg gaaggggcag   1080

cgctctgggt tcgtcatggt gcccgatcga aacttcgcca tgaccgtgct cactaactct   1140

gatggcggat ttcatatgat caacgacctt ttcgcatccg actgggcatt gcagagattc   1200

gccgggctca gcaatcttcc ggccacgccg caacgccttg gtgccgtcga cctggcgccc   1260

tacgagggcc ggtacatcgc caagcaagtc gcccaaaatg gcgacctcga gacaacggtc   1320

atcgacttcc gggccaggga cggccagctt gctggaagca tgagcaccga cgatgccaac   1380

ccggatggcc aaaacagcgc caatctgggc ctcgccttct atcggcccga ctatgggctc   1440

gaccttggac ccgacaacaa gcccaccggc agtcgctcca acttcgtgcg cgggccggac   1500

ggcaacatcg cctggttctg tagccagcac ggccgtctgt tccgacgcca a            1551
```

<210> SEQ ID NO 119
<211> LENGTH: 108
<212> TYPE: PRT
<213> ORGANISM: Mycobacterium tuberculosis

<400> SEQUENCE: 119

```
Met Ser Gly Gly Ser Ser Arg Arg Tyr Pro Pro Glu Leu Arg Glu Arg
1               5                   10                  15

Ala Val Arg Met Val Ala Glu Ile Arg Gly Gln His Asp Ser Glu Trp
            20                  25                  30

Ala Ala Ile Ser Glu Val Ala Arg Leu Leu Gly Val Gly Cys Ala Glu
        35                  40                  45

Thr Val Arg Lys Trp Val Arg Gln Ala Gln Val Asp Ala Gly Ala Arg
    50                  55                  60

Pro Gly Thr Thr Thr Glu Glu Ser Ala Glu Leu Lys Arg Leu Arg Arg
65                  70                  75                  80

Asp Asn Ala Glu Leu Arg Arg Ala Asn Ala Ile Leu Lys Thr Ala Ser
                85                  90                  95

Ala Phe Phe Ala Ala Glu Leu Asp Arg Pro Ala Arg
            100                 105
```

<210> SEQ ID NO 120
<211> LENGTH: 324
<212> TYPE: DNA
<213> ORGANISM: Mycobacterium tuberculosis

<400> SEQUENCE: 120

```
atgtcaggtg gttcatcgag gaggtacccg ccggagctgc gtgagcgggc ggtgcggatg     60

gtcgcagaga tccgcggtca gcacgattcg gagtgggcag cgatcagtga ggtcgcccgt    120

ctacttggtg ttggctgcgc ggagacggtg cgtaagtggg tgcgccaggc gcaggtcgat    180

gccggcgcac ggcccgggac cacgaccgaa gaatccgctg agctgaagcg cttgcggcgg    240

gacaacgccg aattgcgaag ggcgaacgcg attttaaaga ccgcgtcggc tttcttcgcg    300

gccgagctcg accggccagc acgc                                           324
```

<210> SEQ ID NO 121
<211> LENGTH: 365
<212> TYPE: PRT
<213> ORGANISM: Mycobacterium tuberculosis

<400> SEQUENCE: 121

Met Ser Ser Thr Ala Thr Ser Gly Ala Ala Val Val Ser Pro Ala Glu
1 5 10 15

Arg Val Glu Val Leu Phe Glu Glu Leu Ala Glu Leu Ala Gly Gln Arg
20 25 30

Asn Ala Ile Asp Gly Arg Ile Val Glu Ile Val Ala Glu Leu Asp Arg
35 40 45

Asp Gly Leu Trp Gly Val Thr Gly Ala Arg Ser Val Ala Gly Leu Val
50 55 60

Ala Trp Lys Met Gly Cys Ser Ser Gly Asn Ala His Thr Ile Ala Thr
65 70 75 80

Val Ala Arg Arg Leu Pro Glu Phe Pro Arg Cys Ala Arg Gly Met Arg
85 90 95

Glu Gly Arg Leu Ser Leu Asp Gln Val Gly Val Ile Ala Gly Arg Ala
100 105 110

Gly Glu Gly Ser Asp Ala His Tyr Ala Gln Leu Ala Gly Val Ala Thr
115 120 125

Val Asn Gln Leu Arg Thr Ala Leu Lys Leu Glu Pro Arg Pro Glu Pro
130 135 140

Glu Pro Asp Phe Arg Pro Glu Pro Arg Pro Ser Ile Thr Arg Ser Ala
145 150 155 160

Asp Glu Gln Phe Ser Cys Trp Arg Ile Lys Leu Pro His Val Glu Ala
165 170 175

Ala Lys Phe Asp Ala Ala Leu Gln Ser His Leu Asp Ala Leu Ile Ala
180 185 190

Glu Tyr Lys Arg Asp His Asp Asn Ser Asp Gly Val Ser Asp Gln Arg
195 200 205

Pro Pro Leu Pro Gly Asn Val Glu Ala Phe Leu Arg Leu Val Glu Ala
210 215 220

Gly Trp Asp Ala Glu Val Ala Arg Arg Pro His Gly Gln His Thr Thr
225 230 235 240

Val Val Met His Leu Asp Val Gln Glu Arg Ala Ala Gly Leu His Leu
245 250 255

Gly Pro Leu Leu Ser Glu Ser Glu Arg Arg Tyr Leu Leu Cys Asp Ala
260 265 270

Thr Phe Glu Ala Trp Phe Glu Arg Asp Gly Gln Val Ile Gly Cys Gly
275 280 285

Arg Thr Thr Arg Gln Ile Asn Arg Arg Leu Arg Arg Ala Leu Glu His
290 295 300

Arg Asp Arg Thr Cys Val Val Pro Gly Cys Gly Ala Thr Arg Gly Leu
305 310 315 320

His Ala His His Ile Arg His Trp Gln Asp Gly Gly Ala Thr Glu Leu
325 330 335

Ala Asn Leu Val Leu Val Cys Pro Tyr His His Arg Ala His His Arg
340 345 350

Gly Leu Asn Arg Pro Gly Glu Ser Gly Asp Ser Leu Ile
355 360 365

<210> SEQ ID NO 122
<211> LENGTH: 1095
<212> TYPE: DNA
<213> ORGANISM: Mycobacterium tuberculosis

<400> SEQUENCE: 122
atgtcctcga ccgcgacgtc tggcgcagcg gtagtcagtc ctgccgagcg tgtggaggtg 60

```
ttgtttgagg agttggcgga gttggccggt cagcgcaatg cgattgatgg gcgcattgtg      120

gagatcgtgg ctgagctgga tcgcgacggg ttgtggggtg tgacgggggc gcggtcggtg      180

gcggggttgg tggcctggaa gatgggctgc tcgtcaggca acgcccacac gatcgccacg      240

gtggcgcggc ggttgccgga gtttccgcgc tgcgcccggg gtatgcggga ggggcggttg      300

tcgttggatc aggttggggt gatcgcgggg cgggcgggtg agggttcgga tgcgcattat      360

gcgcagttgg ccggcgttgc cacggtgaat cagctgcgga ccgcgctcaa gttggaaccg      420

cgacccgaac ccgaaccgga ttttcggccg gaaccgcggc cctcgatcac caggagcgcc      480

gatgagcagt tcagttgttg gcgaatcaag cttccgcacg tggaggcggc gaagttcgat      540

gcggcgttgc agtctcatct ggatgcgttg atcgccgagt acaagcgtga tcacgacaac      600

agcgacggtg tgtcggatca gcggcccccg ttgccgggca atgttgaggc gtttctgcgt      660

ctggttgagg ccggctggga cgccgaggtg gctcgtcggc cacatgggca gcacaccacc      720

gtggtgatgc atctagacgt gcaggagcgt gccgctggcc tgcacctggg tccgctgctc      780

agcgagtccg aacgccgata tctgctctgt gatgccacct ttgaggcctg gtttgaacgt      840

gacgggcagg tcattggctg cggtcgaacg actcgtcaga tcaatcgtcg gttgcgtcgt      900

gcgcttgagc atcgcgaccg cacgtgtgtg gttcccggtt gtggggccac ccggggtttg      960

cacgcccacc acatccgaca ttggcaggac ggtggggcca ccgagctggc caacctggtg     1020

ctggtgtgcc cgtatcacca ccgggcacac catcggggcc tgaaccgccc cggtgagtcc     1080

ggagactctc tgatc                                                     1095

<210> SEQ ID NO 123
<211> LENGTH: 434
<212> TYPE: PRT
<213> ORGANISM: Mycobacterium tuberculosis

<400> SEQUENCE: 123

Val Arg Arg Ser Pro Lys Gly Ser Pro Gly Ala Val Leu Asp Leu Gln
1               5                   10                  15

Arg Arg Val Asp Gln Ala Val Ser Ala Asp His Ala Glu Leu Met Thr
            20                  25                  30

Ile Ala Lys Asp Ala Asn Thr Phe Phe Gly Ala Glu Ser Val Gln Asp
        35                  40                  45

Pro Tyr Pro Leu Tyr Glu Arg Met Arg Ala Ala Gly Ser Val His Arg
    50                  55                  60

Ile Ala Asn Ser Asp Phe Tyr Ala Val Cys Gly Trp Asp Ala Val Asn
65                  70                  75                  80

Glu Ala Ile Gly Arg Pro Glu Asp Phe Ser Ser Asn Leu Thr Ala Thr
                85                  90                  95

Met Thr Tyr Thr Ala Glu Gly Thr Ala Lys Pro Phe Glu Met Asp Pro
            100                 105                 110

Leu Gly Gly Pro Thr His Val Leu Ala Thr Ala Asp Asp Pro Ala His
        115                 120                 125

Ala Val His Arg Lys Leu Val Leu Arg His Leu Ala Ala Lys Arg Ile
    130                 135                 140

Arg Val Met Glu Gln Phe Thr Val Gln Ala Ala Asp Arg Leu Trp Val
145                 150                 155                 160

Asp Gly Met Gln Asp Gly Cys Ile Glu Trp Met Gly Ala Met Ala Asn
                165                 170                 175

Arg Leu Pro Met Met Val Val Ala Glu Leu Ile Gly Leu Pro Asp Pro
            180                 185                 190
```

-continued

```
Asp Ile Ala Gln Leu Val Lys Trp Gly Tyr Ala Ala Thr Gln Leu Leu
        195                 200                 205

Glu Gly Leu Val Glu Asn Asp Gln Leu Val Ala Ala Gly Val Ala Leu
    210                 215                 220

Met Glu Leu Ser Gly Tyr Ile Phe Glu Gln Phe Asp Arg Ala Ala Ala
225                 230                 235                 240

Asp Pro Arg Asp Asn Leu Leu Gly Glu Leu Ala Thr Ala Cys Ala Ser
                245                 250                 255

Gly Glu Leu Asp Thr Leu Thr Ala Gln Val Met Met Val Thr Leu Phe
            260                 265                 270

Ala Ala Gly Gly Glu Ser Thr Ala Ala Leu Leu Gly Ser Ala Val Trp
        275                 280                 285

Ile Leu Ala Thr Arg Pro Asp Ile Gln Gln Gln Val Arg Ala Asn Pro
    290                 295                 300

Glu Leu Leu Gly Ala Phe Ile Glu Glu Thr Leu Arg Tyr Glu Pro Pro
305                 310                 315                 320

Phe Arg Gly His Tyr Arg His Val Arg Asn Ala Thr Thr Leu Asp Gly
                325                 330                 335

Thr Glu Leu Pro Ala Asp Ser His Leu Leu Leu Leu Trp Gly Ala Ala
            340                 345                 350

Asn Arg Asp Pro Ala Gln Phe Glu Ala Pro Gly Glu Phe Arg Leu Asp
        355                 360                 365

Arg Ala Gly Gly Lys Gly His Ile Ser Phe Gly Lys Gly Ala His Phe
    370                 375                 380

Cys Val Gly Ala Ala Leu Ala Arg Leu Glu Ala Arg Ile Val Leu Arg
385                 390                 395                 400

Leu Leu Leu Asp Arg Thr Ser Val Ile Glu Ala Ala Asp Val Gly Gly
                405                 410                 415

Trp Leu Pro Ser Ile Leu Val Arg Arg Ile Glu Arg Leu Glu Leu Ala
            420                 425                 430

Val Gln
```

<210> SEQ ID NO 124
<211> LENGTH: 1302
<212> TYPE: DNA
<213> ORGANISM: Mycobacterium tuberculosis

<400> SEQUENCE: 124

```
gtgagacgtt cgccgaaagg ctccccgggc gcagttctcg acttgcagcg acgcgttgac      60

caggcggtat ccgccgatca cgctgaacta atgacaattg ccaaggatgc caacacgttc     120

tttggtgccg aatccgtgca ggacccctac ccgctgtatg agcgcatgcg cgccgcaggc     180

tcggtccacc ggatcgctaa ctcggacttc tatgccgtgt gcggttggga cgctgtcaat     240

gaggccatcg gtcgtccgga ggacttctcc tcgaatttga ccgccacgat gacctatacg     300

gccgagggca ccgctaaacc gttcgagatg gacccactcg gcggacccac acacgtgttg     360

gccaccgccg acgatcctgc ccacgccgtg caccgcaagc tcgtgctgcg tcacttggcg     420

gccaagcgga tccgcgttat ggagcagttc accgtacagg ctgccgaccg gctgtgggtc     480

gacggcatgc aggatgggtg catcgaatgg atgggcgcca tggccaatcg cctaccgatg     540

atggtcgtag ctgagctcat cggcctgccc gaccccgaca tcgcccagct ggtgaagtgg     600

ggatacgcgg ccactcagct actcgaaggg ttggtcgaaa acgatcagct cgtcgccgcg     660

ggtgtggcgt tgatggagct cagcggttac atcttcgagc agtttgaccg tgccgcggcc     720
```

```
gatccgcggg acaatctgct cggtgagctt gccaccgcct gcgcatcggg ggagctggac    780

actctcaccg cccaggtcat gatggtcacc ttgttcgccg ccggcggcga gtccacggcg    840

gcgctgctgg gcagcgcggt atggatactg gcgacacgtc ccgatatcca gcaacaggtg    900

cgcgcgaacc ccgagctgct gggagcgttt atcgaagaga cgctgcgtta cgagccgcca    960

tttcgcggcc actaccgcca cgtgcgaaac gccaccacct tggacggcac ggaactgccc   1020

gcggattcgc acctgctgct gttgtggggc gcggccaacc gcgatccagc ccagttcgag   1080

gcacccggcg agttccgtct tgaccgtgca ggaggcaaag gccacatcag tttcggaaaa   1140

ggggcccact tctgtgtcgg cgctgcactg gcacgcttgg aggctcgaat cgtcttgcgt   1200

ctgctgctcg atcgcacctc ggtaattgag gcagccgatg tcggcgggtg gttgcccagt   1260

atcctggtgc gccgcatcga gcggctagag ctagctgtac aa                      1302
```

```
<210> SEQ ID NO 125
<211> LENGTH: 99
<212> TYPE: PRT
<213> ORGANISM: Mycobacterium tuberculosis

<400> SEQUENCE: 125

Met Ala Phe Val Leu Val Cys Pro Asp Ala Leu Ala Ile Ala Ala Gly
1               5                   10                  15

Gln Leu Arg His Val Gly Ser Val Ile Ala Ala Arg Asn Ala Val Ala
            20                  25                  30

Ala Pro Ala Thr Ala Glu Leu Ala Pro Ala Ala Ala Asp Glu Val Ser
        35                  40                  45

Ala Leu Thr Ala Thr Gln Phe Asn Phe His Ala Ala Met Tyr Gln Ala
    50                  55                  60

Val Gly Ala Gln Ala Ile Ala Met Asn Glu Ala Phe Val Ala Met Leu
65                  70                  75                  80

Gly Ala Ser Ala Asp Ser Tyr Ala Ala Thr Glu Ala Ala Asn Ile Ile
                85                  90                  95

Ala Val Ser
```

```
<210> SEQ ID NO 126
<211> LENGTH: 297
<212> TYPE: DNA
<213> ORGANISM: Mycobacterium tuberculosis

<400> SEQUENCE: 126

atggcgtttg ttcttgtctg tccagatgcg ctggccatcg cggccggtca gttgcgccat     60

gttggatcgg tgatagccgc gcggaatgcg gtcgcggcac cggcaactgc cgaattggcc    120

ccggcggccg ctgacgaagt atcagctttg actgcaacac aattcaactt ccatgccgcc    180

atgtaccaag cggtcggcgc ccaggcgatc gccatgaatg aggcgttcgt cgcgatgttg    240

ggcgccagcg cggattctta cgcggctacc gaagccgcca acatcattgc tgtgagc       297
```

```
<210> SEQ ID NO 127
<211> LENGTH: 778
<212> TYPE: PRT
<213> ORGANISM: Mycobacterium tuberculosis

<400> SEQUENCE: 127

Met Val Thr Arg Leu Leu Ala Asp Leu Gly Ala Asp Val Leu Lys Val
1               5                   10                  15

Glu Pro Pro Gly Gly Ser Pro Gly Arg His Val Arg Pro Thr Leu Ala
            20                  25                  30
```

-continued

```
Gly Thr Ser Ile Gly Phe Ala Met His Asn Ala Asn Lys Arg Ser Ala
        35                  40                  45

Val Leu Asn Pro Leu Asp Glu Ser Asp Arg Arg Arg Phe Leu Asp Leu
    50                  55                  60

Ala Ala Ser Ala Asp Ile Val Val Asp Cys Gly Leu Pro Gly Gln Ala
65                  70                  75                  80

Ala Ala Tyr Gly Ala Ser Cys Ala Glu Leu Ala Asp Arg Tyr Arg His
                85                  90                  95

Leu Val Ala Leu Ser Ile Thr Asp Phe Gly Ala Ala Gly Pro Arg Ser
            100                 105                 110

Ser Trp Arg Ala Thr Asp Pro Val Leu Tyr Ala Met Ser Gly Ala Leu
        115                 120                 125

Ser Arg Ser Gly Pro Thr Ala Gly Thr Pro Val Leu Pro Pro Asp Gly
    130                 135                 140

Ile Ala Ser Ala Thr Ala Ala Val Gln Ala Ala Trp Ala Val Leu Val
145                 150                 155                 160

Ala Tyr Phe Asn Arg Leu Arg Cys Gly Thr Gly Asp Tyr Ile Asp Phe
                165                 170                 175

Ser Arg Phe Asp Ala Val Val Met Ala Leu Asp Pro Pro Phe Gly Ala
            180                 185                 190

His Gly Gln Val Ala Ala Gly Ile Arg Ser Thr Gly Arg Trp Arg Gly
        195                 200                 205

Arg Pro Lys Asn Gln Asp Ala Tyr Pro Ile Tyr Pro Cys Arg Asp Gly
    210                 215                 220

Tyr Val Arg Phe Cys Val Met Ala Pro Arg Gln Trp Arg Gly Leu Arg
225                 230                 235                 240

Arg Trp Leu Gly Glu Pro Glu Asp Phe Gln Asp Pro Lys Tyr Asp Val
                245                 250                 255

Ile Gly Ala Arg Leu Ala Ala Trp Pro Gln Ile Ser Val Leu Val Ala
            260                 265                 270

Lys Leu Cys Ala Glu Lys Thr Met Lys Glu Leu Val Ala Ala Gly Gln
        275                 280                 285

Ala Leu Gly Val Pro Ile Thr Ala Val Leu Thr Pro Ser Arg Ile Leu
    290                 295                 300

Ala Ser Glu His Phe Gln Ala Val Gly Ala Ile Thr Asp Ala Glu Leu
305                 310                 315                 320

Val Pro Gly Val Arg Thr Gly Val Pro Thr Gly Tyr Phe Val Val Asp
                325                 330                 335

Gly Lys Arg Ala Gly Phe Arg Thr Pro Ala Pro Ala Ala Gly Gln Asp
            340                 345                 350

Glu Pro Arg Trp Leu Ala Asp Pro Ala Pro Val Pro Pro Pro Ser Gly
        355                 360                 365

Arg Val Gly Gly Tyr Pro Phe Glu Gly Leu Arg Ile Leu Asp Leu Gly
    370                 375                 380

Ile Ile Val Ala Gly Gly Glu Leu Ser Arg Leu Phe Gly Asp Leu Gly
385                 390                 395                 400

Ala Glu Val Ile Lys Val Glu Ser Ala Asp His Pro Asp Gly Leu Arg
                405                 410                 415

Gln Thr Arg Val Gly Asp Ala Met Ser Glu Ser Phe Ala Trp Thr His
            420                 425                 430

Arg Asn His Leu Ala Leu Gly Leu Asp Leu Arg Asn Ser Glu Gly Lys
        435                 440                 445

Ala Ile Phe Gly Arg Leu Val Ala Glu Ser Asp Ala Val Phe Ala Asn
    450                 455                 460
```

```
Phe Lys Pro Gly Thr Leu Thr Ser Leu Gly Phe Ser Tyr Asp Val Leu
465                 470                 475                 480

His Ala Phe Asn Pro Arg Ile Val Leu Ala Gly Ser Ser Ala Phe Gly
                485                 490                 495

Asn Arg Gly Pro Trp Ser Thr Arg Met Gly Tyr Gly Pro Leu Val Arg
            500                 505                 510

Ala Ala Thr Gly Val Thr Arg Val Trp Thr Ser Asp Glu Ala Gln Pro
        515                 520                 525

Asp Asn Ser Arg His Pro Phe Tyr Asp Ala Thr Thr Ile Phe Pro Asp
    530                 535                 540

His Val Val Gly Arg Val Gly Ala Leu Leu Ala Leu Ala Ala Leu Ile
545                 550                 555                 560

His Arg Asp Arg Thr Gly Gly Gly Ala His Val His Ile Ser Gln Ala
                565                 570                 575

Glu Val Val Val Asn Gln Leu Asp Thr Met Phe Val Ala Glu Ala Ala
                580                 585                 590

Arg Ala Thr Asp Val Ala Glu Ile His Pro Asp Thr Ser Val His Ala
            595                 600                 605

Val Tyr Pro Cys Ala Gly Asp Asp Glu Trp Cys Val Ile Ser Ile Arg
        610                 615                 620

Ser Asp Asp Glu Trp Arg Arg Ala Thr Ser Val Phe Gly Gln Pro Glu
625                 630                 635                 640

Leu Ala Asn Asp Pro Arg Phe Gly Ala Ser Arg Ser Arg Val Ala Asn
                645                 650                 655

Arg Ser Glu Leu Val Ala Ala Val Ser Ala Trp Thr Ser Thr Arg Thr
                660                 665                 670

Pro Val Gln Ala Ala Gly Ala Leu Gln Ala Ala Gly Val Ala Ala Gly
            675                 680                 685

Pro Met Asn Arg Pro Ser Asp Ile Leu Glu Asp Pro Gln Leu Ile Glu
        690                 695                 700

Arg Asn Leu Phe Arg Asp Met Val His Pro Leu Ile Ala Arg Pro Leu
705                 710                 715                 720

Pro Ala Glu Thr Gly Pro Ala Pro Phe Arg His Ile Pro Gln Ala Pro
                725                 730                 735

Gln Arg Pro Ala Pro Leu Pro Gly Gln Asp Ser Val Gly Ile Cys Arg
            740                 745                 750

Lys Leu Leu Gly Met Thr Ala Asp Glu Thr Glu Arg Leu Ile Asn Glu
        755                 760                 765

Arg Val Met Phe Gly Pro Ala Val Thr Ala
770                 775

<210> SEQ ID NO 128
<211> LENGTH: 2334
<212> TYPE: DNA
<213> ORGANISM: Mycobacterium tuberculosis

<400> SEQUENCE: 128

atggtgacac gactgctcgc cgacctgggc gcagacgttc tcaaggtgga accccccggc      60

ggcagcccag gacgccacgt gcggcccacg ctggccggca ccagcatcgg gttcgccatg     120

cacaacgcga acaaacgcag cgcagtgctc aacccgctcg acgagagcga ccgtcggcgg     180

ttcttggacc tcgccgccag cgccgacatc gtcgtcgact gtggtcttcc gggacaggcc     240

gccgcgtacg gggcatcgtg tgccgagttg gccgatcgct accgacacct ggtggcgctg     300

tcgatcaccg actttggcgc tgccggtccg cggtcgtcat ggcgcgcgac cgatccggtg     360
```

-continued ctgtacgcga tgagtggtgc tctctcgcgg tcgggcccta ccgccggcac gccggtactg 420
ccgccggacg gtatcgcttc ggcaaccgca gcggtgcagg cagcctgggc cgtactggtc 480
gcctatttca accgattacg ttgtggtact ggggattaca tcgacttctc ccggtttgac 540
gccgtcgtta tggcgttgga tccccccttc ggggcgcacg ggcaggtcgc agccggcatc 600
cgcagcaccg ggcgatggcg gggacggccc aagaaccagg acgcttaccc gatttatccg 660
tgccgggacg gctacgtacg gttctgcgtg atggcgccgc ggcagtggcg cgggctgcgc 720
cgctggttgg gggagcccga agattttcag gaccccaagt acgacgtgat cggcgcacgt 780
ttggccgcat ggccgcagat cagcgtgttg gtcgcgaagt tgtgcgccga gaagaccatg 840
aaggagttgg tggcagccgg ccaagcgctc ggggttccca ttaccgcggt gctgacaccg 900
tcgagaatcc tggcctccga acacttccag gcggtgggtg cgatcaccga tgccgagctc 960
gttccggggg tgcgcaccgg ggtgcctacc ggatacttcg ttgtcgacgg gaagcgcgcc 1020
ggtttccgta ctccggcccc cgccgcgggg caggacgaac cgcgctggct cgcggatcca 1080
gcgccggtgc ccccaccctc aggccgggtc ggcggctatc cattcgaagg tctgcggatt 1140
cttgatctgg gcatcatcgt ggccggcggc gagctcagcc ggctgttcgg cgacttgggc 1200
gccgaggtca tcaaggtcga aagtgccgac caccccgacg ggttgcggca gacccgagtc 1260
ggggatgcga tgagtgaatc attcgcgtgg acccatcgca atcacctcgc gctgggcctg 1320
gacctgcgca acagcgaggg caaagcgatc ttcggtcgcc tggtcgctga atccgacgcg 1380
gtgttcgcca acttcaaacc gggaaccctt acctcacttg ggttttccta cgatgtactg 1440
cacgccttca acccccggat cgtgctcgcc gggagtagtg cattcgggaa ccgagggccg 1500
tggagcaccc ggatgggcta cgggccactg gtgcgcgccg ccaccggggt cacccgtgtt 1560
tggacatccg atgaggcgca gccggacaac tctcggcatc ccttctacga cgcgacgacg 1620
atcttccccg accacgttgt cgggcgggtc ggtgccctgc tcgcgctggc ggccctgatc 1680
caccgcgatc gaactggcgg cggagcccac gtccacatct cccaggccga agtcgtcgtc 1740
aatcagctag acaccatgtt cgttgccgag gccgcccgag cgaccgacgt tgccgagatc 1800
cacccggaca ccagtgtgca tgcggtctac ccttgtgctg gcgacgacga atggtgcgtc 1860
atctcaatcc gctccgacga tgaatggcgt cgcgcgacat ctgttttcgg ccagcctgaa 1920
ttggcgaacg acccacgctt cggggcaagc cggtcacgcg tggccaaccg ttcggagttg 1980
gtggccgcag tgtcggcctg gaccagcacc cgtaccccgg tgcaagcggc cggcgcgctg 2040
caggcggccg gagttgcggc cggcccgatg aatcgcccgt cggatatcct cgaggatccc 2100
cagctgatcg agcgaaacct gttccgcgac atggtgcatc cgctgatcgc ccgtccgctg 2160
cccgccgaga cgggtccggc tccgtttcgt cacattccgc aggcaccccca acgcccggcg 2220 ccgctgcccg gacaggacag cgttcagatc tgccgcaagc tgctcggcat gaccgcggac 2280
gagaccgaac gcctaatcaa cgagcgcgta atgttcgggc cggccgtcac tgcc 2334

<210> SEQ ID NO 129
<211> LENGTH: 1459
<212> TYPE: PRT
<213> ORGANISM: Mycobacterium tuberculosis

<400> SEQUENCE: 129

Met Asn Phe Ser Thr Leu Pro Pro Glu Ile Asn Ser Ala Leu Ile Phe
1 5 10 15

Gly Gly Ala Gly Ser Glu Pro Met Ser Ala Ala Ala Val Ala Trp Asp
20 25 30

```
Gln Leu Ala Met Glu Leu Ala Ser Ala Ala Ala Ser Phe Asn Ser Val
        35                  40                  45

Thr Ser Gly Leu Val Gly Glu Ser Trp Leu Gly Pro Ser Ser Ala Ala
    50                  55                  60

Met Ala Ala Ala Val Ala Pro Tyr Leu Gly Trp Leu Ala Ala Ala Ala
65                  70                  75                  80

Ala Gln Ala Gln Arg Ser Ala Thr Gln Ala Ala Ala Leu Val Ala Glu
                85                  90                  95

Phe Glu Ala Val Arg Ala Ala Met Val Gln Pro Ala Leu Val Ala Ala
            100                 105                 110

Asn Arg Ser Asp Leu Val Ser Leu Val Phe Ser Asn Phe Phe Gly Gln
        115                 120                 125

Asn Ala Pro Ala Ile Ala Ala Ile Glu Ala Ala Tyr Glu Gln Met Trp
    130                 135                 140

Ala Ile Asp Val Ser Val Met Ser Ala Tyr His Ala Gly Ala Ser Ala
145                 150                 155                 160

Val Ala Ser Ala Leu Thr Pro Phe Thr Ala Pro Pro Gln Asn Leu Thr
                165                 170                 175

Asp Leu Pro Ala Gln Leu Ala Ala Ala Pro Ala Ala Val Val Thr Ala
            180                 185                 190

Ala Ile Thr Ser Ser Lys Gly Val Leu Ala Asn Leu Ser Leu Gly Leu
        195                 200                 205

Ala Asn Ser Gly Phe Gly Gln Met Gly Ala Ala Asn Leu Gly Ile Leu
    210                 215                 220

Asn Leu Gly Ser Leu Asn Pro Gly Gly Asn Asn Phe Gly Leu Gly Asn
225                 230                 235                 240

Val Gly Ser Asn Asn Val Gly Leu Gly Asn Thr Gly Asn Gly Asn Ile
                245                 250                 255

Gly Phe Gly Asn Thr Gly Asn Gly Asn Ile Gly Phe Gly Leu Thr Gly
            260                 265                 270

Asp Asn Gln Gln Gly Phe Gly Gly Trp Asn Ser Gly Thr Gly Asn Ile
        275                 280                 285

Gly Leu Phe Asn Ser Gly Thr Gly Asn Ile Gly Ile Gly Asn Thr Gly
    290                 295                 300

Thr Gly Asn Phe Gly Ile Gly Asn Ser Gly Thr Ser Tyr Asn Thr Gly
305                 310                 315                 320

Ile Gly Asn Thr Gly Gln Ala Asn Thr Gly Phe Phe Asn Ala Gly Ile
                325                 330                 335

Ala Asn Thr Gly Ile Gly Asn Thr Gly Asn Tyr Asn Thr Gly Ser Phe
            340                 345                 350

Asn Leu Gly Ser Phe Asn Thr Gly Asp Phe Asn Thr Gly Ser Ser Asn
        355                 360                 365

Thr Gly Phe Phe Asn Pro Gly Asn Leu Asn Thr Gly Val Gly Asn Thr
    370                 375                 380

Gly Asn Val Asn Thr Gly Gly Phe Asn Ser Gly Asn Tyr Ser Asn Gly
385                 390                 395                 400

Phe Phe Trp Arg Gly Asp Tyr Gln Gly Leu Ile Gly Phe Ser Gly Thr
                405                 410                 415

Leu Thr Ile Pro Ala Ala Gly Leu Asp Leu Asn Gly Leu Gly Ser Val
            420                 425                 430

Gly Pro Ile Thr Ile Pro Ser Ile Thr Ile Pro Glu Ile Gly Leu Gly
        435                 440                 445

Ile Asn Ser Ser Gly Ala Leu Val Gly Pro Ile Asn Val Pro Pro Ile
```

-continued

```
    450                 455                 460

Thr Val Pro Ala Ile Gly Leu Gly Ile Asn Ser Thr Gly Ala Leu Val
465                 470                 475                 480

Gly Pro Ile Asn Ile Pro Pro Ile Thr Leu Asn Ser Ile Gly Leu Glu
                485                 490                 495

Leu Ser Ala Phe Gln Val Ile Asn Val Gly Ser Ile Ser Ile Pro Ala
            500                 505                 510

Ser Pro Leu Ala Ile Gly Leu Phe Gly Val Asn Pro Thr Val Gly Ser
        515                 520                 525

Ile Gly Pro Gly Ser Ile Ser Ile Gln Leu Gly Thr Pro Glu Ile Pro
    530                 535                 540

Ala Ile Pro Pro Phe Phe Pro Gly Phe Pro Pro Asp Tyr Val Thr Val
545                 550                 555                 560

Ser Gly Gln Ile Gly Pro Ile Thr Phe Leu Ser Gly Gly Tyr Ser Leu
                565                 570                 575

Pro Ala Ile Pro Leu Gly Ile Asp Val Gly Gly Gly Leu Gly Pro Phe
            580                 585                 590

Thr Val Phe Pro Asp Gly Tyr Ser Leu Pro Ala Ile Pro Leu Gly Ile
        595                 600                 605

Asp Val Gly Gly Gly Leu Gly Pro Phe Thr Val Phe Pro Asp Gly Tyr
    610                 615                 620

Ser Leu Pro Ala Ile Pro Leu Gly Ile Asp Val Gly Gly Gly Leu Gly
625                 630                 635                 640

Pro Phe Thr Val Phe Pro Asp Gly Tyr Ser Leu Pro Ala Ile Pro Leu
                645                 650                 655

Gly Ile Asp Val Gly Gly Ala Ile Gly Pro Leu Thr Thr Pro Pro Ile
            660                 665                 670

Thr Ile Pro Ser Ile Pro Leu Gly Ile Asp Val Ser Gly Ser Leu Gly
        675                 680                 685

Pro Ile Asn Ile Pro Ile Glu Ile Ala Gly Thr Pro Gly Phe Gly Asn
    690                 695                 700

Ser Thr Thr Thr Pro Ser Ser Gly Phe Phe Asn Ser Gly Thr Gly Gly
705                 710                 715                 720

Thr Ser Gly Phe Gly Asn Val Gly Ser Gly Gly Ser Gly Phe Trp Asn
                725                 730                 735

Ile Ala Gly Asn Leu Gly Asn Ser Gly Phe Leu Asn Val Gly Pro Leu
            740                 745                 750

Thr Ser Gly Ile Leu Asn Phe Gly Asn Thr Val Ser Gly Leu Tyr Asn
        755                 760                 765

Thr Ser Thr Leu Gly Leu Ala Thr Ser Ala Phe His Ser Gly Val Gly
    770                 775                 780

Asn Thr Asp Ser Gln Leu Ala Gly Phe Met Arg Asn Ala Ala Gly Gly
785                 790                 795                 800

Thr Leu Phe Asn Phe Gly Phe Ala Asn Asp Gly Thr Leu Asn Leu Gly
                805                 810                 815

Asn Ala Asn Leu Gly Asp Tyr Asn Val Gly Ser Gly Asn Val Gly Ser
            820                 825                 830

Tyr Asn Phe Gly Ser Gly Asn Ile Gly Asn Gly Ser Phe Gly Phe Gly
        835                 840                 845

Asn Ile Gly Ser Asn Asn Phe Gly Phe Gly Asn Val Gly Ser Asn Asn
    850                 855                 860

Leu Gly Phe Ala Asn Thr Gly Pro Gly Leu Thr Glu Ala Leu His Asn
865                 870                 875                 880
```

```
Ile Gly Phe Gly Asn Ile Gly Gly Asn Asn Tyr Gly Phe Ala Asn Ile
                885                 890                 895

Gly Asn Gly Asn Ile Gly Phe Gly Asn Thr Gly Thr Gly Asn Ile Gly
            900                 905                 910

Ile Gly Leu Thr Gly Asp Asn Gln Val Gly Phe Gly Ala Leu Asn Ser
        915                 920                 925

Gly Ser Gly Asn Ile Gly Phe Phe Asn Ser Gly Asn Gly Asn Ile Gly
    930                 935                 940

Phe Phe Asn Ser Gly Asn Gly Asn Val Gly Ile Gly Asn Ser Gly Asn
945                 950                 955                 960

Tyr Asn Thr Gly Leu Gly Asn Val Gly Asn Ala Asn Thr Gly Leu Phe
                965                 970                 975

Asn Thr Gly Asn Val Asn Thr Gly Ile Gly Asn Ala Gly Ser Tyr Asn
            980                 985                 990

Thr Gly Ser Tyr Asn Ala Gly Asp  Thr Asn Thr Gly Asp  Leu Asn Pro
        995                 1000                1005

Gly Asn  Ala Asn Thr Gly Tyr  Leu Asn Leu Gly Asp  Leu Asn Thr
    1010                 1015                 1020

Gly Trp  Gly Asn Ile Gly Asp  Leu Asn Thr Gly Ala  Leu Ile Ser
    1025                 1030                 1035

Gly Ser  Tyr Ser Asn Gly Ile  Leu Trp Arg Gly Asp  Tyr Gln Gly
    1040                 1045                 1050

Leu Ile  Gly Tyr Ser Asp Thr  Leu Ser Ile Pro Ala  Ile Pro Leu
    1055                 1060                 1065

Ser Val  Glu Val Asn Gly Gly  Ile Gly Pro Ile Val  Val Pro Asp
    1070                 1075                 1080

Ile Thr  Ile Pro Gly Ile Pro  Leu Ser Leu Asn Ala  Leu Gly Gly
    1085                 1090                 1095

Val Gly  Pro Ile Val Val Pro  Asp Ile Thr Ile Pro  Gly Ile Pro
    1100                 1105                 1110

Leu Ser  Leu Asn Ala Leu Gly  Gly Val Gly Pro Ile  Val Val Pro
    1115                 1120                 1125

Asp Ile  Thr Ile Pro Gly Ile  Pro Leu Ser Leu Asn  Ala Leu Gly
    1130                 1135                 1140

Gly Val  Gly Pro Ile Val Val  Pro Asp Ile Thr Ile  Pro Gly Ile
    1145                 1150                 1155

Pro Leu  Ser Leu Asn Ala Leu  Gly Gly Val Gly Pro  Ile Val Val
    1160                 1165                 1170

Pro Asp  Ile Thr Ile Pro Gly  Ile Pro Leu Ser Leu  Asn Ala Leu
    1175                 1180                 1185

Gly Gly  Val Gly Pro Ile Thr  Val Pro Gly Val Pro  Ile Ser Arg
    1190                 1195                 1200

Ile Pro  Leu Thr Ile Asn Ile  Arg Ile Pro Val Asn  Ile Thr Leu
    1205                 1210                 1215

Asn Glu  Leu Pro Phe Asn Val  Ala Gly Ile Phe Thr  Gly Tyr Ile
    1220                 1225                 1230

Gly Pro  Ile Pro Leu Ser Thr  Phe Val Leu Gly Val  Thr Leu Ala
    1235                 1240                 1245

Gly Gly  Thr Leu Glu Ser Gly  Ile Gln Gly Phe Ser  Val Asn Pro
    1250                 1255                 1260

Phe Gly  Leu Asn Ile Pro Leu  Ser Gly Ala Thr Asn  Ala Val Thr
    1265                 1270                 1275

Ile Pro  Gly Phe Ala Ile Asn  Pro Phe Gly Leu Asn  Val Pro Leu
    1280                 1285                 1290
```

Ser Gly Gly Thr Ser Pro Val Thr Ile Pro Gly Phe Ala Ile Asn
1295 1300 1305

Pro Phe Gly Leu Asn Val Pro Leu Ser Gly Gly Thr Ser Pro Val
1310 1315 1320

Thr Ile Pro Gly Phe Thr Ile Pro Gly Ser Pro Leu Asn Leu Thr
1325 1330 1335

Ala Asn Gly Gly Leu Gly Pro Ile Asn Ile Pro Ile Asn Ile Thr
1340 1345 1350

Ser Ala Pro Gly Phe Gly Asn Ser Thr Thr Thr Pro Ser Ser Gly
1355 1360 1365

Phe Phe Asn Ser Gly Asp Gly Ser Ala Ser Gly Phe Gly Asn Val
1370 1375 1380

Gly Pro Gly Ile Ser Gly Leu Trp Asn Gln Val Pro Asn Ala Leu
1385 1390 1395

Gln Gly Gly Val Ser Gly Ile Tyr Asn Val Gly Gln Leu Ala Ser
1400 1405 1410

Gly Val Ala Asn Leu Gly Asn Thr Val Ser Gly Phe Asn Asn Thr
1415 1420 1425

Ser Thr Val Gly His Leu Thr Ala Ala Phe Asn Ser Gly Val Asn
1430 1435 1440

Asn Ile Gly Gln Met Leu Leu Gly Phe Phe Ser Pro Gly Ala Gly
1445 1450 1455

Pro

<210> SEQ ID NO 130
<211> LENGTH: 4377
<212> TYPE: DNA
<213> ORGANISM: Mycobacterium tuberculosis

<400> SEQUENCE: 130 atgaatttt caacattgcc accagagatc aactcggccc tcatattcgg cggggcggga 60
tcagaaccca tgtcggcggc cgcggtcgcc tgggaccaac tggcgatgga attggcctcg 120
gcagcggcct ctttcaactc cgtgacgtcg ggcctggtcg gcgaatcgtg gctcggaccg 180
tcatcggcgg cgatggccgc tgcggtagcg ccgtacctag gatggcttgc cgcggcagcg 240
gcccaggccc agcggtcggc aacccaagcc gcggccctcg tggccgagtt cgaggctgtc 300
cgggcggcga tggtgcaacc ggcgctggtg gcggccaacc gctccgacct ggtgtcattg 360
gtgttctcaa acttcttcgg gcagaatgct ccggcgatcg ctgcgattga ggccgcatac 420
gaacagatgt gggccatcga tgtgtcggtg atgtcggcct accatgccgg ggcatcggcg 480
gtggcgtcgg ccctgacgcc gttcactgcg ccgccgcaga atctgacaga cctgcccgcc 540
cagttggcgg ccgctccggc ggccgtcgtc accgcggcga tcaccagttc caagggtgtg 600
ctggcaaatc ttagcttagg cctggcaaac tcgggcttcg gacagatggg cgccgctaac 660
cttggcattt tgaacttggg cagcctaaat cccggcggca acaacttcgg ccttggaaat 720
gtcggcagca acaacgttgg cttgggcaac accggcaacg gaaacatcgg cttcggcaac 780
acgggcaacg gaaacatcgg cttcggcctc accggcgaca accagcaggg gttcggcggc 840
tggaactcgg ggaccggcaa tatcggcttg ttcaactcag gcaccggcaa catcggcatc 900
ggcaatacgg gcaccggaaa cttcggcatc gggaactcag gtaccagcta caacacgggt 960
atcggcaaca cgggccaagc caacacgggc ttcttcaacg ccggcatcgc caacactggc 1020
atcggcaaca cgggcaacta caacacgggc agcttcaatc taggcagctt caacacgggc 1080

-continued

```
gacttcaaca cgggcagctc caacacaggc ttcttcaacc ccggcaacct caacaccggc   1140
gtgggaaaca ccggcaacgt caacaccggt ggattcaact ctggcaacta cagcaacggc   1200
ttcttctggc gaggcgacta ccagggcttg atcggcttct ccggcacact gaccattccc   1260
gctgctggcc tagacctcaa cggcctcggc tccgtcggcc ccatcaccat cccgtccatc   1320
accattcccg aaatcggcct gggcattaac agttccggag cgttggtggg gccgatcaat   1380
gttccgccta ttactgttcc cgccatcggg ctgggcatca acagtaccgg ggcactcgtt   1440
ggccccatca acatcccgcc gatcactcta aattctattg gcctagagct atcggcgttc   1500
caggtcatta acgtgggatc gatttcgatc cccgcgtctc cgcttgcgat cggcttattc   1560
ggcgtaaatc ccaccgttgg cagcataggc ccgggtagca tatcgataca gctaggcact   1620
cctgagattc ccgcgattcc gccatttttc cccggattcc ctccagatta cgtgacagtg   1680
agtggtcaaa tcggtcccat caccttctta tcgggtggtt atagtttgcc ggctattccg   1740
ttgggtattg atgtgggtgg agggttaggc ccgtttacgg tgttcccgga tggctactca   1800
cttccggcaa tcccgttggg tattgatgtg ggcggagggt taggcccgtt tacggtgttc   1860
ccggatggct actcacttcc ggcaatcccg ttgggtattg atgtgggcgg agggttaggc   1920
ccgtttacgg tgttcccgga tggctactca cttccggcaa tcccgttggg tattgatgtg   1980
ggcggcgcca tcggcccccct cactaccccg ccaatcacga tcccctcaat cccgttgggc   2040
atcgacgtgt ccggcagcct cgggccgatc aacatcccga tcgaaatcgc gggcacccca   2100
ggcttcggaa actcgaccac caccccgtca tcgggcttct tcaacagcgg tacgggcggc   2160
acatcgggtt tcgggaacgt cggttcgggc ggatctggct tctggaacat tgctgggaat   2220
ctcggcaact ccggattcct taacgtcggg ccactgacat cgggaatctt gaacttcggc   2280
aacacagtct caggcctcta caacaccagc acgctgggcc tagcgacatc ggcctttcac   2340
tccggcgtcg gtaacaccga cagccaactc gccggcttca tgcgcaacgc cgcaggtggg   2400
acgttattca acttcggctt cgccaacgac ggcacactca acttgggcaa cgcaaacctc   2460
ggcgactaca acgtgggtag cggaaacgtc ggtagctaca acttcggtag cggaaacatc   2520
ggcaacggaa gtttcggttt cggaaacatc ggaagcaaca acttcggttt tggaaacgtc   2580
ggcagcaaca accttgggtt tgcaaacacg ggtccggggt tgacggaggc cctgcacaac   2640
attggctttg ggaacatcgg cggcaacaac tacggcttcg cgaacatcgg taacggcaac   2700
atcggcttcg gcaacacggg cactggaaat attggtatcg ggctcaccgg cgacaatcag   2760
gtcggattcg gggcgctgaa ctccggcagc ggcaacatcg gcttcttcaa ctccggcaac   2820
ggcaacatcg gcttcttcaa ctcaggcaac ggaaacgtcg gcatcggcaa ctccggcaac   2880
tacaacaccg gcctgggtaa cgtgggcaac gccaacacgg gcctgttcaa caccggcaac   2940
gtcaacactg gaatcggcaa cgcaggaagc tacaacacag gcagctacaa cgccggcgac   3000
accaacacgg gcgacctcaa cccgggcaac gccaacacgg ggtacctaaa cctcggcgac   3060
ctcaacaccg gctggggaaa cattggcgac cttaacaccg gcgccctgat ctcgggcagc   3120
tacagcaacg gcatactgtg gaggggcgat taccagggtc tgattggcta ctcagacaca   3180
ctcagcattc ccgccatccc actgagcgtc gaagtgaatg gtggcatcgg tccgattgtg   3240
gtgccggata ttactattcc tggtattccg ttgagcctga acgcgctggg tggtgtcggt   3300
ccgattgtgg tgccggatat tactattcct ggtattccgt tgagcctgaa cgcgctgggt   3360
ggtgtcggtc cgattgtggt gccggatatt actattcctg gtattccgtt gagcctgaac   3420
gcgctgggtg gtgtcggtcc gattgtggtg ccggatatta ctattcctgg tattccgttg   3480
```

-continued

```
agcctgaacg cgctgggtgg tgtcggtccg attgtggtgc ctgatattac tattcctggt    3540

attccgttga gcctgaacgc gctgggtggt gtcggtccga tcaccgttcc cggcgtccct    3600

atttcccgca tccccttac gattaacatc aggataccgg tcaacatcac tctcaacgaa    3660

cttccgttta acgtcgctgg tatcttcacg ggctacatcg cccccatccc gcttagcaca    3720

ttcgtattag gcgtcacgct ggccggcggc accctggagt ctggcatcca gggattcagt    3780

gttaatccgt tcggtttgaa tattccgctg agcggtgcta ccaacgctgt cacgatccct    3840

ggtttcgcga ttaatccgtt tgggttgaat gttccgttga gcgggggcac gagcccggtt    3900

acgatccctg gtttcgcgat taatccgttt gggttgaatg ttccgttgag cgggggcacg    3960

agcccggtta cgatccccgg cttcaccatt cccggatccc ccctgaactt gaccgccaac    4020

ggcggcttgg gaccgatcaa catcccgatc aacatcacga gcgccccggg cttcggaaac    4080

tccaccacca ccccgtcttc gggcttcttc aacagtggcg atggaagcgc atccggcttc    4140

ggcaacgtcg ggcccggcat ttcgggcctc tggaaccagg tgccgaacgc gctgcaaggc    4200

ggagtctcgg gaatctacaa cgtcgggcag ctggcgtcgg gcgtggcgaa cctaggcaac    4260

accgtctcgg gcttcaacaa cacgagcacc gttggtcacc tcaccgctgc gtttaactcg    4320

ggcgtcaaca acatcggcca aatgctcctg ggcttcttct caccgggtgc cgggccg     4377
```

<210> SEQ ID NO 131
<211> LENGTH: 171
<212> TYPE: PRT
<213> ORGANISM: Mycobacterium tuberculosis

<400> SEQUENCE: 131

```
Val Ser Cys Thr Phe Asp Met Val Pro Glu Thr Val Asp His Leu Asp
1               5                   10                  15

Glu Val Gly Leu Arg Arg Val Phe Gly Cys Phe Pro Cys Gly Val Ile
            20                  25                  30

Ala Val Cys Ala Met Val Asp Asp Gln Pro Val Gly Met Ala Ala Ser
        35                  40                  45

Ser Phe Thr Ser Val Ser Val Asp Pro Pro Leu Val Ser Ile Cys Val
    50                  55                  60

Gln Asn Cys Ser Thr Thr Trp Pro Lys Leu Arg Asp Arg Pro Arg Leu
65                  70                  75                  80

Gly Val Ser Val Leu Ala Glu Gly His Asp Ala Ala Cys Met Ser Leu
                85                  90                  95

Ser Arg Lys Glu Gly Asn Arg Phe Ala Gly Val Phe Trp Ser Glu Leu
            100                 105                 110

Ser Ser Gly Gly Val Val Ile Ala Gly Ala Gly Ala Trp Leu Asp Cys
        115                 120                 125

Arg Pro Tyr Ala Glu Ile Pro Ala Gly Asp His Leu Ile Ala Leu Leu
    130                 135                 140

Glu Ile Cys Ala Val Arg Ala Asp Pro Glu Thr Pro Pro Leu Val Phe
145                 150                 155                 160

His Gly Ser Arg Phe Arg Arg Leu Glu Ser Arg
                165                 170
```

<210> SEQ ID NO 132
<211> LENGTH: 513
<212> TYPE: DNA
<213> ORGANISM: Mycobacterium tuberculosis

<400> SEQUENCE: 132

```
gtgagctgca ccttcgacat ggtcccggag accgtcgatc atctcgacga ggtcgggctg    60
```

```
cggcgggtct tcggctgctt tccgtgcggc gtgatcgccg tctgcgcgat ggtcgacgac    120

cagccggtcg gcatggcggc cagctcgttc acgtcggttt cagttgaccc gccgctggta    180

tcgatctgtg tgcagaactg ttcgacgacg tggccgaagt tgcgcgaccg cccacggctc    240

ggtgtgagcg tgctcgccga ggggcacgac gcggcctgta tgagcctgtc gcgcaaggaa    300

ggtaaccggt tcgccggggt gttctggagc gaattgtcca gcgggggtgt ggtgatcgcc    360

ggggccggcg cctggctgga ttgccgcccg tacgcggaga tcccggcggg ggatcacctg    420

atcgccctgc tggagatctg cgcggtgcgc gccgatcccg agacaccgcc gctggtgttt    480

cacggtagcc ggttccgccg gttggagtct cga                                 513
```

```
<210> SEQ ID NO 133
<211> LENGTH: 233
<212> TYPE: PRT
<213> ORGANISM: Mycobacterium tuberculosis

<400> SEQUENCE: 133

Ala Ala Gln Thr Thr Thr Leu Pro Asp Glu Pro Arg Asn Gly Val Thr
1               5                   10                  15

Gly Gly Ile Asp Trp Ala Arg Asp Asp His Ala Ala Ser Ile Val Asp
            20                  25                  30

Ala Arg Gly Arg Glu Val Arg Arg Ala Thr Ile Glu His Asn Ala Ala
        35                  40                  45

Gly Leu Arg Glu Leu Leu Glu Leu Leu Ser Arg Ala Gly Ala Arg Glu
    50                  55                  60

Val Ala Ile Glu Arg Pro Asp Gly Pro Val Val Asp Thr Leu Leu Glu
65                  70                  75                  80

Ala Gly Ile Thr Val Val Val Ile Ser Pro Asn Gln Leu Lys Asn Leu
                85                  90                  95

Arg Gly Arg Tyr Gly Ser Ala Gly Asn Lys Asp Asp Arg Phe Asp Ala
            100                 105                 110

Phe Val Leu Ala Asp Thr Leu Arg Thr Asp Arg Ser Arg Leu Arg Pro
        115                 120                 125

Leu Leu Pro Asp Thr Pro Ala Thr Ala Thr Leu Arg Arg Thr Cys Arg
    130                 135                 140

Pro Arg Lys Asp Leu Val Ala His Arg Val Ala Leu Ala Asn Gln Leu
145                 150                 155                 160

Arg Ala His Leu Arg Val Val Phe Pro Gly Val Val Gly Leu Phe Ala
                165                 170                 175

Asp Leu Asp Ser Pro Ile Ser Leu Ala Phe Leu Thr Phe Leu Pro Arg
            180                 185                 190

Phe Asp Cys Gln Asp Arg Ala Asp Trp Leu Ser Val Lys Arg Leu Ala
        195                 200                 205

Gly Trp Leu Ala Ala Ala Gly Tyr Cys Gly Arg Ala Pro Arg Pro Ala
    210                 215                 220

His Arg Cys Pro Ala Arg Arg His Arg
225                 230
```

```
<210> SEQ ID NO 134
<211> LENGTH: 699
<212> TYPE: DNA
<213> ORGANISM: Mycobacterium tuberculosis

<400> SEQUENCE: 134

gcggcccaaa ccactaccct gcccgacgag ccgcggaacg gcgtcacggg tggaatcgat     60
```

-continued

```
tgggcgcgag atgatcacgc ggcgtcgatc gtcgatgcgc gtgggcgcga ggttcgccgc    120

gccacgatcg agcacaacgc cgccggactg cgcgagctgc tcgagctgct gagccgggcc    180

ggtgcccgcg aggtcgccat cgaacgcccg gacggcccgg tcgtggatac cctgctcgag    240

gccgggatca cggtggtggt gatcagcccc aaccagctga agaatctgcg cggtcgttac    300

ggctcggctg gcaacaagga cgaccggttc gacgcgttcg tgctcgccga cacgttgcgc    360

accgaccggt cccggctgcg ccccctgctg cccgacaccc cggccacggc caccctgcgc    420

cggacctgcc gcccccgcaa agacctcgtc gcccaccggg ttgcgttggc caatcagctg    480

cgcgcgcacc tgcgcgtcgt ctttccgggt gtggtcgggt tgttcgctga ccttgactcg    540

ccgatcagcc tcgcgttttt gacgtttttg ccccgtttcg actgccagga ccgcgcggac    600

tggctgtcgg tcaagcgcct ggccggctgg ctggccgccg ctggctactg cggccgtgct    660

ccacgaccgg ctcaccggtg ccccgcgcgg cgccaccgg                           699
```

<210> SEQ ID NO 135
<211> LENGTH: 573
<212> TYPE: PRT
<213> ORGANISM: Mycobacterium tuberculosis

<400> SEQUENCE: 135

```
Val Thr His Pro Asp Arg Ala Asn Val Asn Pro Gly Ser Pro Pro Leu
1               5                   10                  15

Arg Glu Thr Leu Ser Gln Leu Arg Leu Arg Glu Leu Leu Leu Glu Val
            20                  25                  30

Gln Asp Arg Ile Glu Gln Ile Val Glu Gly Arg Asp Arg Leu Asp Gly
        35                  40                  45

Leu Ile Asp Ala Ile Leu Ala Ile Thr Ser Gly Leu Lys Leu Asp Ala
    50                  55                  60

Thr Leu Arg Ala Ile Val His Thr Ala Ala Glu Leu Val Asp Ala Arg
65                  70                  75                  80

Tyr Gly Ala Leu Gly Val Arg Gly Tyr Asp His Arg Leu Val Glu Phe
                85                  90                  95

Val Tyr Glu Gly Ile Asp Glu Glu Thr Arg His Leu Ile Gly Ser Leu
            100                 105                 110

Pro Glu Gly Arg Gly Val Leu Gly Ala Leu Ile Glu Glu Pro Lys Pro
        115                 120                 125

Ile Arg Leu Asp Asp Ile Ser Arg His Pro Ala Ser Val Gly Phe Pro
    130                 135                 140

Leu His His Pro Pro Met Arg Thr Phe Leu Gly Val Pro Val Arg Ile
145                 150                 155                 160

Arg Asp Glu Val Phe Gly Asn Leu Tyr Leu Thr Glu Lys Ala Asp Gly
                165                 170                 175

Gln Pro Phe Ser Asp Asp Asp Glu Val Leu Val Gln Ala Leu Ala Ala
            180                 185                 190

Ala Ala Gly Ile Ala Val Asp Asn Ala Arg Leu Phe Glu Glu Ser Arg
        195                 200                 205

Thr Arg Glu Ala Trp Ile Glu Ala Thr Arg Asp Ile Gly Thr Gln Met
    210                 215                 220

Leu Ala Gly Ala Asp Pro Ala Met Val Phe Arg Leu Ile Ala Glu Glu
225                 230                 235                 240

Ala Leu Thr Leu Met Ala Gly Ala Ala Thr Leu Val Ala Val Pro Leu
                245                 250                 255

Asp Asp Glu Ala Pro Ala Cys Glu Val Asp Asp Leu Val Ile Val Glu
            260                 265                 270
```

```
Val Ala Gly Glu Ile Ser Pro Ala Val Lys Gln Met Thr Val Ala Val
        275                 280                 285

Ser Gly Thr Ser Ile Gly Gly Val Phe His Asp Arg Thr Pro Arg Arg
    290                 295                 300

Phe Asp Arg Leu Asp Leu Ala Val Asp Gly Pro Val Glu Pro Gly Pro
305                 310                 315                 320

Ala Leu Val Leu Pro Leu Arg Ala Ala Asp Thr Val Ala Gly Val Leu
                325                 330                 335

Val Ala Leu Arg Ser Ala Asp Glu Gln Pro Phe Ser Asp Lys Gln Leu
            340                 345                 350

Asp Met Met Ala Ala Phe Ala Asp Gln Ala Ala Leu Ala Trp Arg Leu
        355                 360                 365

Ala Thr Ala Gln Arg Gln Met Arg Glu Val Glu Ile Leu Thr Asp Arg
    370                 375                 380

Asp Arg Ile Ala Arg Asp Leu His Asp His Val Ile Gln Arg Leu Phe
385                 390                 395                 400

Ala Val Gly Leu Thr Leu Gln Gly Ala Ala Pro Arg Ala Arg Val Pro
                405                 410                 415

Ala Val Arg Glu Ser Ile Tyr Ser Ser Ile Asp Asp Leu Gln Glu Ile
            420                 425                 430

Ile Gln Glu Ile Arg Ser Ala Ile Phe Asp Leu His Ala Gly Pro Ser
        435                 440                 445

Arg Ala Thr Gly Leu Arg His Arg Leu Asp Lys Val Ile Asp Gln Leu
    450                 455                 460

Ala Ile Pro Ala Leu His Thr Thr Val Gln Tyr Thr Gly Pro Leu Ser
465                 470                 475                 480

Val Val Asp Thr Val Leu Ala Asn His Ala Glu Ala Val Leu Arg Glu
                485                 490                 495

Ala Val Ser Asn Ala Val Arg His Ala Asn Ala Thr Ser Leu Ala Ile
            500                 505                 510

Asn Val Ser Val Glu Asp Asp Val Arg Val Glu Val Val Asp Asp Gly
        515                 520                 525

Val Gly Ile Ser Gly Asp Ile Thr Glu Ser Gly Leu Arg Asn Leu Arg
    530                 535                 540

Gln Arg Ala Asp Asp Ala Gly Gly Glu Phe Thr Val Glu Asn Met Pro
545                 550                 555                 560

Thr Gly Gly Thr Leu Leu Arg Trp Ser Ala Pro Leu Arg
                565                 570
```

```
<210> SEQ ID NO 136
<211> LENGTH: 1719
<212> TYPE: DNA
<213> ORGANISM: Mycobacterium tuberculosis

<400> SEQUENCE: 136

gtgacacacc ctgacagggc gaacgttaac cctggcagcc cgccattgcg cgagacactg      60

tcgcagcttc ggttgcgaga gctgctgctg gaagtccaag accggattga acagatcgtc     120

gaaggccgcg accggctgga tggtctgatc gacgccatct tggcgatcac atcgggactc     180

aagctcgacg ccaccctgcg cgccattgtg cataccgccg ccgagttggt ggatgcccgc     240

tacggggcgc tcggggtgcg cggttacgac catagattgg tcgaattcgt ctacgagggg     300

atcgacgaag agacccggca cctcatcggc tcattgccgg aggggcgagg tgttctcggc     360

gcgctgatcg aggagccaaa gccgatccgg ctggacgata tctcgcggca tcccgcatcg     420
```

```
gttggatttc cgctgcacca tccgccgatg cggaccttcc tcggggttcc agtgcgcatc    480

cgcgacgagg tgttcggcaa tctttacttg accgagaagg cagatggcca gccgttcagc    540

gatgacgacg aggtgctggt gcaggcgctg gccgccgcgg ccgggattgc cgttgacaat    600

gcccgtctct tcgaggaatc acggacccgg gaagcgtgga tcgaggcaac ccgcgacatc    660

ggaacgcaga tgctggccgg tgcggacccg gccatggtgt ttcggctcat cgccgaggaa    720

gcgttgacgt tgatggctgg ggcagccacc ttggtggcgg tgccgctcga cgacgaagcg    780

ccggcttgcg aggtcgacga cctggtcatc gtagaggtgg ccggagagat ctccccggcg    840

gtcaagcaaa tgacggttgc cgtcagcgga acgtcgatcg ggggagtctt tcacgaccgt    900

acgccccgcc ggttcgaccg gcttgacctc gcggtcgacg gcccggtgga gcccgggccc    960

gccctggtgc tgccgctgcg tgccgccgac actgttgccg gtgtgctggt cgcacttcgc   1020

agtgccgatg aacagccgtt cagcgacaaa cagctcgata tgatggccgc cttcgctgac   1080

caggctgcgc tcgcctggcg gctggcgacc gcgcagcgac agatgcgaga agtggagatc   1140

ctgaccgatc gcgaccggat cgcacgtgat ctgcatgacc acgtcatcca gcggctcttc   1200

gcagtcgggc tcaccctgca gggtgccgct ccgcgagcac gtgtccccgc cgtccgggaa   1260

tccatctaca gcagcatcga cgatctccag gaaatcattc aggagattcg atctgcgatc   1320

ttcgacctac acgccgggcc ctcccgggcg acgggtctgc gccaccgact ggacaaggtc   1380

atcgaccaac tcgcgatccc cgcgctgcac accacggtcc agtacacggg cccgctgtcc   1440

gttgtcgaca ccgtcctggc caaccacgcc gaagcggttc tgcgggaggc ggttagcaac   1500

gctgtccggc acgcgaacgc gaccagcctg gccatcaacg tcagcgtcga ggatgatgtg   1560

cgggtcgagg tcgtcgacga cggtgtcggc atctccggcg acatcaccga aagcggcctg   1620

cgcaatctcc gccagcgtgc cgacgacgcg ggcggcgaat tcacagtcga gaacatgccg   1680

accggaggca ccttgctgcg gtggtctgca ccgctgcgc                           1719
```

<210> SEQ ID NO 137
<211> LENGTH: 217
<212> TYPE: PRT
<213> ORGANISM: Mycobacterium tuberculosis

<400> SEQUENCE: 137

```
Ala Asn His Arg Asn Thr Gln Gly Arg Asn Glu Phe Leu Arg Ala Glu
1               5                   10                  15

Val Arg Pro Ala Thr Pro Leu Ile Cys Ala Phe Gly Asp Lys His Lys
            20                  25                  30

His Thr Tyr Gly Val Thr Pro Ile Cys Arg Ala Leu Ala Val His Gly
        35                  40                  45

Val Gln Ile Ala Ser Arg Thr Tyr Phe Ala Asp Arg Ala Ala Ala Pro
    50                  55                  60

Ser Lys Arg Ala Leu Trp Asp Thr Thr Ile Thr Glu Ile Leu Ala Gly
65                  70                  75                  80

Tyr Tyr Glu Pro Asp Ala Glu Gly Lys Arg Pro Pro Glu Cys Leu Tyr
                85                  90                  95

Gly Ser Leu Lys Met Trp Ala His Leu Gln Arg Gln Gly Phe Arg Trp
            100                 105                 110

Pro Ser Ala Thr Val Lys Thr Ile Met Arg Ala Asn Gly Trp Arg Gly
        115                 120                 125

Val Pro Leu Ala Ala His Ile Thr His His Arg Thr Arg Pro Gly Arg
    130                 135                 140

Gly Pro Gly Pro Arg Pro Gly Gly Ser Ala Met Ala Gly Phe Ser Asn
```

```
145                 150                 155                 160

Glu Pro Ala Gly Ser Gly Arg Leu His Leu Arg Ala Asp Asp Val Glu
                165                 170                 175

Phe Arg Leu His Arg Val Arg Gly Arg Arg Leu Arg Arg Cys Asp Arg
            180                 185                 190

Gly Leu Gly Met Leu Ala Asp Gln Arg Arg Ser Val Arg Arg Thr Arg
        195                 200                 205

Ile Thr Pro Arg Pro Ser Arg Leu Thr
    210                 215


<210> SEQ ID NO 138
<211> LENGTH: 651
<212> TYPE: DNA
<213> ORGANISM: Mycobacterium tuberculosis

<400> SEQUENCE: 138

gcaaaccatc gaaatactca aggtcgcaac gagtttcttc gcgcggaagt gcgacccgcg      60

acaccgctga tctgtgcgtt cggcgacaag cacaagcaca cctacggggt cacaccgatc     120

tgtcgggcac tggccgtgca cggcgtgcag atcgcctcgc gcacctattt cgcggatcgc     180

gcggcagcgc cttcgaaacg cgcactgtgg gacaccacaa tcaccgaaat cctggccggc     240

tactacgaac ccgacgccga gggcaaacgc ccaccggaat gcctgtacgg cagcctgaag     300

atgtgggcgc acctgcagcg ccagggcttc cggtggccct ctgccacggt gaagacgatc     360

atgcgggcca acggttggcg cggagtgccc ctcgcagcgc acatcacaca ccaccgaacc     420

agacccggcc gcggcccagg ccctagacct ggcgggtcgg caatggcggg ctttagcaac     480

gaacctgctg gaagcggccg acttcaccta cgcgccgatg acgtggagtt ccggctacac     540

cgcgttcgtg gtcgacgcct acgccggtgt gatcgcgggc tgggaatgct cgctgaccaa     600

agacgcagcg ttcgtcgaac gcgcattacg ccacggcctt ccagactcac c               651


<210> SEQ ID NO 139
<211> LENGTH: 121
<212> TYPE: PRT
<213> ORGANISM: Mycobacterium tuberculosis

<400> SEQUENCE: 139

Pro Lys Thr Gln Arg Ser Ser Asn Ala His Tyr Ala Thr Ala Phe Gln
1               5                   10                  15

Thr His Leu Gly His Pro Phe Gly Gly Ala Ile His His Arg Asp Ala
            20                  25                  30

Gly Ser Gln Tyr Thr Ala Ile Tyr Phe Gly Lys Thr Pro Met Leu Ala
        35                  40                  45

Gly Leu Arg Pro Ser Ile Gly Ile Val Gly Asp Ala Leu Asp Asn Ala
    50                  55                  60

Leu Cys Glu Thr Thr Thr Gly Pro His Arg Thr Glu Cys Ser His Gly
65                  70                  75                  80

Ser Pro Phe Arg Ser Gly Pro Ile Arg Thr Leu Ala Asp Leu Glu Asp
                85                  90                  95

Ile Ala Ser Ala Trp Val Glu His Thr Cys His Thr Gln Gln Gly Val
            100                 105                 110

Arg Ile Pro Gly Arg Leu Gln Pro Ala
        115                 120


<210> SEQ ID NO 140
<211> LENGTH: 363
<212> TYPE: DNA
```

<213> ORGANISM: Mycobacterium tuberculosis

<400> SEQUENCE: 140
ccaaagacgc agcgttcgtc gaacgcgcat tacgccacgg ccttccagac tcacctaggt 60
cacccgtttg gcggagctat tcatcatcgc gacgccggaa gtcagtatac tgcaatatat 120
ttcggcaaga caccgatgct agccgggctg cggccgtcga taggcattgt tggcgacgcc 180
ctcgacaacg ccttatgtga aaccacgaca gggccccaca ggaccgaatg cagccacggc 240
agcccgtttc gtagcgggcc gatccgcacc ctggctgacc tggaagacat cgcctcggcg 300
tgggtggagc acacctgtca cacacaacaa ggtgtgcgaa tacccgggag gcttcaacct 360
gcg 363

<210> SEQ ID NO 141
<211> LENGTH: 375
<212> TYPE: PRT
<213> ORGANISM: Mycobacterium tuberculosis

<400> SEQUENCE: 141

Met Gly Ser Arg Arg Phe Asp Ala Glu Val Tyr Ala Arg Arg Leu Ala
1 5 10 15

Leu Ala Ala Ala Ala Thr Ala Asp Ala Gly Leu Ala Gly Leu Val Ile
20 25 30

Thr Pro Gly Tyr Asp Leu Cys Tyr Leu Ile Gly Ser Arg Ala Glu Thr
35 40 45

Phe Glu Arg Leu Thr Ala Leu Val Leu Pro Ala Ala Gly Ala Pro Ala
50 55 60

Val Val Leu Pro Arg Leu Glu Leu Ala Ala Leu Lys Gln Ser Ala Ala
65 70 75 80

Ala Glu Leu Gly Leu Arg Val Cys Asp Trp Val Asp Gly Asp Asp Pro
85 90 95

Tyr Gly Leu Val Ser Ala Val Leu Gly Gly Ala Pro Val Ala Thr Ala
100 105 110

Val Thr Asp Ser Met Pro Ala Leu His Met Leu Pro Leu Ala Asp Ala
115 120 125

Leu Gly Val Leu Pro Val Leu Ala Thr Asp Val Leu Arg Arg Leu Arg
130 135 140

Met Val Lys Glu Glu Thr Glu Ile Asp Ala Leu Arg Lys Ala Gly Ala
145 150 155 160

Ala Ile Asp Arg Val His Ala Arg Val Pro Glu Phe Leu Val Pro Gly
165 170 175

Arg Thr Glu Ala Asp Val Ala Ala Asp Ile Ala Glu Ala Ile Val Ala
180 185 190

Glu Gly His Ser Glu Val Ala Phe Val Ile Val Gly Ser Gly Pro His
195 200 205

Gly Ala Asp Pro His His Gly Tyr Ser Asp Arg Glu Leu Arg Glu Gly
210 215 220

Asp Ile Val Val Val Asp Ile Gly Gly Thr Tyr Gly Pro Gly Tyr His
225 230 235 240

Ser Asp Ser Thr Arg Thr Tyr Ser Ile Gly Glu Pro Asp Ser Asp Val
245 250 255

Ala Gln Ser Tyr Ser Met Leu Gln Arg Ala Gln Arg Ala Ala Phe Glu
260 265 270

Ala Ile Arg Pro Gly Val Thr Ala Glu Gln Val Asp Ala Ala Ala Arg
275 280 285

```
Asp Val Leu Ala Glu Ala Gly Leu Ala Glu Tyr Phe Val His Arg Thr
    290                 295                 300

Gly His Gly Ile Gly Leu Cys Val His Glu Glu Pro Tyr Ile Val Ala
305                 310                 315                 320

Gly Asn Asp Leu Val Leu Val Pro Gly Met Ala Phe Ser Ile Glu Pro
                325                 330                 335

Gly Ile Tyr Phe Pro Gly Arg Trp Gly Ala Arg Ile Glu Asp Ile Val
            340                 345                 350

Ile Val Thr Glu Asp Gly Ala Val Ser Val Asn Asn Cys Pro His Glu
        355                 360                 365

Leu Ile Val Val Pro Val Ser
    370                 375


<210> SEQ ID NO 142
<211> LENGTH: 1125
<212> TYPE: DNA
<213> ORGANISM: Mycobacterium tuberculosis

<400> SEQUENCE: 142

atgggttctc gccgattcga cgccgaggtt tatgcacggc ggctggcttt agcggcggcc     60

gcgacggcgg acgccggtct ggcgggtctg gtgataactc ccggctacga cctgtgttac    120

ctcatcgggt cgcgagcgga gacgttcgag cggctcaccg cgttggtgtt gccggccgcc    180

ggtgcgccgg cggttgtgct gccgcggctg gagctcgccg ccctcaagca atccgccgca    240

gcggaattgg gtctgcgcgt gtgcgattgg gtcgacggtg acgacccccta cgggttggtg    300

agtgccgtgt tgggcggagc tccggtagcg accgcggtca ccgattccat gccggcgttg    360

cacatgttgc cgctggccga cgcactgggt gtgctgccgg tattggccac cgacgtgctg    420

cgcaggctgc ggatggtcaa ggaggaaacc gagatcgacg cgctgcgtaa ggccggcgcg    480

gcgatcgatc gagtgcatgc ccgagtgccg gagtttctgg tcccgggccg aacggaagcc    540

gacgtagccg ccgacatcgc cgaagcaatt gtcgccgaag ggcattcgga ggtagcgttc    600

gtcatcgtgg gttccgggcc gcacggcgcc gacccgcatc acggatattc ggaccgcgaa    660

ttgcgggagg gtgacatcgt tgtcgtcgac atcggcggca cgtatgggcc tggataccac    720

tccgactcca cccgaaccta cagcatcggc gagcctgatt ctgatgtagc gcagtcatat    780

tcgatgttgc agcgagccca gcgggcggcg ttcgaggcca tccgcccagg ggtgacagcg    840

gagcaggtgg acgccgccgc gcgtgacgtg ctcgccgagg ccgggctcgc ggagtatttt    900

gtgcaccgca ccgggcacgg catcgggctg tgcgtgcacg aggagcccta tatcgtcgcc    960

ggcaatgacc tggtgttggt tcccggcatg gcgttttcca tcgagccggg aatctatttc   1020

ccgggccggt ggggcgcccg catcgaggac atcgtgatcg tgaccgagga cggtgctgtg   1080

tctgtcaaca actgcccgca cgagttgatc gtggtgccgg tgtcc                   1125


<210> SEQ ID NO 143
<211> LENGTH: 244
<212> TYPE: PRT
<213> ORGANISM: Mycobacterium tuberculosis

<400> SEQUENCE: 143

Met Ser Gly Pro Gln Gly Ser Asp Pro Arg Gln Pro Trp Gln Pro Pro
1               5                   10                  15

Gly Gln Gly Ala Asp His Ser Ser Asp Pro Thr Val Ala Ala Gly Tyr
            20                  25                  30

Pro Trp Gln Gln Gln Pro Thr Gln Glu Ala Thr Trp Gln Ala Pro Ala
        35                  40                  45
```

```
Tyr Thr Pro Gln Tyr Gln Gln Pro Ala Asp Pro Ala Tyr Pro Gln Gln
    50                  55                  60

Tyr Pro Gln Pro Thr Pro Gly Tyr Ala Gln Pro Glu Gln Phe Gly Ala
65                  70                  75                  80

Gln Pro Thr Gln Leu Gly Val Pro Gly Gln Tyr Gly Gln Tyr Gln Gln
                85                  90                  95

Pro Gly Gln Tyr Gly Gln Pro Gly Gln Tyr Gly Gln Pro Gly Gln Tyr
            100                 105                 110

Ala Pro Pro Gly Gln Tyr Pro Gly Gln Tyr Gly Pro Tyr Gly Gln Ser
        115                 120                 125

Gly Gln Gly Ser Lys Arg Ser Val Ala Val Ile Gly Gly Val Ile Ala
    130                 135                 140

Val Met Ala Val Leu Phe Ile Gly Ala Val Leu Ile Leu Gly Phe Trp
145                 150                 155                 160

Ala Pro Gly Phe Phe Val Thr Thr Lys Leu Asp Val Ile Lys Ala Gln
                165                 170                 175

Ala Gly Val Gln Gln Val Leu Thr Asp Glu Thr Thr Gly Tyr Gly Ala
            180                 185                 190

Lys Asn Val Lys Asp Val Lys Cys Asn Asn Gly Ser Asp Pro Thr Val
        195                 200                 205

Lys Lys Gly Ala Thr Phe Glu Cys Thr Val Ser Ile Asp Gly Thr Ser
    210                 215                 220

Lys Arg Val Thr Val Thr Phe Gln Asp Asn Lys Gly Thr Tyr Glu Val
225                 230                 235                 240

Gly Arg Pro Gln
```

<210> SEQ ID NO 144
<211> LENGTH: 732
<212> TYPE: DNA
<213> ORGANISM: Mycobacterium tuberculosis

<400> SEQUENCE: 144

```
atgagcggac cgcagggatc ggacccaagg cagccgtggc agccgcccgg ccagggcgcc      60

gaccattcct cggaccccac cgtggccgcg ggatatccct ggcagcagca gccgacccag     120

gaggcgacgt ggcaggcccc ggcgtacaca ccgcagtacc aacagccggc tgacccggcg     180

tacccgcagc agtacccgca gcccacaccc ggctatgcgc agcccgaaca gttcggtgca     240

cagcccaccc agctcggcgt gcccggtcag tacggccaat accagcagcc gggccaatat     300

ggccagccgg gacagtacgg ccagcccggc cagtacgcac cgcccggtca gtaccccggg     360

caatacggcc cgtatggcca gtcgggtcag ggtcgaagc gttcggttgc ggtgatcggc     420

ggcgtgatcg ccgtgatggc cgtgctgttc atcggcgcgg ttctaatact cggcttctgg     480

gcacccggat tcttcgtcac caccaagctg gacgtcatta aggcgcaggc cggtgtgcag     540

caggttctca ccgatgagac cacggggtac ggcgccaaga acgtcaaaga cgtcaagtgc     600

aacaacggtt cagaccccac ggtcaaaaag ggcgccacct tcgaatgcac ggtgagcatc     660

gacggcacct caaagcgcgt gaccgtgacc ttccaggaca acaagggcac ctacgaggtc     720

ggccggccac ag                                                         732
```

<210> SEQ ID NO 145
<211> LENGTH: 308
<212> TYPE: PRT
<213> ORGANISM: Mycobacterium tuberculosis

<400> SEQUENCE: 145

-continued

Val Arg Ala Ala Gly Leu Leu Lys Arg Leu Asn Pro Arg Asn Arg Arg
1 5 10 15

Ser Arg Val Asn Pro Asp Ala Thr Met Ser Leu Val Asp His Leu Thr
20 25 30

Glu Leu Arg Thr Arg Leu Leu Ile Ser Leu Ala Ala Ile Leu Val Thr
35 40 45

Thr Ile Phe Gly Phe Val Trp Tyr Ser His Ser Ile Phe Gly Leu Asp
50 55 60

Ser Leu Gly Glu Trp Leu Arg His Pro Tyr Cys Ala Leu Pro Gln Ser
65 70 75 80

Ala Arg Ala Asp Ile Ser Ala Asp Gly Glu Cys Arg Leu Leu Ala Thr
85 90 95

Ala Pro Phe Asp Gln Phe Met Leu Arg Leu Lys Val Gly Met Ala Ala
100 105 110

Gly Ile Val Leu Ala Cys Pro Val Trp Phe Tyr Gln Leu Trp Ala Phe
115 120 125

Ile Thr Pro Gly Leu Tyr Gln Arg Glu Arg Arg Phe Ala Val Ala Phe
130 135 140

Val Ile Pro Ala Ala Val Leu Phe Val Ala Gly Ala Val Leu Ala Tyr
145 150 155 160

Leu Val Leu Ser Lys Ala Leu Gly Phe Leu Leu Thr Val Gly Ser Asp
165 170 175

Val Gln Val Thr Ala Leu Ser Gly Asp Arg Tyr Phe Gly Phe Leu Leu
180 185 190

Asn Leu Leu Val Val Phe Gly Val Ser Phe Glu Phe Pro Leu Leu Ile
195 200 205

Val Met Leu Asn Leu Ala Gly Leu Leu Thr Tyr Glu Arg Leu Lys Ser
210 215 220

Trp Arg Arg Gly Leu Ile Phe Ala Met Phe Val Phe Ala Ala Ile Phe
225 230 235 240

Thr Pro Gly Ser Asp Pro Phe Ser Met Thr Ala Leu Gly Ala Ala Leu
245 250 255

Thr Val Leu Leu Glu Leu Ala Ile Gln Ile Ala Arg Val His Asp Lys
260 265 270

Arg Lys Ala Lys Arg Glu Ala Ala Ile Pro Asp Asp Glu Ala Ser Val
275 280 285

Ile Asp Pro Pro Ser Pro Val Pro Ala Pro Ser Val Ile Gly Ser His
290 295 300

Asp Asp Val Thr
305

<210> SEQ ID NO 146
<211> LENGTH: 924
<212> TYPE: DNA
<213> ORGANISM: Mycobacterium tuberculosis

<400> SEQUENCE: 146
gtgcgcgccg ccggtcttct caaacggctc aacccacgta acaggcgcag ccgcgtcaat 60
cctgacgcga cgatgtcgct ggtcgaccac ctgaccgagt tacgcaccag gttgctgatc 120
tccctggccg cgatcttggt caccacaatc ttcgggttcg tctggtattc gcattcgatt 180
ttcgggttgg acagcctcgg agagtggctg cggcatccct actgtgccct gccgcagtcg 240
gcccgggcgg atatcagcgc cgacggagag tgccgtttgt tggccaccgc gccgttcgac 300
cagttcatgt tgcggctcaa ggtcgggatg gccgccggca ttgtgctggc ttgcccggtg 360

```
tggttctacc agctgtgggc gttcatcacg cctggtctct accagaggga gcgccgcttc    420

gcggtggcct tcgtgatccc agcagcggtg ctgttcgtcg ccggtgccgt actggcctac    480

ctggtgttgt ccaaggcgtt gggctttttg ttgaccgtcg gcagcgacgt gcaggtgacc    540

gcgctgtctg gcgaccgcta ctttggcttt ctgctcaacc tgctggtggt gttcggggtc    600

agcttcgaat tcccctgct gatcgtgatg ctgaacctgg cgggcctgct gacctatgag    660

cggctcaagt cttggcggcg cgggttgatc tttgcgatgt tcgtcttcgc ggcgatcttc    720

acgcccggat ccgatccgtt ctcgatgacc gcgctcggtg cggcgttgac cgtgctgcta    780

gagctcgcca ttcagatcgc ccgcgtgcat gacaagcgaa aagccaagcg cgaagccgcg    840

attcccgacg acgaagcttc ggtcatcgac ccgccctcgc cggtgccggc gccatcggtc    900

atcggatctc atgacgacgt cacg                                           924


<210> SEQ ID NO 147
<211> LENGTH: 108
<212> TYPE: PRT
<213> ORGANISM: Mycobacterium tuberculosis

<400> SEQUENCE: 147

Met Ser Gly Gly Ser Ser Arg Arg Tyr Pro Pro Glu Leu Arg Glu Arg
1               5                   10                  15

Ala Val Arg Met Val Ala Glu Ile Arg Gly Gln His Asp Ser Glu Trp
            20                  25                  30

Ala Ala Ile Ser Glu Val Ala Arg Leu Leu Gly Val Gly Cys Ala Glu
        35                  40                  45

Thr Val Arg Lys Trp Val Arg Gln Ala Gln Val Asp Ala Gly Ala Arg
    50                  55                  60

Pro Gly Thr Thr Thr Glu Glu Ser Ala Glu Leu Lys Arg Leu Arg Arg
65                  70                  75                  80

Asp Asn Ala Glu Leu Arg Arg Ala Asn Ala Ile Leu Lys Thr Ala Ser
                85                  90                  95

Ala Phe Phe Ala Ala Glu Leu Asp Arg Pro Ala Arg
            100                 105


<210> SEQ ID NO 148
<211> LENGTH: 324
<212> TYPE: DNA
<213> ORGANISM: Mycobacterium tuberculosis

<400> SEQUENCE: 148

atgtcaggtg gttcatcgag gaggtacccg ccggagctgc gtgagcgggc ggtgcggatg     60

gtcgcagaga tccgcggtca gcacgattcg gagtgggcag cgatcagtga ggtcgcccgt    120

ctacttggtg ttggctgcgc ggagacggtg cgtaagtggg tgcgccaggc gcaggtcgat    180

gccggcgcac ggcccgggac cacgaccgaa gaatccgctg agctgaagcg cttgcggcgg    240

gacaacgccg aattgcgaag ggcgaacgcg attttaaaga ccgcgtcggc tttcttcgcg    300

gccgagctcg accggccagc acgc                                           324


<210> SEQ ID NO 149
<211> LENGTH: 108
<212> TYPE: PRT
<213> ORGANISM: Mycobacterium tuberculosis

<400> SEQUENCE: 149

Met Ser Gly Gly Ser Ser Arg Arg Tyr Pro Pro Glu Leu Arg Glu Arg
1               5                   10                  15
```

```
Ala Val Arg Met Val Ala Glu Ile Arg Gly Gln His Asp Ser Glu Trp
            20                  25                  30

Ala Ala Ile Ser Glu Val Ala Arg Leu Leu Gly Val Gly Cys Ala Glu
        35                  40                  45

Thr Val Arg Lys Trp Val Arg Gln Ala Gln Val Asp Ala Gly Ala Arg
    50                  55                  60

Pro Gly Thr Thr Thr Glu Glu Ser Ala Glu Leu Lys Arg Leu Arg Arg
65                  70                  75                  80

Asp Asn Ala Glu Leu Arg Arg Ala Asn Ala Ile Leu Lys Thr Ala Ser
                85                  90                  95

Ala Phe Phe Ala Ala Glu Leu Asp Arg Pro Ala Arg
            100                 105


<210> SEQ ID NO 150
<211> LENGTH: 324
<212> TYPE: DNA
<213> ORGANISM: Mycobacterium tuberculosis

<400> SEQUENCE: 150

atgtcaggtg gttcatcgag gaggtacccg ccggagctgc gtgagcgggc ggtgcggatg      60

gtcgcagaga tccgcggtca gcacgattcg gagtgggcag cgatcagtga ggtcgcccgt     120

ctacttggtg ttggctgcgc ggagacggtg cgtaagtggg tgcgccaggc gcaggtcgat     180

gccggcgcac ggcccgggac cacgaccgaa gaatccgctg agctgaagcg cttgcggcgg     240

gacaacgccg aattgcgaag ggcgaacgcg attttaaaga ccgcgtcggc tttcttcgcg     300

gccgagctcg accggccagc acgc                                            324


<210> SEQ ID NO 151
<211> LENGTH: 414
<212> TYPE: PRT
<213> ORGANISM: Mycobacterium tuberculosis

<400> SEQUENCE: 151

Val Asn Asp Asn Gln Leu Ala Pro Val Ala Arg Pro Arg Ser Pro Leu
1               5                   10                  15

Glu Leu Leu Asp Thr Val Pro Asp Ser Leu Leu Arg Arg Leu Lys Gln
            20                  25                  30

Tyr Ser Gly Arg Leu Ala Thr Glu Ala Val Ser Ala Met Gln Glu Arg
        35                  40                  45

Leu Pro Phe Phe Ala Asp Leu Glu Ala Ser Gln Arg Ala Ser Val Ala
    50                  55                  60

Leu Val Val Gln Thr Ala Val Val Asn Phe Val Glu Trp Met His Asp
65                  70                  75                  80

Pro His Ser Asp Val Gly Tyr Thr Ala Gln Ala Phe Glu Leu Val Pro
                85                  90                  95

Gln Asp Leu Thr Arg Arg Ile Ala Leu Arg Gln Thr Val Asp Met Val
            100                 105                 110

Arg Val Thr Met Glu Phe Phe Glu Glu Val Val Pro Leu Leu Ala Arg
        115                 120                 125

Ser Glu Glu Gln Leu Thr Ala Leu Thr Val Gly Ile Leu Lys Tyr Ser
    130                 135                 140

Arg Asp Leu Ala Phe Thr Ala Ala Thr Ala Tyr Ala Asp Ala Ala Glu
145                 150                 155                 160

Ala Arg Gly Thr Trp Asp Ser Arg Met Glu Ala Ser Val Val Asp Ala
                165                 170                 175
```

```
Val Val Arg Gly Asp Thr Gly Pro Glu Leu Leu Ser Arg Ala Ala Ala
            180                 185                 190

Leu Asn Trp Asp Thr Thr Ala Pro Ala Thr Val Leu Val Gly Thr Pro
        195                 200                 205

Ala Pro Gly Pro Asn Gly Ser Asn Ser Asp Gly Asp Ser Glu Arg Ala
    210                 215                 220

Ser Gln Asp Val Arg Asp Thr Ala Ala Arg His Gly Arg Ala Ala Leu
225                 230                 235                 240

Thr Asp Val His Gly Thr Trp Leu Val Ala Ile Val Ser Gly Gln Leu
                245                 250                 255

Ser Pro Thr Glu Lys Phe Leu Lys Asp Leu Leu Ala Ala Phe Ala Asp
            260                 265                 270

Ala Pro Val Val Ile Gly Pro Thr Ala Pro Met Leu Thr Ala Ala His
        275                 280                 285

Arg Ser Ala Ser Glu Ala Ile Ser Gly Met Asn Ala Val Ala Gly Trp
    290                 295                 300

Arg Gly Ala Pro Arg Pro Val Leu Ala Arg Glu Leu Leu Pro Glu Arg
305                 310                 315                 320

Ala Leu Met Gly Asp Ala Ser Ala Ile Val Ala Leu His Thr Asp Val
                325                 330                 335

Met Arg Pro Leu Ala Asp Ala Gly Pro Thr Leu Ile Glu Thr Leu Asp
            340                 345                 350

Ala Tyr Leu Asp Cys Gly Gly Ala Ile Glu Ala Cys Ala Arg Lys Leu
        355                 360                 365

Phe Val His Pro Asn Thr Val Arg Tyr Arg Leu Lys Arg Ile Thr Asp
    370                 375                 380

Phe Thr Gly Arg Asp Pro Thr Gln Pro Arg Asp Ala Tyr Val Leu Arg
385                 390                 395                 400

Val Ala Ala Thr Val Gly Gln Leu Asn Tyr Pro Thr Pro His
                405                 410


<210> SEQ ID NO 152
<211> LENGTH: 1242
<212> TYPE: DNA
<213> ORGANISM: Mycobacterium tuberculosis

<400> SEQUENCE: 152

gtgaacgaca atcagttggc tccagttgcc cgcccgaggt cgccgctcga actgctggac     60

actgtgcccg attcgctgct gcggcggttg aagcagtact cgggccggct ggccaccgag    120

gcagtttcgg ccatgcaaga acggttgccg ttcttcgccg acctagaagc gtcccagcgc    180

gccagcgtgg cgctggtggt gcagacggcc gtggtcaact tcgtcgaatg gatgcacgac    240

ccgcacagtg acgtcggcta taccgcgcag gcattcgagc tggtgcccca ggatctgacg    300

cgacggatcg cgctgcgcca gaccgtggac atggtgcggg tcaccatgga gttcttcgaa    360

gaagtcgtgc ccctgctcgc ccgttccgaa gagcagttga ccgccctcac ggtgggcatt    420

ttgaaataca gccgcgacct ggcattcacc gccgccacgg cctacgccga tgcggccgag    480

gcacgaggca cctgggacag ccggatggag gccagcgtgg tggacgcggt ggtacgcggc    540

gacaccggtc ccgagctgct gtcccgggcg gccgcgctga attgggacac caccgcgccg    600

gcgaccgtac tggtgggaac tccggcgccc ggtccaaatg gctccaacag cgacggcgac    660

agcgagcggg ccagccagga tgtccgcgac accgcggctc gccacggccg cgctgcgctg    720

accgacgtgc acggcacctg gctggtggcg atcgtctccg gccagctgtc gccaaccgag    780

aagttcctca aagacctgct ggcagcattc gccgacgccc cggtggtcat cggccccacg    840
```

```
gcgcccatgc tgaccgcggc gcaccgcagc gctagcgagg cgatctccgg gatgaacgcc    900

gtcgccggct ggcgcggagc gccgcggccc gtgctggcta gggaactttt gcccgaacgc    960

gccctgatgg gcgacgcctc ggcgatcgtg gccctgcata ccgacgtgat gcggccccta   1020

gccgatgccg gaccgacgct catcgagacg ctagacgcat atctggattg tggcggcgcg   1080

attgaagctt gtgccagaaa gttgttcgtt catccaaaca cagtgcggta ccggctcaag   1140

cggatcaccg acttcaccgg gcgcgatccc acccagccac gcgatgccta tgtccttcgg   1200

gtggcggcca ccgtgggtca actcaactat ccgacgccgc ac                      1242
```

<210> SEQ ID NO 153
<211> LENGTH: 312
<212> TYPE: PRT
<213> ORGANISM: Mycobacterium tuberculosis

<400> SEQUENCE: 153

```
Met Pro Leu Ser Ser Arg Met Pro Gly Leu Thr Cys Phe Glu Ile Phe
1               5                   10                  15

Leu Ala Ile Ala Glu Ala Gly Ser Leu Gly Gly Ala Ala Arg Glu Leu
            20                  25                  30

Gly Leu Thr Gln Gln Ala Val Ser Arg Arg Leu Ala Ser Met Glu Ala
        35                  40                  45

Gln Ile Gly Val Arg Leu Ala Ile Arg Thr Thr Arg Gly Ser Gln Leu
    50                  55                  60

Thr Pro Ala Gly Ile Val Val Ala Glu Trp Ala Ala Arg Leu Leu Glu
65                  70                  75                  80

Val Ala Asp Glu Ile Asp Ala Gly Leu Gly Ser Leu Arg Thr Glu Gly
                85                  90                  95

Arg Gln Arg Ile Arg Val Val Ala Ser Gln Thr Ile Ala Glu Gln Leu
            100                 105                 110

Met Pro His Trp Met Leu Ser Leu Arg Ala Ala Asp Met Arg Arg Gly
        115                 120                 125

Gly Thr Val Pro Glu Val Ile Leu Thr Ala Thr Asn Ser Glu His Ala
    130                 135                 140

Ile Ala Ala Val Arg Asp Gly Ile Ala Asp Leu Gly Phe Ile Glu Asn
145                 150                 155                 160

Pro Cys Pro Pro Thr Gly Leu Gly Ser Val Val Val Ala Arg Asp Glu
                165                 170                 175

Leu Val Val Val Val Pro Pro Gly His Lys Trp Ala Arg Arg Ser Arg
            180                 185                 190

Val Val Ser Ala Arg Glu Leu Ala Gln Thr Pro Leu Val Thr Arg Glu
        195                 200                 205

Pro Asn Ser Gly Ile Arg Asp Ser Leu Thr Ala Ala Leu Arg Asp Thr
    210                 215                 220

Leu Gly Glu Asp Met Gln Gln Ala Pro Pro Val Leu Glu Leu Ser Ser
225                 230                 235                 240

Ala Ala Ala Val Arg Ala Ala Val Leu Ala Gly Ala Gly Pro Ala Ala
                245                 250                 255

Met Ser Arg Leu Ala Ile Ala Asp Asp Leu Ala Phe Gly Arg Leu Leu
            260                 265                 270

Ala Val Asp Ile Pro Ala Leu Asn Leu Arg Arg Gln Leu Arg Ala Ile
        275                 280                 285

Trp Val Gly Gly Arg Thr Pro Pro Ala Gly Ala Ile Arg Asp Leu Leu
    290                 295                 300
```

-continued

Ser His Ile Thr Ser Arg Ser Thr
305 310

<210> SEQ ID NO 154
<211> LENGTH: 936
<212> TYPE: DNA
<213> ORGANISM: Mycobacterium tuberculosis

<400> SEQUENCE: 154
atgccgctca gctctcgtat gcccggactc acctgcttcg aaatctttct ggccatcgct 60
gaggccggca gtcttggcgg cgccgcacgc gaactcgggt tgactcaaca agctgtgtca 120
aggcggctcg catcgatgga ggcccagatc ggggtgcgat tggccatccg gacgacacgt 180
ggctcccaac tcacgcctgc cggcatcgtc gtcgccgaat gggcggcccg cttgctcgaa 240
gtcgccgacg agatcgatgc cggcctcggc tcgctgcgca ccgaaggccg ccagcgcatc 300
agagtggtgg ccagccagac gatagccgaa cagctgatgc cgcattggat gctgtccttg 360
cgggccgccg acatgcgccg cggtggtact gtccctgagg taatcctgac cgccaccaat 420
agcgagcatg cgatcgcagc cgttcgtgac ggcatcgcag atcttggatt catcgaaaac 480
ccctgtcctc ccacgggatt aggcagcgtt gtggttgcac gcgacgaact ggtcgtcgtc 540
gtgccgccgg gtcacaagtg ggcccgacgg tcacgagtag tgagcgcccg ggagctcgct 600
cagacgcctt tggtgactcg cgaaccgaac tctggcatcc gcgattcact caccgcggcg 660
ttacgtgaca cgctcgggga ggacatgcag caagcgccac cggtgctgga attatcatcg 720
gctgcggccg tgcgggccgc ggtcttggcc ggcgctggac cggctgcgat gagccggcta 780
gcgatagccg atgacctggc gttcggtcga ttactcgcgg tcgacatccc cgcgttgaac 840
ctgcggcgcc agcttcgagc catctgggtc ggtgggcgca ccccgccggc gggtgcgata 900
cgagacctgc tcagccacat cacttcccgc agcacg 936

<210> SEQ ID NO 155
<211> LENGTH: 74
<212> TYPE: PRT
<213> ORGANISM: Mycobacterium tuberculosis

<400> SEQUENCE: 155

Val Asn Pro Gly Phe Asp Ala Val Asp Gln Glu Thr Ala Ala Ala Gln
1 5 10 15

Ala Val Ala Asp Ala His Gly Val Pro Phe Leu Gly Ile Arg Gly Met
20 25 30

Ser Asp Gly Pro Gly Asp Pro Leu His Leu Pro Gly Phe Pro Val Gln
35 40 45

Phe Phe Val Tyr Lys Gln Ile Ala Ala Asn Asn Ala Ala Arg Val Thr
50 55 60

Glu Ala Phe Leu Gln Asn Trp Ala Gly Val
65 70

<210> SEQ ID NO 156
<211> LENGTH: 222
<212> TYPE: DNA
<213> ORGANISM: Mycobacterium tuberculosis

<400> SEQUENCE: 156
gtgaaccccg gcttcgacgc ggttgaccag gagacggcag ccgcgcaggc ggtcgccgat 60
gcacacggcg tcccgttcct gggaattcgc ggtatgtccg acgggcccgg cgacccgctg 120
catctgccgg gcttccccgt ccagttcttc gtttacaagc agattgcggc caacaacgcc 180
gcccgggtca ccgaagcctt cctgcagaac tgggccggcg tc 222

<210> SEQ ID NO 157
<211> LENGTH: 114
<212> TYPE: PRT
<213> ORGANISM: Mycobacterium tuberculosis

<400> SEQUENCE: 157

Val Val Ala Ala Leu His Ala Gly Lys Ala Val Thr Ile Ala Pro Gln
1 5 10 15

Ser Met Thr Leu Thr Thr Gln Gln Ala Ala Asp Leu Leu Gly Val Ser
20 25 30

Arg Pro Thr Val Val Arg Leu Ile Lys Ser Gly Glu Leu Ala Ala Glu
35 40 45

Arg Ile Gly Asn Arg His Arg Leu Val Leu Asp Asp Val Leu Ala Tyr
50 55 60

Arg Glu Ala Arg Arg Gln Arg Gln Tyr Asp Ala Leu Ala Glu Ser Ala
65 70 75 80

Met Asp Ile Asp Ala Asp Glu Asp Pro Glu Val Ile Cys Glu Gln Leu
85 90 95

Arg Glu Ala Arg Arg Val Val Ala Ala Arg Arg Arg Thr Glu Arg Arg
100 105 110

Arg Ala

<210> SEQ ID NO 158
<211> LENGTH: 342
<212> TYPE: DNA
<213> ORGANISM: Mycobacterium tuberculosis

<400> SEQUENCE: 158
gtggtggctg cgctgcacgc cggcaaggcg gtgaccatcg cgccgcagag catgacgctg 60
accacccagc aggccgccga ccttctcggg gtgagtcgtc cgaccgtggt gcgtctgatc 120
aagagcggcg agctggccgc cgagcgcatc gggaatcgcc accggctcgt gctcgacgac 180
gtgttggcct accgggaggc ccgccggcag cgccagtacg acgcgcttgc cgagagcgca 240
atggacatcg acgccgacga ggatcccgag gtgatttgcg agcagttgcg tgaggcgcgg 300
cgtgttgtcg ccgcgcgccg tagaactgag cggcggcgcg cc 342

<210> SEQ ID NO 159
<211> LENGTH: 221
<212> TYPE: PRT
<213> ORGANISM: Mycobacterium tuberculosis

<400> SEQUENCE: 159

Met Thr Asn Leu Ala Asp Ala Thr Gln Ala Thr Met Ala Leu Val Glu
1 5 10 15

Arg His Ala Ala His Asn Tyr Ser Pro Leu Pro Val Val Ala Ala Ser
20 25 30

Ala Glu Gly Ala Trp Ile Ala Asp Ile Asp Gly Leu Arg Tyr Leu Asp
35 40 45

Trp Leu Ala Ala Tyr Ser Ala Val Asn Leu Gly His Arg Asn Pro Ala
50 55 60

Ser Thr Ala Thr Ala His Ala Gln Val Asp Thr Val Thr Leu Leu Asn
65 70 75 80

Arg Ala Leu His Ala Asp Arg Leu Gly Pro Leu Gly Ala Ala Leu Ala
85 90 95

Gln Leu Cys Gly Lys Asp Val Val Leu Pro Met Asn Ser Asp Ala Glu

```
            100                 105                 110

Ala Val Glu Ser Gly Leu Arg Val Ala Arg Lys Trp Gly Ala Asp Val
        115                 120                 125

Asn Gly Leu Pro Ala Gly Arg His Asp Ile Ile Leu Ala Asn Asn Asn
    130                 135                 140

Phe His Gly His Thr Ser Ser Val Val Ser Phe Ser Ser Asp Pro Ala
145                 150                 155                 160

Ala Gly Ser Gly Val Glu Pro Ser Thr Pro Gly Leu Arg Ser Val Pro
                165                 170                 175

Phe Gly Asp Ala Ala Ala Pro Ala Gln Thr Ile Asp Asp Asn Thr Val
            180                 185                 190

Ala Asp Leu Leu Glu Pro Ile Pro Gly Gln Ala Gly Ile Ile Val Pro
        195                 200                 205

Ala Asp Asp Tyr Leu Pro Ala Ala Ser Ser Thr Thr Cys
    210                 215                 220


<210> SEQ ID NO 160
<211> LENGTH: 663
<212> TYPE: DNA
<213> ORGANISM: Mycobacterium tuberculosis

<400> SEQUENCE: 160

atgacaaatc tcgcggatgc cactcaggcc actatggcac tggtcgaaag gcatgcagcg      60

cacaattatt cgccgctgcc tgtggtggcg gccagcgctg agggtgcgtg gatcgccgat     120

atcgacggcc tgcgctacct ggactggctg gctgcgtact cggcggtcaa ccttggccat     180

cgcaaccccg cgagcaccgc cacggctcat gcccaagtcg acaccgtcac cctgctgaat     240

cgggccttgc atgccgaccg actcgggccg ttgggcgccg cgcttgccca gctgtgcggc     300

aaagacgtgg tgttgccaat gaactctgat gctgaagcgg tggagagcgg tcttagggtc     360

gcccgcaagt ggggagccga cgtcaacggc ctccccgcgg gccggcacga tatcattttg     420

gcaaacaaca actttcatgg ccacaccagc agtgtcgtca gcttctcgtc ggacccggct     480

gcgggcagcg gcgtcgaacc ttctaccccg ggactccgct cggtaccgtt tggcgatgct     540

gcggcaccgg cgcagacaat cgacgacaac accgtcgctg acctgctcga gccgattccc     600

ggccaggcgg gcatcatcgt cccggccgac gactacctgc cggctgcgtc gagcacaacg     660

tgc                                                                   663


<210> SEQ ID NO 161
<211> LENGTH: 302
<212> TYPE: PRT
<213> ORGANISM: Mycobacterium tuberculosis

<400> SEQUENCE: 161

Met Glu Asn Thr Gln Arg Pro Ser Phe Asp Cys Glu Ile Arg Ala Lys
1               5                   10                  15

Tyr Arg Trp Phe Met Thr Asp Ser Tyr Val Ala Ala Ala Arg Leu Gly
            20                  25                  30

Ser Pro Ala Arg Arg Thr Pro Arg Thr Arg Arg Tyr Ala Met Thr Pro
        35                  40                  45

Pro Ala Phe Phe Ala Val Ala Tyr Ala Ile Asn Pro Trp Met Asp Val
    50                  55                  60

Thr Ala Pro Val Asp Val Gln Val Ala Gln Ala Gln Trp Glu His Leu
65                  70                  75                  80

His Gln Thr Tyr Leu Arg Leu Gly His Ser Val Asp Leu Ile Glu Pro
                85                  90                  95
```

-continued

```
Ile Ser Gly Leu Pro Asp Met Val Tyr Thr Ala Asn Gly Gly Phe Ile
            100                 105                 110

Ala His Asp Ile Ala Val Val Ala Arg Phe Arg Phe Pro Glu Arg Ala
        115                 120                 125

Gly Glu Ser Arg Ala Tyr Ala Ser Trp Met Ser Ser Val Gly Tyr Arg
    130                 135                 140

Pro Val Thr Thr Arg His Val Asn Glu Gly Gln Gly Asp Leu Leu Met
145                 150                 155                 160

Val Gly Glu Arg Val Leu Ala Gly Tyr Gly Phe Arg Thr Asp Gln Arg
                165                 170                 175

Ala His Ala Glu Ile Ala Ala Val Leu Gly Leu Pro Val Val Ser Leu
            180                 185                 190

Glu Leu Val Asp Pro Arg Phe Tyr His Leu Asp Thr Ala Leu Ala Val
        195                 200                 205

Leu Asp Asp His Thr Ile Ala Tyr Tyr Pro Pro Ala Phe Ser Thr Ala
    210                 215                 220

Ala Gln Glu Gln Leu Ser Ala Leu Phe Pro Asp Ala Ile Val Val Gly
225                 230                 235                 240

Ser Ala Asp Ala Phe Val Phe Gly Leu Asn Ala Val Ser Asp Gly Leu
                245                 250                 255

Asn Val Val Leu Pro Val Ala Ala Met Gly Phe Ala Ala Gln Leu Arg
            260                 265                 270

Ala Ala Gly Phe Glu Pro Val Gly Val Asp Leu Ser Glu Leu Leu Lys
        275                 280                 285

Gly Gly Gly Ser Val Lys Cys Cys Thr Leu Glu Ile His Pro
    290                 295                 300
```

<210> SEQ ID NO 162
<211> LENGTH: 906
<212> TYPE: DNA
<213> ORGANISM: Mycobacterium tuberculosis

<400> SEQUENCE: 162

```
atggaaaata cgcaacgacc atcgtttgat tgtgaaatca gagccaaata tcgttggttt      60

atgacggatt cctacgtcgc tgctgcccgt ctagggtcac ctgcacgccg caccccccgg     120

acgcggcggt atgcaatgac cccgccggcc ttctttgccg tcgcatacgc gatcaacccc     180

tggatggacg tcaccgcgcc agtcgacgtc caagtcgcgc aagcacagtg ggagcacctc     240

caccagacct atcttcggct aggccacagc gtggatctga tcgagcccat ttccgggtta     300

ccggacatgg tgtacaccgc caacggtggg ttcatcgcgc acgacatcgc cgtggtcgcc     360

cggttccggt tccccgaacg agctggtgag tctagagcct atgccagctg gatgtcctcg     420

gtcggatatc gcccggtgac cacccgccac gtcaacgagg gacagggcga cctgctgatg     480

gttggcgaaa gggtgttggc gggctacggc tttcgcacag accagcgcgc acacgccgaa     540

atcgccgcgg tgcttggtct gccggtggtc tccctcgagt tggtcgaccc acggttctat     600

cacctggaca ccgcgctggc cgtgctcgac gaccacacga tcgcctacta cccgccggcg     660

ttcagtacgg cagcgcagga acagttgtcg gcgctgttcc ccgacgcgat tgtggtcggc     720

agtgccgacg cgttcgtgtt cggactcaac gccgtctctg acggtctgaa cgtagtgctt     780

ccggtcgcgg ccatgggttt tgcggcgcag ttacgcgcag ccggcttcga gccggtcggt     840

gtcgatctgt ccgagctgct caagggcggc ggttccgtca agtgctgcac gctggagata     900

caccca                                                               906
```

<210> SEQ ID NO 163
<211> LENGTH: 652
<212> TYPE: PRT
<213> ORGANISM: Mycobacterium tuberculosis

<400> SEQUENCE: 163

Met Val Glu Ser Gly Thr Gly Ile Pro Leu Pro Ala Ser Cys Trp Ser
1 5 10 15

Arg Thr Arg Ser Arg Arg Cys Met Pro Lys Asp Ser Ser Pro His Trp
20 25 30

Ile Trp His Ser Ser Ala Ala Arg Ala Ala Leu Tyr Val Arg Gly Lys
35 40 45

Arg Arg Pro Asp Gly Gln Gly Arg Arg Ser Cys Ala Leu Arg Asn Arg
50 55 60

Gly Arg Thr Pro Ala Thr Gly Pro Gly Pro Gly Gln Ser Pro Ser Pro
65 70 75 80

Val Gly Ala Arg Gln Pro Ala Leu Pro Ser Arg Arg Pro Leu Asn Pro
85 90 95

Ala Arg Ser Arg Thr Glu Val Val Met Ser Asp Ala Arg Val Pro Arg
100 105 110

Ile Pro Ala Ala Leu Ser Ala Pro Ser Leu Asn Arg Gly Val Gly Phe
115 120 125

Thr His Ala Gln Arg Arg Arg Leu Gly Leu Thr Gly Arg Leu Pro Ser
130 135 140

Ala Val Leu Thr Leu Asp Gln Gln Ala Glu Arg Val Trp His Gln Leu
145 150 155 160

Gln Ser Leu Ala Thr Glu Leu Gly Arg Asn Leu Leu Leu Glu Gln Leu
165 170 175

His Tyr Arg His Glu Val Leu Tyr Phe Lys Val Leu Ala Asp His Leu
180 185 190

Pro Glu Leu Met Pro Val Val Tyr Thr Pro Thr Val Gly Glu Ala Ile
195 200 205

Gln Arg Phe Ser Asp Glu Tyr Arg Gly Gln Arg Gly Leu Phe Leu Ser
210 215 220

Ile Asp Glu Pro Asp Glu Ile Glu Glu Ala Phe Asn Thr Leu Gly Leu
225 230 235 240

Gly Pro Glu Asp Val Asp Leu Ile Val Cys Thr Asp Ala Glu Ala Ile
245 250 255

Leu Gly Ile Gly Asp Trp Gly Val Gly Gly Ile Gln Ile Ala Val Gly
260 265 270

Lys Leu Ala Leu Tyr Thr Ala Gly Gly Gly Val Asp Pro Arg Arg Cys
275 280 285

Leu Ala Val Ser Leu Asp Val Gly Thr Asp Asn Glu Gln Leu Leu Ala
290 295 300

Asp Pro Phe Tyr Leu Gly Asn Arg His Ala Arg Arg Arg Gly Arg Glu
305 310 315 320

Tyr Asp Glu Phe Val Ser Arg Tyr Ile Glu Thr Ala Gln Arg Leu Phe
325 330 335

Pro Arg Ala Ile Leu His Phe Glu Asp Phe Gly Pro Ala Asn Ala Arg
340 345 350

Lys Ile Leu Asp Thr Tyr Gly Thr Asp Tyr Cys Val Phe Asn Asp Asp
355 360 365

Met Gln Gly Thr Gly Ala Val Val Leu Ala Ala Val Tyr Ser Gly Leu
370 375 380

-continued

Lys Val Thr Gly Ile Pro Leu Arg Asp Gln Thr Ile Val Val Phe Gly
385 390 395 400

Ala Gly Thr Ala Gly Met Gly Ile Ala Asp Gln Ile Arg Asp Ala Met
405 410 415

Val Ala Asp Gly Ala Thr Leu Glu Gln Ala Val Ser Gln Ile Trp Pro
420 425 430

Ile Asp Arg Pro Gly Leu Leu Phe Asp Asp Met Asp Asp Leu Arg Asp
435 440 445

Phe Gln Val Pro Tyr Ala Lys Asn Arg His Gln Leu Gly Val Ala Val
450 455 460

Gly Asp Arg Val Gly Leu Ser Asp Ala Ile Lys Ile Ala Ser Pro Thr
465 470 475 480

Ile Leu Leu Gly Cys Ser Thr Val Tyr Gly Ala Phe Thr Lys Glu Val
485 490 495

Val Glu Ala Met Thr Ala Ser Cys Lys His Pro Met Ile Phe Pro Leu
500 505 510

Ser Asn Pro Thr Ser Arg Met Glu Ala Ile Pro Ala Asp Val Leu Ala
515 520 525

Trp Ser Asn Gly Arg Ala Leu Leu Ala Thr Gly Ser Pro Val Ala Pro
530 535 540

Val Glu Phe Asp Glu Thr Thr Tyr Val Ile Gly Gln Ala Asn Asn Val
545 550 555 560

Leu Ala Phe Pro Gly Ile Gly Leu Gly Val Ile Val Ala Gly Ala Arg
565 570 575

Leu Ile Thr Arg Arg Met Leu His Ala Ala Ala Lys Ala Ile Ala His
580 585 590

Gln Ala Asn Pro Thr Asn Pro Gly Asp Ser Leu Leu Pro Asp Val Gln
595 600 605

Asn Leu Arg Ala Ile Ser Thr Thr Val Ala Glu Ala Val Tyr Arg Ala
610 615 620

Ala Val Gln Asp Gly Val Ala Ser Arg Thr His Asp Asp Val Arg Gln
625 630 635 640

Ala Ile Val Asp Thr Met Trp Leu Pro Ala Tyr Asp
645 650

<210> SEQ ID NO 164
<211> LENGTH: 1956
<212> TYPE: DNA
<213> ORGANISM: Mycobacterium tuberculosis

<400> SEQUENCE: 164
atggttgagt cgggaaccgg gatcccccta ccggcttcct gctggagccg gacgagatcg 60
aggcgatgca tgccgaagga ttcctcgccg cactggatct ggcactcttc tgcggccagg 120
gcagcgctgt acgttcgcgg caaacgccga cccgatggcc aagggcgtcg atcgtgcgct 180
ctgcgaaatc gtggccgaac gccggcaact ggacctggac ctggccaaag cccaagtccg 240
gtcggcgctc gccaaccagc gttaccatcg cgacgtccat taaacccagc acggtcacga 300
acggaggttg tgatgagcga cgcccgcgtg ccacggatcc cggccgcgtt gtccgcacca 360
agtctcaacc gtggagtcgg cttcacccac gcgcagcggc ggcggctggg gctgaccggc 420
cggcttccgt cggccgtgct cacgctcgac caacaggccg aacgcgtatg gcatcagttg 480
cagagcttgg ccaccgagct gggccgcaac ctgcttctcg aacagctgca ctaccgccac 540
gaggtgctgt acttcaaggt gctggccgac catttgcccg aactgatgcc ggtggtgtac 600
acgcccaccg ttggcgaggc aatccaacgc ttctccgacg aataccgcgg gcaacgcgga 660

```
ctgtttctga gcatcgacga acccgacgaa atcgaggaag ccttcaacac gttggggctg     720

gggcccgagg acgtcgacct gatcgtgtgc accgatgccg aggcgatcct gggtatcggt     780

gactggggtg tgggtggcat ccagatcgct gtgggcaaat tggccctcta caccgccggc     840

ggcggcgtcg atccgcgccg ctgcctcgcg gtgtctctgg atgtcggcac cgacaatgag     900

cagctgctgg ccgatccgtt ctatctgggc aatcgccacg cccggcggcg cggtcgggaa     960

tacgacgagt tcgtcagtcg ctatatcgaa acggctcaac ggttatttcc gcgtgccatt    1020

ctgcatttcg aggacttcgg gccggcgaac gcgcggaaga tcctagacac atacggcacg    1080

gattactgcg tgttcaacga tgacatgcaa ggaaccggcg cggtggtctt ggccgccgta    1140

tacagcggtc tgaaggttac cggtatcccg ctgcgcgatc agacaatagt cgtcttcggc    1200

gcaggcaccg cagggatggg gatcgccgat cagatccggg acgcgatggt ggcagacggt    1260

gccacgctcg agcaggcggt gtcccagatc tggccgatcg acaggccggg cctgttgttc    1320

gacgacatgg atgacctgcg cgacttccaa gtgccgtacg cgaaaaaccg ccaccagctc    1380

ggtgtggccg tcggggatcg ggtcgggctg agcgacgcga tcaagatcgc atcgcccact    1440

atcctgctcg gctgctcaac ggtctacgga gcgttcacca aagaggtggt cgaggcgatg    1500

acggcgtcct gcaaacaccc gatgatcttt ccgctgtcca acccgacgtc gcgcatggaa    1560

gccatccccg ccgacgtgct ggcgtggtcg aatggcaggg cgctgcttgc caccggcagc    1620

ccagtcgccc cagtggaatt cgacgaaacc acctacgtca tcggtcaggc caacaacgtg    1680

ttggcgtttc ccggcatcgg actgggcgtc attgtcgctg gtgcccggtt gataaccagg    1740

cgcatgctgc atgcagcagc gaaggccatt gcgcaccagg ccaatccgac aaatcccgga    1800

gactcgctgt tgccggatgt ccaaaatctg cgggccatct cgacaacggt cgccgaagct    1860

gtctatcggg ccgccgtcca agacggggtg gcttccagga cgcacgacga cgtcaggcag    1920

gccatagtcg acaccatgtg gctcccggca tatgac                              1956
```

<210> SEQ ID NO 165
<211> LENGTH: 356
<212> TYPE: PRT
<213> ORGANISM: Mycobacterium tuberculosis

<400> SEQUENCE: 165

```
Met Leu Ser Leu Thr Leu Ser Glu Ala Ser Cys Ile Ala Ser Ala Ser
1               5                   10                  15

Arg Trp Arg His Ile Ile Pro Ala Gly Val Val Cys Ala Leu Ile Ala
            20                  25                  30

Gly Ile Gly Val Gly Cys His Gly Gly Pro Ser Asp Val Val Gly Arg
        35                  40                  45

Ala Gly Pro Asp Arg Ala His Thr Ser Ile Thr Leu Val Ala Tyr Ala
    50                  55                  60

Val Pro Glu Pro Gly Trp Ser Ala Val Ile Pro Ala Phe Asn Ala Ser
65                  70                  75                  80

Glu Gln Gly Arg Gly Val Gln Val Ile Thr Ser Tyr Gly Ala Ser Ala
                85                  90                  95

Asp Gln Ser Arg Gly Val Ala Asp Gly Lys Pro Ala Asp Leu Val Asn
            100                 105                 110

Phe Ser Val Glu Pro Asp Ile Ala Arg Leu Val Lys Ala Gly Lys Val
        115                 120                 125

Asp Lys Asp Trp Asp Ala Asp Ala Thr Lys Gly Ile Pro Phe Gly Ser
    130                 135                 140
```

-continued

```
Val Val Thr Phe Val Val Arg Ala Gly Asn Pro Lys Asn Ile Arg Asp
145                 150                 155                 160

Trp Asp Asp Leu Leu Arg Pro Gly Ile Glu Val Ile Thr Pro Ser Pro
                165                 170                 175

Leu Ser Ser Gly Ser Ala Lys Trp Asn Leu Leu Ala Pro Tyr Ala Ala
            180                 185                 190

Lys Ser Asp Gly Gly Arg Asn Asn Gln Ala Gly Ile Asp Phe Val Asn
        195                 200                 205

Thr Leu Val Asn Glu His Val Lys Leu Arg Pro Gly Ser Gly Arg Glu
    210                 215                 220

Ala Thr Asp Val Phe Val Gln Gly Ser Gly Asp Val Leu Ile Ser Tyr
225                 230                 235                 240

Glu Asn Glu Ala Ile Ala Thr Glu Arg Ala Gly Lys Pro Val Gln His
                245                 250                 255

Val Thr Pro Pro Gln Thr Phe Lys Ile Glu Asn Pro Leu Ala Val Val
            260                 265                 270

Ala Thr Ser Thr His Leu Gly Ala Ala Thr Ala Phe Arg Asn Phe Gln
        275                 280                 285

Tyr Thr Val Gln Ala Gln Lys Leu Trp Ala Gln Ala Gly Phe Arg Pro
    290                 295                 300

Val Asp Pro Ala Val Ala Ala Asp Phe Ala Asp Leu Phe Pro Val Pro
305                 310                 315                 320

Ala Lys Leu Trp Thr Ile Ala Asp Leu Gly Gly Trp Gly Ser Val Asp
                325                 330                 335

Pro Gln Leu Phe Asp Lys Ala Thr Gly Ser Ile Thr Lys Ile Tyr Leu
            340                 345                 350

Arg Ala Thr Gly
        355
```

<210> SEQ ID NO 166
<211> LENGTH: 1068
<212> TYPE: DNA
<213> ORGANISM: Mycobacterium tuberculosis

<400> SEQUENCE: 166

```
atgctctcct tgacgctttc tgaagcgagc tgcatcgcta gcgcatcccg ctggcggcac      60

attatccctg ccggggtggt gtgcgcattg atcgccggta tcggcgtggg gtgtcatggc     120

ggtcccagcg acgtggtcgg ccgtgcggga ccggaccgtg cgcatacgag catcaccctg     180

gtcgcctacg ccgtcccgga acccggctgg agtgcggtga ttcccgcgtt caacgcttcc     240

gaacagggcc ggggagtcca ggtgattacc tcatatggcg cgtcggccga ccagtcgcgc     300

ggtgttgccg acggtaaacc ggccgacctg gtgaacttct cggtcgaacc ggacatcgct     360

cgcctggtca aggccggcaa ggttgacaag gactgggacg ccgatgccac caagggcatc     420

ccgttcgggt cggtggtgac gtttgtggtc cgcgcgggta acccgaagaa catcagagat     480

tgggatgacc tgttgcgccc gggtattgag gtcatcacgc ccagtccgct gagttcgggt     540

tctgccaagt ggaatctgct agccccctac gccgcgaaaa gtgacggtgg ccggaataac     600

caagcgggga tcgactttgt caatacattg gtgaatgaac acgtcaaatt gcgccccggg     660

tcggggcggg aagccaccga tgtttttgtc cagggcagcg gtgacgtgtt gatcagctac     720

gagaacgaag ccatcgccac cgagcgggcg ggcaaaccgg tgcagcacgt caccccgccg     780

cagacgttca agatcgaaaa tccgttggcc gtagtggcga ccagcacaca ccttggagcg     840

gcgaccgcat tcagaaactt ccagtacacc gtgcaggcgc agaagttatg ggcgcaggcc     900
```

-continued

```
ggtttccggc cggtcgatcc ggcggtcgcc gccgattttg ccgacctgtt tccggtgccg    960

gcgaaactgt ggacgatcgc cgacctcggt ggctggggca gcgtggatcc tcagctgttc   1020

gacaaggcga ccggcagcat caccaagatt tatctgcggg ccaccgga                1068


<210> SEQ ID NO 167
<211> LENGTH: 514
<212> TYPE: PRT
<213> ORGANISM: Mycobacterium tuberculosis

<400> SEQUENCE: 167

Met Gly Phe Gly Ala Ser Arg Leu Asp Val Arg Leu Val Pro Ala Ala
1               5                   10                  15

Leu Val Ser Trp Ile Val Thr Ala Ala Gly Ile Val Trp Pro Ile Gly
            20                  25                  30

Asn Val Cys Ala Leu Cys Cys Val Val Val Ala Leu Gly Gly Gly Ala
        35                  40                  45

Leu Trp Trp Cys Val Ala Arg Arg Ser Trp His Ala Pro Arg Leu Gly
    50                  55                  60

Ser Ile Ser Ala Gly Leu Val Ala Val Gly Met Val Gly Ala Gly Tyr
65                  70                  75                  80

Gly Leu Ala Val Ala Leu Arg Ser Glu Ala Val Asp Arg His Pro Ile
                85                  90                  95

Thr Val Ala Phe Gly Thr Ser Ala Leu Val Thr Val Thr Pro Ser Glu
            100                 105                 110

Ser Pro Val Ser Leu Gly Arg Gly Arg Leu Met Phe Arg Ala Thr Val
        115                 120                 125

Gln Arg Leu Arg Asp Asp Glu Thr Ser Gly Arg Val Val Val Phe Ala
    130                 135                 140

Arg Ala Leu Asp Phe Gly Glu Leu Met Val Gly Gln Pro Val Gln Phe
145                 150                 155                 160

Arg Ala Arg Ile Ser Arg Pro Ala Arg His Asp Leu Thr Val Ala Val
                165                 170                 175

Phe Asn Ala Thr Gly Arg Pro Thr Val Gly Arg Ala Gly Pro Val His
            180                 185                 190

Arg Ala Ala His Ile Val Arg His Arg Phe Ala Ala Ala Val Arg Glu
        195                 200                 205

Val Leu Pro Ala Asp Gln Ala Thr Met Leu Pro Ala Leu Val Leu Gly
    210                 215                 220

Asp Thr Ser Thr Val Thr Ala Leu Thr Ser Arg Glu Phe Arg Ala Ala
225                 230                 235                 240

Gly Leu Thr His Leu Thr Ala Val Ser Gly Ala Asn Val Thr Ile Val
                245                 250                 255

Cys Ala Ala Ala Leu Val Ser Ala Arg Leu Ile Gly Pro Arg Ala Ala
            260                 265                 270

Val Val Cys Ala Ala Val Ala Leu Val Ala Phe Val Ile Leu Val Gln
        275                 280                 285

Pro Thr Ala Ser Val Leu Arg Ala Ala Val Met Gly Ala Ile Ala Leu
    290                 295                 300

Val Gly Met Leu Ser Ala Arg Arg Arg Gln Ala Ile Pro Ala Leu Ser
305                 310                 315                 320

Gly Ser Val Leu Val Leu Leu Ala Ala Ala Pro His Leu Ala Val Asp
                325                 330                 335

Ile Gly Phe Ala Leu Ser Val Ala Ala Thr Gly Ala Leu Val Val Ile
            340                 345                 350
```

```
Ala Pro Val Trp Ser Arg Arg Leu Val Asp Arg Gly Cys Pro Lys Val
        355                 360                 365

Leu Ala Asp Ala Leu Ala Val Ala Ala Ala Ala Gln Leu Val Thr Ala
    370                 375                 380

Pro Leu Val Ala Ala Ile Ser Gly Arg Val Ser Leu Val Ala Val Val
385                 390                 395                 400

Ala Asn Leu Ala Val Ala Ala Val Ile Ala Pro Ile Thr Val Leu Gly
                405                 410                 415

Ser Val Ala Ala Val Leu Val Val Pro Trp Pro Ala Gly Ala Gln Val
            420                 425                 430

Leu Ile Arg Phe Thr Gly Pro Glu Val Trp Trp Val Leu Arg Val Ala
        435                 440                 445

His Trp Ala Ser Gly Val Pro Ala Ala Thr Val Pro Val Ala Ala Gly
    450                 455                 460

Leu Pro Gly Val Leu Leu Val Gly Gly Ala Thr Val Phe Thr Val Ala
465                 470                 475                 480

Gln Trp Arg Trp Arg Trp Phe Arg Ala Ala Met Cys Lys Thr Met Ala
                485                 490                 495

Val Ala Val Ile Cys Leu Leu Ala Trp Ser Leu Ser Gly Leu Val Gly
            500                 505                 510

Pro Ser
```

<210> SEQ ID NO 168
<211> LENGTH: 1542
<212> TYPE: DNA
<213> ORGANISM: Mycobacterium tuberculosis

<400> SEQUENCE: 168

```
atgggcttcg gcgcgtcccg tttggacgta cgcctggtcc cggcggcgct ggtcagctgg      60

attgtgacgg cggccgggat cgtgtggccg atcggcaacg tgtgtgcctt gtgctgcgtc     120

gtggtggccc tcggcggcgg cgcactgtgg tggtgtgtgg cgcgccggtc gtggcacgct     180

ccgcgactgg gttcgatcag cgccggcctg gtcgcggtcg gtatggtggg cgcggggtac     240

gggcttgcgg tcgcgttgcg ctccgaggcg gtcgatcgcc acccaatcac cgtggcattt     300

ggcacctccg cgctggtcac ggtcaccccc agcgagagcc cagtgtcgct ggggcggggc     360

cggttgatgt tccgggcgac ggttcaacgg ctgcgggatg acgagacatc cggccgggta     420

gtggttttcg cgcgagcgct ggacttcggc gagctgatgg tcggacagcc cgtccagttc     480

cgcgcgcgta tcagtcgccc ggcgcgtcac gacctgacgg tcgcggtgtt caatgcgacc     540

ggtcggccga ccgtgggccg tgccggcccg gtacaccgcg ccgctcacat cgtccgccat     600

cgattcgcgg ccgcggttcg tgaggtgctg cccgctgacc aggccacgat gttgccggcc     660

ctggttctcg gcgatacctc gacggtcacc gccttaacca gccgcgagtt ccgtgcggcg     720

ggcctgacgc acttgacggc ggtctcgggg gccaatgtca cgatcgtgtg tgcggcggcg     780

ctggtttcgg cacggttgat cggaccgcgt gcggccgtgg tgtgcgcggc cgtcgcgttg     840

gtggcattcg tcatcctggt gcagccgacg gccagcgtgt tgcgggcagc tgtgatgggc     900

gccattgccc tcgtggggat gctgtctgcg cgccggcggc aggcgattcc agctttgtcg     960

ggtagcgtgc tggttttgct ggctgccgct ccccatcttg ctgtggacat cggcttcgcg    1020

ctgtccgtgg cggccacggg tgcactggtc gtcatcgcgc cggtttggtc acgccgcttg    1080

gtcgaccgcg gatgtccgaa ggtgctggcc gatgccctcg cagtcgcggc ggccgcgcag    1140

ctggtgacgg cgccactggt ggccgccatc tccggccggg tcagtctggt ggccgtggtg    1200
```

gccaatctgg cggtggcggc cgtgatcgcg ccgatcaccg tgctgggcag cgttgcggcc 1260
gtgctggtcg tgccgtggcc ggccggcgcg caggtgctga tccggttcac cgggcccgaa 1320
gtgtggtggg tgttgcgcgt ggcgcattgg gcgtcgggtg tgcccgcggc gaccgttccg 1380
gtggccgcag gtctgcccgg cgtactgctg gtcggtggcg ccaccgtgtt cacggttgcg 1440
cagtggcgct ggcgctggtt tcgcgcggcc atgtgcaaaa cgatggcggt ggccgtcata 1500
tgtctgcttg cctggtcgct gtccgggctg gtcggccctt cg 1542

<210> SEQ ID NO 169
<211> LENGTH: 139
<212> TYPE: PRT
<213> ORGANISM: Mycobacterium tuberculosis

<400> SEQUENCE: 169

Val Leu Gln Arg Thr Asn Val Val Gln Pro Leu Asn Thr Leu Arg Met
1 5 10 15

Val Trp Ile Gln Val Ala Gly Ile Ile Pro Ala Thr Ala Gly Ile Ala
20 25 30

Ala Thr Val Tyr Ala Gln Leu Ala Met Gly Asp Ser Trp Arg Ile Gly
35 40 45

Val Asp Glu Gln Glu Asn Thr Thr Leu Val Arg Thr Gly Pro Phe Lys
50 55 60

Trp Val Arg His Pro Ile Tyr Thr Ala Met Met Ala Phe Gly Leu Gly
65 70 75 80

Leu Leu Leu Val Thr Pro Asn Leu Val Ala Leu Ala Gly Phe Ile Leu
85 90 95

Leu Val Ala Thr Leu Glu Val His Val Arg Arg Val Glu Glu Pro Tyr
100 105 110

Leu Leu Arg Thr His Ser Ala Val Tyr Arg Gly Tyr Thr Ala Ser Val
115 120 125

Gly Arg Phe Val Pro Gly Val Gly Leu Ile Arg
130 135

<210> SEQ ID NO 170
<211> LENGTH: 417
<212> TYPE: DNA
<213> ORGANISM: Mycobacterium tuberculosis

<400> SEQUENCE: 170
gtgctgcagc ggaccaacgt tgtccaaccg ctgaatactc tgcgcatggt ctggattcag 60
gttgccggca taatcccggc gacggccggg atcgcggcca cggtttacgc ccagcttgcg 120
atgggcgatt cgtggcggat cggggtggac gagcaggaga acaccactct ggtgcgcacc 180
ggcccgttta aatgggtgcg tcaccccatc tacacggcca tgatggcgtt tggcctcggg 240
ctgttgctgg tgactccgaa tctcgttgcc ctcgccgggt ttatcctgct cgttgccacg 300
ctcgaggtgc atgtccgccg cgtcgaagaa ccctacctgt tgcggacgca cagtgccgtc 360
taccgcggct acaccgccag cgtcggccgg ttcgtcccgg gtgtggggtt gatccgc 417

<210> SEQ ID NO 171
<211> LENGTH: 161
<212> TYPE: PRT
<213> ORGANISM: Mycobacterium tuberculosis

<400> SEQUENCE: 171

Val Val Gly His Ile Val Asn Asp Leu Gln Arg Arg Lys Val Gly Asp
1 5 10 15

-continued

```
Gln Glu Val Val Lys Phe Arg Val Ala Ser Asn Ser Arg Arg Arg Thr
            20                  25                  30

Ser Asp Gly Gly Trp Glu Pro Gly Asn Ser Leu Phe Ile Thr Val Asn
        35                  40                  45

Cys Trp Gly Arg Leu Val Thr Gly Val Gly Ala Ala Leu Gly Lys Gly
    50                  55                  60

Ala Pro Val Ile Val Val Gly His Val Tyr Thr Ser Glu Tyr Glu Asp
65                  70                  75                  80

Arg Asp Gly Ile Arg Arg Ser Ser Leu Glu Met Arg Ala Thr Ser Val
                85                  90                  95

Gly Pro Asp Leu Ser Arg Val Ile Val Arg Ile Glu Lys Pro Ala Tyr
            100                 105                 110

Thr Gly Pro Ser Ala Gly Asp Leu Pro Ala Ala Thr Gly Thr Gly Ala
        115                 120                 125

Ala Gly Ala Ala Asp Ala Pro Ala Ser Ala Ala Asp Ser Val Ser Asp
    130                 135                 140

Val Val Val Asp Asp Ala Ile Thr Gly His Asn Pro Leu Pro Ile Ser
145                 150                 155                 160

Ala
```

<210> SEQ ID NO 172
<211> LENGTH: 483
<212> TYPE: DNA
<213> ORGANISM: Mycobacterium tuberculosis

<400> SEQUENCE: 172

```
gtggtcggtc acatcgtcaa cgatttgcag cgccgcaaag tcggtgatca agaggtcgtc      60

aagttccggg tggccagcaa ttcgcgccgg cgcaccagcg acggcggttg ggagcccggc     120

aactcgctgt ttatcaccgt caattgctgg ggaaggctgg tcaccggggt gggcgcagca     180

ttgggcaagg gcgcaccggt gattgtggtg ggacacgtgt acaccagtga atatgaggac     240

cgggacggca ttcgtcgctc gtcgctggag atgcgggcga cgtcggtagg gccggatttg     300

tcgcgcgtga tcgtgcgcat cgaaaagccg gcctacaccg gtccaagcgc cggtgatctc     360

ccggccgcca cggggaccgg ggcggccggt gccgccgacg ccccagcgtc ggcagccgac     420

tcggtttccg atgtcgtggt cgacgacgcc atcactggcc acaacccccct gcccatatcg     480

gct                                                                   483
```

<210> SEQ ID NO 173
<211> LENGTH: 256
<212> TYPE: PRT
<213> ORGANISM: Mycobacterium tuberculosis

<400> SEQUENCE: 173

```
Met Ala Gln Tyr Asp Pro Val Leu Leu Ser Val Asp Lys His Val Ala
1               5                   10                  15

Leu Ile Thr Val Asn Asp Pro Asp Arg Arg Asn Ala Val Thr Asp Glu
            20                  25                  30

Met Ser Ala Gln Leu Arg Ala Ala Ile Gln Arg Ala Glu Gly Asp Pro
        35                  40                  45

Asp Val His Ala Val Val Val Thr Gly Ala Gly Lys Ala Phe Cys Ala
    50                  55                  60

Gly Ala Asp Leu Ser Ala Leu Gly Ala Gly Val Gly Asp Pro Ala Glu
65                  70                  75                  80

Pro Arg Leu Leu Arg Leu Tyr Asp Gly Phe Met Ala Val Ser Ser Cys
                85                  90                  95
```

```
Asn Leu Pro Thr Ile Ala Ala Val Asn Gly Ala Ala Val Gly Ala Gly
            100                 105                 110

Leu Asn Leu Ala Leu Ala Ala Asp Val Arg Ile Ala Gly Pro Ala Ala
        115                 120                 125

Leu Phe Asp Ala Arg Phe Gln Lys Leu Gly Leu His Pro Gly Gly Gly
    130                 135                 140

Ala Thr Trp Met Leu Gln Arg Ala Val Gly Pro Gln Val Ala Arg Ala
145                 150                 155                 160

Ala Leu Leu Phe Gly Met Cys Phe Asp Ala Glu Ser Ala Val Arg His
                165                 170                 175

Gly Leu Ala Leu Met Val Ala Asp Asp Pro Val Thr Ala Ala Leu Glu
            180                 185                 190

Leu Ala Ala Gly Pro Ala Ala Ala Pro Arg Glu Val Val Leu Ala Ser
        195                 200                 205

Lys Ala Thr Met Arg Ala Thr Ala Ser Pro Gly Ser Leu Asp Leu Glu
    210                 215                 220

Gln His Glu Leu Ala Lys Arg Leu Glu Leu Gly Pro Gln Ala Lys Ser
225                 230                 235                 240

Val Gln Ser Pro Glu Phe Ala Ala Arg Leu Ala Ala Ala Gln His Arg
                245                 250                 255
```

<210> SEQ ID NO 174
<211> LENGTH: 768
<212> TYPE: DNA
<213> ORGANISM: Mycobacterium tuberculosis

<400> SEQUENCE: 174

```
atggcccaat acgacccggt cttgctcagc gtcgacaagc acgttgcgct catcacggtc     60

aacgacccgg accgacggaa cgccgtcacc gacgagatgt cggcgcagtt gcgtgcggcg    120

atccaacgcg ccgaaggcga ccccgacgta cacgccgtag tcgtgaccgg ggcgggcaag    180

gccttctgcg ccggggccga cctgagtgcg ctgggcgccg gggtcggcga tccagccgag    240

ccgagattgt tacggctcta cgacggtttc atggccgtca gtagttgtaa tctgcccacc    300

atcgccgcgg tcaacggcgc ggctgtgggc gccggactca atctggcgtt ggccgccgat    360

gtgcgcatcg ccggaccggc cgcattgttc gacgcccgct tccaaaagct gggactgcat    420

ccaggtggcg gcgcaacctg gatgctgcag cgagcggtgg gtccgcaggt cgcccgtgcg    480

gccttattgt tcggcatgtg cttcgacgcc gaatccgctg tgcggcacgg cttggcgcta    540

atggttgccg acgatcccgt caccgcggcg ctggagctgg ccgccgggcc cgcagccgcc    600

ccgcgcgagg tcgtgctggc gagcaaagcc accatgcgcg ccacagccag ccccggatcg    660

ctggaccttg agcaacacga actcgccaaa cgcttagaac ttgggccgca ggcgaaatcg    720

gtccagtcgc ccgagttcgc cgctcgcttg gctgccgctc aacacagg                 768
```

<210> SEQ ID NO 175
<211> LENGTH: 547
<212> TYPE: PRT
<213> ORGANISM: Mycobacterium tuberculosis

<400> SEQUENCE: 175

```
Val Ala Ala Ala Glu Val Val Asp Pro Asn Arg Leu Ser Tyr Asp Arg
1               5                   10                  15

Gly Pro Ser Ala Pro Ser Leu Leu Glu Ser Thr Ile Gly Ala Asn Leu
            20                  25                  30

Ala Ala Thr Ala Ala Arg Tyr Gly His Arg Glu Ala Leu Val Asp Met
```

-continued

```
        35                  40                  45

Val Ala Arg Arg Arg Phe Asn Tyr Ser Glu Leu Leu Thr Asp Val His
    50                  55                  60

Arg Leu Ala Thr Gly Leu Val Arg Ala Gly Ile Gly Pro Gly Asp Arg
65                  70                  75                  80

Val Gly Ile Trp Ala Pro Asn Arg Trp Glu Trp Val Leu Val Gln Tyr
                85                  90                  95

Ala Thr Ala Glu Ile Gly Ala Ile Leu Val Thr Ile Asn Pro Ala Tyr
            100                 105                 110

Arg Val Arg Glu Val Glu Tyr Ala Leu Arg Gln Ser Gly Val Ala Met
        115                 120                 125

Val Ile Ala Val Ala Ser Phe Lys Asp Ala Asp Tyr Ala Ala Met Leu
    130                 135                 140

Ala Glu Val Gly Pro Arg Cys Pro Asp Leu Ala Asp Val Ile Leu Leu
145                 150                 155                 160

Glu Ser Asp Arg Trp Asp Ala Leu Ala Gly Ala Glu Pro Asp Leu Pro
                165                 170                 175

Ala Leu Gln Gln Thr Ala Ala Arg Leu Asp Gly Ser Asp Pro Val Asn
            180                 185                 190

Ile Gln Tyr Thr Ser Gly Thr Thr Ala Tyr Pro Lys Gly Val Thr Leu
        195                 200                 205

Ser His Arg Asn Ile Leu Asn Asn Gly Tyr Leu Val Gly Glu Leu Leu
    210                 215                 220

Gly Tyr Thr Ala Gln Asp Arg Ile Cys Ile Pro Val Pro Phe Tyr His
225                 230                 235                 240

Cys Phe Gly Met Val Met Gly Asn Leu Ala Ala Thr Ser His Gly Ala
                245                 250                 255

Ala Met Val Ile Pro Ala Pro Gly Phe Asp Pro Ala Ala Thr Leu Arg
            260                 265                 270

Ala Val Gln Asp Glu Arg Cys Thr Ser Leu Tyr Gly Val Pro Thr Met
        275                 280                 285

Phe Ile Ala Glu Leu Gly Leu Pro Asp Phe Thr Asp Tyr Glu Leu Gly
    290                 295                 300

Ser Leu Arg Thr Gly Ile Met Ala Gly Ala Ala Cys Pro Val Glu Val
305                 310                 315                 320

Met Arg Lys Val Ile Ser Arg Met His Met Pro Gly Val Ser Ile Cys
                325                 330                 335

Tyr Gly Met Thr Glu Thr Ser Pro Val Ser Thr Gln Thr Arg Ala Asp
            340                 345                 350

Asp Ser Val Asp Arg Arg Val Gly Thr Val Gly Arg Val Gly Pro His
        355                 360                 365

Leu Glu Ile Lys Val Val Asp Pro Ala Thr Gly Glu Thr Val Pro Arg
    370                 375                 380

Gly Val Val Gly Glu Phe Cys Thr Arg Gly Tyr Ser Val Met Ala Gly
385                 390                 395                 400

Tyr Trp Asn Asp Pro Gln Lys Thr Ala Glu Val Ile Asp Ala Asp Gly
                405                 410                 415

Trp Met His Thr Gly Asp Leu Ala Glu Met Asp Pro Ser Gly Tyr Val
            420                 425                 430

Arg Ile Ala Gly Arg Ile Lys Asp Leu Val Val Arg Gly Gly Glu Asn
        435                 440                 445

Ile Ser Pro Arg Glu Ile Glu Glu Leu Leu His Thr His Pro Asp Ile
    450                 455                 460
```

```
Val Asp Gly His Val Ile Gly Val Pro Asp Ala Lys Tyr Gly Glu Glu
465                 470                 475                 480

Leu Met Ala Val Val Lys Leu Arg Asn Asp Ala Pro Glu Leu Thr Ile
                485                 490                 495

Glu Arg Leu Arg Glu Tyr Cys Met Gly Arg Ile Ala Arg Phe Lys Ile
            500                 505                 510

Pro Arg Tyr Leu Trp Ile Val Asp Glu Phe Pro Met Thr Val Thr Gly
        515                 520                 525

Lys Val Arg Lys Val Glu Met Arg Gln Gln Ala Leu Glu Tyr Leu Arg
    530                 535                 540

Gly Gln Gln
545
```

<210> SEQ ID NO 176
<211> LENGTH: 1641
<212> TYPE: DNA
<213> ORGANISM: Mycobacterium tuberculosis

<400> SEQUENCE: 176

```
gtggcagccg cggaagtcgt agaccccaat cggctttcct atgatcgcgg tccgagtgcg     60

ccatcattgc tcgagtcgac catcggcgcc aacctcgcag cgaccgctgc caggtacgga    120

catcgggaag cactcgtgga catggtggcc cggcgacggt tcaattacag cgaactgctg    180

actgacgtgc accggctggc gacggggctg gtgcgggcgg ggatcggccc gggcgatcgg    240

gtcggcatct gggcgccgaa ccggtgggag tgggtgctcg tccagtacgc gaccgctgag    300

atcggcgcga tcctagtgac cataaacccc gcctatcggg tccgcgaagt ggagtatgcg    360

cttaggcagt ccggtgtcgc gatggtgatt gccgtagcga gtttcaagga tgcggactat    420

gccgcgatgc tggccgaggt tgggccgcga tgccccgatc tggccgacgt gattttgctg    480

gaaagcgatc gctgggacgc gctggcgggt gccgagcccg atctgcctgc gctgcagcag    540

accgcggcga ggctagacgg cagtgatccg gtaaacatcc aatacacctc cggcacaacg    600

gcatacccga agggtgtcac gctaagccac cgcaatatcc tcaacaacgg ctacctggtg    660

ggcgagctgc tcgggtacac cgcacaagat cggatttgca tcccggtgcc cttctaccac    720

tgcttcggca tggtaatggg aaatctggcg gccaccagtc acggggcggc catggtgatc    780

ccggcgccgg gctttgaccc tgcggccacg ctgcgcgcgg tgcaggacga gcgatgcacc    840

agcttgtacg gcgtgccgac gatgttcatc gccgagctgg gcctgccgga cttcaccgac    900

tacgaactgg gcagtctgcg caccgggatt atggccggcg ccgcgtgccc ggtcgaggtg    960

atgcgcaagg tgatctcacg catgcatatg cccggggtct cgatctgcta tggaatgacc   1020

gaaacgtcac cggtttccac gcagacgcgc gccgacgact cggtggatcg acgggtcggc   1080

acggtcggtc gggtgggtcc acaccttgag atcaaggtgg tggatccggc cacgggcgag   1140

acggtcccgc gcggggtggt cggcgagttc tgcacgcgag gctattcggt gatggccggg   1200

tactggaatg acccgcagaa gactgcggag gtgatcgacg ccgacggctg gatgcacacc   1260

ggagatctgg ctgagatgga cccgtccggg tacgtgcgga tcgccggccg gatcaaagac   1320

ctcgtcgtcc ggggcggcga gaacatctcg ccgcgggaga tcgaggaact cctccacacg   1380

catcccgata ttgtcgacgg tcacgtcatc ggggtgcccg acgccaaata cggcgaagag   1440

ctcatggcgg tggtcaagct gagaaacgac gcgccggaac tgaccatcga gcggctgcgc   1500

gagtactgca tgggccgcat cgcgcgattc aagatcccgc ggtacctgtg gatcgtcgac   1560

gagttcccga tgaccgtcac cggcaaagta cgcaaagtgg agatgcgaca acaggcgctc   1620
```

gaatacctcc gcggccaaca g 1641

<210> SEQ ID NO 177
<211> LENGTH: 463
<212> TYPE: PRT
<213> ORGANISM: Mycobacterium tuberculosis

<400> SEQUENCE: 177

Val His Leu Ala His Arg Val Ala Ser Ser Arg Asp Thr Pro Ser Ser
1 5 10 15

Ser Ala Thr Pro Asn Ala Val Ser Gly Ser Ala Ser Asn Ala Ala Asp
20 25 30

Arg Pro Cys Leu Val Arg Pro Pro Thr Ala Pro Pro Trp Ala His Gly
35 40 45

Pro Arg Leu Arg Arg Asp Pro Thr Gly Gly Gly Ser Thr Pro Ser Ile
50 55 60

Val Leu Ser Arg Ser Thr Asp Arg Ser Lys Asp Gly His Arg Ile Val
65 70 75 80

Pro Ala Gly Ala Arg Lys Ser Gly Val Arg Ala Ser Thr Gly Arg Leu
85 90 95

Pro Ser Thr Arg Lys Thr Thr Arg Ser Pro Asp Cys Arg Pro Ser Ala
100 105 110

Ser Arg Thr Ala Phe Gly Thr Val Thr Cys Pro Phe Asp Val Thr Met
115 120 125

Gly Ser Ser Glu Cys Leu Leu His Arg Cys Arg Thr Pro Pro Val Pro
130 135 140

Ser His Ser Val Glu Leu Leu Val Ala Ala Asn Pro Ala Glu Asp Ser
145 150 155 160

Arg Leu Pro Tyr Leu Ile Arg Leu Pro Val Gly Ala Gly Leu Val Phe
165 170 175

Ala Thr Ser Asp Val Trp Pro Arg Thr Lys Ala Leu Tyr Cys His Arg
180 185 190

Leu Asp Ile Ala Asp Trp Pro Ala Asp Pro Val Val Val Asp Arg Val
195 200 205

Glu Leu Arg Ser Cys Ser Arg Arg Gly Ala Ala Ile Asp Val Val Ala
210 215 220

Ala Arg Ala Arg Glu Asn Arg Ser Gln Leu Val His Thr Met Ala Arg
225 230 235 240

Gly Arg Gln Val Val Phe Trp Gln Ser Pro Lys Thr Arg Lys Gln Ser
245 250 255

Arg Pro Gly Val Arg Thr Pro Thr Ala Arg Ala Ala Gly Ile Pro Glu
260 265 270

Leu His Ile Val Val Asp Ala His Glu Arg Tyr Pro Tyr Thr Phe Ala
275 280 285

Asp Lys Pro Ala Lys Thr Thr Arg Glu Ala Leu Pro Cys Gly Asp Tyr
290 295 300

Gly Leu Lys Val Ala Gly Gln Leu Val Ala Ala Val Glu Arg Lys Ala
305 310 315 320

Leu Ala Asp Leu Thr Ser Gly Val Leu Asn Gly Asn Leu Lys Tyr Gln
325 330 335

Leu Thr Glu Leu Ala Ala Leu Pro Arg Ala Ala Val Val Val Glu Asp
340 345 350

Arg Tyr Ser Glu Ile Phe Ala His Ser Phe Ala Arg Pro Thr Ala Ile
355 360 365

Ala Asp Gly Leu Ala Glu Leu Gln Ile Gly Phe Pro Asn Val Pro Ile 370 375 380

Val Phe Cys Gln Thr Arg Lys Leu Ala Gln Glu Tyr Thr Tyr Arg Tyr
385 390 395 400

Leu Ala Ala Ala Leu Thr Trp Phe Val Asp Asp Ala Asp Ala Thr Thr
405 410 415

Val Phe Glu Pro Ala Ala Ala Glu Pro Glu Pro Ser Ser Ala Glu Leu
420 425 430

Arg Ala Trp Ala Lys Ser Val Gly Leu Pro Val Ser Asp Arg Gly Arg
435 440 445

Leu Arg Pro Gln Ile Leu Gln Ala Trp Arg Ala Ala His Pro Arg
450 455 460

<210> SEQ ID NO 178
<211> LENGTH: 1389
<212> TYPE: DNA
<213> ORGANISM: Mycobacterium tuberculosis

<400> SEQUENCE: 178
gtgcacctcg cgcaccgggt cgccagcagc cgcgacacgc cgtcgtccag tgccacaccg 60
aatgcggtgt cgggctcggc gtcaaacgct gccgatcggc cttgcctcgt caggccgccg 120
acagcaccgc cctgggctca cggtccgcgg ctccgccggg atccgaccgg cggcggctca 180
accccctcga tcgtcttgag ccggtcgaca gaccgatcga aagacggcca ccggatcgtc 240
ccggcagggg cgaggaagtc cggcgtccga gcaagcaccg ggcgattgcc ctcaacgcgg 300
aagacaaccc gatcacccga ttgcaggccg agcgcgtcgc gcaccgcttt cggaaccgtc 360
acctgcccct tcgacgtgac gatgggttcg tcggagtgcc tgcttcaccg ttgccgtacg 420
ccgcccgtac cctcacactc tgtggagctg ctcgtcgccg ccaaccccgc tgaagactcg 480
cgcctgccct acctgatccg gctgccggtg ggcgcgggac tggtcttcgc cacctcagac 540
gtgtggccgc gcaccaaggc gctgtattgc catcgcctcg acatcgccga ctggcccgcc 600
gaccccgtcg tcgtcgaccg ggtcgagcta cgcagctgca gccgccgggg cgcggccatc 660
gacgtcgtcg ccgcccgcgc gcgggagaac cgatcgcaac tggtgcacac catggcgcgc 720
ggccgccagg tggtgttctg gcagagcccc aaaacgcgca aacagtcgcg gccgggcgtg 780
cgcaccccca ccgcccgcgc cgccggcatc cccgagctgc acatcgtcgt cgacgcccac 840
gaacgctacc cctacacctt tgccgacaaa cccgcgaaga cgacgcggga agccctgccc 900
tgcggcgact acggcctgaa agtggccggc caactcgtgg cggccgtcga gcgtaaagcg 960
ttggcggacc ttacttctgg cgtgctgaac ggcaacctga aataccaact gaccgaactg 1020
gccgcgctgc cacgggccgc cgtggtggtc gaggaccgct actcggagat cttcgcgcac 1080
tccttcgccc gcccgacggc gatcgccgat gggctggccg aattgcagat cggctttccc 1140
aacgtgccga tcgtgttctg ccaaacccgc aagctcgccc aggaatacac ctaccgctat 1200
ctagccgccg ccctcacctg gttcgtcgac gatgccgacg ccaccacggt tttcgagccg 1260
gctgccgccg agcccgagcc cagcagcgcc gagctgcgcg cgtgggccaa aagcgtcggc 1320
ctgccggtgt ccgaccgggg gcgcctgcgc ccgcagatcc tgcaggcctg gcgagccgcc 1380
catccccgg 1389

<210> SEQ ID NO 179
<211> LENGTH: 134
<212> TYPE: PRT
<213> ORGANISM: Mycobacterium tuberculosis

<400> SEQUENCE: 179

```
Val Ile Ala Pro Asp Thr Ser Val Leu Val Ala Gly Phe Ala Thr Trp
1               5                   10                  15

His Glu Gly His Glu Ala Ala Val Arg Ala Leu Asn Arg Gly Val His
            20                  25                  30

Leu Ile Ala His Ala Ala Val Glu Thr Tyr Ser Val Leu Thr Arg Leu
        35                  40                  45

Pro Pro Pro His Arg Ile Ala Pro Val Ala Val His Ala Tyr Leu Ala
    50                  55                  60

Asp Ile Thr Ser Ser Asn Tyr Leu Ala Leu Asp Ala Cys Ser Tyr Arg
65                  70                  75                  80

Gly Leu Thr Asp His Leu Ala Glu His Asp Val Thr Gly Gly Ala Thr
                85                  90                  95

Tyr Asp Ala Leu Val Gly Phe Thr Ala Lys Ala Ala Gly Ala Lys Leu
            100                 105                 110

Leu Thr Arg Asp Leu Arg Ala Val Glu Thr Tyr Glu Arg Leu Arg Val
        115                 120                 125

Glu Val Glu Leu Val Thr
    130


<210> SEQ ID NO 180
<211> LENGTH: 402
<212> TYPE: DNA
<213> ORGANISM: Mycobacterium tuberculosis

<400> SEQUENCE: 180

gtgatcgcac cagacaccag cgtgctggtt gccggattcg cgacctggca cgaagggcac      60

gaggccgccg tgcgcgcgct caaccgtggc gtccatctga tcgcgcacgc ggctgtggaa     120

acctattcgg tcttgacccg gctaccaccg ccgcatcgta ttgcccctgt tgccgtccac     180

gcctacttgg cggacatcac ctccagcaac tacctggcac tggatgcctg ctcatatcgc     240

ggcttgaccg accacctcgc cgagcacgat gtcaccggtg gcgcaaccta cgatgccctg     300

gtcggcttca cggcgaaagc tgccggcgca aagctgctga ctcgcgacct gcgcgcggtc     360

gaaacgtacg agcgattgcg ggtcgaggtt gagctggtga cc                        402


<210> SEQ ID NO 181
<211> LENGTH: 405
<212> TYPE: PRT
<213> ORGANISM: Mycobacterium tuberculosis

<400> SEQUENCE: 181

Val Thr Glu Asn Pro Tyr Leu Val Gly Leu Arg Leu Ala Gly Lys Lys
1               5                   10                  15

Val Val Val Val Gly Gly Gly Thr Val Ala Gln Arg Arg Leu Pro Leu
            20                  25                  30

Leu Ile Ala Ser Gly Ala Asp Val His Val Ile Ala Pro Ser Val Thr
        35                  40                  45

Pro Ala Val Glu Ala Met Asp Gln Ile Thr Leu Ser Val Arg Asp Tyr
    50                  55                  60

Arg Asp Gly Asp Leu Asp Gly Ala Trp Tyr Ala Ile Ala Ala Thr Asp
65                  70                  75                  80

Asp Ala Arg Val Asn Val Ala Val Val Ala Glu Ala Glu Arg Arg Arg
                85                  90                  95

Ile Phe Cys Val Arg Ala Asp Ile Ala Val Glu Gly Thr Ala Val Thr
            100                 105                 110

Pro Ala Ser Phe Ser Tyr Ala Gly Leu Ser Val Gly Val Leu Ala Gly
```

```
        115                 120                 125

Gly Glu His Arg Arg Ser Ala Ala Ile Arg Ser Ala Ile Arg Glu Ala
    130                 135                 140

Leu Gln Gln Gly Val Ile Thr Ala Gln Ser Ser Asp Val Leu Ser Gly
145                 150                 155                 160

Gly Val Ala Leu Val Gly Gly Gly Pro Gly Asp Pro Glu Leu Ile Thr
                165                 170                 175

Val Arg Gly Arg Arg Leu Leu Ala Gln Ala Asp Val Val Val Ala Asp
            180                 185                 190

Arg Leu Ala Pro Pro Glu Leu Leu Ala Glu Leu Pro Pro His Val Glu
        195                 200                 205

Val Ile Asp Ala Ala Lys Ile Pro Tyr Gly Arg Ala Met Ala Gln Asp
    210                 215                 220

Ala Ile Asn Ala Val Leu Ile Glu Arg Ala Arg Ser Gly Asn Phe Val
225                 230                 235                 240

Val Arg Leu Lys Gly Gly Asp Pro Phe Val Phe Ala Arg Gly Tyr Glu
                245                 250                 255

Glu Val Leu Ala Cys Ala His Ala Gly Ile Pro Val Thr Val Val Pro
            260                 265                 270

Gly Val Thr Ser Ala Ile Ala Val Pro Ala Met Ala Gly Val Pro Val
        275                 280                 285

Thr His Arg Ala Met Thr His Glu Phe Val Val Val Ser Gly His Leu
    290                 295                 300

Ala Pro Gly His Pro Glu Ser Leu Val Asn Trp Asp Ala Leu Ala Ala
305                 310                 315                 320

Leu Thr Gly Thr Ile Val Leu Leu Met Ala Val Glu Arg Ile Glu Leu
                325                 330                 335

Phe Val Asp Val Leu Leu Lys Gly Gly Arg Thr Ala Asp Thr Pro Val
            340                 345                 350

Leu Val Val Gln His Gly Thr Thr Ala Ala Gln Gln Thr Leu Arg Ala
        355                 360                 365

Thr Leu Ala Asp Thr Pro Glu Lys Val Arg Ala Ala Gly Ile Arg Pro
    370                 375                 380

Pro Ala Ile Ile Val Ile Gly Ala Val Val Gly Leu Ser Gly Val Arg
385                 390                 395                 400

Gly Leu Asn Asn Ser
                405
```

<210> SEQ ID NO 182
<211> LENGTH: 1215
<212> TYPE: DNA
<213> ORGANISM: Mycobacterium tuberculosis

<400> SEQUENCE: 182

```
gtgaccgaga acccctatct ggtcgggtta cggctggctg gcaagaaggt cgtcgtggtt      60

ggcgggggca cggtcgccca gcgccggtta cccctgctga tcgccagtgg cgcggacgtg     120

cacgtgatcg cccccagcgt cacccccgcc gtcgaggcga tggaccagat caccttgtcg     180

gtgcgtgact accgcgacgg cgaccttgac ggcgcctggt atgcgatcgc ggccaccgat     240

gacgcgcggg tgaacgtggc tgtcgtcgcc gaggcggagc gccgacggat cttttgcgtc     300

cgggccgata tcgcggtgga ggggacggcg gtgaccccgg cgtcattcag ctatgcgggc     360

ctgtcggtgg gggtgctcgc cggtggtgag caccgccgtt cggcggcgat ccgctcggca     420

atccgggagg cgttgcagca gggcgtcatc actgcgcaga gttccgacgt cctcagcggc     480
```

-continued

```
ggagtggcgt tggtcggcgg cggtcccggc gatcccgaac tgatcacggt tcgcggtcgc    540

cggctgcttg cccaggccga tgtcgtggtc gccgaccggc tcgccccgcc cgaactgctg    600

gccgagctgc cgccgcacgt agaagtcatc gacgcggcca agatccctta cggccgggcc    660

atggcccagg acgcgatcaa cgctgtcctg atcgaacggg ccagatccgg caactttgtg    720

gtccgtctca aagggggcga ccccttcgtg ttcgcccggg gctatgaaga agtgctggca    780

tgtgcccacg ccggaatccc ggtcaccgtg gtgccaggtg tgacgagtgc catagccgtg    840

cccgctatgg cgggcgttcc agtcactcac cgggccatga cccacgaatt cgtggtggtc    900

agtggccatc ttgcgcccgg tcatcccgaa tcgttagtga attgggatgc attggctgca    960

ttgacgggca ccatcgtttt gctgatggcg gtcgaacgca tcgagctttt cgttgacgtt   1020

ctgctaaagg gtggccgaac tgcggatacg ccggtactgg tggttcaaca cggaacgacc   1080

gccgctcaac agacgttgcg ggccaccctt gccgacacgc cggagaaggt ccgcgcggcg   1140

gggatccgac ctcccgcgat catcgtgatc ggggctgtag tcggcctgag cggcgttcgg   1200

ggtttaaaca attct                                                    1215
```

<210> SEQ ID NO 183
<211> LENGTH: 591
<212> TYPE: PRT
<213> ORGANISM: Mycobacterium tuberculosis

<400> SEQUENCE: 183

```
Met Pro Ala Pro Arg Met Pro Arg Val Ala Leu Val Ala Val Leu Leu
1               5                   10                  15

Ile Thr Val Gln Leu Val Val Arg Val Val Leu Ala Phe Gly Gly Tyr
            20                  25                  30

Phe Tyr Trp Asp Asp Leu Ile Leu Val Gly Arg Ala Gly Thr Gly Gly
        35                  40                  45

Leu Leu Ser Pro Ser Tyr Leu Phe Asp Asp His Asp Gly His Val Met
    50                  55                  60

Pro Gly Ala Phe Leu Val Ala Gly Ala Ile Ile Arg Val Ala Pro Leu
65                  70                  75                  80

Val Trp Thr Gly Pro Ala Ile Ser Leu Val Val Leu Gln Leu Leu Glu
                85                  90                  95

Ser Leu Ala Leu Leu Arg Ala Leu Tyr Val Ile Ser Ser Trp Arg Pro
            100                 105                 110

Val Leu Leu Ile Pro Leu Thr Phe Ala Leu Phe Thr Pro Leu Ala Val
        115                 120                 125

Pro Gly Phe Ala Trp Trp Ala Ala Ala Leu Asn Ser Leu Pro Met Leu
    130                 135                 140

Ala Ala Leu Ala Trp Val Cys Ala Asp Ala Ile Leu Leu Val Arg Thr
145                 150                 155                 160

Gly Asn His Arg Tyr Ala Val Thr Gly Val Leu Val Tyr Leu Gly Gly
                165                 170                 175

Leu Leu Phe Phe Glu Lys Ala Ala Val Ile Pro Phe Val Ser Phe Ala
            180                 185                 190

Val Ala Ala Leu Gln Cys His Val Arg Gly Asp Arg Ser Ala Leu Ala
        195                 200                 205

Thr Val Trp Arg Ala Gly Val Arg Leu Trp Thr Pro Ser Leu Ala Leu
    210                 215                 220

Thr Val Gly Trp Val Ala Leu Tyr Leu Ala Val Val Asp Gln Arg Arg
225                 230                 235                 240

Trp Ser Ser Asp Leu Ser Met Thr Trp Asp Leu Leu Cys Arg Ser Val
```

```
                245                 250                 255

Thr His Gly Ile Val Pro Ala Leu Ala Gly Gly Pro Trp Asp Trp Ala
            260                 265                 270

Arg Trp Ala Pro Ala Ser Pro Trp Ala Thr Pro Pro Ala Val Val Met
        275                 280                 285

Val Leu Gly Trp Leu Val Leu Ile Ala Val Leu Ala Leu Ser Leu Val
    290                 295                 300

Arg Lys Arg Arg Ile Gly Pro Val Trp Leu Thr Ala Ala Gly Tyr Ala
305                 310                 315                 320

Val Ala Cys Gln Val Pro Ile Phe Leu Met Arg Ser Ser Pro Phe Thr
                325                 330                 335

Ala Leu Glu Leu Ala Gln Thr Leu Arg Tyr Phe Pro Asp Leu Val Val
            340                 345                 350

Val Leu Ala Leu Leu Ala Ala Val Ala Leu Gln Ala Pro Asn Arg Ala
        355                 360                 365

Gly Thr Arg Trp Leu Asp Ala Ser Pro Ala Arg Ala Val Ala Thr Val
    370                 375                 380

Ala Ser Ala Val Leu Phe Leu Thr Ser Ser Leu Tyr Ser Thr Ala Thr
385                 390                 395                 400

Phe Leu Ala Ser Trp Arg Asp Asn Pro Thr Glu Gly Tyr Leu Lys Asn
                405                 410                 415

Ala Gln Ala Ser Leu Ala Ala Ala Ala Ser Gly Ala Pro Leu Leu Asp
            420                 425                 430

Gln Glu Val Asp Pro Leu Val Leu Gln Arg Val Ala Trp Pro Glu Asn
        435                 440                 445

Leu Ala Ser His Met Phe Ala Leu Leu Arg Val Arg Pro Glu Phe Ala
    450                 455                 460

Thr Thr Thr Thr Gln Leu Arg Met Phe Thr Ser Thr Gly Arg Leu Val
465                 470                 475                 480

Asp Ala Lys Val Thr Trp Val Arg Thr Ile Ile Ala Gly Pro Val Pro
                485                 490                 495

Gln Cys Gly Tyr Phe Val Gln Pro Asp Arg Pro Glu Arg Leu Ile Leu
            500                 505                 510

Asp Gly Pro Leu Leu Pro Gly Asp Trp Thr Val Glu Leu Asn Tyr Leu
        515                 520                 525

Ala Asn Ser Asp Gly Ser Met Ala Leu Ala Leu Ser Asp Gly Pro Glu
    530                 535                 540

Arg Lys Val Pro Val His Pro Gly Leu Asn Arg Val Tyr Ala Arg Leu
545                 550                 555                 560

Pro Gly Ala Gly Asp Ala Ile Thr Val Arg Ala Asn Thr Thr Ala Leu
                565                 570                 575

Ser Leu Cys Ile Gly Ala Ala Pro Val Gly Phe Leu Ala Pro Ala
            580                 585                 590
```

<210> SEQ ID NO 184
<211> LENGTH: 1773
<212> TYPE: DNA
<213> ORGANISM: Mycobacterium tuberculosis

<400> SEQUENCE: 184

```
atgccagcgc cccgtatgcc tcgggtcgcc ctggtcgccg tattgctgat cacggtgcag     60

ctggtggttc gcgtggtgct ggcatttggg ggctatttct attgggacga cttgatcctc    120

gtcggcaggg ccggcactgg gggcctgttg tcgccgtcgt acctgttcga cgaccacgac    180

ggccacgtga tgcccggtgc cttcctggtt gcgggcgcca ttatccgggt ggcacccctg    240
```

gtgtggaccg gaccagcgat cagcctggtg gtgctgcagc tgctggagtc gctggcgttg 300
ctgcgcgcgt tgtatgtgat atcgagctgg cggccggtac tcctgatccc attgacgttc 360
gcgctgttca caccgctagc ggtgccgggg ttcgcgtggt gggcggctgc gctcaactcg 420
ctgccgatgc tggccgcgct ggcgtgggtg tgcgccgatg ccatcctgct ggtgcggacc 480
ggcaaccacc gctacgccgt caccggtgtc ctggtttacc tcggtggcct gctgttcttc 540
gagaaggccg cggtgatccc gttcgtctcc ttcgcggtgg ccgcgctgca gtgccatgtg 600
cgcggcgacc ggtcagcttt ggcgacggtg tggcgggccg gtgtccggtt gtggacgccg 660
tcgctggcac tgaccgtcgg ctgggtagcc ctttatctgg cggtggtgga tcaacggcga 720
tggagttccg atctgtcgat gacgtgggat ctgctgtgcc gttcggtcac ccacggcata 780
gtgccggcac tggccggcgg gccgtgggac tgggcgcgct gggctccggc atccccgtgg 840
gccactcccc cggcggtggt gatggtgctc ggctggctgg tgttgatcgc agtgcttgcg 900
ctgtcactgg tccgcaagcg acgcatcggc ccggtgtggc tgaccgcggc cggctacgcg 960
gtggcctgcc aggtgccgat ctttctgatg cgctcgtcgc cgttcaccgc gctcgagttg 1020
gcccagaccc tccggtactt cccggatctt gtcgtcgtgc tggcgctgct agccgccgtc 1080
gcgctgcagg cacccaatcg cgccggcacc cgctggctgg acgcctcgcc ggcccgagcc 1140
gttgcgacag tcgcttcggc cgtgttgttt ttgaccagca gcctgtattc gaccgcgacg 1200
tttctggcca gttggcgtga caaccccacc gagggatacc tgaagaacgc ccaggcaagt 1260
ctggccgcgg ccgcgtcagg tgcgccgcta ctggatcagg aagtcgatcc gctggtgttg 1320
caacgagtgg cctggccgga gaacttggcc agccacatgt tcgccctgct gcgcgtccga 1380
ccggaattcg ctacgacaac aacacaattg agaatgttca ccagcacagg tcggctggtc 1440
gacgcgaaag tgacctgggt ccggacgatc atcgcggggc cggtgccgca gtgcggctac 1500
ttcgtccagc cggaccggcc ggaacgtctg atcctcgacg gccccttgct gcccggcgac 1560
tggaccgtcg aactcaacta cctggccaac agcgacggct cgatggcgct ggcactttct 1620
gacggacctg agcggaaggt tccggtgcat ccgggtctca atcgggtgta cgcccggcta 1680
ccaggggccg gcgacgcaat cacggtgcga gccaacacca ccgcgctttc gctgtgcatc 1740
ggagcggcgc cggtgggatt tctggcaccg gcc 1773

<210> SEQ ID NO 185
<211> LENGTH: 498
<212> TYPE: PRT
<213> ORGANISM: Mycobacterium tuberculosis

<400> SEQUENCE: 185

Met Thr Glu Thr Val Thr Arg Thr Ala Ala Pro Ala Val Val Gly Lys
1 5 10 15

Leu Ser Thr Leu Asp Arg Phe Leu Pro Val Trp Ile Gly Ser Ala Met
20 25 30

Ala Ala Gly Leu Leu Leu Gly Arg Trp Ile Pro Gly Leu His Thr Ala
35 40 45

Leu Glu Gly Val Gln Leu Asp Gly Ile Ser Leu Pro Ile Ala Leu Gly
50 55 60

Leu Leu Ile Met Met Tyr Pro Val Leu Ala Lys Val Arg Tyr Asp Arg
65 70 75 80

Leu Asp Thr Val Thr Gly Asp Arg Lys Leu Leu Leu Ser Ser Leu Leu
85 90 95

Leu Asn Trp Val Leu Gly Pro Ala Leu Met Phe Ala Leu Ala Trp Leu

-continued

```
            100                 105                 110

Leu Leu Ala Asp Leu Pro Glu Tyr Arg Thr Gly Leu Ile Ile Val Gly
        115                 120                 125

Leu Ala Arg Cys Ile Ala Met Val Ile Ile Trp Asn Asp Leu Ala Cys
    130                 135                 140

Gly Asp Arg Glu Ala Ala Ala Val Leu Val Ala Leu Asn Ser Ile Phe
145                 150                 155                 160

Gln Val Ala Met Phe Ala Ala Leu Gly Trp Phe Tyr Leu Ser Val Leu
                165                 170                 175

Pro Gly Trp Leu Gly Leu Glu Gln Thr Thr Ile Ala Thr Ser Pro Trp
            180                 185                 190

Gln Ile Ala Lys Ser Val Leu Ile Phe Leu Gly Ile Pro Leu Leu Ala
        195                 200                 205

Gly Tyr Leu Ser Arg Arg Ile Gly Glu Lys Thr Lys Gly Arg Asn Trp
    210                 215                 220

Tyr Glu Ser Arg Phe Leu Pro Lys Val Gly Pro Trp Ala Leu Tyr Gly
225                 230                 235                 240

Leu Leu Phe Thr Ile Val Ile Leu Phe Ala Leu Gln Gly Asp Gln Ile
                245                 250                 255

Thr Gly Arg Pro Leu Asp Val Ala Arg Ile Ala Leu Pro Leu Leu Ala
            260                 265                 270

Tyr Phe Ala Ile Met Trp Val Gly Gly Tyr Leu Leu Gly Ala Ala Leu
        275                 280                 285

Arg Leu Gly Tyr Arg Arg Thr Thr Thr Leu Ala Phe Thr Ala Ala Ser
    290                 295                 300

Asn Asn Phe Glu Leu Ala Ile Ala Val Ala Ile Ala Thr Tyr Gly Ala
305                 310                 315                 320

Thr Ser Gly Gln Ala Leu Ala Gly Val Val Gly Pro Leu Ile Glu Val
                325                 330                 335

Pro Val Leu Val Gly Leu Val Tyr Val Ser Leu Ala Leu Arg Asn Arg
            340                 345                 350

Leu Ala Gly Pro Asn Ala Thr His Asp Ala Asp Lys Pro Ser Val Leu
        355                 360                 365

Phe Val Cys Val His Asn Ala Gly Arg Ser Gln Met Ala Ala Gly Leu
    370                 375                 380

Leu Thr His Leu Ala Gly Asp Arg Ile Glu Val Arg Ser Ala Gly Thr
385                 390                 395                 400

Glu Pro Ala Gly Gln Val Asn Pro Thr Ala Val Ala Ala Met Ala Glu
                405                 410                 415

Met Gly Ile Asp Ile Thr Ala Asn Ala Pro Thr Leu Leu Thr Gly Gly
            420                 425                 430

Gln Val Gln Ser Ser Asp Val Val Ile Thr Met Gly Cys Gly Asp Ala
        435                 440                 445

Cys Pro Tyr Phe Pro Gly Val Ser Tyr Arg Asn Trp Lys Leu Pro Asp
    450                 455                 460

Pro Ala Gly Gln Pro Leu Asp Val Val Arg Met Ile Arg Asp Asp Ile
465                 470                 475                 480

Ala Asp Arg Val Gln Ala Leu Ile Ala Glu Leu Leu Ala Thr Ala Lys
                485                 490                 495

Thr Arg
```

<210> SEQ ID NO 186
<211> LENGTH: 1494
<212> TYPE: DNA

<213> ORGANISM: Mycobacterium tuberculosis

<400> SEQUENCE: 186

```
atgacggaga cggtcacccg caccgccgcc ccggcggtgg tgggcaaact ctcgacgctg     60
gaccgcttct tgccggtgtg gatcgggtcg gcaatggccg ccgggctact actgggccgg    120
tggattcccg gcctgcacac cgccctagaa ggggttcagc tcgacgggat ttcgctgccg    180
atcgcgctag gcctgctgat catgatgtat ccggtgctgg ccaaggtgcg ctacgaccgc    240
ctcgacaccg tcaccggtga ccgcaagctg ctactcagct cgctgctgct gaactgggta    300
ctgggcccgg cgttgatgtt cgcgctggct tggctgctac tggcggatct gcccgagtac    360
cgcaccgggc tgatcatcgt gggcctggct cgctgcatcg ccatggtgat catctggaac    420
gacctggcct gcggggatcg cgaagccgcc gccgtgctcg tcgcgttgaa ctcgatcttt    480
caggtggcca tgttcgccgc gctcggctgg ttctacctgt cggtgctacc gggttggctg    540
ggcctcgagc agaccaccat cgccacatcc ccgtggcaga tcgccaagtc ggtgctgatc    600
ttcctcggca tcccgctgct ggccggctac ctgtcgcggc ggatcggcga aaagaccaag    660
ggccgcaact ggtatgaatc ccgcttcctg cccaaggtgg gaccgtgggc gctctacggt    720
ttgctgttca ccatcgtgat tctctttgcg ctgcaaggag atcagatcac cggccgaccg    780
ctggacgtcg cacgcattgc gctgccgctg ctggcctact tcgccatcat gtgggtaggc    840
ggctacctac tgggggcggc gctgcggcta gggtatcggc gcaccaccac gctggcgttc    900
accgccgcga gcaacaactt cgagctggcc atcgcggtgg ccatcgccac ctacggcgcc    960
acctccgggc aagccctggc cggagtcgtc gggcccctga tcgaggtacc cgtcctggtg   1020
gggttggtct atgtgtccct ggcgctgcgc aaccgcctcg ccggtcccaa cgcgacccac   1080
gatgccgaca aacccagcgt cctattcgtc tgtgtgcaca acgccggacg ttcccagatg   1140
gccgccgggc tattgaccca cttggccggt gaccgcatcg aagtccgttc ggccggaacc   1200
gagcccgccg gtcaggtcaa tccgacggct gtggccgcga tggccgaaat gggcatcgat   1260
atcaccgcca atgcccccac attgctcacc ggcgggcagg tccagtccag cgacgtcgtc   1320
atcacgatgg gctgcggcga tgcctgccct tacttcccgg gtgtctccta ccgcaactgg   1380
aaactacccg atcccgccgg ccagcccctc gacgttgtgc gcatgatccg cgacgacatc   1440
gcagaccgcg tccaagccct gatcgccgag ctgctggcca ccgccaagac caga         1494
```

<210> SEQ ID NO 187
<211> LENGTH: 108
<212> TYPE: PRT
<213> ORGANISM: Mycobacterium tuberculosis

<400> SEQUENCE: 187

```
Met Ser Gly Gly Ser Ser Arg Arg Tyr Pro Pro Glu Leu Arg Glu Arg
1               5                   10                  15

Ala Val Arg Met Val Ala Glu Ile Arg Gly Gln His Asp Ser Glu Trp
            20                  25                  30

Ala Ala Ile Ser Glu Val Ala Arg Leu Leu Gly Val Gly Cys Ala Glu
        35                  40                  45

Thr Val Arg Lys Trp Val Arg Gln Ala Gln Val Asp Ala Gly Ala Arg
    50                  55                  60

Pro Gly Thr Thr Thr Glu Glu Ser Ala Glu Leu Lys Arg Leu Arg Arg
65                  70                  75                  80

Asp Asn Ala Glu Leu Arg Arg Ala Asn Ala Ile Leu Lys Thr Ala Ser
                85                  90                  95
```

Ala Phe Phe Ala Ala Glu Leu Asp Arg Pro Ala Arg
100 105

<210> SEQ ID NO 188
<211> LENGTH: 324
<212> TYPE: DNA
<213> ORGANISM: Mycobacterium tuberculosis

<400> SEQUENCE: 188
atgtcaggtg gttcatcgag gaggtacccg ccggagctgc gtgagcgggc ggtgcggatg 60
gtcgcagaga tccgcggtca gcacgattcg gagtgggcag cgatcagtga ggtcgcccgt 120
ctacttggtg ttggctgcgc ggagacggtg cgtaagtggg tgcgccaggc gcaggtcgat 180
gccggcgcac ggcccgggac cacgaccgaa gaatccgctg agctgaagcg cttgcggcgg 240
gacaacgccg aattgcgaag ggcgaacgcg attttaaaga ccgcgtcggc tttcttcgcg 300
gccgagctcg accggccagc acgc 324

<210> SEQ ID NO 189
<211> LENGTH: 475
<212> TYPE: PRT
<213> ORGANISM: Mycobacterium tuberculosis

<400> SEQUENCE: 189

Met Ala Asp Ile Pro Tyr Gly Arg Asp Tyr Pro Asp Pro Ile Trp Cys
1 5 10 15

Asp Glu Asp Gly Gln Pro Met Pro Pro Val Gly Ala Glu Leu Leu Asp
20 25 30

Asp Ile Arg Ala Phe Leu Arg Arg Phe Val Val Tyr Pro Ser Asp His
35 40 45

Glu Leu Ile Ala His Thr Leu Trp Ile Ala His Cys Trp Phe Met Glu
50 55 60

Ala Trp Asp Ser Thr Pro Arg Ile Ala Phe Leu Ser Pro Glu Pro Gly
65 70 75 80

Ser Gly Lys Ser Arg Ala Leu Glu Val Thr Glu Pro Leu Val Pro Arg
85 90 95

Pro Val His Ala Ile Asn Cys Thr Pro Ala Tyr Leu Phe Arg Arg Val
100 105 110

Ala Asp Pro Val Gly Arg Pro Thr Val Leu Tyr Asp Glu Cys Asp Thr
115 120 125

Leu Phe Gly Pro Lys Ala Lys Glu His Glu Glu Ile Arg Gly Val Ile
130 135 140

Asn Ala Gly His Arg Lys Gly Ala Val Ala Gly Arg Cys Val Ile Arg
145 150 155 160

Gly Lys Ile Val Glu Thr Glu Glu Leu Pro Ala Tyr Cys Ala Val Ala
165 170 175

Leu Ala Gly Leu Asp Asp Leu Pro Asp Thr Ile Met Ser Arg Ser Ile
180 185 190

Val Val Arg Met Arg Arg Arg Ala Pro Thr Glu Pro Val Glu Pro Trp
195 200 205

Arg Pro Arg Val Asn Gly Pro Glu Ala Glu Lys Leu His Asp Arg Leu
210 215 220

Ala Asn Trp Ala Ala Ala Ile Asn Pro Leu Glu Ser Gly Trp Pro Ala
225 230 235 240

Met Pro Asp Gly Val Thr Asp Arg Arg Ala Asp Val Trp Glu Ser Leu
245 250 255

Val Ala Val Ala Asp Thr Ala Gly Gly His Trp Pro Lys Thr Ala Arg

```
            260                 265                 270

Ala Thr Ala Glu Thr Asp Ala Thr Ala Asn Arg Gly Ala Lys Pro Ser
        275                 280                 285

Ile Gly Val Leu Leu Leu Arg Asp Ile Arg Arg Val Phe Ser Asp Arg
    290                 295                 300

Asp Arg Met Arg Thr Ser Asp Ile Leu Thr Gly Leu Asn Arg Met Glu
305                 310                 315                 320

Glu Gly Pro Trp Gly Ser Ile Arg Arg Gly Asp Pro Leu Asp Ala Arg
                325                 330                 335

Gly Leu Ala Thr Arg Leu Gly Arg Tyr Gly Ile Gly Pro Lys Phe Gln
            340                 345                 350

His Ser Gly Gly Glu Pro Pro Tyr Lys Gly Tyr Ser Arg Thr Gln Phe
        355                 360                 365

Glu Asp Ala Trp Ser Arg Tyr Leu Ser Ala Asp Asp Glu Thr Pro Glu
    370                 375                 380

Glu Arg Asp Leu Ser Val Ser Ala Val Ser Ala Val Ser Pro Pro Val
385                 390                 395                 400

Gly Asp Pro Gly Asp Ala Thr Gly Ala Thr Asp Ala Thr Asp Leu Pro
                405                 410                 415

Glu Ala Gly Asp Leu Pro Tyr Glu Pro Pro Ala Pro Asn Gly His Pro
            420                 425                 430

Asn Gly Asp Ala Pro Leu Cys Ser Gly Pro Gly Cys Pro Asn Lys Leu
        435                 440                 445

Leu Ser Thr Glu Ala Lys Ala Ala Gly Lys Cys Arg Pro Cys Arg Gly
    450                 455                 460

Arg Ala Ala Ala Ser Ala Arg Asp Gly Ala Arg
465                 470                 475
```

<210> SEQ ID NO 190
<211> LENGTH: 1425
<212> TYPE: DNA
<213> ORGANISM: Mycobacterium tuberculosis

<400> SEQUENCE: 190

```
atggctgaca tcccctacgg ccgtgactat cccgacccga tctggtgtga cgaggacggc      60

cagccgatgc cgccggtcgg cgccgaattg ctcgacgaca ttagggcatt cttgcggcgg     120

ttcgtagtct atccaagcga ccatgaactg atcgcgcaca ccctctggat tgcgcattgc     180

tggtttatgg aggcgtggga ctcaacgccc cgaatcgctt ttttgtcacc ggaacccggc     240

tctggcaaga gccgcgcact cgaagtcacg gaaccgctag tgccccggcc ggtgcatgcc     300

atcaactgca caccggccta cctgttccgt cgggtggccg atccggtcgg gcggccgacc     360

gtcctgtacg acgagtgtga caccctgttt ggcccgaaag ctaaagaaca cgaggaaatt     420

cgcggcgtga tcaacgccgg ccaccgcaag ggagccgtcg cgggccgctg cgtcatccgc     480

ggcaagatcg ttgagaccga ggaactgcca gcgtactgtg cggtcgcctt ggccggcctc     540

gacgacctgc ccgacaccat catgtctcgg tcgatcgtgg tgaggatgcg caggagggca     600

ccaaccgaac ccgtggagcc gtggcgcccc cgcgtcaacg gccccgaggc cgagaagctg     660

cacgaccggt tggcgaactg ggcggccgcc attaacccgc tggaaagcgg ttggccggcg     720

atgccggacg gggtgaccga ccggcgcgcc gacgtctggg agtccctggt tgcggttgct     780

gacaccgcgg gcgggcactg gcccaaaacc gcccgtgcaa ccgcagaaac ggatgcaacc     840

gcaaatcgag gagccaagcc cagcataggc gtgctgctgc tgcgggatat ccgtcgagtc     900

ttcagcgacc gggaccggat gcgcaccagc gacatcctga ccggactgaa ccggatggag     960
```

-continued

```
gagggaccgt ggggctccat ccgccgcggc gacccgctcg acgcgcgcgg cctcgcgacc   1020

cggctcggca gatacggcat cgggccgaag ttccagcaca gtggtggcga accaccctac   1080

aaagggtatt cgcggaccca gttcgaggat gcgtggtccc ggtatctctc tgccgacgac   1140

gaaacccccg aggaacgaga tttatcggtt tccgcggttt ccgcggtttc accgccggtt   1200

ggcgatcccg gtgatgcaac cggcgcaacc gatgcaaccg atctcccgga ggcgggcgac   1260

ttgccgtacg agccgccggc gcccaacggg caccccaacg gcgacgcgcc gctgtgctcc   1320

gggccgggat gccccaacaa gctcctcagt actgaggcca aggccgccgg caaatgccgg   1380

ccctgccgag gtcgagcggc ggctagcgct cgggacggcg cccga                   1425
```

<210> SEQ ID NO 191
<211> LENGTH: 429
<212> TYPE: PRT
<213> ORGANISM: Mycobacterium tuberculosis

<400> SEQUENCE: 191

```
Val Ser Val Val Ala Val Thr Ile Phe Val Ala Ala Tyr Val Leu Ile
1               5                   10                  15

Ala Ser Asp Arg Val Asn Lys Thr Met Val Ala Leu Thr Gly Ala Ala
            20                  25                  30

Ala Val Val Val Leu Pro Val Ile Thr Ser His Asp Ile Phe Tyr Ser
        35                  40                  45

His Asp Thr Gly Ile Asp Trp Asp Val Ile Phe Leu Leu Val Gly Met
    50                  55                  60

Met Ile Ile Val Gly Val Leu Arg Gln Thr Gly Val Phe Glu Tyr Thr
65                  70                  75                  80

Ala Ile Trp Ala Ala Lys Arg Ala Arg Gly Ser Pro Leu Arg Ile Met
                85                  90                  95

Ile Leu Leu Val Leu Val Ser Ala Leu Ala Ser Ala Leu Leu Asp Asn
            100                 105                 110

Val Thr Thr Val Leu Leu Ile Ala Pro Val Thr Leu Leu Val Cys Asp
        115                 120                 125

Arg Leu Asn Ile Asn Thr Thr Ser Phe Leu Met Ala Glu Val Phe Ala
    130                 135                 140

Ser Asn Ile Gly Gly Ala Ala Thr Leu Val Gly Asp Pro Pro Asn Ile
145                 150                 155                 160

Ile Val Ala Ser Arg Ala Gly Leu Thr Phe Asn Asp Phe Met Leu His
                165                 170                 175

Leu Thr Pro Leu Val Val Ile Val Leu Ile Ala Leu Ile Ala Val Leu
            180                 185                 190

Pro Arg Leu Phe Gly Ser Ile Thr Val Glu Ala Asp Arg Ile Ala Asp
        195                 200                 205

Val Met Ala Leu Asp Glu Gly Glu Ala Ile Arg Asp Arg Gly Leu Leu
    210                 215                 220

Val Lys Cys Gly Ala Val Leu Val Leu Val Phe Ala Ala Phe Val Ala
225                 230                 235                 240

His Pro Val Leu His Ile Gln Pro Ser Leu Val Ala Leu Leu Gly Ala
                245                 250                 255

Gly Met Leu Ile Val Val Ser Gly Leu Thr Arg Ser Glu Tyr Leu Ser
            260                 265                 270

Ser Val Glu Trp Asp Thr Leu Leu Phe Phe Ala Gly Leu Phe Ile Met
        275                 280                 285

Val Gly Ala Leu Val Lys Thr Gly Val Val Asn Asp Leu Ala Arg Ala
```

```
    290                 295                 300

Ala Thr Gln Leu Thr Gly Gly Asn Ile Val Ala Thr Ala Phe Leu Ile
305                 310                 315                 320

Leu Gly Val Ser Ala Pro Ile Ser Gly Ile Ile Asp Asn Ile Pro Tyr
                325                 330                 335

Val Ala Thr Met Thr Pro Leu Val Ala Glu Leu Val Ala Val Met Gly
            340                 345                 350

Gly Gln Pro Ser Thr Asp Thr Pro Trp Trp Ala Leu Ala Leu Gly Ala
        355                 360                 365

Asp Phe Gly Gly Asn Leu Thr Ala Ile Gly Ala Ser Ala Asn Val Val
    370                 375                 380

Met Leu Gly Ile Ala Arg Arg Ala Gly Ala Pro Ile Ser Phe Trp Glu
385                 390                 395                 400

Phe Thr Arg Lys Gly Ala Val Val Thr Ala Val Ser Ile Ala Leu Ala
                405                 410                 415

Ala Ile Tyr Leu Trp Leu Arg Tyr Phe Val Leu Leu His
            420                 425


<210> SEQ ID NO 192
<211> LENGTH: 1287
<212> TYPE: DNA
<213> ORGANISM: Mycobacterium tuberculosis

<400> SEQUENCE: 192

gtgagcgtcg tcgcggtcac catcttcgtg gcggcctacg ttctgattgc cagcgatcgc      60

gtcaacaaga cgatggtggc gctgaccggc gcggcggccg tggtcgtcct accagtgatc     120

acatcccacg acatcttcta ttcccacgac accggaatcg actgggacgt cattttcttg     180

ttggtgggca tgatgatcat cgtcggagtg ctgcggcaga cgggggtgtt cgaatacacc     240

gcgatctggg ccgccaagcg cgcccgcggc tcgccgctac gcatcatgat cctgctggta     300

ttggtgagcg cgttggcgtc agccttgctg gataacgtca ccacggtgtt gttgatcgcg     360

ccggtcacgc tattggtgtg cgaccggtta aacatcaaca cgacgtcgtt cctgatggcc     420

gaagtcttcg cctccaacat tggtggcgcc gcgacgttgg tgggtgaccc gccgaacatc     480

atcgtggcca gccgggcggg attgacgttc aacgacttca tgctgcactt gacaccgctg     540

gtagtcattg tgctgatcgc cctcatcgct gtgctgcccc gcctgttcgg ctcgatcacg     600

gtcgaagccg atcgaattgc cgatgtcatg gcgctcgacg agggtgaagc catccgcgac     660

cgcggactgc tggtcaaatg tggcgccgtg ctggtgctgg tgttcgcggc cttcgtcgcc     720

catccggtgc tgcacatcca gccttctcta gtggcgctgc tgggcgctgg gatgctgatc     780

gtggtctcgg gtctgacgcg atccgagtat ctatccagcg tcgagtggga cacgctgctg     840

tttttcgccg ggctgttcat tatggtcgga gcgctggtca agaccggtgt cgtcaacgat     900

ctcgcgcggg cagcgaccca gctgaccggc ggcaatattg tggccaccgc gttcctaatc     960

ctcggcgtct ccgccccgat ctcgggaatt atcgacaaca ttccctacgt cgccacgatg    1020

acgcccctcg tcgcggagct ggtcgcggtc atggggggtc aacccagcac cgacaccccc    1080

tggtgggcgc tggccctggg tgccgacttc ggcggcaacc tgaccgcaat cggcgccagc    1140

gcgaacgtcg tcatgctcgg aatcgcccgg cgcgcaggag ctcccatctc gttctgggag    1200

ttcacccgca aaggggcggt ggtcacggcc gtctcgatcg cgctcgcggc gatctacctg    1260

tggttgcggt acttcgtgtt gttgcac                                        1287


<210> SEQ ID NO 193
```

<211> LENGTH: 237
<212> TYPE: PRT
<213> ORGANISM: Mycobacterium tuberculosis

<400> SEQUENCE: 193

```
Met Thr Arg Leu Val Pro Ala Leu Arg Leu Glu Leu Thr Leu Gln Val
1               5                   10                  15

Arg Gln Lys Phe Leu His Ala Ala Val Phe Ser Gly Leu Ile Trp Leu
            20                  25                  30

Ala Val Leu Leu Pro Met Pro Val Ser Leu Arg Pro Val Ala Glu Pro
        35                  40                  45

Tyr Val Leu Val Gly Asp Ile Ala Ile Ile Gly Phe Phe Phe Val Gly
    50                  55                  60

Gly Thr Val Phe Phe Glu Lys Gln Glu Arg Thr Ile Gly Ala Ile Val
65                  70                  75                  80

Ser Thr Pro Leu Arg Phe Trp Glu Tyr Leu Ala Ala Lys Leu Thr Val
                85                  90                  95

Leu Leu Ala Ile Ser Leu Phe Val Ala Val Val Val Ala Thr Ile Val
            100                 105                 110

His Gly Leu Gly Tyr His Leu Leu Pro Leu Val Ala Gly Ile Val Leu
        115                 120                 125

Gly Thr Leu Leu Met Leu Leu Val Gly Phe Ser Ser Ser Leu Pro Phe
    130                 135                 140

Ala Ser Val Thr Asp Trp Phe Leu Ala Ala Val Ile Pro Leu Ala Ile
145                 150                 155                 160

Met Leu Ala Pro Pro Val Val His Tyr Ser Gly Leu Trp Pro Asn Pro
                165                 170                 175

Val Leu Tyr Leu Ile Pro Thr Gln Gly Pro Leu Leu Leu Leu Gly Ala
            180                 185                 190

Ala Phe Asp Gln Val Ser Leu Ala Pro Trp Gln Val Gly Tyr Ala Val
        195                 200                 205

Val Tyr Pro Ile Val Cys Ala Ala Gly Leu Cys Arg Ala Ala Lys Ala
    210                 215                 220

Leu Phe Gly Arg Tyr Val Val Gln Arg Ser Gly Val Leu
225                 230                 235
```

<210> SEQ ID NO 194
<211> LENGTH: 711
<212> TYPE: DNA
<213> ORGANISM: Mycobacterium tuberculosis

<400> SEQUENCE: 194

```
atgacccggt tggtgcctgc gctgcggctc gagctgacgc tacaggtgcg gcagaagttc      60

ttgcatgccg ccgttttctc cggactgatt tggctggcag tgctgctgcc gatgccggtc     120

agcctgcgcc cggtcgccga accctatgtc ctggtgggtg atatcgcgat catcgggttc     180

ttcttcgtcg gcgggaccgt gttcttcgag aagcaggagc gcacgatcgg cgcgatcgtc     240

tcgacgccgc tgcggttctg ggagtacctg gctgccaaac taactgtgct gctggcgatc     300

tcgctgttcg ttgcggttgt cgtggccacc atcgttcacg ggcttggtta ccacctgctg     360

ccgctggtgg ccggcatcgt gctgggcaca ctgctgatgc tgctggtcgg cttcagttcc     420

tcgttgccgt tcgcctcggt gaccgattgg ttcctggcgg cggtcatccc gctcgcgatc     480

atgctggcgc cgccggtggt gcactactcc ggcctgtggc ccaacccggt gctttacctc     540

atccccaccc aggggccgct gctcttgctc ggcgcggcgt tcgatcaggt gagcttggcg     600

ccctggcagg tcgggtatgc ggtggtctac ccaatcgtgt gtgcggcggg attgtgccgg     660
```

gcggccaagg cgctattcgg ccgttatgtc gtgcaaagat cgggtgtgct g 711

<210> SEQ ID NO 195
<211> LENGTH: 657
<212> TYPE: PRT
<213> ORGANISM: Mycobacterium tuberculosis

<400> SEQUENCE: 195

```
Val Ser Lys Leu Ser Thr Ala Ala Arg Arg Leu Leu Ile Gly Arg Pro
1               5                   10                  15

Phe Arg Ser Asp Arg Leu Ser His Thr Leu Leu Pro Lys Arg Ile Ala
            20                  25                  30

Leu Pro Val Phe Ala Ser Asp Ala Met Ser Ser Ile Ala Tyr Ala Pro
        35                  40                  45

Glu Glu Ile Phe Leu Val Leu Ser Val Ala Gly Leu Ala Ala Tyr Ser
    50                  55                  60

Met Ala Pro Leu Ile Gly Leu Ala Val Ala Ala Val Leu Leu Val Val
65                  70                  75                  80

Val Ser Ser Tyr Arg Gln Asn Val His Ala Tyr Pro Ser Gly Gly Gly
                85                  90                  95

Asp Tyr Glu Val Val Thr Thr Asn Leu Gly Ala Thr Gly Gly Leu Val
            100                 105                 110

Val Ala Ser Ala Leu Met Val Asp Tyr Val Leu Thr Val Ala Val Ser
        115                 120                 125

Ile Ser Ser Ala Ala Ser Asn Ile Gly Ser Val Ser Pro Phe Val Tyr
    130                 135                 140

Glu His Lys Val Leu Phe Ala Val Gly Ala Ile Val Leu Ile Met Ala
145                 150                 155                 160

Met Asn Leu Arg Gly Val Arg Glu Ser Gly Leu Ala Phe Ala Ile Pro
                165                 170                 175

Thr Tyr Ala Phe Ile Ala Gly Ile Gly Thr Met Leu Val Trp Gly Leu
            180                 185                 190

Phe Arg Ile Phe Val Leu Gly Asn Pro Val Arg Ala Glu Ser Ala Ala
        195                 200                 205

Phe Glu Met His Ala Glu His Gly Gln Ile Val Gly Phe Ala Leu Val
    210                 215                 220

Phe Leu Val Ala Arg Ser Phe Ser Ser Gly Cys Ala Ala Leu Thr Gly
225                 230                 235                 240

Val Glu Ala Ile Ser Asn Gly Val Pro Ala Phe Gln Lys Pro Lys Ser
                245                 250                 255

Arg Asn Ala Ala Thr Thr Leu Leu Met Leu Gly Ile Ile Ala Val Ser
            260                 265                 270

Met Phe Met Gly Met Ile Val Leu Ala Val Glu Thr Gly Val Gln Val
        275                 280                 285

Val Asp Asp Pro Asp Thr Gln Leu Thr Gly Ala Pro Pro Gly Tyr Gln
    290                 295                 300

Gln Lys Thr Leu Val Ala Gln Leu Ala Gln Ala Val Phe Gly Gly Phe
305                 310                 315                 320

Tyr Leu Gly Phe Leu Leu Ile Ala Ala Val Thr Ala Leu Ile Leu Val
                325                 330                 335

Leu Ala Ala Asn Thr Ala Phe Asn Gly Phe Pro Val Leu Gly Ser Val
            340                 345                 350

Leu Ala Gln His Ser Tyr Leu Pro Arg Gln Leu His Thr Arg Gly Asp
        355                 360                 365
```

Arg Leu Ala Phe Ser Asn Gly Ile Leu Phe Leu Ala Ala Ala Ala Ile
370 375 380

Gly Ala Val Val Ala Phe Arg Ala Glu Leu Thr Ala Leu Ile Gln Leu
385 390 395 400

Tyr Ile Val Gly Val Phe Ile Ser Phe Thr Met Ser Gln Val Gly Met
405 410 415

Val Arg His Trp Thr Arg Leu Leu Ser Ala Glu Thr Asp Pro Arg Ala
420 425 430

Arg Arg Ala Met Leu Arg Ser Arg Ala Val Asn Thr Val Gly Phe Val
435 440 445

Ser Thr Gly Thr Val Leu Leu Ile Val Leu Val Thr Lys Phe Leu Ala
450 455 460

Gly Ala Trp Ile Ala Ile Val Ala Met Gly Gly Phe Phe Met Met Met
465 470 475 480

Lys Leu Ile His Arg His Tyr Asp Ala Val Asn Arg Glu Leu Ala Glu
485 490 495

Gln Ala Glu Glu Ala Glu Ile Thr Leu Pro Ser Arg Asn His Ala Val
500 505 510

Val Leu Val Ser Lys Leu His Leu Pro Thr Leu Arg Ala Leu Thr Tyr
515 520 525

Ala Arg Ala Thr Arg Pro Asp Val Leu Glu Ala Val Thr Val Asn Val
530 535 540

Asp Asp Ala Glu Thr Arg Glu Leu Val Arg Gln Trp Gln Asp Ser Asp
545 550 555 560

Val Ser Val Pro Leu Lys Val Ile Ala Ser Pro Tyr Arg Glu Ile Thr
565 570 575

Arg Pro Val Leu Asp Tyr Val Lys Arg Val Ser Lys Glu Ser Pro Arg
580 585 590

Thr Val Val Thr Val Phe Ile Pro Glu Tyr Val Val Gly Arg Trp Trp
595 600 605

Glu Gln Leu Leu His Asn Gln Ser Ala Leu Arg Leu Lys Gly Arg Leu
610 615 620

Leu Phe Met Pro Gly Val Met Val Thr Ser Val Pro Trp Gln Leu Thr
625 630 635 640

Ser Ser Glu Arg Ile Lys Thr Leu Gln Pro His Ala Ala Pro Gly Asp
645 650 655

Thr

<210> SEQ ID NO 196
<211> LENGTH: 1971
<212> TYPE: DNA
<213> ORGANISM: Mycobacterium tuberculosis

<400> SEQUENCE: 196
gtgtccaaac tttcaaccgc ggcgcgtcgg ttgctgatcg gccggccgtt tcgcagtgac 60
cggctcagtc acaccttgtt gcccaagcgg atcgccttgc cggtgttcgc ctcggatgcg 120
atgtcgtcga tagcctacgc ccccgaggag atatttctgg tgctctcggt ggccggcctg 180
gcggcctatt cgatggcgcc gttgatcggc ctggcggtcg ccgcggttct gctcgtggtg 240
gtgtctagtt accggcagaa cgtgcacgct tacccctccg gtgggggcga ctacgaggtt 300
gtcaccacca acctgggtgc taccggcggt ctcgtggttg ccagcgccct gatggtggat 360
tacgttctca ccgttgctgt ttcgatatcg tcggcggcgt ccaacatcgg ctctgtgagc 420
ccgttcgtgt acgagcacaa ggtgttgttt gccgtcggcg cgatcgtgct gatcatggcg 480

-continued

```
atgaacttgc gtggggttcg ggaatccggg ttggcgttcg cgatcccgac ctatgcgttc     540

atcgccggaa tcggcaccat gctcgtgtgg gggttgttcc ggattttcgt gctgggcaat     600

ccggttcggg ccgagtccgc ggcttttgaa atgcacgcag agcacggcca gatcgtcggt     660

ttcgcgctgg tgttcttggt ggcgcgctcg ttttcgtcgg ggtgtgcggc gctgacgggt     720

gtcgaggcga tcagcaacgg ggtgccggcg tttcaaaagc ccaagtcgcg taacgcggca     780

accacgctgc tgatgctggg catcattgcg gtgagcatgt ttatgggcat gatcgtgctg     840

gccgtagaga ccggggtcca ggtcgtcgac gatccggaca cccagctgac gggcgccccg     900

ccgggttatc agcaaaagac gctggtcgca caactggcgc aggccgtgtt cgggggcttt     960

tacctggggt tcttgctgat cgccgcggtg acagcgctga tcctggtgtt ggccgctaac    1020

accgccttca acggcttccc ggtgctgggc tcggtgctgg cgcagcacag ctatctgccg    1080

cgccagttgc acacccgtgg ggaccggctg gcgttctcca acggaatcct gttcctggcg    1140

gcggcggcga tcggggcggt ggtcgcgttt cgtgccgagt tgaccgcgct gatccagctg    1200

tacatcgtcg gtgtgttcat ctcgttcacc atgagtcagg tcggcatggt ccggcactgg    1260

acccggttgc tgagcgccga gaccgatccg cgcgcccgtc gcgcgatgct gcgctcccgc    1320

gcggttaaca cggtcggctt cgtgtccacc ggtaccgtcc tgctcatcgt gctggtaacg    1380

aaattccttg ccggagcatg gatcgcgatc gtcgccatgg gagggttctt catgatgatg    1440

aagctcatcc acaggcacta tgacgccgtc aaccgggagt tggcggaaca ggccgaggaa    1500

gccgagataa cgttgcccag ccgcaatcac gccgtcgtgc tggtgtcgaa gctgcacctg    1560

ccgacgttgc gcgcgttgac ctacgcacga gcgacccggc ccgacgtgtt ggaagccgtg    1620

acggtcaacg tcgacgatgc ggaaacccgc gagctggtgc gccagtggca ggacagcgat    1680

gtgagcgtgc cactcaaggt catcgcctcg ccgtaccgtg agatcacccg gccggtgctc    1740

gattacgtca agcgggtcag caaggaatcg ccacggaccg tggtgacggt attcattccg    1800

gagtatgtcg tggggcgctg gtgggaacag ctgctgcaca accagagtgc gctgcggctc    1860

aagggccggt tgctgttcat gcccggcgtg atggtgactt cggtgccttg gcaactgacg    1920

tcgtcggagc ggatcaagac gttacagccg cacgcggctc ccggtgacac g             1971
```

<210> SEQ ID NO 197
<211> LENGTH: 549
<212> TYPE: PRT
<213> ORGANISM: Mycobacterium tuberculosis

<400> SEQUENCE: 197

```
Val Ser Thr Thr Ser Ala Arg Pro Glu Arg Pro Lys Leu Arg Ala Leu
1               5                   10                  15

Thr Gly Arg Val Gly Gly Gln Ala Leu Gly Gly Leu Leu Gly Leu Pro
            20                  25                  30

Arg Ala Thr Thr Arg Tyr Thr Val Gly His Val Arg Val Pro Met Arg
        35                  40                  45

Asp Gly Val Gln Leu Val Ala Asp His Tyr Ala Pro Ala Thr Ser Gln
    50                  55                  60

Pro Val Gly Thr Leu Leu Val Arg Gly Pro Tyr Gly Arg Arg Phe Pro
65                  70                  75                  80

Phe Ser Leu Val Phe Ala Arg Ile Tyr Ala Ala Arg Gly Tyr His Val
                85                  90                  95

Val Leu Gln Ser Val Arg Gly Thr Phe Gly Ser Gly Gly Val Phe Glu
            100                 105                 110

Pro Met Val Asn Glu Ala Ala Asp Gly Ala Asp Thr Val Ala Trp Leu
```

```
        115                 120                 125

Arg Glu Gln Pro Trp Phe Thr Gly Arg Phe Gly Thr Ile Gly Leu Pro
    130                 135                 140

Tyr Leu Gly Phe Thr Gln Trp Ala Leu Leu His Asp Pro Pro Pro Glu
145                 150                 155                 160

Leu Ala Ala Ala Val Ile Thr Val Gly Pro His Asp Phe Arg Ala Ser
                165                 170                 175

Val Trp Gly Thr Gly Ser Phe Thr Val Asn Asp Phe Leu Gly Trp Ser
            180                 185                 190

Asp Leu Val Ser His Gln Glu Asp Pro Gly Arg Ile Arg Ala Gly Ile
        195                 200                 205

Arg Gln Leu Thr Ala Pro Arg Arg Val Ala Arg Thr Ala Ala Thr Leu
    210                 215                 220

Pro Leu Gly Glu Ser Ala Arg Thr Leu Leu Gly Thr Gly Ala Pro Trp
225                 230                 235                 240

Phe Glu Ser Trp Val Glu His Thr Asp Arg Asp Asp Pro Phe Trp Asp
                245                 250                 255

Arg Leu Arg Phe Pro Ala Ala Leu Asp Arg Val Gln Val Pro Val Leu
            260                 265                 270

Leu Val Gly Gly Trp Gln Asp Ile Phe Leu Arg Gln Thr Leu Gln Gln
        275                 280                 285

Tyr Arg His Leu Arg Asp Arg Gly Val His Val Ala Leu Thr Val Gly
    290                 295                 300

Pro Trp Thr His Thr Gln Met Leu Thr Lys Gly Leu Ala Thr Gly Ala
305                 310                 315                 320

Arg Glu Ser Leu Asp Trp Leu Asp Ala His Leu Gly Arg Ala Pro Ala
                325                 330                 335

Leu Arg Pro Ser Pro Val Arg Val Phe Val Thr Gly Gln Gly Trp Arg
            340                 345                 350

His Leu Pro Asp Trp Pro Pro Ala Thr Thr Glu Arg Ala Trp Tyr Leu
        355                 360                 365

Gln Pro Gly Gly Arg Leu Gly Glu Ser Ala Pro Ala Ser Gly Thr Pro
    370                 375                 380

Pro Ala Thr Phe Arg Tyr His Pro Ala Asp Pro Thr Pro Thr Thr Gly
385                 390                 395                 400

Gly Pro Leu Leu Ser Ser Asn Gly Gly Tyr Arg Asp Asp Ser Arg Leu
                405                 410                 415

Ala Thr Arg Ala Asp Val Leu Cys Phe Thr Gly Ala Pro Leu Thr His
            420                 425                 430

Asp Leu Cys Val His Gly Asn Pro Val Val Glu Leu Val His Ser Ser
        435                 440                 445

Asp Asn Pro Tyr Val Asp Val Phe Val Arg Val Ser Glu Val Asp Ala
    450                 455                 460

Lys Gly Arg Ser Arg Asn Val Ser Asp Gly Tyr Arg Arg Leu Gly Asp
465                 470                 475                 480

Ala Pro Glu Leu Val Arg Val Glu Leu Asp Ala Ile Ala His Arg Phe
                485                 490                 495

Arg Ala Asp Ser Arg Ile Arg Val Leu Ile Ala Gly Ser Trp Phe Pro
            500                 505                 510

Arg Tyr Ala Arg Asn Leu Gly Thr Pro Glu Pro Ile Leu Thr Gly Arg
        515                 520                 525

Gln Leu Lys Pro Ala Thr His Ala Val His Phe Gly Arg Ser Arg Leu
    530                 535                 540
```

Leu Leu Pro Val Gly
545

<210> SEQ ID NO 198
<211> LENGTH: 1647
<212> TYPE: DNA
<213> ORGANISM: Mycobacterium tuberculosis

<400> SEQUENCE: 198
gtgagtacca cctccgctcg gcccgagcgg cccaagctgc gcgccctgac cggacgagtc 60
ggtgggcagg ccctgggcgg actgttgggt ctgccccgcg caaccacccg ctacaccgtc 120
ggtcacgtcc gagtcccgat gcgcgacggc gtccagctgg tggccgacca ctacgcaccc 180
gccacgtcgc agcccgtcgg caccctgctg gtgcgtgggc catacgggcg ccggtttccg 240
ttttcgctgg tgtttgccag gatttacgcc gcccgcggtt atcacgtcgt gctgcagagc 300
gtgcgcggga cgttcgggtc cggtggcgtg ttcgagccca tggtcaacga ggccgccgac 360
ggcgccgata cggtggcgtg gctgcgtgaa cagccctggt tcaccggccg gttcggcacc 420
atcggcctgc cctatctggg tttcacccag tgggcgttgc tgcacgatcc gcccccggag 480
ctggccgcgg ccgtgatcac ggtggggccg cacgacttcc gggcctcggt gtggggcacc 540
ggatcgttta cggtcaacga cttcctgggc tggagcgatc tggtttccca ccaggaagac 600
cccggtcgca tccgggccgg aatccgccag ctcaccgcgc cgcgacgggt ggcgcggacg 660
gccgccacgt tgccgctggg tgagtcggcc cggacgctgc tcggcacggg tgcgccgtgg 720
ttcgaatcct gggtggaaca caccgaccgc gacgatccgt tctgggaccg actgcggttt 780
cccgccgcgt tggaccgcgt ccaggtcccg gtgctgctcg tcggcggctg gcaggacatc 840
ttcctgcggc agacgctgca gcagtaccgg cacctgcgcg accggggtgt gcacgtcgcg 900
ctgacggtcg gtccctggac acacacccag atgctcacca aggggctggc caccggcgct 960
cgggaatcgt tggactggtt ggacgcccac ctcggccggg cgccggcgct gcgccccagc 1020
ccggtgcggg tcttcgtcac cggccagggc tggcggcacc tgccggactg gcctccggcg 1080
accaccgagc gggcgtggta cctgcagccc ggtggccgcc tgggtgagag cgctccggct 1140
tccggcacgc caccggcgac gtttcgctac caccccgccg acccgacacc gaccaccggt 1200
ggtccgctac tgtcatccaa cggcggttac cgcgacgaca gccggctggc cacgcgcgcc 1260
gatgtgctgt gcttcaccgg ggcgcccctc acccacgacc tctgcgtgca cggaaacccc 1320
gtcgtcgagc tggtgcacag ctcggacaac ccctacgtcg acgtgttcgt tcgggtcagc 1380
gaggtggacg cgaagggccg gtcccgcaat gtcagcgacg gctaccggcg ccttggtgac 1440
gcgccggagc tggtccgcgt cgagctggac gccatcgccc accgattccg cgccgactcc 1500
cgcatccggg tgctgatcgc cggtagttgg tttccccgct atgcgcgaaa cctcggcacc 1560
ccggaaccga tactcaccgg acggcagctc aagccggcta cccacgcggt gcatttcggg 1620
cgctcccggc tgctgctgcc cgtcggc 1647

<210> SEQ ID NO 199
<211> LENGTH: 469
<212> TYPE: PRT
<213> ORGANISM: Mycobacterium tuberculosis

<400> SEQUENCE: 199

Val Ala Val Gly Asp Asp Glu Glu Lys Val Arg Ala Glu Arg Ala Arg
1 5 10 15

Ala Ile Gly Leu Phe Arg Tyr Gln Leu Ile Trp Glu Ala Ala Asp Ala
20 25 30

Ala His Ser Thr Lys Gln Arg Gly Lys Met Val Arg Glu Leu Ala Ser
35 40 45

Arg Glu His Thr Asp Pro Phe Gly Arg Arg Val Arg Ile Ser Arg Gln
50 55 60

Thr Ile Asp Arg Trp Ile Arg Gly Trp Arg Ala Gly Gly Phe Asp Ala
65 70 75 80

Leu Val Pro Asn Pro Arg Gln Cys Thr Pro Arg Thr Pro Ala Glu Val
85 90 95

Leu Glu Leu Ala Val Ala Leu Arg Arg Glu Asn Pro Gln Arg Thr Ala
100 105 110

Ala Ala Ile Arg Arg Ile Leu Arg Thr Gln Leu Gly Trp Ala Pro Asp
115 120 125

Glu Arg Thr Leu Gln Arg Asn Phe His Arg Leu Gly Leu Thr Gly Ala
130 135 140

Thr Thr Gly Ser Ala Pro Ala Val Phe Gly Arg Phe Glu Ala Glu His
145 150 155 160

Pro Asn Ala Leu Trp Thr Gly Asp Val Leu His Gly Ile Arg Ile Asp
165 170 175

Leu Arg Lys Thr Tyr Leu Phe Ala Phe Leu Asp Asp His Ser Arg Leu
180 185 190

Val Pro Gly Tyr Arg Trp Gly His Ala Glu Asp Thr Val Arg Leu Ala
195 200 205

Ala Ala Leu Arg Pro Ala Leu Ala Ser Arg Gly Val Pro Asn Ala Val
210 215 220

Tyr Val Asp Asn Gly Ser Pro Tyr Val Asp Ala Trp Leu Leu Arg Ala
225 230 235 240

Cys Ala Lys Leu Gly Val Arg Leu Val His Ser Thr Pro Gly Arg Pro
245 250 255

Gln Gly Arg Gly Lys Ile Glu Arg Phe Phe Arg Thr Val Arg Glu Gln
260 265 270

Phe Leu Val Glu Ile Thr Gly Glu Pro Asp Val Val Gly Arg His Tyr
275 280 285

Val Ala Asp Leu Ala Glu Leu Asn Arg Leu Phe Thr Ala Trp Val Glu
290 295 300

Thr Val Tyr His Arg Ser Val His Ser Glu Thr Gly Gln Thr Pro Leu
305 310 315 320

Ala Arg Trp Ser Ala Gly Gly Pro Ile Pro Leu Pro Ala Pro Glu Thr
325 330 335

Leu Thr Glu Ala Phe Leu Trp Glu Glu His Arg Arg Val Thr Lys Thr
340 345 350

Ala Thr Val Ser Leu His Gly Asn Arg Tyr Glu Ile Asp Pro Ala Leu
355 360 365

Val Gly Arg Lys Val Glu Leu Val Phe Asp Pro Phe Asp Leu Thr Arg
370 375 380

Ile Glu Val Arg Leu Ala Gly Ala Pro Met Arg Arg Ala Ile Pro Tyr
385 390 395 400

His Ile Gly Arg His Ser His Pro Lys Ala Lys Pro Glu Thr Pro Thr
405 410 415

Ala Pro Pro Lys Pro Ser Gly Ile Asp Tyr Ala Gln Leu Ile Glu Thr
420 425 430

Ala His Ala Ala Glu Leu Ala Arg Gly Val Asn Tyr Thr Ala Leu Thr
435 440 445

Gly Ala Ala Asp Gln Ile Pro Gly Gln Leu Asp Leu Leu Thr Gly Gln 450 455 460

Glu Ala Gln Pro Lys
465

<210> SEQ ID NO 200
<211> LENGTH: 1407
<212> TYPE: DNA
<213> ORGANISM: Mycobacterium tuberculosis

<400> SEQUENCE: 200
gtggcggtcg gcgatgacga ggagaaggtg cgcgcggagc gcgcgagggc gatcgggttg 60
tttcgctacc agttgatttg ggaggccgcc gatgcggcgc attccaccaa gcagcgggga 120
aagatggtgc gcgagttggc ctcacgcgag cacaccgatc cgttcgggcg gcgggtgcgc 180
atcagccgcc aaaccatcga ccgctggatc cggggctggc gggccggcgg gttcgacgcg 240
ctggtgccca acccacgcca gtgcacaccg cgtaccccgg ccgaggtgct ggagctggcg 300
gtggcgctgc ggcgggaaaa cccgcagcgc acggcggcgg caatccggcg gatcctgcgt 360
acccagttgg gctgggcgcc cgatgaacgc accctgcaac gcaacttcca ccggctcggg 420
ctcaccggcg ccaccaccgg gtcggcgccg gcggtgttcg gccggttcga agccgagcac 480
ccgaacgccc tgtggaccgg ggatgtgttg cacggcatac ggattgatct ccgcaagacc 540
tatctgttcg cgttcttaga cgaccattcc cggttggtgc ccggctaccg gtggggccat 600
gccgaggaca cggtgcggct ggccgccgca ctgcgcccgg cgctggcctc ccgcggcgtg 660
cccaacgcgg tgtatgtcga taacggctcg ccctatgtgg atgcgtggtt gttgcgggca 720
tgcgcgaaac tcggtgtgcg ccttgttcat tccacgccag gtcggccgca aggcaggggc 780
aagatagaga ggttcttccg caccgtgcgc gagcagttcc tggtcgagat caccggcgaa 840
cccgacgtcg tcggccgaca ttacgtcgct gatctggccg agttgaatcg gctgtttacg 900
gcctgggtcg aaacggttta tcaccgcagc gtgcattccg aaaccgggca gacccccgctg 960 gcccgctggt cagccggcgg ccccatcccg ctgcccgccc ccgagacgct caccgaggcc 1020
ttcctgtggg aggagcaccg ccgcgtgacc aagaccgcca ccgtctcgct gcacggcaac 1080
cgctacgaga tcgacccggc gctggtcggc cggaaagtgg agttggtgtt cgacccgttc 1140
gatttgaccc gcatcgaggt gcggctggcc ggcgcgccga tgaggcgggc cattccgtat 1200
cacatcgggc gccattcaca cccgaaagcc aaacccgaaa cccccaccgc accgcccaaa 1260
cccagcggca tcgactacgc gcagttaatc gagaccgcgc acgcagccga actcgcccgc 1320
ggcgtcaact acaccgccct caccggggct gccgatcaga tccccggcca gctcgacctg 1380
ctcaccggcc aggaggccca accgaaa 1407

<210> SEQ ID NO 201
<211> LENGTH: 270
<212> TYPE: PRT
<213> ORGANISM: Mycobacterium tuberculosis

<400> SEQUENCE: 201

Met Met His Lys Leu Ile Ser Tyr Tyr Gly Phe Ser Arg Met Pro Phe
1 5 10 15

Gly Arg Asp Leu Ala Pro Gly Met Leu His Arg His Ser Ala His Asn
20 25 30

Glu Ala Val Ala Arg Ile Gly Trp Cys Ile Ala Asp Arg Arg Ile Gly
35 40 45

Val Ile Thr Gly Glu Val Gly Ala Gly Lys Thr Val Ala Val Arg Ala
50 55 60

```
Ala Leu Ala Ser Leu Asp Arg Ser Arg His Thr Ile Ile Tyr Leu Pro
65                  70                  75                  80

Asp Pro Thr Val Gly Val Gln Gly Ile His His Arg Ile Val Ala Ser
                85                  90                  95

Leu Gly Gly Gln Pro Leu Thr His His Ala Thr Leu Ala Pro Gln Ala
            100                 105                 110

Ala Asp Ala Leu Ala Ala Glu Gln Ala Glu Arg Gly Arg Thr Pro Val
        115                 120                 125

Val Val Val Glu Glu Ala His Leu Leu Gly Tyr Asp Gln Leu Glu Ala
    130                 135                 140

Leu Arg Leu Leu Thr Asn His Asp Leu Asp Ser Ser Ser Pro Phe Ala
145                 150                 155                 160

Cys Leu Leu Ile Gly Gln Pro Thr Leu Arg Arg Arg Met Lys Leu Gly
                165                 170                 175

Val Leu Ala Ala Leu Asp Gln Arg Ile Gly Leu Arg Tyr Ala Met Pro
            180                 185                 190

Pro Met Thr Asp Thr Asn Thr Gly Ser Tyr Leu Arg His His Leu Lys
        195                 200                 205

Leu Ala Gly Arg Asp Asp Ala Leu Phe Ser Asp Asp Ala Ile Gly Leu
    210                 215                 220

Ile His Gln Thr Ser Arg Gly Tyr Pro Arg Ala Val Asn Asn Leu Ala
225                 230                 235                 240

Leu Gln Ala Leu Val Ala Ala Phe Ala Ala Asp Lys Ala Ile Val Asp
                245                 250                 255

Glu Ser Thr Thr Arg Thr Ala Ile Ala Glu Val Thr Ala Asp
            260                 265                 270
```

<210> SEQ ID NO 202
<211> LENGTH: 810
<212> TYPE: DNA
<213> ORGANISM: Mycobacterium tuberculosis

<400> SEQUENCE: 202

```
atgatgcaca aactgatctc gtattacggt ttttcgcgca tgccattcgg ccgcgatctg      60

gcaccgggca tgctgcatcg ccacagcgcg cacaacgaag cggtcgcccg catcggctgg     120

tgcatcgccg accgccgcat cggcgtcatc accggcgaag tcggcgccgg caagaccgtc     180

gccgtgcgcg ccgcactagc gagcctggat cgcagccgcc acaccatcat ctacctgccc     240

gaccccaccg tcggcgtcca gggcatccac caccgcatcg tcgcctcgct cggcggacaa     300

cccctcaccc accacgccac cctggcccca caggccgccg acgcgctagc cgccgaacaa     360

gccgagcgcg gacgcacccc cgtcgtggtc gtcgaggaag cgcacctgct cggctatgac     420

caactggagg cgttgcggct cttgacaaat cacgacctcg actcgtcaag cccgttcgcc     480

tgcctgctca tcggccaacc caccctgcgg cggcggatga aactcggcgt gctcgccgcg     540

cttgaccagc gcatcggact ccgatatgcc atgccgccca tgaccgacac caacaccggc     600

agctacctac gccaccacct caagctagcc ggacgcgacg atgccctgtt ctccgacgac     660

gccatcgggt tgatccacca gaccagccgg ggctaccccc gcgcggtcaa caacctcgcc     720

ctgcaagccc tcgtcgccgc cttcgccgcc gacaaggcca tcgtcgacga atccaccacc     780

cgcaccgcca tcgccgaagt cacggcagac                                      810
```

<210> SEQ ID NO 203
<211> LENGTH: 303
<212> TYPE: PRT

<213> ORGANISM: Mycobacterium tuberculosis

<400> SEQUENCE: 203

Met Ala Ala Pro Gln Arg Ala Arg Leu Arg Ser Ser Lys Glu Arg Val
1 5 10 15

Arg Asp Tyr Ala Leu Phe Val Val Leu Val Gly Pro Asn Val Ala Leu
20 25 30

Leu Leu Leu Phe Val Tyr Arg Pro Leu Ala Asp Asn Ile Arg Leu Ser
35 40 45

Phe Phe Asp Trp Asn Val Ser Asp Pro Ser Ala Arg Phe Val Gly Leu
50 55 60

Ser Asn Tyr Thr Glu Trp Phe Thr Arg Ser Asp Thr Arg Gln Ile Val
65 70 75 80

Phe Asn Thr Ala Val Phe Thr Gly Ala Ala Val Val Gly Ser Met Val
85 90 95

Leu Gly Leu Ala Leu Ala Met Leu Leu Asp Arg Pro Leu Arg Gly Arg
100 105 110

Asn Leu Val Arg Ser Thr Val Phe Ala Pro Phe Val Ile Ser Gly Ala
115 120 125

Ala Val Gly Leu Ala Ala Gln Phe Val Phe Asp Pro His Phe Gly Leu
130 135 140

Ile Gln Asp Leu Leu Arg Arg Ile Gly Val Gly Val Pro Asp Phe Tyr
145 150 155 160

Gln Asp Ala Arg Trp Ala Leu Phe Met Val Thr Ile Thr Tyr Val Trp
165 170 175

Lys Asn Leu Gly Tyr Thr Phe Val Ile Tyr Leu Ala Ala Leu Gln Gly
180 185 190

Val Arg Arg Asp Leu Leu Glu Ala Ala Glu Ile Asp Gly Ala Ser Arg
195 200 205

Trp Ala Val Phe Arg Arg Val Leu Leu Pro Gln Leu Arg Pro Thr Thr
210 215 220

Phe Phe Leu Ser Ile Thr Val Leu Ile Asn Ser Leu Gln Val Phe Asp
225 230 235 240

Val Ile Asn Val Met Thr Arg Gly Gly Pro Glu Gly Thr Gly Thr Thr
245 250 255

Thr Met Val Tyr Gln Val Tyr Val Glu Thr Phe Arg Asn Phe Arg Ala
260 265 270

Gly Tyr Gly Ala Thr Val Ala Thr Ile Met Phe Leu Val Leu Leu Ala
275 280 285

Val Thr Tyr Tyr Gln Val Arg Val Met Asp Arg Gly Gln Arg Gln
290 295 300

<210> SEQ ID NO 204
<211> LENGTH: 909
<212> TYPE: DNA
<213> ORGANISM: Mycobacterium tuberculosis

<400> SEQUENCE: 204
atggcggcgc cgcaacgagc acggcttcgg tcatcgaaag agcgcgtgcg cgattatgcg 60
ctgttcgtcg tgttggtcgg ccccaatgtg gcgctattgc tgctgttcgt ctatcgcccg 120
ttggccgaca acatccggct gtcgttcttc gactggaacg tctccgatcc gtcggcccga 180
tttgtggggt tatccaacta caccgagtgg ttcacccggt cggacacccg ccagatcgtg 240
ttcaacacgg cggttttcac cggtgccgcg gtggtcggct cgatggtgct ggggttggcg 300
ctggcgatgc tgctcgatcg accgttgcgt ggacgaaacc tggtgcgctc cactgttttc 360

```
gcgccgttcg tgatctccgg tgccgctgtc ggcctggccg cccagttcgt cttcgacccg    420

catttcggtc tgattcaaga cctgttgcgc cggatcgggg tcggggtgcc cgacttttac    480

caggatgcgc gctgggcgtt gttcatggtg accatcacct acgtctggaa gaacctcggc    540

tataccttcg tgatctatct ggccgcgttg caggggggtac gccgagatct gttggaggcg    600

gccgaaatcg acggcgccag ccggtgggcc gtgttccgtc gagtgctgtt gccgcagctg    660

cggccgacca cgtttttctt gtcgatcacc gtgctgatca actcgctgca ggtgttcgat    720

gtgatcaacg tgatgacccg gggcgggccg gagggcaccg gcaccaccac catggtgtac    780

caggtgtatg tggagacgtt ccgcaatttc cgggccggtt atggcgccac ggtggccacg    840

atcatgttcc tggtgctgct ggccgtgacg tactaccagg tgcgggtgat ggatcggggg    900

cagcggcag                                                           909
```

<210> SEQ ID NO 205
<211> LENGTH: 695
<212> TYPE: PRT
<213> ORGANISM: Mycobacterium tuberculosis

<400> SEQUENCE: 205

```
Met Val Glu Ser Arg Arg Ala Ala Ala Ala Ala Ser Ala Tyr Ala Ser
1               5                   10                  15

Arg Cys Gly Ile Ala Pro Ala Thr Ser Gln Arg Ser Leu Ala Thr Pro
            20                  25                  30

Pro Thr Ile Ser Val Pro Ser Gly Glu Gly Arg Cys Arg Cys His Val
        35                  40                  45

Ala Arg Gly Ala Gly Arg Asp Pro Arg Arg Arg Leu Arg Arg Arg Arg
    50                  55                  60

Trp Cys Gly Arg Cys Gly Tyr His Ser His Leu Thr Gly Gly Glu Phe
65                  70                  75                  80

Asp Val Asn Arg Leu Cys Gln Gln Arg Ser Arg Glu Arg Ser Cys Gln
                85                  90                  95

Leu Val Ala Val Pro Ala Asp Pro Arg Pro Lys Arg Gln Arg Ile Thr
            100                 105                 110

Asp Val Leu Thr Leu Ala Leu Val Gly Phe Leu Gly Gly Leu Ile Thr
        115                 120                 125

Gly Ile Ser Pro Cys Ile Leu Pro Val Leu Pro Val Ile Phe Phe Ser
    130                 135                 140

Gly Ala Gln Ser Val Asp Ala Ala Gln Val Ala Lys Pro Glu Gly Ala
145                 150                 155                 160

Val Ala Val Arg Arg Lys Arg Ala Leu Ser Ala Thr Leu Arg Pro Tyr
                165                 170                 175

Arg Val Ile Gly Gly Leu Val Leu Ser Phe Gly Met Val Thr Leu Leu
            180                 185                 190

Gly Ser Ala Leu Leu Ser Val Leu His Leu Pro Gln Asp Ala Ile Arg
        195                 200                 205

Trp Ala Ala Leu Val Ala Leu Val Ala Ile Gly Ala Gly Leu Ile Phe
    210                 215                 220

Pro Arg Phe Glu Gln Leu Leu Glu Lys Pro Phe Ser Arg Ile Pro Gln
225                 230                 235                 240

Lys Gln Ile Val Thr Arg Ser Asn Gly Phe Gly Leu Gly Leu Ala Leu
                245                 250                 255

Gly Val Leu Tyr Val Pro Cys Ala Gly Pro Ile Leu Ala Ala Ile Val
            260                 265                 270
```

-continued

```
Val Ala Gly Ala Thr Ala Thr Ile Gly Leu Gly Thr Val Val Leu Thr
        275                 280                 285

Ala Thr Phe Ala Leu Gly Ala Ala Leu Pro Leu Leu Phe Phe Ala Leu
    290                 295                 300

Ala Gly Gln Arg Ile Ala Glu Arg Val Gly Ala Phe Arg Arg Arg Gln
305                 310                 315                 320

Arg Glu Ile Arg Ile Ala Thr Gly Ser Val Thr Ile Leu Leu Ala Val
                325                 330                 335

Ala Leu Val Phe Asp Leu Pro Ala Ala Leu Gln Arg Ala Ile Pro Asp
            340                 345                 350

Tyr Thr Ala Ser Leu Gln Gln Gln Ile Ser Thr Gly Thr Glu Ile Arg
        355                 360                 365

Glu Gln Leu Asn Leu Gly Gly Ile Val Asn Ala Gln Asn Ala Gln Leu
    370                 375                 380

Ser Asn Cys Ser Asp Gly Ala Ala Gln Leu Glu Ser Cys Gly Thr Ala
385                 390                 395                 400

Pro Asp Leu Lys Gly Ile Thr Gly Trp Leu Asn Thr Pro Gly Asn Lys
                405                 410                 415

Pro Ile Asp Leu Lys Ser Leu Arg Gly Lys Val Val Leu Ile Asp Phe
            420                 425                 430

Trp Ala Tyr Ser Cys Ile Asn Cys Gln Arg Ala Ile Pro His Val Val
        435                 440                 445

Gly Trp Tyr Gln Ala Tyr Lys Asp Ser Gly Leu Ala Val Ile Gly Val
    450                 455                 460

His Thr Pro Glu Tyr Ala Phe Glu Lys Val Pro Gly Asn Val Ala Lys
465                 470                 475                 480

Gly Ala Ala Asn Leu Gly Ile Ser Tyr Pro Ile Ala Leu Asp Asn Asn
                485                 490                 495

Tyr Ala Thr Trp Thr Asn Tyr Arg Asn Arg Tyr Trp Pro Ala Glu Tyr
            500                 505                 510

Leu Ile Asp Ala Thr Gly Thr Val Arg His Ile Lys Phe Gly Glu Gly
        515                 520                 525

Asp Tyr Asn Val Thr Glu Thr Leu Val Arg Gln Leu Leu Asn Asp Ala
    530                 535                 540

Lys Pro Gly Val Lys Leu Pro Gln Pro Ser Ser Thr Thr Thr Pro Asp
545                 550                 555                 560

Leu Thr Pro Arg Ala Ala Leu Thr Pro Glu Thr Tyr Phe Gly Val Gly
                565                 570                 575

Lys Val Val Asn Tyr Gly Gly Gly Gly Ala Tyr Asp Glu Gly Ser Ala
            580                 585                 590

Val Phe Asp Tyr Pro Pro Ser Leu Ala Ala Asn Ser Phe Ala Leu Arg
        595                 600                 605

Gly Arg Trp Ala Leu Asp Tyr Gln Gly Ala Thr Ser Asp Gly Asn Asp
    610                 615                 620

Ala Ala Ile Lys Leu Asn Tyr His Ala Lys Asp Val Tyr Ile Val Val
625                 630                 635                 640

Gly Gly Thr Gly Thr Leu Thr Val Val Arg Asp Gly Lys Pro Ala Thr
                645                 650                 655

Leu Pro Ile Ser Gly Pro Pro Thr Thr His Gln Val Val Ala Gly Tyr
            660                 665                 670

Arg Leu Ala Ser Glu Thr Leu Glu Val Arg Pro Ser Lys Gly Leu Gln
        675                 680                 685

Val Phe Ser Phe Thr Tyr Gly
    690                 695
```

<210> SEQ ID NO 206
<211> LENGTH: 2085
<212> TYPE: DNA
<213> ORGANISM: Mycobacterium tuberculosis

<400> SEQUENCE: 206
atggttgagt cgagacgagc tgctgcggcg gcttcggcat acgcaagcag atgcgggatt 60
gcacccgcga cctcgcaacg ctcactggcg acaccaccga cgatctcggt cccgtccggt 120
gagggccgct gccgttgcca cgtcgcaagg ggtgccggtc gtgacccacg acggcgactt 180
cgacgccgtc gatggtgtgg ccgatgtggc tatcattcgc atctgacggg tggcgagttc 240
gacgtgaacc gactctgtca acagcgctcg cgtgagcggt cctgccaact cgttgccgtc 300
ccggcagatc caagacctaa acggcaacga ataaccgatg tgttgaccct cgcactagtc 360
ggcttcctcg gcggcctcat caccggaata tcaccatgca ttctgccggt cctgccagta 420
atcttcttct ccggcgcgca gagcgtcgat gcagcgcagg tggcgaaacc cgaaggcgcc 480
gtagcagtcc ggcgcaaacg tgcgctatca gcgacattgc ggccctaccg ggtgatcggt 540
ggtctggtgc tcagtttcgg catggtcacc ctgctcggct cggcattgct gtcagtgctg 600
catctaccgc aggacgccat ccgctgggcc gcactggtcg ccttggtggc aatcggcgcc 660
ggcctcattt tcccgcggtt tgaacaactt ctggaaaaac cgttctcccg tattccgcag 720
aagcaaatcg tcactcgcag caacggtttc gggctgggtc tagccctggg cgtgttgtat 780
gtcccctgcg ccggcccgat tctagctgcg atcgtcgtgg ccggggctac tgccaccatc 840
gggttgggaa ccgtcgtgct caccgcgaca ttcgcactcg gagccgcgtt gccgttgttg 900
ttcttcgccc tcgccggcca acggatagct gagcgggtgg gcgcttttcg gcgccgccag 960
cgtgagatca ggatcgccac cggttccgtg acgatcctgc tggcggtggc gttggtgttc 1020
gatctgccgg ccgcgctgca gcgggctatt cctgactaca ccgcatcgct gcagcagcag 1080
atcagcaccg gcacggagat acgggaacaa ctgaaccttg gcggcatcgt caacgcccag 1140
aacgcacagc tgtcgaattg cagcgacggg gccgcacaac tcgaaagctg cggcactgca 1200
ccagatctca aaggcatcac cggctggctc aacacgcccg gcaacaagcc gatcgacctg 1260
aaatcattgc gtggcaaggt ggtgctgatt gacttttggg cctactcctg cattaactgc 1320
caacgggcca tcccccacgt cgtcggttgg tatcaggcct acaaagacag tggtttggcg 1380
gtcatcggcg tgcacacccc cgagtacgct ttcgagaagg tcccgggcaa cgtcgccaaa 1440
ggcgcggcca atctgggcat cagctatccg attgcgctcg acaacaacta cgccacttgg 1500
accaactacc ggaatcgcta ttggcccgcc gagtatctga tcgacgctac cgggacggtg 1560
cggcacatca agttcggaga aggcgattac aacgtcaccg agacgttggt caggcagttg 1620
ctcaacgatg ccaagcccgg cgtcaaactc ccccagccca gcagcaccac cacgcccgac 1680
cttaccccgc gggccgcact tactcccgag acgtacttcg gagtcggcaa ggtggtcaac 1740
tacggcggcg gcggcgcata tgacgaaggg tcggccgtgt ttgactaccc gcccagtttg 1800
gcagccaaca gctttgcact gcgcggccgg tgggcgctgg actatcaggg tgccacgtcc 1860
gacggcaacg acgccgctat caaattgaat taccacgcca aagacgtcta catcgttgtc 1920
ggtggcaccg gcaccctcac ggtcgtgagg gacggaaagc cagccacact accgatcagc 1980
gggccgccga ccacccatca ggtggtcgcc ggctatcggc tggcgtccga aacacttgag 2040
gtgcggccca gcaaggggct acaggttttt tccttcacct acgga 2085

-continued

<210> SEQ ID NO 207
<211> LENGTH: 287
<212> TYPE: PRT
<213> ORGANISM: Mycobacterium tuberculosis

<400> SEQUENCE: 207

```
Val Asn Glu Ala Leu Ile Gly Leu Ala Phe Ala Ala Gly Leu Val Ala
1               5                   10                  15

Ala Leu Asn Pro Cys Gly Phe Ala Met Leu Pro Ala Tyr Leu Leu Leu
            20                  25                  30

Val Val Tyr Gly Gln Asp Ser Ala Gly Arg Thr Gly Pro Leu Ser Ala
        35                  40                  45

Val Gly Arg Ala Ala Ala Ala Thr Val Gly Met Ala Leu Gly Phe Leu
    50                  55                  60

Thr Val Phe Gly Ile Phe Gly Ala Leu Thr Ile Ser Ala Ala Thr Ala
65                  70                  75                  80

Val Gln Arg Tyr Leu Pro Tyr Ala Thr Val Leu Ile Gly Leu Ala Leu
                85                  90                  95

Ile Ala Leu Gly Gly Trp Leu Leu Leu Gly Arg Gly Leu Thr Ala Leu
            100                 105                 110

Thr Pro Arg Ser Leu Gly Val Arg Trp Ala Pro Thr Val Arg Leu Gly
        115                 120                 125

Ser Met Tyr Gly Tyr Gly Ile Ser Tyr Ala Val Ala Ser Leu Ser Cys
    130                 135                 140

Thr Ile Gly Pro Phe Leu Ala Val Thr Gly Ala Gly Leu Arg Gly Gly
145                 150                 155                 160

Ser Val Val Gly Ser Val Ala Ile Tyr Leu Ala Tyr Val Ala Gly Leu
                165                 170                 175

Thr Leu Val Val Gly Val Leu Ala Val Ala Ala Ala Thr Ala Ser Ser
            180                 185                 190

Ala Leu Ala Asp Arg Leu Arg Arg Ile Leu Pro Phe Val Asn Arg Ile
        195                 200                 205

Ser Gly Ala Leu Leu Val Val Val Gly Leu Tyr Val Gly Tyr Tyr Gly
    210                 215                 220

Leu Tyr Glu Leu Arg Leu Ile Ala Gly Val Gly Ala Asn Pro Gln Asp
225                 230                 235                 240

Ala Val Ile Ala Ala Ala Gly Arg Leu Gln Gly Ala Leu Ala Gly Trp
                245                 250                 255

Val Asn Gln His Gly Ala Trp Pro Trp Ala Val Leu Leu Val Val Leu
            260                 265                 270

Val Val Gly Ala Phe Ala Gly Thr Trp Phe Arg Arg Val Arg Arg
        275                 280                 285
```

<210> SEQ ID NO 208
<211> LENGTH: 861
<212> TYPE: DNA
<213> ORGANISM: Mycobacterium tuberculosis

<400> SEQUENCE: 208

```
gtgaacgagg cgctgatcgg tttggcgttc gccgccgggt tggtggctgc gctgaaccca     60

tgcgggtttg ccatgttgcc ggcctacctg ctgttggtgg tgtatgggca ggattcggcg    120

ggccggacgg ggccgcttag cgcagtgggc cgagcggcag ccgccacggt cgggatggcg    180

ctgggcttct tgacggtgtt cggcatcttc ggagccctga ccatttccgc ggccacggcg    240

gtgcagcgat acctgcccta tgccacggtg ctgatcggtc tggcgctcat cgccctcggc    300

gggtggctgc tgttgggacg agggctgacg gcgttgacgc cccgatccct cggcgtgcgt    360
```

```
tgggctccaa cggtacggct gggttccatg tatggctacg gcatcagcta tgcggttgct    420

tcgctgtcat gcaccatcgg gccgtttctc gcggttaccg gggcaggcct gcggggcggt    480

tcggtcgtcg ggagcgtagc gatctatctg gcttatgtcg cgggcctgac cctcgttgtc    540

ggcgtgcttg ccgtcgcggc cgcgaccgcg agctcggcgc tggccgaccg cctacggcga    600

atcttgccgt tcgtcaaccg gatcagtggc gcgctgctgg tggtggtcgg gctgtacgtg    660

ggttactacg gtctctacga gctgcgcctg attgccggtg tcggggcgaa tccccaggat    720

gcggtgattg ccgcggccgg ccgcctgcaa ggtgccctgg ctggctgggt taaccagcac    780

ggtgcatggc cttgggcggt gttgctggtt gtgctggtgg tcggtgcctt cgccggtacc    840

tggtttcggc gggtgcggcg c                                              861
```

<210> SEQ ID NO 209
<211> LENGTH: 413
<212> TYPE: PRT
<213> ORGANISM: Mycobacterium tuberculosis

<400> SEQUENCE: 209

```
Met Leu Thr Val Glu Asp Trp Ala Glu Ile Arg Arg Leu His Arg Ala
1               5                   10                  15

Glu Gly Leu Pro Ile Lys Met Ile Ala Arg Val Leu Gly Ile Ser Lys
            20                  25                  30

Asn Thr Val Lys Ser Ala Leu Glu Ser Asn Gln Gln Pro Lys Tyr Glu
        35                  40                  45

Arg Ala Pro Gln Gly Ser Ile Val Asp Ala Val Glu Pro Arg Ile Arg
    50                  55                  60

Glu Leu Leu Gln Ala Tyr Pro Thr Met Pro Ala Thr Val Ile Ala Glu
65                  70                  75                  80

Arg Ile Gly Trp Glu Arg Ser Ile Arg Val Leu Ser Ala Arg Val Ala
                85                  90                  95

Glu Leu Arg Pro Val Tyr Leu Pro Pro Asp Pro Ala Ser Arg Thr Thr
            100                 105                 110

Tyr Val Ala Gly Glu Ile Ala Gln Cys Asp Phe Trp Phe Pro Pro Ile
        115                 120                 125

Glu Leu Pro Val Gly Phe Gly Gln Thr Arg Thr Ala Lys Gln Leu Pro
    130                 135                 140

Val Leu Thr Met Val Cys Ala Tyr Ser Arg Trp Leu Leu Ala Met Leu
145                 150                 155                 160

Leu Pro Ser Arg Cys Ala Glu Asp Leu Phe Ala Gly Trp Trp Arg Leu
                165                 170                 175

Ile Glu Ala Leu Gly Ala Val Pro Arg Val Leu Val Trp Asp Gly Glu
            180                 185                 190

Gly Ala Ile Gly Arg Trp Arg Gly Gly Arg Ser Glu Leu Thr Thr Glu
        195                 200                 205

Cys Gln Ala Phe Arg Gly Thr Leu Ala Ala Lys Val Leu Ile Cys Arg
    210                 215                 220

Pro Ala Asp Pro Glu Ala Lys Gly Leu Ile Glu Arg Ala His Asp Tyr
225                 230                 235                 240

Leu Glu Arg Ser Phe Leu Pro Gly Arg Val Phe Ala Ser Pro Ala Asp
                245                 250                 255

Phe Asn Ala Gln Leu Gly Ala Trp Leu Ala Leu Val Asn Thr Arg Thr
            260                 265                 270

Arg Arg Ala Leu Gly Cys Ala Pro Thr Asp Arg Ile Gly Ala Asp Arg
        275                 280                 285
```

```
Ala Ala Met Leu Ser Leu Pro Pro Val Ala Pro Ala Thr Gly Trp Cys
    290                 295                 300

Thr Ser Leu Arg Leu Pro Arg Asp His Tyr Val Arg Cys Asp Ser Asn
305                 310                 315                 320

Asp Tyr Ser Val His Pro Gly Val Ile Gly His Arg Val Leu Val Arg
                325                 330                 335

Ala Asp Leu Glu Arg Val His Val Phe Cys Asp Gly Glu Leu Val Ala
            340                 345                 350

Asp His Glu Arg Ile Trp Ala Val His Gln Thr Val Ser Asp Pro Ala
        355                 360                 365

His Val Glu Ala Ala Lys Val Leu Arg Arg Arg His Phe Ser Ala Ala
    370                 375                 380

Ser Pro Val Val Glu Pro Gln Val Gln Val Arg Ser Leu Ser Asp Tyr
385                 390                 395                 400

Asp Asp Ala Leu Gly Val Asp Ile Asp Gly Gly Val Ala
                405                 410
```

<210> SEQ ID NO 210
<211> LENGTH: 1239
<212> TYPE: DNA
<213> ORGANISM: Mycobacterium tuberculosis

<400> SEQUENCE: 210

```
atgttgactg tggaagattg ggctgagatt cgccgattgc atcgcgcgga gggtttgccg     60

atcaagatga tcgcccgggt gctggggatt tccaagaaca cggtgaagtc agcgttggaa    120

tcaaaccagc agccgaaata tgaacgggca ccgcagggtt cgatcgttga tgcggttgag    180

ccgcggatcc gggagttgtt gcaggcctat ccgacgatgc cggcgacggt gatcgccgag    240

cggatcggct gggagcgctc gattcgggtg ctctcggcgc gggtggccga gctgcgcccg    300

gtgtatctgc cgccggaccc ggcgtcgcgc accacgtatg tggcaggcga aattgcccag    360

tgcgacttct ggtttccgcc gatcgagttg ccggtagggt tcgggcagac ccgcacggcc    420

aaacagttgc cggtgctgac catggtgtgc gcctattcgc gctggctgtt ggcgatgctg    480

ctgcccagca ggtgtgccga ggacctgttc gccggctggt ggcggctgat cgaggcgttg    540

ggggcggtgc cgcgggtgtt ggtgtgggat ggcgagggcg cgatcgggcg ctggcgcggc    600

gggcggtcgg agttgaccac tgagtgtcag gcgttccgcg gcacgctggc ggccaaggtg    660

ctcatctgcc ggccggccga cccggaggcc aagggcctca ttgaacgggc ccacgactac    720

ctggagcgct cgtttttgcc cgggcgggtg tttgcctcgc cggccgattt caacgcccaa    780

ctgggcgcct ggctggcgct ggtgaacacc cgcacccgcc gggcgctggg ttgtgcgccc    840

accgatcgca tcggcgcgga tcgggccgcg atgctgagct tgccgccggt ggcgccggcc    900

accgggtggt gcacctcgct gcggctgccc cgggatcact atgtgcgctg cgattccaac    960

gactactcgg tgcacccggg tgtgatcggg catcgggtgc tggtgcgcgc cgacctggag   1020

cgggtgcatg tgttctgcga cggtgagctg gtcgccgacc acgagcggat ctgggcggtc   1080

catcagacgg tctccgatcc cgcacatgtg gaggcggcga aggtgttgcg ccgccggcac   1140

ttcagtgcag catcaccggt agttgagccg caggtgcagg tccgctcact gagcgactac   1200

gatgacgcgc tgggagtcga catcgatggc ggggtggcc                          1239
```

<210> SEQ ID NO 211
<211> LENGTH: 153
<212> TYPE: PRT
<213> ORGANISM: Mycobacterium tuberculosis

<400> SEQUENCE: 211

Val Asp Val Ile Trp Ser Ala Thr Ile Ala Thr Thr Val Ala Thr Gly
1               5                   10                  15

Met Arg Lys Pro Arg Met His Gly Met Pro Pro Ile Thr Ser Gly Ser
            20                  25                  30

Met Val Thr Arg Val Thr Arg Met Ser Ile Arg Leu Ala Gly Asp Ser
        35                  40                  45

Thr Leu Gly Arg Phe Ser Thr Ser Arg Leu Gly Leu Ser Ser Ala Lys
    50                  55                  60

Ser Lys Pro Glu Gly Asp Phe Gly Thr Ala Cys Gly Ala Val Ser Gly
65                  70                  75                  80

Gly Asp Ala Gly Val Val Ala Leu Ala Glu Gly Val Asp Asp Gly Gln
                85                  90                  95

Ser Lys Pro Gly Ala Ala Gly Gly Ala Arg Gly Val Gly Gly Phe Arg
            100                 105                 110

Glu Ser Arg Ala Asp Cys Gly Glu Gln Phe Gly Val Ala Ser Trp Thr
        115                 120                 125

Pro Gln Gly Glu Phe Glu Phe Gly Gly Gln Glu Ala Lys Gly Val Arg
    130                 135                 140

Ser Ser Trp Pro Ala Ser Leu Thr Asn
145                 150

<210> SEQ ID NO 212
<211> LENGTH: 459
<212> TYPE: DNA
<213> ORGANISM: Mycobacterium tuberculosis

<400> SEQUENCE: 212
gtggatgtca tttggtccgc gaccatcgcg accacagtcg ccactgggat gcgcaagccc 60
cggatgcatg gcatgcctcc catcacgtcg gggtcgatgg tgacgcgggt gactcgcatg 120
tctataaggc tagccggtga cagcacgctg ggcggttct ccaccagccg tcttggctta 180
agctcagcca agagcaagcc ggagggagat ttcggcaccg cctgcggcgc ggtttcgggc 240
ggtgacgctg gcgtggttgc gttggctgag ggtgtcgacg atggccagtc caagcccggt 300
gccgccggtg gtgcgcgcgg tgtcggtggt ttccgcgaga gccgagcgga ttgcggcgag 360
cagttcgggg ttgcttcgtg gacgccgcag ggcgagttcg agttcggtgg tcaggaggct 420
aagggggtgc gaagttcgtg gcccgcatcg ctgacgaat 459

<210> SEQ ID NO 213
<211> LENGTH: 337
<212> TYPE: PRT
<213> ORGANISM: Mycobacterium tuberculosis

<400> SEQUENCE: 213

Val Ser Val Phe Ala Thr Ala Thr Gly Ile Gly Ser Trp Pro Gly Thr
1               5                   10                  15

Ala Ala Arg Glu Ala Ala Gln Val Val Val Gly Glu Leu Ala Gly Ala
            20                  25                  30

Leu Ala Tyr Leu Thr Glu Leu Pro Ala Arg Gly Val Gly Ala Asp Met
        35                  40                  45

Leu Gly Arg Ala Gly Gly Leu Leu Val Asp Val Ala Ile Asp Thr Val
    50                  55                  60

Pro Arg Gly Tyr Arg Ile Ala Ala Arg Pro Gly Ala Val Thr Arg Arg
65                  70                  75                  80

-continued

```
Ala Ala Ser Leu Leu Asp Glu Asp Met Asp Ala Leu Glu Glu Ala Trp
                85                  90                  95

Glu Thr Ala Gly Leu Arg Gly Cys Gly Arg Ala Val Lys Val Gln Ala
            100                 105                 110

Pro Gly Pro Val Thr Leu Val Ala Gly Leu Glu Leu Ala Asn Gly His
        115                 120                 125

Arg Ala Ile Thr Asp Pro Gly Ala Val Arg Asp Leu Ala Ala Ser Leu
    130                 135                 140

Ala Glu Gly Val Ala Ala His Arg Ala Ala Leu Ala Arg Arg Leu Asp
145                 150                 155                 160

Thr Pro Val Val Val Gln Phe Asp Glu Pro Ser Leu Pro Ala Ala Leu
                165                 170                 175

Gly Gly Arg Leu Thr Gly Val Thr Ala Leu Ser Pro Val Ala Pro Leu
            180                 185                 190

Asp Glu Thr Val Ala Glu Ala Leu Leu Asp Thr Cys Ile Ala Ala Val
        195                 200                 205

Asp Ala Asp Val Ala Leu His Ser Cys Ser Pro Asp Leu Pro Trp Asp
    210                 215                 220

Leu Leu Gln Arg Ser Arg Ile Ser Ala Val Ser Val Asp Ala Ser Thr
225                 230                 235                 240

Leu Gln Ala Ala Asp Leu Asp Ala Val Ala Ala Phe Val Glu Ser Gly
                245                 250                 255

Arg Thr Val Val Leu Gly Leu Val Pro Val Thr Ala Pro Glu Arg Ala
            260                 265                 270

Pro Ser Met Glu Glu Val Ala Ala Ala Ala Val Ala Val Thr Asp Arg
        275                 280                 285

Leu Gly Val Pro Arg Ser Ala Leu Arg Asp Arg Leu Gly Val Ser Pro
    290                 295                 300

Ala Cys Gly Leu Ala Asn Ala Thr Gly Gln Trp Ala Arg Thr Ala Val
305                 310                 315                 320

Gly Leu Ala Arg Asp Val Ala Glu Ala Phe Ala Arg Asp Pro Glu Ala
                325                 330                 335

Ile


<210> SEQ ID NO 214
<211> LENGTH: 1011
<212> TYPE: PRT
<213> ORGANISM: Mycobacterium tuberculosis

<400> SEQUENCE: 214

Gly Thr Gly Ala Gly Thr Gly Thr Thr Thr Thr Cys Gly Cys Ala Ala
1               5                   10                  15

Cys Gly Gly Cys Cys Ala Cys Cys Gly Gly Gly Ala Thr Cys Gly Gly
            20                  25                  30

Ala Thr Cys Gly Thr Gly Gly Cys Cys Gly Gly Gly Cys Ala Cys Cys
        35                  40                  45

Gly Cys Cys Gly Cys Gly Cys Gly Ala Gly Ala Gly Gly Cys Cys Gly
    50                  55                  60

Cys Gly Cys Ala Gly Gly Thr Cys Gly Thr Gly Gly Thr Cys Gly Gly
65                  70                  75                  80

Gly Gly Ala Gly Thr Thr Gly Gly Cys Gly Gly Gly Thr Gly Cys Ala
                85                  90                  95

Thr Thr Gly Gly Cys Cys Thr Ala Thr Cys Thr Cys Ala Cys Cys Gly
            100                 105                 110

Ala Gly Cys Thr Gly Cys Cys Cys Gly Cys Cys Ala Gly Gly Gly Gly
```

-continued

```
        115                 120                 125

Cys Gly Thr Cys Gly Gly Cys Gly Cys Cys Gly Ala Cys Ala Thr Gly
    130                 135                 140

Cys Thr Gly Gly Gly Gly Cys Gly Ala Gly Cys Cys Gly Gly Cys Gly
145                 150                 155                 160

Gly Ala Cys Thr Gly Cys Thr Gly Gly Thr Cys Gly Ala Cys Gly Thr
                165                 170                 175

Gly Gly Cys Gly Ala Thr Thr Gly Ala Cys Ala Cys Cys Gly Thr Gly
            180                 185                 190

Cys Cys Thr Cys Gly Thr Gly Gly Cys Thr Ala Cys Cys Gly Cys Ala
        195                 200                 205

Thr Cys Gly Cys Thr Gly Cys Thr Cys Gly Ala Cys Cys Cys Gly Gly
    210                 215                 220

Cys Gly Cys Gly Gly Thr Gly Ala Cys Ala Cys Gly Gly Cys Gly Gly
225                 230                 235                 240

Gly Cys Cys Gly Cys Gly Ala Gly Cys Cys Thr Cys Cys Thr Cys Gly
                245                 250                 255

Ala Cys Gly Ala Gly Gly Ala Thr Ala Thr Gly Gly Ala Thr Gly Cys
            260                 265                 270

Cys Thr Thr Ala Gly Ala Ala Gly Ala Gly Gly Cys Cys Thr Gly Gly
        275                 280                 285

Gly Ala Gly Ala Cys Cys Gly Cys Gly Gly Gly Cys Cys Thr Gly Cys
    290                 295                 300

Gly Thr Gly Gly Cys Thr Gly Thr Gly Gly Gly Cys Gly Gly Gly Cys
305                 310                 315                 320

Gly Gly Thr Gly Ala Ala Gly Gly Thr Gly Cys Ala Gly Gly Cys Gly
                325                 330                 335

Cys Cys Cys Gly Gly Gly Cys Cys Ala Gly Thr Cys Ala Cys Ala Thr
            340                 345                 350

Thr Gly Gly Thr Cys Gly Cys Gly Gly Gly Gly Thr Thr Gly Gly Ala
        355                 360                 365

Gly Cys Thr Gly Gly Cys Cys Ala Ala Cys Gly Gly Thr Cys Ala Cys
    370                 375                 380

Cys Gly Gly Gly Cys Gly Ala Thr Cys Ala Cys Cys Gly Ala Cys Cys
385                 390                 395                 400

Cys Cys Gly Gly Ala Gly Cys Cys Gly Thr Gly Cys Gly Thr Gly Ala
                405                 410                 415

Cys Cys Thr Gly Gly Cys Cys Gly Cys Cys Thr Cys Gly Cys Thr Gly
            420                 425                 430

Gly Cys Cys Gly Ala Ala Gly Gly Cys Gly Thr Thr Gly Cys Cys Gly
        435                 440                 445

Cys Gly Cys Ala Thr Cys Gly Cys Gly Cys Gly Gly Cys Gly Cys Thr
    450                 455                 460

Gly Gly Cys Gly Cys Gly Thr Cys Gly Ala Cys Thr Thr Gly Ala Cys
465                 470                 475                 480

Ala Cys Ala Cys Cys Gly Gly Thr Gly Gly Thr Gly Gly Thr Gly Cys
                485                 490                 495

Ala Gly Thr Thr Cys Gly Ala Cys Gly Ala Gly Cys Cys Gly Thr Cys
            500                 505                 510

Gly Thr Thr Gly Cys Cys Gly Gly Cys Gly Gly Cys Gly Thr Thr Gly
        515                 520                 525

Gly Gly Cys Gly Gly Cys Cys Gly Gly Cys Thr Gly Ala Cys Cys Gly
    530                 535                 540
```

-continued

```
Gly Gly Gly Thr Gly Ala Cys Cys Gly Cys Gly Thr Thr Gly Ala Gly
545                 550                 555                 560

Cys Cys Cys Gly Gly Thr Thr Gly Cys Cys Cys Cys Gly Cys Thr Cys
                565                 570                 575

Gly Ala Cys Gly Ala Gly Ala Cys Gly Gly Thr Gly Gly Cys Cys Gly
            580                 585                 590

Ala Ala Gly Cys Gly Cys Thr Gly Cys Thr Cys Gly Ala Cys Ala Cys
        595                 600                 605

Thr Thr Gly Cys Ala Thr Cys Gly Cys Gly Gly Cys Thr Gly Thr Cys
    610                 615                 620

Gly Ala Cys Gly Cys Gly Gly Ala Cys Gly Thr Ala Gly Cys Gly Cys
625                 630                 635                 640

Thr Ala Cys Ala Cys Ala Gly Cys Thr Gly Cys Ala Gly Thr Cys Cys
                645                 650                 655

Gly Gly Ala Thr Thr Thr Gly Cys Cys Gly Thr Gly Gly Gly Ala Thr
            660                 665                 670

Cys Thr Gly Cys Thr Gly Cys Ala Gly Cys Gly Cys Ala Gly Cys Ala
        675                 680                 685

Gly Ala Ala Thr Thr Ala Gly Thr Gly Cys Gly Gly Thr Ala Thr Cys
    690                 695                 700

Gly Gly Thr Gly Gly Ala Thr Gly Cys Gly Ala Gly Cys Ala Cys Ala
705                 710                 715                 720

Cys Thr Gly Cys Ala Gly Gly Cys Thr Gly Cys Gly Gly Ala Thr Thr
                725                 730                 735

Thr Gly Gly Ala Thr Gly Cys Thr Gly Thr Cys Gly Cys Gly Gly Cys
            740                 745                 750

Ala Thr Thr Thr Gly Thr Cys Gly Ala Gly Thr Cys Gly Gly Gly Cys
        755                 760                 765

Cys Gly Ala Ala Cys Cys Gly Thr Cys Gly Thr Gly Cys Thr Gly Gly
    770                 775                 780

Gly Cys Cys Thr Gly Gly Thr Cys Cys Cys Gly Gly Thr Gly Ala Cys
785                 790                 795                 800

Cys Gly Cys Cys Cys Cys Gly Gly Ala Gly Cys Gly Ala Gly Cys Ala
                805                 810                 815

Cys Cys Thr Thr Cys Gly Ala Thr Gly Gly Ala Ala Gly Ala Gly Gly
            820                 825                 830

Thr Cys Gly Cys Thr Gly Cys Thr Gly Cys Gly Gly Cys Gly Gly Thr
        835                 840                 845

Cys Gly Cys Gly Gly Thr Cys Ala Cys Cys Gly Ala Thr Cys Gly Gly
    850                 855                 860

Cys Thr Cys Gly Gly Cys Gly Thr Thr Cys Cys Thr Cys Gly Cys Thr
865                 870                 875                 880

Cys Gly Gly Cys Gly Cys Thr Ala Cys Gly Cys Gly Ala Thr Cys Gly
                885                 890                 895

Ala Cys Thr Cys Gly Gly Cys Gly Thr Cys Ala Gly Cys Cys Cys Gly
            900                 905                 910

Gly Cys Gly Thr Gly Thr Gly Gly Thr Cys Thr Gly Gly Cys Cys Ala
        915                 920                 925

Ala Thr Gly Cys Gly Ala Cys Gly Gly Gly Gly Cys Ala Gly Thr Gly
    930                 935                 940

Gly Gly Cys Cys Cys Gly Cys Ala Cys Cys Gly Cys Gly Gly Thr Cys
945                 950                 955                 960

Gly Gly Gly Cys Thr Thr Gly Cys Cys Cys Gly Thr Gly Ala Thr Gly
                965                 970                 975
```

```
Thr Cys Gly Cys Thr Gly Ala Gly Gly Cys Gly Thr Thr Cys Gly Cys
            980                 985                 990

Gly Cys Gly Gly Gly Ala Cys Cys  Cys Ala Gly Ala Gly  Gly Cys Cys
        995                 1000                1005

Ala Thr  Cys
    1010


<210> SEQ ID NO 215
<211> LENGTH: 81
<212> TYPE: PRT
<213> ORGANISM: Mycobacterium tuberculosis

<400> SEQUENCE: 215

Val Thr Ala Pro Val Trp Leu Ala Ser Pro Pro Glu Val His Ser Ala
1               5                   10                  15

Leu Leu Ser Ala Gly Pro Gly Pro Gly Ser Leu Gln Ala Ala Ala Ala
            20                  25                  30

Gly Trp Ser Ala Leu Ser Ala Glu Tyr Ala Ala Val Ala Gln Glu Leu
        35                  40                  45

Ser Val Val Val Ala Ala Val Gly Ala Gly Val Trp Gln Gly Pro Ser
    50                  55                  60

Ala Glu Leu Phe Val Ala Ala Tyr Val Pro Tyr Val Ala Trp Leu Val
65                  70                  75                  80

Gln


<210> SEQ ID NO 216
<211> LENGTH: 243
<212> TYPE: DNA
<213> ORGANISM: Mycobacterium tuberculosis

<400> SEQUENCE: 216

gtgacggcgc cggtgtggtt ggcgtcgccg ccggaggtgc attcggcgct gctaagtgct      60

ggtccggggc cgggttcgtt gcaggcggcc gcggcggggt ggagcgcgtt aagcgccgag     120

tacgccgctg tggcgcaaga gttgagcgtg gtggtggccg cggtgggggc cggggtgtgg     180

cagggtccca gtgctgagtt gtttgtggcc gcctatgtgc cgtatgtggc gtggttggtg     240

cag                                                                   243


<210> SEQ ID NO 217
<211> LENGTH: 254
<212> TYPE: PRT
<213> ORGANISM: Mycobacterium tuberculosis

<400> SEQUENCE: 217

Val Pro Glu Phe Val Asn Val Val Val Ser Asp Gly Ser Gln Asp Ala
1               5                   10                  15

Gly Leu Ala Met Leu Leu Leu Ser Arg Pro Pro Thr Asn Ala Met Thr
            20                  25                  30

Arg Gln Val Tyr Arg Glu Val Val Ala Ala Ala Asn Glu Leu Gly Arg
        35                  40                  45

Arg Asp Asp Val Ala Ala Val Ile Leu Tyr Gly Gly His Glu Ile Phe
    50                  55                  60

Ser Ala Gly Asp Asp Met Pro Glu Leu Arg Thr Leu Ser Ala Gln Glu
65                  70                  75                  80

Ala Asp Thr Ala Ala Arg Ile Arg Gln Gln Ala Val Asp Ala Val Ala
                85                  90                  95

Ala Ile Pro Lys Pro Thr Val Ala Ala Ile Thr Gly Tyr Ala Leu Gly
```

```
            100                 105                 110

Ala Gly Leu Thr Leu Ala Leu Ala Ala Asp Trp Arg Val Ser Gly Asp
        115                 120                 125

Asn Val Lys Phe Gly Ala Thr Glu Ile Leu Ala Gly Leu Ile Pro Ser
    130                 135                 140

Gly Asp Gly Met Ala Arg Leu Thr Arg Ala Ala Gly Pro Ser Arg Ala
145                 150                 155                 160

Lys Glu Leu Val Phe Ser Gly Arg Phe Phe Asp Ala Glu Glu Ala Leu
                165                 170                 175

Ala Leu Gly Leu Ile Asp Asp Met Val Ala Pro Asp Asp Val Tyr Asp
            180                 185                 190

Ala Ala Ala Ala Trp Ala Arg Arg Phe Leu Asp Gly Pro Pro His Ala
        195                 200                 205

Leu Ala Ala Ala Lys Ala Gly Ile Ser Asp Val Tyr Glu Leu Ala Pro
    210                 215                 220

Ala Glu Arg Ile Ala Ala Glu Arg Arg Arg Tyr Val Glu Val Phe Ala
225                 230                 235                 240

Ala Gly Gln Gly Gly Gly Ser Lys Gly Asp Arg Gly Gly Arg
                245                 250
```

<210> SEQ ID NO 218
<211> LENGTH: 762
<212> TYPE: DNA
<213> ORGANISM: Mycobacterium tuberculosis

<400> SEQUENCE: 218

```
gtgcccgagt tcgtcaacgt cgtggtcagt gacggctccc aggatgccgg cctggccatg      60

ttgctcctat cgcgaccgcc taccaacgcg atgacccgcc aggtctaccg ggaagtggtc     120

gccgcggcca acgagctggg gcgacgcgac gacgtggccg cagtgatcct gtatggcggc     180

cacgaaatct tctccgccgg cgacgacatg cccgaactgc ggacattgag cgcgcaggag     240

gccgacaccg ccgcccggat tcggcagcag gccgtcgacg ccgttgcggc gatccccaag     300

ccgaccgtgg ccgccatcac cggatacgcg ttgggtgccg gccttacgct ggccctagcc     360

gccgattggc gagtcagcgg tgacaacgtg aaattcggcg cgaccgagat cctggccggc     420

ctgatcccca gcggcgacgg aatggcccgg ctgacccgtg cggccggtcc gagcagagcc     480

aaggagctgg tgttcagcgg gcgcttcttc gacgccgagg aggccttggc gctgggcctg     540

atcgacgaca tggtggcccc cgacgacgtt tacgacgccg cggcggcctg ggcgaggcgc     600

tttcttgacg gcccgccgca cgcgctggcc gcggccaaag ccgggatcag cgacgtctac     660

gagctggcgc cggccgagcg gatcgccgct gagcgtcggc gctatgtcga ggtgttcgcc     720

gctggtcaag gtggtggcag caagggtgac cggggcggcc gt                        762
```

<210> SEQ ID NO 219
<211> LENGTH: 721
<212> TYPE: PRT
<213> ORGANISM: Mycobacterium tuberculosis

<400> SEQUENCE: 219

```
Met Gly Ile Ala Leu Thr Asp Asp His Arg Glu Leu Ser Gly Val Ala
1               5                   10                  15

Arg Ala Phe Leu Thr Ser Gln Lys Val Arg Trp Ala Ala Arg Ala Ser
            20                  25                  30

Leu Asp Ala Ala Gly Asp Ala Arg Pro Pro Phe Trp Gln Asn Leu Ala
        35                  40                  45
```

-continued

```
Glu Leu Gly Trp Leu Gly Leu His Ile Asp Glu Arg His Gly Gly Ser
    50                  55                  60

Gly Tyr Gly Leu Ser Glu Leu Val Val Val Ile Glu Glu Leu Gly Arg
65                  70                  75                  80

Ala Val Ala Pro Gly Leu Phe Val Pro Thr Val Ile Ala Ser Ala Val
                85                  90                  95

Val Ala Lys Glu Gly Thr Asp Asp Gln Arg Ala Arg Leu Leu Pro Ala
            100                 105                 110

Leu Ile Asp Gly Thr Leu Thr Ala Gly Val Gly Leu Asp Ser Gln Val
        115                 120                 125

Gln Val Thr Asp Gly Val Ala Asp Gly Glu Ala Gly Ile Val Leu Gly
    130                 135                 140

Ala Gly Leu Ala Glu Leu Leu Leu Val Ala Ala Gly Asp Asp Val Leu
145                 150                 155                 160

Val Leu Glu Arg Gly Arg Lys Gly Val Ser Val Asp Val Pro Glu Asn
                165                 170                 175

Phe Asp Pro Thr Arg Arg Ser Gly Arg Val Arg Leu Asp Asn Val Arg
            180                 185                 190

Val Thr Thr Asp Asp Ile Leu Leu Gly Ala Tyr Glu Ser Ala Leu Ala
        195                 200                 205

Arg Ala Arg Thr Leu Leu Ala Ala Glu Ala Val Gly Gly Ala Ala Asp
    210                 215                 220

Cys Val Asp Ser Ala Val Ala Tyr Ala Lys Val Arg Gln Gln Phe Gly
225                 230                 235                 240

Arg Thr Ile Ala Thr Phe Gln Ala Val Lys His His Cys Ala Asn Met
                245                 250                 255

Leu Val Ala Ala Glu Ser Ala Ile Ala Ala Val Trp Asp Ala Ala Arg
            260                 265                 270

Ala Ala Ala Glu Asp Glu Glu Gln Phe Arg Leu Ala Ala Ala Val Ala
        275                 280                 285

Ala Ala Leu Ala Phe Pro Ala Tyr Ala Arg Asn Ala Glu Leu Asn Ile
    290                 295                 300

Gln Val His Gly Gly Ile Gly Phe Thr Trp Glu His Asp Ala His Leu
305                 310                 315                 320

His Leu Arg Arg Ala Leu Val Thr Val Gly Leu Phe Gly Gly Asp Ala
                325                 330                 335

Pro Val Arg Asp Val Phe Glu Arg Thr Ala Ala Gly Val Thr Arg Ala
            340                 345                 350

Ile Ser Leu Asp Leu Pro Ala Gln Ala Glu Glu Leu Arg Ala Arg Ile
        355                 360                 365

Arg Ser Asp Ala Ala Glu Ile Ala Ala Leu Glu Lys Asp Ala Gln Arg
    370                 375                 380

Asp Lys Leu Ile Glu Thr Gly Tyr Val Met Pro His Trp Pro Arg Pro
385                 390                 395                 400

Trp Gly Arg Ala Ala Gly Ala Val Glu Gln Leu Val Ile Glu Glu Glu
                405                 410                 415

Phe Ser Ala Ala Gly Ile Glu Arg Pro Asp Tyr Ser Ile Thr Gly Trp
            420                 425                 430

Val Ile Leu Thr Leu Ile Gln His Gly Thr Pro Trp Gln Ile Glu Arg
        435                 440                 445

Phe Val Glu Lys Ala Leu Arg Gln Gln Glu Ile Trp Cys Gln Leu Phe
    450                 455                 460

Ser Glu Pro Asp Ala Gly Ser Asp Ala Ala Ser Val Lys Thr Arg Ala
465                 470                 475                 480
```

Thr Arg Val Glu Gly Gly Trp Lys Ile Asn Gly Gln Lys Val Trp Thr
485 490 495

Ser Gly Ala Gln Tyr Cys Ala Arg Gly Leu Ala Thr Val Arg Thr Asp
500 505 510

Pro Asp Ala Pro Lys His Ala Gly Ile Thr Thr Val Ile Ile Asp Met
515 520 525

Leu Ala Pro Gly Val Glu Val Arg Pro Leu Arg Gln Ile Thr Gly Asp
530 535 540

Ser Glu Phe Asn Glu Val Phe Phe Asn Asp Val Phe Val Pro Asp Glu
545 550 555 560

Asp Val Val Gly Ala Pro Asn Ser Gly Trp Thr Val Ala Arg Ala Thr
565 570 575

Leu Gly Asn Glu Arg Val Ser Ile Gly Gly Ser Gly Ser Tyr Tyr Glu
580 585 590

Ala Met Ala Ala Lys Leu Val Gln Leu Val Gln Arg Arg Ser Asp Ala
595 600 605

Phe Ala Gly Ala Pro Ile Arg Val Gly Ala Phe Leu Ala Glu Asp His
610 615 620

Ala Leu Arg Leu Leu Asn Leu Arg Arg Ala Ala Arg Ser Val Glu Gly
625 630 635 640

Ala Gly Pro Gly Pro Glu Gly Asn Ile Thr Lys Leu Lys Val Ala Glu
645 650 655

His Met Ile Glu Gly Ala Ala Ile Ala Ala Ala Leu Trp Gly Pro Glu
660 665 670

Ile Ala Leu Leu Asp Gly Pro Gly Arg Val Ile Gly Arg Thr Val Met
675 680 685

Gly Ala Arg Gly Met Ala Ile Ala Gly Gly Thr Ser Glu Val Thr Arg
690 695 700

Asn Gln Ile Ala Glu Arg Ile Leu Gly Met Pro Arg Asp Pro Leu Ile
705 710 715 720

Ser

<210> SEQ ID NO 220
<211> LENGTH: 2163
<212> TYPE: DNA
<213> ORGANISM: Mycobacterium tuberculosis

<400> SEQUENCE: 220
atgggtattg cattgaccga cgaccatcgc gagctctccg gggtggctcg cgcgttcttg 60
acttcgcaga aggtgcgctg ggcggcgcgt gcatcactgg acgcggcggg ggacgcccgc 120
ccgccgttct ggcagaacct cgccgagctg ggctggctcg gcctgcatat cgacgagcga 180
cacggtggct ctggctatgg cctgtccgag cttgtggtgg tgatcgaaga gctcggtcgt 240
gcggtggcac cggggctgtt tgtgccgacc gtgatcgcct cagcggtggt cgccaaagaa 300
ggtactgatg accaacgggc acggctgttg ccggcgctga ttgacggaac cctgacggcg 360
ggtgtgggac tggatagtca ggtgcaggtt accgacggtg ttgccgacgg tgaggcggga 420
atcgtgttgg gcgccgggct tgccgagctg ctgttggttg ccgccggtga cgacgtgctg 480
gtgttggaac gcggccgcaa gggcgtctcg gttgatgtgc cggaaaactt tgatccgacc 540
cggcggagtg gccgcgtgcg cctggacaac gtgcgcgtca cgaccgacga catcctgctt 600
ggtgcgtatg aatcggcttt ggcccgcgcg cgcacattgc tggccgccga ggccgtcggt 660
ggggcggccg actgcgtgga cagcgccgtg gcctatgcca aggtgcgaca gcaattcggc 720

```
cgtaccatcg ccacgtttca agcggtgaag catcactgcg cgaacatgct ggtggccgcc    780

gagtcggcga tcgccgcggt ctgggatgcc gcgcgtgcgg cagcagagga tgaggagcag    840

tttcggctgg ccgccgcggt cgctgcggcc ctggcgtttc cggcctatgc acgcaatgcc    900

gagctcaaca tccaggtgca cggcggtatt ggctttacct gggagcatga cgcgcatctg    960

catctgcgcc gggcgttggt gaccgtggga ttgttcggcg gtgatgcgcc cgtccgagac   1020

gttttcgagc gcaccgcggc tggcgttacc cgggcgatca gcttggacct gccggcacag   1080

gccgaggagc tgcgcgcccg catccgttcg gacgccgctg aaatcgctgc tctggaaaag   1140

gatgcacagc gcgacaagct gatcgagacg ggctatgtga tgccgcattg gcccaggccg   1200

tggggtcgtg ccgcgggcgc ggtggagcag ttggtgatcg aggaagagtt cagcgcggcg   1260

ggcatcgagc gcccggatta ctcgatcacc gggtgggtga tcttgacgct gattcagcac   1320

ggaacgcctt ggcagattga aagattcgtc gagaaagcgc tgcgccagca ggagatatgg   1380

tgccaactgt tctccgaacc tgacgcgggg tctgacgcgg cctcggtcaa gacccgcgca   1440

actcgggtgg agggcggctg gaagatcaac gggcaaaagg tgtggaccag cggagcgcag   1500

tactgcgcgc gtggcctggc taccgtgcgt accgatccgg atgcccccaa acacgctggc   1560

atcaccacgg tgatcatcga catgttggcc cccggtgtcg aggtgcggcc gctgcggcag   1620

atcaccggcg actcggaatt caacgaggtg ttcttcaacg atgtcttcgt ccccgatgag   1680

gacgttgtcg gggcgccgaa ctccgggtgg acggtggcgc gggcaacgct gggcaacgag   1740

cgggtcagca tcggcggcag tggctcgtac tacgaagcaa tggcggcgaa gctggtgcaa   1800

ttggtccagc ggcggtcaga tgcgtttgcg ggcgccccaa ttcgagtcgg cgctttcctc   1860

gcagaggatc acgcactgcg gctgctgaac ctgcgccgtg ccgctcgcag cgtcgaagga   1920

gccggccctg gtccggaggg caacatcacc aagctcaaag tggcagagca catgatcgag   1980

ggcgccgcca tcgcggccgc gctatggggg cccgagattg cgttgctgga cggccccggc   2040

agggtgattg gccgaacggt gatgggcgcc cgtggcatgg cgatcgccgg cggcacgtcg   2100

gaggtgaccc gcaatcagat tgccgagcgg atcctgggca tgccgcgtga tcccctgatt   2160

agc                                                                 2163
```

```
<210> SEQ ID NO 221
<211> LENGTH: 141
<212> TYPE: PRT
<213> ORGANISM: Mycobacterium tuberculosis

<400> SEQUENCE: 221

Met Val Lys Asp Leu Asp Arg Arg Leu Ala Gly Cys Leu Pro Ala Val
1               5                   10                  15

Leu Ser Leu Phe Arg Leu Val Tyr Gly Leu Leu Phe Ala Gly Tyr Gly
            20                  25                  30

Ser Met Ile Leu Phe Gly Trp Pro Val Thr Ser Ala Gln Pro Val Glu
        35                  40                  45

Phe Gly Ser Trp Pro Gly Trp Tyr Ala Gly Val Ile Glu Leu Val Ala
    50                  55                  60

Gly Leu Leu Ile Ala Thr Gly Leu Phe Thr Arg Ala Val Ala Phe Val
65                  70                  75                  80

Ala Ser Gly Glu Met Ala Val Ala Tyr Phe Trp Met His Gln Pro Tyr
                85                  90                  95

Ala Leu Trp Pro Ile Gly Gly Pro Pro Asp Gly Asn Gly Gly Thr Pro
            100                 105                 110

Ala Ile Leu Phe Cys Phe Gly Phe Phe Leu Leu Val Phe Thr Gly Gly
```

```
        115                 120                 125

Gly Ile Tyr Ser Ile Asp Ala Arg Arg Thr Val Thr Ala
    130                 135                 140


<210> SEQ ID NO 222
<211> LENGTH: 423
<212> TYPE: DNA
<213> ORGANISM: Mycobacterium tuberculosis

<400> SEQUENCE: 222

atggtgaaag atctcgaccg tcggctcgcc ggctgtttgc cggctgtgct gagcctcttt     60

cggttggtat acgggctgct gttcgccggc tacggatcga tgatcctttt cggctggccc    120

gtcacctcgg ctcaacccgt cgaatttgga tcctggcccg gctggtatgc cggggtcatc    180

gagttggtgg caggtctgct gatcgcaacc gggctgttta cccgcgctgt ggcgttcgtt    240

gcctcgggcg aaatggcggt cgcctacttc tggatgcatc aaccgtatgc actgtggccg    300

atcggcggtc caccggacgg caatggcgga actccggcga tactgttctg cttcggcttc    360

ttcctgctgg tgttcaccgg tggtgggatc tactcaattg atgctcgacg cactgtcact    420

gca                                                                  423


<210> SEQ ID NO 223
<211> LENGTH: 437
<212> TYPE: PRT
<213> ORGANISM: Mycobacterium tuberculosis

<400> SEQUENCE: 223

Val Val Ser Tyr Val Val Ala Leu Pro Glu Val Met Ser Ala Ala Ala
1               5                   10                  15

Thr Asp Val Ala Ser Ile Gly Ser Val Val Ala Thr Ala Ser Gln Gly
            20                  25                  30

Val Ala Gly Ala Thr Thr Thr Val Leu Ala Ala Ala Glu Asp Glu Val
        35                  40                  45

Ser Ala Ala Ile Ala Ala Leu Phe Ser Gly His Gly Gln Asp Tyr Gln
    50                  55                  60

Ala Leu Ser Ala Gln Leu Ala Val Phe His Glu Arg Phe Val Gln Ala
65                  70                  75                  80

Leu Thr Gly Ala Ala Lys Gly Tyr Ala Ala Ala Glu Leu Ala Asn Ala
                85                  90                  95

Ser Leu Leu Gln Ser Glu Phe Ala Ser Gly Ile Gly Asn Gly Phe Ala
            100                 105                 110

Thr Ile His Gln Glu Ile Gln Arg Ala Pro Thr Ala Leu Ala Ala Gly
        115                 120                 125

Phe Thr Gln Val Pro Pro Phe Ala Ala Ala Gln Ala Gly Ile Phe Thr
    130                 135                 140

Gly Thr Pro Ser Gly Ala Ala Gly Phe Asp Ile Ala Ser Leu Trp Pro
145                 150                 155                 160

Val Lys Pro Leu Leu Ser Leu Ser Ala Leu Glu Thr His Phe Ala Ile
                165                 170                 175

Pro Asn Asn Pro Leu Leu Ala Leu Ile Ala Ser Asp Ile Pro Pro Leu
            180                 185                 190

Ser Trp Phe Leu Gly Asn Ser Pro Pro Pro Leu Leu Asn Ser Leu Leu
        195                 200                 205

Gly Gln Thr Val Gln Tyr Thr Thr Tyr Asp Gly Met Ser Val Val Gln
    210                 215                 220

Ile Thr Pro Ala His Pro Thr Gly Glu Tyr Val Val Ala Ile His Gly
```

-continued 225 230 235 240

Gly Ala Phe Ile Leu Pro Pro Ser Ile Phe His Trp Leu Asn Tyr Ser
245 250 255

Val Thr Ala Tyr Gln Thr Gly Ala Thr Val Gln Val Pro Ile Tyr Pro
260 265 270

Leu Val Gln Glu Gly Gly Thr Ala Gly Thr Val Val Pro Ala Met Ala
275 280 285

Gly Leu Ile Ser Thr Gln Ile Ala Gln His Gly Val Ser Asn Val Ser
290 295 300

Val Val Gly Asp Ser Ala Gly Gly Asn Leu Ala Leu Ala Ala Ala Gln
305 310 315 320

Tyr Met Val Ser Gln Gly Asn Pro Val Pro Ser Ser Met Val Leu Leu
325 330 335

Ser Pro Trp Leu Asp Val Gly Thr Trp Gln Ile Ser Gln Ala Trp Ala
340 345 350

Gly Asn Leu Ala Val Asn Asp Pro Leu Val Ser Pro Leu Tyr Gly Ser
355 360 365

Leu Asn Gly Leu Pro Pro Thr Tyr Val Tyr Ser Gly Ser Leu Asp Pro
370 375 380

Leu Ala Gln Gln Ala Val Val Leu Glu His Thr Ala Val Val Gln Gly
385 390 395 400

Ala Pro Phe Ser Phe Val Leu Ala Pro Trp Gln Ile His Asp Trp Ile
405 410 415

Leu Leu Thr Pro Trp Gly Leu Leu Ser Trp Pro Gln Ile Asn Gln Gln
420 425 430

Leu Gly Ile Ala Ala
435

<210> SEQ ID NO 224
<211> LENGTH: 1311
<212> TYPE: DNA
<213> ORGANISM: Mycobacterium tuberculosis

<400> SEQUENCE: 224
gtggtgtctt atgttgttgc gttgccggag gtgatgtccg ccgcggccac agacgtggct 60
tcgattggtt cggtggtcgc gacggcgagc cagggtgtcg cgggtgccac cacgacggta 120
ttagccgctg ccgaggacga ggtgtcagcc gcgatcgcgg ctttgttttc cggccatggt 180
caggactatc aagctcttag cgcacagctt gcggtgtttc atgagcggtt tgtgcaggca 240
ttgacaggcg cggccaaggg gtatgccgcc gccgagctgg ccaacgcttc gctgttgcag 300
agtgaattcg ccagcggtat cgggaacggt tttgccacga ttcaccagga aattcagcgg 360
gcccccacgg cgctggccgc cggattcacg caggttccgc ctttcgcggc ggcgcaggca 420
gggatcttca ccggcacgcc gtcaggggct gccggattcg acatcgcttc gctgtggccg 480
gtgaaacccc tgctgagttt gtctgcgctc gaaactcact ttgcaatccc aaacaatcca 540
cttttagcgc tcattgccag cgacataccg ccgctgtcgt ggtttcttgg caactcccca 600
ccgccgttgc tgaactcgct gctgggacag acggtccagt acaccaccta tgacgggatg 660
agcgtcgtgc agatcacgcc ggctcatcca accggcgaat acgtggttgc cattcacggc 720
ggcgcgttta tcctgccgcc gtcaatcttc cactggctca actactcggt gacggcttac 780
cagaccggcg cgaccgtgca agtgccgatt tacccgttgg tgcaggaagg aggcactgcc 840
gggacggtag taccggcgat ggccgggctc atctccacgc aaatcgcgca acacggggtc 900
tccaacgtca gcgtggtcgg ggactccgcg ggcggcaacc tcgcactggc ggccgcccaa 960

-continued

```
tacatggtga gccagggcaa cccagtaccg tcgtccatgg tgttgctgtc cccgtggctc   1020

gatgtgggga cctggcagat cagccaggcg tgggcaggca atcttgcggt caacgacccg   1080

ctggtcagtc cgctgtatgg gtcgctgaac ggtcttccgc cgacgtatgt ctattcgggc   1140

tcgcttgatc cgctcgcaca acaagcggtt gtcctcgagc acacagccgt agtccaagga   1200

gcgccgttca gcttcgtact ggccccctgg caaatccacg actggatact gctcaccccc   1260

tggggtttgc tgtcctggcc gcagattaac cagcaactcg gtatcgccgc c            1311
```

<210> SEQ ID NO 225
<211> LENGTH: 527
<212> TYPE: PRT
<213> ORGANISM: Mycobacterium tuberculosis

<400> SEQUENCE: 225

```
Met Arg Ser Trp Trp Gly Trp Gly Thr Val Glu Asp Ala Leu Ser Asp
1               5                   10                  15

Gln Glu Thr Gln Ala Leu Gln Ser Arg Val Ala Ala Leu Val Ser Gly
            20                  25                  30

His Asp Leu Ser Asp His Pro Pro Pro Asp Leu Thr Ala Leu Gly Leu
        35                  40                  45

Ala Ala Pro Arg Val Ser Pro Pro Ala Ser Leu Ala Ala Leu Cys Ser
    50                  55                  60

Ser Asp Leu Val Asp Arg Ala Gly His Ala Arg Gly Lys Ala Tyr Arg
65                  70                  75                  80

Asp Ile Ala Arg Asn Leu Gln Gly Gln Leu Asp His Leu Pro Asp Leu
                85                  90                  95

Ile Ala Arg Pro Arg Ser Glu Gln Asp Val Ile Asp Val Leu Asp Trp
            100                 105                 110

Cys Ala Arg Glu Gly Ile Ala Val Ile Pro Tyr Gly Gly Gly Ser Ser
        115                 120                 125

Val Val Gly Gly Val Glu Pro Arg Phe Asp Glu Pro Val Val Thr Val
    130                 135                 140

Asp Val Thr Ala Met Ser Ala Val Leu Glu Ile Asp Arg Val Ser Arg
145                 150                 155                 160

Ala Ala Arg Ile Gln Ala Gly Ala Phe Gly Pro Ser Ile Glu His Gln
                165                 170                 175

Leu Arg Pro His Asp Leu Thr Leu Arg His Phe Pro Gln Ser Phe Gly
            180                 185                 190

Phe Ser Thr Leu Gly Gly Trp Leu Ala Thr Arg Ser Gly Gly His Phe
        195                 200                 205

Ala Thr Leu Tyr Thr His Ile Asp Asp Leu Thr Glu Ser Leu Arg Ile
    210                 215                 220

Val Thr Pro Val Gly Ile Ser Glu Ser Arg Arg Leu Pro Gly Ser Gly
225                 230                 235                 240

Ala Gly Pro Ser Pro Asp Arg Leu Phe Leu Gly Ser Glu Gly Thr Leu
                245                 250                 255

Gly Ile Ile Thr Glu Ala Trp Met Arg Leu Gln His Arg Pro Arg Trp
            260                 265                 270

Gln Val Thr Val Ser Val Val Phe Asp Asp Trp Ala Ala Ala Val Ala
        275                 280                 285

Ala Thr Arg Thr Ile Ala Gln Ala Gly Leu Tyr Pro Ala Asn Cys Arg
    290                 295                 300

Leu Leu Asp Pro Ala Glu Ala Leu Leu Asn Ala Gly Thr Ser Val Gly
305                 310                 315                 320
```

```
Gly Gly Leu Leu Val Leu Ala Phe Glu Ser Ala Asp His Pro Ile Asp
                325                 330                 335

Pro Trp Leu His Arg Ala Val Ala Ile Thr Ala Glu His Gly Gly Thr
            340                 345                 350

Val Thr Ala Gln Arg Ser Arg Gly Thr Thr Ser Asp Ala Thr Glu His
        355                 360                 365

Asn Ala Ala Ala Asn Trp Arg Ser Ala Phe Leu Arg Met Pro Tyr Gln
    370                 375                 380

Arg Asp Ala Leu Val Arg Arg Gly Val Ile Ala Glu Thr Phe Glu Thr
385                 390                 395                 400

Ala Cys Thr Trp Asp Gly Phe Asp Thr Leu His Ala Ala Val Thr Asp
                405                 410                 415

Ala Ala Arg Thr Ala Ile Trp Lys Val Cys Gly Thr Gly Val Val Thr
            420                 425                 430

Cys Arg Phe Thr His Val Tyr Pro Asp Gly Pro Ala Pro Tyr Tyr Gly
        435                 440                 445

Ile Tyr Ala Gly Gly Arg Trp Gly Ser Leu Asp Ala Gln Trp Asp Glu
    450                 455                 460

Ile Lys Ala Ala Val Ser Glu Ala Ile Ser Ala Ser Gly Gly Thr Ile
465                 470                 475                 480

Thr His His His Ala Val Gly Arg Asp His Arg Ala Trp Tyr Asp Arg
                485                 490                 495

Gln Arg Pro Asp Pro Phe Ala Ala Ala Leu Arg Ala Ala Lys Ser Ala
            500                 505                 510

Leu Asp Pro Ala Gly Ile Leu Asn Pro Gly Val Leu Leu Gly Arg
        515                 520                 525
```

<210> SEQ ID NO 226
<211> LENGTH: 1581
<212> TYPE: DNA
<213> ORGANISM: Mycobacterium tuberculosis

<400> SEQUENCE: 226

```
atgcgttcgt ggtggggttg gggcacagtc gaggacgcgc tctccgatca ggagacgcaa      60

gcgctacagt cgcgagtcgc ggcactggtg tccggccatg acctgagcga ccacccgccg     120

ccggacctga ccgcgctcgg tttggcggcc ccacgggtca gcccgccggc atcgctggcc     180

gcgctctgct caagcgatct cgtcgatcgg gccggacacg cgcgcggcaa agcgtatcgc     240

gacatcgcac gcaacctgca gggccagctc gaccacctgc ccgacctcat cgcccgaccc     300

cgcagcgagc aggacgtgat cgacgtgctg gattggtgtg cgcgcgaggg gattgcggtc     360

atcccatacg gtggtggcag ctcggtggtt ggcggtgtcg agccgcgctt cgatgagccg     420

gtggtcacgg tcgacgtcac tgccatgagc gcggtgcttg agattgaccg tgtcagccgt     480

gccgcgcgca tccaggcggg tgcgttcggc ccctcgatcg agcatcagct tcgcccacac     540

gatttgacac tgcgccattt cccgcagtcc ttcggcttct cgactctcgg tggctggttg     600

gccacccgct ccggcggaca cttcgccacg ctctataccc atatcgacga cttgaccgaa     660

tcgctgcgga ttgtcacccc ggtggggatc agcgagtccc ggcggctgcc cggaagcggt     720

gccggaccat ccccggaccg gttgttcctc gggtccgagg ggacgcttgg catcatcacc     780

gaggcgtgga tgcggctgca acaccgtccg cgatggcagg tcacggtgtc cgtggtgttt     840

gacgactggg ccgccgcggt cgccgcgacc cggacgatcg ctcaggcggg gctgtacccg     900

gccaactgcc ggctgttgga tccggccgag gcgttgctga atgccggcac gtccgttggt     960
```

```
ggcgggctgt tggtgttggc gttcgagtct gccgaccacc cgatagaccc gtggctgcac   1020

cgggcggtgg cgatcaccgc cgaacacggc ggcacggtga ccgcgcaacg tagccgcgga   1080

actacaagcg acgcaacgga acacaacgca gccgcgaact ggcgctcggc gtttctgcgc   1140

atgccgtatc aacgagacgc gctggttcgc cgcggagtta tcgccgaaac attcgaaacc   1200

gcttgcacct gggacggatt cgatactcta catgccgcgg tgaccgatgc cgctcggacc   1260

gcgatctgga aggtatgcgg gaccggagta gtgacctgtc gattcaccca tgtctacccg   1320

gacggcccgg ctccttacta cggcatctat gccggcgggc gctgggggtc gctcgacgcg   1380

cagtgggacg agatcaaggc tgccgtgtcc gaggcgatca gcgccagtgg cggtaccatc   1440

acccaccacc atgcggtcgg tcgcgaccac cgcgcttggt atgaccggca gcgtcccgac   1500

ccgttcgcgg cggccctgcg ggcggcgaag tccgcactcg acccggccgg gatcctcaac   1560

ccaggggtgt tgctcggtcg c                                             1581
```

<210> SEQ ID NO 227
<211> LENGTH: 145
<212> TYPE: PRT
<213> ORGANISM: Mycobacterium tuberculosis

<400> SEQUENCE: 227

```
Met Thr Ser Phe Ala His Pro Gly Thr Arg Gly Leu Ser Thr Val Phe
1               5                   10                  15

Gly Leu Met Met Val Gly Ser Ala Ala Val Gly Ser His Gly Leu Ala
            20                  25                  30

Val Val Val Gly Leu Ala Ala Val Ile Ala Val Gly Val Ala Ala Val
        35                  40                  45

Phe Arg Leu Ala Ala Thr Leu Ala Val Val Leu Ser Val Val Met Ile
    50                  55                  60

Val Val Ser Gly Pro Thr His Val Leu Ala Ala Leu Ser Gly Phe Cys
65                  70                  75                  80

Ala Ala Val Tyr Leu Val Cys Arg Tyr Gly Ala Gly Val Val Ala Gly
                85                  90                  95

Ser Trp Pro Thr Thr Val Ala Ala Val Gly Phe Thr Phe Ala Gly Leu
            100                 105                 110

Ala Ala Thr Ser Phe Pro Leu Gln Val Pro Trp Leu Pro Leu Ala Ala
        115                 120                 125

Pro Leu Ala Val Leu Ala Thr Tyr Val Leu Ala Thr Arg Pro Phe Ser
    130                 135                 140

Arg
145
```

<210> SEQ ID NO 228
<211> LENGTH: 435
<212> TYPE: DNA
<213> ORGANISM: Mycobacterium tuberculosis

<400> SEQUENCE: 228

```
atgacctcgt ttgcgcaccc gggtactcgt gggctctcca cggtgttcgg actgatgatg     60

gtggggtcgg ccgctgtggg atcgcacggg ctggctgttg tcgtggggct tgccgcggtg    120

attgcggtag gggtggcggc ggtgtttcgc ctggcggcaa cgcttgccgt ggtgttgtcg    180

gtggtgatga tcgtggtgtc cggcccgacg catgtgcttg ccgcattgtc ggggttttgc    240

gccgccgtct acctggtgtg ccgatacggg gccggtgttg tcgccgggag ctggccgacg    300

accgttgccg ccgttggttt cacgttcgct gggttggctg cgacgtcgtt cccgctgcaa    360
```

gtgccatggc tgccgttggc ggcaccgttg gccgtgttgg ctacctacgt gctggccacc 420
cgtccgttct cgagg 435

<210> SEQ ID NO 229
<211> LENGTH: 119
<212> TYPE: PRT
<213> ORGANISM: Mycobacterium tuberculosis

<400> SEQUENCE: 229

Leu Arg Leu Gly Ala Gly Phe Arg Lys Pro Val Pro Thr Leu Leu Leu
1 5 10 15

Glu His Arg Ser Arg Lys Ser Gly Lys Asn Phe Val Ala Pro Leu Leu
20 25 30

Tyr Ile Thr Asp Arg Asn Asn Val Ile Val Val Ala Ser Ala Leu Gly
35 40 45

Gln Ala Glu Asn Pro Gln Trp Tyr Arg Asn Leu Pro Pro Asn Pro Asp
50 55 60

Thr His Ile Gln Ile Gly Ser Asp Arg Arg Pro Val Arg Ala Val Val
65 70 75 80

Ala Ser Ser Asp Glu Arg Ala Arg Leu Trp Pro Arg Pro Val Asp Ala
85 90 95

Tyr Ala Asp Phe Asp Ser Cys Gln Ser Trp Thr Glu Arg Gly Ile Pro
100 105 110

Val Ile Ile Leu Arg Pro Arg
115

<210> SEQ ID NO 230
<211> LENGTH: 357
<212> TYPE: DNA
<213> ORGANISM: Mycobacterium tuberculosis

<400> SEQUENCE: 230
ttgcgactcg gcgccggatt ccgcaaaccg gtgccgacac tgctactcga acaccggagc 60
cgcaagtccg gcaagaactt cgtcgcacca ctgctttaca tcaccgaccg taacaatgtc 120
atcgtcgttg cctctgccct tgggcaggca gaaaacccgc agtggtatcg caacctgccg 180
cccaatcccg acacccacat tcagatcgga tccgatcgcc gcccggtgag agccgtcgtg 240
gccagctcgg acgagcgggc gcgcctatgg ccgcgcccag tagacgccta cgccgacttc 300
gattcttgcc aaagctggac cgagcgtggg attccggtga tcatcttgcg gccacgc 357

<210> SEQ ID NO 231
<211> LENGTH: 108
<212> TYPE: PRT
<213> ORGANISM: Mycobacterium tuberculosis

<400> SEQUENCE: 231

Met Ser Gly Gly Ser Ser Arg Arg Tyr Pro Pro Glu Leu Arg Glu Arg
1 5 10 15

Ala Val Arg Met Val Ala Glu Ile Arg Gly Gln His Asp Ser Glu Trp
20 25 30

Ala Ala Ile Ser Glu Val Ala Arg Leu Leu Gly Val Gly Cys Ala Glu
35 40 45

Thr Val Arg Lys Trp Val Arg Gln Ala Gln Val Asp Ala Gly Ala Arg
50 55 60

Pro Gly Thr Thr Thr Glu Glu Ser Ala Glu Leu Lys Arg Leu Arg Arg
65 70 75 80

Asp Asn Ala Glu Leu Arg Arg Ala Asn Ala Ile Leu Lys Thr Ala Ser 85 90 95

Ala Phe Phe Ala Ala Glu Leu Asp Arg Pro Ala Arg
100 105

<210> SEQ ID NO 232
<211> LENGTH: 324
<212> TYPE: DNA
<213> ORGANISM: Mycobacterium tuberculosis

<400> SEQUENCE: 232
atgtcaggtg gttcatcgag gaggtacccg ccggagctgc gtgagcgggc ggtgcggatg 60
gtcgcagaga tccgcggtca gcacgattcg gagtgggcag cgatcagtga ggtcgcccgt 120
ctacttggtg ttggctgcgc ggagacggtg cgtaagtggg tgcgccaggc gcaggtcgat 180
gccggcgcac ggcccgggac cacgaccgaa gaatccgctg agctgaagcg cttgcggcgg 240
gacaacgccg aattgcgaag ggcgaacgcg attttaaaga ccgcgtcggc tttcttcgcg 300
gccgagctcg accggccagc acgc 324

<210> SEQ ID NO 233
<211> LENGTH: 133
<212> TYPE: PRT
<213> ORGANISM: Mycobacterium tuberculosis

<400> SEQUENCE: 233

Met Pro Asp Val Asp Trp Asn Met Leu Arg Gly Asn Ala Thr Gln Ala
1 5 10 15

Ala Ala Gly Ala Tyr Val Pro Tyr Ser Arg Phe Ala Val Gly Ala Ala
20 25 30

Ala Leu Val Asp Asp Gly Arg Val Val Thr Gly Cys Asn Val Glu Asn
35 40 45

Val Ser Tyr Gly Leu Thr Leu Cys Ala Glu Cys Ala Val Val Cys Ala
50 55 60

Leu His Ser Thr Gly Gly Gly Arg Leu Leu Ala Leu Ala Cys Val Asp
65 70 75 80

Gly His Gly Ser Val Leu Met Pro Cys Gly Arg Cys Arg Gln Val Leu
85 90 95

Leu Glu His Gly Gly Ser Glu Leu Leu Ile Asp His Pro Val Arg Pro
100 105 110

Arg Arg Leu Gly Asp Leu Leu Pro Asp Ala Phe Gly Leu Asp Asp Leu
115 120 125

Pro Arg Glu Arg Arg
130

<210> SEQ ID NO 234
<211> LENGTH: 399
<212> TYPE: DNA
<213> ORGANISM: Mycobacterium tuberculosis

<400> SEQUENCE: 234
atgcctgatg tcgattggaa tatgctgcgg ggcaatgcaa cccaggcagc agccggagcc 60
tatgtgccgt attcgcggtt tgcggtgggt gcggccgcac tggtcgacga tggtcgcgtg 120
gtgaccggat gcaacgtgga aaacgtctcg tatggcttga ctttgtgcgc cgaatgtgcg 180
gtggtgtgcg ccctgcattc gaccggcggc ggccggctgc tcgcgctggc ctgcgtcgac 240
ggccatggat ccgtgctgat gccgtgcggg cgatgccgtc aggtgctgct cgaacacggg 300
ggttccgagc tactgatcga ccatccggtg cgaccccgcc ggctcggcga cctgctgccc 360

-continued gacgccttcg gcctcgacga cctcccccgg gaacgccgg 399

<210> SEQ ID NO 235
<211> LENGTH: 204
<212> TYPE: PRT
<213> ORGANISM: Mycobacterium tuberculosis

<400> SEQUENCE: 235

Met Ser Val Gln Thr Asp Pro Ala Leu Arg Glu His Pro Asn Arg Val
1 5 10 15

Asp Trp Asn Ala Arg Tyr Glu Arg Ala Gly Ser Ala His Ala Pro Phe
20 25 30

Ala Pro Val Pro Trp Leu Ala Asp Val Leu Arg Ala Gly Val Pro Asp
35 40 45

Gly Pro Val Leu Glu Leu Ala Ser Gly Arg Ser Gly Thr Ala Leu Ala
50 55 60

Leu Ala Ala His Gly Arg Gln Val Thr Ala Ile Asp Val Ser Asp Val
65 70 75 80

Ala Leu Leu Gln Leu Asp Ser Glu Ala Val Arg Arg Gly Val Ala Asp
85 90 95

Arg Leu Asn Leu Val Gln Ala Asp Leu Gly Cys Trp Glu Pro Gly Glu
100 105 110

Thr Arg Phe Ala Leu Val Leu Ser Arg Leu Phe Trp Asp Ala Ala Ile
115 120 125

Phe His Arg Ala Cys Glu Ala Val Met Pro Gly Gly Val Leu Ala Trp
130 135 140

Glu Ser Leu Ala Leu Ser Gly Ala Glu Ala Gly Thr Ala Ser Ala Lys
145 150 155 160

Arg Arg Val Lys Pro Gly Glu Pro Ala Cys Leu Leu Pro Ala Asp Phe
165 170 175

Thr Val Val His Glu Gly Gln Gly Asn Cys Asp Ser Ala Pro Ser Arg
180 185 190

Ile Met Ile Ala Arg Arg Ser Pro Leu Pro Gly Ala
195 200

<210> SEQ ID NO 236
<211> LENGTH: 612
<212> TYPE: DNA
<213> ORGANISM: Mycobacterium tuberculosis

<400> SEQUENCE: 236
atgagcgtgc agacggatcc ggcgctgcgg gagcacccca accgcgtcga ctggaacgcg 60
cgatacgaac gcgcgggttc ggcgcacgcg ccgtttgccc cggtgccttg gctcgccgat 120
gtcctcagag caggcgttcc ggacggtccc gttctggagt tagccagcgg tcgatcgggt 180
accgcactgg cgttggccgc ccacggccgc caggtcaccg caatcgatgt gtccgatgtc 240
gcgctgctgc agctggacag cgaggccgtg cgtcgaggcg tggccgatcg gctcaacctc 300
gtgcaggccg acttgggctg ctgggaaccc ggcgagacgc gtttcgcgct ggtgctcagc 360
aggctctttt gggatgcggc gatatttcac cgcgcctgtg aggcggtgat gccaggcggc 420
gtattggcat gggagtcgct ggctctcagt ggcgccgagg cgggcacagc cagcgcgaag 480
cgacgtgtca agccgggaga gccagcgtgt ctgcttcctg ccgacttcac cgttgtacac 540
gaggggcagg gtaactgcga ttcggcgccg tcgcggatca tgatcgcgcg gcgctcaccg 600
ttgccagggg ca 612

<210> SEQ ID NO 237
<211> LENGTH: 264
<212> TYPE: PRT
<213> ORGANISM: Mycobacterium tuberculosis

<400> SEQUENCE: 237

```
Val Leu Ala Ser Cys Pro Ala Arg Ser Gly Ala Ala Val Ala Asp Ala
1               5                   10                  15

Ile Lys Ser Ala Val Gly Val Gln Pro Ser Gly Val Glu His Lys Thr
            20                  25                  30

Leu Arg Arg Met Asp Leu Val Arg Tyr Leu Ala Gly Gly His Thr Thr
        35                  40                  45

Tyr Pro Pro Glu Gly Phe Val Ala Gly Ser Asp Val Ile Gly Thr Thr
    50                  55                  60

Asn Pro Ala Ala Ala Gln Ala Ile Val Ala Ala Ile Gly Thr Trp Pro
65                  70                  75                  80

Pro Ala Ala Gly Arg Ala Ser Ala Leu Ile Asp Ser Leu Gly Gly Ala
                85                  90                  95

Val Gly Asp Met Asp Pro Glu Gly Ser Ala Phe Pro Trp Cys Arg Gln
            100                 105                 110

Ser Ala Val Val Gln Trp Tyr Val Asn Thr Pro Ser Asp Gly Gln Val
        115                 120                 125

Ala Thr Ala Asn Lys Trp Leu Ser Asp Ala His His Ala Val Gln His
    130                 135                 140

Phe Ser Val Gly Gly Tyr Val Asn Tyr Leu Glu Ala Asn Ala Ala Ala
145                 150                 155                 160

Ser Gln Tyr Phe Gly Ala Asn Leu Ser Arg Leu Thr Thr Val Arg Arg
                165                 170                 175

Lys Tyr Asp Pro Asp Arg Ile Met Tyr Ser Gly Leu Asp Phe Ser Thr
            180                 185                 190

Arg Gln Val Ala Glu Arg Leu Leu Pro Ala Leu Gly Phe Arg Val Arg
        195                 200                 205

Phe Gly Val Leu Val Ile Arg Cys Ala Leu Cys Thr Asp Thr Val Lys
    210                 215                 220

Arg Leu Gly Thr Leu Pro Asn Leu Thr Trp Ser Arg Leu Lys Val Asn
225                 230                 235                 240

Val Ala Val Thr Gln Glu Gln Ala Gly Val Met Asp Leu Pro Ala Leu
                245                 250                 255

Pro Val Arg Arg Thr Pro Arg Arg
            260
```

<210> SEQ ID NO 238
<211> LENGTH: 792
<212> TYPE: DNA
<213> ORGANISM: Mycobacterium tuberculosis

<400> SEQUENCE: 238

```
gtgctggcga gctgcccggc gcggtccggc gcggctgtcg cggatgcgat caagtccgcg     60
gttggagtgc aacccagtgg agttgagcac aagacgctgc gccgtatgga cctggtgagg    120
tatctggccg gcggccatac gacctatccg ccggagggct tcgtggctgg atccgatgtc    180
atcgggacga cgaatccggc cgcggcccaa gccatcgtcg ccgccatcgg aacatggcca    240
cccgctgcgg gccgcgcgtc ggctctgatc gattcgctgg gcggcgcggt gggcgacatg    300
gacccggagg gctcggcatt tccctggtgc cgccagtccg ctgtggtgca gtggtatgtc    360
aacaccccca gcgacggcca ggtggcgacg gccaacaaat ggctgagcga cgcacaccac    420
```

```
gcggtgcaac acttttcggt cggcggctat gtcaactacc tggaggccaa cgccgcggcg    480

tcacaatact tcggcgcgaa cctgtcgcgg ctgaccacag tgcggcgcaa gtacgatccc    540

gaccggatca tgtactcggg tctggatttc tctaccagac aggtcgctga acgactttta    600

cccgctctcg gctttcgagt gaggttcggg gttttggtaa tcaggtgcgc actgtgcact    660

gacactgtga aacgcttggg aactttgccc aaccttacgt ggtcgcgctt aaaagtgaac    720

gtcgcagtga cccaagaaca ggctggggtc atggatttgc cggcgctgcc ggttcggcgc    780

acgccgcggc gg                                                        792


<210> SEQ ID NO 239
<211> LENGTH: 123
<212> TYPE: PRT
<213> ORGANISM: Mycobacterium tuberculosis

<400> SEQUENCE: 239

Val Ser Ala Ala Thr Asp Leu Tyr Ala Val His Gln Ala Leu Ala Gly
1               5                   10                  15

Glu Ser Arg Ala Ile Pro Thr Gly Ser Cys Pro Thr Val Gly Val Ala
            20                  25                  30

Gly Leu Thr Leu Gly Gly Gly Leu Gly Ala Asp Ser Arg His Ala Gly
        35                  40                  45

Leu Thr Cys Asp Ala Leu Lys Ser Ala Thr Val Val Leu Pro Gly Gly
    50                  55                  60

Asp Ala Val Ser Ala Ser Ala Asp Asp His Ala Glu Leu Phe Trp Ala
65                  70                  75                  80

Leu Arg Gly Gly Gly Gly Gly Asn Phe Gly Val Thr Thr Ser Met Thr
                85                  90                  95

Phe Ala Arg Phe Pro Thr Ala Asp Cys Asp Val Val Arg Val Asp Phe
            100                 105                 110

Ala Pro Ser Ala Ala Ala Gln Val Leu Val Gly
        115                 120


<210> SEQ ID NO 240
<211> LENGTH: 369
<212> TYPE: DNA
<213> ORGANISM: Mycobacterium tuberculosis

<400> SEQUENCE: 240

gtgtcggccg cgaccgatct ctatgcggtc catcaagcgt tggccggtga gagccgggcg     60

attccgaccg gcagctgccc gaccgtgggt gtggcgggtt tgaccctggg cggcgggtta    120

ggcgccgatt ctcgccatgc ggggttgacc tgcgatgcgc tcaagtcggc gacggtggtg    180

ttgcccggcg gtgatgcggt gagcgcgtct gccgacgacc acgcggagct gttctgggcg    240

cttcgtggcg gcgggggcgg caacttcggg gtgacgacat cgatgacgtt cgcgaggttc    300

cccaccgcgg actgcgatgt cgtccgtgtc gatttcgcgc cgtctgcggc cgcgcaggtg    360

ctggtcggc                                                            369


<210> SEQ ID NO 241
<211> LENGTH: 213
<212> TYPE: PRT
<213> ORGANISM: Mycobacterium tuberculosis

<400> SEQUENCE: 241

Met Arg Arg Arg Ala Met Thr Lys Met Asp Glu Ala Ser Asn Pro Cys
1               5                   10                  15

Gly Gly Asp Ile Glu Ala Glu Met Cys Gln Leu Met Arg Glu Gln Pro
```

-continued

```
            20                  25                  30

Pro Ala Glu Gly Val Val Asp Arg Val Ala Leu Gln Arg His Arg Asn
        35                  40                  45

Val Ala Leu Ile Thr Leu Ser His Pro Gln Ala Gln Asn Ala Leu Asn
    50                  55                  60

Leu Ala Ser Trp Arg Arg Leu Lys Arg Leu Leu Asp Asp Leu Ala Gly
65                  70                  75                  80

Glu Ser Gly Leu Arg Ala Val Val Leu Arg Gly Ala Gly Asp Lys Ala
                85                  90                  95

Phe Ala Ala Gly Ala Asp Ile Lys Glu Phe Pro Asn Thr Arg Met Ser
            100                 105                 110

Ala Ala Asp Ala Ala Glu Tyr Asn Glu Ser Leu Ala Val Cys Leu Arg
        115                 120                 125

Ala Leu Thr Thr Met Pro Ile Pro Val Ile Ala Ala Val Arg Gly Leu
    130                 135                 140

Ala Val Gly Gly Gly Cys Glu Leu Ala Thr Ala Cys Asp Val Cys Ile
145                 150                 155                 160

Ala Thr Asp Asp Ala Arg Phe Gly Ile Pro Leu Gly Lys Leu Gly Val
                165                 170                 175

Thr Thr Gly Phe Thr Glu Ala Asp Thr Val Ala Arg Leu Ile Gly Pro
            180                 185                 190

Ala Ala Leu Lys Tyr Leu Leu Phe Ser Gly Glu Leu Ile Gly Ile Glu
        195                 200                 205

Glu Ala Ala Arg Trp
    210


<210> SEQ ID NO 242
<211> LENGTH: 639
<212> TYPE: DNA
<213> ORGANISM: Mycobacterium tuberculosis

<400> SEQUENCE: 242

atgaggcggc gtgcaatgac gaagatggac gaggctagca atccgtgcgg cggggacatc      60

gaagctgaga tgtgccagtt gatgcgcgag caaccacccg ccgaaggcgt cgtcgatcgt     120

gtcgcgctgc aacgccatcg aaacgttgcg ttgatcacgc tgagccatcc gcaggcgcag     180

aacgcactca acctggcgag ctggcgtcgg ctgaagcggc tgctggacga tctcgccggc     240

gaatcggggc tgcgggcggt ggtgctgcgg ggcgccggtg acaaggcgtt cgccgcgggt     300

gccgacatca aggagtttcc gaacacccgc atgagcgccg cggacgccgc ggagtacaac     360

gagagcctgg ccgtctgcct gagggcgttg accacgatgc cgatcccagt catcgcggcg     420

gtccgggggc tcgccgtcgg tggcggctgt gagctggcga cggcctgcga tgtgtgcatc     480

gcgaccgacg acgcgcgctt cggcatcccg ctgggcaagc tcggcgtcac gacgggcttc     540

accgaggcgg acaccgtcgc gcgcctcatc ggtccggcgg cgctgaagta tctgttgttc     600

agcggagaac tgatcggcat tgaggaagcc gcccgctgg                            639


<210> SEQ ID NO 243
<211> LENGTH: 467
<212> TYPE: PRT
<213> ORGANISM: Mycobacterium tuberculosis

<400> SEQUENCE: 243

Val Ala Asp Arg Leu Asn Val Ala Glu Arg Leu Ala Glu Gly Arg Pro
1               5                   10                  15

Ala Ala Glu His Thr Gln Ser Tyr Val Arg Ala Cys His Leu Val Gly
```

```
            20                  25                  30

Tyr Gln His Pro Asp Leu Thr Ala Tyr Pro Ala Gln Ile His Asp Trp
        35                  40                  45

Tyr Gly Ser Glu Asp Gly Leu Asp Leu His Ala Leu Asp Ala Asp Cys
    50                  55                  60

Ala Gln Leu Arg Ala Ala Ala Ser Val Leu Met Glu Ala Leu Arg Met
65                  70                  75                  80

Glu Arg Ser Gln Val Ala Val Leu Ala Ala Ala Trp Thr Gly Ser Gly
                85                  90                  95

Ala Asp Ala Ala Val His Phe Val Gln Arg His Cys Glu Thr Gly Asn
            100                 105                 110

Ser Val Val Thr Glu Val Arg Ala Ala Ala Gln Arg Cys Glu Ser Leu
        115                 120                 125

Arg Asp Asn Leu Trp Gln Leu Val Asp Ser Lys Val Ala Thr Ala Ile
    130                 135                 140

Ala Ile Asp Glu Arg Ala Leu Ala Gln Arg Pro Ala Trp Leu Ala Ala
145                 150                 155                 160

Ala Glu Ala Leu Thr Thr Glu Gly Ala Asp Arg Pro Thr Ala Val Glu
                165                 170                 175

Val Val Arg Gln Gln Ile Gln Pro Tyr Val Asp Asp Asp Val Arg Asn
            180                 185                 190

Asp Trp Leu Thr Thr Met Arg Ser Thr Thr Ala Gly Val Ala Ala Ser
        195                 200                 205

Tyr Asp Ala Val Thr Asp Gln Leu Ala Ser Ala Pro Arg Ala His Phe
    210                 215                 220

Glu Ile Pro Asp Asp Leu Gly Pro Gly Arg Gln Pro Ser Pro Ala Ser
225                 230                 235                 240

Val Pro Ala Gln Pro Ser Ala Thr Ala Ala Ile Thr Pro Ala Ala Ala
                245                 250                 255

Leu Pro Pro Pro Asp Pro Val Pro Ala Val Thr Ser Arg Pro Val Thr
            260                 265                 270

Pro Ser Asp Phe Gly Ser Ala Pro Gly Asp Gly Ser Ala Thr Pro Ala
        275                 280                 285

Gly Val Gly Ser Ala Gly Gly Phe Gly Asp Ala Gly Gly Thr Gly Gly
    290                 295                 300

Leu Gly Gly Phe Ala Gly Leu Ala Gly Leu Ala Asn Arg Ile Val Asp
305                 310                 315                 320

Ala Val Asp Ser Leu Leu Gly Ser Val Ala Glu Gln Leu Gly Asp Pro
                325                 330                 335

Leu Ala Ala Asp Asn Pro Pro Gly Ala Val Asp Pro Phe Ala Glu Asp
            340                 345                 350

Ala Ala Asp Asn Ala Asp Asp Gly Asp Asp Ala His Pro Glu Glu Ala
        355                 360                 365

Asp Glu Ala Ala Glu Pro Lys Glu Ala Thr Glu Pro Asp Glu Ala Asp
    370                 375                 380

Glu Val Asp Asp Ala Asp Glu Ser Val Pro Ala Glu Arg Ala Gln Asp
385                 390                 395                 400

Val Ala Glu Glu Ala Thr Leu Pro Pro Val Ala Glu Pro Pro Pro Pro
                405                 410                 415

Ala Ala Pro Pro Val Ala Glu Pro Pro Pro Pro Val Ala Ala Pro Ala
            420                 425                 430

Pro Pro Gly Ala Pro Glu Pro Ala Asn Gly Pro Ser Pro Glu Ala Leu
        435                 440                 445
```

Ser Glu Gly Ala Thr Pro Cys Glu Ile Ala Ala Asp Glu Leu Pro Gln
450 455 460

Ala Gly Pro
465

<210> SEQ ID NO 244
<211> LENGTH: 1401
<212> TYPE: DNA
<213> ORGANISM: Mycobacterium tuberculosis

<400> SEQUENCE: 244
gtggctgacc ggttgaacgt cgctgagcgt ctcgccgagg gcaggcccgc agccgagcac 60
acgcaaagct acgtgcgggc ttgccacctg gtgggctacc aacatcccga cctgaccgcc 120
taccctgccc agatccacga ctggtacggc agcgaagacg gacttgacct gcacgcgctc 180
gacgctgact gcgcgcagct gcgggctgcc gccagtgtgc tcatggaggc gctgcggatg 240
gagcgtagcc aggtcgccgt cttggcagcg gcatggacgg gatcgggggc cgacgcggcg 300
gtgcactttg tgcagcgtca ctgtgagact ggaaattcgg tggtcaccga agtccgtgcc 360
gcggcccaac gctgcgaatc gctgcgcgac aacctctggc agctggtgga ctccaaagtc 420
gcgacggcca ttgcgatcga cgagcgtgcc ctggcgcagc ggccggcatg gttggctgcg 480
gccgaagcgc tcacgacgga gggggcagat cggccgacgg ccgtcgaagt ggttcgccaa 540
cagatacagc cctacgtgga cgacgatgtt cgcaacgact ggctgaccac gatgcgatcg 600
acaacggccg gtgtggcggc gtcgtatgat gcggtcaccg atcagctggc cagcgcgccg 660
cgcgcgcact tcgagattcc ggacgatctc gggcccggtc gccaaccttc tccggcatcg 720
gtgccggctc aaccgagcgc gacggcagcg attacgcccg cggccgctct tcccccgccg 780
gatccggtgc cggccgtgac ctcgcggcca gtgacgccgt cggattttgg atcggcgcca 840
ggtgatggtt ccgcgacgcc ggcgggtgtt ggcagcgccg gtggtttcgg cgatgccggc 900
ggcaccggcg gtctgggcgg gtttgccggg cttgccgggc ttgccaaccg gatcgtcgat 960
gcggtggata gcctgctggg ttcggtggcc gaacagctgg gggatccgtt ggcagctgac 1020
aatccgccgg gtgccgtcga tccgttcgct gaagacgcgg ccgacaacgc tgatgacggc 1080
gacgatgccc acccggaaga ggccgacgag gcagcggagc cgaaggaagc aacagagccc 1140
gacgaagcag acgaggtcga cgacgccgac gaatcggtgc ccgctgaacg tgcccaggat 1200
gtcgccgagg aggccacgct gccgccggtc gccgaaccgc cgccgcctgc cgcgcctccg 1260
gtcgccgaac caccgcctcc ggtcgctgcg ccggcgccgc cgggtgcgcc ggaaccggcg 1320
aatgggcctt cgccggaagc gctgtccgag ggagccaccc cctgtgagat cgccgccgac 1380
gagcttccgc aggcggggcc g 1401

<210> SEQ ID NO 245
<211> LENGTH: 404
<212> TYPE: PRT
<213> ORGANISM: Mycobacterium tuberculosis

<400> SEQUENCE: 245

Val Ser Pro His Arg Ala Val Ile Glu Ala Gly Pro Gly Ala Ile Arg
1 5 10 15

Arg Leu Cys Cys Gly Ala Asp Val Val Ala Asp Thr Ala Val Ser Ala
20 25 30

Ala Ala Leu Ala Ala Ile Asp Asp Gln Val Ala Leu Leu Asp Glu Arg
35 40 45

Pro Val Ala Val Asp Ser Leu Trp Phe Asp Ala Leu Arg Ser Val Ala

-continued

```
    50                  55                  60

Val Asp His Arg Asp Gly Pro Val Val Val His Pro Ser Trp Trp Ser
65                  70                  75                  80

Ala Ala Arg Val Glu Val Val Thr Ala Ala Ala Arg Thr Leu Thr Arg
                85                  90                  95

Asp Val Val Val His Pro Arg Ser Trp Leu Leu Arg Gln Ala Ser Ser
            100                 105                 110

Gly Val Ser Ala Ala Thr Val Val Val Glu Ile Ala Glu Arg Leu Val
        115                 120                 125

Leu Val Ala Gly Ala Glu Val Ala Ala Val Ala Arg Arg Thr Asp Ala
    130                 135                 140

Glu Ser Val Ala Gly Gln Val Gly Ser Val Ile Ala Arg Met Thr Arg
145                 150                 155                 160

Gly Ile Thr Ala Val Val Leu Ile Asp Val Pro Ser Thr Val Ala Gly
                165                 170                 175

Ala Ala Ala Leu Ala Ala Ala Ile Ala Gly Ala Val Arg Gly Thr Gly
            180                 185                 190

Ser Ser Val Val Glu Ile Asp Gly Val Arg Leu Ala Arg Leu Ala Arg
        195                 200                 205

Ala Ala Leu Pro Pro Ser Asp Glu Pro Ala Asp Pro Ala Ala Arg Pro
    210                 215                 220

Ala Thr Arg Ser Arg Val Pro Thr Leu Ala Arg Val Ala Ala Ala Gly
225                 230                 235                 240

Val Ala Leu Ala Leu Leu Ala Pro Ala Ala Val Val Arg His Gly Ala
                245                 250                 255

Thr Thr Leu Gln Arg Pro Pro Thr Thr Leu Leu Val Glu Gly Arg Val
            260                 265                 270

Ala Leu Thr Ile Pro Ala Asp Trp Ser Thr Gln Arg Val Val Ser Gly
        275                 280                 285

Pro Gly Ser Ala Arg Val Gln Val Thr Ser Pro Ala Asp Pro Glu Val
    290                 295                 300

Ala Leu His Val Thr Gln Ser Pro Val Pro Gly Glu Thr Leu Pro Gly
305                 310                 315                 320

Thr Ala Gln Arg Leu Lys Arg Ala Ile Asp Ala Ser Pro Ala Gly Val
                325                 330                 335

Phe Val Asp Phe Asn Pro Ser Asp Ile Arg Ala Gly Arg Pro Ala Val
            340                 345                 350

Thr Tyr Arg Glu Val Arg Ala Gly His Gln Val Arg Trp Thr Ile Leu
        355                 360                 365

Leu Asp Gly Ala Val Arg Ile Ser Val Gly Cys Gln Ser Gly Pro Gly
    370                 375                 380

His Glu Asp Leu Leu Arg Glu Val Cys Ala Gln Ala Val Arg Ser Val
385                 390                 395                 400

His Ala Val Gly
```

<210> SEQ ID NO 246
<211> LENGTH: 1212
<212> TYPE: DNA
<213> ORGANISM: Mycobacterium tuberculosis

<400> SEQUENCE: 246

```
gtgagcccac atcgcgcggt gatcgaggcg ggtccgggtg ccatccgccg attgtgttgt      60

ggcgcagacg tagtcgcgga caccgcagtg tctgccgccg cgctggcggc gatcgacgac     120

caggtagcgc tgctggacga acggccagtc gccgtggatt cgctgtggtt cgacgccctg     180
```

```
cgatcggtgg ccgtcgacca ccgtgacggc ccggtcgtcg tgcacccgtc gtggtggtcg    240

gcggctcggg tcgaggtggt caccgcagcc gcacgcacgc tgacccgcga tgtcgtcgtg    300

cacccgcggt cgtggctgct gaggcaggcg tcctcggggg tttcggccgc aacggtggtg    360

gtggagatcg cggagcgact ggtgttggtg gccggcgccg aggtcgccgc ggtggcccgc    420

cgcacggacg ccgagtccgt tgccggccag gtaggcagtg tcattgcgcg gatgacgcgg    480

ggtattaccg cggtggtgct gatcgacgtg cccagtacgg tcgccggggc ggcagcgctc    540

gcggcggcaa tcgccggtgc ggtgcggggt accggtagca gcgtggtcga gatcgacggc    600

gtgcggctgg cgcggttggc cagggccgcc ctgccgcctt ccgacgagcc cgccgatccg    660

gcggcgcggc ctgccacccg ctctcgggtc ccgacacttg cccgggttgc ggccgccggt    720

gtcgccttgg cgttactggc gccggctgcc gtggtccgcc acggtgcgac aaccctgcaa    780

agaccaccga cgacgcttct ggtagagggc cgggtggcgc tgacgattcc ggcggactgg    840

tccacgcagc gggtggtctc cggtcccggt tcggcgcggg tacaggtcac ttcaccggcc    900

gatcccgagg tggcgttgca cgtcacacaa tcaccggttc ccggtgagac gctgcctggc    960

accgcgcagc ggttgaagcg ggcgatcgac gcgtcaccgg ccggggtatt cgtcgacttc   1020

aacccctccg atatcagagc cggccggccc gcggtgacct atcgagaggt ccgcgccggg   1080

catcaggtgc ggtggacgat tctgctcgac ggagcggtcc ggatcagcgt cggctgccag   1140

agcgggcccg gccatgaaga cctcctcagg gaggtgtgtg cgcaagccgt acggtccgtc   1200

cacgccgttg gt                                                       1212
```

<210> SEQ ID NO 247
<211> LENGTH: 1236
<212> TYPE: PRT
<213> ORGANISM: Mycobacterium tuberculosis

<400> SEQUENCE: 247

```
Met Asn Ser Gly Pro Ala Cys Ala Thr Ala Asp Ile Leu Val Ala Pro
1               5                   10                  15

Pro Pro Glu Leu Arg Arg Ser Glu Pro Ser Ser Leu Leu Ile Arg Leu
            20                  25                  30

Leu Pro Val Val Met Ser Val Ala Thr Val Gly Val Met Val Thr Val
        35                  40                  45

Phe Leu Pro Gly Ser Pro Ala Thr Arg His Pro Thr Phe Leu Ala Phe
    50                  55                  60

Pro Met Met Met Leu Val Ser Leu Val Val Thr Ala Val Thr Gly Arg
65                  70                  75                  80

Gly Arg Arg His Val Ser Gly Ile His Asn Asp Arg Val Asp Tyr Leu
                85                  90                  95

Gly Tyr Leu Ser Val Leu Arg Thr Ser Val Thr Gln Thr Ala Ala Ala
            100                 105                 110

Gln His Val Ser Leu Asn Trp Thr His Pro Asp Pro Ala Thr Leu Trp
        115                 120                 125

Thr Leu Ile Gly Gly Pro Arg Met Trp Glu Arg Arg Pro Gly Ala Ala
    130                 135                 140

Asp Phe Cys Arg Ile Arg Val Gly Val Gly Ser Ala Pro Leu Ala Thr
145                 150                 155                 160

Arg Leu Val Val Gly Gln Leu Pro Pro Ala Gln Arg Ala Asp Pro Val
                165                 170                 175

Thr Arg Ala Ala Leu Arg Cys Phe Leu Ala Ala His Ala Thr Ile Ala
            180                 185                 190
```

```
Asp Ala Pro Ile Ala Ile Pro Leu Arg Val Gly Gly Pro Ile Ala Ile
        195                 200                 205

Asp Gly Asp Pro Thr Lys Val Arg Gly Leu Leu Arg Ala Met Ile Cys
    210                 215                 220

Gln Leu Ala Val Trp His Ser Pro Glu Glu Leu Leu Ile Ala Gly Val
225                 230                 235                 240

Val Ser Asp Arg Asn Arg Ala His Trp Asp Trp Leu Lys Trp Leu Pro
                245                 250                 255

His Asn Gln His Pro Asn Ala Cys Asp Ala Leu Gly Pro Ala Pro Met
            260                 265                 270

Val Tyr Ser Thr Leu Ala Glu Met Gln Asn Ala Leu Ala Ala Thr Val
        275                 280                 285

Leu Ala His Val Val Ala Ile Val Asp Thr Ala Glu Arg Gly Asn Gly
    290                 295                 300

Ala Ile Thr Gly Val Ile Thr Ile Glu Val Gly Ala Arg Arg Asp Gly
305                 310                 315                 320

Ala Pro Pro Val Val Arg Cys Ala Gly Glu Val Thr Ala Leu Ala Cys
                325                 330                 335

Pro Asp Gln Leu Glu Pro Gln Asp Ala Leu Val Cys Ala Arg Arg Leu
            340                 345                 350

Ala Ala His Arg Val Gly His Ser Gly Arg Thr Phe Ile Arg Gly Ser
        355                 360                 365

Gly Trp Ala Glu Leu Val Gly Ile Gly Asp Val Ala Ala Phe Asp Pro
    370                 375                 380

Ser Thr Leu Trp Arg Asn Val Asn Gln His Asp Arg Leu Arg Val Pro
385                 390                 395                 400

Ile Gly Val Thr Pro Asp Gly Thr Ala Val Gln Leu Asp Ile Lys Glu
                405                 410                 415

Ala Ala Glu Gln Gly Met Gly Pro His Gly Leu Cys Val Gly Ala Thr
            420                 425                 430

Gly Ser Gly Lys Ser Glu Leu Leu Arg Thr Ile Ala Leu Gly Met Met
        435                 440                 445

Ala Arg Asn Ser Pro Glu Val Leu Asn Leu Leu Leu Val Asp Phe Lys
    450                 455                 460

Gly Gly Ala Thr Phe Leu Asp Leu Ala Gly Ala Pro His Val Ala Ala
465                 470                 475                 480

Val Ile Thr Asn Leu Ala Glu Glu Ala Pro Leu Val Ala Arg Met Gln
                485                 490                 495

Asp Ala Leu Ala Gly Glu Met Ser Arg Arg Gln Gln Leu Leu Arg Met
            500                 505                 510

Ala Gly His Leu Val Ser Val Thr Ala Tyr Gln Arg Ala Arg Gln Thr
        515                 520                 525

Gly Ala Gln Leu Pro Cys Leu Pro Ile Leu Phe Ile Val Val Asp Glu
    530                 535                 540

Phe Ser Glu Leu Leu Ser Gln His Pro Glu Phe Val Asp Val Phe Leu
545                 550                 555                 560

Ala Ile Gly Arg Val Gly Arg Ser Leu Gly Met His Leu Leu Leu Ala
                565                 570                 575

Ser Gln Arg Leu Asp Glu Gly Arg Leu Arg Gly Leu Glu Thr His Leu
            580                 585                 590

Ser Tyr Arg Met Cys Leu Lys Thr Trp Ser Ala Ser Glu Ser Arg Asn
        595                 600                 605

Val Leu Gly Thr Gln Asp Ala Tyr Gln Leu Pro Asn Thr Pro Gly Ala
```

-continued

```
    610                 615                 620

Gly Leu Leu Gln Thr Gly Thr Gly Glu Leu Ile Arg Phe Gln Thr Ala
625                 630                 635                 640

Phe Val Ser Gly Pro Leu Arg Arg Ala Ser Pro Ser Ala Val His Pro
                645                 650                 655

Val Ala Pro Pro Ser Val Arg Pro Phe Thr Thr His Ala Ala Ala Pro
            660                 665                 670

Val Thr Ala Gly Pro Val Gly Gly Thr Ala Glu Val Pro Thr Pro Thr
        675                 680                 685

Val Leu His Ala Val Leu Asp Arg Leu Val Gly His Gly Pro Ala Ala
    690                 695                 700

His Gln Val Trp Leu Pro Pro Leu Asp Glu Pro Pro Met Leu Gly Ala
705                 710                 715                 720

Leu Leu Arg Asp Ala Glu Pro Ala Gln Ala Glu Leu Ala Val Pro Ile
                725                 730                 735

Gly Ile Val Asp Arg Pro Phe Glu Gln Ser Arg Val Pro Leu Thr Ile
            740                 745                 750

Asp Leu Ser Gly Ala Ala Gly Asn Val Ala Val Val Gly Ala Pro Gln
        755                 760                 765

Thr Gly Lys Ser Thr Ala Leu Arg Thr Leu Ile Met Ala Leu Ala Ala
    770                 775                 780

Thr His Asp Ala Gly Arg Val Gln Phe Tyr Cys Leu Asp Phe Gly Gly
785                 790                 795                 800

Gly Ala Leu Ala Gln Val Asp Glu Leu Pro His Val Gly Ala Val Ala
                805                 810                 815

Gly Arg Ala Gln Pro Gln Leu Ala Ser Arg Met Leu Ala Glu Leu Glu
            820                 825                 830

Ser Ala Val Arg Phe Arg Glu Ala Phe Phe Arg Asp His Gly Ile Asp
        835                 840                 845

Ser Val Ala Arg Tyr Arg Gln Leu Arg Ala Lys Ser Ala Ala Glu Ser
    850                 855                 860

Phe Ala Asp Ile Phe Leu Val Ile Asp Gly Trp Ala Ser Leu Arg Gln
865                 870                 875                 880

Glu Phe Ala Ala Leu Glu Glu Ser Ile Val Ala Leu Ala Ala Gln Gly
                885                 890                 895

Leu Ser Phe Gly Val His Val Ala Leu Ser Ala Ala Arg Trp Ala Glu
            900                 905                 910

Ile Arg Pro Ser Leu Arg Asp Gln Ile Gly Ser Arg Ile Glu Leu Arg
        915                 920                 925

Leu Ala Asp Pro Ala Asp Ser Glu Leu Asp Arg Arg Gln Ala Gln Arg
    930                 935                 940

Val Pro Val Asp Arg Pro Gly Arg Gly Leu Ser Arg Asp Gly Met His
945                 950                 955                 960

Met Val Ile Ala Leu Pro Asp Leu Asp Gly Val Ala Leu Arg Arg Arg
                965                 970                 975

Ser Gly Asp Pro Val Ala Pro Pro Ile Pro Leu Leu Pro Ala Arg Val
            980                 985                 990

Asp Tyr Asp Ser Val Val Ala Arg  Ala Gly Asp Glu Leu  Gly Ala His
        995                 1000                1005

Ile Leu  Leu Gly Leu Glu Glu  Arg Arg Gly Gln Pro  Val Ala Val
    1010                1015                1020

Asp Phe  Gly Arg His Pro His  Leu Leu Val Leu Gly  Asp Asn Glu
    1025                1030                1035
```

```
Cys Gly  Lys Thr Ala Ala Leu  Arg Thr Leu Cys Arg  Glu Ile Val
    1040                 1045                 1050

Arg Thr  His Thr Ala Ala Arg  Ala Gln Leu Leu Ile  Val Asp Phe
    1055                 1060                 1065

Arg His  Thr Leu Leu Asp Val  Ile Glu Ser Glu His  Met Ser Gly
    1070                 1075                 1080

Tyr Val  Ser Ser Pro Ala Ala  Leu Gly Ala Lys Leu  Ser Ser Leu
    1085                 1090                 1095

Val Asp  Leu Leu Gln Ala Arg  Met Pro Ala Pro Asp  Val Ser Gln
    1100                 1105                 1110

Ala Gln  Leu Arg Ala Arg Ser  Trp Trp Ser Gly Pro  Asp Ile Tyr
    1115                 1120                 1125

Val Val  Val Asp Asp Tyr Asp  Leu Val Ala Val Ser  Ser Gly Asn
    1130                 1135                 1140

Pro Leu  Met Val Leu Leu Glu  Tyr Leu Pro His Ala  Arg Asp Leu
    1145                 1150                 1155

Gly Leu  His Leu Val Val Ala  Arg Arg Ser Gly Gly  Ala Ala Arg
    1160                 1165                 1170

Ala Leu  Phe Glu Pro Val Leu  Ala Ser Leu Arg Asp  Leu Gly Cys
    1175                 1180                 1185

Arg Ala  Leu Leu Met Ser Gly  Arg Pro Asp Glu Gly  Ala Leu Phe
    1190                 1195                 1200

Gly Ser  Ser Arg Pro Met Pro  Leu Pro Pro Gly Arg  Gly Ile Leu
    1205                 1210                 1215

Val Thr  Gly Ala Gly Asp Glu  Gln Leu Val Gln Val  Ala Trp Ser
    1220                 1225                 1230

Pro Pro  Pro
    1235

<210> SEQ ID NO 248
<211> LENGTH: 3708
<212> TYPE: DNA
<213> ORGANISM: Mycobacterium tuberculosis

<400> SEQUENCE: 248
atgaattcag ggccggcgtg cgcgactgcg gacatcctgg ttgccccgcc gcccgagttg     60
cggcggtcgg aaccgtccag cctgctgatt cgcctgctcc cggtcgtcat gtcggtggcg    120
accgtgggtg tcatggtgac ggtgttcttg ccgggctcgc cggccacgcg ccaccccacg    180
tttctggcct tcccaatgat gatgctggtc tcgttggtgg tgactgcggt aaccggacgc    240
ggccggcggc atgtctccgg tatccacaac gaccgtgtcg actacctcgg gtacctgagt    300
gtcttgcgca catctgtcac ccaaacggct gcagcacaac acgtatcact gaactggacg    360
catcccgatc ctgccacctt gtggacattg atcggtggtc cgcgaatgtg ggagcgtcga    420
ccgggtgctg ccgacttctg tcgcatccgt gtcggagttg gatctgcacc gctggccacc    480
cgcttggtgg tcgggcagct tccgccggcg cagcgtgcgg atccggtcac ccgcgccgcg    540
ctgcgctgtt tccttgccgc acacgcgacc attgcggatg cgcccatcgc gatccccttg    600
cgggtcggcg gtccgatcgc catcgacggt gacccgacca aggtccgcgg gctgctgcgg    660
gcgatgatct gccagctggc cgtatggcac tcaccggagg agttgctgat cgccggcgtg    720
gtcagtgacc gcaaccgcgc gcactgggat tggctgaaat ggctgccgca caaccaacat    780
ccgaatgcct gtgatgcctt ggggccagcc ccgatggtgt actcgaccct ggcagagatg    840
caaaatgcgc tagccgcaac ggtattggcc cacgttgttg cgatcgtcga cacggccgaa    900
```

-continued

```
cgtggcaacg gcgcgatcac cggcgtgatc acgatcgagg tgggcgccag acgagacggt    960
gcaccgccgg tggtcagatg tgccggcgaa gtgacagcgc tagcgtgccc ggaccagctg   1020
gagcctcaag acgcgctggt atgcgcccgt cggctggccg ctcaccgggt cgggcactcg   1080
ggtcgcacgt tcatccgtgg ctcgggttgg gcggaactgg tcggcatcgg cgatgtggcc   1140
gctttcgatc cgagcacgtt gtggcgcaac gtaaaccaac atgatcggct ccgtgtcccg   1200
atcggagtca cgcccgacgg taccgccgtg cagctagaca tcaaggaagc cgcggaacag   1260
ggcatgggtc cacacgggct gtgcgtcggc gccaccggat caggcaaatc ggagctgctg   1320
cgtaccatcg cgctggggat gatggcacgc aattcgcccg aagtcctcaa cctccttctg   1380
gtcgacttca agggtggtgc aacatttctc gacctcgcgg gagccccaca tgtagccgcg   1440
gtcatcacca accttgccga ggaagcaccg ctggtcgcac ggatgcaaga cgcattggcc   1500
ggcgagatga gccgccggca acagctgctg cggatggcag gccacttggt cagtgtcacg   1560
gcatatcagc gggcacgcca aacgggtgcg caacttccct gcctgccgat cctgttcatc   1620
gtcgtcgacg agttttccga attgctgagc caacatcccg aattcgtcga cgtgttcctc   1680
gcgatcggtc gggtgggccg gtcgctgggc atgcatttgc tgctggccag tcagcggctc   1740
gacgagggcc gactgcgtgg actggaaacc catctgtcct atcgaatgtg cctgaaaacg   1800
tggtccgcca gtgaatcacg caacgtgctc gggacgcagg acgcatatca actgcccaac   1860
acccccggtg cgggcttgct gcaaacggga accggagagc tgatccgatt tcagaccgcg   1920
ttcgtttccg ggccgcttcg acgggcgagt ccctcagcgg tccacccggt agccccgccg   1980
tcggtgcgac cgttcaccac gcacgctgcg gcgccggtca cagccggtcc cgtcggcggg   2040
acagccgagg tgcccacgcc taccgtcttg catgcggtgc tcgaccggct ggtcggtcat   2100
ggaccggctg cgcatcaagt ctggctaccg ccgctggacg agccaccgat gctgggcgcc   2160
ctactgcgtg acgctgagcc ggcgcaggcc gagctggccg tacccatcgg cattgtcgat   2220
cggccgttcg agcagtcacg ggtgccgctg acgatcgact tgtccggggc cgcaggcaat   2280
gtcgcggtcg taggtgcacc gcaaacgggc aagtcaaccg cgctgcggac gctgatcatg   2340
gcgttggctg ctacccacga tgcgggccgg gtgcagttct attgtttgga cttcggcggc   2400
ggggcgctgg cccaggtgga cgaactgccg catgtgggtg ccgtggccgg cagggcgcag   2460
ccgcagctgg catcgcggat gctcgccgaa ctggagtcgg ccgtgcgatt tcgggaggca   2520
ttcttccgcg accacggcat cgactcggtg gcgcggtacc gccagctgcg agcaaagtcg   2580
gccgctgagt cttttgcgga catatttctt gtcatcgacg gctgggcaag cttacgccag   2640
gagttcgcgg cccttgagga gtcgatcgtt gccctggcag ctcaagggct ttcattcggc   2700
gtacatgtgg cgctatcggc agcacggtgg gcggagatca ggccgtcgct gcgggatcag   2760
atcggcagtc gaatcgagtt acggctggcg gatcccgcgg attccgaatt ggaccgtagg   2820
caggcgcaac gggtgccggt cgacagaccg ggccgtggcc tctcccgcga cgggatgcac   2880
atggtgatcg ccctgcccga cctggatgga gttgcgctac gacgccgaag tggtgatccg   2940
gtggcgcccc cgataccgct actgcccgcg cgcgtggact acgacagcgt cgtggcccga   3000
gccggcgacg aactcggtgc gcacatcttg ctcggcctcg aggaacgtcg aggccagccg   3060
gtggccgtcg atttcggacg ccacccgcac ctgctggtgc tgggcgacaa cgagtgcgga   3120
aagacggccg cgttgcggac cctgtgccgc gagatcgtcc ggacccatac cgccgcgcga   3180
gcccaacttc tcatcgtcga cttccggcac accctgctcg acgtcatcga gtcggaacat   3240
atgagcggct acgtcagctc gccggcggcg ctgggtgcca agctgtcgag tctggtcgac   3300
```

```
ctgctccagg cgcggatgcc cgccccggat gtgagccagg cgcagctgcg agccaggtcc   3360

tggtggtcgg gtccggatat ctatgtcgtg gtcgacgact acgacctggt tgcggtctca   3420

tcgggcaacc cgctgatggt cttgctcgaa tatttgccgc acgcaagaga tctcggttta   3480

cacctggtgg tggcgcggcg cagcgggggt gctgctcggg cgctgttcga gccggtgctt   3540

gccagcctgc gtgacctggg ctgccgggca ctgctgatga gcggacgtcc ggatgaaggc   3600

gcactgttcg ggtcgagccg cccgatgccg ctgccaccgg gccggggcat cctggtcacc   3660

ggtgccggtg acgagcaact ggttcaagtc gcctggagcc cacccccg                 3708


<210> SEQ ID NO 249
<211> LENGTH: 470
<212> TYPE: PRT
<213> ORGANISM: Mycobacterium tuberculosis

<400> SEQUENCE: 249

Val Pro Ser Pro Ala Thr Thr Trp Leu His Val Ser Gly Tyr Arg Phe
1               5                   10                  15

Leu Leu Arg Arg Ile Glu Cys Ala Leu Leu Phe Gly Asp Val Cys Ala
            20                  25                  30

Ala Thr Gly Ala Leu Arg Ala Arg Thr Thr Ser Leu Ala Leu Gly Cys
        35                  40                  45

Val Leu Ala Ile Val Ala Ala Met Gly Cys Ala Phe Val Ala Leu Leu
    50                  55                  60

Arg Pro Gln Ser Ala Leu Gly Gln Ala Pro Ile Val Met Gly Arg Glu
65                  70                  75                  80

Ser Gly Ala Leu Tyr Val Arg Val Asp Asp Val Trp His Pro Val Leu
                85                  90                  95

Asn Leu Ala Ser Ala Arg Leu Ile Ala Ala Thr Asn Ala Asn Pro Gln
            100                 105                 110

Pro Val Ser Glu Ser Glu Leu Gly His Thr Lys Arg Gly Pro Leu Leu
        115                 120                 125

Gly Ile Pro Gly Ala Pro Gln Leu Leu Asp Gln Pro Leu Ala Gly Ala
    130                 135                 140

Glu Ser Ala Trp Ala Ile Cys Asp Ser Asp Asn Gly Gly Ser Thr Thr
145                 150                 155                 160

Val Val Val Gly Pro Ala Glu Asp Ser Ser Ala Gln Val Leu Thr Ala
                165                 170                 175

Glu Gln Met Ile Leu Val Ala Thr Glu Ser Gly Ser Pro Thr Tyr Leu
            180                 185                 190

Leu Tyr Gly Gly Arg Arg Ala Val Val Asp Leu Ala Asp Pro Ala Val
        195                 200                 205

Val Trp Ala Leu Arg Leu Gln Gly Arg Val Pro His Val Val Ala Gln
    210                 215                 220

Ser Leu Leu Asn Ala Val Pro Glu Ala Pro Arg Ile Thr Ala Pro Arg
225                 230                 235                 240

Ile Arg Gly Gly Gly Arg Ala Ser Val Gly Leu Pro Gly Phe Leu Val
                245                 250                 255

Gly Gly Val Val Arg Ile Thr Arg Ala Ser Gly Asp Glu Tyr Tyr Val
            260                 265                 270

Val Leu Glu Asp Gly Val Gln Arg Ile Gly Gln Val Ala Ala Asp Leu
        275                 280                 285

Leu Arg Phe Gly Asp Ser Gln Gly Ser Val Asn Val Pro Thr Val Ala
    290                 295                 300

Pro Asp Val Ile Arg Val Ala Pro Ile Val Asn Thr Leu Pro Val Ser
```

-continued 305 310 315 320

Ala Phe Pro Asp Arg Pro Pro Thr Pro Val Asp Gly Ser Pro Gly Arg
325 330 335

Ala Val Thr Thr Leu Cys Val Thr Trp Thr Pro Ala Gln Pro Gly Ala
340 345 350

Ala Arg Val Ala Phe Leu Ala Gly Ser Gly Pro Pro Val Pro Leu Gly
355 360 365

Gly Val Pro Val Thr Leu Ala Gln Ala Asp Gly Arg Gly Pro Ala Leu
370 375 380

Asp Ala Val Tyr Leu Pro Pro Gly Arg Ser Ala Tyr Val Ala Ala Arg
385 390 395 400

Ser Leu Ser Gly Gly Gly Thr Gly Thr Arg Tyr Leu Val Thr Asp Thr
405 410 415

Gly Val Arg Phe Ala Ile His Asp Asp Asp Val Ala His Asp Leu Gly
420 425 430

Leu Pro Thr Ala Ala Ile Pro Ala Pro Trp Pro Val Leu Ala Thr Leu
435 440 445

Pro Ser Gly Pro Glu Leu Ser Arg Ala Asn Ala Ser Val Ala Arg Asp
450 455 460

Thr Val Ala Pro Gly Pro
465 470

<210> SEQ ID NO 250
<211> LENGTH: 1410
<212> TYPE: DNA
<213> ORGANISM: Mycobacterium tuberculosis

<400> SEQUENCE: 250
gtgccgagcc cagcgacgac ctggctgcac gtcagcgggt accgatttct gctgcggcgc 60
atcgagtgcg cgttgctgtt cggggatgtc tgcgcagcga ccggagcact gcgcgcgcgc 120
acaacatcgc tggccctcgg gtgcgtgctg gcgatcgtcg ccgcgatggg atgcgcattc 180
gttgcgctgc tgcggccaca gtcggcgctc ggtcaggcgc cgatcgtgat gggtcgggaa 240
tccggggcac tctacgtgcg agtggacgat gtctggcatc cggtgttgaa cctggcttcg 300
gcgcggttga tcgcggcgac gaacgccaac ccgcaaccgg tgtccgagtc cgaattgggc 360
cacaccaaac gcggtccact gctcggtatt ccaggtgcgc cgcagctgct tgaccagccg 420
ctagccggcg ccgaatcggc gtgggcgatc tgcgatagcg acaatggcgg atcaacgact 480
gtcgtcgtcg ggcccgccga agactcgtcg gcgcaggtgc tgaccgccga acagatgatc 540
ctggtggcga ccgaatcagg ttcgcccacc tacctgctct acggcggtcg gcgggccgtg 600
gtggatctgg ccgacccggc ggtggtgtgg gcgctgcggc tgcagggccg ggtcccgcac 660
gtggtcgcgc aatcgttgct caacgccgtc ccggaggcac cgcgcatcac ggctccccgg 720
attcgtggcg gcgggcgggc ctcggtcggg ctgcccgggt ttctggtcgg cggtgtggtg 780
cgcatcactc gcgcgagcgg tgatgagtat tacgtggtgc tggaggacgg cgtgcagcgc 840
atcggccagg tcgccgcgga tttgttgcgg ttcggcgatt cgcagggcag cgtcaacgtc 900
ccgacggtgg cccccgatgt gattcgcgtc gctccgatcg tgaacacctt gccggtgtcg 960
gcctttcccg accggccgcc aacaccggtg gacggctcgc cgggaagggc ggtcaccacg 1020
ttgtgcgtga cctggacgcc cgcgcagccg ggtgctgctc gcgtcgcgtt cttggcgggc 1080
agcggcccgc cggtgcccct cggaggggtt ccggtgacac tggcacaagc cgacggtcgc 1140
ggccccgcac tggacgcggt gtacctgccg ccgggacgca gcgcctacgt agccgcgcgc 1200
agcctgtccg gcggcggcac cggcacgcgc tacctggtca ccgacaccgg agtgcggttc 1260
gcgatccacg acgacgacgt ggcacacgac ctcggtctgc cgacggctgc catcccggcg 1320
ccgtggccgg tgttggcgac actgccgtcc ggaccggagc tgagtagagc caacgcgtca 1380
gtcgcccgcg ataccgttgc gcccgggccg 1410

<210> SEQ ID NO 251
<211> LENGTH: 317
<212> TYPE: PRT
<213> ORGANISM: Mycobacterium tuberculosis

<400> SEQUENCE: 251

Val Ser Thr Arg Gln Ala Ala Glu Ala Asp Leu Ala Gly Lys Ala Ala
1 5 10 15

Gln Tyr Arg Pro Asp Glu Leu Ala Arg Tyr Ala Gln Arg Val Met Asp
20 25 30

Trp Leu His Pro Asp Gly Asp Leu Thr Asp Thr Glu Arg Ala Arg Lys
35 40 45

Arg Gly Ile Thr Leu Ser Asn Gln Gln Tyr Asp Gly Met Ser Arg Leu
50 55 60

Ser Gly Tyr Leu Thr Pro Gln Ala Arg Ala Thr Phe Glu Ala Val Leu
65 70 75 80

Ala Lys Leu Ala Ala Pro Gly Ala Thr Asn Pro Asp Asp His Thr Pro
85 90 95

Val Ile Asp Thr Thr Pro Asp Ala Ala Ala Ile Asp Arg Asp Thr Arg
100 105 110

Ser Gln Ala Gln Arg Asn His Asp Gly Leu Leu Ala Gly Leu Arg Ala
115 120 125

Leu Ile Ala Ser Gly Lys Leu Gly Gln His Asn Gly Leu Pro Val Ser
130 135 140

Ile Val Val Thr Thr Thr Leu Thr Asp Leu Gln Thr Gly Ala Gly Lys
145 150 155 160

Gly Phe Thr Gly Gly Gly Thr Leu Leu Pro Met Ala Asp Val Ile Arg
165 170 175

Met Thr Ser His Ala His His Tyr Ser Pro Ala Ser Gly Arg Tyr Pro
180 185 190

Gln Ala Ile Phe Asp His Gly Thr Pro Leu Ala Leu Tyr His Thr Lys
195 200 205

Arg Leu Ala Ser Pro Ala Gln Arg Ile Met Leu Phe Ala Asn Asp Arg
210 215 220

Gly Cys Thr Lys Pro Gly Cys Asp Ala Pro Ala Tyr His Ser Gln Ala
225 230 235 240

His His Val Thr Ala Trp Thr Ser Thr Gly Arg Thr Asp Ile Thr Glu
245 250 255

Leu Thr Leu Ala Cys Gly Pro Asp Asn Arg Leu Ala Glu Lys Gly Trp
260 265 270

Thr Thr His Asn Asn Thr His Gly His Thr Glu Trp Leu Pro Pro Pro
275 280 285

His Leu Asp His Gly Gln Pro Arg Thr Asn Thr Phe His His Pro Glu
290 295 300

Arg Phe Leu His Asn Gln Asp Asp Asp Asp Lys Pro Asp
305 310 315

<210> SEQ ID NO 252
<211> LENGTH: 951
<212> TYPE: DNA

<213> ORGANISM: Mycobacterium tuberculosis

<400> SEQUENCE: 252
gtgtccaccc gccaggccgc cgaagccgac ctggccggca aagccgctca atatcgtccc 60
gacgagctgg cccgctacgc ccagcgggtc atggactggc tacaccccga cggcgacctc 120
accgacaccg aacgcgcccg caaacgcggc atcaccctga gcaaccagca atacgacggc 180
atgtcacggc taagtggcta cctgaccccc caagcgcggg ccacctttga agccgtgcta 240
gccaaactgg ccgcccccgg cgcgaccaac cccgacgacc acaccccggt catcgacacc 300
acccccgatg cggccgccat cgaccgcgac acccgcagcc aagcccaacg caaccacgac 360
gggctgctgg ccgggctgcg cgcgctgatc gcctccggga aactgggcca acacaacggt 420
cttcccgtct cgatcgtggt caccaccacc ctgaccgacc tgcaaaccgg cgccggcaag 480
ggcttcaccg gcggcggcac cctgctaccc atggccgatg tgatccgcat gaccagccac 540
gcccaccact actcccccgc aagcgggagg tacccccagg cgatcttcga ccacggcaca 600
cccctggcgc tgtatcacac caaacgccta gcctccccgg cccagcggat catgctgttc 660
gccaacgacc gcggctgcac caaacccggc tgtgacgcac cggcctacca cagccaagcc 720
caccacgtca ccgcctggac cagcaccgga cgcaccgaca tcaccgagct gaccctggcc 780
tgcggccccg acaaccgact cgccgaaaaa ggctggacca cccacaacaa cacccacggc 840
cacaccgaat ggctaccacc accccacctc gaccacggcc aaccccgcac caacaccttc 900
caccaccccg aacgattcct ccacaaccaa gacgacgacg acaaacccga t 951

<210> SEQ ID NO 253
<211> LENGTH: 373
<212> TYPE: PRT
<213> ORGANISM: Mycobacterium tuberculosis

<400> SEQUENCE: 253

Met Asp Phe Thr Thr Thr Glu Ala Ala Gln Asp Leu Gly Gly Leu Val
1               5                   10                  15

Asp Thr Ile Val Asp Ala Val Cys Thr Pro Glu His Gln Arg Glu Leu
            20                  25                  30

Asp Lys Leu Glu Gln Arg Phe Asp Arg Glu Leu Trp Arg Lys Leu Ile
        35                  40                  45

Asp Ala Gly Ile Leu Ser Ser Ala Ala Pro Glu Ser Leu Gly Gly Asp
    50                  55                  60

Gly Phe Gly Val Leu Glu Gln Val Ala Val Leu Val Ala Leu Gly His
65                  70                  75                  80

Gln Leu Ala Ala Val Pro Tyr Leu Glu Ser Val Val Leu Ala Ala Gly
                85                  90                  95

Ala Leu Ala Arg Phe Gly Ser Pro Glu Leu Gln Gln Gly Trp Gly Val
            100                 105                 110

Ser Ala Val Ser Gly Asp Arg Ile Leu Thr Val Ala Leu Asp Gly Glu
        115                 120                 125

Met Gly Glu Gly Pro Val Gln Ala Ala Gly Thr Gly His Gly Tyr Arg
    130                 135                 140

Leu Thr Gly Thr Arg Thr Gln Val Gly Tyr Gly Pro Val Ala Asp Ala
145                 150                 155                 160

Phe Leu Val Pro Ala Glu Thr Asp Ser Gly Ala Ala Val Phe Leu Val
                165                 170                 175

Ala Ala Gly Asp Pro Gly Val Ala Val Thr Ala Leu Ala Thr Thr Gly
            180                 185                 190

-continued

```
Leu Gly Ser Val Gly His Leu Glu Leu Asn Gly Ala Lys Val Asp Ala
        195                 200                 205

Ala Arg Arg Val Gly Gly Thr Asp Val Ala Val Trp Leu Gly Thr Leu
    210                 215                 220

Ser Thr Leu Ser Arg Thr Ala Phe Gln Leu Gly Val Leu Glu Arg Gly
225                 230                 235                 240

Leu Gln Met Thr Ala Glu Tyr Ala Arg Thr Arg Glu Gln Phe Asp Arg
                245                 250                 255

Pro Ile Gly Ser Phe Gln Ala Val Gly Gln Arg Leu Ala Asp Gly Tyr
            260                 265                 270

Ile Asp Val Lys Gly Leu Arg Leu Thr Leu Thr Gln Ala Ala Trp Arg
        275                 280                 285

Val Ala Glu Asp Ser Leu Ala Ser Arg Glu Cys Pro Gln Pro Ala Asp
    290                 295                 300

Ile Asp Val Ala Thr Ala Gly Phe Trp Ala Ala Glu Ala Gly His Arg
305                 310                 315                 320

Val Ala His Thr Ile Val His Val His Gly Gly Val Gly Val Asp Thr
                325                 330                 335

Asp His Pro Val His Arg Tyr Phe Leu Ala Ala Lys Gln Thr Glu Phe
            340                 345                 350

Ala Leu Gly Gly Ala Thr Gly Gln Leu Arg Arg Ile Gly Arg Glu Leu
        355                 360                 365

Ala Glu Thr Pro Ala
    370
```

<210> SEQ ID NO 254
<211> LENGTH: 1119
<212> TYPE: DNA
<213> ORGANISM: Mycobacterium tuberculosis

<400> SEQUENCE: 254

```
atggatttca cgacaaccga agccgcccag gatcttggtg gtctggtcga caccatcgtg     60

gacgcggtgt gcacgccgga gcatcaacgt gagctggaca agctcgagca gcggttcgac    120

cgcgagctgt ggcgcaagct gatagacgcc ggcatcctgt ccagtgcggc gccggagtcg    180

ctgggcggcg atggcttcgg cgtgctcgag caggttgcgg tgctggtggc gttggggcat    240

caactggccg cggtgccgta cctggagtcg gtggtgctcg ccgccggcgc cctggcccgg    300

ttcggctcgc cggaactgca gcagggctgg ggggtgtcgg cggtctccgg cgatcggatc    360

ctcaccgtcg ccctcgacgg tgagatgggc gagggtccgg tgcaggccgc cggcaccgga    420

catggctacc gcctcaccgg cacacgcacc caggtcgggt acggcccggt ggccgacgca    480

tttctggtac ccgccgaaac cgattccggt gcagccgttt tcctggttgc cgccggcgac    540

ccaggggttg cggtgaccgc actggccacc accggactgg gcagcgtcgg acacctcgag    600

ctaaacgggg ccaaagtgga cgccgcccgc agggtcggcg gaaccgatgt cgcggtttgg    660

ctcggcacgc tttccaccct gagccgcacc gcttttcagc tcggtgtgct cgagcgcgga    720

ctgcaaatga cggccgaata tgcgcgcacc cgtgaacaat tcgaccgccc gatcggcagc    780

ttccaggcgg tggggcaacg gttggctgac ggctacatcg acgtcaaggg attgcgactg    840

acgcttaccc aggcggcctg gcgggtggcc gaagattccc tggcaagccg ggagtgcccc    900

cagccagccg acatcgacgt cgccaccgcg gggttctggg ccgccgaagc cgggcatcgg    960

gtggcgcata ccatcgtgca tgtgcatggc ggcgtcggcg tcgacaccga tcatcccgta   1020

caccggtatt tcctggccgc caagcagacc gagttcgcgt tgggcggcgc caccggtcag   1080
```

```
ctccgccgaa tcggccgtga actggcggaa acccctgcc                        1119


<210> SEQ ID NO 255
<211> LENGTH: 386
<212> TYPE: PRT
<213> ORGANISM: Mycobacterium tuberculosis

<400> SEQUENCE: 255

Val Leu Ser Gly Gln Ala Ala Ile Val Gly Ile Gly Ala Thr Asp Phe
1               5                   10                  15

Ser Lys Asn Ser Gly Arg Ser Glu Leu Arg Leu Ala Ala Glu Ala Val
            20                  25                  30

Leu Asp Ala Leu Ala Asp Ala Gly Leu Ser Pro Thr Asp Val Asp Gly
        35                  40                  45

Leu Thr Thr Phe Thr Met Asp Thr Asn Thr Glu Ile Ala Val Ala Arg
    50                  55                  60

Ala Ala Gly Ile Gly Glu Leu Thr Phe Phe Ser Lys Ile His Tyr Gly
65                  70                  75                  80

Gly Gly Ala Ala Cys Ala Thr Val Gln His Ala Ala Met Ala Val Ala
                85                  90                  95

Thr Gly Val Ala Asp Val Val Val Ala Tyr Arg Ala Phe Asn Glu Arg
            100                 105                 110

Ser Gly Met Arg Phe Gly Gln Val Gln Thr Arg Leu Thr Glu Asn Ala
        115                 120                 125

Asp Ser Thr Gly Val Asp Asn Ser Phe Ser Tyr Pro His Gly Leu Ser
    130                 135                 140

Thr Pro Ala Ala Gln Val Ala Met Ile Ala Arg Arg Tyr Met His Leu
145                 150                 155                 160

Ser Gly Ala Thr Ser Arg Asp Phe Gly Ala Val Ser Val Ala Asp Arg
                165                 170                 175

Lys His Ala Ala Asn Asn Pro Lys Ala Tyr Phe Tyr Gly Lys Pro Ile
            180                 185                 190

Thr Ile Glu Asp His Gln Asn Ser Arg Trp Ile Ala Glu Pro Leu Arg
        195                 200                 205

Leu Leu Asp Cys Cys Gln Glu Thr Asp Gly Ala Val Ala Ile Val Val
    210                 215                 220

Thr Ser Ala Ala Arg Ala Arg Asp Leu Lys Gln Arg Pro Val Val Ile
225                 230                 235                 240

Glu Ala Ala Ala Gln Gly Cys Ser Pro Asp Gln Tyr Thr Met Val Ser
                245                 250                 255

Tyr Tyr Arg Pro Glu Leu Asp Gly Leu Pro Glu Met Gly Leu Val Gly
            260                 265                 270

Arg Gln Leu Trp Ala Gln Ser Gly Leu Thr Pro Ala Asp Val Gln Thr
        275                 280                 285

Ala Val Leu Tyr Asp His Phe Thr Pro Phe Thr Leu Ile Gln Leu Glu
    290                 295                 300

Glu Leu Gly Phe Cys Gly Lys Gly Glu Ala Lys Asp Phe Ile Ala Asp
305                 310                 315                 320

Gly Ala Ile Glu Val Gly Gly Arg Leu Pro Ile Asn Thr His Gly Gly
                325                 330                 335

Gln Leu Gly Glu Ala Tyr Ile His Gly Met Asn Gly Ile Ala Glu Gly
            340                 345                 350

Val Arg Gln Leu Arg Gly Thr Ser Val Asn Pro Val Ala Gly Val Glu
        355                 360                 365

His Val Leu Val Thr Ala Gly Thr Gly Val Pro Thr Ser Gly Leu Ile
```

```
    370                 375                 380

Leu Gly
385


<210> SEQ ID NO 256
<211> LENGTH: 1158
<212> TYPE: DNA
<213> ORGANISM: Mycobacterium tuberculosis

<400> SEQUENCE: 256

gtgttatcgg gtcaggcggc catcgtcggt atcggcgcca ccgacttttc gaagaactcc      60

ggtcgaagtg agctgcggct ggcggccgag gcggtgttgg atgcgttggc cgatgcgggc     120

ctgagcccga ccgatgtcga cgggctgacc acgttcacga tggacaccaa caccgaaatc     180

gccgtggcgc gtgcggccgg catcggcgag ctgacgttct tctccaagat ccactacggc     240

ggtggcgccg catgtgcgac cgtgcagcac gccgctatgg cagtggccac cggggtggct     300

gacgtcgtgg tggcgtatcg ggcattcaac gaacgatccg gcatgcggtt cggtcaggtg     360

caaactcgtt tgaccgagaa tgccgactcc accggcgtgg acaattcgtt ttcgtatccg     420

cacgggctct ccacgcccgc cgcgcaagtg gcgatgatcg ctcgccggta catgcacctg     480

tctggtgcga ccagccggga cttcggtgct gtctcggtgg ccgaccgcaa gcatgccgcc     540

aacaacccca aggcgtactt ctacggcaag ccgataacca ttgaggacca ccagaattcg     600

aggtggatcg ccgagccgct gcggctgctg gactgctgcc aggagaccga cggcgcggtc     660

gcgatcgtgg tgacgtcagc tgcgcgcgca cgggacctca agcagcgccc ggtggtcatt     720

gaggcggctg cgcagggctg cagtccagac cagtacacga tggtcagcta ctaccggccg     780

gaactcgacg gcctgcccga gatgggcctg gtgggccggc agctatgggc gcagtcgggg     840

ctgacgccgg ccgatgtcca gaccgcagtc ctctacgacc acttcacgcc gtttaccctg     900

attcagttgg aggagttggg attctgcggc aagggcgaag cgaaagactt catcgccgac     960

ggcgcgatcg aggtgggcgg gcggctgccc atcaacaccc acggcggtca actcggcgaa    1020

gcctacatcc atggcatgaa cggcatcgcg gagggggtgc ggcagctgcg cggcacctcg    1080

gtgaacccgg tggcgggcgt cgagcatgtg ctcgtcaccg cgggcaccgg ggtgcctacg    1140

tccgggctga tcctgggt                                                  1158


<210> SEQ ID NO 257
<211> LENGTH: 391
<212> TYPE: PRT
<213> ORGANISM: Mycobacterium tuberculosis

<400> SEQUENCE: 257

Met Gly Tyr Pro Val Ile Val Glu Ala Thr Arg Ser Pro Ile Gly Lys
1               5                   10                  15

Arg Asn Gly Trp Leu Ser Gly Leu His Ala Thr Glu Leu Leu Gly Ala
            20                  25                  30

Val Gln Lys Ala Val Val Asp Lys Ala Gly Ile Gln Ser Gly Leu His
        35                  40                  45

Ala Gly Asp Val Glu Gln Val Ile Gly Gly Cys Val Thr Gln Phe Gly
    50                  55                  60

Glu Gln Ser Asn Asn Ile Ser Arg Val Ala Trp Leu Thr Ala Gly Leu
65                  70                  75                  80

Pro Glu His Val Gly Ala Thr Thr Val Asp Cys Gln Cys Gly Ser Gly
                85                  90                  95

Gln Gln Ala Asn His Leu Ile Ala Gly Leu Ile Ala Ala Gly Ala Ile
```

```
            100                 105                 110

Asp Val Gly Ile Ala Cys Gly Ile Glu Ala Met Ser Arg Val Gly Leu
        115                 120                 125

Gly Ala Asn Ala Gly Pro Asp Arg Ser Leu Ile Arg Ala Gln Ser Trp
    130                 135                 140

Asp Ile Asp Leu Pro Asn Gln Phe Glu Ala Ala Glu Arg Ile Ala Lys
145                 150                 155                 160

Arg Arg Gly Ile Thr Arg Glu Asp Val Asp Val Phe Gly Leu Glu Ser
                165                 170                 175

Gln Arg Arg Ala Gln Arg Ala Trp Ala Glu Gly Arg Phe Asp Arg Glu
            180                 185                 190

Ile Ser Pro Ile Gln Ala Pro Val Leu Asp Glu Gln Asn Gln Pro Thr
        195                 200                 205

Gly Glu Arg Arg Leu Val Phe Arg Asp Gln Gly Leu Arg Glu Thr Thr
    210                 215                 220

Met Ala Gly Leu Gly Glu Leu Lys Pro Val Leu Glu Gly Gly Ile His
225                 230                 235                 240

Thr Ala Gly Thr Ser Ser Gln Ile Ser Asp Gly Ala Ala Ala Val Leu
                245                 250                 255

Trp Met Asp Glu Ala Val Ala Arg Ala His Gly Leu Thr Pro Arg Ala
            260                 265                 270

Arg Ile Val Ala Gln Ala Leu Val Gly Ala Glu Pro Tyr Tyr His Leu
        275                 280                 285

Asp Gly Pro Val Gln Ser Thr Ala Lys Val Leu Glu Lys Ala Gly Met
    290                 295                 300

Lys Ile Gly Asp Ile Asp Ile Val Glu Ile Asn Glu Ala Phe Ala Ser
305                 310                 315                 320

Val Val Leu Ser Trp Ala Arg Val His Glu Pro Asp Met Asp Arg Val
                325                 330                 335

Asn Val Asn Gly Gly Ala Ile Ala Leu Gly His Pro Val Gly Cys Thr
            340                 345                 350

Gly Ser Arg Leu Ile Thr Thr Ala Leu His Glu Leu Glu Arg Thr Asp
        355                 360                 365

Gln Ser Leu Ala Leu Ile Thr Met Cys Ala Gly Gly Ala Leu Ser Thr
    370                 375                 380

Gly Thr Ile Ile Glu Arg Ile
385                 390
```

<210> SEQ ID NO 258
<211> LENGTH: 1173
<212> TYPE: DNA
<213> ORGANISM: Mycobacterium tuberculosis

<400> SEQUENCE: 258

```
atgggttacc cggtcatcgt tgaagccacc cgcagcccca tcggcaaacg caacggatgg      60

ctgtcggggc tgcatgccac cgagttgttg ggcgcggtgc aaaaggcggt ggtcgacaag     120

gccggcatcc agtccggcct tcacgccggt gacgtcgaac aggtcatcgg cggttgcgtg     180

acccagttcg gggagcaatc caacaacatc agccgggtgg cctggctgac ggccggtttg     240

cccgaacacg tcggcgccac caccgtcgac tgccagtgcg gcagcggcca gcaggccaac     300

catctgattg ccgggttgat cgcggccggt gccatcgatg tcggcatcgc ctgcggcatc     360

gaggcgatga gccgggtcgg gctgggcgcc aacgccgggc cggaccgctc gctgatccgc     420

gcgcagtcat gggatatcga cctgccgaac cagttcgagg ccgccgagcg gatcgccaag     480
```

```
cggcgcggca tcacccgcga ggacgtggat gtcttcgggc tcgagtcgca gcgacgcgcg    540

cagcgggcct gggcggaggg ccgctttgac cgcgagatct cgccgatcca ggcgccggtg    600

ctcgacgagc agaatcagcc caccggcgag cggcgcctgg tctttcgcga ccagggcctg    660

cgcgagacca cgatggcggg gctaggcgag ctgaaaccgg tgctcgaggg cggcatccac    720

accgcgggca cgtcgtcgca gatctccgac ggcgcggcag ccgtgttgtg gatggacgaa    780

gccgtggcac gtgcgcacgg cctgaccccg cgggcccgga tcgtcgccca ggcactcgtc    840

ggcgccgagc cctactacca cctggacggc ccggtgcagt ccaccgcgaa ggtgctggag    900

aaggccggca tgaagatcgg cgacatcgac atcgtcgaga tcaacgaggc gttcgcgtcc    960

gtggtgctgt cctgggcgcg ggtgcacgag cccgacatgg accgggtcaa cgtcaacggc   1020

ggggcgatcg cgctggggca tccggtgggc tgcaccggca gccggctgat caccaccgcc   1080

ctgcacgagc tcgagcgcac cgaccagagc ctcgcgctga tcaccatgtg cgccggcggg   1140

gccctgtcca ccggcaccat catcgagcgg att                                1173


<210> SEQ ID NO 259
<211> LENGTH: 247
<212> TYPE: PRT
<213> ORGANISM: Mycobacterium tuberculosis

<400> SEQUENCE: 259

Met Pro Ile Thr Ser Thr Thr Pro Glu Pro Gly Ile Val Ala Val Thr
1               5                   10                  15

Val Asp Tyr Pro Pro Val Asn Ala Ile Pro Ser Lys Ala Trp Phe Asp
            20                  25                  30

Leu Ala Asp Ala Val Thr Ala Ala Gly Ala Asn Ser Asp Thr Arg Ala
        35                  40                  45

Val Ile Leu Arg Ala Glu Gly Arg Gly Phe Asn Ala Gly Val Asp Ile
    50                  55                  60

Lys Glu Met Gln Arg Thr Glu Gly Phe Thr Ala Leu Ile Asp Ala Asn
65                  70                  75                  80

Arg Gly Cys Phe Ala Ala Phe Arg Ala Val Tyr Glu Cys Ala Val Pro
                85                  90                  95

Val Ile Ala Ala Val Asn Gly Phe Cys Val Gly Gly Gly Ile Gly Leu
            100                 105                 110

Val Gly Asn Ser Asp Val Ile Val Ala Ser Glu Asp Ala Thr Phe Gly
        115                 120                 125

Leu Pro Glu Val Glu Arg Gly Ala Leu Gly Ala Ala Thr His Leu Ser
    130                 135                 140

Arg Leu Val Pro Gln His Leu Met Arg Arg Leu Phe Phe Thr Ala Ala
145                 150                 155                 160

Thr Val Asp Ala Ala Thr Leu Gln His Phe Gly Ser Val His Glu Val
                165                 170                 175

Val Ser Arg Asp Gln Leu Asp Glu Ala Ala Leu Arg Val Ala Arg Asp
            180                 185                 190

Ile Ala Ala Lys Asp Thr Arg Val Ile Arg Ala Ala Lys Glu Ala Leu
        195                 200                 205

Asn Phe Ile Asp Val Gln Arg Val Asn Ala Ser Tyr Arg Met Glu Gln
    210                 215                 220

Gly Phe Thr Phe Glu Leu Asn Leu Ala Gly Val Ala Asp Glu His Arg
225                 230                 235                 240

Asp Ala Phe Val Lys Lys Ser
                245
```

<210> SEQ ID NO 260
<211> LENGTH: 741
<212> TYPE: DNA
<213> ORGANISM: Mycobacterium tuberculosis

<400> SEQUENCE: 260
atgccgatca cctccaccac gcccgaaccg ggcatcgtcg cggtcaccgt cgactacccg 60
ccggtcaacg ccatcccgtc gaaagcgtgg ttcgacctgg ccgacgcggt gacggccgcg 120
ggcgccaact ccgacacccg cgcggtgatc ctgcgggccg aggggcgcgg cttcaacgcc 180
ggggtggaca tcaaagagat gcaacgaacc gaaggtttca cggcgctgat cgacgccaac 240
cgcggctgct tcgccgcatt ccgcgccgtc tacgagtgcg cggtgccggt gatcgccgcc 300
gtgaacggat tctgcgtggg cggcggcatc ggcctggtcg gcaactccga cgtcatcgtg 360
gcctccgagg acgccacctt cggcctgccc gaggtggaac ggggcgcgct gggcgcggcc 420
acgcacctct cgcggctggt gccccagcac ctgatgcgac ggctgttctt tacggcggcc 480
accgtggacg cggccacctt gcagcacttc ggctcggtgc acgaggtggt gtcccgcgat 540
cagctggacg aggccgcttt gcgggtggcc cgcgacatcg ccgccaaaga cacccgggtc 600
atccgcgccg ccaaggaggc gctgaacttc atcgacgtgc aacgggtcaa tgcgagttac 660
cggatggagc aaggttttac cttcgagctc aacctcgccg gagtcgccga cgagcaccgc 720
gacgcctttg tgaagaagtc a 741

<210> SEQ ID NO 261
<211> LENGTH: 250
<212> TYPE: PRT
<213> ORGANISM: Mycobacterium tuberculosis

<400> SEQUENCE: 261

Val Ser Thr Arg Ala Glu Val Cys Ala Val Ala Cys Ala Glu Leu Phe
1               5                   10                  15

Arg Asp Ala Gly Glu Ile Met Ile Ser Pro Met Thr Asn Met Ala Ser
            20                  25                  30

Val Gly Ala Arg Leu Ala Arg Leu Thr Phe Ala Pro Asp Ile Leu Leu
        35                  40                  45

Thr Asp Gly Glu Ala Gln Leu Leu Ala Asp Thr Pro Ala Leu Gly Lys
    50                  55                  60

Thr Gly Ala Pro Asn Arg Ile Glu Gly Trp Met Pro Phe Gly Arg Val
65                  70                  75                  80

Phe Glu Thr Leu Ala Trp Gly Arg Arg His Val Val Met Gly Ala Asn
                85                  90                  95

Gln Val Asp Arg Tyr Gly Asn Gln Asn Ile Ser Ala Phe Gly Pro Leu
            100                 105                 110

Gln Arg Pro Thr Arg Gln Met Phe Gly Val Arg Gly Ser Pro Gly Asn
        115                 120                 125

Thr Ile Asn His Ala Thr Ser Tyr Trp Val Gly Asn His Cys Lys Arg
    130                 135                 140

Val Phe Val Glu Ala Val Asp Val Val Ser Gly Ile Gly Tyr Asp Lys
145                 150                 155                 160

Val Asp Pro Asp Asn Pro Ala Phe Arg Phe Val Asn Val Tyr Arg Val
                165                 170                 175

Val Ser Asn Leu Gly Val Phe Asp Phe Gly Gly Pro Asp His Ser Met
            180                 185                 190

Arg Ala Val Ser Leu His Pro Gly Val Thr Pro Gly Asp Val Arg Asp
        195                 200                 205

Ala Thr Ser Phe Glu Val His Asp Leu Asp Ala Ala Glu Gln Thr Arg
    210                 215                 220

Leu Pro Thr Asp Asp Glu Leu His Leu Ile Arg Ala Val Ile Asp Pro
225                 230                 235                 240

Lys Ser Leu Arg Asp Arg Glu Ile Arg Ser
                245                 250

<210> SEQ ID NO 262
<211> LENGTH: 750
<212> TYPE: DNA
<213> ORGANISM: Mycobacterium tuberculosis

<400> SEQUENCE: 262
gtgagcaccc gagccgaagt gtgtgccgtc gcctgcgccg agttgttccg cgatgcaggc 60
gaaatcatga tcagccccat gaccaacatg gcctcggtag gggcgcggct ggcgcggctc 120
accttcgcgc cggacattct gctgaccgac ggcgaggctc agctgctcgc ggacacaccg 180
gcattgggca agacgggcgc cccaaacagg attgaggggt ggatgccgtt cggccgggtt 240
ttcgaaaccc tggcctgggg gcgccggcac gtggtgatgg gcgccaatca ggtcgaccgc 300
tatggcaatc agaacatctc ggcgttcggg ccgctgcagc ggccgacccg gcagatgttc 360
ggcgtccgcg gctcgccggg caacaccatc aaccacgcca ccagttactg ggtgggcaac 420
cactgcaagc gggtctttgt cgaggccgtc gatgtggtct ccggcatcgg ctacgacaag 480
gtggatccgg acaatccggc cttccggttc gtcaacgtct accgggtggt gtccaaccta 540
ggcgtgttcg acttcggcgg ccccgaccac tccatgcggg cggtatccct acaccccggg 600
gtgacgcccg gcgacgtccg cgacgccacc tcgttcgagg tgcatgacct cgacgcggcc 660
gagcagacca ggctgcccac cgacgacgaa ctgcacctga tccgcgcggt aatcgatccg 720
aagtcgttgc gggacaggga gatacgatca 750

<210> SEQ ID NO 263
<211> LENGTH: 388
<212> TYPE: PRT
<213> ORGANISM: Mycobacterium tuberculosis

<400> SEQUENCE: 263

Val Thr Asp Arg Val Ala Leu Arg Ala Gly Val Pro Pro Phe Tyr Val
1               5                   10                  15

Met Asp Val Trp Leu Ala Ala Ala Glu Arg Gln Arg Thr His Gly Asp
            20                  25                  30

Leu Val Asn Leu Ser Ala Gly Gln Pro Ser Ala Gly Ala Pro Glu Pro
        35                  40                  45

Val Arg Ala Ala Ala Ala Ala Ala Leu His Leu Asn Gln Leu Gly Tyr
    50                  55                  60

Ser Val Ala Leu Gly Ile Pro Glu Leu Arg Asp Ala Ile Ala Ala Asp
65                  70                  75                  80

Tyr Gln Arg Arg His Gly Ile Thr Val Glu Pro Asp Ala Val Val Ile
                85                  90                  95

Thr Thr Gly Ser Ser Gly Gly Phe Leu Leu Ala Phe Leu Ala Cys Phe
            100                 105                 110

Asp Ala Gly Asp Arg Val Ala Met Ala Ser Pro Gly Tyr Pro Cys Tyr
        115                 120                 125

Arg Asn Ile Leu Ser Ala Leu Gly Cys Glu Val Val Glu Ile Pro Cys
    130                 135                 140

Gly Pro Gln Thr Arg Phe Gln Pro Thr Ala Gln Met Leu Ala Glu Ile

```
145                 150                 155                 160

Asp Pro Pro Leu Arg Gly Val Val Val Ala Ser Pro Ala Asn Pro Thr
                165                 170                 175

Gly Thr Val Ile Pro Pro Glu Glu Leu Ala Ala Ile Ala Ser Trp Cys
            180                 185                 190

Asp Ala Ser Asp Val Arg Leu Ile Ser Asp Glu Val Tyr His Gly Leu
        195                 200                 205

Val Tyr Gln Gly Ala Pro Gln Thr Ser Cys Ala Trp Gln Thr Ser Arg
    210                 215                 220

Asn Ala Val Val Val Asn Ser Phe Ser Lys Tyr Tyr Ala Met Thr Gly
225                 230                 235                 240

Trp Arg Leu Gly Trp Leu Leu Val Pro Thr Val Leu Arg Arg Ala Val
                245                 250                 255

Asp Cys Leu Thr Gly Asn Phe Thr Ile Cys Pro Pro Val Leu Ser Gln
            260                 265                 270

Ile Ala Ala Val Ser Ala Phe Thr Pro Glu Ala Thr Ala Glu Ala Asp
        275                 280                 285

Gly Asn Leu Ala Ser Tyr Ala Ile Asn Arg Ser Leu Leu Leu Asp Gly
    290                 295                 300

Leu Arg Arg Ile Gly Ile Asp Arg Leu Ala Pro Thr Asp Gly Ala Phe
305                 310                 315                 320

Tyr Val Tyr Ala Asp Val Ser Asp Phe Thr Ser Asp Ser Leu Ala Phe
                325                 330                 335

Cys Ser Lys Leu Leu Ala Asp Thr Gly Val Ala Ile Ala Pro Gly Ile
            340                 345                 350

Asp Phe Asp Thr Ala Arg Gly Gly Ser Phe Val Arg Ile Ser Phe Ala
        355                 360                 365

Gly Pro Ser Gly Asp Ile Glu Glu Ala Leu Arg Arg Ile Gly Ser Trp
    370                 375                 380

Leu Pro Ser Gln
385
```

<210> SEQ ID NO 264
<211> LENGTH: 1164
<212> TYPE: DNA
<213> ORGANISM: Mycobacterium tuberculosis

<400> SEQUENCE: 264

```
gtgacggatc gtgtcgccct gcgtgccggc gttccccgt  tctacgtgat ggacgtctgg      60

ttggcggccg cggagcgcca gcgcacccat ggggatctgg tgaatctttc ggcgggccaa     120

cccagtgcgg gcgctccgga accggtgcgt gcggccgcgg ccgccgccct gcatctcaac     180

cagttgggat actcggtggc gctgggtatt ccggagctgc gcgacgctat cgccgcggat     240

taccaacgcc ggcatggcat caccgtcgaa cccgatgcgg tggtgatcac cacgggctcc     300

tcgggcggct ttctgctcgc gtttctggcg tgcttcgacg ccggtgatcg ggtcgcgatg     360

gccagtcccg gctacccgtg ctaccggaat atcctgtcag cgctgggatg tgaggtcgtg     420

gagatcccgt gcggaccgca gacccgattc caaccgaccg cgcagatgct ggccgagatc     480

gacccaccgc tgcgcggtgt cgtcgtcgcc agcccggcca acccgaccgg aaccgtcatc     540

ccgcccgaag aactggcggc catcgcgtcg tggtgtgacg catcggatgt ccggttgatc     600

agtgatgagg tctaccacgg cctggtgtac cagggggcac cgcaaaccag ctgcgcctgg     660

cagacgtcgc gaaacgcggt ggtagtcaac agcttttcca agtattacgc gatgacgggc     720

tggcggctgg gctggctgct ggtgccgacg gtgctgcgcc gcgcggtgga ctgcctgacc     780
```

-continued

```
ggcaacttca ccatctgccc gccggtcttg tcgcagatcg ccgcggtgtc cgcgttcacc    840

ccggaggcga ccgccgaggc cgacggcaac ctggccagct acgcgatcaa ccgctcgctg    900

ttgctggacg gtctgcgtcg catcggcatc gaccggctgg cacccaccga cggcgcattc    960

tacgtctacg ccgacgtctc ggacttcacc agcgattcgc tggccttctg ctcaaagttg   1020

ctggccgaca ccggtgttgc gatcgcaccc ggaatcgatt tcgacaccgc acgggggggt   1080

tcgtttgttc ggatatcgtt tgccgggcca agcggcgaca tcgaagaagc cttacggcgc   1140

atcggctcct ggctgccgag ccaa                                          1164
```

<210> SEQ ID NO 265
<211> LENGTH: 291
<212> TYPE: PRT
<213> ORGANISM: Mycobacterium tuberculosis

<400> SEQUENCE: 265

```
Met Thr Ala Thr Glu Glu Leu Thr Phe Glu Ser Thr Ser Arg Phe Ala
1               5                   10                  15

Glu Val Asp Val Asp Gly Pro Leu Lys Leu His Tyr His Glu Ala Gly
            20                  25                  30

Val Gly Asn Asp Gln Thr Val Val Leu Leu His Gly Gly Gly Pro Gly
        35                  40                  45

Ala Ala Ser Trp Thr Asn Phe Ser Arg Asn Ile Ala Val Leu Ala Arg
    50                  55                  60

His Phe His Val Leu Ala Val Asp Gln Pro Gly Tyr Gly His Ser Asp
65                  70                  75                  80

Lys Arg Ala Glu His Gly Gln Phe Asn Arg Tyr Ala Ala Met Ala Leu
                85                  90                  95

Lys Gly Leu Phe Asp Gln Leu Gly Leu Gly Arg Val Pro Leu Val Gly
            100                 105                 110

Asn Ser Leu Gly Gly Gly Thr Ala Val Arg Phe Ala Leu Asp Tyr Pro
        115                 120                 125

Ala Arg Ala Gly Arg Leu Val Leu Met Gly Pro Gly Gly Leu Ser Ile
    130                 135                 140

Asn Leu Phe Ala Pro Asp Pro Thr Glu Gly Val Lys Arg Leu Ser Lys
145                 150                 155                 160

Phe Ser Val Ala Pro Thr Arg Glu Asn Leu Glu Ala Phe Leu Arg Val
                165                 170                 175

Met Val Tyr Asp Lys Asn Leu Ile Thr Pro Glu Leu Val Asp Gln Arg
            180                 185                 190

Phe Ala Leu Ala Ser Thr Pro Glu Ser Leu Thr Ala Thr Arg Ala Met
        195                 200                 205

Gly Lys Ser Phe Ala Gly Ala Asp Phe Glu Ala Gly Met Met Trp Arg
    210                 215                 220

Glu Val Tyr Arg Leu Arg Gln Pro Val Leu Leu Ile Trp Gly Arg Glu
225                 230                 235                 240

Asp Arg Val Asn Pro Leu Asp Gly Ala Leu Val Ala Leu Lys Thr Ile
                245                 250                 255

Pro Arg Ala Gln Leu His Val Phe Gly Gln Cys Gly His Trp Val Gln
            260                 265                 270

Val Glu Lys Phe Asp Glu Phe Asn Lys Leu Thr Ile Glu Phe Leu Gly
        275                 280                 285

Gly Gly Arg
    290
```

-continued

<210> SEQ ID NO 266
<211> LENGTH: 873
<212> TYPE: DNA
<213> ORGANISM: Mycobacterium tuberculosis

<400> SEQUENCE: 266
atgacagcta ccgaggaatt gacgttcgaa tccacctcgc gctttgcgga agtggacgtc 60
gacgggccgc tgaaactgca ctaccacgag gccggcgtgg gcaacgacca gacggtggtg 120
ctactgcacg gcggtgggcc cggcgcggcg agctggacga acttctcgcg taatatcgcg 180
gtgctggcgc ggcactttca tgtgctggcc gtcgaccagc ccggttacgg ccattccgac 240
aagcgggccg agcacggcca gttcaatcgc tatgccgcga tggcgctgaa ggggctcttc 300
gatcagctgg ggctggggcg ggtaccgctg gtgggcaact cgttgggcgg gggaaccgcg 360
gtccggtttg cgctggacta cccggcccgg gcaggacggt tagtgctgat gggcccgggg 420
ggcctgagta tcaacctgtt tgcgcccgac ccgaccgagg gagtcaaacg gctgtcgaag 480
ttctccgttg cgcccacccg ggagaacctc gaggcgttcc tgcgggtcat ggtctacgac 540
aagaacctga tcacccccga gttggtggat cagcggtttg cgctggccag caccccggag 600
tcgttgacgg caacacgggc gatgggaaag tcgttcgccg gagccgactt cgaggccggc 660
atgatgtggc gcgaggtgta tcggctgcgc cagccggtgt tgctgatctg ggtcgtgag 720 gaccgggtca acccgctgga cggcgcgctg gttgcgttga aaacgattcc gcgtgcgcag 780
ctgcacgtat tcgggcagtg tgggcattgg gtgcaggtgg agaagttcga cgagttcaac 840
aagctgacga ttgaatttct gggaggtggc aga 873

<210> SEQ ID NO 267
<211> LENGTH: 188
<212> TYPE: PRT
<213> ORGANISM: Mycobacterium tuberculosis

<400> SEQUENCE: 267

Met Thr Arg Val Val Leu Ser Val Gly Ser Asn Leu Gly Asp Arg Leu
1               5                   10                  15

Ala Arg Leu Arg Ser Val Ala Asp Gly Leu Gly Asp Ala Leu Ile Ala
            20                  25                  30

Ala Ser Pro Ile Tyr Glu Ala Asp Pro Trp Gly Gly Val Glu Gln Gly
        35                  40                  45

Gln Phe Leu Asn Ala Val Leu Ile Ala Asp Asp Pro Thr Cys Glu Pro
    50                  55                  60

Arg Glu Trp Leu Arg Arg Ala Gln Glu Phe Glu Arg Ala Ala Gly Arg
65                  70                  75                  80

Val Arg Gly Gln Arg Trp Gly Pro Arg Asn Leu Asp Val Asp Leu Ile
                85                  90                  95

Ala Cys Tyr Gln Thr Ser Ala Thr Glu Ala Leu Val Glu Val Thr Ala
            100                 105                 110

Arg Glu Asn His Leu Thr Leu Pro His Pro Leu Ala His Leu Arg Ala
        115                 120                 125

Phe Val Leu Ile Pro Trp Ile Ala Val Asp Pro Thr Ala Gln Leu Thr
    130                 135                 140

Val Ala Gly Cys Pro Arg Pro Val Thr Arg Leu Leu Ala Glu Leu Glu
145                 150                 155                 160

Pro Ala Asp Arg Asp Ser Val Arg Leu Phe Arg Pro Ser Phe Asp Leu
                165                 170                 175

Asn Ser Arg His Pro Val Ser Arg Ala Pro Glu Ser 180 185

<210> SEQ ID NO 268
<211> LENGTH: 564
<212> TYPE: DNA
<213> ORGANISM: Mycobacterium tuberculosis

<400> SEQUENCE: 268
atgacgcggg tagtgctctc ggttggctcc aacctgggtg accgcctggc acgattgcgg 60
tcggtcgccg acggtctcgg cgatgcgttg attgcggctt ccccgatata tgaggccgac 120
ccctggggtg gggtggagca ggggcagttc ctcaatgcgg tgctgatcgc cgacgatcct 180
acctgcgaac cgcgggagtg gctgcggcgg gcgcaggagt tcgagcgcgc tgcgggcagg 240
gtgcgtggcc agcgctgggg tccacgaaat ctcgacgtcg acctgatcgc ctgctaccag 300
acctcggcca ccgaggctct ggtcgaagtg accgcgcggg agaaccacct cacgctgccg 360
cacccactgg cgcatctgcg ggcctttgtg ttgatcccgt ggattgccgt cgacccaacg 420
gcgcagctga cggttgccgg gtgcccgcgg cccgtcacgc gactgctggc cgagctggag 480
cccgccgacc gcgacagtgt gcggttgttt aggccgtcgt tcgatctgaa tagcagacac 540
cccgtcagtc gggcaccgga aagc 564

<210> SEQ ID NO 269
<211> LENGTH: 166
<212> TYPE: PRT
<213> ORGANISM: Mycobacterium tuberculosis

<400> SEQUENCE: 269

Leu Pro Gly Arg Val Phe Ala Ser Pro Ala Asp Phe Asn Thr Gln Leu
1 5 10 15

Gln Ala Trp Leu Val Arg Ala Asn His Arg Gln His Arg Val Leu Gly
20 25 30

Cys Arg Pro Ala Asp Arg Ile Glu Ala Asp Thr Ala Ala Met Leu Thr
35 40 45

Leu Pro Pro Val Gly Pro Ser Ile Gly Trp Arg Thr Ser Thr Arg Leu
50 55 60

Pro Arg Asp His Tyr Val Arg Leu Asp Gly Asn Asp Tyr Ser Val His
65 70 75 80

Pro Val Ala Ile Gly Arg Arg Ile Glu Ile Thr Ala Asp Leu Ser Arg
85 90 95

Val Arg Val Trp Cys Gly Gly Thr Leu Val Ala Asp His Asp Arg Ile
100 105 110

Trp Ala Lys His Gln Thr Ile Ser Asp Pro Glu His Val Val Ala Ala
115 120 125

Lys Leu Leu Arg Arg Lys Arg Phe Asp Ile Val Gly Pro Pro His His
130 135 140

Val Glu Val Glu Gln Arg Leu Leu Thr Thr Tyr Asp Thr Val Leu Gly
145 150 155 160

Leu Asp Gly Pro Val Ala
165

<210> SEQ ID NO 270
<211> LENGTH: 498
<212> TYPE: DNA
<213> ORGANISM: Mycobacterium tuberculosis

<400> SEQUENCE: 270
ttgccgggtc gggtctttgc ctctccggcg gatttcaata cccagttgca ggcctggctg 60
gtgcgggcca atcaccgcca gcaccgagtg ctgggatgtc gaccggcaga tcgcatcgag 120
gccgataccg cagcgatgct gacattgccg ccggtcgggc ccagcatcgg gtggcgaacc 180
tcgacacggc tgccgcgcga tcattacgtg cgcctcgacg gcaacgacta ctcggtgcat 240
ccggtcgcga tcggccggcg catcgagatc accgcagatc tgagccgggt ccgggtctgg 300
tgtggcggca ccctggtcgc cgatcatgac cgcatctggg ccaaacacca gacgatcagc 360
gatcccgagc atgtcgtggc cgccaaactg ctgcgacgca aacggttcga catcgtcggt 420
ccaccccacc acgttgaggt cgaacaacgt ctcctgacca cctacgacac cgtgttgggc 480
cttgacgggc cggtggcc 498

<210> SEQ ID NO 271
<211> LENGTH: 350
<212> TYPE: PRT
<213> ORGANISM: Mycobacterium tuberculosis

<400> SEQUENCE: 271

Met Leu Thr Asp Pro Gly Leu Arg Asp Glu Leu Asp Arg Val Ala Ala
1 5 10 15

Ala Val Gly Val Arg Val Val His Leu Gly Gly Arg His Pro Val Ser
20 25 30

Arg Lys Thr Trp Ser Ala Ala Ala Ala Val Val Leu Asp His Ala Ala
35 40 45

Ala Asp Arg Cys Gly Arg Leu Ala Leu Pro Arg Arg Thr His Val Ser
50 55 60

Val Leu Thr Gly Thr Glu Ala Ala Thr Ala Thr Trp Ala Ala Ala Ile
65 70 75 80

Thr Val Gly Ala Gln His Val Leu Arg Met Pro Glu Gln Glu Gly Glu
85 90 95

Leu Val Arg Glu Leu Ala Glu Ala Ala Glu Ser Ala Arg Asp Asp Gly
100 105 110

Ile Cys Gly Ala Val Val Ala Val Ile Gly Gly Arg Gly Gly Ala Gly
115 120 125

Ala Ser Leu Phe Ala Val Ala Leu Ala Gln Ala Ala Ala Asp Ala Leu
130 135 140

Leu Val Asp Leu Asp Pro Trp Ala Gly Gly Ile Asp Leu Leu Val Gly
145 150 155 160

Gly Glu Thr Ala Pro Gly Leu Arg Trp Pro Asp Leu Ala Leu Gln Gly
165 170 175

Gly Arg Leu Asn Trp Ser Ala Val Arg Ala Ala Leu Pro Arg Pro Arg
180 185 190

Gly Ile Ser Val Leu Ser Gly Thr Arg Arg Gly Tyr Glu Leu Asp Ala
195 200 205

Gly Pro Val Asp Ala Val Ile Asp Ala Gly Arg Arg Gly Gly Val Thr
210 215 220

Val Val Cys Asp Leu Pro Arg Arg Leu Thr Asp Ala Thr Gln Ala Ala
225 230 235 240

Leu Asp Ala Ala Asp Leu Val Val Leu Val Ser Pro Cys Asp Val Arg
245 250 255

Ala Cys Ala Ala Ala Ala Thr Met Ala Pro Val Leu Thr Ala Ile Asn
260 265 270

Pro Asn Leu Gly Leu Val Val Arg Gly Pro Ser Pro Gly Gly Leu Arg
275 280 285

Ala Ala Glu Val Ala Asp Val Ala Gly Val Pro Leu Leu Ala Ser Met

```
    290                 295                 300

Arg Ala Gln Pro Arg Leu Ala Glu Gln Leu Glu His Gly Gly Leu Arg
305                 310                 315                 320

Leu Arg Arg Arg Ser Val Leu Ala Ser Ala Ala Arg Arg Val Leu Gly
                325                 330                 335

Val Leu Pro Arg Ala Gly Ser Gly Arg His Gly Arg Ala Ala
            340                 345                 350


<210> SEQ ID NO 272
<211> LENGTH: 1050
<212> TYPE: DNA
<213> ORGANISM: Mycobacterium tuberculosis

<400> SEQUENCE: 272

atgctgaccg atccggggtt gcgcgacgag ctggaccgag tcgccgcagc cgtcggggtt      60

cgcgttgttc atctcggcgg ccgccatccg gtgagcagaa agacgtggtc ggcggcggcg     120

gctgtggtgc tcgaccacgc ggcggcggac cggtgtgggc ggctcgcgct accccggcgc     180

acccacgtca gcgtgttgac cggaaccgaa gccgcgacgg cgacctgggc ggctgccata     240

accgtcgggg cccagcacgt gctgaggatg cccgagcagg agggtgaact ggtccgcgag     300

ctcgccgaag ctgctgaatc ggcacgcgat gacgggatct gcggggcggt ggtcgcggtc     360

atcgggggtc gcggtggcgc tggggcatcg ttgtttgcgg ttgccctggc gcaggccgcc     420

gctgatgcgc tgttggtcga tctcgatccg tgggccggcg gcatcgatct tctggtgggc     480

ggcgaaaccg cccccggtct gcgttggccc gacctggcgc tacagggtgg acggctgaat     540

tggtcggcgg tgcgtgcggc attgccgcga ccgcggggga tcagcgtgct ctcgggaact     600

cggcgcggct acgagttaga cgccgggccg gtggacgccg tgatcgacgc cggccgacgt     660

gggggagtca ccgtggtctg cgatcttcca cgtcgtctga ccgatgccac ccaagcagcg     720

ctggatgccg ccgatctcgt cgtcctggtc agcccatgcg atgtgcgggc atgtgcggcc     780

gccgcgacga tggcgcctgt gctgaccgcg atcaacccca acctgggtct ggtggtgcgg     840

gggccctccc cgggggatt gcgggcggca gaggtcgcgg acgtcgccgg ggtgccgcta      900

ctggcatcca tgagggccca gccgcggcta gccgaacagc tggaacacgg gggtcttcga     960

ctgcgacggc gatcggtgct ggcatcggct gcccgacggg tacttggtgt gctgccacgt    1020

gctgggtcag ggcgacacgg tagggcggca                                     1050


<210> SEQ ID NO 273
<211> LENGTH: 70
<212> TYPE: PRT
<213> ORGANISM: Mycobacterium tuberculosis

<400> SEQUENCE: 273

Met Ser Asp Cys Asn Val Leu Gly Gly Ala Leu Glu Gln Gly Gly Thr
1               5                   10                  15

Asp Pro Leu Thr Gly Phe Tyr Arg Asp Gly Cys Cys Ala Thr Gly Pro
            20                  25                  30

Glu Asp Leu Gly Trp His Thr Ile Cys Ala Val Met Thr Thr Glu Phe
        35                  40                  45

Leu Ala His Gln Arg Ser Val Gly Asn Asp Leu Ser Ile Ala Arg Pro
    50                  55                  60

Pro Arg Trp Leu Arg Pro
65                  70


<210> SEQ ID NO 274
```

<211> LENGTH: 210
<212> TYPE: DNA
<213> ORGANISM: Mycobacterium tuberculosis

<400> SEQUENCE: 274
atgtccgatt gcaatgtgct gggcggcgcc ctggaacagg gtggcaccga tccgcttacc 60
ggcttctatc gtgacggctg ctgtgcgacc ggacccgagg acctcggttg gcacaccatc 120
tgcgccgtca tgaccaccga attcctggca caccagcgct cggtcggcaa cgacctgtcg 180
attgcgcgcc cgccacggtg gctgcgccct 210

<210> SEQ ID NO 275
<211> LENGTH: 846
<212> TYPE: PRT
<213> ORGANISM: Mycobacterium tuberculosis

<400> SEQUENCE: 275

Met Ala Pro Leu Ala Val Asp Pro Ala Ala Leu Asp Ser Ala Gly Gly
1 5 10 15

Ala Val Val Ala Ala Gly Ala Gly Leu Gly Ala Val Ile Ser Ser Leu
20 25 30

Thr Ala Ala Leu Ala Gly Cys Ala Gly Met Ala Gly Asp Asp Pro Ala
35 40 45

Gly Ala Val Phe Gly Arg Ser Tyr Asp Gly Ser Ala Ala Ala Leu Val
50 55 60

Gln Ala Met Ser Val Ala Arg Asn Gly Leu Cys Asn Leu Gly Asp Gly
65 70 75 80

Val Arg Met Ser Ala His Asn Tyr Ser Leu Ala Glu Ala Met Ser Asp
85 90 95

Val Ala Gly Arg Ala Ala Pro Leu Pro Ala Pro Pro Pro Ser Gly Cys
100 105 110

Val Gly Val Gly Ala Pro Pro Ser Ala Val Gly Gly Gly Gly Gly Ala
115 120 125

Pro Lys Gly Trp Gly Trp Val Ala Pro Tyr Ile Gly Met Ile Trp Pro
130 135 140

Asn Gly Asp Ser Thr Lys Leu Arg Ala Ala Ala Val Ala Trp Arg Ser
145 150 155 160

Ala Gly Thr Gln Phe Ala Leu Thr Glu Ile Gln Ser Thr Ala Gly Pro
165 170 175

Met Gly Val Ile Arg Ala Gln Gln Leu Pro Glu Ala Gly Leu Ile Glu
180 185 190

Ser Ala Phe Ala Asp Ala Tyr Ala Ser Thr Thr Ala Val Val Gly Gln
195 200 205

Cys His Gln Leu Ala Ala Gln Leu Asp Ala Tyr Ala Ala Arg Ile Asp
210 215 220

Ala Val His Ala Ala Val Leu Asp Leu Leu Ala Arg Ile Cys Asp Pro
225 230 235 240

Leu Thr Gly Ile Lys Glu Val Trp Glu Phe Leu Thr Asp Gln Asp Glu
245 250 255

Asp Glu Ile Gln Arg Ile Ala His Asp Ile Ala Val Val Val Asp Gln
260 265 270

Phe Ser Gly Glu Val Asp Ala Leu Ala Ala Glu Ile Thr Ala Val Val
275 280 285

Ser His Ala Glu Ala Val Ile Thr Ala Met Ala Asp His Ala Gly Lys
290 295 300

Gln Trp Asp Arg Phe Leu His Ser Asn Pro Val Gly Val Val Ile Asp

-continued

```
305                 310                 315                 320

Gly Thr Gly Gln Gln Leu Lys Gly Phe Gly Glu Glu Ala Phe Gly Met
                325                 330                 335

Ala Lys Asp Ser Trp Asp Leu Gly Pro Leu Arg Ala Ser Ile Asp Pro
            340                 345                 350

Phe Gly Trp Tyr Arg Ser Trp Glu Glu Met Leu Thr Gly Met Ala Pro
        355                 360                 365

Leu Ala Gly Leu Gly Gly Glu Asn Ala Pro Gly Val Val Glu Ser Trp
    370                 375                 380

Lys Gln Phe Gly Lys Ser Leu Ile His Trp Asp Glu Trp Thr Thr Asn
385                 390                 395                 400

Pro Asn Glu Ala Leu Gly Lys Thr Val Phe Asp Ala Ala Thr Leu Ala
                405                 410                 415

Leu Pro Gly Gly Pro Leu Ser Lys Leu Gly Ser Lys Gly Arg Asp Ile
            420                 425                 430

Leu Ala Gly Val Arg Gly Leu Lys Glu Arg Leu Glu Pro Thr Thr Pro
        435                 440                 445

His Leu Glu Pro Pro Ala Thr Pro Pro Arg Pro Gly Pro Gln Pro Pro
    450                 455                 460

Arg Ile Glu Pro Pro Glu Ser Gly His Pro Ala Pro Ala Pro Ala Ala
465                 470                 475                 480

Lys Pro Ala Pro Val Pro Ala Asn Gly Pro Leu Pro His Ser Pro Thr
                485                 490                 495

Glu Ser Lys Pro Pro Pro Val Asp Arg Pro Ala Glu Pro Val Ala Pro
            500                 505                 510

Ser Ser Ala Ser Ala Gly Gln Pro Arg Val Ser Ala Ala Thr Thr Pro
        515                 520                 525

Gly Thr His Val Pro His Gly Leu Pro Gln Pro Gly Glu His Val Pro
    530                 535                 540

Ala Gln Ala Pro Pro Ala Thr Thr Leu Leu Gly Gly Pro Pro Val Glu
545                 550                 555                 560

Ser Ala Pro Ala Thr Ala His Gln Pro Gln Trp Ala Thr Thr Pro Ala
                565                 570                 575

Ala Pro Ala Ala Ala Pro His Ser Thr Pro Gly Gly Val His Ser Thr
            580                 585                 590

Glu Ser Gly Pro His Gly Arg Ser Leu Ser Ala His Gly Ser Glu Pro
        595                 600                 605

Thr His Asp Gly Ala Ser His Gly Ser Gly His Gly Ser Gly Ser Glu
    610                 615                 620

Pro Pro Gly Leu His Ala Pro His Arg Glu Gln Gln Leu Ala Met His
625                 630                 635                 640

Ser Asn Glu Pro Ala Gly Glu Gly Trp His Arg Leu Ser Asp Glu Ala
                645                 650                 655

Val Asp Pro Gln Tyr Gly Glu Pro Leu Ser Arg His Trp Asp Phe Thr
            660                 665                 670

Asp Asn Pro Ala Asp Arg Ser Arg Ile Asn Pro Val Val Ala Gln Leu
        675                 680                 685

Met Glu Asp Pro Asn Ala Pro Phe Gly Arg Asp Pro Gln Gly Gln Pro
    690                 695                 700

Tyr Thr Gln Glu Arg Tyr Gln Glu Arg Phe Asn Ser Val Gly Pro Trp
705                 710                 715                 720

Gly Gln Gln Tyr Ser Asn Phe Pro Pro Asn Asn Gly Ala Val Pro Gly
                725                 730                 735
```

-continued

```
Thr Arg Ile Ala Tyr Thr Asn Leu Glu Lys Phe Leu Ser Asp Tyr Gly
            740                 745                 750

Pro Gln Leu Asp Arg Ile Gly Gly Asp Gln Gly Lys Tyr Leu Ala Ile
        755                 760                 765

Met Glu His Gly Arg Pro Ala Ser Trp Glu Gln Arg Ala Leu His Val
    770                 775                 780

Thr Ser Leu Arg Asp Pro Tyr His Ala Tyr Thr Ile Asp Trp Leu Pro
785                 790                 795                 800

Glu Gly Trp Phe Ile Glu Val Ser Glu Val Ala Pro Gly Cys Gly Gln
                805                 810                 815

Pro Gly Gly Ser Ile Gln Val Arg Ile Phe Asp His Gln Asn Glu Met
            820                 825                 830

Arg Lys Val Glu Glu Leu Ile Arg Arg Gly Val Leu Arg Gln
        835                 840                 845
```

<210> SEQ ID NO 276
<211> LENGTH: 2538
<212> TYPE: DNA
<213> ORGANISM: Mycobacterium tuberculosis

<400> SEQUENCE: 276

```
atggcgccgt tggcggtcga tcccgcggcc cttgatagcg cgggcggcgc ggtggtggct      60

gcgggtgcgg gtttgggtgc ggtgatctcg tcgctgaccg cggcgctggc cgggtgtgcg     120

gggatggccg gtgatgatcc ggctggggcg gtgttcgggc gctcctatga cggttcggcg     180

gccgcgctgg tgcaggcgat gtcggtggcg cgcaacggat tgtgcaacct cggcgatggg     240

gtgcgcatga gcgcgcacaa ctactcgttg gccgaggcga tgtcggatgt cgctgggcgg     300

gcggcgccgt tgccggcgcc gccgccgagc ggctgtgtcg gcgtgggtgc gccgccgtcg     360

gcggtcggtg gcggcggtgg cgccccgaag ggctgggggt gggtggcccc gtatatcggg     420

atgatctggc cgaacgggga ttcgacaaag ctacgtgcgg cggctgtggc gtggcgcagc     480

gcgggcacgc agttcgcgct gactgagatt cagtcgacgg cggggccgat gggcgttatt     540

cgcgcccagc agctcccgga ggcggggctg atcgagtcgg cgtttgctga cgcgtacgcc     600

agcaccaccg ctgtcgtggg ccaatgccac cagctggcgg cccagctaga cgcctatgcc     660

gcccgcatcg acgcggtgca tgcggcggtc ctggatttgt tggcccgcat ctgcgatccg     720

ctgaccggga tcaaagaggt gtgggagttt ctgaccgacc aggacgaaga cgagatccag     780

cgcatcgccc atgacatcgc ggtggtggtc gaccagttca gcggggaagt ggacgcgttg     840

gctgcggaga tcaccgcggt ggtgtcgcac gccgaggcgg tgatcaccgc gatggcagac     900

cacgcaggca aacaatggga tcggttcttg cacagcaacc cggtgggtgt ggtcatcgat     960

ggcaccgggc agcagctcaa aggcttcggc gaggaggcct tcgggatggc caaggactcc    1020

tgggacctag ggccactgcg cgcctcgata gacccgttcg ggtggtatcg ctcctgggag    1080

gagatgctga ctgggatggc gccgctggcg ggcctgggcg gcgagaacgc tcccggcgtt    1140

gtggagtcgt ggaagcagtt cggcaaaagc ctcatccatt gggatgagtg gacgaccaac    1200

cctaatgagg cgctaggcaa gaccgtattc gacgccgcga cgctagcttt gccgggcggg    1260

ccgctgtcga aacttggcag caagggccgc gacattctcg cgggcgtgcg aggcctcaag    1320

gagcggcttg agccgacgac accgcacctt gagcccccag caacgccgcc gcggccagga    1380

ccgcaaccac cacggatcga accaccagaa tcgggccacc cggcacccgc gcccgcggcg    1440

aaaccggcgc ccgtgcccgc caacggtcca ctgccgcaca gccccaccga atccaaaccg    1500

ccgcccgtcg acagaccggc tgaaccggtg gcgccgtcgt cggcgtcggc aggccagccc    1560
```

```
cgggtatccg cagccaccac gcccggcaca catgtgccgc atggcctgcc gcaaccgggt   1620

gaacatgtcc cggcgcaagc accaccggcg acgacgttgc ttggcggacc tcctgtcgag   1680

tcagcgcccg ctaccgcgca ccaaccccag tgggcgacca caccagcagc acccgcggcg   1740

gcgccgcatt ccacgcccgg aggcgttcac tcaaccgaat cggggcctca cggccgatca   1800

ctgagcgcac acggatccga gccgacccac gacggtgcgt ctcacgggtc aggccacggt   1860

agcggtagcg agccacctgg gctgcatgcg ccgcatcgcg agcagcagct tgcaatgcat   1920

tcgaacgaac cagctggaga gggttggcat cggttatccg acgaagcggt tgacccgcag   1980

tatggcgagc cattatcgcg ccactgggac tttacagaca atccggccga tcgcagtcgg   2040

ataaacccgg ttgtggccca gctcatggag gaccccaacg ccccattcgg ccgcgatcct   2100

cagggacagc cctataccca agaacggtat caagagcgat ttaatagtgt aggcccatgg   2160

ggccagcagt actctaattt tccgcctaac aatggtgcgg ttccagggac aaggatcgcc   2220

tacactaatc tcgaaaaatt tcttagtgac tacggccccc agctagatcg tataggcggc   2280

gatcagggca agtacctggc gatcatggaa catgggcgcc cggcatcatg ggaacaacgt   2340

gccctgcacg tgacgtcgtt acgcgacccc taccacgcgt ataccattga ttggttgcct   2400

gagggatggt tcatcgaagt atctgaggtc gcgccggggt gcggccagcc gggcggatcc   2460

atccaagtgc ggatattcga tcatcagaac gagatgcgca aagtggaaga gttaataagg   2520

cgcggggtgt tgcgacag                                                 2538
```

<210> SEQ ID NO 277
<211> LENGTH: 115
<212> TYPE: PRT
<213> ORGANISM: Mycobacterium tuberculosis

<400> SEQUENCE: 277

```
Met Phe Leu Ala Gly Val Leu Cys Met Cys Ala Ala Ala Ala Ser Ala
1               5                   10                  15

Leu Phe Gly Ser Trp Ser Leu Cys His Thr Pro Thr Ala Asp Pro Thr
            20                  25                  30

Ala Leu Ala Leu Arg Ala Met Ala Pro Thr Gln Leu Ala Ala Ala Val
        35                  40                  45

Met Leu Ala Ala Gly Gly Val Val Ala Val Ala Ala Pro Gly His Thr
    50                  55                  60

Ala Leu Met Val Val Ile Val Cys Ile Ala Gly Ala Val Gly Thr Leu
65                  70                  75                  80

Ala Ala Gly Ser Trp Gln Ser Ala Gln Tyr Ala Leu Arg Arg Glu Thr
                85                  90                  95

Ala Ser Pro Thr Ala Asn Cys Val Gly Ser Cys Ala Val Cys Thr Gln
            100                 105                 110

Ala Cys His
        115
```

<210> SEQ ID NO 278
<211> LENGTH: 345
<212> TYPE: DNA
<213> ORGANISM: Mycobacterium tuberculosis

<400> SEQUENCE: 278

```
atgttcctcg cgggtgtgct gtgcatgtgt gcggcggcgg cgtccgccct gttcgggagc     60

tggtcgctgt gccatacgcc cactgccgac ccccacggcgc tggcgctgcg cgcgatggcg   120

cccacgcagt tggcagccgc agtaatgctg gccgccgggg gagtggtggc ggtggccgcg    180
```

```
cccgggcaca ccgccttgat ggtggtgatc gtctgcattg cgggcgcggt cggcacgctg    240

gccgcggggt cgtggcagag cgcccagtac gcgctgcgcc gtgaaaccgc tagccccacc    300

gccaactgcg ttggcagctg cgcggtctgc acccaggcct gtcat                    345
```

<210> SEQ ID NO 279
<211> LENGTH: 236
<212> TYPE: PRT
<213> ORGANISM: Mycobacterium tuberculosis

<400> SEQUENCE: 279

```
Met Gly Gly Met Asp Thr Gly Val Thr Ser Pro Arg Val Leu Val Val
1               5                   10                  15

Asp Asp Asp Ser Asp Val Leu Ala Ser Leu Glu Arg Gly Leu Arg Leu
            20                  25                  30

Ser Gly Phe Glu Val Ala Thr Ala Val Asp Gly Ala Glu Ala Leu Arg
        35                  40                  45

Ser Ala Thr Glu Asn Arg Pro Asp Ala Ile Val Leu Asp Ile Asn Met
    50                  55                  60

Pro Val Leu Asp Gly Val Ser Val Val Thr Ala Leu Arg Ala Met Asp
65                  70                  75                  80

Asn Asp Val Pro Val Cys Val Leu Ser Ala Arg Ser Ser Val Asp Asp
                85                  90                  95

Arg Val Ala Gly Leu Glu Ala Gly Ala Asp Asp Tyr Leu Val Lys Pro
            100                 105                 110

Phe Val Leu Ala Glu Leu Val Ala Arg Val Lys Ala Leu Leu Arg Arg
        115                 120                 125

Arg Gly Ser Thr Ala Thr Ser Ser Ser Glu Thr Ile Thr Val Gly Pro
    130                 135                 140

Leu Glu Val Asp Ile Pro Gly Arg Arg Ala Arg Val Asn Gly Val Asp
145                 150                 155                 160

Val Asp Leu Thr Lys Arg Glu Phe Asp Leu Leu Ala Val Leu Ala Glu
                165                 170                 175

His Lys Thr Ala Val Leu Ser Arg Ala Gln Leu Leu Glu Leu Val Trp
            180                 185                 190

Gly Tyr Asp Phe Ala Ala Asp Thr Asn Val Val Asp Val Phe Ile Gly
        195                 200                 205

Tyr Leu Arg Arg Lys Leu Glu Ala Gly Gly Gly Pro Arg Leu Leu His
    210                 215                 220

Thr Val Arg Gly Val Gly Phe Val Leu Arg Met Gln
225                 230                 235
```

<210> SEQ ID NO 280
<211> LENGTH: 708
<212> TYPE: DNA
<213> ORGANISM: Mycobacterium tuberculosis

<400> SEQUENCE: 280

```
atgggcggca tggacactgg tgtgacctca cctcgggtgt tggtcgtcga cgacgactcc     60

gatgtgctcg cctcgctgga acgcggctta cggctgtccg gattcgaggt agcgaccgcg    120

gtggacggcg ccgaggcctt gcgcagcgcc accgagaacc ggccggacgc gatcgtgctc    180

gacatcaaca tgccagtgct cgatggagtc agcgtcgtga cggcactacg cgcgatggac    240

aacgacgtcc cggtctgtgt gctatccgca cgcagctctg tcgatgaccg agtggccgga    300

ttggaggccg gcgccgacga ttacctggtg aaaccgttcg tgctggccga gctggtggca    360
```

-continued

```
cgggtgaagg cgctgctgcg ccgccgcggc tccactgcaa cgtcgtcctc ggaaaccatc    420

acggtgggcc cgctggaggt ggacatcccc ggccggcggg cccgggtcaa cggcgtcgac    480

gtcgacctga ccaagcgcga attcgacctg ctcgcggtgc tggccgagca caagaccgcg    540

gtgctctccc gagcgcaact cctggaattg gtgtggggct acgacttcgc cgccgacacc    600

aacgtggtgg acgtcttcat cgggtacctg cggcgcaaac tggaggccgg cggtggccct    660

aggctgctgc ataccgtccg cggagtcgga ttcgtgctgc gtatgcag                 708
```

```
<210> SEQ ID NO 281
<211> LENGTH: 112
<212> TYPE: PRT
<213> ORGANISM: Mycobacterium tuberculosis

<400> SEQUENCE: 281

Met Ala Ala Leu Val Arg Glu Val Val Gly Asp Val Leu Arg Gly Ala
1               5                   10                  15

Arg Met Ser Gln Gly Arg Thr Leu Arg Glu Val Ser Asp Ser Ala Arg
            20                  25                  30

Val Ser Leu Gly Tyr Leu Ser Glu Ile Glu Arg Gly Arg Lys Glu Pro
        35                  40                  45

Ser Ser Glu Leu Leu Ser Ala Ile Cys Thr Ala Leu Gln Leu Pro Leu
    50                  55                  60

Ser Val Val Leu Ile Asp Ala Gly Glu Arg Met Ala Arg Gln Glu Arg
65                  70                  75                  80

Leu Ala Arg Ala Thr Pro Ala Gly Arg Ala Thr Gly Ala Thr Ile Asp
                85                  90                  95

Ala Ser Thr Lys Val Val Ile Ala Pro Val Val Ser Leu Ala Val Ala
            100                 105                 110
```

```
<210> SEQ ID NO 282
<211> LENGTH: 336
<212> TYPE: DNA
<213> ORGANISM: Mycobacterium tuberculosis

<400> SEQUENCE: 282

atggcggctt tggtgcgtga ggtcgttggt gacgtgctgc gcggagcgcg gatgtcgcag     60

ggtcggacgc tgcgcgaggt gtccgattcg gcgcgggtga gcctcgggta tctgtcggag    120

atcgagcgcg gtcgcaagga gccttccagc gagctgctca gtgcgatttg tacggctctg    180

cagctcccgt tgtcggtggt gctcatcgat gcgggcgagc ggatggcgcg tcaagagcgc    240

cttgcccgcg ccaccccggc tggcagagca accggcgcca ccattgacgc cagcaccaag    300

gtcgtcattg cgccggtggt gtcgctggcg gtggcc                              336
```

MYCOBACTERIAL ANTIGENS EXPRESSED DURING LATENCY

CROSS REFERENCE TO RELATED APPLICATION

This application is a divisional application of co-pending U.S. application Ser. No. 12/140,163, now U.S. Pat. No. 8,003,776, filed on Jun. 16, 2008, which is a divisional of U.S. application Ser. No. 10/482,706, now U.S. Pat. No. 7,393,540, filed Jul. 19, 2004 having international filing date Jul. 4, 2002, entitled "MYCOBACTERIAL ANTIGENS EXPRESSED DURING LATENCY."

SEQUENCE LISTING INCORPORATION BY REFERENCE

A sequence listing in an ASCII text file, having the name "MSQ01-012-DIV2-US_SEQUENCE_LISTING_AS_FILED.txt", created on 22 Aug. 2011, and having a size of 606 kb, is hereby incorporated by reference in its entirety.

The present invention relates to a method of identifying a gene in mycobacteria the expression of which is induced or up-regulated during mycobacterial latency, to the isolated peptide products, variants, derivatives or fragments thereof, to antibodies that bind to said peptides, variants, derivatives or fragments, to DNA and RNA vectors that express said peptides, variants, derivatives or fragments, to attenuated mycobacteria in which the activity of at least one of said induced or up-regulated genes has been modified, to vaccines against mycobacterial infections, and to methods of detecting the presence of a mycobacterial infection.

Many microorganisms are capable of forming intracellular infections. These include: infections caused by species of *Salmonella, Yersinia, Shigella, Campylobacter, Chlamydia* and *Mycobacteria*. Some of these infections are exclusively intracellular, others contain both intracellular and extracellular components. However, it is the intracellular survival cycle of bacterial infection which is suspected as a main supportive factor for disease progression.

Generally, these microorganisms do not circulate freely in the body, for example, in the bloodstream, and are often not amenable to drug treatment regimes. Where drugs are available, this problem has been exacerbated by the development of multiple drug resistant microorganisms.

A number of factors have contributed to the problem of microbial resistance. One is the accumulation of mutations over time and the subsequent horizontal and vertical transfer of the mutated genes to other organisms. Thus, for a given pathogen, entire classes of antibiotics have been rendered inactive. A further factor has been the absence of a new class of antibiotics in recent years. The emergence of multiple drug-resistant pathogenic bacteria represents a serious threat to public health and new forms of therapy are urgently required.

For similar reasons, vaccine therapies have not proved effective against such intracellular microorganisms. Also, increased systemic concentration of antibiotics to improve bioavailability within cells may result in severe side effects.

*Mycobacterium tuberculosis* (TB) and closely related species make up a small group of mycobacteria known as the *Mycobacterium tuberculosis* complex (MTC). This group comprises four species *M. tuberculosis, M. microti, M. bovis* and *M. africanum* which are the causative agent in the majority of tuberculosis (TB) cases throughout the world.

*M. tuberculosis* is responsible for more than three million deaths a year world-wide. Other mycobacteria are also pathogenic in man and animals, for example *M. avium* subsp. *paratuberculosis* which causes Johne's disease in ruminants, *M. bovis* which causes tuberculosis in cattle, *M. avium* and *M. intracellulare* which cause tuberculosis in immunocompromised patients (eg. AIDS patients, and bone marrow transplant patients) and *M. leprae* which causes leprosy in humans. Another important mycobacterial species is *M. vaccae*.

*M. tuberculosis* infects macrophage cells within the body. Soon after macrophage infection, most *M. tuberculosis* bacteria enter and replicate within cellular phagosome vesicles, where the bacteria are sequestered from host defences and extracellular factors.

It is the intracellular survival and multiplication or replication of bacterial infection which is suspected as a main supportive factor for mycobacterial disease progression.

A number of drug therapy regimens have been proposed for combating *M. tuberculosis* infections, and currently combination therapy including the drug isoniazid has proved most effective. However, one problem with such treatment regimes is that they are long-term, and failure to complete such treatment can promote the development of multiple drug resistant microorganisms.

A further problem is that of providing an adequate bioavailability of the drug within the cells to be treated. Whilst it is possible to increase the systemic concentration of a drug (eg. by administering a higher dosage) this may result in severe side effects caused by the increased drug concentration.

The effectiveness of vaccine prevention against *M. tuberculosis* has varied widely. The current *M. tuberculosis* vaccine, BCG, is an attenuated strain of *M. bovis*. It is effective against severe complications of TB in children, but it varies greatly in its effectiveness in adults particularly across ethnic groups. BCG vaccination has been used to prevent tuberculous meningitis and helps prevent the spread of *M. tuberculosis* to extra-pulmonary sites, but does not prevent infection.

The limited efficacy of BCG and the global prevalence of TB has led to an international effort to generate new, more effective vaccines. The current paradigm is that protection will be mediated by the stimulation of a Th1 immune response.

BCG vaccination in man was given orally when originally introduced, but that route was discontinued because of loss of viable BCG during gastric passage and of frequent cervical adenopathy. In experimental animal species, aerosol or intratracheal delivery of BCG has been achieved without adverse effects, but has varied in efficacy from superior protection than parenteral inoculation in primates, mice and guinea pigs to no apparent advantage over the subcutaneous route in other studies.

There is therefore a need for an improved and/or alternative vaccine or therapeutic agent for combating mycobacterial infections.

An additional major problem associated with the control of mycobacterial infections, especially *M. tuberculosis* infections, is the presence of a large reservoir of asymptomatic individuals infected with mycobacteria. Dormant mycobacteria are even more resistant to front-line drugs.

Infection with mycobacteria (eg. *M. tuberculosis*) rarely leads to active disease, and most individuals develop a latent infection which may persist for many years before reactivating to cause disease (Wayne, 1994). The current strategy for controlling such infection is early detection and treatment of patients with active disease. Whilst this is essential to avoid deaths and control transmission, it has no effect on eliminating the existing reservoir of infection or on preventing new cases of disease through reactivation.

Conventional mycobacterial vaccines, including BCG, protect against disease and not against infection. Ideally a new mycobacterial vaccine will impart sterile immunity, and a post-exposure vaccine capable of boosting the immune system to kill latent mycobacteria or prevent reactivation to active disease-causing microorganisms would also be valuable against latent infection.

Conventional detection of latent mycobacterial infection by skin testing may be compromised. For example, current TB detection methods based on tuberculin skin testing are compromised by BCG vaccination and by exposure to environmental mycobacteria.

New strategies are therefore required for more effective diagnosis, treatment and prevention of mycobacterial latent infection.

To develop specific strategies for addressing latent mycobacterial infection it is necessary to elucidate the physiological, biochemical and molecular properties of these microorganisms.

At present, there is no suitable in vivo model for studying mycobacterial latent infection and such a model is unlikely to provide sufficient microbial material to enable detailed analysis of the physiological and molecular changes that occur.

Studies to date have used either static cultures which allow tubercle bacilli to generate oxygen-depletion gradients and enter a non-replicating persistent state in the sediment layer, or agitated sealed liquid cultures (Wayne and Lin, 1982; Cunningham and Spreadbury, 1998; Wayne and Hayes, 1996). Transition to a non-replicating persistent state in these models coincides with a shift-down to glyoxylate metabolism, resistance to isoniazid and rifampicin and susceptibility to the anaerobic bactericidal action of metronidazole (Wayne and Hayes, 1996).

For example, a number of publications have described the analysis of mycobacterial gene and protein expression profiles following exposure of the mycobacteria to various environmental stimuli. These include Sherman, D. R. et al (2001) PNAS, vol. 98, no. 13, pp. 7534-7539; Hutter, B. (2000) FEMS Microbiol. Letts. 188, pp. 141-146; Michele, T. M. et al. (1999) Antimicrobial Agents and Chemotherapy, vol. 43, no. 2, pp. 216-225; Yuan, Y. et al. (1998) PNAS, vol. 95, pp. 9578-9583; Boon, C. et al (2001) J. Bacteriol., vol. 183, no. 8, pp. 2672-2676; Cunningham, A. F. et al (1998) J. Bacteriol., vol. 180, no. 4, pp. 801-808; Murugasu-Oei, B. et al (1999) Mol. Gen. Genet., vol. 262, pp. 677-682; and a number of patent publications such as WO99/24067, WO99/04005, WO97/35611, and WO92/08484. The mycobacteria employed in these analyses have been grown in crude, batch systems, with the result that there is little or no control of the environmental stimuli to which the mycobacteria have been exposed. Accordingly, the bacteria experience a large number of complex, interactive environmental stimuli, some of which may have rapid and transient effects in terms of gene and protein expression.

Such studies are poorly defined and controlled, and experiments relying on self-generated oxygen-depletion gradients have yielded inconsistent results. In addition, the described studies have been conducted over a relatively short duration in terms of post-inoculation growth, in many cases up to approximately 2 weeks post-inoculation, with the result that the cultured bacteria are exposed to environmental stimuli associated with the mid to late exponential phase, and/or the early stationary phase.

In view of the above, there is a need for a defined and controlled model for studying mycobacterial (eg. TB) persistence which simulates key features of the in vivo environment.

According to a first aspect of the present invention there is provided an isolated mycobacterial peptide, or a fragment or derivative or variant of said peptide, wherein the peptide is encoded by a mycobacterial gene the expression of which is induced or up-regulated under culture conditions that are nutrient-starving and which maintain mycobacterial latency, said conditions being obtainable by batch fermentation of a mycobacterium for at least 20 days post-inoculation, when compared with culture conditions that are not nutrient-starving and which support exponential growth of said mycobacterium.

Latency is synonymous with persistence. These terms describe a reversible state of low metabolic activity in which mycobacterial cells can survive for extended periods without cell division.

In contrast to the various prior art analyses, the present invention is concerned with the induction or up-regulation of mycobacterial genes (and the corresponding gene products) during long term latency conditions rather than during the onset of latency (ie. late exponential phase, or early stationary phase).

The preferred culture method of the present invention is that of batch fermenter culture. This method permits careful monitoring and control of growth culture parameters such as pH, temperature, available nutrients, and dissolved oxygen tension (DOT). In particular, temperature and DOT may be strictly controlled. In contrast, careful monitoring and control is not possible with convention, crude batch culture systems, with the result that mycobacteria cultured by such systems are exposed to a multiplicity of complex, interactive environmental stimuli, some of which may have rapid and transient effects in terms of gene and protein expression. Thus, the batch fermenter system of the present invention allows relatively careful control of environmental stimuli so that a mycobacterial response to a particular stimulus (eg. nutrient starvation) can be analysed in relative isolation from other environmental stimuli that may otherwise obscure or modify the particular mycobacterial response of interest.

In use of the present method it is possible to ensure that the principal latency induction parameter employed is starvation of carbon, and preferably the starvation of carbon and energy. This means that the accidental induction or up-regulation of genes that are solely responsive to other environmental switches may be substantially prevented. Accordingly, false-positive identification of genes that are induced or up-regulated under conditions unrelated to carbon starvation and/or energy limitation may be substantially avoided.

The term "nutrient-starving" in the context of the present invention means that the concentration of the primary carbon, and preferably the primary energy source, is insufficient to support growth of the mycobacteria. "Nutrient-starving" is a term associated with an established mid to late stationary phase of a batch culture growth curve. Under such conditions the mycobacteria are metabolically stressed, rather than simply reduced in growth rate.

In more detail, exponential growth is that period of growth which is associated with a logarithmic increase in mycobacterial cell mass (also known as the "log" phase) in which the bacteria are multiplying at a maximum specific growth rate for the prevailing culture conditions. During this period of growth the concentrations of essential nutrients diminish and those of end products increase. However, once the primary carbon and/or primary energy source falls to below a critical level, it is no longer possible for all of the mycobacterial cells within the culture to obtain sufficient carbon and/or energy needed to support optimal cellular function and cell division. Once this occurs, exponential growth slows and the mycobacteria enter stationary phase. Thereafter, the mycobacteria become nutrient starved, and enter latency. It is this latent state in the growth phase, rather than the late exponential phase or early stationary phase, with which the present invention is concerned.

Carbon starvation refers to a growth state in which the concentration of exogenous carbon is insufficient to enable the bacteria to grow and or replicate. However, when in this state, there may be other energy sources (eg. endogenous reserves, secondary metabolites) that are available to maintain essential cellular functions and viability without supporting growth. Thus, carbon starvation is associated with a mid or late stationary phase condition in which the exogenous carbon source has become depleted and bacterial growth has substantially ceased. In terms of a batch fermenter culture of mycobacteria, this typically occurs at 20 days (or later) post inoculation.

The onset of stationary phase vis-a-vis the time of inoculation will depend on a number of factors such as the particular mycobacterial species/strain, the composition of the culture media (eg. the particular primary carbon and energy source), and the physical culture parameters employed.

However, as a guide, the end of exponential phase and the onset of stationary phase generally corresponds to that point in the growth phase associated with the maximum number of viable counts of mycobacteria.

In use of the present invention, the exponential phase mycobacterial cells are harvested from the culture vessel at a point in the growth phase before the maximum number of total viable counts has been achieved. This point in the growth phase may be mimicked under continuous culture conditions employing a steady state growth rate approximating $\mu_{max}$ and providing a generation time of approximately 18-24 hours. In a preferred embodiment, the exponential phase mycobacterial cells are harvested when a value of between 2 and 0.5 (more preferably between 1 and 0.5) log units of viable counts per ml of culture medium less than the maximum number of viable counts per ml of culture medium has been achieved. Thus, the "exponential" phase cells are generally harvested during mid-log phase.

For example, if the maximum viable count value is $1\times10^{10}$ per ml, then the "exponential" phase cells would be preferably harvested once a value of between $1\times10^{8}$ and $1\times10^{9.5}$ (more preferably between $1\times10^{9}$ and $1\times10^{9.5}$) viable counts per ml has been achieved. In the case of *M. tuberculosis*, this would be approximately 3-10, preferably 4-7 days post-inoculation.

In use of the present invention, the nutrient-starved, batch fermenter cultured mycobacterial cells are harvested from the culture vessel at a point in the growth phase after the maximum number of total viable counts has been achieved. This point in the growth phase may be mimicked under continuous culture conditions supporting a generation time of at least 3 days. In a preferred embodiment, the stationary phase mycobacterial cells are harvested when the viable counts per ml of culture medium has fallen by at least 0.5, preferably at least 1, more preferably at least 2 log units less than the maximum number of viable counts per ml of culture medium. Thus, the nutrient-starved cells are generally harvested during mid- to late-stationary phase.

For example, if the maximum viable count value is $1\times10^{10}$ per ml, then the stationary phase cells would be preferably harvested once the viable count number had fallen to a value of at least $1\times10^{9.5}$, preferably at least $1\times10^{9}$, more preferably at least $1\times10^{8}$ viable counts per ml. In the case of *M. tuberculosis*, this would be approximately at least day 20, preferably at least day 30, typically day 40-50 post-inoculation. Longer post-inoculation harvesting times of at least 100 days, even at least 150 days may be employed. For mycobacteria generally, the mid to late stationary phase cells are preferably harvested at least 20 days, preferably at least 30 days, more preferably at least 40 days post-inoculation.

Suitable media for culturing mycobacteria are described in Wayne, L. G. (1994) [in Tuberculosis: Pathogenesis, Protection, and Control published by the American Society for Microbiology, pp. 73-83]. These include Middlebrook 7H9 Medium [see Barker, L. P., et al. (1998) Molec. Microbiol., vol. 29(5), pp. 1167-1177], and WO00/52139 in the name of the present Applicant.

In use of the batch fermenter culture method, the starting concentration of the primary carbon source (and preferably the primary energy source) is at least 0.5, preferably at least 1 $gl^{-1}$ of culture medium. Such concentrations are considered to be not nutrient-starving. Conversely, "nutrient-starving" conditions are associated with a primary carbon and energy source concentration of less than 0.5, preferably less than 0.2, and more preferably less than 0.1 $gl^{-1}$ of culture medium. The preferred carbon and energy source is glycerol.

In a preferred embodiment, the starting concentration of glycerol is at least 1, preferably 1-3, more preferably approximately 2 $gl^{-1}$ of culture medium. The onset of "nutrient-starving" conditions is associated with a concentration of less than 0.2, preferably less than 0.1 $gl^{-1}$ of culture medium.

Other primary carbon and energy sources may be employed such as glucose, pyruvate, and fatty acids (eg. palmitate, and butyrate). These sources may be employed at substantially the same concentrations as for glycerol.

The pH of the culture medium is preferably maintained between pH 6 and 8, more preferably between pH 6.5 and 7.5, most preferably at about pH 6.9.

In one embodiment, the dissolved oxygen tension (DOT) is maintained throughout the culture process at least 40% air saturation, more preferably between 50 and 70% air saturation, most preferably at 50% air saturation.

The dissolved oxygen tension parameter is calculated by means of an oxygen electrode and conventional laboratory techniques. Thus, 100% air saturation corresponds to a solution that is saturated with air, whereas 0% corresponds to a solution that has been thoroughly purged with an inert gas such as nitrogen. Calibration is performed under standard atmospheric pressure conditions and measured at 37° C., and with conventional air comprising approximately 21% oxygen.

In another embodiment of the present invention, latency may be induced by a combination of carbon and/or energy source starvation, and a low DOT.

In a preferred embodiment, the DOT is maintained at least 40% air saturation, more preferably between 50 and 70% air saturation, until the mycobacterial culture has entered early-mid log phase. The DOT may be then lowered so as to become limiting, for example in increments over a 5 or 6 day period, and the culture maintained at a DOT of 0-10, preferably at a DOT of approximately 5% until the stationary phase cells are harvested.

The carbon and energy starvation, and optional low oxygen tension latency induction conditions of the present invention are culture conditions that are conducive for a mycobacterium to express at least one gene which would be normally expressed in vivo during latency of the mycobacterium's natural target environment which is believed to involve a low carbon and energy, and low oxygen environment.

The mycobacterium is selected from the species *M. phlei, M. smegmatis, M. africanum, M. caneti, M. fortuitum, M. marinum, M. ulcerans, M. tuberculosis, M. bovis, M. microti,*

*M. avium, M. paratuberculosis, M. leprae, M. lepraemurium, M. intracellulare, M. scrofulaceum, M. xenopi, M. genavense, M. kansasii, M. simiae, M. szulgai, M. haemophilum, M. asiaticum, M. malmoense, M. vaccae* and *M. shimoidei*. Of particular interest are members of the MTC, preferably *M. tuberculosis*.

In use, it is preferred that those genes (ie. as represented by cDNAs in the detection assay) which are up-regulated by at least 1.5-fold under stationary phase conditions vis-a-vis exponential phase conditions are selected. In more preferred embodiments, the corresponding up-regulation selection criterium is at least 2-fold, more preferably 3-fold, most preferably 4-fold. In further embodiments up-regulation levels of at least 10-fold, preferably 50-fold may be employed.

The term peptide throughout this specification is synonymous with protein.

Use of mycobacterial peptide compositions, which peptides are associated with mycobacterial latency, provide excellent vaccine candidates for targeting latent mycobacteria in asymptomatic patients infected with mycobacteria.

The terms "isolated," "substantially pure," and "substantially homogenous" are used interchangeably to describe a peptide which has been separated from components which naturally accompany it. A peptide is substantially pure when at least about 60 to 75% of a sample exhibits a single peptide sequence. A substantially pure peptide will typically comprise about 60 to 90% w/w of a protein sample, more usually about 95%, and preferably will be over about 99% pure. Peptide purity or homogeneity may be indicated by, for example, polyacrylamide gel electrophoresis of a protein sample, followed by visualizing a single polypeptide band upon staining the gel. Alternatively, higher resolution may be provided by using, for example, HPLC. A peptide is considered to be isolated when it is separated from the contaminants which accompany it in its natural state. Thus, a peptide which is chemically synthesized or synthesized in a cellular system different from the cell from which it naturally originates will be substantially free from its naturally associated components. The present invention provides peptides which may be purified from mycobacteria as well as from other types of cells transformed with recombinant nucleic acids encoding these peptides. If desirable, the amino acid sequence of the proteins of the present invention may be determined by protein sequencing methods.

The terms "peptide", "oligopeptide", "polypeptide", and "protein" are used interchangeably and do not refer to a specific length of the product. These terms embrace post-translational modifications such as glycosylation, acetylation, and phosphorylation.

The term "fragment" means a peptide having at least five, preferably at least ten, more preferably at least twenty, and most preferably at least thirty-five amino acid residues of the peptide which is the gene product of the induced or up-regulated gene in question. The fragment preferably includes an epitope of the gene product in question.

The term "variant" means a peptide or peptide "fragment" having at least seventy, preferably at least eighty, more preferably at least ninety percent amino acid sequence homology with the peptide that is the gene product of the induced or up-regulated gene in question. An example of a "variant" is a peptide or peptide fragment of an induced/up-regulated gene which contains one or more analogues of an amino acid (eg. an unnatural amino acid), or a substituted linkage. The terms "homology" and "identity" are considered synonymous in this specification. In a further embodiment, a "variant" may be a mimic of the peptide or peptide fragment, which mimic reproduces at least one epitope of the peptide or peptide fragment. The mimic may be, for example, a nucleic acid mimic, preferably a DNA mimic.

For sequence comparison, typically one sequence acts as a reference sequence, to which test sequences may be compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Optimal alignment of sequences for comparison may be conducted, for example, by the local homology alignment algorithm of Smith and Waterman [Adv. Appl. Math. 2: 484 (1981)], by the algorithm of Needleman & Wunsch [J. Mol. Biol. 48: 443 (1970)] by the search for similarity method of Pearson & Lipman [Proc. Nat'l. Acad. Sci. USA 85: 2444 (1988)], by computer implementations of these algorithms (GAP, BESTFIT, FASTA, and TFASTA—Sequence Analysis Software Package of the Genetics Computer Group, University of Wisconsin Biotechnology Center, 1710 University Avenue, Madison, Wis. 53705), or by visual inspection [see Current Protocols in Molecular Biology, F. M. Ausbel et al, eds, Current Protocols, a joint venture between Greene Publishing Associates, Inc. and John Wiley & Sons, Inc. (1995 Supplement) Ausbubel].

Examples of algorithms suitable for determining percent sequence similarity are the BLAST and BLAST 2.0 algorithms [see Altschul (1990) J. Mol. Biol. 215: pp. 403-410; and www.ncbi.nlm.nih.gov/" of the National Center for Biotechnology Information].

In a preferred homology comparison, the identity exists over a region of the sequences that is at least 10 amino acid residues in length.

The term "derivative" means a peptide comprising the peptide (or fragment, or variant thereof) which is the gene product of the induced or up-regulated gene in question. Thus, a derivative may include the peptide in question, and a further peptide sequence which may introduce one or more additional epitopes. The further peptide sequence should preferably not interfere with the basic folding and thus conformational structure of the peptide in question. Examples of a "derivative" are a fusion protein, a conjugate, and a graft. Thus, two or more peptides (or fragments, or variants) may be joined together to form a derivative. Alternatively, a peptide (or fragment, or variant) may be joined to an unrelated molecule (eg. a peptide). Derivatives may be chemically synthesized, but will be typically prepared by recombinant nucleic acid methods. Additional components such as lipid, and/or polysaccharide, and/or polyketide components may be included.

All of the molecules "fragment", "variant" and "derivative" have a common antigenic cross-reactivity and/or substantially the same in vivo biological activity as the gene product of the induced or up-regulated gene in question from which they are derived. For example, an antibody capable of binding to a fragment, variant or derivative would be also capable of binding to the gene product of the induced or up-regulated gene in question. It is a preferred feature that the fragment, variant and derivative each possess the active site of the peptide which is the induced or up-regulated peptide in question. Alternatively, all of the above embodiments of a peptide of the present invention share a common ability to induce a "recall response" of a T-lymphocyte which has been previously exposed to an antigenic component of a mycobacterial infection.

In a preferred embodiment, the peptide is selected from the group consisting of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279 and 281.

According to a second aspect of the invention there is provided a method of identifying a mycobacterial gene the expression of which is induced or up-regulated during mycobacterial latency, said method comprising:— culturing a first mycobacterium under culture conditions that are nutrient-starving and which maintain mycobacterial latency, said conditions being obtainable by batch fermentation of the first mycobacterium for at least 20 days post-inoculation;

culturing a second mycobacterium under culture conditions that are not nutrient-starving and which support exponential growth of the second mycobacterium;

obtaining first and second mRNA populations from said first and second mycobacteria respectively, wherein said first mRNA population is obtained from the first mycobacterium which has been cultured under nutrient-starving conditions obtainable by batch fermentation of the first mycobacterium for at least 20 days post-inoculation, and wherein said second mRNA is obtained from the second mycobacterium which has been cultured under conditions that are not nutrient-starving and which support exponential growth of said second mycobacterium;

preparing first and second cDNA populations from said first and second mRNA populations respectively, during which cDNA preparation a detectable label is introduced into the cDNA molecules of the first and second cDNA populations;

isolating corresponding first and second cDNA molecules from the first and second cDNA populations, respectively;

comparing relative amounts of label or corresponding signal emitted from the label present in the isolated first and second cDNA molecules;

identifying a greater amount of label or signal provided by the isolated first cDNA molecule than that provided by the isolated second cDNA molecule; and identifying the first cDNA and the corresponding mycobacterial gene which is induced or up-regulated during mycobacterial latency.

Reference to gene throughout this specification embraces open reading frames (ORFs).

The various embodiments described for the first aspect of the present invention apply equally to the second and subsequent aspects of the present invention.

The term "corresponding first and second cDNA molecules from the first and second cDNA populations" refers to cDNAs having substantially the same nucleotide sequence. Thus, by isolating the cDNA copies relating to a given gene under each culture condition (ie. exponential phase, and stationary phase), it is possible to quantify the relative copy number of cDNA for that gene for each culture condition. Since each cDNA copy has been produced from an mRNA molecule, the cDNA copy number reflects the corresponding mRNA copy number for each culture condition, and thus it is possible to identify induced or up-regulated genes.

In one embodiment, the first and second cDNA molecules are isolated from the corresponding first and second cDNA populations by hybridisation to an array containing immobilised DNA sequences that are representative of each known gene (or ORE) within a particular mycobacterial species genome. Thus, a first cDNA may be considered "corresponding" to a second cDNA if both cDNAs hybridise to the same immobilised DNA sequence.

In another embodiment, the first and second cDNAs are prepared by incorporation of a fluorescent label. The first and second cDNAs may incorporate labels which fluoresce at different wavelengths, thereby permitting dual fluorescence and simultaneous detection of two cDNA samples.

The type of label employed naturally determines how the output of the detection method is read. When using fluorescent labels, a confocal laser scanner is preferably employed.

According to one embodiment, fluorescently labelled cDNA sequences from stationary and exponential phase cultured systems were allowed to hybridise with a whole mycobacterial genome array. The first cDNA population was labelled with fluorescent label A, and the second cDNA population was labelled with fluorescent label B. The array was scanned at two different wavelengths corresponding to the excitable maxima of each dye and the intensity of the emitted light was recorded. Multiple arrays were preferably prepared for each cDNA and a mean intensity value was calculated across the two cDNA populations for each spot with each dye, against which relative induction or up-regulation was quantified.

In addition to the above mRNA isolation and cDNA preparation and labelling, genomic DNA may be isolated from the first and second mycobacteria. Thus, in a preferred embodiment, labelled DNA is also prepared from the isolated DNA. The labelled DNA may be then included on each array as a control.

According to a third aspect of the present invention, there is provided an inhibitor of a mycobacterial peptide, wherein the peptide is encoded by a gene the expression of which is induced or up-regulated under culture conditions that are nutrient-starving and which maintain mycobacterial latency, said conditions being obtainable by batch fermentation of a mycobacterium for at least 20 days post-inoculation, when compared with culture conditions that are not nutrient-starving and which support exponential growth of said mycobacterium, wherein the inhibitor is capable of preventing or inhibiting the mycobacterial peptide, from exerting its native biological effect.

Such inhibitors may be employed to prevent the onset of, or to cause a break in the period of mycobacterial latency (ie. induce re-activation). In this respect, mycobacteria are more susceptible to treatment regimens when in a non-latent state, and the combined use of drugs to kill latent mycobacteria (eg. TB) would significantly reduce the incidence of mycobacteria by targeting the reservoir for new disease and would thereby help reduce the problem of emerging drug-resistant strains.

The inhibitor may be a peptide, carbohydrate, synthetic molecule, or an analogue thereof. Inhibition of the mycobacterial peptide may be effected at the nucleic acid level (ie. DNA, or RNA), or at the peptide level. Thus, the inhibitor may act directly on the peptide. Alternatively, the inhibitor may act indirectly on the peptide by, for example, causing inactivation of the induced or up-regulated mycobacterial gene.

In preferred embodiments, the inhibitor is capable of inhibiting one or more of the following:—2-nitropropane dioxygenase, acetyltransferase, oxidoreductase, transcriptional regulator, acyl transferase, UDP-glucose dehydrogenase, phosphoribosylglycinamide formyltransferase, 1,4-dihydroxy-2-naphthoate octaprenyl, gmc-type oxidoreductase, 3-hydroxyisobutyrate dehydrogenase, methylmalonate semialdehyde dehydrogenase, dehydrogenase, mercuric reductase, glutathione reductase, dihydrolipoamide, transposase, proline iminopeptidase, prolyl aminopeptidase, quinolone efflux pump, glycine betaine transporter, phosphatidylethanolamine N-methyltransferase, chalcone synthase 2, sulfotransferase, glycosyl transferase, fumarate reductase flavoprotein, 8-amino-7-oxononanoate synthase, aminotransferase class-II pyridoxal-phosphate, bacteriophage HK97 prohead protease, penicillin-binding protein, fatty acyl-CoA racemase, nitrilotriacetate monooxygenase, histidine kinase response regulator, peptidase, LysR transcription regulator, excisionase, ornithine aminotransferase, malate oxidoreductase, thiosulphate binding protein, enoyl-CoA hydratase, acyl-CoA synthetase, methyltransferase, siroheme synthase, permease, glutaryl 7-aca acylase, sn-glycerol-3-phosphate transport system permease, enoyl-CoA hydratase/isomerase, acyl-CoA dehydrogenase, esterase, lipase, cytidine deaminase, crotonase, lipid-transfer protein, acetyl-CoA C-acetyltransferase, aminotransferase, hydrolase, and 2-amino-4-hydroxy-6-hydroxymethyldihydropterine pyrophosphokinase.

In a further embodiment, the inhibitor may be an antibiotic capable of targeting the induced or up-regulated mycobacterial gene identifiable by the present invention, or the gene product thereof. The antibiotic is preferably specific for the gene and/or gene product.

In a further embodiment, the inhibitor may act on a gene or gene product the latter of which interacts with the induced or up-regulated gene. Alternatively, the inhibitor may act on a gene or gene product thereof upon which the gene product of the induced or up-regulated gene acts.

Inhibitors of the present invention may be prepared utilizing the sequence information of provided herein. For example, this may be performed by overexpressing the peptide, purifying the peptide, and then performing X-ray crystallography on the purified peptide to obtain its molecular structure. Next, compounds are created which have similar molecular structures to all or portions of the polypeptide or its substrate. The compounds may be then combined with the peptide and attached thereto so as to block one or more of its biological activities.

Also included within the invention are isolated or recombinant polynucleotides that bind to the regions of the mycobacterial chromosome containing sequences that are associated with induction/up-regulation under low oxygen tension (ie. virulence), including antisense and triplex-forming polynucleotides. As used herein, the term "binding" refers to an interaction or complexation between an oligonucleotide and a target nucleotide sequence, mediated through hydrogen bonding or other molecular forces. The term "binding" more specifically refers to two types of internucleotide binding mediated through base-base hydrogen bonding. The first type of binding is "Watson-Crick-type" binding interactions in which adenine-thymine (or adenine-uracil) and guanine-cytosine base-pairs are formed through hydrogen bonding between the bases. An example of this type of binding is the binding traditionally associated with the DNA double helix and in RNA-DNA hybrids; this type of binding is normally detected by hybridization procedures. The second type of binding is "triplex binding". In general, triplex binding refers to any type of base-base hydrogen bonding of a third polynucleotide strand with a duplex DNA (or DNA-RNA hybrid) that is already paired in a Watson-Crick manner.

In a preferred embodiment, the inhibitor may be an antisense nucleic acid sequence which is complementary to at least part of the inducible or up-regulatable gene.

The inhibitor, when in the form of a nucleic acid sequence, in use, comprises at least 15 nucleotides, preferably at least 20 nucleotides, more preferably at least 30 nucleotides, and most preferably at least 50 nucleotides.

According to a fourth aspect of the invention, there is provided an antibody that binds to a peptide encoded by a gene, or to a fragment or variant or derivative of said peptide, the expression of which gene is induced or up-regulated during culture of a mycobacterium under culture conditions that are nutrient-starving and which maintain mycobacterial latency, said conditions being obtainable by batch fermentation of a mycobacterium for at least 20 days post-inoculation, when compared with culture conditions that are not nutrient-starving and which support exponential growth of said mycobacterium.

The antibody preferably has specificity for the peptide in question, and following binding thereto may initiate coating of the mycobacterium. Coating of the bacterium preferably leads to opsonization thereof. This, in turn, leads to the bacterium being destroyed. It is preferred that the antibody is specific for the mycobacterium (eg. species and/or strain) which is to be targeted.

In use, the antibody is preferably embodied in an isolated form.

Opsonization by antibodies may influence cellular entry and spread of mycobacteria in phagocytic and non-phagocytic cells by preventing or modulating receptor-mediated entry and replication in macrophages.

The peptides, fragments, variants or derivatives of the present invention may be used to produce antibodies, including polyclonal and monoclonal antibodies. If polyclonal antibodies are desired, a selected mammal (eg. mouse, rabbit, goat, horse, etc.) is immunized with an immunogenic polypeptide. Serum from the immunized animal is collected and treated according to known procedures. If serum containing polyclonal antibodies to a desired mycobacterial epitope contains antibodies to other antigens, the polyclonal antibodies may be purified by immunoaffinity chromatography. Alternatively, general methodology for making monoclonal antibodies by hybridomas involving, for example, preparation of immortal antibody-producing cell lines by cell fusion, or other techniques such as direct transformation of B lymphocytes with oncogenic DNA, or transfection with Epstein-Barr virus may be employed.

The antibody employed in this aspect of the invention may belong to any antibody isotype family, or may be a derivative or mimic thereof. Reference to antibody throughout this specification embraces recombinantly produced antibody, and any part of an antibody which is capable of binding to a mycobacterial antigen.

In one embodiment the antibody belongs to the IgG, IgM or IgA isotype families.

In a preferred embodiment, the antibody belongs to the IgA isotype family. Reference to the IgA isotype throughout this specification includes the secretory form of this antibody (ie. sIgA). The secretory component (SC) of sIgA may be added in vitro or in vivo. In the latter case, the use of a patient's natural SC labelling machinery may be employed.

In one embodiment, the antibody may be raised against a peptide from a member of the MTC, preferably against *M. tuberculosis.*

In a preferred embodiment, the antibody is capable of binding to a peptide selected from the group consisting of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281 and a fragment, variant, and derivative of said SEQ IDs.

In a further embodiment, the antigen is an exposed component of a mycobacterial *bacillus*. In another embodiment, the antigen is a cell surface component of a mycobacterial *bacillus*.

The antibody of the present invention may be polyclonal, but is preferably monoclonal.

Without being bound by any theory, it is possible that following mycobacterial infection of a macrophage, the macrophage is killed and the bacilli are released. It is at this stage that the mycobacteria are considered to be most vulnerable to antibody attack. Thus, it is possible that the antibodies of the present invention act on released bacilli following macrophage death, and thereby exert a post-infection effect.

It is possible that the passive protection aspect (ie. delivery of antibodies) of the present invention is facilitated by enhanced accessibility of the antibodies of the present invention to antigens on mycobacterial bacilli harboured by the infected macrophages. Indeed, acr expression is low during logarithmic growth, but increases at the stationary or oxygen limiting stage, and particularly in organisms which replicate within macrophages. As acr expression appears to be necessary for mycobacterial infectivity, it is possible that antibody binding may block macrophage infection by steric hindrance or disruption of its oligomeric structure. Thus, antibodies acting on mycobacterial bacilli released from killed, infected macrophages may interfere with the spread of re-infection to fresh macrophages. This hypothesis involves a synergistic action between antibodies and cytotoxic T cells, acting early after infection, eg. γδ and NK T cells, but could later involve also CD8 and CD4 cytotoxic T cells.

According to a fifth aspect of the invention, there is provided an attenuated mycobacterium in which a gene has been modified thereby rendering the mycobacterium substantially non-pathogenic, wherein said gene is a gene the expression of which is induced or up-regulated during culture conditions that are nutrient-starving and which maintain mycobacterial latency, said conditions being obtainable by batch fermentation of a mycobacterium for at least 20 days post-inoculation, when compared with culture conditions that are not nutrient-starving and which support exponential growth of said mycobacterium.

The modification preferably inactivates the gene in question, and preferably renders the mycobacterium substantially non-pathogenic.

The term "modified" refers to any genetic manipulation such as a nucleic acid or nucleic acid sequence replacement, a deletion, or an insertion which renders the mycobacterium substantially reduced in ability to persist in a latent state. In one embodiment the entire inducible or up-regulatable gene may be deleted.

In a preferred embodiment, gene to be modified has a wild-type coding sequence selected from the group consisting of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280 and 282.

It will be appreciated that the above wild-type sequences may include minor variations depending on the Database employed. The term "wild-type" indicates that the sequence in question exists as a coding sequence in nature.

According to a sixth aspect of the invention, there is provided an attenuated microbial carrier, comprising a peptide encoded by a gene, or a fragment or variant or derivative of said peptide, the expression of which gene is induced or up-regulated under culture conditions that are nutrient-starving and which maintain mycobacterial latency, said conditions being obtainable by batch fermentation of a mycobacterium for at least 20 days post-inoculation, when compared with culture conditions that are not nutrient-starving and which support exponential growth of said mycobacterium.

In use, the peptide (or fragment, variant or derivative) is either at least partially exposed at the surface of the carrier, or the carrier becomes degraded in vivo so that at least part of the peptide (or fragment, variant or derivative) is otherwise exposed to a host's immune system.

In a preferred embodiment, the attenuated microbial carrier is attenuated *salmonella*, attenuated vaccinia virus, attenuated fowlpox virus, or attenuated *M. bovis* (eg. BCG strain).

In a preferred embodiment, the peptide is selected from the group consisting of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279 and 281.

According to a seventh aspect of the invention, there is provided a DNA plasmid comprising a promoter, a polyadenylation signal, and a DNA sequence that is the coding sequence of a mycobacterial gene or a fragment or variant of derivative of said coding sequence, the expression of which gene is induced or up-regulated under culture conditions that are nutrient-starving and which maintain mycobacterial latency, said conditions being obtainable by batch fermentation of a mycobacterium for at least 20 days post-inoculation, when compared with culture conditions that are not nutrient-starving and which support exponential growth of said mycobacterium, wherein the promoter and polyadenylation signal are operably linked to the DNA sequence.

The term DNA "fragment" used in this invention will usually comprise at least about 5 codons (15 nucleotides), more usually at least about 7 to 15 codons, and most preferably at least about 35 codons. This number of nucleotides is usually about the minimal length required for a successful probe that would hybridize specifically with such a sequence.

In preferred embodiments, the DNA "fragment" has a nucleotide length which is at least 50%, preferably at least 70%, and more preferably at least 80% that of the coding sequence of the corresponding induced/up-regulated gene.

The term DNA "variant" means a DNA sequence that has substantial homology or substantial similarity to the coding sequence (or a fragment thereof) of an induced/up-regulated gene. A nucleic acid or fragment thereof is "substantially homologous" (or "substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95 to 98% of the nucleotide bases. Homology determination is performed as described supra for peptides.

Alternatively, a DNA "variant" is substantially homologous (or substantially similar) with the coding sequence (or a fragment thereof) of an induced/up-regulated gene when they are capable of hybridizing under selective hybridization conditions. Selectivity of hybridization exists when hybridization occurs which is substantially more selective than total lack of specificity. Typically, selective hybridization will occur when there is at least about 65% homology over a stretch of at least about 14 nucleotides, preferably at least about 70%, more preferably at least about 75%, and most preferably at least about 90%. See, Kanehisa (1984) Nuc. Acids Res. 12:203-213. The length of homology comparison, as described, may be over longer stretches, and in certain embodiments will often be over a stretch of at least about 17 nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration (eg. NaCl), temperature, or organic solvents, in addition to the base composition, length of the complementary strands, and the number of nucleotide base mismatches between the hybridizing nucleic acids, as will be readily appreciated by those skilled in the art. Stringent temperature conditions are preferably employed, and generally include temperatures in excess of 30° C., typically in excess of 37° C. and preferably in excess of 45° C. Stringent salt conditions will ordinarily be less than 1000 mM, typically less than 500 mM, and preferably less than 200 mM. The pH is typically between 7.0 and 8.3. However, the combination of parameters is much more important than the measure of any single parameter. See, eg., Wetmur and Davidson (1968) J. Mol. Biol. 31:349-370.

The term DNA "derivative" means a DNA polynucleotide which comprises a DNA sequence (or a fragment, or variant thereof) corresponding to the coding sequence of the induced/up-regulated gene and an additional DNA sequence which is not naturally associated with the DNA sequence corresponding to the coding sequence.

The comments on peptide derivative supra also apply to DNA "derivative". A "derivative" may, for example, include two or more coding sequences of a mycobacterial operon that is induced during nutrient-starvation. Thus, depending on the presence or absence of a non-coding region between the coding sequences, the expression product/s of such a "derivative" may be a fusion protein, or separate peptide products encoded by the individual coding regions.

The above terms DNA "fragment", "variant", and "derivative" have in common with each other that the resulting peptide products have cross-reactive antigenic properties which are substantially the same as those of the corresponding wild-type peptide. Preferably all of the peptide products of the above DNA molecule embodiments of the present invention bind to an antibody which also binds to the wild-type peptide. Alternatively, all of the above peptide products are capable of inducing a "recall response" of a T lymphocyte which has been previously exposed to an antigenic component of a mycobacterial infection.

The promoter and polyadenylation signal are preferably selected so as to ensure that the gene is expressed in a eukaryotic cell. Strong promoters and polyadenylation signals are preferred.

In a related aspect, the present invention provides an isolated RNA molecule which is encoded by a DNA sequence of the present invention, or a fragment or variant or derivative of said DNA sequence.

An "isolated" RNA is an RNA which is substantially separated from other mycobacterial components that naturally accompany the sequences of interest, eg., ribosomes, polymerases, and other mycobacterial polynucleotides such as DNA and other chromosomal sequences.

The above RNA molecule may be introduced directly into a host cell as, for example, a component of a vaccine.

Alternatively the RNA molecule may be incorporated into an RNA vector prior to administration.

The polynucleotide sequences (DNA and RNA) of the present invention include a nucleic acid sequence which has been removed from its naturally occurring environment, and recombinant or cloned DNA isolates and chemically synthesized analogues or analogues biologically synthesized by heterologous systems.

The term "recombinant" as used herein intends a polynucleotide of genomic, cDNA, semisynthetic, or synthetic origin which, by virtue of its origin or manipulation: (1) is not associated with all or a portion of a polynucleotide with which it is associated in nature; or (2) is linked to a polynucleotide other than that to which it is linked in nature; and (3) does not occur in nature. This artificial combination is often accomplished by either chemical synthesis means, or by the artificial manipulation of isolated segments of nucleic acids, eg., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

In embodiments of the invention the polynucleotides may encode a peptide (or fragment, variant, or derivative) which is induced or up-regulated under nutrient-starving conditions. A nucleic acid is said to "encode" a peptide if, in its native state or when manipulated, it can be transcribed and/or translated to produce the peptide (or fragment, variant or derivative thereof). The anti-sense strand of such a nucleic acid is also said to encode the peptide (or fragment, variant, or derivative).

Also contemplated within the invention are expression vectors comprising the polynucleotide of interest. Expression vectors generally are replicable polynucleotide constructs that encode a peptide operably linked to suitable transcriptional and translational regulatory elements. Examples of regulatory elements usually included in expression vectors are promoters, enhancers, ribosomal binding sites, and transcription and translation initiation and termination sequences. These regulatory elements are operably linked to the sequence to be translated. A nucleic acid sequence is operably linked when it is placed into a functional relationship with another nucleic acid sequence. For instance, a promoter is operably linked to a coding sequence if the promoter affects its transcription or expression. Generally, operably linked means that the DNA sequences being linked are contiguous and, where necessary to join two protein coding regions, contiguous and in reading frame. The regulatory elements employed in the expression vectors containing a polynucleotide encoding a virulence factor are functional in the host cell used for expression.

The polynucleotides of the present invention may be prepared by any means known in the art. For example, large amounts of the polynucleotides may be produced by replication in a suitable host cell. The natural or synthetic DNA fragments coding for a desired fragment will be incorporated into recombinant nucleic acid constructs, typically DNA constructs, capable of introduction into and replication in a prokaryotic or eukaryotic cell. Usually the DNA constructs will be suitable for autonomous replication in a unicellular host, such as yeast or bacteria, but may also be intended for introduction to and integration within the genome of a cultured insect, mammalian, plant or other eukaryotic cell lines. The polynucleotides of the present invention may also be produced by chemical synthesis, e.g., by the phosphoramidite method or the triester method, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence. DNA constructs prepared for introduction into a prokaryotic or eukaryotic host will typically comprise a replication system recognized by the host, including the intended DNA fragment encoding the desired peptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals from polypeptides secreted from the host cell of choice may also be included where appropriate, thus allowing the protein to cross and/or lodge in cell membranes, and thus attain its functional topology or be secreted from the cell. Appropriate promoter and other necessary vector sequences will be selected so as to be functional in the host, and may, when appropriate, include those naturally associated with mycobacterial genes. Promoters such as the trp, lac and phage promoters, tRNA promoters and glycolytic enzyme promoters may be used in prokaryotic hosts. Useful yeast promoters include the promoter regions for metallothionein, 3-phosphoglycerate kinase or other glycolytic enzymes such as enolase or glyceraldehyde-3-phosphate dehydrogenase, enzymes responsible for maltose and galactose utilization, and others.

Appropriate non-native mammalian promoters may include the early and late promoters from SV40 or promoters derived from murine moloney leukemia virus, mouse mammary tumour virus, avian sarcoma viruses, adenovirus II, bovine papilloma virus or polyoma. In addition, the construct may be joined to an amplifiable gene (e.g., DHFR) so that multiple copies of the gene may be made. While such expression vectors may replicate autonomously, they may less preferably replicate by being inserted into the genome of the host cell. Expression and cloning vectors will likely contain a selectable marker, a gene encoding a protein necessary for the survival or growth of a host cell transformed with the vector. The presence of this gene ensures the growth of only those host cells which express the inserts. Typical selection genes encode proteins that (a) confer resistance to antibiotics or other toxic substances, e.g. ampicillin, neomycin, methotrexate, etc.; (b) complement auxotrophic deficiencies; or (c) supply critical nutrients not available from complex media, e.g. the gene encoding D-alanine racemase for Bacilli. The choice of appropriate selectable marker will depend on the host cell. The vectors containing the nucleic acids of interest can be transcribed in vitro and the resulting RNA introduced into the host cell (e.g., by injection), or the vectors can be introduced directly into host cells by methods which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome). The cells into which have been introduced nucleic acids described above are meant to also include the progeny of such cells. Large quantities of the nucleic acids and peptides of the present invention may be prepared by expressing the nucleic acids or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or *Pseudomonas* may also be used. Mammalian or other eukaryotic host cells, such as those of yeast, filamentous fungi, plant, insect, amphibian or avian species, may also be useful for production of the proteins of the present invention. Propagation of mammalian cells in culture is per se well known. Examples of commonly used mammalian host cell lines are VERO and HeLa cells, Chinese hamster ovary (CHO) cells, and WI38, BHK, and COS cell lines, although other cell lines may be appropriate, e.g., to provide higher expression, desirable glycosylation patterns. Clones are selected by using markers depending on the mode of the vector construction. The marker may be on the same or a different DNA molecule, preferably the same DNA molecule. The transformant may be screened or, preferably, selected by any of the means well known in the art, e.g., by resistance to such antibiotics as ampicillin, tetracycline.

The polynucleotides of the invention may be inserted into the host cell by any means known in the art, including for example, transformation, transduction, and electroporation. As used herein, “recombinant host cells”, “host cells”, “cells”, “cell lines”, “cell cultures”, and other such terms denoting microorganisms or higher eukaryotic cell lines cultured as unicellular entities refer to cells which can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. “Transformation”, as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

In one embodiment, a DNA plasmid or RNA vector may encode a component of the immune system which is specific to an immune response following challenge with a peptide, wherein said peptide is encoded by a mycobacterial gene that is induced or up-regulated during nutrient-starvation, and optionally oxygen starvation.

An example of such a component is an antibody to the peptide product of the induced or up-regulated gene. Thus, in one embodiment, the nucleic acid sequence (eg. DNA plasmid, or RNA vector) encodes the antibody in question.

An eighth aspect provides use of the aforementioned aspects of the present invention, namely a peptide or fragment or variant or derivative thereof, an inhibitor, an antibody, an attenuated mycobacterium, an attenuated microbial carrier, a DNA sequence that is the coding sequence of an induced or up-regulated mycobacterial gene or a fragment or variant or derivative of said coding sequence, a DNA plasmid comprising said DNA sequence, an RNA sequence encoded by said DNA sequence (including DNA fragment, variant, derivative), and/or an RNA vector comprising said RNA sequence, in the manufacture of a medicament for treating or preventing a mycobacterial infection.

The term "preventing" includes reducing the severity/intensity of, or initiation of, a mycobacterial infection.

The term "treating" includes post-infection therapy and amelioration of a mycobacterial infection.

In a related aspect, there is provided a method of treating or preventing a mycobacterial infection, comprising administration of a medicament (namely the aforementioned aspects of the present invention) selected from the group consisting of a peptide or fragment or variant or derivative thereof, an inhibitor, an antibody, an attenuated mycobacterium, an attenuated microbial carrier, a DNA sequence that is the coding sequence of an induced or up-regulated mycobacterial gene or a fragment or variant or derivative of said coding sequence, a DNA plasmid comprising said DNA sequence, an RNA sequence encoded by said DNA sequence, and/or an RNA vector comprising said RNA sequence, to a patient.

The immunogenicity of the epitopes of the peptides of the invention may be enhanced by preparing them in mammalian or yeast systems fused with or assembled with particle-forming proteins such as, for example, that associated with hepatitis B surface antigen. Vaccines may be prepared from one or more immunogenic peptides of the present invention. Typically, such vaccines are prepared as injectables, either as liquid solutions or suspensions; solid forms suitable for solution in, or suspension in, liquid prior to injection may also be prepared. The preparation may also be emulsified, or the peptide encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-s n-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The vaccines are conventionally administered parenterally, by injection, for example, either subcutaneously or intramuscularly. Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25%-70%. The peptides may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like. The vaccines are administered in a manner compatible with the dosage formulation, and in such amount as will be prophylactically and/or therapeutically effective. The quantity to be administered, which is generally in the range of 5 micrograms to 250 micrograms of antigen per dose, depends on the subject to be treated, capacity of the subject's immune system to synthesize antibodies, and the degree of protection desired. Precise amounts of active ingredient required to be administered may depend on the judgment of the practitioner and may be peculiar to each subject. The vaccine may be given in a single dose schedule, or preferably in a multiple dose schedule. A multiple dose schedule is one in which a primary course of vaccination may be with 1-10 separate doses, followed by other doses given at subsequent time intervals required to maintain and or re-enforce the immune response, for example, at 1-4 months for a second dose, and if needed, a subsequent dose(s) after several months. The dosage regimen will also, at least in part, be determined by the need of the individual and be dependent upon the judgment of the practitioner. In addition, the vaccine containing the immunogenic mycobacterial antigen(s) may be administered in conjunction with other immunoregulatory agents, for example, immunoglobulins, as well as antibiotics.

The medicament may be administered by conventional routes, eg. intravenous, intraperitoneal, intranasal routes.

The outcome of administering antibody-containing compositions may depend on the efficiency of transmission of antibodies to the site of infection. In the case of a mycobacterial respiratory infection (eg. a *M. tuberculosis* infection), this may be facilitated by efficient transmission of antibodies to the lungs.

In one embodiment the medicament may be administered intranasally (i.n.). This mode of delivery corresponds to the route of delivery of a *M. tuberculosis* infection and, in the case of antibody delivery, ensures that antibodies are present at the site of infection to combat the bacterium before it becomes intracellular and also during the period when it spreads between cells.

An intranasal composition may be administered in droplet form having approximate diameters in the range of 100-5000 μm, preferably 500-4000 μm, more preferably 1000-3000 μm. Alternatively, in terms of volume, the droplets would be in the approximate range of 0.001-100 μl, preferably 0.1-50 μl, more preferably 1.0-25 μl.

Intranasal administration may be achieved by way of applying nasal droplets or via a nasal spray.

In the case of nasal droplets, the droplets may typically have a diameter of approximately 1000-3000 μm and/or a volume of 1-25 μl.

In the case of a nasal spray, the droplets may typically have a diameter of approximately 100-1000 μm and/or a volume of 0.001-1 μl.

It is possible that, following i.n. delivery of antibodies, their passage to the lungs is facilitated by a reverse flow of mucosal secretions, although mucociliary action in the respiratory tract is thought to take particles within the mucus out of the lungs. The relatively long persistence in the lungs' lavage, fast clearance from the bile and lack of transport to the saliva of some antibodies suggest the role of mucosal site specific mechanisms.

In a different embodiment, the medicament may be delivered in an aerosol formulation. The aerosol formulation may take the form of a powder, suspension or solution.

The size of aerosol particles is one factor relevant to the delivery capability of an aerosol. Thus, smaller particles may travel further down the respiratory airway towards the alveoli than would larger particles. In one embodiment, the aerosol particles have a diameter distribution to facilitate delivery along the entire length of the bronchi, bronchioles, and alveoli. Alternatively, the particle size distribution may be selected to target a particular section of the respiratory airway, for example the alveoli.

The aerosol particles may be delivered by way of a nebulizer or nasal spray.

In the case of aerosol delivery of the medicament, the particles may have diameters in the approximate range of 0.1-50 μm, preferably 1-25 μm, more preferably 1-5 μm.

The aerosol formulation of the medicament of the present invention may optionally contain a propellant and/or surfactant.

By controlling the size of the droplets which are to be administered to a patient to within the defined range of the present invention, it is possible to avoid/minimise inadvertent antigen delivery to the alveoli and thus avoid alveoli-associated pathological problems such as inflammation and fibrotic scarring of the lungs.

I.n. vaccination engages both T and B cell mediated effector mechanisms in nasal and bronchus associated mucosal tissues, which differ from other mucosae-associated lymphoid tissues.

The protective mechanisms invoked by the intranasal route of administration may include: the activation of T lymphocytes with preferential lung homing; upregulation of co-stimulatory molecules, eg. B7.2; and/or activation of macrophages or secretory IgA antibodies.

Intranasal delivery of antigens may facilitate a mucosal antibody response is invoked which is favoured by a shift in the T cell response toward the Th2 phenotype which helps antibody production. A mucosal response is characterised by enhanced IgA production, and a Th2 response is characterised by enhanced IL-4 production.

Intranasal delivery of mycobacterial antigens allows targeting of the antigens to submucosal B cells of the respiratory system. These B cells are the major local IgA-producing cells in mammals and intranasal delivery facilitates a rapid increase in IgA production by these cells against the mycobacterial antigens.

In one embodiment administration of the medicament comprising a mycobacterial antigen stimulates IgA antibody production, and the IgA antibody binds to the mycobacterial antigen. In another embodiment, a mucosal and/or Th2 immune response is stimulated.

In another embodiment monoclonal antibodies, in particular, may be used to raise anti-idiotype antibodies. Anti-idiotype antibodies are immunoglobulins which carry an "internal image" of the antigen of the infectious agent against which protection is desired. These anti-idiotype antibodies may also be useful for treatment, vaccination and/or diagnosis of mycobacterial infections.

According to a ninth aspect of the present invention, the peptides (including fragments, variants, and derivatives thereof) of the present invention and antibodies which bind thereto are useful in immunoassays to detect the presence of antibodies to mycobacteria, or the presence of the virulence associated antigens in biological samples. Design of the immunoassays is subject to a great deal of variation, and many formats are known in the art. The immunoassay may utilize at least one epitope derived from a peptide of the present invention. In one embodiment, the immunoassay uses a combination of such epitopes. These epitopes may be derived from the same or from different bacterial peptides, and may be in separate recombinant or natural peptides, or together in the same recombinant peptides.

An immunoassay may use, for example, a monoclonal antibody directed towards a virulence associated peptide epitope(s), a combination of monoclonal antibodies directed towards epitopes of one mycobacterial antigen, monoclonal antibodies directed towards epitopes of different mycobacterial antigens, polyclonal antibodies directed towards the same antigen, or polyclonal antibodies directed towards different antigens. Protocols may be based, for example, upon competition, or direct reaction, or sandwich type assays. Protocols may also, for example, use solid supports, or may be by immunoprecipitation. Most assays involve the use of labelled antibody or polypeptide; the labels may be, for example, enzymatic, fluorescent, chemiluminescent, radioactive, or dye molecules. Assays which amplify the signals from the probe are also known; examples of which are assays which utilize biotin and avidin, and enzyme-labelled and mediated immunoassays, such as ELISA assays. Typically, an immunoassay for an antibody(s) to a peptide, will involve selecting and preparing the test sample suspected of containing the antibodies, such as a biological sample, then incubating it with an antigenic (i.e., epitope-containing) peptide(s) under conditions that allow antigen-antibody complexes to form, and then detecting the formation of such complexes. The immunoassay may be of a standard or competitive type. The peptide is typically bound to a solid support to facilitate separation of the sample from the peptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immulon), diazotized paper, nylon membranes, activated beads, and Protein A beads. For example, Dynatech Immulon microtiter plates or 60 mm diameter polystyrene beads (Precision Plastic Ball) may be used. The solid support containing the antigenic peptide is typically washed after separating it from the test sample, and prior to detection of bound antibodies. Complexes formed comprising antibody (or, in the case of competitive assays, the amount of competing antibody) are detected by any of a number of known techniques, depending on the format. For example, unlabelled antibodies in the complex may be detected using a conjugate of antixenogeneic Ig complexed with a label, (e.g., an enzyme label). In immunoassays where the peptides are the analyte, the test sample, typically a biological sample, is incubated with antibodies directed against the peptide under conditions that allow the formation of antigen-antibody complexes. It may be desirable to treat the biological sample to release putative bacterial components prior to testing. Various formats can be employed. For example, a "sandwich assay" may be employed, where antibody bound to a solid support is incubated with the test sample; washed; incubated with a second, labelled antibody to the analyte, and the support is washed again. Analyte is detected by determining if the second antibody is bound to the support. In a competitive format, a test sample is usually incubated with antibody and a labelled, competing antigen is also incubated, either sequentially or simultaneously.

Also included as an embodiment of the invention is an immunoassay kit comprised of one or more peptides of the invention, or one or more antibodies to said peptides, and a buffer, packaged in suitable containers.

As used herein, a "biological sample" refers to a sample of tissue or fluid isolated from an individual, including but not limited to, for example, plasma, serum, spinal fluid, lymph fluid, the external sections of the skin, respiratory, intestinal, and genitourinary tracts, tears, saliva, milk, blood cells, tumours, organs, and also samples of in vitro cell culture constituents (including but not limited to conditioned medium resulting from the growth of cells in cell culture medium, putatively virally infected cells, recombinant cells, and cell components).

In a related diagnostic assay, the present invention provides nucleic acid probes for detecting a mycobacterial infection.

Using the polynucleotides of the present invention as a basis, oligomers of approximately 8 nucleotides or more can be prepared, either by excision from recombinant polynucleotides or synthetically, which hybridize with the mycobacterial sequences, and are useful in identification of mycobacteria. The probes are a length which allows the detection of the induced or up-regulated sequences by hybridization. While 6-8 nucleotides may be a workable length, sequences of 10-12 nucleotides are preferred, and at least about 20 nucleotides appears optimal. These probes can be prepared using routine methods, including automated oligonucleotide synthetic methods. For use as probes, complete complementarity is desirable, though it may be unnecessary as the length of the fragment is increased. For use of such probes as diagnostics, the biological sample to be analyzed, such as blood or serum, may be treated, if desired, to extract the nucleic acids contained therein. The resulting nucleic acid from the sample may be subjected to gel electrophoresis or other size separation techniques; alternatively, the nucleic acid sample may be dot blotted without size separation. The probes are usually labeled. Suitable labels, and methods for labeling probes are known in the art, and include, for example, radioactive labels incorporated by nick translation or kinasing, biotin, fluorescent probes, and chemiluminescent probes. The nucleic acids extracted from the sample are then treated with the labeled probe under hybridization conditions of suitable stringencies. The probes may be made completely complementary to the virulence encoding polynucleotide. Therefore, usually high stringency conditions are desirable in order to prevent false positives. The stringency of hybridization is determined by a number of factors during hybridization and during the washing procedure, including temperature, ionic strength, length of time, and concentration of formamide. It may be desirable to use amplification techniques in hybridization assays. Such techniques are known in the art and include, for example, the polymerase chain reaction (PCR) technique. The probes may be packaged into diagnostic kits. Diagnostic kits include the probe DNA, which may be labelled; alternatively, the probe DNA may be unlabeled and the ingredients for labelling may be included in the kit in separate containers. The kit may also contain other suitably packaged reagents and materials needed for the particular hybridization protocol, for example, standards, as well as instructions for conducting the test.

In a preferred embodiment, a peptide (or fragment or variant or derivative) of the present invention is used in a diagnostic assay to detect the presence of a T-lymphocyte which T lymphocyte has been previously exposed to an antigenic component of a mycobacterial infection in a patient.

In more detail, a T-lymphocyte which has been previously exposed to a particular antigen will be activated on subsequent challenge by the same antigen. This activation provides a means for identifying a positive diagnosis of mycobacterial infection. In contrast, the same activation is not achieved by a T-lymphocyte which has not been previously exposed to the particular antigen.

The above "activation" of a T-lymphocyte is sometimes referred to as a "recall response" and may be measured, for example, by determining the release of interferon (eg. IFN-Y) from the activated T-lymphocyte. Thus, the presence of a mycobacterial infection in a patient may be determined by the release of a minimum concentration of interferon from a T-lymphocyte after a defined time period following in vitro challenge of the T-lymphocyte with a peptide (or fragment or variant or derivative) of the present invention.

In use, a biological sample containing T-lymphocytes is taken from a patient, and then challenged with a peptide (or fragment, variant, or derivative thereof) of the present invention.

The above T-lymphocyte diagnostic assay may include an antigen presenting cell (APC) expressing at least one major histocompatibility complex (MHC) class II molecule expressed by the patient in question. The APC may be inherently provided in the biological sample, or may be added exogenously. In one embodiment, the T-lymphocyte is a CD4 T-lymphocyte.

Brief mention is now made to the Figures of the present application, in which:—

EXAMPLE 1

Culture of Mycobacteria

Figure 1:
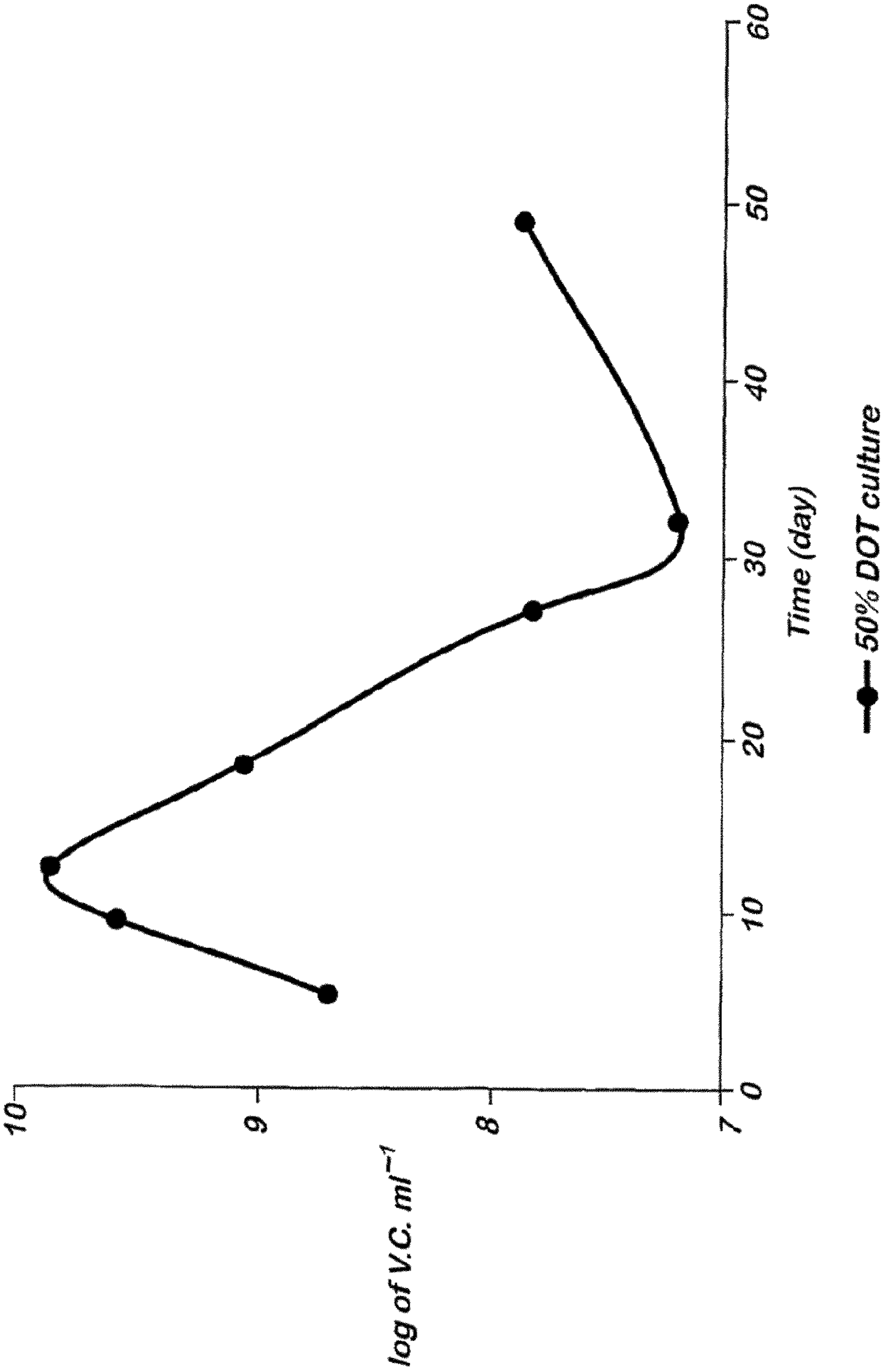
FIG. 1 illustrates the viable counts for *M. tuberculosis* during culture under batch fermentation conditions at a DOT of 50% air saturation (37° C.)

Two alternative mycobacterial culture methods have been employed to study genes which are up-regulated or induced during mycobacterial latency.

Model 1—In Vitro Model of Mycobacterial Persistence Under Aerobic, Nutrient-Starved Conditions Materials and Methods Strain Studies were performed with *M. tuberculosis* strain H37Rv (NCTC cat. no. 7416)—a representative strain of *M. tuberculosis*. Stock cultures were grown on Middlebrook 7H10+OADC for 3 weeks at 37±2° C.

Culture Medium

Persistence cultures were established in Middlebrook 7H9 medium supplemented with Middlebrook ADC enrichment, 0.2% Tween 80 and 0.2% glycerol (Table 1). The medium was prepared with high quality water from a Millipore water purification system and filter sterilised by passage through a 0.1 μm pore size cellulose acetate membrane filter capsule (Sartorius Ltd). The pH was adjusted to 6.6 with concentrated hydrochloric acid.

Middlebrook 7H10+OADC agar was used to prepare inoculum cultures, enumerate the number of culturable bacteria in samples, and to assess culture purity.

Culture System

We previously developed a process for the culture of mycobacteria under controlled and defined conditions—patent application No. PCT/GB00/00760 (WO00/52139). We used this culture system operated as a batch fermenter for the following studies of mycobacterial persistence.

Culture experiments were performed in a one litre glass vessel operated at a working volume of 750 ml. The culture was agitated by a magnetic bar placed in the culture vessel coupled to a magnetic stirrer positioned beneath the vessel. Culture conditions were continuously monitored by an Anglicon Microlab Fermentation System (Brighton Systems, New Haven), linked to sensor probes inserted into the culture through sealed ports in the top plate. The oxygen concentration was monitored with a galvanic oxygen electrode (Uniprobe, Cardiff) and was controlled through sparging the culture with a mixture of air and oxygen free-nitrogen. Temperature was monitored by an Anglicon temperature probe, and maintained by a heating pad positioned beneath the culture vessel. Culture pH was measured using an Ingold pH electrode (Mettler-Toledo, Leicester).

Inoculation and Culture

The vessel was filled with 750 ml of sterile culture medium and parameters were allowed to stabilise at 37° C.±2° C., pH 6.9±0.3 and a dissolved oxygen tension of approximately 70% air saturation. A dense inoculum suspension was prepared by resuspending Middlebrook agar cultures, grown at 37° C.±2° C. for 3 weeks, in sterile deionised water. The inoculum was aseptically transferred to the culture vessel, to provide an initial culture turbidity of approximately 0.25 at 540 nm.

The culture were maintained at 37° C. with an agitation rate of 500 to 750 rpm. The dissolved oxygen tension was maintained between 50-70% air saturation with the aid of culture sparging. The initial culture pH was set at approximately 6.7 and was monitored through-out the experiment.

The culture was maintained for 50 days and samples were removed regularly to monitor growth and survival, nutrient utilisation and gene expression.

Growth and Survival

Bacterial growth and survival was assessed by determining the number of viable cells in the culture system at specific time points. This was achieved by preparing a decimal dilution series of the sample in sterile water and plating 100 μl aliquots onto Middlebrook 7H10+OADC plates. The plates were incubated at 37° C. for up to 4 weeks before enumerating the number of colonies formed.

Nutrient Utilisation

Glycerol is the primary carbon and energy source present in Middlebrook 7H9 medium with ADC, 0.2% Tween and 0.2% Glycerol. The rate at which glycerol was utilised was determined using the Glycerol Determination Kit Cat. No. 148 270 Boehringer Mannheim.

Microarray Experiments

RNA was extracted from culture samples collected at different time points during the experiment. A fluorescently-labelled cDNA was then transcribed from each sample of RNA. The cDNA was labelled by the incorporation of either Cy3 or Cy5 labelled dCTP (Dyes are supplied by Amersham Pharmacia Biotech).

Whole *M. tuberculosis* genome arrays were prepared from *M. tuberculosis* genomic DNA using ORF-specific primers. PCR products corresponding to each ORF were spotted in a grid onto a standard glass microscope slide using a BioRobotics microgrid robot (MWG Biotech) at a resolution of >4000 spots/$cm^2$.

In each microarray experiment a whole genome array was hybridised with labelled cDNA from one culture sample (Test sample). Each array was also hybridised with control DNA incorporating a different Cy dye and prepared from DNA extracted from *M. tuberculosis* strain H37Rv (control sample).

Each array was scanned at two different wavelengths corresponding to the excitation maxima of each dye and the intensity of the emitted light was recorded. The ration of the intensity values for the test and control samples was determined for each array.

The slides were scanned using an Affymetrix 428 scanner. The raw data was initially analysed by ImaGene software. The scanned images were then transferred to another software package known as GeneSpring to analyse the expression of each gene.

Results

After inoculation the culture entered exponential growth and continued to grow exponentially until 10 days after inoculation (see FIG. 1). Cessation of exponential growth coincided with depletion of the primary carbon and energy source—glycerol (see FIG. 2). As the culture entered stationary phase, viability started to decline and continued to decline steadily over the duration of the study. After 40 days in stationary phase, approximately 1% of the culture was still culturable on Middlebrook agar.

The gene expression profiles for samples collect at day 5 and day 50 were compared. Three arrays were prepared for each sample and the ratio of the intensity values for the test and control samples was determined for each array.

Two different approaches were used to analyse the data:—

1. The ratio values for the 3 arrays prepared for each sample were averaged and compared. Genes which produced intensity ratios that were 3-fold higher on day 50 than on day 5 were selected.
2. Data from each array was treated as a separate data set and self-organising maps were used to select all the genes that were consistently up-regulated in all 3 arrays at day 50 relative to day 5.

The two data sets were then compared and those genes that were at least 1.5-fold, preferably at least 3-fold up-regulated at day 50, relative to exponential growth at day 5, and which were consistently up-regulated in all 3 arrays (experiments) were selected. The identified sequences (protein, followed by nucleic acid) are presented in Table 2.

Model 2—In Vitro Model of Mycobacterial Persistence Under Low Oxygen, and Nutrient-Starved Conditions A second model which simulated low-oxygen availability and nutrient depletion has also been developed. This model was established as outlined for Model 1 above, but with the following modifications.

After inoculation, the dissolved oxygen tension (DOT) of the culture was maintained at approximately 40% air saturation at 37° C. until the culture had entered early exponential growth. The DOT was then lowered in increments down to 1% air saturation over a six day period. The culture was then maintained at a DOT of 0-5% until 50 days after inoculation. Samples were collected for analysis, and the identified sequences (protein, followed by nucleic acid) are presented in Table 2.

TABLE 1 liquid medium formulation for persistence cultures - Middlebrook 7H9 medium supplemented with ADC, 0.2% Tween 80 and 0.2% Glycerol

| Composition per liter | |
|---|---|
| $Na_2HPO_4$ | 2.5 g |
| $KH_2PO_4$ | 1.0 g |
| Monosodium glutamate | 0.5 g |
| $(NH_4)_2SO_4$ | 0.5 g |
| Sodium citrate | 0.1 g |
| $MgSO_4 \cdot 7H_2O$ | 0.05 g |
| Ferric ammonium citrate | 0.04 g |
| $CuSO_4 \cdot 5H_2O$ | 1.0 mg |
| Pyridoxine | 1.0 mg |
| $ZnSO_4 \cdot 7H_2O$ | 1.0 mg |
| Biotin | 0.5 mg |
| $CaCl_2 \cdot 2H_20$ | 0.5 mg |
| Middlebrook ADC enrichment | 100 ml |
| Glycerol | 2.0 ml |
| Tween 80 | 2.0 ml |
| Middlebrook ADC enrichment - per 100 ml | |
| Bovine serum albumin | 5.0 g |
| Glucose | 2.0 g |
| Catalase | 3.0 mg |

EXAMPLE 2

RNA Extraction from *M. tuberculosis* for Microarray Analysis

Materials and Methods

Trizol (Life Technologies)—Formulation of Phenol and Guanidine Thiocyanate.

GTC lysis solution containing: 5 M guanidine thiocyanate, 0.5% N-lauryl sarcosine, 25 mM tri-sodium citrate, 0.1 M 2-mercaptoethanol, and 0.5% Tween 80.

Chloroform

Isopropanol 3M sodium acetate

70% Ethanol microfuge ribolyser

Sterile plasticware—Falcon tubes, screw capped eppendorfs, gilson tips—all RNase free Glassware—baked at 160° C. for at least 16 hours Method Steps performed at Containment level 3; within a Class III microbiological safety cabinet.

Remove 10 or 20 ml of culture ($10^9$/ml) and immediately add this to 4 volumes of GTC lysis buffer in a plastic specimen pot. Seal the pot tightly.

Incubate the cells in GTC lysis buffer for 1 hour at room temperature. Surface decontaminate the plastic pot with 5% Hycolin for 5 minutes. Transfer the sample to the pass box and place it into a plastic carry tin with a sealable lid. Close the container securely and transport it to a non-toxic cabinet CL3 cabinet.

Equally distribute the lysis mixture between Falcon tubes. Place these tubes into centrifuge buckets and seal the buckets tightly. Surface-decontaminate the buckets for 5 minutes with 5% Hycolin. Then transfer them to the centrifuge (Baird and Tatlock Mark IV refrigerated bench-top centrifuge). Spin the tubes at 3,000 rpm for 30 minutes.

Return the unopened buckets to the cabinet. Remove the centrifuge tubes and pour the supernatant into a waste bottle for GTC lysis buffer.

Resuspend each pellet in 1 ml of Trizol (formulation of phenol and GTC cat no. 15596-026). The manufacturers guidelines recommend lysing cells by repetitive pipetting. Although this action alone will not lyse *M. tuberculosis*, it is important to completely resuspend the pellet in Trizol.

Transfer 1 ml of cells into a FastRNA tube and ribolyse it at power setting 6.5 for 45 seconds.

Leave the tube to incubate at room temperature for 5 minutes.

Remove the aqueous layer from the tube and add this to 200 µl of chloroform in a screw-capped eppendorf tube. Shake each tube vigorously for about 15 seconds. Incubate for 2-3 minutes at room temperature.

Spin the tube at 13,000 rpm for 15 minutes. Following centrifugation, the liquid separates into red phenol/chloroform phase, an interface, and a clear aqueous phase.

Carefully remove the aqueous phase and transfer it to a fresh eppendorf tube containing 500 µl of chloroform/isoamyl alcohol (24:1). Spin the tubes at 13,000 rpm for 15 minutes.

Transfer the aqueous phase to an eppendorf tube containing 50 µl of sodium acetate and 500 µl of isopropanol.

Surface decontaminate the eppendorf tubes with 5% Hycolin for 5 minutes. Remove the tubes from the CL3 laboratory and continue with the procedure in laboratory.

Steps Performed at Containment Level 2:

Precipitate the RNA at −70° C. for at least 30 minutes—can do this step overnight.

Spin the precipitated RNA down at 13,000 rpm for 10 minutes. Remove the supernatant and wash the pellet in 70% ethanol. Repeat centrifugation.

Remove the 70% ethanol and air-dry the pellet. Dissolve the pellet in RNAse free water.

Freeze the RNA at −70° C. to store it.

EXAMPLE 3

Isolation of Genomic DNA from *Mycobacterium tuberculosis* Grown in Chemostat Culture. DNA then Used to Generate Cy3 or Cy6 Labelled DNA for Use as a Control in Microarray Experiments Materials and Methods Beads 0.5 mm in diameter Bead beater Bench top centrifuge Platform rocker Heat block Falcon 50 ml centrifuge tubes Sorvall RC-5C centrifuge 250 ml polypropylene centrifuge pots.

Screw capped eppendorf tubes

Pipettes 1 ml, 200 µl, 10 ml, 5 ml

Breaking Buffer 50 mM Tris HCl pH 8.0

10 mM EDTA 100 mM NaCl

Procedure

Mechanical Disruption of *M. tuberculosis* Cells 150 ml of chemostat cells (O.D of 2.5 at 540 nm) are spun down at 15,000 rpm for 15 minutes in 250 ml polypropylene pots using centrifuge Sorvall RC-5C.

The supernatant is discarded.

Cells are re-suspended in 5 ml of breaking buffer in a 50 ml Falcon tube and centrifuged at 15,000 rpm for a further 15 minutes.

The supernatant is removed and additional breaking buffer is added at a volume of 5 ml. Beads are used to disrupt the cells. These are used at a quantity of 1 ml of beads for 1 ml of cells. Place the sample into the appropriate sized chamber. Place in the bead beater and secure the outer unit (containing ice) and process at the desired speed for 30 seconds.

Allow the beads to settle for 10 minutes and transfer cell lysate to a 50 ml Falcon centrifuge tube Wash beads with 2-5 ml of breaking buffer by pipetting washing buffer up and down over the beads.

Add this washing solution to the lysate in the falcon tube

Removal of Proteins and Cellular Components

Add 0.1 volumes of 10% SDS and 0.01 volumes proteinase K.

Mix by inversion and heat at 55° C. in a heat block for 2-3 hours

The resulting mix should be homogenous and viscous. Additional SDS may be added to assist here to bring the concentration up to 0.2%

Add an equal volume of phenol/chloroform/Isoamyl alcohol in the ratio: 25/24/1.

Gently mix on a platform rocker until homogenous

Spin down at 3,000 rpm for 20 minutes

Remove the aqueous phase and place in a fresh tube

Extract the aqueous phase with an equal volume of chloroform to remove traces of cell debris and phenol. Chloroform extractions may need to be repeated to remove all the debris.

Precipitate the DNA with 0.3 M sodium acetate and an equal volume of isopropanol.

Spool as much DNA as you can with a glass rod

Wash the spooled DNA in 70% ethanol followed by 100% ethanol

Leave to air dry

Dissolve the DNA in sterile deionised water (500 μl)

Allow DNA to dissolve at 4° C. for approximately 16 hours.

Add RNase 1 (500U) to the dissolved DNA

Incubate for 1 hour at 37° C.

Re-extract with an equal volume of phenol/chloroform followed by a chloroform extraction and precipitate as before Spin down the DNA at 13,000 rpm Remove the supernatant and wash the pellet in 70% ethanol Air dry Dissolve in 200-500 μl of sterile water.

EXAMPLE 4

Preparation of Cy3 or Cy5 Labelled DNA from DNA a) Prepare One Cy3 or One Cy5 Labelled DNA Sample Per Microarray Slide.

Each Sample:

| | |
|---|---|
| DNA | 2-5 μg |
| Random primers (3 μg/μl) | 1 μl |
| $H_2O$ | to 41.5 μl |

Heat at 95° C. for 5 min, snap cool on ice and briefly centrifuge.

Add to Each:

| | |
|---|---|
| 10 × REact 2 buffer | 5 μl |
| dNTPs (5 mM dA/G/TTP, 2 mM dCTP) | 1 μl |
| Cy3 OR Cy5 dCTP | 1.5 μl |
| Klenow (5 U/μl) | 1 μl |

Incubate at 37° C. in dark for 90 min.

b) Prehybridise Slide

Mix the prehybridisation solution in a Coplin jar and incubate at 65° C. during the labelling reaction to equilibrate.

Prehybridisation:

| | |
|---|---|
| 20 x SSC | 8.75 ml (3.5 x SSC) |
| 20% SDS | 250 μl (0.1% SDS) |
| BSA (100 mg/ml) | 5 ml (10 mg/ml) |
| $H_2O$ | to 50 ml |

Incubate the microarray slide in the pre-heated prehybridisation solution at 65° C. for 20 min. Rinse slide thoroughly in 400 ml $H_2O$ for 1 min followed by rinse in 400 ml propan-2-ol for 1 min and centrifuge slide in 50 ml centrifuge tube at 1,500 rpm for 5 min to dry. Store slide in dark, dust-free box until hybridisation (<1 h).

c) Purify Cy3/Cy5 Labelled DNA-Qiagen MinElute Purification

Combine Cy3 and Cy5 labelled DNA samples in single tube and add 500 μl Buffer PB.

Apply to MinElute column in collection tube and centrifuge at 13,000 rpm for 1 min.

Discard flow-through and place MinElute column back into same collection tube.

Add 500 μl Buffer PE to MinElute column and centrifuge at 13,000 rpm for 1 min.

Discard flow-through and place MinElute column back into same collection tube.

Add 250 μl Buffer PE to MinElute column and centrifuge at 13,000 rpm for 1 min.

Discard flow-through and place MinElute column back into same collection tube.

Centrifuge at 13,000 rpm for an additional 1 min to remove residual ethanol.

Place the MinElute column into a fresh 1.5 ml tube.

Add 10.5 μl $H_2O$ to the centre of the membrane and allow to stand for 1 min.

Centrifuge at 13,000 rpm for 1 min.

EXAMPLE 5

Preparation of Cy3 or Cy5 Label cDNA from RNA a) Prepare One Cy3 and One Cy5 Labelled cDNA Sample Per Microarray Slide Each Sample:

| | |
|---|---|
| RNA | 2-10 μg |
| Random primers (3 μg/μl) | 1 μl |
| $H_2O$ | to 11 μl |

Heat at 95° C. for 5 min, snap cool on ice and briefly centrifuge.

Add to Each:

| | |
|---|---|
| 5Î First Strand Buffer | 5 µl |
| DTT (100 mM) | 2.5 µl |
| dNTPs (5 mM dA/G/TTP, 2 mM dCTP) | 2.3 µl |
| Cy3 OR Cy5 dCTP | 1.7 µl |
| SuperScript II (200 U/µl) | 2.5 µl |

Incubate at 25° C. in dark for 10 min followed by 42° C. in dark for 90 min.

b) Prehybridise Slide

Mix the prehybridisation solution in a Coplin jar and incubate at 65° C. during the labelling reaction to equilibrate.

Prehybridisation:

| | |
|---|---|
| 20 × SSC | 8.75 ml (3.5 × SSC) |
| 20% SDS | 250 µl (0.1% SDS) |
| BSA (100 mg/ml) | 5 ml (10 mg/ml) |
| $H_2O$ | to 50 ml |

Incubate the microarray slide in the pre-heated prehybridisation solution at 65° C. for 20 min. Rinse slide thoroughly in 400 ml $H_2O$ for 1 min followed by rinse in 400 ml propan-2-ol for 1 min and centrifuge slide in 50 ml centrifuge tube at 1500 rpm for 5 min to dry. Store slide in dark, dust-free box until hybridisation (<1 h).

c) Purify Cy3/Cy5 Labelled cDNA-Qiagen MinElute Purification

Combine Cy3 and Cy5 labelled DNA samples in single tube and add 250 µl Buffer PB.

Apply to MinElute column in collection tube and centrifuge at 13,000 rpm for 1 min.

Discard flow-through and place MinElute column back into same collection tube.

Add 500 µl Buffer PE to MinElute column and centrifuge at 13,000 rpm for 1 min.

Discard flow-through and place MinElute column back into same collection tube.

Add 250 µl Buffer PE to MinElute column and centrifuge at 13,000 rpm for 1 min.

Discard flow-through and place MinElute column back into same collection tube.

Centrifuge at 13,000 rpm for an additional 1 min to remove residual ethanol.

Place the MinElute column into a fresh 1.5 ml tube.

Add 10.5 µl $H_2O$ to the centre of the membrane and allow to stand for 1 min.

Centrifuge at 13,000 rpm for 1 min.

EXAMPLE 6

Hybridise Slide with Cy3/Cy5 Labelled cDNA

Place the prehybridise microarray slide in the hybridisation cassette and add two 15 ml aliquots of $H_2O$ to the wells in the cassette. Mix resuspended Cy3/Cy5 labelled cDNA sample with hybridisation solution.

Hybridisation:

| | |
|---|---|
| Cy3/Cy5 labelled cDNA sample | 10.5 ml |
| 20 × SSC | 3.2 ml (4 × SSC) |
| 2% SDS | 2.3 ml (0.3% SDS) |

Heat hybridisation solution at 95° C. for 2 min. Do not snap cool on ice but allow to cool slightly and briefly centrifuge. Pipette the hybridisation solution onto the slide at the edge of the arrayed area avoiding bubble formation. Using forceps carefully drag the edge of a cover slip along the surface of the slide towards the arrayed area and into the hybridisation solution at the edge of the array. Carefully lower the cover slip down over the array avoiding any additional movement once in place. Seal the hybridisation cassette and submerge in a water bath at 60° C. for 16-20 h.

Wash Slide.

Remove microarray slide from hybridisation cassette and initially wash slide carefully in staining trough of Wash A to remove cover slip. Once cover slip is displaced place slide(s) in slide rack and continue agitating in Wash A for a further 2 min.

Wash A:

| | |
|---|---|
| 20 × SSC | 20 ml (1 × SSC) |
| 20% SDS | 1 ml (0.05% SDS) |
| $H_2O$ | to 400 ml |

Transfer slide(s) to a clean slide rack and agitate in first trough of Wash B for 2 min. Wash in second trough of Wash B with agitation for 2 min.

Wash B (×2):

| | |
|---|---|
| 20 × SSC | 1.2 ml (0.06 × SSC) |
| $H_2O$ | to 400 ml |

Place slide into a 50 ml centrifuge tube and centrifuge at 1500 rpm for 5 mins to dry slide, and then scan fluorescence using a ScanArray 3000 dual-laser confocal scanner and analyse data.

EXAMPLE 7

Preparation of the Arrays

PCR-amplified products are generated from *M. tuberculosis* genomic DNA using ORF-specific primers. Each gene of the genome is represented. These are spotted in a grid onto a standard glass microscope slide using a BioRobotics microgrid robot (MWG Biotech) at a resolution of >4000 spots/$cm^2$.

EXAMPLE 8

Scanning and Analysis of Data

The slides were scanned using an Affymetrix 428 scanner.

Dual fluorescence is used, allowing simultaneous detection of two cDNA samples. The output of the arrays is read using a confocal laser scanner (Affymetrix 428 scanner from MWG Biotech). More detailed information can be found in web site www.sghms.ac.uk/depts/medmicro/bugs; Mujumdar, R.B. (1993) Bioconjugate Chemistry, 4(2), pp.105-111;

Yu, H. (1994) Nucl. Acids Res. 22, pp.3226-3232; and Zhu, Z. (1994) Nucl. Acids Res. 22, pp. 3418-3422.

The raw data were initially analysed in software known as ImaGene, which was supplied with the scanner. The scanned images were then transferred to another software package known as GeneSpring. This is a very powerful tool, which draws information from many databases allowing the complete analysis of the expression of each gene.

EXAMPLE 9

Delete One or More of the Genes from *M. tuberculosis* in Order to Attenuate its Virulence while Retaining Immunogenicity One or more genes that are identified may be disrupted using allelic exchange. In brief, the gene of interest is cloned with 1-2 kb of flanking DNA either side and is inactivated by deletion of part of the coding region and insertion of an antibiotic resistance marker, such as hygromycin.

The manipulated fragment is then transferred to a suitable suicide vector e.g. pPR23 and is transformed into the wild-type parent strain of *M. tuberculosis*. Mutants are recovered by selecting for antibiotic resistant strains. Genotypic analysis (Southern Blotting with a fragment specific to the gene of interest) is performed on the selected strains to confirm that the gene has been disrupted.

The mutant strain is then studied to determine the effect of the gene disruption on the phenotype. In order to use it as a vaccine candidate it would be necessary to demonstrated attenuated virulence. This can be done using either a guinea pig or mouse model of infection. Animals are infected with the mutant strain and the progression of disease is monitored by determining the bacterial load in different organs, in particular the lung and spleen, at specific time points post infection, typically up to 16 weeks.

Comparison is made to animals infected with the wild-type strain which should have a significantly higher bacterial load in the different organs. Long-term survival studies and histopathology can also be used to assess virulence and pathogenicity.

Once attenuated virulence has been established, protection and immunogenicity studies can be performed to assess the potential of the strain as a vaccine. Suitable references for allelic exchange and preparation of TB mutants are McKinney et al., 2000 and Pelicic et al., 1997, [1, 2].

EXAMPLE 10

Select One or More of the Genes Identifiable by the Present Invention, which Encode Proteins that are Immunogenic, and Put them into BCG or an Attenuated Strain of *M. tuberculosis* to Enhance its Overall Immunogenicity The gene of interest is amplified from the *M. tuberculosis* genome by PCR. The amplified product is purified and cloned into a plasmid (pMV306) that integrates site specifically into the mycobacterial genome at the attachment site (attB) for mycobacteriophage L5 [3].

BCG is transformed with the plasmid by electroporation, which involves damaging the cell envelope with high voltage electrical pulses, resulting in uptake of the DNA. The plasmid integrates into the BCG chromosome at the attB site generating stable recombinants. Recombinants are selected and are checked by PCR or Southern blotting to ensure that the gene has been integrated. The recombinant strain is then used for protection studies.

EXAMPLE 11

Use of Recombinant Carriers Such as Attenuated *Salmonella* and the Vaccinia Virus to Express and Present TB Genes One of the best examples of this type of approach is the use of Modified Vaccinia virus Ankara (MVA) [4]. The gene of interest is cloned into a vaccinia virus shuttle vector, e.g. pSC11. Baby Hamster Kidney (BHK) cells are then infected with wild-type MVA and are transfected with the recombinant shuttle vector. Recombinant virus is then selected using a suitable selection marker and viral plaques, selected and purified.

Recombinant virus is normally delivered as part of a prime-boost regime where animals are vaccinated initially with a DNA vaccine encoding the TB genes of interest under the control of a constitutive promoter. The immune response is boosted by administering recombinant MVA carrying the genes of interest to the animals at least 2 weeks later.

EXAMPLE 12

Sub-Unit Vaccines Containing a Single Peptide/Protein or a Combination of Proteins To prepare sub-unit vaccines with one or more peptides or proteins it is first of all necessary to obtain a supply of protein or peptide to prepare the vaccine. Up to now, this has mainly been achieved in mycobacterial studies by purifying proteins of interest from TB culture. However, it is becoming more common to clone the gene of interest and produce a recombinant protein.

The coding sequence for the gene of interest is amplified by PCR with restriction sites inserted at the N terminus and C terminus to permit cloning in-frame into a protein expression vector such as pET-15b. The gene is inserted behind an inducible promoter such as lacZ. The vector is then transformed into *E. coli* which is grown in culture. The recombinant protein is over-expressed and is purified.

One of the common purification methods is to produce a recombinant protein with an N-terminal His-tag. The protein can then be purified on the basis of the affinity of the His-tag for metal ions on a Ni-NTA column after which the His-tag is cleaved. The purified protein is then administered to animals in a suitable adjuvant [5].

EXAMPLE 13

Plasmid DNA Vaccines Carrying One or More of, the Identified Genes

DNA encoding a specific gene is amplified by PCR, purified and inserted into specialised vectors developed for vaccine development, such as pVAX1. These vectors contain promoter sequences, which direct strong expression of the introduced DNA (encoding candidate antigens) in eukaryotic cells (e.g. CMV or SV40 promoters), and polyadenylation signals (e.g. SV40 or bovine growth hormone) to stabilise the mRNA transcript.

The vector is transformed into *E. coli* and transformants are selected using a marker, such as kanamycin resistance, encoded by the plasmid. The plasmid is then recovered from transformed colonies and is sequenced to check that the gene of interest is present and encoded properly without PCR generated mutations.

Large quantities of the plasmid is then produced in *E. coli* and the plasmid is recovered and purified using commercially available kits (e.g. Qiagen Endofree-plasmid preparation). The vaccine is then administered to animals for example by intramuscular injection in the presence or absence of an adjuvant.

EXAMPLE 14

Preparation of DNA Expression Vectors

DNA vaccines consist of a nucleic acid sequence of the present invention cloned into a bacterial plasmid. The plasmid vector pVAX1 is commonly used in the preparation of DNA vaccines. The vector is designed to facilitate high copy number replication in *E. coli* and high level transient expression of the peptide of interest in most mammalian cells (for details see manufacturers protocol for pVAX1 (catalog No. V260-20 www.invitrogen.com).

The vector contains the following elements:—

- Human cytomegalovirus immediate-early (CMV) promoter for high-level expression in a variety of mammalian cells
- T7 promoter/priming site to allow in vitro transcription in the sense orientation and sequencing through the insert
- Bovine growth hormone (BGH) polyadenylation signal for efficient transcription termination and polyadenylation of mRNA
- Kanamycin resistance gene for selection in *E. coli*
- A multiple cloning site
- pUC origin for high-copy number replication and growth in *E. coli*
- BGH reverse priming site to permit sequencing through the insert Vectors may be prepared by means of standard recombinant techniques which are known in the art, for example Sambrook et al., (1989). Key stages in preparing the vaccine are as follows:

- The gene of interest is ligated into pVAX1 via one of the multiple cloning sites
- The ligation mixture is then transformed into a competent *E. coli* strain (e.g. TOP10) and LB plates containing 50 μg/ml kanamycin are used to select transformants.
- Clones are selected and may be sequenced to confirm the presence and orientation of the gene of interest.
- Once the presence of the gene has been verified, the vector can be used to transfect a mammalian cell line to check for protein expression. Methods for transfection are known in the art and include, for example, electroporation, calcium phosphate, and lipofection.
- Once peptide expression has been confirmed, large quantities of the vector can be produced and purified from the appropriate cell host, e.g. *E. coli.* pVAX1 does not integrate into the host chromosome. All non-essential sequences have been removed to minimise the possibility of integration. When constructing a specific vector, a leader sequence may be included to direct secretion of the encoded protein when expressed inside the eukaryotic cell.

Other examples of vectors that have been used are V1Jns.tPA and pCMV4 (Lefevre et al., 2000 and Vordermeier et al., 2000).

Expression vectors may be used that integrate into the genome of the host, however, it is more common and more preferable to use a vector that does not integrate. The example provided, pVAX1, does not integrate. Integration would lead to the generation of a genetically modified host which raises other issues.

EXAMPLE 15

RNA Vaccine

As discussed on page 15 of U.S. Pat. No. 5,783,386, one approach is to introduce RNA directly into the host.

Thus, the vector construct (Example 10) may be used to generate RNA in vitro and the purified RNA then injected into the host. The RNA would then serve as a template for translation in the host cell. Integration would not occur.

Another option is to use an infectious agent such as the retroviral genome carrying RNA corresponding to the gene of interest. Here you will get integration into the host genome Another option is the use of RNA replicon vaccines which can be derived from virus vectors such as Sindbis virus or Semliki Forest virus. These vaccines are self-replicating and self-limiting and may be administered as either RNA or DNA which is then transcribed into RNA replicons in vivo. The vector eventually causes lysis of the transfected cells thereby reducing concerns about integration into the host genome. Protocols for RNA vaccine construction are detailed in Cheng et al., (2001).

EXAMPLE 16

Diagnostic Assays Based on Assessing T Cell Responses

For a diagnostic assay based on assessing T cell responses it would be sufficient to obtain a sample of blood from the patient. Mononuclear cells (monocytes, T and B lymphocytes) can be separated from the blood using density gradients such as Ficoll gradients.

Both monocytes and B-lymphocytes are both able to present antigen, although less efficiently than professional antigen presenting cells (APCs) such as dendritic cells. The latter are more localised in lymphoid tissue.

The simplest approach would be to add antigen to the separated mononuclear cells and incubate for a week and then assess the amount of proliferation. If the individual had been exposed to the antigen previously through infection, then T-cell clones specific to the antigen should be more prevalent in the sample and should respond.

It is also possible to separate the different cellular populations should it be desired to control the ratio of T cells to APC's.

Another variation of this type of assay is to measure cytokine production by the responding lymphocytes as a measure of response. The ELISPOT assay described below in Example 17 is a suitable example of this variation.

EXAMPLE 17

Detection of Latent Mycobacteria

A major problem for the control of tuberculosis is the presence of a large reservoir of asymptomatic individuals infected with tubercle bacilli. Dormant bacilli are more resistant to front-line drugs.

The presence of latent mycobacteria-associated antigen may be detected indirectly either by detecting antigen specific antibody or T-cells in blood samples.

The following method is based on the method described in Lalvani et al. (2001) in which a secreted antigen, ESAT-6, was identified as being expressed by members of the *M. tuberculosis* complex but is absent from *M. Bovis* BCG vaccine strains and most environmental mycobacteria. 60-80% of patients also have a strong cellular immune response to ESAT-6. An ex-vivo ELISPOT assay was used to detect ESAT-6 specific T cells.

As applied to the present invention:

A 96 well plate is coated with cytokine (e.g. interferon-γ, IL-2)-specific antibody. Peripheral blood monocytes are then isolated from patient whole blood and are applied to the wells.

Antigen (ie. one of the peptides, fragments, derivatives or variants of the present invention) is added to stimulate specific T cells that may be present and the plates are incubated for 24 h. The antigen stimulates cytokine production which then binds to the specific antibody.

The plates are washed leaving a footprint where antigen-specific T cells were present.

A second antibody coupled with a suitable detection system, e.g. enzyme, is then added and the number of spots are enumerated after the appropriate substrate has been added.

The number of spots, each corresponding to a single antigen-specific T cell, is related to the total number of cells originally added.

The above Example also describes use of an antigen that may be used to distinguish TB infected individuals from BCG vaccinated individuals. This could be used in a more discriminative diagnostic assay.

EXAMPLE 18

In Vitro Model for Mycobacterial Persistence Under the Joint Conditions of Carbon-Starvation and Oxygen-Limitation (a Variation on Examples 1-7)

Materials and Methods

Strain

Studies were performed with *M. tuberculosis* strain H37Rv (NCTC cat. No. 7416) —a representative strain of *M. tuberculosis*. Stock cultures were grown on Middlebrook 7H10+ OADC for 3 weeks at 37±2° C.

Culture Medium

Persistence cultures were established in Middlebrook 7H9 medium supplemented with Middlebrook ADC enrichment, 0.2% Tween 80 and 0.2% glycerol (see below). The medium was prepared with high quality water from a Millipore water purification system and filter sterilised by passage through a 0.1 μm pore size cellulose acetate membrane filter capsule (Sartorius Ltd). The pH was adjusted to 6.6 with concentrated hydrochloric acid.

Middlebrook 7H10+OADC agar was used to prepare inoculum cultures, enumerate the number of culturable bacteria in samples, and to assess culture purity.

Culture System

The culture system described in WO00/52139, operated as a batch fermenter, was employed for this Example.

Culture experiments were performed in a one litre glass vessel operated at a working volume of 750 ml. The culture was agitated by a magnetic bar placed in the culture vessel coupled to a magnetic stirrer positioned beneath the vessel. Culture conditions were continuously monitored by an Anglicon Microlab Fermentation System (Brighton Systems, Newhaven), linked to sensor probes inserted into the culture through sealed ports in the top plate. The oxygen concentration was monitored with a galvanic oxygen electrode (Uniprobe, Cardiff) and was controlled through sparging the culture with a mixture of air and oxygen free-nitrogen. Temperature was monitored by an Anglicon temperature probe, and maintained by a heating pad positioned beneath the culture vessel. Culture pH was measured using an Ingold pH electrode (Mettler-Toledo, Leicester).

Inoculation and Culture

The vessel was filled with 750 ml of sterile culture medium and parameters were allowed to stabilise at 37° C.±2° C., pH 6.9±0.3 and a dissolved oxygen tension of approximately 70% air saturation. A dense inoculum suspension was prepared by resuspending Middlebrook agar cultures, grown at 37±2° C. for 3 week, in sterile deionised water. The inoculum was aseptically transferred to the culture vessel, to provide an initial culture turbidity of approximately 0.25 at 540 nm. The culture was maintained at 37° C. with an agitation rate of 500 to 750 rpm.

Figure 3:
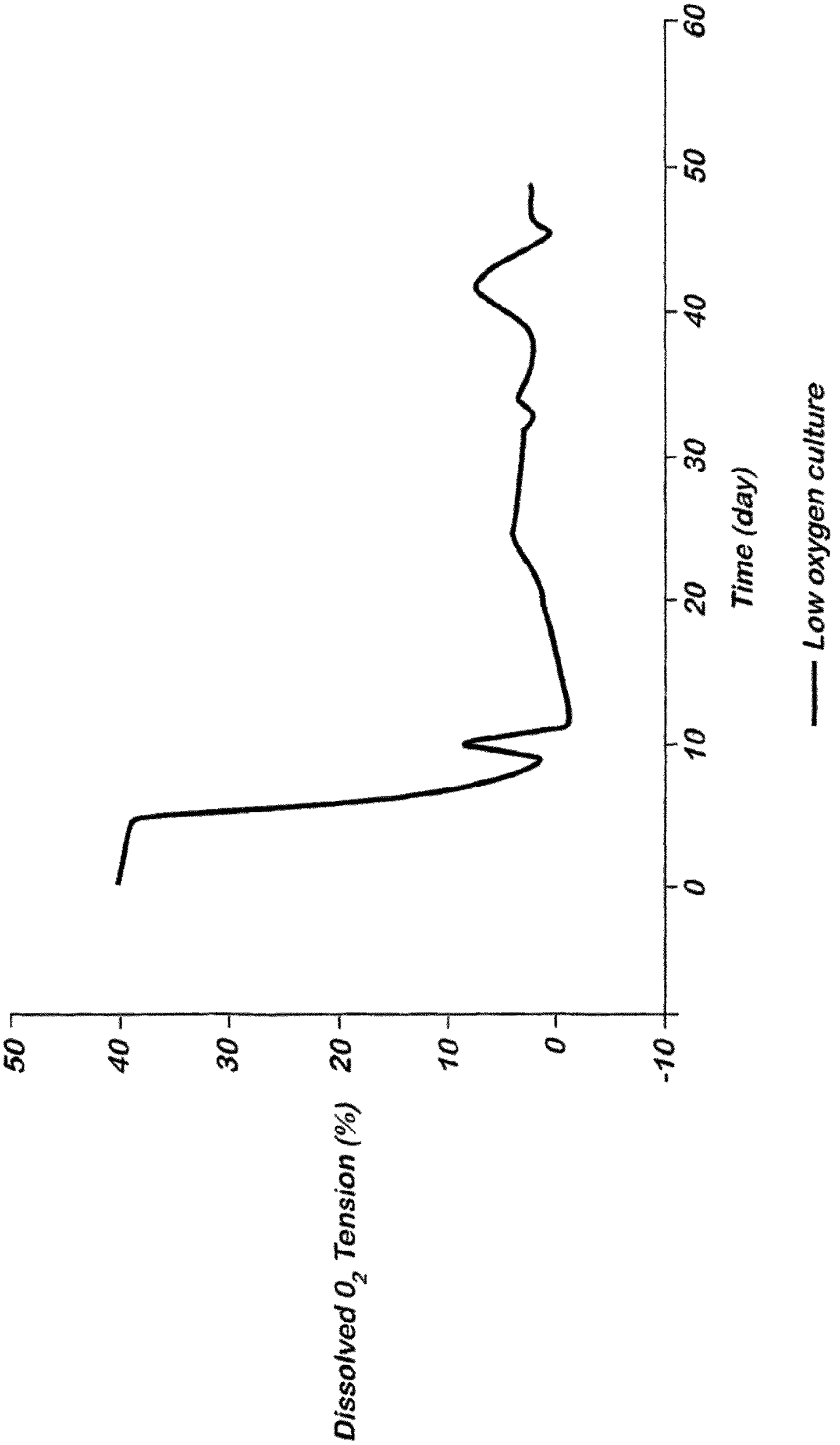
FIG. 3 illustrates the DOT within the medium of the mycobacterial culture described in Example 18.

After inoculation, the dissolved oxygen tension (DOT) of the culture was maintained at approximately 40% air saturation at 37° C. until the culture had entered early exponential growth. The DOT was then lowered in increments down to 1% air saturation over a six day period (FIG. 3). The culture was then maintained at a DOT of 0-5% until 50 days after inoculation and samples were removed regularly to Monitor growth and survival, nutrient utilisation and gene expression.

Growth and Survival

Bacterial growth and survival was assessed by determining the number of viable cells in the culture system at specific time points. This was achieved by preparing a decimal dilution series of the sample in sterile water and plating 100 μl aliquots onto Middlebrook 7H10+OADC plates. The plates were incubated at 37° C. for up to 4 weeks before enumerating the number of colonies formed.

Nutrient Utilisation

Glycerol is the primary carbon and energy source present in Middlebrook 7H9 medium with ADC, 0.2% Tween and Glycerol. The rate at which glycerol was utilised was determined using the Glycerol Determination Kit Cat. No. 148 270 Boehringer Mannheim.

Microarray Experiments

RNA was extracted from culture samples collected at different time points during the experiment. A fluorescently-labelled cDNA was then transcribed from each sample of RNA. The cDNA was labelled by the incorporation of either Cy3 or Cy5 labelled dCTP (Dyes are supplied by Amersham Pharmacia Biotech).

Whole *M. tuberculosis* genome arrays were prepared from *M. tuberculosis* genomic DNA using ORF-specific primers. PCR products corresponding to each ORF were spotted in a grid onto a standard glass microscope slide using a BioRobotics microgrid robot (MWG Biotech) at a resolution of >4000 spots/$cm^2$. Arrays were supplied by Dr P Butcher, St George's Hospital Medical School London.

In each microarray experiment a whole genome array was hybridised with labelled cDNA from one culture sample (Test sample). Each array was also hybridised with control DNA incorporating a different Cy dye and prepared from DNA extracted from *M. tuberculosis* strain H37Rv (control sample). Each array was scanned, using an Affymetrix 428 scanner, at two different wavelengths corresponding to the excitation maxima of each dye and the intensity of the emitted light was recorded. The raw data was processed by ImaGene software before performing comparative analysis using GeneSpring.

Results

Figure 2:
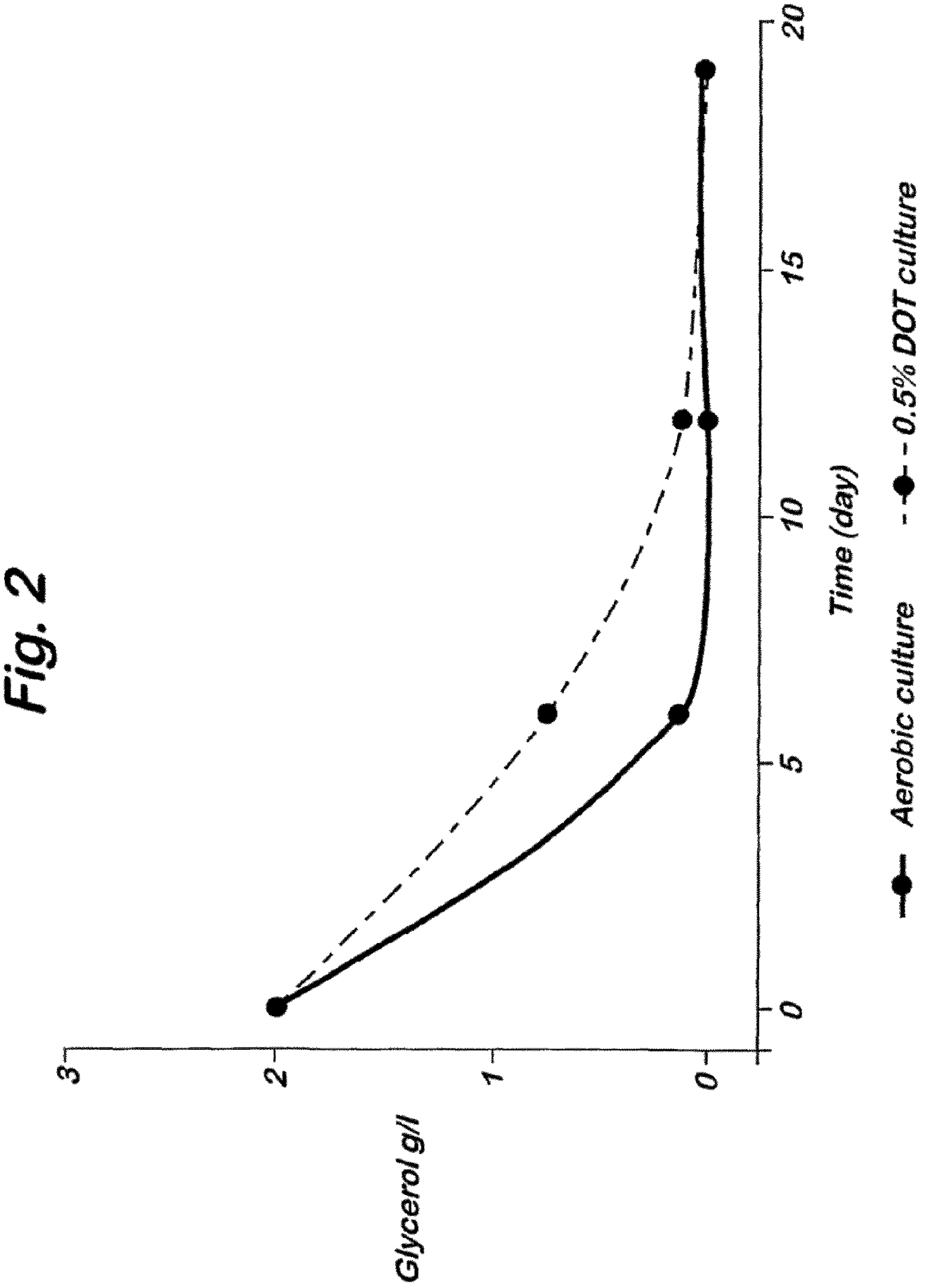
FIG. 2 illustrates the concentration of glycerol (as the primary carbon and energy source during culture of *M. tuberculosis* under batch fermentation conditions at a DOT of 50% air saturation (37° C.).
Figure 4:
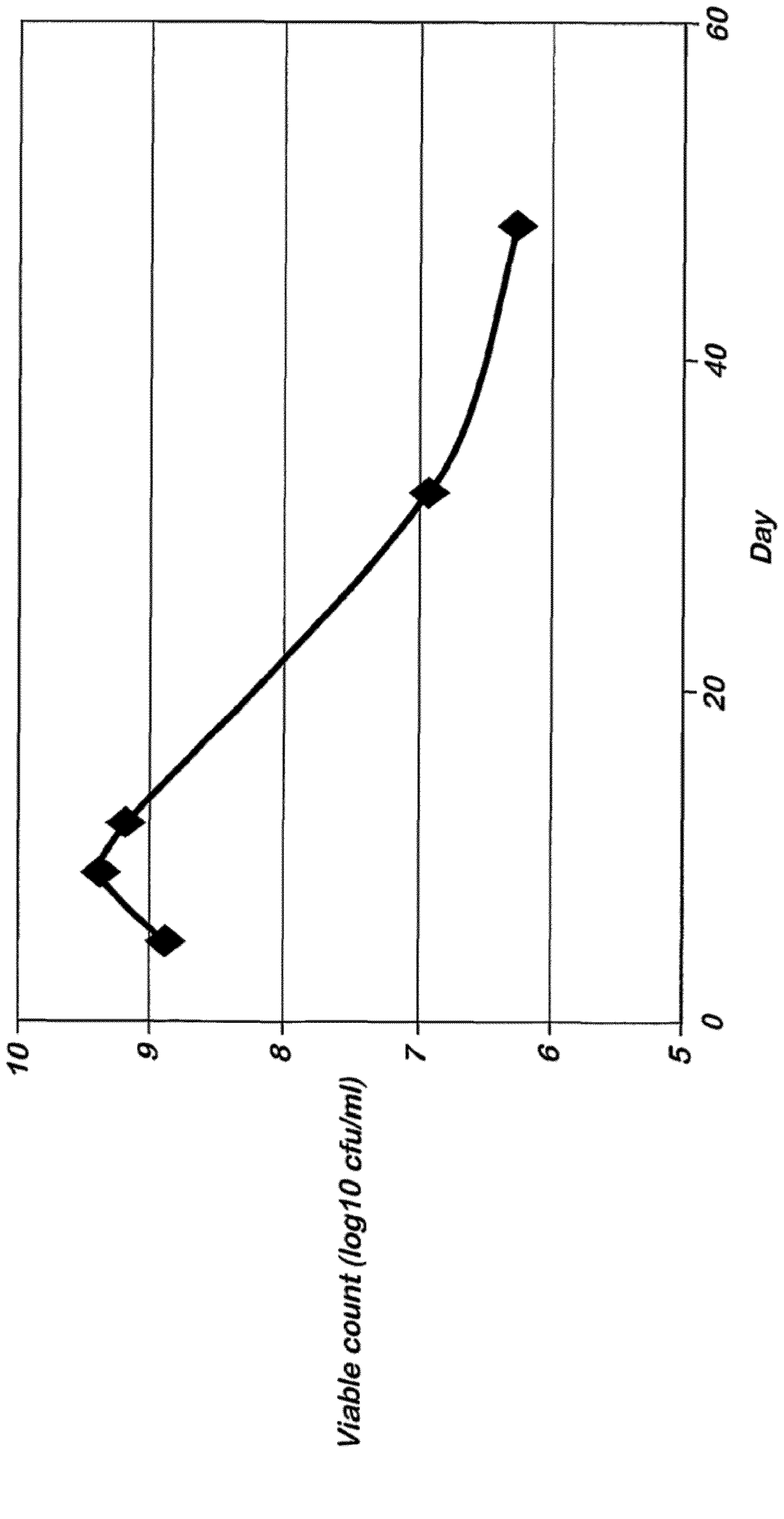
FIG. 4 illustrates the viable counts for *M. tuberculosis* during the batch fermentation conditions of Example 18 (ie. carbon-starvation, and oxygen limiting conditions).

Analysis of viable count data indicated that the culture grew exponentially until 10 to 12 days post infection (FIG. 4). As the culture entered stationary phase, viability started to decline and continued to decline steadily over the duration of the study. After 40 days in stationary phase, approximately 0.1% of the culture was still culturable on Middlebrook agar. The rate of glycerol utilisation was slower than observed in the culture established under aerobic conditions, indicating that the metabolic activity of the low-oxygen culture was restricted by limited oxygen availability. Nevertheless, the principal carbon and energy source was depleted within 15 days after inoculation (FIG. 2).

Samples were collected for microarray analysis as outlined. The gene expression profiles for samples collected at day 5 and 50 were compared. Three arrays were prepared for each sample and the test data was normalised against the control data on each chip. The normalised data for each set of arrays was then averaged and the two data sets were compared. Those genes that were expressed at least 1.5-fold, preferably at least 5-fold higher at day 50 relative to day 5 were selected. The gene list was then added to those genes identified under "nutrient-starving" conditions, and the complete set listed in Table 2.

Liquid medium formulation for persistence cultures—Middlebrook 7H9 medium supplemented with ADC, 0.2% Tween 80 and 0.2% Glycerol

| Composition per liter: | |
|---|---|
| $Na_2HPO_4$ | 2.5 g |
| $KH_2PO_4$ | 1.0 g |
| Monosodium glutamate | 0.5 g |
| $(NH4)_2SO_4$ | 0.5 g |
| Sodium citrate | 0.1 g |
| $MgSO_4$•$7H_2O$ | 0.05 g |
| Ferric ammonium citrate | 0.04 g |
| $CuSO_4$•$5H_2O$ | 1.0 mg |
| Pyridoxine | 1.0 mg |
| $ZnSO_4$•$7H_2O$ | 1.0 mg |
| Biotin | 0.5 mg |
| $CaCl_2$•$2H_20$ | 0.5 mg |
| Middlebrook ADC enrichment | 100 ml |
| Glycerol | 2.0 ml |
| Tween 80 | 2.0 ml |
| Middlebrook ADC enrichment - per 100 ml | |
| Bovine serum albumin | 5.0 g |
| Glucose | 2.0 g |
| Catalase | 3.0 mg |

Microarray Protocols

1. RNA Extraction from *M. tuberculosis* for Microarray Analysis

Materials and Methods

Trizol (Life Technologies)—formulation of phenol and guanidine thiocyanate.

GTC lysis solution containing: 5 M guanidine thiocyanate, 0.5% N-lauryl sarcosine, 25 mM tri-sodium citrate, 0.1 M 2-mercaptoethanol, and 0.5% Tween 80.

Chloroform

Isopropanol

3 M sodium acetate

70% Ethanol microfuge ribolyser

Sterile plasticware—Falcon tubes, screw capped eppendorfs, gilson tips—all RNase free Glassware—baked at 160° C. for at least 16 hours Method Steps performed at Containment level 3; within a Class III microbiological safety cabinet.

Remove 10 or 20 ml of culture ($10^9$/ml) and immediately add this to 4 volumes of GTC lysis buffer in a plastic specimen pot. Seal the pot tightly.

Incubate the cells in GTC lysis buffer for 1 hour at room temperature. Surface decontaminate the plastic pot with 5% Hycolin for 5 minutes. Transfer the sample to the pass box and place it into a plastic carry tin with a sealable lid. Close the container securely and transport it to a non-toxic cabinet CL3 cabinet.

Equally distribute the lysis mixture between Falcon tubes. Place these tubes into centrifuge buckets and seal the buckets tightly. Surface-decontaminate the buckets for 5 minutes with 5% Hycolin. Then transfer them to the centrifuge (Baird and Tatlock Mark IV refrigerated bench-top centrifuge). Spin the tubes at 3,000 rpm for 30 minutes.

Return the unopened buckets to the cabinet. Remove the centrifuge tubes and pour the supernatant into a waste bottle for GTC lysis buffer.

Resuspend each pellet in 5 ml of Trizol (formulation of phenol and GTC cat No. 15596-026). The manufacturers guidelines recommend lysing cells by repetitive pipetting. Although this action alone will not lyse *M. tuberculosis*, it is important to completely resuspend the pellet in Trizol.

Transfer 1 ml of cells into each FastRNA tube and ribolyse them at power setting 6.5 for 45 seconds.

Leave the tubes to incubate at room temperature for 5 minutes.

Remove the aqueous layer from each tube and add this to 200 µl of chloroform in a screw-capped eppendorf tube. Shake each tube vigorously for about 15 seconds. Incubate for 2-3 minutes at room temperature.

Spin the tubes at 13,000 rpm for 15 minutes. Following centrifugation, the liquid separates into red phenol/chloroform phase, an interface, and a clear aqueous phase.

Carefully remove the aqueous phase and transfer it to fresh eppendorf tubes containing 500 µl of chloroform/isoamyl alcohol (24:1). Spin the tubes at 13,000 rpm for 15 minutes.

Transfer the aqueous phase to eppendorf tubes containing 50 µl of sodium acetate and 500 µl of isopropanol.

Surface decontaminate the eppendorf tubes with 5% Hycolin for 5 minutes. Remove the tubes from the CL3 laboratory and continue with the procedure in laboratory.

Steps performed at Containment level 2:

Precipitate the RNA at −70° C. for at least 30 minutes (optionally overnight).

Spin the precipitated RNA down at 13,000 rpm for 10 minutes. Remove the supernatant and wash the pellet in 70% ethanol. Repeat centrifugation.

Remove the 70% ethanol and air-dry the pellet. Dissolve the pellet in RNAse free water.

Freeze the RNA at −70° C. to store it.

2. Isolation of Genomic DNA from *Mycobacterium tuberculosis* Grown in Chemostat Culture. DNA then Used to Generate Cy3 or Cy5 Labelled DNA for Use as a Control in Microarray Experiments Materials and Methods Beads 0.5 mm in diameter Bead beater Bench top centrifuge Platform rocker Heat block Falcon 50 ml centrifuge tubes Sorvall RC-5C centrifuge 250 ml polypropylene centrifuge pots.

Screw capped eppendorf tubes
Pipettes 1 ml, 200 μl, 10 ml, 5 ml
Breaking Buffer
50 mM Tris HCL pH 8.0
10 mM EDTA
100 mM NaCl
Procedure
Mechanical Disruption of Mtb Cells 150 ml of chemostat cells (O.D of 2.5 at 540 nm) are spun down at 15,000 rpm for 15 minutes in 250 ml polypropylene pots using centrifuge Sorvall RC-5C.

The supernatant is discarded.

Cells are re-suspended in 5 ml of breaking buffer in a 50 ml Falcon tube and centrifuged at 15,000 rpm for a further 15 minutes.

The supernatant is removed and additional breaking buffer is added at a volume of 5 ml. Beads are used to disrupt the cells. These are used at a quantity of 1 ml of beads for 1 ml of cells. Place the sample into the appropriate sized chamber. Place in the bead beater and secure the outer unit (containing ice) and process at the desired speed for 30 seconds.

Allow the beads to settle for 10 minutes and transfer cell lysate to a 50 ml Falcon centrifuge tube Wash beads with 2-5 ml of breaking buffer by pipetting washing buffer up and down over the beads.

Add this washing solution to the lysate in the falcon tube

Removal of Proteins and Cellular Components.

Add 0.1 volumes of 10% SDS and 0.01 volumes proteinase K.

Mix by inversion and heat at 55° C. in a heat block for 2-3 hours

The resulting mix should be homogenous and viscous. If it isn't then add more SDS to bring the concentration up to 0.2%

Add an equal volume of phenol/chloroform/Isoamyl alcohol in the ratio: 25/24/1.

Gently mix on a platform rocker until homogenous

Spin down at 3,000 rpm for 20 minutes

Remove the aqueous phase and place in a fresh tube

Extract the aqueous phase with an equal volume of chloroform to remove traces of cell debris and phenol. Chloroform extractions may need to be repeated to remove all the debris.

Precipitate the DNA with 0.3 M sodium acetate and an equal volume of isopropanol.

Spool as much DNA as you can with a glass rod

Wash the spooled DNA in 70% ethanol followed by 100% ethanol

Leave to air dry

Dissolve the DNA in sterile deionised water (500 μl)

Allow DNA to dissolve at 4° C. for approximately 16 hours.

Add RNase 1 (500U) to the dissolved DNA

Incubate for 0.1 hour at 37° C.

Re-extract with an equal volume of phenol/chloroform followed by a chloroform extraction and precipitate as before.

Spin down the DNA at 13,000 rpm

Remove the supernatant and wash the pellet in 70% ethanol

Air dry

Dissolve in 200-500 μl of sterile water.

3. Preparation of Cy3 or Cy5 Labelled DNA from DNA a) Prepare One Cy3 or One Cy5 Labelled DNA Sample Per Microarray Slide.

Each Sample:

| | |
|---|---|
| DNA | 2-5 μg |
| Random primers (3 μg/μl) | 1 μl |
| $H_2O$ | to 41.5 μl |

Heat at 95° C. for 5 min, snap cool on ice and briefly centrifuge.

Add to Each:

| | |
|---|---|
| 10 * REact 2 buffer | 5 μl |
| dNTPs (5 mM dA/G/TTP, 2 mM dCTP) | 1 μl |
| Cy3 OR Cy5 dCTP | 1.5 μl |
| Klenow (5 U/μl) | 1 μl |

Incubate at 37° C. in dark for 90 min.

b) Prehybridise Slide

Mix the prehybridisation solution in a Coplin jar and incubate at 65° C. during the labelling reaction to equilibrate.

Prehybridisation:

| | |
|---|---|
| 20 * SSC | 8.75 ml (3.5 * SSC) |
| 20% SDS | 250 μl (0.1% SDS) |
| BSA (100 mg/ml) | 5 ml (10 mg/ml) |
| $H_2O$ | to 50 ml |

Incubate the microarray slide in the pre-heated prehybridisation solution at 65° C. for 20 min. Rinse slide thoroughly in 400 ml $H_2O$ for 1 min followed by rinse in 400 ml propan-2-ol for 1 min and centrifuge slide in 50 ml centrifuge tube at 1,500 rpm for 5 min to dry. Store slide in dark, dust-free box until hybridisation (<1 h).

c) Purify Cy3/Cy5 Labelled DNA-Qiagen MinElute Purification

Combine Cy3 and Cy5 labelled DNA samples in single tube and add 500 μl Buffer PB.

Apply to MinElute column in collection tube and centrifuge at 13,000 rpm for 1 min.

Discard flow-through and place MinElute column back into same collection tube.

Add 500 μl Buffer PE to MinElute column and centrifuge at 13,000 rpm for 1 min.

Discard flow-through and place MinElute column back into same collection tube.

Add 250 μl Buffer PE to MinElute column and centrifuge at 13,000 rpm for 1 min.

Discard flow-through and place MinElute column back into same collection tube.

Centrifuge at 13,000 rpm for an additional 1 min to remove residual ethanol.

Place the MinElute column into a fresh 1.5 ml tube.

Add 10.5 μl $H_2O$ to the centre of the membrane and allow to stand for 1 min.

Centrifuge at 13,000 rpm for 1 min.

4. Preparation of Cy3 or Cy5 Label cDNA from RNA a) Prepare One Cy3 and One Cy5 Labelled cDNA Sample Per Microarray Slide.

Each Sample:

| | |
|---|---|
| RNA | 2-10 μg |
| Random primers (3 μg/μl) | 1 μl |
| $H_2O$ | to 11 μl |

Heat at 95° C. for 5 min, snap cool on ice and briefly centrifuge.

Add to Each:

| | |
|---|---|
| 5 * First Strand Buffer | 5 μl |
| DTT (100 mM) | 2.5 μl |
| dNTPs (5 mM dA/G/TTP, 2 mM dCTP) | 2.3 μl |
| Cy3 OR Cy5 dCTP | 1.7 μl |
| SuperScript II (200 U/μl) | 2.5 μl |

Incubate at 25° C. in dark for 10 min followed by 42° C. in dark for 90 min.

b) Prehybridise Slide

Mix the prehybridisation solution in a Coplin jar and incubate at 65° C. during the labelling reaction to equilibrate.

Prehybridisation:

| | |
|---|---|
| 20 * SSC | 8.75 ml (3.5 * SSC) |
| 20% SDS | 250 μl (0.1% SDS) |
| BSA (100 mg/ml) | 5 ml (10 mg/ml) |
| $H_2O$ | to 50 ml |

Incubate the microarray slide in the pre-heated prehybridisation solution at 65° C. for 20 min. Rinse slide thoroughly in 400 ml $H_2O$ for 1 min followed by rinse in 400 ml propan-2-ol for 1 min and centrifuge slide in 50 ml centrifuge tube at 1500 rpm for 5 min to dry. Store slide in dark, dust-free box until hybridisation (<1 h).

c) Purify Cy3/Cy5 Labelled cDNA-Qiagen MinElute Purification

Combine Cy3 and Cy5 labelled DNA samples in single tube and add 250 μl Buffer PB.

Apply to MinElute column in collection tube and centrifuge at 13,000 rpm for 1 min.

Discard flow-through and place MinElute column back into same collection tube.

Add 500 μl Buffer PE to MinElute column and centrifuge at 13,000 rpm for 1 min.

Discard flow-through and place MinElute column back into same collection tube.

Add 250 μl Buffer PE to MinElute column and centrifuge at 13,000 rpm for 1 min.

Discard flow-through and place MinElute column back into same collection tube.

Centrifuge at 13,000 rpm for an additional 1 min to remove residual ethanol.

Place the MinElute column into a fresh 1.5 ml tube.

Add 10.5 μl $H_2O$ to the centre of the membrane and allow to stand for 1 min.

Centrifuge at 13,000 rpm for 1 min.

5. Hybridise Slide with Cy3/Cy5 Labelled cDNA/DNA

Place the prehybridise microarray slide in the hybridisation cassette and add two 15 μl aliquots of $H_2O$ to the wells in the cassette. Mix resuspended Cy3/Cy5 labelled cDNA sample with hybridisation solution.

Hybridisation:

| | |
|---|---|
| Cy3/Cy5 labelled cDNA sample | 10.5 μl |
| 20 × SSC | 3.2 μl (4 × SSC) |
| 2% SDS | 2.3 μl (0.3% SDS) |

Heat hybridisation solution at 95° C. for 2 min. Do NOT snap cool on ice but allow to cool slightly and briefly centrifuge. Pipette the hybridisation solution onto the slide at the edge of the arrayed area avoiding bubble formation. Using forceps carefully drag the edge of a cover slip along the surface of the slide towards the arrayed area and into the hybridisation solution at the edge of the array. Carefully lower the cover slip down over the array avoiding any additional movement once in place. Seal the hybridisation cassette and submerge in a water bath at 65° C. for 16-20 hours.

Wash Slide

Remove microarray slide from hybridisation cassette and initially wash slide carefully in staining trough of Wash A preheated to 65° C. to remove cover slip. Once cover slip is displaced place slide(s) in slide rack and continue agitating in Wash A for a further 2 min.

Wash A:

| | |
|---|---|
| 20 × SSC | 20 ml (1 × SSC) |
| 20% SDS | 1 ml (0.05% SDS) |
| $H_2O$ | to 400 ml |

Transfer slide(s) to a clean slide rack and agitate in first trough of Wash B for 2 min. Wash in second trough of Wash B with agitation for 2 min.

Wash B (×2):

| | |
|---|---|
| 20 × SSC | 1.2 ml (0.06 × SSC) |
| $H_2O$ | to 400 ml |

Place slide into a 50 ml centrifuge tube and centrifuge at 1500 rpm for 5 mins to dry slide and then scan fluorescence.

TABLE 2

Genes induced or up-regulated under nutrient-starving conditions, or under nutrient-starving and oxygen-limiting conditions.

| Gene | Assigned function | SEQ. ID. NO. |
|---|---|---|
| Rv0021c | 2-nitropropane dioxygenase | 1, 2 |
| Rv0029 | | 3, 4 |
| Rv0076c | peptide with a membrane-spanning domain at its C-terminus | 5, 6 |
| Rv0111 | acetyltransferase | 7, 8 |
| Rv0161 | oxidoreductase | 9, 10 |
| Rv0212c | transcriptional regulator | 11, 12 |
| Rv0228 | acyl transferase | 13, 14 |
| Rv0260c | two-component response regulator | 15, 16 |
| Rv0311 | | 17, 18 |
| Rv0322 | UDP-glucose dehydrogenase | 19, 20 |
| Rv0325 | | 21, 22 |
| Rv0389 | phosphoribosylglycinamide formyltransferase | 23, 24 |
| Rv0390 | | 25, 26 |
| Rv0395 | | 27, 28 |
| Rv0480c | | 29, 30 |
| Rv493c | | 31, 32 |
| Rv0534c | 1,4-dihydroxy-2-naphthoate octaprenyl | 33, 34 |
| Rv0557 | | 35, 36 |

TABLE 2-continued

Genes induced or up-regulated under nutrient-starving conditions, or under nutrient-starving and oxygen-limiting conditions.

| Gene | Assigned function | SEQ. ID. NO. |
|---|---|---|
| Rv0614 | | 37, 38 |
| Rv0621 | peptide containing a membrane-spanning region | 39, 40 |
| Rv0622 | peptide containing a membrane-spanning region | 41, 42 |
| Rv0697 | gmc-type oxidoreductase | 43, 44 |
| Rv0698 | | 45, 46 |
| Rv0736 | | 47, 48 |
| Rv0751c | 3-hydroxyisobutyrate dehydrogenase; methylmalonate semialdehyde dehydrogenase | 49, 50 |
| Rv0775 | | 51, 52 |
| Rv0776c | | 53, 54 |
| Rv0785 | dehydrogenase | 55, 56 |
| Rv0790c | | 57, 58 |
| Rv0794c | mercuric reductase; glutathione reductase; dihydrolipoamide dehydrogenase | 59, 60 |
| Rv0795 | transposase | 61, 62 |
| Rv0836c | | 63, 64 |
| Rv0837c | | 65, 66 |
| Rv0840c | proline iminopeptidase; prolyl aminopeptidase | 67, 68 |
| Rv0849 | integral membrane transport protein; quinolone efflux pump | 69, 70 |
| Rv0917 | glycine betaine transporter | 71, 72 |
| Rv978c | | 73, 74 |
| Rv1051c | | 75, 76 |
| Rv1056 | | 77, 78 |
| Rv1089 | | 79, 80 |
| Rv1146 | membrane protein | 81, 82 |
| Rv1147 | phosphatidylethanolamine N-methyltransferase | 83, 84 |
| Rv1370c | transposase | 85, 86 |
| Rv1371 | membrane protein | 87, 88 |
| Rv1372 | chalcone synthase 2 | 89, 90 |
| Rv1373 | sulfotransferase | 91, 92 |
| Rv1429 | | 93, 94 |
| Rv1455 | | 95, 96 |
| Rv1482c | | 97, 98 |
| Rv1496 | | 99, 100 |
| Rv1526c | glycosyl transferase | 101, 102 |
| Rv1528c | PKS-associated protein | 103, 104 |
| Rv1552 | fumarate reductase flavoprotein | 105, 106 |
| Rv1569 | 8-amino-7-oxononanoate synthase; aminotransferase class-II pyridoxal-phosphate | 107, 108 |
| Rv1573 | phage phiRv1 protein | 109, 110 |
| Rv1577c | bacteriophage HK97 prohead protease; phage phiRv1 protein | 111, 112 |
| Rv1670 | | 113, 114 |
| Rv1725c | | 115, 116 |
| Rv1730 | penicillin-binding protein | 117, 118 |
| Rv1763 | transposase | 119, 120 |
| Rv1765c | | 121, 122 |
| Rv1777 | cytochrome p450 | 123, 124 |
| Rv1806 | | 125, 126 |
| Rv1866 | fatty acyl-CoA racemase | 127, 128 |
| Rv1917c | | 129, 130 |
| Rv1939 | nitrilotriacetate monooxygenase | 131, 132 |
| Rv2013 | transposase | 133, 134 |
| Rv2027c | histidine kinase response regulator | 135, 136 |
| Rv2086 | transposase | 137, 138 |
| Rv2087 | transposase | 139, 140 |
| Rv2089c | pepQ; peptidase | 141, 142 |
| Rv2091c | peptide containing a transmembrane region | 143, 144 |
| Rv2093c | TatC component of twin-arginine translocation protein export system | 145, 146 |
| Rv2105 | transposase | 147, 148 |
| Rv2168c | transposase | 149, 150 |
| Rv2242 | | 151, 152 |
| Rv2282c | LysR transcription regulator | 153, 154 |
| Rv2292c | | 155, 156 |
| Rv2310 | excisionase | 157, 158 |
| Rv2322c | ornithine aminotransferase | 159, 160 |
| Rv2323c | | 161, 162 |
| Rv2332 | malate oxidoreductase | 163, 164 |
| Rv2400c | thiosulphate-binding protein | 165, 166 |
| Rv2414c | | 167, 168 |
| Rv2437 | | 169, 170 |
| Rv2478c | | 171, 172 |

TABLE 2-continued

Genes induced or up-regulated under nutrient-starving conditions, or under nutrient-starving and oxygen-limiting conditions.

| Gene | Assigned function | SEQ. ID. NO. |
|---|---|---|
| Rv2486 | enoyl-coA hydratase | 173, 174 |
| Rv2505c | acyl-CoA synthetase | 175, 176 |
| Rv2529 | methyltransferase | 177, 178 |
| Rv2596 | | 179, 180 |
| Rv2847c | multifunctional enzyme; siroheme synthase | 181, 182 |
| Rv3635 | transmembrane protein | 183, 184 |
| Rv2643 | membrane protein | 185, 186 |
| Rv2648 | transposase | 187, 188 |
| Rv2655c | | 189, 190 |
| Rv2684 | transmembrane protein; arsenical pump | 191, 192 |
| Rv2687c | regulatory protein | 193, 194 |
| Rv2690c | transport protein; permease | 195, 196 |
| Rv2800 | glutaryl 7-aca acylase | 197, 198 |
| Rv2812 | transposase | 199, 200 |
| Rv2813 | secretion pathway protein | 201, 202 |
| Rv2835c | sn-glycerol-3-phosphate transport system permease protein | 203, 204 |
| Rv2874 | integral membrane protein | 205, 206 |
| Rv2877c | mercury resistance protein | 207, 208 |
| Rv2943 | transposase | 209, 210 |
| Rv2998 | | 211, 212 |
| Rv3015c | | 213, 214 |
| Rv3022c | | 215, 216 |
| Rv3039c | enoyl-CoA hydratase/isomerase | 217, 218 |
| Rv3061c | acyl-CoA dehydrogenase | 219, 220 |
| Rv3064c | | 221, 222 |
| Rv3097c | esterase; lipase | 223, 224 |
| Rv3107c | dehydrogenase | 225, 226 |
| Rv3162c | | 227, 228 |
| Rv3178 | | 229, 230 |
| Rv3184 | transposase | 231, 232 |
| Rv3315c | cytidine deaminase | 233, 234 |
| Rv3322c | methyltransferase | 235, 236 |
| Rv3351c | | 237,238 |
| Rv3352c | oxidoreductase | 239, 240 |
| Rv3373 | enoyl-CoA hydratase (crotonase) | 241, 242 |
| Rv3439c | | 243, 244 |
| Rv3446c | | 245, 246 |
| Rv3447c | membrane protein | 247, 248 |
| Rv3450c | | 249, 250 |
| Rv3467 | | 251, 252 |
| Rv3505 | acyl-CoA dehydrogenase | 253, 254 |
| Rv3540c | lipid-transfer protein | 255, 256 |
| Rv3546 | acetyl-CoA C-acetyltransferase | 257, 258 |
| Rv3550 | enoyl-CoA hydratase/isomerase | 259, 260 |
| Rv3552 | | 261, 262 |
| Rv3565 | aminotransferase | 263, 264 |
| Rv3569c | hydrolase | 265, 266 |
| Rv3606c | 2-amino-4-hydroxy-6-hydroxymethyldihydropterine pyrophosphokinase | 267, 268 |
| Rv3637 | transposase | 269, 270 |
| Rv3660c | | 271, 272 |
| Rv3745c | | 273, 274 |
| Rv3903c | | 275, 276 |
| Rv0039c | | 277, 278 |
| Rv0903c | | 279, 280 |
| Rv2745c | | 281, 282 |

References

1. McKinney, J. D., et al., Persistence of *Mycobacterium tuberculosis* in macrophages and mice requires the glyoxylate shunt enzyme isocitrate lyase [see comments]. Nature, 2000. 406(6797): p. 735-8.
2. Pelicic, V., et al., Efficient allelic exchange and transposon mutagenesis in *Mycobacterium tuberculosis*. Proc Natl Acad Sci USA, 1997. 94(20): p. 10955-60.
3. Lee, M. H., et al., Site-specific integration of mycobacteriophage L5: integration-proficient vectors for *Mycobacterium smegmatis, Mycobacterium tuberculosis*, and bacille Calmette-Guerin. Proc Natl Acad Sci USA, 1991. 88(8): p. 3111-5.

4. McShane, H., et al., Enhanced immunogenicity of CD4(+) t-cell responses and protective efficacy of a DNA-modified vaccinia virus Ankara prime-boost vaccination regimen for murine tuberculosis. Infect Immun, 2001. 69(2): p. 681-6.

5. Movahedzadeh, F., M. J. Colston, and E. O. Davis, Characterization of *Mycobacterium tuberculosis* LexA: recognition of a Cheo (Bacillus-type SOS) box. Microbiology, 1997. 143(Pt 3): p. 929-36.

Additional References

Cunningham, A. F. and C. L. Spreadbury. 1998. Mycobacterial stationary phase induced by low oxygen tension: cell wall thickening and localization of the 16-kilodalton alpha-crystallin homolog. J. Bacteriol. 180:801-808.

Lalvani, A. et al., 2001. Enhanced contact tracing and spatial tracking of *Mycobacterium tuberculosis* infection by enumeration of antigen-specific T cells. The Lancet 357:2017-2021.

Rook, G. A. W. and B. R. Bloom. 1994. Mechanisms of pathogenesis in tuberculosis, pp 460-485. In B. R. Bloom (ed), Tuberculosis-pathogenesis, protection and control. ASM Press, Washington D.C.

Wayne, L. G. 1994. Dormancy of *Mycobacterium tuberculosis* and latency of disease. Eur. J. Clin. Microbiol. Infect. Dis. 13:908-914.

Wayne, L. G. and L. G. Hayes. 1996. An in vitro model for sequential study of shift-down of *Mycobacterium tuberculosis* through two stages of non-replicating persistence. Infect. Immun. 642062-2069.

Wayne, L. G. and K. Lin. 1982. Glyoxylate metabolism and adaptation of *Mycobacterium tuberculosis* to survival under anaerobic conditions. Infect. Immun. 37:1042-1049.

Sambrook, J., E. F. Fritsch, and T. Maniatis. 1989. Molecular cloning: a laboratory manual, 2nd ed. Cold Spring Harbour Laboratory Press, Cold Spring Harbour, N.Y.

Lefever, P., O. Denis, L. De Wit, A. Tanghe, P. Vandenbussche, J. Content, and K. Huygen. 2000. Cloning of the gene encoding a 22-kilodalton cell surface antigen of *Mycobacterium bovis* BCG and analysis of its potential for DNA vaccination against tuberculosis. Infection and Immunity. 68:1040-1047.

Vordermeire, H. M., P. J. Cockle, A. O. Whelan, S. Rhodes, M. A. Chambers, D. Clifford, K. Huygen, R. Tascon, D. Lowrie, M. J. Colston, and R. G. Hewinson. 2000. Effective DNA vaccination of cattle with the mycobacterial antigens MPB83 and MPB70 does not compromise the specificity of the comparative intradermal tuberculin skin test. Vaccine. 19:1246-1255.

Cheng, W., C. Hung, C. Chai, K. Hsu, L. He, C. Rice, M. Ling, and T. Wu. 2001. Enhancement of Sindbis virus self-replicating RNA vaccine potency by linkage of *Mycobacterium tuberculosis* heat shock protein 70 gene to an antigen. J. Immunol. 166:6218-6226.

The invention claimed is:

1. A vector selected from the group consisting of (i) a DNA plasmid comprising a promoter, a polyadenylation signal, a selectable marker and a DNA sequence, wherein the promoter and polyadenylation signal are operably linked to the DNA sequence, the selectable marker encodes a protein that confers resistance to an antibiotic, the promoter is a CMV promoter, and the polyadenylation signal is a bovine growth hormone polyadenylation signal;

(ii) an RNA vector comprising an isolated RNA sequence that is encoded by the DNA sequence, wherein the RNA vector contains an integration site for a chromosome of a host cell; and (iii) a viral vector comprising an RNA sequence that is encoded by the DNA sequence;

wherein the DNA sequence is selected from the group consisting of SEQ ID NOs: 8, 56, 126 and 130, or a variant thereof having at least 70% nucleotide sequence identity therewith, or a fragment thereof having at least 15 nucleotides, or a derivative thereof, wherein the peptide encoded by said variant, fragment or derivative has a common antigenic cross-reactivity to the peptide encoded by the DNA sequence;

wherein the DNA sequence is the coding sequence of a *M. tuberculosis* gene, the expression of which is induced or up-regulated under culture conditions that are nutrient-starving and which maintain mycobacterial latency, said conditions being obtainable by batch fermentation of a

*M. tuberculosis* mycobacterium for at least 40 days post-inoculation, when compared with culture conditions that are not nutrient-starving and which support exponential growth of said mycobacterium.

2. A viral vector comprising a *M. tuberculosis* DNA sequence selected from the group consisting of SEQ ID NOs: 8, 56, 126 and 130, or a variant thereof having at least 70% nucleotide sequence identity therewith, or a derivative thereof, wherein the peptide encoded by said variant or derivative has a common antigenic cross-reactivity to the peptide encoded by the DNA sequence;

wherein the *M. tuberculosis* DNA sequence is the coding sequence of a *M. tuberculosis* gene, the expression of which is induced or up-regulated under culture conditions that are nutrient-starving and which maintain mycobacterial latency, said conditions being obtainable by batch fermentation of a *M. tuberculosis* mycobacterium for at least 40 days post-inoculation, when compared with culture conditions that are not nutrient-starving and which support exponential growth of said mycobacterium.

3. A viral vector comprising a DNA sequence, wherein the DNA sequence is:

(i) a fragment of a *M. tuberculosis* DNA sequence selected from the group consisting of SEQ ID NOs: 8, 56, 126 and 130; wherein the fragment has at least 15 nucleotides;

(ii) a variant of (i) having at least 70% nucleotide sequence identity therewith; or (iii) a derivative of (i) or (ii);

wherein the peptide encoded by said fragment, variant or derivative has a common antigenic cross-reactivity to the peptide encoded by said *M. tuberculosis* DNA sequence;

wherein said *M. tuberculosis* DNA sequence is the coding sequence of a *M. tuberculosis* gene, the expression of which is induced or up-regulated under culture conditions and which maintain mycobacterial latency, said conditions being obtainable by batch fermentation of a *M. tuberculosis* mycobacterium for at least 40 days post-inoculation, when compared with culture conditions that are not nutrient-starving and which support exponential growth of said mycobacterium.

4. The vector according to claim 1, wherein said vector is (i) the DNA plasmid.

5. The vector according to claim 1, wherein said vector is (ii) the RNA vector.

6. The vector according to claim 1, wherein said vector is (iii) the viral vector.

7. The viral vector according to claim 3, wherein the DNA sequence is (i) the fragment of the *M. tuberculosis* DNA sequence.

8. The viral vector according to claim 3, wherein the DNA sequence is (ii) the variant of (i).

9. The viral vector according to claim 3, wherein the DNA sequence is (iii) the derivative of (i) or (ii).

10. The viral vector according to claim 7, wherein the length of the DNA fragment is at least 70% of the length of SEQ ID NOs: 8, 56, 126 or 130 respectively.

11. The viral vector according to claim 7, wherein the length of the DNA fragment is at least 80% of the length of SEQ ID NOs: 8, 56, 126 or 130 respectively.

12. A viral vector comprising a DNA sequence, wherein the DNA sequence is:

(i) a fragment of a DNA sequence variant, wherein:

(a) the DNA sequence variant has at least 98% nucleotide sequence identity with isolated *M. tuberculosis* DNA sequence SEQ ID NO: 8, 56 or 130;

wherein the length of the fragment is at least 50% of the length of SEQ ID NOs: 8, 56 or 130 respectively; or (b) the DNA sequence variant has at least 95% nucleotide sequence identity with isolated *M. tuberculosis* DNA sequence SEQ ID NO: 126, wherein the length of the fragment is at least 50% of the length of SEQ ID NO: 126; or (ii) a derivative of (i);

wherein the peptide encoded by said fragment, variant or derivative has a common antigenic cross-reactivity to the peptide encoded by said *M. tuberculosis* DNA sequence; and wherein said *M. tuberculosis* DNA sequence is the coding sequence of a *M. tuberculosis* gene, the expression of which is induced or up-regulated under culture conditions that are nutrient starving and which maintain mycobacterial latency, said conditions being obtainable by batch fermentation of a *M. tuberculosis* mycobacterium for at least 40 days post-inoculation, when compared with culture conditions that are not nutrient-starving and which support exponential growth of said mycobacterium.

13. The viral vector according to claim 12, wherein the DNA sequence is (i) the fragment of (a) the DNA sequence variant.

14. The viral vector according to claim 12, wherein the DNA sequence is (i) the fragment of (b) the DNA sequence variant.

15. The viral vector according to claim 12, wherein the DNA sequence is (ii) the derivative of (i).

16. The viral vector according to claim 13, wherein the length of the (i) fragment of (a) the DNA sequence variant is at least 70% of the length of SEQ ID NOs: 8, 56 or 130.

17. The viral vector according to claim 13, wherein the length of the (i) fragment of (a) the DNA sequence variant is at least 80% of the length of SEQ ID NOs: 8, 56 or 130.

18. The viral vector according to claim 14, wherein the length of the (i) fragment of (b) the DNA sequence variant is at least 70% of the length of SEQ ID NO: 126.

19. The viral vector according to claim 14, wherein the length of the (i) fragment of (b) the DNA sequence variant is at least 80% of the length of SEQ ID NO: 126.

* * * * *

UNITED STATES PATENT AND TRADEMARK OFFICE

CERTIFICATE OF CORRECTION

| | |
|---|---|
| PATENT NO. | : 8,399,650 B2 |
| APPLICATION NO. | : 13/214776 |
| DATED | : March 19, 2013 |
| INVENTOR(S) | : Brian W. James et al. |

It is certified that error appears in the above-identified patent and that said Letters Patent is hereby corrected as shown below:

On the Title Page, Item (56):

Other Publications, line 7, please insert --virus-- after vaccinia.

Other Publications:

Page 1
Col. 1, line 8, please delete “CDF” and insert --CD4--.
Col. 1, line 67, please delete “Nutrlional” and insert --Nutritional--.

Page 3
Col. 1, line 10, please delete “Lefevre” and insert --Lefèver--.
Col. 1, line 29, please delete “issue 5” and insert --issue 4--.
Col. 2, line 22, please delete “Mold.” and insert --Moled.--.
Col. 2, line 38, please delete “marX” and insert --narX--.

In the claims:
Col. 456, line 12, please delete “130” and insert --130--.

Signed and Sealed this
Twelfth Day of August, 2014

Michelle K. Lee
*Deputy Director of the United States Patent and Trademark Office*